United States Patent
Atkinson et al.

(10) Patent No.: US 10,927,080 B2
(45) Date of Patent: *Feb. 23, 2021

(54) PYRIDINONE DICARBOXAMIDE FOR USE AS BROMODOMAIN INHIBITORS

(71) Applicant: GlaxoSmithKline Intellectual Property (No.2) Limited, Brentford (GB)

(72) Inventors: Stephen John Atkinson, Stevenage (GB); Helen Elizabeth Aylott, Stevenage (GB); Anthony William James Cooper, Stevenage (GB); Emmanuel Hubert Demont, Stevenage (GB); Lee Andrew Harrison, Stevenage (GB); Thomas George Christopher Hayhow, Stevenage (GB); Matthew J. Lindon, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GLAXOSMITHKLINE INTELLECTUAL PROPERTY (NO.2) LIMITED, Brentford (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/535,139

(22) Filed: Aug. 8, 2019

(65) Prior Publication Data
US 2019/0359572 A1  Nov. 28, 2019

Related U.S. Application Data

(63) Continuation of application No. 15/757,199, filed as application No. PCT/EP2016/070519 on Aug. 31, 2016, now Pat. No. 10,428,026.

(60) Provisional application No. 62/213,137, filed on Sep. 2, 2015.

(51) Int. Cl.
| | |
|---|---|
| C07D 213/82 | (2006.01) |
| A61K 31/44 | (2006.01) |
| C07D 401/06 | (2006.01) |
| C07D 405/06 | (2006.01) |
| C07D 413/06 | (2006.01) |
| C07D 471/04 | (2006.01) |

(52) U.S. Cl.
CPC ......... *C07D 213/82* (2013.01); *C07D 401/06* (2013.01); *C07D 405/06* (2013.01); *C07D 413/06* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 7,476,681 B2 | 1/2009 | Paruch et al. | |
| 7,998,984 B2 | 8/2011 | Hansen et al. | |
| 8,716,274 B2 | 5/2014 | Crawford et al. | |
| 9,561,231 B2 | 2/2017 | Hubbard et al. | |
| 10,428,026 B2 * | 10/2019 | Atkinson | C07D 405/06 |
| 10,441,576 B2 | 10/2019 | Diethelm et al. | |
| 2009/0131483 A1 | 5/2009 | Hansen et al. | |
| 2012/0208814 A1 | 8/2012 | Demont et al. | |
| 2014/0179648 A1 | 6/2014 | Liu et al. | |
| 2015/0158873 A1 | 6/2015 | Bogdan et al. | |

FOREIGN PATENT DOCUMENTS

| | | |
|---|---|---|
| EP | 1 357 111 B1 | 10/2003 |
| EP | 1 433 788 A1 | 6/2004 |
| EP | 1 477 186 A1 | 11/2004 |
| EP | 1 663 974 B1 | 1/2009 |
| JP | 2015-523347 A | 8/2015 |
| WO | WO 2004/033446 A1 | 4/2004 |
| WO | WO 2009/158315 A1 | 12/2009 |
| WO | WO 2013/188381 A1 | 12/2013 |
| WO | WO 2014/074675 A1 | 5/2014 |
| WO | WO 2014/096965 A2 | 6/2014 |

(Continued)

OTHER PUBLICATIONS

Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).

Gallenkamp et al., "Bromodomains and Their Pharmacological Inhibitors", *ChemMedChem*, vol. 9, No. 3, pp. 438-464 (2014).

Garnier et al., "BET bromodomain inhibitors: a patent review", *Expert Opinion on Therapeutic Patents*, vol. 24, No. 2, pp. 185-199 (2014).

International Search Report for International application No. PCT/EP2016/070519, dated Oct. 20, 2016, 4 pages.

(Continued)

*Primary Examiner* — Zinna Northington Davis
(74) *Attorney, Agent, or Firm* — Robert H. Brink; Duke M. Fitch; Edward R. Gimmi

(57) ABSTRACT

The present invention relates to compounds of formula (I) and salts thereof, pharmaceutical compositions containing such compounds and to their use in therapy

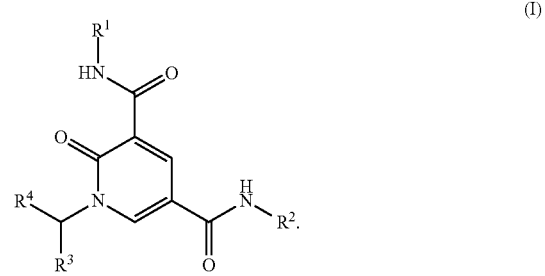

(I)

8 Claims, No Drawings

(56) References Cited

FOREIGN PATENT DOCUMENTS

| | | |
|---|---|---|
| WO | WO 2015/015318 A2 | 2/2015 |
| WO | WO 2015/022322 A1 | 2/2015 |
| WO | WO 2017/037116 A1 | 3/2017 |
| WO | WO 2017/060180 A1 | 4/2017 |
| WO | WO 2017/174621 A1 | 10/2017 |
| WO | WO 2017/202742 A1 | 11/2017 |

OTHER PUBLICATIONS

International Search Report for International application No. PCT/EP2016/072216, International filing date: Sep. 20, 2016, 3 pages.
International Search Report for International application No. PCT/EP2016/073532, dated Nov. 30, 2016, 5 pages.
International Search Report for International application No. PCT/EP2017/058050, dated May 24, 2017, 5 pages.
International Search Report for International application No. PCT/EP2017/062208, dated Jul. 6, 2017, 5 pages.
International Search Report for International application No. PCT/EP2018/054730, dated May 4, 2018, 4 pages.
International Search Report for International application No. PCT/EP2018/054733, dated Jun. 11, 2018, 4 pages.
Non-Final Office Action for U.S. Appl. No. 15/766,222, USPTO, dated Oct. 4, 2018, 9 pages.
Notice of Allowance for U.S. Appl. No. 15/762,229, USPTO, dated Dec. 11, 2018, 9 pages.
Notice of Allowance for U.S. Appl. No. 15/766,222, USPTO, dated Jan. 17, 2019, 6 pages.
Notice of Allowance for U.S. Appl. No. 15/762,229, USPTO, dated Mar. 20, 2019, 7 pages.

* cited by examiner

PYRIDINONE DICARBOXAMIDE FOR USE AS BROMODOMAIN INHIBITORS

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions. Compounds which are bromodomain inhibitors may be useful in the treatment of various diseases and conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.*, 2011, 54, 3827-3838).

Chan et al. report that BET bromodomain inhibition suppresses transcriptional responses to cytokine-Jak-STAT signalling in a gene-specific maner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

Funabashi et al describe 1,2,3,4,-tetrahydroquinolines and conduct a configuration and conformation analysis (Funabashi et a, *Bulletin of the Chemical Society of Japan*, 1969, 42, 2885-2894).

WO2014/140076 discloses 2,3-disubstituted 1-acyl-4-amino-1,2,3,4-tetrahydroquinoline derivatives and their use as bromodomain inhibitors.

SUMMARY OF THE INVENTION

The invention is directed to compounds of formula (I)

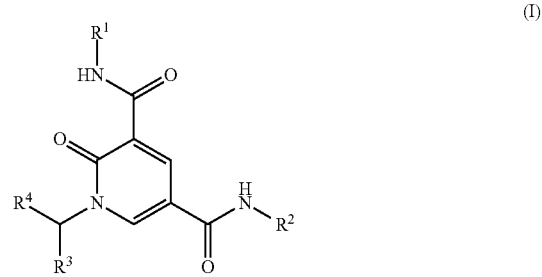

and salts thereof;
wherein:
$R^1$ is —$C_{1-3}$alkyl or cyclopropyl;
$R^2$ is H or —$C_{0-3}$alkyl-$C_{3-7}$cycloalkyl, wherein the cycloalkyl group is unsubstituted or substituted with one, two or three $R^5$ groups which may be the same or different;
$R^3$ is —H, —$C_{1-4}$alkyl, cyclopropyl or —$(CH_2)_pOR^{10}$;
$R^4$ is a) phenyl (which may be unsubstituted or substituted by one, two or three $R^7$ groups which may be the same or different); b) a 5 or 6 membered heteroaryl group (which may be unsubstituted or substituted by —$C_{1-3}$alkyl, —O—$C_{1-3}$alkyl or halo); c) a 9 to 11 membered heteroaryl group (which may be unsubstituted or substituted by one, two or three groups, which may be the same or different, selected from —$C_{1-3}$alkyl-$R^8$, —$OCH_3$, —O—$C_{2-3}$alkyl-$R^8$, halo, oxo, —O—$CF_3$ and —CN); or d) —$(CH_2)_n$-phenyl;
p is 1 or 2;
n is 1 or 2;
$R^5$ is halo, phenyl, —$C_{1-6}$alkyl-$R^8$, —$CO_2H$, —$OCH_3$, —O—$C_{2-6}$alkyl-$R^8$, —CN, —OH or —$NHR^6$;
$R^6$ is —H, —$C(O)OC(CH_3)_3$, —$C_{1-6}$alkyl, —$C_{3-7}$cycloalkyl, a 4 to 7 membered heterocyclyl group, or —$C_{2-3}$alkyl-O—$C_{1-3}$alkyl wherein the —$C_{1-6}$alkyl and —$C_{3-7}$cycloalkyl groups may be optionally substituted by one, two or three fluoro;
$R^7$ is —$NR^{11}R^{12}$, —$C_{1-3}$alkyl, halo, —$CO_2R^{10}$, —$CH_2OH$, —$CH(R^{11})OR^{10}$, —$C(O)C_{1-3}$alkyl, —$CH(R^{10})NR^{11}R^{12}$, —CN, —CHF$_2$, —CF$_3$, —OH, —OCHF$_2$, —OCF$_3$, —OCH$_3$, —O—C$_{2-6}$alkyl-R$^9$, —C$_{1-6}$alkyl-R$^9$ or —O-piperidinyl;

R$^8$ is —H, —OR$^{10}$, —CO$_2$C(CH$_3$)$_3$ or —NR$^{11}$R$^{12}$;

R$^9$ is —H, —OR$^{10}$ or —NR$^{11}$R$^{12}$;

R$^{10}$ is —H or —C$_{1-3}$alkyl;

R$^{11}$ and R$^{12}$ are each independently selected from —H, —C$_{1-3}$alkyl and —C$_{1-3}$alkylNR$^{13}$R$^{14}$; or R$^{11}$ and R$^{12}$ may join together with the nitrogen to which they are attached, to form a 4 to 7 membered heterocyclyl group optionally substituted by one or two substituents independently selected from —C$_{1-3}$alkyl, —OH and F; and R$^{13}$ and R$^{14}$ are each independently selected from —H, —C$_{1-3}$alkyl and —C(O)CH$_3$.

Certain compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "C$_{1-6}$alkyl" as used herein refers to a straight or branched alkyl group having from 1 to 6 carbon atoms, for example 1 to 3 carbon atoms. For example the term "C$_{0-3}$alkyl" refers to a straight or branched alkyl group having from 0 (i.e. is absent) to 3 carbon atoms, for example 0 to 2 carbon atoms. Representative branched alkyl groups have one, two or three branches. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon ring or a saturated spiro-linked bicyclic hydrocarbon ring, having the specified number of member atoms in the ring. For example, the term "C$_{3-7}$cycloalkyl" as used herein refers to a cycloakyl group having from 3 to 7 member atoms, for example 3 member atoms. Examples of C$_{3-7}$cycloalkyl groups include, but are not limited to, cyclopropyl, cyclobutyl, cyclopentyl, cyclohexyl, and spiro[3.3]heptane.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a cyclic or bicyclic group having the specified number of member atoms wherein at least a portion of the group is aromatic. The point of attachment to the rest of the molecule may be by any suitable carbon or nitrogen atom. For example, the term "5 or 6 membered heteroaryl" as used herein refers to a heteroaryl group having 5 or 6 member atoms, including 1 or 2 heteroatoms independently selected from nitrogen, sulphur and oxygen. Examples of "5 or 6 membered heteroaryl" groups include, but are not limited to, thiophene, pyrazolyl and pyridinyl. The term "9 to 11 membered heteroaryl" as used herein refers to a bicyclic structure having 9, 10 or 11 member atoms, including 1 or 2 heteroatoms independently selected from nitrogen and oxygen. Examples of "9 to 11 membered heteroaryl" groups include, but are not limited to, 2,3-dihydrobenzo[b][1,4]dioxinyl, 1H-benzo[d]imidazolyl, benzoimidazolyl, benzazepinyl, 2,3,4,5-tetrahydro-1H-benzo[d]azepinyl, quinoxalinyl, quinolinyl, indazolyl, indolyl, 1,2,3,4-tetrahydroquinolinyl, 1,2,3,4-tetrahydroisoquinolinyl, indolinyl, benzofuranyl, isoquinolinyl, and 2,3-dihydrobenzofuranyl.

"Heteroatom" refers to a nitrogen, sulfur, or oxygen atom, for example a nitrogen atom or an oxygen atom.

"Heterocyclyl" refers to an aliphatic cyclic group having the specified number of member atoms. The point of attachment may be by any suitable carbon or nitrogen atom. For example the term "4 to 7 membered heterocyclyl" as used herein refers to a heterocycle group having 4, 5, 6 or 7 member atoms including one nitrogen atom and optionally containing a further heteroatom selected from nitrogen, oxygen or sulphur. Examples of "4 to 7 membered heterocycle" groups include, but are not limited to, morpholinyl, piperidinyl, piperazinyl, homopiperazinyl and pyrrolidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I). For example, "rac-(2S,3R,4R)" means a racemic mixture of the (2S,3R,4R) enantiomer and the (2R,3S,4S) enantiomer.

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols ( ▬/ ⅢⅢ ) are used. Where the absolute stereochemistry is known and the compound is a single enantiomer, the bold or hashed wedges symbols ( ▬/ ⅢⅢ ) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

STATEMENT OF THE INVENTION

In a first aspect there are provided compounds of formula (I):

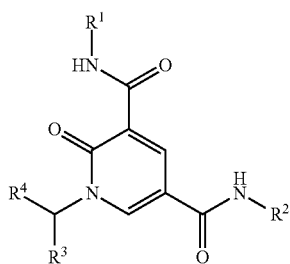

and salts thereof;

wherein:
$R^1$ is —$C_{1-3}$alkyl or cyclopropyl;
$R^2$ is H or —$C_{0-3}$alkyl-$C_{3-7}$cycloalkyl, wherein the cycloalkyl group is unsubstituted or substituted with one, two or three $R^5$ groups which may be the same or different;
$R^3$ is —H, —$C_{1-4}$alkyl, cyclopropyl or —$(CH_2)_pOR^{10}$;
$R^4$ is a) phenyl (which may be unsubstituted or substituted by one, two or three $R^7$ groups which may be the same or different); b) a 5 or 6 membered heteroaryl group (which may be unsubstituted or substituted by —$C_{1-3}$alkyl, —O—$C_{1-3}$alkyl or halo); c) a 9 to 11 membered heteroaryl group (which may be unsubstituted or substituted by one, two or three groups, which may be the same or different, selected from —$C_{1-3}$alkyl$R^8$, —$OCH_3$, —O—$C_{2-3}$alkyl-$R^8$, halo, oxo, —O—$CF_3$ and —CN); or d) —$(CH_2)_n$-phenyl;
p is 1 or 2;
n is 1 or 2;
$R^5$ is halo, phenyl, —$C_{1-6}$alkyl-$R^8$, —$CO_2H$, —$OCH_3$, —O—$C_{2-6}$alkyl-$R^8$, —CN, —OH or —$NHR^6$;
$R^6$ is —H, —$C(O)OC(CH_3)_3$, —$C_{1-6}$alkyl, —$C_{3-7}$cycloalkyl, a 4 to 7 membered heterocyclyl group, or —$C_{2-3}$alkyl-O—$C_{1-3}$alkyl wherein the —$C_{1-6}$alkyl and —$C_{3-7}$cycloalkyl groups may be optionally substituted by one, two or three fluoro;
$R^7$ is —$NR^{11}R^{12}$, —$C_{1-3}$alkyl, halo, —$CO_2R^{10}$, —$CH_2OH$, —$CH(R^{11})OR^{10}$, —$C(O)C_{1-3}$alkyl, —$CH(R^{10})NR^{11}R^{12}$, —CN, —$CHF_2$, —$CF_3$, —OH, —$OCHF_2$, —$OCF_3$, —$OCH_3$, —O—$C_{2-6}$alkyl-$R^9$, —$C_{1-6}$alkyl-$R^9$ or —O-piperidinyl;
$R^8$ is —H, —$OR^{10}$, —$CO_2C(CH_3)_3$ or —$NR^{11}R^{12}$;
$R^9$ is —H, —$OR^{10}$ or —$NR^{11}R^{12}$;
$R^{10}$ is —H or —$C_{1-3}$alkyl;
$R^{11}$ and $R^{12}$ are each independently selected from —H, —$C_{1-3}$alkyl and —$C_{1-3}$alkyl$NR^{13}R^{14}$; or $R^{11}$ and $R^{12}$ may join together with the nitrogen to which they are attached, to form a 4 to 7 membered heterocyclyl group optionally substituted by one or two substituents indecently selected from —$C_{1-3}$alkyl, —OH and F; and
$R^{13}$ and $R^{14}$ are each independently selected from —H, —$C_{1-3}$alkyl and —$C(O)CH_3$.

In one embodiment there are provided compounds of formula (I) and salts thereof wherein:
$R^1$ is —$C_{1-3}$alkyl or cyclopropyl;
$R^2$ is —$C_{0-3}$alkyl-$C_{3-7}$cycloalkyl, wherein the cycloalkyl group is unsubstituted or substituted with one, two or three $R^5$ groups which may be the same or different;
$R^3$ is —H, —$C_{1-4}$alkyl, cyclopropyl or —$(CH_2)_pOR^{10}$;
$R^4$ is a) phenyl (which may be unsubstituted or substituted by one, two or three $R^7$ groups which may be the same or different); b) a 5 or 6 membered heteroaryl group (which may be unsubstituted or substituted by —$C_{1-3}$alkyl, —O—$C_{1-3}$alkyl or halo); c) a 9 to 11 membered heteroaryl group (which may be unsubstituted or substituted by one, two or three groups, which may be the same or different, selected from —$C_{1-3}$alkyl$R^8$, —$OCH_3$, —O—$C_{2-3}$alkyl-$R^8$, halo, oxo, —O—$CF_3$ and —CN); or d) —$(CH_2)_n$-phenyl;
p is 1 or 2;
n is 1 or 2;
$R^5$ is halo, phenyl, —$C_{1-6}$alkyl-$R^8$, —$CO_2H$, —$OCH_3$, —O—$C_{2-6}$alkyl-$R^8$, —CN, —OH or —$NHR^6$;
$R^6$ is —H, —$C(O)OC(CH_3)_3$, —$C_{1-6}$alkyl, —$C_{3-7}$cycloalkyl, a 4 to 7 membered heterocyclyl group, or —$C_{2-3}$alkyl-O—$C_{1-3}$alkyl wherein the —$C_{1-6}$alkyl and —$C_{3-7}$cycloalkyl groups may be optionally substituted by one, two or three fluoro;
$R^7$ is —$NR^{11}R^{12}$, —$C_{1-3}$alkyl, halo, —$CO_2R^{10}$, —$CH_2OH$, —$CH(R^{11})OR^{10}$, —$C(O)C_{1-3}$alkyl, —$CH(R^{10})NR^{11}R^{12}$, —CN, —OH, —OCHF$_2$, —OCF$_3$, —OCH$_3$, —O—C$_{2-6}$alkyl-R$^9$, —C$_{1-6}$alkyl-R$^9$ or —O-piperidinyl;
R$^8$ is —H, —OR$^{10}$ or —NR$^{11}$R$^{12}$;
R$^9$ is —H, —OR$^{10}$ or —NR$^{11}$R$^{12}$;
R$^{10}$ is —H or —C$_{1-3}$alkyl; and
R$^{11}$ and R$^{12}$ are each independently selected from —H and —C$_{1-3}$alkyl; or R$^{11}$ and R$^{12}$ may join together with the nitrogen to which they are attached, to form a 4 to 7 membered heterocyclyl group optionally substituted by one or two substituents independently selected from —C$_{1-3}$alkyl, —OH and F.

In one embodiment there are provided compounds of formula (Ia):

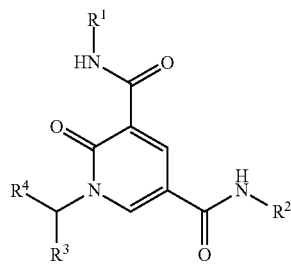

(Ia)

and salts thereof;
wherein:
R$^1$ is —C$_{1-3}$alkyl or cyclopropyl;
R$^2$ is —C$_{0-3}$alkyl-C$_{3-7}$cycloalkyl, wherein the cycloalkyl group is unsubstituted or substituted with 1, 2 or 3 R$^5$ groups which may be the same or different;
R$^3$ is —H, —C$_{1-4}$alkyl or cyclopropyl;
R$^4$ is a) phenyl (which may be unsubstituted or substituted by 1 or 2 R$^7$ groups which may be the same or different); or b) a 5 or 6 membered heteroaryl group (which may be unsubstituted or substituted by methyl or methoxy); or c) a 9 to 11 membered heteroaryl group (which may be unsubstituted or substituted by 1, 2 or 3 groups, which may be the same or different, selected from methyl, fluoro and oxo); or d) —(CH$_2$)$_n$-phenyl;
p is 1 or 2;
n is 1 or 2;
R$^5$ is halo, phenyl, —C$_{1-6}$alkyl-R$^8$, —CO$_2$H, —O—C$_{1-6}$alkyl-R$^8$, —CN, —OH or —NHR$^6$;
R$^6$ is —H or —C(O)OC(CH$_3$)$_3$;
R$^7$ is —NHCH$_3$, —N(CH$_3$)$_2$, —CH$_3$, —F, —CO$_2$H, —CH$_2$OH, —Cl, —C(O)CH$_3$, —C(O)OCH$_3$, —CH$_2$N(CH$_3$)$_2$, —CN, —OH, —O—C$_{1-6}$alkyl-R$^9$, —C$_{1-6}$alkyl-R$^9$ or —O-piperidinyl;
R$^8$ is —H, —OH, —N(CH$_3$)$_2$ or —OCH$_3$;
R$^9$ is —H, —OH, —N(CH$_3$)$_2$ or morpholinyl; and
R$^{10}$ is —H, methyl or ethyl.

In one embodiment R$^1$ is methyl, ethyl or cyclopropyl.
In one embodiment R$^1$ is methyl.
In one embodiment R$^2$ is H.
In one embodiment R$^2$ is cyclopropyl, cyclobutyl, cyclohexyl, methylcyclobutyl, methycyclopentyl, methylcyclohexyl, ethylcyclopropyl, ethyl cyclohexyl or spiro[3.3]heptanyl, wherein the cyclopropyl cyclobutyl, cyclopentyl, and cyclohexyl groups may be unsubstituted or substituted with 1 or 2 R$^5$ groups which may be the same or different.
In one embodiment R$^2$ is cyclopropyl, cyclobutyl, 3-fluorocyclobutyl, 3-phenylcyclobutyl, 6-aminoprio[3,3]heptanyl, 2-cyclopropylethyl, (trans)-2-methylcyclopropyl, (trans)-4-hydroxycyclohexyl, 2-hydroxymethylcyclopropyl, 2-methoxycyclopropyl, 1-cyanocyclopropyl, 2,2-diflourocyclopropyl, 3-(tert)-butoxycarbonylaminocyclobutyl, (1R*,2R*)-2-ethoxycylcpropyl, (1S*,2S*)-2-ethoxycyclopropyl, (trans)-2-ethylcyclopropyl, (1S,2S)-2-hydroxymethylcyclopropyl, (1R,2R)—, 2-hydroxymethylcyclopropyl, (1S,2S)-2-ethylcyclopropyl, (1R,2R)-2-ethylcyclopropyl, (1R,2R)-2-methylcyclopropyl, 2-ethoxycyclopropyl, (cis)-4-hydroxycyclohexyl, (1S*,2S*)-2-methoxycyclopropyl, (trans)-2-ethoxycyclopropyl, (cis)-2-methylcyclopropyl, (trans)-2-hydroxymethylcyclopropyl, (trans)-2-ethoxycyclopropyl, (1R*,2R*)-2-methylcyclopropyl, (1R,2R)-2-hydroxymethylcyclopropyl, (1S,2S)-2-methylcyclopropyl, (1S*,2S*)-2-hydroxymethylcyclobutylmethyl, (cis)-3-hydroxycyclobutyl, 6-(ter)-butoxycarbonylaminospiro[3.3]heptanyl, 2-phenylcyclobutyl, (cis)-3-hydroxycarbonylcyclobutyl, 1-isobutylcyclopropyl, 3-methoxy-2,2-dimethylcyclobutyl, 3-ethoxycyclobutyl, 3-methylcyclobutyl, 3-ethoxy-2-methoxycyclobutyl, 1-propylcyclobutyl, (1S,3R)-3-hydroxycyclopenyl, (trans)-2-hydroxycyclohexyl, (cis)-2-hydroxycyclohexyl, 2,2-difluorocyclopropyl, 2-hydroxycyclopenyl, (trans)-2-methoxycyclopropyl, 2-hydroxycyclohexyl, (1R,2S)-2-hydroxycyclopenylmethyl, (cis)-2-hydroxycyclopenylmethyl, (trans)-3-hydroxycyclopenylmethyl, (cis)-3-hydroxycyclopenylmethyl, (trans)-4-hydroxycyclohexyl methyl, (cis)-4-hydroxycyclohexylmethyl, (1R*,2R*)-2-methylcyclopropyl, (1R,3S)-3-hydroxycyclohexylmethyl, (1R,2R)-2-hydroxycyclobutyl, (1S*,3S*)-3-hydroxycyclohexyl, (1R*,3R*)-3-hydroxycyclohexyl, (1S*,3R*)-3-hydroxycyclohexyl, (1R,3S)-3-hydroxycyclohexyl, 2,2-dimethylcyclopropyl, (1S*,2S*)-2-methylcyclopropyl, (trans)-2-methoxycyclobutyl, (1R*)-2,2-dimethylcyclopropyl, or (1S*)-2,2-dimethylcyclopropyl.

In one embodiment R$^2$ is cyclopropyl.
In one embodiment R$^2$ is (1S,2S)-2-methylcyclopropyl.
In one embodiment R$^3$ is —H, —C$_{1-4}$alkyl or cyclopropyl.
In one embodiment R$^3$ is H, methyl, ethyl or cyclopropyl.
In one embodiment R$^3$ is H.

In one embodiment R$^4$ is a) phenyl (which may be unsubstituted or substituted by 1 or 2 R$^7$ groups which may be the same or different); b) a 5 or 6 membered heteroaryl (which may be unsubstituted or substituted by methyl) or c) a 9 to 11 membered heteroaryl (which may be unsubstituted or substituted by methyl).

In one embodiment R$^4$ is phenyl, unsubstituted or substituted with 1 or 2 R$^7$ groups which may be the same or different.

In one embodiment, R$^4$ is phenyl, 3-methylaminophenyl, 3-dimethylaminophenyl, 3,5-dimethylphenyl, 4-methoxyphenyl, 2,3-dimethylphenyl, 2-fluoro-3-methylphenyl, 4-fluoro-3-methylphenyl, 4-methoxy-3-methylphenyl, 3-fluoro-5-methylphenyl, 3-methylphenyl, 2-fluoro-5-methylphenyl, 3-methoxycarbonylphenyl, 3-hydroxymethylphenyl, 3-methoxyphenyl, 3-hydroxyphenyl, 3-(2-hydroxyethoxy)phenyl, 3-fluorophenyl, 4-fluorophenyl, 4-methylphenyl, 2-fluorophenyl, 3-(morpholino)phenyl, 3-chlorophenyl, 3-acetylphenyl, 2-methylphenyl, 3-2-(dimethylaminoethoxy)phenyl, 2-fluoro-3-methylphenyl, 3-(1-hydroxyethyl)phenyl, 3-hyddroxyphenyl, 2,5-dimethylphenyl, 4-methoxycarbonylphenyl, 3-cyanophenyl, 3-(morpholinomethyl)phenyl, 3-(dimethylaminomethyl) phenyl, 4-hydroxymethyl, 2-methylphenyl, 2-fluoro-5-methyl, 4-fluoro-3-methoxyphenyl, (R*)-3-(1-hydroxyethyl)phenyl, or (S*)-3-(1-hydroxyethyl)phenyl.

In one embodiment R⁴ is 5 or 6 membered heteroaryl, unsubstituted or substituted with methyl or methoxy.

In one embodiment R⁴ is:

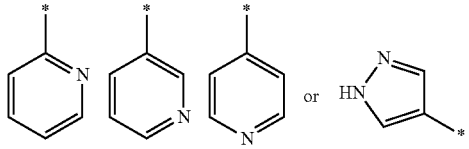

wherein * denotes the point of attachment to the alkyl residue, and which R⁴ may be unsubstituted or substituted by methyl or methoxy.

In one embodiment, R⁴ is 6-methoxypyridin-3-yl, pyridin-2-yl, pyridin-3-yl, pyridin-4-yl, 1-methyl-1Hpyrazol-4-yl or 6-methylpyridin-2-yl.

In one embodiment R⁴ is a 9 to 11 membered heteroaryl, unsubstituted or substituted with methyl.

In one embodiment R⁴ is:

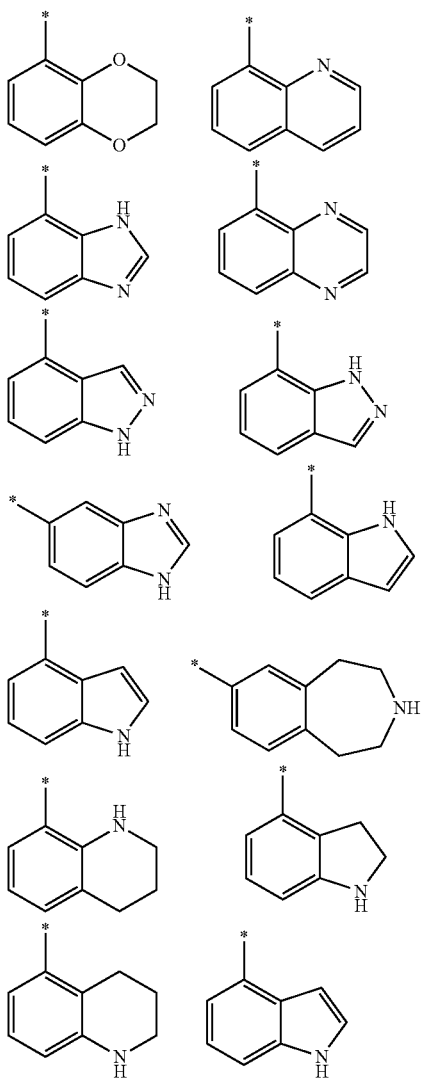

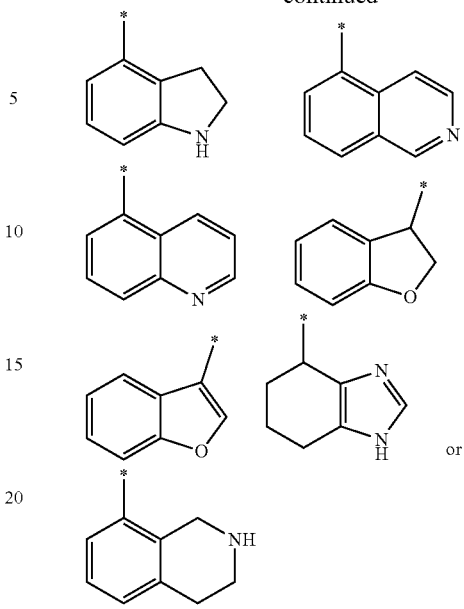

wherein * denotes the point of attachment to the alkyl residue, and which R⁴ may be unsubstituted or substituted by methyl.

In one embodiment R⁴ is (2,3-dihydrobenzo[b][1,4]dioxin-5-yl, quinolin-8-yl, 1H-benzo[d]imidazol-4-yl, 1-methyl-1H-benzo[d]imidazol-7-yl, quinoxalin-5-yl, 1H-indazol-4-yl, 1H-indazol-7-yl, 1H-benzo[d]imidazol-6-yl, 2,3,4,5-tetrahydro-1H-benzo[d]ezepin-7-yl, 1,2,3,4-tetrahydroquinolin-8-yl, 1H-indol-4-yl, indolin-4-yl, 1-methyl-1H-indol-4-yl, 2-methyl-1H-benzo[d]imidazol-4-yl, 3-methyl-1H-indol-4-yl, benzofuran-4-yl, isoquinolin-5-yl, 1,2,3,4-tetrahydroisoquinolin-7-yl, 1,2,3,4-tetrahydroisoquinolin-8-yl, 1,2,3,4-tetrahydroquinolin-5-yl, 1H-indol-3-yl, 1-methyl-1H-benzo[d]imidazol-4-yl, 4,5,6,7-tetrahydro-H-benzo[d]imidazol-4-yl, benzofuran-3-yl or 2,3-dihydrobenzofuran-3-yl.

In one embodiment R⁴ is phenyl, 3-methoxyphenyl, 3-hydroxyethoxyphenyl or indolin-4-yl. In another embodiment R⁴ is phenyl. In a further embodiment R⁴ is 3-hydroxyethoxyphenyl.

In one embodiment R⁵ is halo, phenyl, —C₁₋₆alkyl, —O—C₁₋₆alkyl, —CO₂H, —C₁₋₆alkyl-OH, —CN, —OH or —NHR⁶. In another embodiment R⁵ is —F, phenyl, methyl, ethyl, n-propyl, —OCH₃, —OCH₂CH₃, —CH₂OH, —CN, —OH, —NH₂ or —NHC(O)OC(CH₃)₃. In a further embodiment R⁵ is methyl.

In one embodiment R⁷ is —NHCH₃, —N(CH₃)₂, —CH₃, —OCH₃, —F, —CH₂OH, —CN, —CH₂-morpholinyl, —Cl, —C(O)CH₃, —OCH₂CH₂N(CH₃)₂, —OCH₂CH₂OH, —C(O)OCH₃, —CH₂N(CH₃)₂, —OH, or —CH(CH₃)OH. In another embodiment R⁷ is —NHCH₃, —N(CH₃)₂, —CH₃, —OCH₃, —F, —CH₂OH, —CN, —CH₂-morpholinyl, —Cl, —C(O)CH₃, —OCH₂CH₂N(CH₃)₂, —OCH₂CH₂OH, —C(O)OCH₃, —CH₂N(CH₃)₂, —OH, —CHF₂, —CF₃ or —CH(CH₃)OH. In another embodiment R⁷ is —CH(CH₃)OH.

It is to be understood that the present invention covers all combinations of substituent groups described hereinabove.

Compounds of the invention include the compounds of Examples 1 to 268 and salts thereof.

In a further embodiment there is provided the compounds of Examples 269 to 341 and salts thereof.

In a yet further embodiment there is provided the compounds of Examples 1 to 341 and salts thereof.

In one embodiment the compound of formula (I) is
1-benzyl-N5-cyclopropyl-N3-methyl-2-oxo-1,2-dihydropyridine-3,5-dicarboxamide;
1-benzyl-N5-cyclobutyl-N3-methyl-2-oxo-1,2-dihydropyridine-3,5-dicarboxamide;
N5-cyclopropyl-N3-methyl-2-oxo-1-(1-phenylethyl)-1,2-dihydropyridine-3,5-dicarboxamide;
rac-N5-cyclopropyl-N3-methyl-2-oxo-1-(1-phenylpropyl)-1,2-dihydropyridine-3,5-dicarboxamide;
N5-cyclobutyl-1-((2,3-dihydrobenzo[b][1,4]dioxin-5-yl)methyl)-N3-methyl-2-oxo-1,2-dihydropyridine-3,5-dicarboxamide;
N5-cyclobutyl-N3-methyl-1-(3-(methylamino)benzyl)-2-oxo-1,2-dihydropyridine-3,5-dicarboxamide;
N5-cyclobutyl-1-(3-(dimethylamino)benzyl)-N3-methyl-2-oxo-1,2-dihydropyridine-3,5-dicarboxamide;
1-benzyl-N5-(3-fluorocyclobutyl)-N3-methyl-2-oxo-1,2-dihydropyridine-3,5-dicarboxamide;
N5-cyclobutyl-1-(3,5-dimethylbenzyl)-N3-methyl-2-oxo-1,2-dihydropyridine-3,5-dicarboxamide;
N5-cyclobutyl-1-(4-methoxybenzyl)-N3-methyl-2-oxo-1,2-dihydropyridine-3,5-dicarboxamide;
N5-cyclobutyl-N3-methyl-2-oxo-1-(quinolin-8-ylmethyl)-1,2-dihydropyridine-3,5-dicarboxamide;
N5-cyclobutyl-1-(2,3-dimethylbenzyl)-N3-methyl-2-oxo-1,2-dihydropyridine-3,5-dicarboxamide;
N5-cyclobutyl-1-(2-fluoro-3-methylbenzyl)-N3-methyl-2-oxo-1,2-dihydropyridine-3,5-dicarboxamide;
N5-cyclobutyl-1-(4-fluoro-3-methylbenzyl)-N3-methyl-2-oxo-1,2-dihydropyridine-3,5-dicarboxamide;
N5-cyclobutyl-1-(4-methoxy-3-methylbenzyl)-N3-methyl-2-oxo-1,2-dihydropyridine-3,5-dicarboxamide;
N5-cyclobutyl-1-(3-fluoro-5-methylbenzyl)-N3-methyl-2-oxo-1,2-dihydropyridine-3,5-dicarboxamide;
N5-cyclobutyl-N3-methyl-1-(3-methylbenzyl)-2-oxo-1,2-dihydropyridine-3,5-dicarboxamide;
N5-cyclobutyl-1-(2-fluoro-5-methylbenzyl)-N3-methyl-2-oxo-1,2-dihydropyridine-3,5-dicarboxamide;
1-benzyl-N3-methyl-2-oxo-N5-(3-phenylcyclobutyl)-1,2-dihydropyridine-3,5-dicarboxamide;
N5-(6-aminospiro[3.3]heptan-2-yl)-1-benzyl-N3-methyl-2-oxo-1,2-dihydropyridine-3,5-dicarboxamide;
(+/−)-N5-cyclobutyl-N3-methyl-2-oxo-1-(1-phenylethyl)-1,2-dihydropyridine-3,5-dicarboxamide;
1-benzyl-N5-cyclobutyl-N3-cyclopropyl-2-oxo-1,2-dihydropyridine-3,5-dicarboxamide;
1-((1H-benzo[d]imidazol-4-yl)methyl)-N5-cyclobutyl-N3-methyl-2-oxo-1,2-dihydropyridine-3,5-dicarboxamide;
1-benzyl-N5-(2-cyclopropylethyl)-N3-methyl-2-oxo-1,2-dihydropyridine-3,5-dicarboxamide;
methyl 3-((5-(cyclobutylcarbamoyl)-3-(methylcarbamoyl)-2-oxopyridin-1(2H)-yl)methyl)benzoate;
N5-cyclobutyl-1-(3-(hydroxymethyl)benzyl)-N3-methyl-2-oxo-1,2-dihydropyridine-3,5-dicarboxamide;
N5-cyclobutyl-1-(3-methoxybenzyl)-N3-methyl-2-oxo-1,2-dihydropyridine-3,5-dicarboxamide;
N5-cyclobutyl-1-(3-hydroxybenzyl)-N3-methyl-2-oxo-1,2-dihydropyridine-3,5-dicarboxamide;
N5-cyclobutyl-1-(3-(2-hydroxyethoxy)benzyl)-N3-methyl-2-oxo-1,2-dihydropyridine-3,5-dicarboxamide;
1-((1H-benzo[d]imidazol-4-yl)methyl)-N5-cyclopropyl-N3-methyl-2-oxo-1,2-dihydropyridine-3,5-dicarboxamide;
(R)—N5-cyclopropyl-N3-methyl-2-oxo-1-(1-phenylethyl)-1,2-dihydropyridine-3,5-dicarboxamide;
N5-cyclopropyl-N3-methyl-1-((1-methyl-1H-benzo[d]imidazol-7-yl)methyl)-2-oxo-1,2-dihydropyridine-3,5-dicarboxamide;
(+/−)-1-benzyl-N3-methyl-N5-((trans)-2-methylcyclopropyl)-2-oxo-1,2-dihydropyridine-3,5-dicarboxamide;
(+/−)-1-benzyl-N3-methyl-N5-((cis)-2-methylcyclopropyl)-2-oxo-1,2-dihydropyridine-3,5-dicarboxamide;
1-benzyl-N5-((trans)-4-hydroxycyclohexyl)-N3-methyl-2-oxo-1,2-dihydropyridine-3,5-dicarboxamide;
(+/−)-1-benzyl-N5-(2-(hydroxymethyl)cyclopropyl)-N3-methyl-2-oxo-1,2-dihydropyridine-3,5-dicarboxamide;
(+/−)-1-benzyl-N5-(2-methoxycyclopropyl)-N3-methyl-2-oxo-1,2-dihydropyridine-3,5-dicarboxamide;
N5-Cyclopropyl-1-(3-fluorobenzyl)-N3-methyl-2-oxo-1,2-dihydropyridine-3,5-dicarboxamide;
(+/−)-1-benzyl-N5-(1-cyanocyclopropyl)-N3-methyl-2-oxo-1,2-dihydropyridine-3,5-dicarboxamide;
N5-cyclopropyl-N3-methyl-2-oxo-1-(quinoxalin-5-ylmethyl)-1,2-dihydropyridine-3,5-dicarboxamide;
(S*)-1-benzyl-N5-(2,2-difluorocyclopropyl)-N3-methyl-2-oxo-1,2-dihydropyridine-3,5-dicarboxamide;
tert-butyl (3-(1-benzyl-5-(methylcarbamoyl)-6-oxo-1,6-dihydropyridine-3-carboxamido)cyclobutyl)carbamate;
N5-cyclopropyl-1-(4-fluorobenzyl)-N3-methyl-2-oxo-1,2-dihydropyridine-3,5-dicarboxamide;
N5-cyclopropyl-1-(4-methoxybenzyl)-N3-methyl-2-oxo-1,2-dihydropyridine-3,5-dicarboxamide;
N5-cyclopropyl-1-(3-methoxybenzyl)-N3-methyl-2-oxo-1,2-dihydropyridine-3,5-dicarboxamide;
N5-cyclopropyl-N3-methyl-1-(3-methylbenzyl)-2-oxo-1,2-dihydropyridine-3,5-dicarboxamide;
1-benzyl-N5-((1R*,2R*)-2-ethoxycyclopropyl)-N3-methy-2-oxo-1,2-dihydropyridine-3,5-dicarboxamide;
1-benzyl-N5-((1S*,2S*)-2-ethoxycyclopropyl)-N3-methy-2-oxo-1,2-dihydropyridine-3,5-dicarboxamide;
(+/−)-1-benzyl-N5-((trans)-2-ethylcyclopropyl)-N3-methyl-2-oxo-1,2-dihydropyridine-3,5-dicarboxamide;
N5-cyclopropyl-1-(4-fluoro-3-methylbenzyl)-N3-methyl-2-oxo-1,2-dihydropyridine-3,5-dicarboxamide;
N5-cyclopropyl-N3-methyl-2-oxo-1-(quinolin-8-ylmethyl)-1,2-dihydropyridine-3,5-dicarboxamide;
1-((1H-indazol-4-yl)methyl)-N5-cyclopropyl-N3-methyl-2-oxo-1,2-dihydropyridine-3,5-dicarboxamide;
1-((1H-indazol-7-yl)methyl)-N5-cyclopropyl-N3-methyl-2-oxo-1,2-dihydropyridine-3,5-dicarboxamide;
N5-cyclopropyl-N3-methyl-1-(4-methylbenzyl)-2-oxo-1,2-dihydropyridine-3,5-dicarboxamide;
N5-cyclopropyl-1-(3,5-dimethylbenzyl)-N3-methyl-2-oxo-1,2-dihydropyridine-3,5-dicarboxamide;
N5-cyclopropyl-1-(2-fluoro-3-methylbenzyl)-N3-methyl-2-oxo-1,2-dihydropyridine-3,5-dicarboxamide;
N5-cyclopropyl-1-(2-fluorobenzyl)-N3-methyl-2-oxo-1,2-dihydropyridine-3,5-dicarboxamide;
N5-cyclopropyl-1-(2-fluoro-5-methylbenzyl)-N3-methyl-2-oxo-1,2-dihydropyridine-3,5-dicarboxamide;
1-((1H-benzo[d]imidazol-6-yl)methyl)-N5-cyclopropyl-N3-methyl-2-oxo-1,2-dihydropyridine-3,5-dicarboxamide;
N5-cyclopropyl-N3-methyl-1-(3-(morpholinomethyl)benzyl)-2-oxo-1,2-dihydropyridine-3,5-dicarboxamide;
1-benzyl-N5-((1S,2S)-2-(hydroxymethyl)cyclopropyl)-N3-methyl-2-oxo-1,2-dihydropyridine-3,5-dicarboxamide;
1-benzyl-N5-((1S,2S)-2-(hydroxymethyl)cyclopropyl)-N3-methyl-2-oxo-1,2-dihydropyridine-3,5-dicarboxamide;

(+/−)-1-(2-fluorobenzyl)-N3-methyl-N5-((trans)-2-methylcyclopropyl)-2-oxo-1,2-dihydropyridine-3,5-dicarboxamide;

5-bromo-1-((6-methoxypyridin-3-yl)methyl)-N-methyl-2-oxo-1,2-dihydropyridine-3-carboxamide;

(+/−)-1-(2-fluoro-5-methylbenzyl)-N3-methyl-N5-((trans)-2-methylcyclopropyl)-2-oxo-1,2-dihydropyridine-3,5-dicarboxamide;

1-benzyl-N5-((1R,2R)-2-ethylcyclopropyl)-N3-methyl-2-oxo-1,2-dihydropyridine-3,5-dicarboxamide;

1-benzyl-N5-((1S,2S)-2-ethylcyclopropyl)-N3-methyl-2-oxo-1,2-dihydropyridine-3,5-dicarboxamide;

1-((1H-indol-7-yl)methyl)-N5-cyclopropyl-N3-methyl-2-oxo-1,2-dihydropyridine-3,5-dicarboxamide;

1-((1H-indol-4-yl)methyl)-N5-cyclopropyl-N3-methyl-2-oxo-1,2-dihydropyridine-3,5-dicarboxamide;

1-(3-chlorobenzyl)-N5-cyclopropyl-N3-methyl-2-oxo-1,2-dihydropyridine-3,5-dicarboxamide;

rac-N3-methyl-1-(3-methylbenzyl)-N5-((1R,2R)-2-methylcyclopropyl)-2-oxo-1,2-dihydropyridine-3,5-dicarboxamide;

N5-(2-cyclopropylethyl)-N3-methyl-1-(3-methylbenzyl)-2-oxo-1,2-dihydropyridine-3,5-dicarboxamide;

N5-(6-aminospiro[3.3]heptan-2-yl)-N3-methyl-1-(3-methylbenzyl)-2-oxo-1,2-dihydropyridine-3,5-dicarboxamide;

N5-(3-fluorocyclobutyl)-N3-methyl-1-(3-methylbenzyl)-2-oxo-1,2-dihydropyridine-3,5-dicarboxamide;

N5-(2-ethoxycyclopropyl)-N3-methyl-1-(3-methylbenzyl)-2-oxo-1,2-dihydropyridine-3,5-dicarboxamide;

N5-(2-(hydroxymethyl)cyclopropyl)-N3-methyl-1-(3-methylbenzyl)-2-oxo-1,2-dihydropyridine-3,5-dicarboxamide;

(R)—N5-(3-fluorocyclobutyl)-N3-methyl-2-oxo-1-(1-phenylethyl)-1,2-dihydropyridine-3,5-dicarboxamide;

(R)—N5-(2-cyclopropylethyl)-N3-methyl-2-oxo-1-(1-phenylethyl)-1,2-dihydropyridine-3,5-dicarboxamide;

N5-(2-ethoxycyclopropyl)-N3-methyl-2-oxo-1-((R)-1-phenylethyl)-1,2-dihydropyridine-3,5-dicarboxamide;

N5-(2-(hydroxymethyl)cyclopropyl)-N3-methyl-2-oxo-1-((R)-1-phenylethyl)-1,2-dihydropyridine-3,5-dicarboxamide;

N3-methyl-N5-((trans)-2-methylcyclopropyl)-2-oxo-1-((R)-1-phenylethyl)-1,2-dihydropyridine-3,5-dicarboxamide;

N5-cyclopropyl-N3-methyl-2-oxo-1-((2,3,4,5-tetra hydro-1H-benzo[d]azepin-7-yl)methyl)-1,2-dihydropyridine-3,5-dicarboxamide;

1-benzyl-N5-(2-((cis)-4-hydroxycyclohexyl)ethyl)-N3-methyl-2-oxo-1,2-dihydropyridine-3,5-dicarboxamide;

1-benzyl-N5-(2-((trans)-4-hydroxycyclohexyl)ethyl)-N3-methyl-2-oxo-1,2-dihydropyridine-3,5-dicarboxamide;

(+/−)-1-(4-fluorobenzyl)-N3-methyl-N5-((trans)-2-methylcyclopropyl)-2-oxo-1,2-dihydropyridine-3,5-dicarboxamide;

1-(2-fluorobenzyl)-N5-((1S*,2S)-2-methoxycyclopropyl)-N3-methyl-2-oxo-1,2-dihydropyridine-3,5-dicarboxamide;

1-(4-fluorobenzyl)-N5-(2-(hydroxymethyl)cyclopropyl)-N3-methyl-2-oxo-1,2-dihydropyridine-3,5-dicarboxamide;

N5-(2-ethoxycyclopropyl)-1-(4-fluorobenzyl)-N3-methyl-2-oxo-1,2-dihydropyridine-3,5-dicarboxamide;

rac-N5-cyclopropyl-N3-methyl-2-oxo-1-(1-(m-tolyl)ethyl)-1,2-dihydropyridine-3,5-dicarboxamide;

N5-(3-fluorocyclobutyl)-1-(3-methoxybenzyl)-N3-methyl-2-oxo-1,2-dihydropyridine-3,5-dicarboxamide;

N5-(2-cyclopropylethyl)-1-(3-methoxybenzyl)-N3-methyl-2-oxo-1,2-dihydropyridine-3,5-dicarboxamide;

rac-N5-(2-ethoxycyclopropyl)-1-(3-methoxybenzyl)-N3-methyl-2-oxo-1,2-dihydropyridine-3,5-dicarboxamide;

rac-N5-(2-(hydroxymethyl)cyclopropyl)-1-(3-methoxybenzyl)-N3-methyl-2-oxo-1,2-dihydropyridine-3,5-dicarboxamide;

N5-(6-aminospiro[3.3]heptan-2-yl)-1-(3-methoxybenzyl)-N3-methyl-2-oxo-1,2-dihydropyridine-3,5-dicarboxamide;

rac-1-(3-methoxybenzyl)-N3-methyl-N5-((trans)-2-methylcyclopropyl)-2-oxo-1,2-dihydropyridine-3,5-dicarboxamide;

1-(3-acetyl benzyl)-N5-cyclopropyl-N3-methyl-2-oxo-1,2-dihydropyridine-3,5-dicarboxamide;

rac-N5-cyclopropyl-N3-methyl-2-oxo-1-(1-(o-tolyl)ethyl)-1,2-dihydropyridine-3,5-dicarboxamide;

1-(4-fluoro-3-methylbenzyl)-N5-(2-(hydroxymethyl)cyclopropyl)-N3-methyl-2-oxo-1,2-dihydropyridine-3,5-dicarboxamide;

N5-(2-ethoxycyclopropyl)-1-(4-fluoro-3-methylbenzyl)-N3-methyl-2-oxo-1,2-dihydropyridine-3,5-dicarboxamide;

N5-cyclopropyl-N3-methyl-2-oxo-1-((1,2,3,4-tetrahydroquinolin-8-yl)methyl)-1,2-dihydropyridine-3,5-dicarboxamide;

(+/−)-1-(3-fluorobenzyl)-N3-methyl-N5-((trans)-2-methylcyclopropyl)-2-oxo-1,2-dihydropyridine-3,5-dicarboxamide;

1-benzyl-N3-methyl-N5-((1R,2R)-2-methylcyclopropyl)-2-oxo-1,2-dihydropyridine-3,5-dicarboxamide;

1-benzyl-N3-methyl-N5-((1S,2S)-2-methylcyclopropyl)-2-oxo-1,2-dihydropyridine-3,5-dicarboxamide;

1-(4-fluoro-3-methylbenzyl)-N3-methyl-N5-(2-methylcyclopropyl)-2-oxo-1,2-dihydropyridine-3,5-dicarboxamide;

N5-cyclopropyl-1-(3-(2-(dimethylamino)ethoxy)benzyl)-N3-methyl-2-oxo-1,2-dihydropyridine-3,5-dicarboxamide;

N5-(((+/−)-trans)-2-ethoxycyclopropyl)-1-(3-fluorobenzyl)-N3-methyl-2-oxo-1,2-dihydropyridine-3,5-dicarboxamide;

(+/−)-1-((1H-indol-4-yl)methyl)-N5-((trans)-2-ethylcyclopropyl)-N3-methyl-2-oxo-1,2-dihydropyridine-3,5-dicarboxamide;

N5-(3-fluorocyclobutyl)-1-(3-(2-hydroxyethoxy)benzyl)-N3-methyl-2-oxo-1,2-dihydropyridine-3,5-dicarboxamide;

N5-(2-cyclopropylethyl)-1-(3-(2-hydroxyethoxy)benzyl)-N3-methyl-2-oxo-1,2-dihydropyridine-3,5-dicarboxamide;

rac-N5-(2-ethoxycyclopropyl)-1-(3-(2-hydroxyethoxy)benzyl)-N3-methyl-2-oxo-1,2-dihydropyridine-3,5-dicarboxamide;

rac-1-(3-(2-hydroxyethoxy)benzyl)-N5-(2-(hydroxymethyl)cyclopropyl)-N3-methyl-2-oxo-1,2-dihydropyridine-3,5-dicarboxamide;

N5-(6-aminospiro[3.3]heptan-2-yl)-1-(3-(2-hydroxyethoxy)benzyl)-N3-methyl-2-oxo-1,2-dihydropyridine-3,5-dicarboxamide;

rac-1-(3-(2-hydroxyethoxy)benzyl)-N3-methyl-N5-((trans)-2-methylcyclopropyl)-2-oxo-1,2-dihydropyridine-3,5-dicarboxamide;

(R*)—N5-cyclopropyl-N3-methyl-2-oxo-1-(1-(m-tolyl)ethyl)-1,2-dihydropyridine-3,5-dicarboxamide;

N5-(2-ethoxycyclopropyl)-1-(2-fluoro-5-methylbenzyl)-N3-methyl-2-oxo-1,2-dihydropyridine-3,5-dicarboxamide;

N5-(2-cyclopropylethyl)-1-(2-fluoro-3-methylbenzyl)-N3-methyl-2-oxo-1,2-dihydropyridine-3,5-dicarboxamide;

N5-(2-ethoxycyclopropyl)-1-(2-fluoro-3-methylbenzyl)-N3-methyl-2-oxo-1,2-dihydropyridine-3,5-dicarboxamide;

1-(2-fluoro-3-methylbenzyl)-N5-(3-fluorocyclobutyl)-N3-methyl-2-oxo-1,2-dihydropyridine-3,5-dicarboxamide;

N5-(6-aminospiro[3.3]heptan-2-yl)-1-(2-fluoro-3-methylbenzyl)-N3-methyl-2-oxo-1,2-dihydropyridine-3,5-dicarboxamide;

1-(4-fluorobenzyl)-N5-((1R*,2R*)-2-(hydroxymethyl)cyclopropyl)-N3-methyl-2-oxo-1,2-dihydropyridine-3,5-dicarboxamide;

1-(4-fluorobenzyl)-N5-((1S*,2S*)-2-(hydroxymethyl)cyclopropyl)-N3-methyl-2-oxo-1,2-dihydropyridine-3,5-dicarboxamide;

1-(4-fluorobenzyl)-N3-methyl-N5-((1R*,2R*)-2-methylcyclopropyl)-2-oxo-1,2-dihydropyridine-3,5-dicarboxamide;

1-(4-fluorobenzyl)-N3-methyl-N5-((1S*,2S))-2-methylcyclopropyl)-2-oxo-1,2-dihydropyridine-3,5-dicarboxamide;

N5-((1R*,2R*)-2-ethoxycyclopropyl)-1-(4-fluorobenzyl)-N3-methyl-2-oxo-1,2-dihydropyridine-3,5-dicarboxamide;

N5-((1S*,2S*)-2-ethoxycyclopropyl)-1-(4-fluorobenzyl)-N3-methy-2-oxo-1,2-dihydropyridine-3,5-dicarboxamide;

N5-((1R*,2R*)-2-ethoxycyclopropyl)-1-(4-fluoro-3-methylbenzyl)-N3-methyl-2-oxo-1,2-dihydropyridine-3,5-dicarboxamide;

N5-((1S*,2S*)-2-ethoxycyclopropyl)-1-(4-fluoro-3-methylbenzyl)-N3-methy-2-oxo-1,2-dihydropyridine-3,5-dicarboxamide;

N5-((1R*,2R*)-2-ethoxycyclopropyl)-1-(3-fluorobenzyl)-N3-methyl-2-oxo-1,2-dihydropyridine-3,5-dicarboxamide;

N5-((1S*,2S*)-2-ethoxycyclopropyl)-1-(3-fluorobenzyl)-N3-methy-2-oxo-1,2-dihydropyridine-3,5-dicarboxamide;

N5-cyclopropyl-N3-methyl-2-oxo-1-((1,2,3,4-tetrahydroisoquinolin-5-yl)methyl)-1,2-dihydropyridine-3,5-dicarboxamide;

1-(2-fluoro-5-methylbenzyl)-N5-(2-(hydroxymethyl)cyclopropyl)-N3-methyl-2-oxo-1,2-dihydropyridine-3,5-dicarboxamide;

(+/−)-N5-((trans)-2-(hydroxymethyl)cyclopropyl)-1-(3-methoxybenzyl)-N3-methyl-2-oxo-1,2-dihydropyridine-3,5-dicarboxamide;

1-(2-fluorobenzyl)-N3-methyl-N5-((1S*,2S*)-2-methylcyclopropyl)-2-oxo-1,2-dihydropyridine-3,5-dicarboxamide;

1-(2-fluorobenzyl)-N3-methyl-N5-((1R*,2R*)-2-methylcyclopropyl)-2-oxo-1,2-dihydropyridine-3,5-dicarboxamide;

1-((1H-indol-4-yl)methyl)-N5-(3-fluorocyclobutyl)-N3-methyl-2-oxo-1,2-dihydropyridine-3,5-dicarboxamide;

1-((1H-indol-4-yl)methyl)-N5-(2-cyclopropylethyl)-N3-methyl-2-oxo-1,2-dihydropyridine-3,5-dicarboxamide;

(+/−)-1-((1H-indol-4-yl)methyl)-N5-(2-ethoxycyclopropyl)-N3-methyl-2-oxo-1,2-dihydropyridine-3,5-dicarboxamide;

(+/−)-1-((1H-indol-4-yl)methyl)-N5-(2-(hydroxymethyl)cyclopropyl)-N3-methyl-2-oxo-1,2-dihydropyridine-3,5-dicarboxamide;

(+/−)-1-((1H-indol-4-yl)methyl)-N3-methyl-N5-((trans)-2-methylcyclopropyl)-2-oxo-1,2-dihydropyridine-3,5-dicarboxamide;

(+/−)-N3-methyl-1-(3-methylbenzyl)-N5-((cis)-2-methylcyclopropyl)-2-oxo-1,2-dihydropyridine-3,5-dicarboxamide;

(+/−)-N5-cyclopropyl-1-(3-(1-hydroxyethyl)benzyl)-N3-methyl-2-oxo-1,2-dihydropyridine-3,5-dicarboxamide;

N5-((1R,2R)-2-(hydroxymethyl)cyclopropyl)-1-(3-methoxybenzyl)-N3-methyl-2-oxo-1,2-dihydropyridine-3,5-dicarboxamide;

N5-cyclopropyl-1-(indolin-4-ylmethyl)-N3-methyl-2-oxo-1,2-dihydropyridine-3,5-dicarboxamide;

N5-cyclopropyl-N3-methyl-1-((1-methyl-1H-indol-4-yl)methyl)-2-oxo-1,2-dihydropyridine-3,5-dicarboxamide;

N5-cyclopropyl-N3-methyl-1-((2-methyl-1H-benzo[d]imidazol-4-yl)methyl)-2-oxo-1,2-dihydropyridine-3,5-dicarboxamide;

1-(3-methoxybenzyl)-N3-methyl-N5-((1S,2S)-2-methylcyclopropyl)-2-oxo-1,2-dihydropyridine-3,5-dicarboxamide;

N5-cyclopropyl-N3-methyl-1-((3-methyl-1H-indol-4-yl)methyl)-2-oxo-1,2-dihydropyridine-3,5-dicarboxamide;

1-((1H-indazol-7-yl)methyl)-N3-methyl-N5-((1S,2S)-2-methylcyclopropyl)-2-oxo-1,2-dihydropyridine-3,5-dicarboxamide;

(+/−)-N5-((trans)-2-ethylcyclopropyl)-1-(3-(2-hydroxyethoxy)benzyl)-N3-methyl-2-oxo-1,2-dihydropyridine-3,5-dicarboxamide;

1-(benzofuran-4-ylmethyl)-N5-cyclopropyl-N3-methyl-2-oxo-1,2-dihydropyridine-3,5-dicarboxamide;

N5-((trans)-2-(hydroxymethyl)cyclopropyl)-N3-methyl-2-oxo-1-((S*)-1-(m-tolyl)ethyl)-1,2-dihydropyridine-3,5-dicarboxamide;

(+/−)-1-(1-(1H-indol-4-yl)ethyl)-N5-cyclopropyl-N3-methyl-2-oxo-1,2-dihydropyridine-3,5-dicarboxamide;

1-(3-(2-hydroxyethoxy)benzyl)-N3-methyl-N5-((1S,2S)-2-methylcyclopropyl)-2-oxo-1,2-dihydropyridine-3,5-dicarboxamide;

1-((1H-indol-4-yl)methyl)-N5-((1S*,2S*)-2-(hydroxymethyl)cyclopropyl)-N3-methyl-2-oxo-1,2-dihydropyridine-3,5-dicarboxamide;

1-((1H-indol-4-yl)methyl)-N5-((1R*,2R*)-2-(hydroxymethyl)cyclopropyl)N3-methyl-2-oxo-1,2-dihydropyridine-3,5-dicarboxamide;

1-(3-methoxybenzyl)-N3-methyl-N5-((1R,2R)-2-methylcyclopropyl)-2-oxo-1,2-dihydropyridine-3,5-dicarboxamide;

N5-cyclopropyl-1-(cyclopropyl(phenyl)methyl)-N3-methyl-2-oxo-1,2-dihydropyridine-3,5-dicarboxamide;

1-benzyl-N5-(cyclobutylmethyl)-N3-methyl-2-oxo-1,2-dihydropyridine-3,5-dicarboxamide;

N5-cyclobutyl-N3-methyl-2-oxo-1-(pyridin-4-ylmethyl)-1,2-dihydropyridine-3,5-dicarboxamide;

N5-cyclobutyl-N3-methyl-2-oxo-1-(pyridin-2-ylmethyl)-1,2-dihydropyridine-3,5-dicarboxamide;

N5-cyclobutyl-N3-methyl-2-oxo-1-(pyridin-3-ylmethyl)-1,2-dihydropyridine-3,5-dicarboxamide;

N5-cyclobutyl-1-(2-fluorobenzyl)-N3-methyl-2-oxo-1,2-dihydropyridine-3,5-dicarboxamide;

N5-cyclobutyl-N3-methyl-1-((1-methyl-1H-pyrazol-4-yl)methyl)-2-oxo-1,2-dihydropyridine-3,5-dicarboxamide;

N5-cyclobutyl-1-(2,5-dimethylbenzyl)-N3-methyl-2-oxo-1,2-dihydropyridine-3,5-dicarboxamide;

1-benzyl-N5-((cis)-3-hydroxycyclobutyl)-N3-methyl-2-oxo-1,2-dihydropyridine-3,5-dicarboxamide;

1-benzyl-N5-(3,3-difluorocyclobutyl)-N3-methyl-2-oxo-1,2-dihydropyridine-3,5-dicarboxamide;
tert-cutyl (6-(1-benzyl-5-(methylcarbamoyl)-6-oxo-1,6-dihydropyridine-3-carboxamido)spiro[3.3]heptan-2-yl)carbamate;
1-cenzyl-N3-methyl-2-oxo-N5-(2-phenylcyclobutyl)-1,2-dihydropyridine-3,5-dicarboxamide;
(cis)-3-(1-benzyl-5-(methylcarbamoyl)-6-oxo-1,6-dihydropyridine-3-carboxamido)cyclobutanecarboxylic acid;
N5-cyclobutyl-1-(isoquinolin-5-ylmethyl)-N3-methyl-2-oxo-1,2-dihydropyridine-3,5-dicarboxamide;
(S*)—N5-cyclobutyl-N3-methyl-2-oxo-1-(1-phenylethyl)-1,2-dihydropyridine-3,5-dicarboxamide;
1-benzyl-N5-cyclobutyl-N3-ethyl-2-oxo-1,2-dihydropyridine-3,5-dicarboxamide;
1-benzyl-N5-(1-isobutylcyclopropyl)-N3-methyl-2-oxo-1,2-dihydropyridine-3,5-dicarboxamide;
1-benzyl-N5-(3-methoxy-2,2-dimethylcyclobutyl)-N3-methyl-2-oxo-1,2-dihydropyridine-3,5-dicarboxamide;
1-benzyl-N5-(3-ethoxycyclobutyl)-N3-methyl-2-oxo-1,2-dihydropyridine-3,5-dicarboxamide;
1-benzyl-N3-methyl-N5-(3-methylcyclobutyl)-2-oxo-1,2-dihydropyridine-3,5-dicarboxamide;
1-benzyl-N5-(3-ethoxy-2-methoxycyclobutyl)-N3-methyl-2-oxo-1,2-dihydropyridine-3,5-dicarboxamide;
1-benzyl-N3-methyl-2-oxo-N5-(1-propylcyclopropyl)-1,2-dihydropyridine-3,5-dicarboxamide;
(S*)—N5-cyclopropyl-N3-methyl-2-oxo-1-(1-phenylethyl)-1,2-dihydropyridine-3,5-dicarboxamide;
methyl 4-((5-(cyclobutylcarbamoyl)-3-(methylcarbamoyl)-2-oxopyridin-1(2H)-yl)methyl)benzoate;
1-benzyl-N5-(2-ethoxycyclopropyl)-N3-methyl-2-oxo-1,2-dihydropyridine-3,5-dicarboxamide;
N5-cyclobutyl-N3-methyl-2-oxo-1-(quinolin-5-ylmethyl)-1,2-dihydropyridine-3,5-dicarboxamide;
1-benzyl-N5-((1S,3R)-3-hydroxycyclopentyl)-N3-methyl-2-oxo-1,2-dihydropyridine-3,5-dicarboxamide;
1-(3-cyanobenzyl)-N5-cyclopropyl-N3-methyl-2-oxo-1,2-dihydropyridine-3,5-dicarboxamide;
(+/−)-1-benzyl-N5-((trans)-2-hydroxycyclohexyl)-N3-methyl-2-oxo-1,2-dihydropyridine-3,5-dicarboxamide;
(+/−)-1-benzyl-N5-((cis)-2-hydroxycyclohexyl)-N3-methyl-2-oxo-1,2-dihydropyridine-3,5-dicarboxamide;
N5-cyclopropyl-N3-methyl-1-((6-methylpyridin-2-yl)methyl)-2-oxo-1,2-dihydropyridine-3,5-dicarboxamide;
(R*)-1-benzyl-N5-(2,2-difluorocyclopropyl)-N3-methyl-2-oxo-1,2-dihydropyridine-3,5-dicarboxamide;
(+/−)-1-benzyl-N5-(2-hydroxycyclopentyl)-N3-methyl-2-oxo-1,2-dihydropyridine-3,5-dicarboxamide;
N5-cyclopropyl-N3-methyl-2-oxo-1-(3-phenylpropyl)-1,2-dihydropyridine-3,5-dicarboxamide;
N5-cyclopropyl-N3-methyl-2-oxo-1-phenethyl-1,2-dihydropyridine-3,5-dicarboxamide;
N5-cyclopropyl-N3-methyl-1-(3-(morpholinomethyl)benzyl)-2-oxo-1,2-dihydropyridine-3,5-dicarboxamide;
(+/−)-1-(2-fluorobenzyl)-N3-methyl-N5-((cis)-2-methylcyclopropyl)-2-oxo-1,2-dihydropyridine-3,5-dicarboxamide;
(+/−)-1-(2-fluorobenzyl)-N5-((trans)-2-methoxycyclopropyl)-N3-methyl-2-oxo-1,2-dihydropyridine-3,5-dicarboxamide;
1-benzyl-N5-((2-hydroxycyclohexyl)methyl)-N3-methyl-2-oxo-1,2-dihydropyridine-3,5-dicarboxamide;
N5-cyclopropyl-N3-methyl-2-oxo-1-((1,2,3,4-tetrahydroisoquinolin-7-yl)methyl)-1,2-dihydropyridine-3,5-dicarboxamide;
(+/−)-1-benzyl-N5-(((1R,2S)-2-hydroxycyclopentyl)methyl)-N3-methyl-2-oxo-1,2-dihydropyridine-3,5-dicarboxamide;
(+/−)-1-benzyl-N5-(((cis)-2-hydroxycyclopentyl)methyl)-N3-methyl-2-oxo-1,2-dihydropyridine-3,5-dicarboxamide;
(+/−)-1-benzyl-N5-(((trans)-3-hydroxycyclopentyl)methyl)-N3-methyl-2-oxo-1,2-dihydropyridine-3,5-dicarboxamide;
(+/−)-1-benzyl-N5-(((cis)-3-hydroxycyclopentyl)methyl)-N3-methyl-2-oxo-1,2-dihydropyridine-3,5-dicarboxamide;
1-benzyl-N5-(((trans)-4-hydroxycyclohexyl)methyl)-N3-methyl-2-oxo-1,2-dihydropyridine-3,5-dicarboxamide;
1-benzyl-N5-(((cis)-4-hydroxycyclohexyl)methyl)-N3-methyl-2-oxo-1,2-dihydropyridine-3,5-dicarboxamide;
methyl 4-((5-(cyclopropylcarbamoyl)-3-(methylcarbamoyl)-2-oxopyridin-1(2H)-yl)methyl)benzoate;
N5-cyclopropyl-1-(3-((dimethylamino)methyl)benzyl)-N3-methyl-2-oxo-1,2-dihydropyridine-3,5-dicarboxamide;
1-(2-fluorobenzyl)-N5-((1R*,2R*)-2-methoxycyclopropyl)-N3-methyl-2-oxo-1,2-dihydropyridine-3,5-dicarboxamide;
(R)—N5-(6-aminospiro[3.3]heptan-2-yl)-N3-methyl-2-oxo-1-(1-phenylethyl)-1,2-dihydropyridine-3,5-dicarboxamide;
(+/−)-1-benzyl-N5-(((1R,3S)-3-hydroxycyclohexyl)methyl)-N3-methyl-2-oxo-1,2-dihydropyridine-3,5-dicarboxamide;
N5-cyclopropyl-1-(4-methoxy-3-methylbenzyl)-N3-methyl-2-oxo-1,2-dihydropyridine-3,5-dicarboxamide;
(+/−)-N5-((cis)-2-ethoxycyclopropyl)-1-(3-fluorobenzyl)-N3-methyl-2-oxo-1,2-dihydropyridine-3,5-dicarboxamide;
1-benzyl-N5-((1R,2R)-2-hydroxycyclobutyl)-N3-methyl-2-oxo-1,2-dihydropyridine-3,5-dicarboxamide;
N5-cyclopropyl-1-(4-(hydroxymethyl)benzyl)-N3-methyl-2-oxo-1,2-dihydropyridine-3,5-dicarboxamide;
(S*)—N5-cyclopropyl-N3-methyl-2-oxo-1-(1-(m-tolyl)ethyl)-1,2-dihydropyridine-3,5-dicarboxamide;
(S*)—N5-cyclopropyl-N3-methyl-2-oxo-1-(1-(o-tolyl)ethyl)-1,2-dihydropyridine-3,5-dicarboxamide;
(R*)—N5-cyclopropyl-N3-methyl-2-oxo-1-(1-(o-tolyl)ethyl)-1,2-dihydropyridine-3,5-dicarboxamide;
1-(2-fluoro-3-methylbenzyl)-N5-(2-(hydroxymethyl)cyclopropyl)-N3-methyl-2-oxo-1,2-dihydropyridine-3,5-dicarboxamide;
(+/−)-1-(2-fluoro-3-methylbenzyl)-N3-methyl-N5-((trans)-2-methylcyclopropyl)-2-oxo-1,2-dihydropyridine-3,5-dicarboxamide;
1-benzyl-N5-((1S*,3S*)-3-hydroxycyclohexyl)-N3-methyl-2-oxo-1,2-dihydropyridine-3,5-dicarboxamide;
1-benzyl-N5-(1R*,3R*)-3-hydroxycyclohexyl)-N3-methyl-2-oxo-1,2-dihydropyridine-3,5-dicarboxamide;
1-benzyl-N5-(1S*,3R*)-3-hydroxycyclohexyl)-N3-methyl-2-oxo-1,2-dihydropyridine-3,5-dicarboxamide;
1-benzyl-N5-((1R,3S)-3-hydroxycyclohexyl)-N3-methyl-2-oxo-1,2-dihydropyridine-3,5-dicarboxamide;
N5-cyclopropyl-N3-methyl-2-oxo-1-((1,2,3,4-tetrahydroisoquinolin-8-yl)methyl)-1,2-dihydropyridine-3,5-dicarboxamide;
1-((1H-indol-4-yl)methyl)-N5-(6-aminospiro[3.3]heptan-2-yl)-N3-methyl-2-oxo-1,2-dihydropyridine-3,5-dicarboxamide;
(+/−)-N5-((cis)-2-ethoxycyclopropyl)-N3-methyl-1-(3-methylbenzyl)-2-oxo-1,2-dihydropyridine-3,5-dicarboxamide;

(+/−)-N5-((trans)-2-ethoxycyclopropyl)-N3-methyl-1-(3-methylbenzyl)-2-oxo-1,2-dihydropyridine-3,5-dicarboxamide;

1-benzyl-N5-(2,2-dimethylcyclopropyl)-N3-methyl-2-oxo-1,2-dihydropyridine-3,5-dicarboxamide;

1-(2-fluorobenzyl)-N5-((1R*,2R*)-2-(hydroxymethyl)cyclopropyl)-N3-methyl-2-oxo-1,2-dihydropyridine-3,5-dicarboxamide;

1-(2-fluorobenzyl)-N5-((1S*,2S*)-2-(hydroxymethyl)cyclopropyl)-N3-methy-2-oxo-1,2-dihydropyridine-3,5-dicarboxamide;

N5-cyclopropyl-1-(3-fluoro-5-methoxybenzyl)-N3-methyl-2-oxo-1,2-dihydropyridine-3,5-dicarboxamide;

N5-cyclopropyl-N3-methyl-2-oxo-1-((1,2,3,4-tetrahydroquinolin-5-yl)methyl)-1,2-dihydropyridine-3,5-dicarboxamide;

1-(2-fluoro-5-methylbenzyl)-N5-((1S*,2S*)-2-(hydroxymethyl)cyclopropyl)-N3-methyl-2-oxo-1,2-dihydropyridine-3,5-dicarboxamide;

1-(2-fluoro-5-methylbenzyl)-N5-((1R*,2R*)-2-(hydroxymethyl)cyclopropyl)-N3-methyl-2-oxo-1,2-dihydropyridine-3,5-dicarboxamide;

N5-((1S*,2S'*)-2-(hydroxymethyl)cyclopropyl)-1-(3-methoxybenzyl)-N3-methyl-2-oxo-1,2-dihydropyridine-3,5-dicarboxamide;

N5-((1S*,2S*)-2-ethoxycyclopropyl)-N3-methyl-1-(3-methylbenzyl)-2-oxo-1,2-dihydropyridine-3,5-dicarboxamide;

N5-((1S*,2S*)-2-ethoxycyclopropyl)-N3-methyl-1-(3-methylbenzyl)-2-oxo-1,2-dihydropyridine-3,5-dicarboxamide;

1-(4-fluoro-3-methylbenzyl)-N5-((1R*,2R)-2-(hydroxymethyl)cyclopropyl)-N3-methyl-2-oxo-1,2-dihydropyridine-3,5-dicarboxamide;

1-(4-fluoro-3-methylbenzyl)-N5-((1S*,2S*)-2-(hydroxymethyl)cyclopropyl)-N3-methyl-2-oxo-1,2-dihydropyridine-3,5-dicarboxamide;

1-(3-fluorobenzyl)-N5-((1S*,2S*)-2-(hydroxymethyl)cyclopropyl)-N3-methyl-2-oxo-1,2-dihydropyridine-3,5-dicarboxamide;

1-(3-fluorobenzyl)-N5-((1R*,2R*)-2-(hydroxymethyl)cyclopropyl)N3-methyl-2-oxo-1,2-dihydropyridine-3,5-dicarboxamide;

(+/−)-N5-((trans)-2-ethoxycyclopropyl)-1-(2-fluoro-3-methylbenzyl)-N3-methyl-2-oxo-1,2-dihydropyridine-3,5-dicarboxamide;

N5-cyclopropyl-1-(4-fluoro-3-methoxybenzyl)-N3-methyl-2-oxo-1,2-dihydropyridine-3,5-dicarboxamide;

1-((1H-indol-3-yl)methyl)-N5-cyclopropyl-N3-methyl-2-oxo-1,2-dihydropyridine-3,5-dicarboxamide;

1-(3-fluorobenzyl)-N3-methyl-N5-((1R*,2R*)-2-methylcyclopropyl)-2-oxo-1,2-dihydropyridine-3,5-dicarboxamide;

1-(3-fluorobenzyl)-N3-methyl-N5-((1S*,2S*)-2-methylcyclopropyl)-2-oxo-1,2-dihydropyridine-3,5-dicarboxamide;

(+/−)-1-benzyl-N5-((trans)-2-methoxycyclobutyl)-N3-methyl-2-oxo-1,2-dihydropyridine-3,5-dicarboxamide;

N5-cyclopropyl-1-(2-hydroxybenzyl)-N3-methyl-2-oxo-1,2-dihydropyridine-3,5-dicarboxamide;

N5-cyclopropyl-N3-methyl-1-((1-methyl-1H-benzo[d]imidazol-4-yl)methyl)-2-oxo-1,2-dihydropyridine-3,5-dicarboxamide;

N5-cyclopropyl-1-(3-fluoro-5-methylbenzyl)-N3-methyl-2-oxo-1,2-dihydropyridine-3,5-dicarboxamide;

(+/−)-N3-methyl-N5-((trans)-2-methylcyclopropyl)-1-(3-(morpholinomethyl)benzyl)-2-oxo-1,2-dihydropyridine-3,5-dicarboxamide;

(R*)-1-benzyl-N5-(2,2-dimethylcyclopropyl)-N3-methyl-2-oxo-1,2-dihydropyridine-3,5-dicarboxamide;

(S*)-1-benzyl-N5-(2,2-dimethylcyclopropyl)-N3-methyl-2-oxo-1,2-dihydropyridine-3,5-dicarboxamide;

N5-cyclopropyl-N3-methyl-2-oxo-1-((4,5,6,7-tetrahydro-1H-benzo[d]imidazol-4-yl)methyl)-1,2-dihydropyridine-3,5-dicarboxamide;

N3-methyl-1-(3-methylbenzyl)-N5-((1R*,2R*)-2-methylcyclopropyl)-2-oxo-1,2-dihydropyridine-3,5-dicarboxamide;

N3-methyl-1-(3-methylbenzyl)-N5-((1S*,2S*)-2-methylcyclopropyl)-2-oxo-1,2-dihydropyridine-3,5-dicarboxamide;

N5-((1R*,2R*)-2-ethoxycyclopropyl)-1-(2-fluoro-5-methylbenzyl)-N3-methyl-2-oxo-1,2-dihydropyridine-3,5-dicarboxamide;

N5-((1S*,2S*)-2-ethoxycyclopropyl)-1-(2-fluoro-5-methylbenzyl)-N3-methyl-2-oxo-1,2-dihydropyridine-3,5-dicarboxamide;

N5-((1R*,2R*)-2-ethoxycyclopropyl)-1-(2-fluoro-3-methylbenzyl)-N3-methyl-2-oxo-1,2-dihydropyridine-3,5-dicarboxamide;

N5-((1S*,2S*)-2-ethoxycyclopropyl)-1-(2-fluoro-3-methylbenzyl)-N3-methyl-2-oxo-1,2-dihydropyridine-3,5-dicarboxamide;

1-(4-fluoro-3-methylbenzyl)-N3-methyl-N5-((1R*2R*)-2-methylcyclopropyl)-2-oxo-1,2-dihydropyridine-3,5-dicarboxamide;

1-(4-fluoro-3-methylbenzyl)-N3-methyl-N5-((1S*,2S*)-2-methylcyclopropyl)-2-oxo-1,2-dihydropyridine-3,5-dicarboxamide;

N3-methyl-N5-((1R*,2R*)-2-methylcyclopropyl)-2-oxo-1-((R)-1-phenylethyl)-1,2-dihydropyridine-3,5-dicarboxamide;

N3-methyl-N5-((1S*,2S*)-2-methylcyclopropyl)-2-oxo-1-((R)-1-phenylethyl)-1,2-dihydropyridine-3,5-dicarboxamide;

N5-cyclopropyl-1-(1-(3-methoxyphenyl)ethyl)-N3-methyl-2-oxo-1,2-dihydropyridine-3,5-dicarboxamide;

(+/−)-1-(3-(2-hydroxyethoxy)benzyl)-N5-((trans)-2-(hydroxymethyl)cyclopropyl)-N3-methyl-2-oxo-1,2-dihydropyridine-3,5-dicarboxamide;

1-(benzofuran-3-ylmethyl)-N5-cyclopropyl-N3-methyl-2-oxo-1,2-dihydropyridine-3,5-dicarboxamide;

(+/−)-N5-((trans)-2-ethoxycyclopropyl)-1-(3-(2-hydroxyethoxy)benzyl)-N3-methyl-2-oxo-1,2-dihydropyridine-3,5-dicarboxamide;

(R*)—N5-cyclopropyl-1-(3-(1-hydroxyethyl)benzyl)-N3-methyl-2-oxo-1,2-dihydropyridine-3,5-dicarboxamide;

(S*)—N5-cyclopropyl-1-(3-(1-hydroxyethyl)benzyl)-N3-methyl-2-oxo-1,2-dihydropyridine-3,5-dicarboxamide;

N5-((trans)-2-(hydroxymethyl)cyclopropyl)-N3-methyl-2-oxo-1-((S*)-1-(m-tolyl)ethyl)-1,2-dihydropyridine-3,5-dicarboxamide; or N5-cyclopropyl-1-((2,3-dihydrobenzofuran-3-yl)methyl)-N3-methyl-2-oxo-1,2-dihydropyridine-3,5-dicarboxamide;

1-((1H-indol-4-yl)methyl)-$N^3$-methyl-$N^5$-((1R*,2R*)-2-methylcyclopropyl)-2-oxo-1,2-dihydropyridine-3,5-dicarboxamide;

1-((1H-indol-4-yl)methyl)-$N^3$-methyl-$N^5$-((1S*,2S*)-2-methylcyclopropyl)-2-oxo-1,2-dihydropyridine-3,5-dicarboxamide;

1-((1H-pyrrolo[3,2-c]pyridin-4-yl)methyl)-$N^5$-cyclopropyl-$N^3$-methyl-2-oxo-1,2-dihydropyridine-3,5-dicarboxamide;

$N^5$-cyclopropyl-$N^3$-methyl-1-((2-methyl-1H-indol-4-yl)methyl)-2-oxo-1,2-dihydropyridine-3,5-dicarboxamide;

1-(3-(difluoromethoxy)benzyl)-$N^3$-methyl-$N^5$-((1S,2S)-2-methylcyclopropyl)-2-oxo-1,2-dihydropyridine-3,5-dicarboxamide;

$N^5$-cyclopropyl-1-(3-(difluoromethoxy)benzyl)-$N^3$-methyl-2-oxo-1,2-dihydropyridine-3,5-dicarboxamide;

$N^5$-cyclopropyl-$N^3$-methyl-2-oxo-1-(quinolin-7-ylmethyl)-1,2-dihydropyridine-3,5-dicarboxamide;

1-((S*)-1-(3-methoxyphenyl)ethyl)-$N^3$-methyl-$N^5$-((1S,2S)-2-methylcyclopropyl)-2-oxo-1,2-dihydropyridine-3,5-dicarboxamide;

1-(3-(2-hydroxyethoxy)benzyl)-$N^5$-((1R*,2R*)-2-(hydroxymethyl)cyclopropyl)-$N^3$-methyl-2-oxo-1,2-dihydropyridine-3,5-dicarboxamide;

1-(3-(2-hydroxyethoxy)benzyl)-$N^5$-((1S*,2S*)-2-(hydroxymethyl)cyclopropyl)-$N^3$-methyl-2-oxo-1,2-dihydropyridine-3,5-dicarboxamide;

$N^5$-((1R*,2R*)-2-ethylcyclopropyl)-1-(3-(2-hydroxyethoxy)benzyl)-$N^3$-methyl-2-oxo-1,2-dihydropyridine-3,5-dicarboxamide;

$N^5$-((1S*,2S*)-2-ethylcyclopropyl)-1-(3-(2-hydroxyethoxy)benzyl)-$N^3$-methyl-2-oxo-1,2-dihydropyridine-3,5-dicarboxamide;

$N^5$-((1R*,2R*)-2-ethoxycyclopropyl)-1-(3-(2-hydroxyethoxy)benzyl)-$N^3$-methyl-2-oxo-1,2-dihydropyridine-3,5-dicarboxamide;

$N^5$-((1S*,2S*)-2-ethoxycyclopropyl)-1-(3-(2-hydroxyethoxy)benzyl)-$N^3$-methyl-2-oxo-1,2-dihydropyridine-3,5-dicarboxamide;

$N^5$-(2-((trans)-4-aminocyclohexyl)ethyl)-1-benzyl-$N^3$-methyl-2-oxo-1,2-dihydropyridine-3,5-dicarboxamide;

$N^5$-(2-((cis)-4-aminocyclohexyl)ethyl)-1-benzyl-$N^3$-methyl-2-oxo-1,2-dihydropyridine-3,5-dicarboxamide;

1-((1H-pyrrolo[3,2-c]pyridin-4-yl)methyl)-$N^3$-methyl-$N^5$-((1S,2S)-2-methylcyclopropyl)-2-oxo-1,2-dihydropyridine-3,5-dicarboxamide;

(±)-1-benzyl-$N^5$-((trans)-2-(methoxymethyl)cyclopropyl)-$N^3$-methyl-2-oxo-1,2-dihydropyridine-3,5-dicarboxamide;

$N^5$-cyclopropyl-1-(3-(2-hydroxyethyl)benzyl)-$N^3$-methyl-2-oxo-1,2-dihydropyridine-3,5-dicarboxamide;

(+/−)-tert-butyl 2-((trans)-2-(1-benzyl-5-(methylcarbamoyl)-6-oxo-1,6-dihydropyridine-3-carboxamido)cyclopropyl)acetate;

$N^5$-cyclopropyl-$N^3$-methyl-1-(3-(2-morpholinoethyl)benzyl)-2-oxo-1,2-dihydropyridine-3,5-dicarboxamide;

3-((5-(cyclopropylcarbamoyl)-3-(methylcarbamoyl)-2-oxopyridin-1(2H)-yl)methyl)benzoic acid;

1-((1H-pyrrolo[2,3-b]pyridin-3-yl)methyl)-$N^5$-cyclopropyl-$N^3$-methyl-2-oxo-1,2-dihydropyridine-3,5-dicarboxamide;

$N^5$-cyclopropyl-1-(3-(2-(dimethylamino)ethyl)benzyl)-$N^3$-methyl-2-oxo-1,2-dihydropyridine-3,5-dicarboxamide;

1-(indolin-4-ylmethyl)-$N^3$-methyl-$N^5$-((1S,2S)-2-methylcyclopropyl)-2-oxo-1,2-dihydropyridine-3,5-dicarboxamide;

1-benzyl-$N^5$-((1S,2S)-2-(methoxymethyl)cyclopropyl)-$N^3$-methyl-2-oxo-1,2-dihydropyridine-3,5-dicarboxamide;

(+/−)-$N^5$-((trans)-2-ethylcyclopropyl)-1-(indolin-4-ylmethyl)-N3-methyl-2-oxo-1,2-dihydropyridine-3,5-dicarboxamide;

1-(3-(2-hydroxyethyl)benzyl)-$N^3$-methyl-$N^5$-((1S,2S)-2-methylcyclopropyl)-2-oxo-1,2-dihydropyridine-3,5-dicarboxamide;

1-benzyl-$N^5$-((1S,2R)-2-((dimethylamino)methyl)cyclopropyl)-$N^3$-methyl-2-oxo-1,2-dihydropyridine-3,5-dicarboxamide;

$N^3$-methyl-$N^5$-((1S,2S)-2-methylcyclopropyl)-1-((6-methylpyridin-2-yl)methyl)-2-oxo-1,2-dihydropyridine-3,5-dicarboxamide;

(+/−)-1-benzyl-$N^5$-((trans)-2-(2-hydroxyethyl)cyclopropyl)-$N^3$-methyl-2-oxo-1,2-dihydropyridine-3,5-dicarboxamide;

$N^5$-cyclopropyl-1-((1-(2-hydroxyethyl)-1H-indol-3-yl)methyl)-$N^3$-methyl-2-oxo-1,2-dihydropyridine-3,5-dicarboxamide;

$N^3$-methyl-$N^5$-((1S,2S)-2-methylcyclopropyl)-1-(3-(2-morpholinoethyl)benzyl)-2-oxo-1,2-dihydropyridine-3,5-dicarboxamide;

1-benzyl-$N^5$-((1R,2R)-2-(methoxymethyl)cyclopropyl)-$N^3$-methyl-2-oxo-1,2-dihydropyridine-3,5-dicarboxamide;

1-benzyl-$N^5$-((1R,2R)-2-(ethoxymethyl)cyclopropyl)-$N^3$-methyl-2-oxo-1,2-dihydropyridine-3,5-dicarboxamide;

1-(3-hydroxybenzyl)-$N^3$-methyl-$N^5$-((1S,2S)-2-methylcyclopropyl)-2-oxo-1,2-dihydropyridine-3,5-dicarboxamide;

1-benzyl-$N^5$-((1S,2S)-2-(ethoxymethyl)cyclopropyl)-$N^3$-methyl-2-oxo-1,2-dihydropyridine-3,5-dicarboxamide;

1-(3-(2-methoxyethoxy)benzyl)-$N^3$-methyl-$N^5$-((1S,2S)-2-methylcyclopropyl)-2-oxo-1,2-dihydropyridine-3,5-dicarboxamide;

1-(3-((S)-2-hydroxypropoxy)benzyl)-$N^3$-methyl-$N^5$-((1S,2S)-2-methylcyclopropyl)-2-oxo-1,2-dihydropyridine-3,5-dicarboxamide;

$N^3$-methyl-$N^5$-((1S,2S)-2-methylcyclopropyl)-1-(3-(2-morpholinoethoxy)benzyl)-2-oxo-1,2-dihydropyridine-3,5-dicarboxamide;

1-(3-((R)-2-hydroxypropoxy)benzyl)-$N^3$-methyl-$N^5$-((1S,2S)-2-methylcyclopropyl)-2-oxo-1,2-dihydropyridine-3,5-dicarboxamide;

(+/−)-1-((1H-indol-4-yl)methyl)-$N^3$-ethyl-$N^5$-((trans)-2-methylcyclopropyl)-2-oxo-1,2-dihydropyridine-3,5-dicarboxamide;

1-benzyl-$N^5$-((1S*,2R*)-2-(2-hydroxyethyl)cyclopropyl)-$N^3$-methyl-2-oxo-1,2-dihydropyridine-3,5-dicarboxamide;

1-benzyl-$N^5$-((1R*,2S*)-2-(2-hydroxyethyl)cyclopropyl)-$N^3$-methyl-2-oxo-1,2-dihydropyridine-3,5-dicarboxamide;

(+/−)-1-((1H-indol-4-yl)methyl)-$N^5$-((trans)-2-(2-hydroxyethyl)cyclopropyl)-$N^3$-methyl-2-oxo-1,2-dihydropyridine-3,5-dicarboxamide;

(+/−)-$N^3$-ethyl-1-(indolin-4-yl methyl)-$N^5$-((trans)-2-methylcyclopropyl)-2-oxo-1,2-dihydropyridine-3,5-dicarboxamide;

(+/−)-$N^3$-ethyl-1-(3-(2-hydroxyethoxy)benzyl)-$N^5$-((trans)-2-methylcyclopropyl)-2-oxo-1,2-dihydropyridine-3,5-dicarboxamide;

(+/−)-1-((1H-indol-4-yl)methyl)-$N^5$-((trans)-2-(2-((2-aminoethyl)(methyl)amino)ethyl)cyclopropyl)-$N^3$-methyl-2-oxo-1,2-dihydropyridine-3,5-dicarboxamide;

1-((1H-indol-4-yl)methyl)-$N^5$-(trans-3-hydroxycyclobutyl)-$N^3$-methyl-2-oxo-1,2-dihydropyridine-3,5-dicarboxamide;

$N^5$-cyclopropyl-$N^3$-methyl-2-oxo-1-(3-(trifluoromethyl)benzyl)-1,2-dihydropyridine-3,5-dicarboxamide;

(+/−)-1-((1H-indol-4-yl)methyl)-N$^5$-((trans)-2-(2-((2-acetamidoethyl)(methyl)amino)ethyl)cyclopropyl)-N$^3$-methyl-2-oxo-1,2-dihydropyridine-3,5-dicarboxamide;

1-benzyl-N$^3$-methyl-N$^5$-((1R*,2R*)-2-(2-morpholinoethyl)cyclopropyl)-2-oxo-1,2-dihydropyridine-3,5-dicarboxamide;

1-benzyl-N$^3$-methyl-N$^5$-((1S*,2S*)-2-(2-morpholinoethyl)cyclopropyl)-2-oxo-1,2-dihydropyridine-3,5-dicarboxamide;

(+/−)-1-benzyl-N$^3$-methyl-N$^5$-((trans)-2-(2-morpholinoethyl)cyclopropyl)-2-oxo-1,2-dihydropyridine-3,5-dicarboxamide;

1-benzyl-N$^3$-methyl-2-oxo-1,2-dihydropyridine-3,5-dicarboxamide;

(R*)—N$^5$-cyclopropyl-1-(2-hydroxy-1-phenylethyl)-N$^3$-methyl-2-oxo-1,2-dihydropyridine-3,5-dicarboxamide;

(S*)—N$^5$-cyclopropyl-1-(2-hydroxy-1-phenylethyl)-N$^3$-methyl-2-oxo-1,2-dihydropyridine-3,5-dicarboxamide;

(S*)—N$^5$-cyclopropyl-1-(2-methoxy-1-phenylethyl)-N$^3$-methyl-2-oxo-1,2-dihydropyridine-3,5-dicarboxamide;

N$^5$-cyclopropyl-N$^3$-methyl-1-((2-methylbenzo[d]oxazol-7-yl)methyl)-2-oxo-1,2-dihydropyridine-3,5-dicarboxamide;

1-((R*)-1-(3-methoxyphenyl)ethyl)-N$^3$-methyl-N$^5$-(1S,2S)-2-methylcyclopropyl)-2-oxo-1,2-dihydropyridine-3,5-dicarboxamide;

(+/−)-1-benzyl-N$^5$-((trans)-2-((dimethylamino)methyl)cyclopropyl)-N$^3$-methyl-2-oxo-1,2-dihydropyridine-3,5-dicarboxamide;

1-((1H-pyrrolo[2,3-c]pyridin-3-yl)methyl)-N$^5$-cyclopropyl-N$^3$-methyl-2-oxo-1,2-dihydropyridine-3,5-dicarboxamide;

1-((6-methoxypyridin-2-yl)methyl)-N$^3$-methyl-N$^5$-((1S,2S)-2-methylcyclopropyl)-2-oxo-1,2-dihydropyridine-3,5-dicarboxamide;

N$^3$-methyl-N$^5$-((1S,2S)-2-methylcyclopropyl)-2-oxo-1-(1-(pyridin-2-yl)ethyl)-1,2-dihydropyridine-3,5-dicarboxamide;

N$^3$-methyl-N$^5$-((1S,2S)-2-methylcyclopropyl)-2-oxo-1-(pyridin-2-ylmethyl)-1,2-dihydropyridine-3,5-dicarboxamide;

1-((4-methoxypyridin-2-yl)methyl)-N$^3$-methyl-N$^5$-((1S,2S)-2-methylcyclopropyl)-2-oxo-1,2-dihydropyridine-3,5-dicarboxamide;

N$^3$-methyl-N$^5$-((1S,2S)-2-methylcyclopropyl)-1-((4-methylpyridin-2-yl)methyl)-2-oxo-1,2-dihydropyridine-3,5-dicarboxamide;

1-benzyl-N$^5$-((1R,2S)-2-((dimethylamino)methyl)cyclopropyl)-N$^3$-methyl-2-oxo-1,2-dihydropyridine-3,5-dicarboxamide;

1-(3,5-dimethoxybenzyl)-N$^3$-methyl-N$^5$-((1S,2S)-2-methylcyclopropyl)-2-oxo-1,2-dihydropyridine-3,5-dicarboxamide;

methyl 4-((3-(methylcarbamoyl)-5-(((1S,2S)-2-methylcyclopropyl)carbamoyl)-2-oxopyridin-1(2H)-yl)methyl)benzoate;

4-((3-(methylcarbamoyl)-5-(((1S,2S)-2-methylcyclopropyl)carbamoyl)-2-oxopyridin-1(2H)-yl)methyl)benzoic acid;

1-(4-(2-aminoethoxy)benzyl)-N$^3$-methyl-N$^5$-((1S,2S)-2-methylcyclopropyl)-2-oxo-1,2-dihydropyridine-3,5-dicarboxamide; and 1-benzyl-N$^5$-((trans)-3-hydroxycyclobutyl)-N$^3$-methyl-2-oxo-1,2-dihydropyridine-3,5-dicarboxamide or a salt thereof.

In one embodiment, the compound of formula (I) is:
1-benzyl-N5-cyclopropyl-N3-methyl-2-oxo-1,2-dihydropyridine-3,5-dicarboxamide;

1-benzyl-N3-methyl-N5-((1S,2S)-2-methylcyclopropyl)-2-oxo-1,2-dihydropyridine-3,5-dicarboxamide;

N5-((1R,2R)-2-(hydroxymethyl)cyclopropyl)-1-(3-methoxybenzyl)-N3-methyl-2-oxo-1,2-dihydropyridine-3,5-dicarboxamide;

N5-cyclopropyl-1-(indolin-4-ylmethyl)-N3-methyl-2-oxo-1,2-dihydropyridine-3,5-dicarboxamide; or 1-(3-(2-hydroxyethoxy)benzyl)-N3-methyl-N5-((1S,2S)-2-methylcyclopropyl)-2-oxo-1,2-dihydropyridine-3,5-dicarboxamide;

or a salt thereof.

In one embodiment the compound of formula (I) is:
1-benzyl-N$^3$-methyl-2-oxo-1,2-dihydropyridine-3,5-dicarboxamide;

1-((1H-indol-4-yl)methyl)-N$^3$-methyl-N$^5$-((1R*,2R*)-2-methylcyclopropyl)-2-oxo-1,2-dihydropyridine-3,5-dicarboxamide; or 1-((1H-pyrrolo[3,2-c]pyridin-4-yl)methyl)-N$^3$-methyl-N-((1S,2S)-2-methylcyclopropyl)-2-oxo-1,2-dihydropyridine-3,5-dicarboxamide;

or a salt thereof.

In one embodiment the compound of formula (I) is 1-benzyl-N5-cyclopropyl-N3-methyl-2-oxo-1,2-dihydropyridine-3,5-dicarboxamide or a salt thereof. In another embodiment the compound of formula (I) is 1-benzyl-N5-cyclopropyl-N3-methyl-2-oxo-1,2-dihydropyridine-3,5-dicarboxamide or a pharmaceutically acceptable salt thereof. In a further embodiment the compound of formula (I) is 1-benzyl-N5-cyclopropyl-N3-methyl-2-oxo-1,2-dihydropyridine-3,5-dicarboxamide.

In one embodiment the compound of formula (I) is

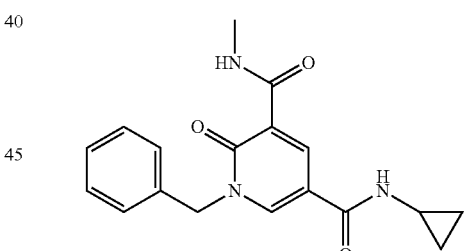

or a salt thereof.

In another embodiment the compound of formula (I) is a pharmaceutically acceptable salt of

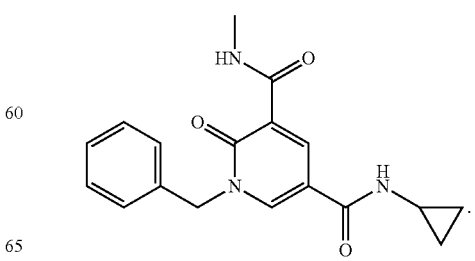

In a further embodiment the compound of formula (I) is

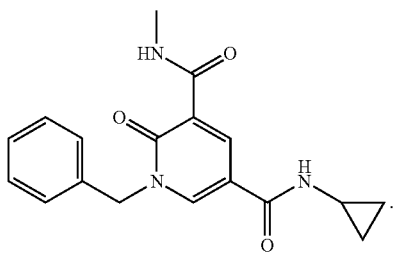 [SMILES: CNC(=O)c1cc(C(=O)NC2CC2)cn(Cc2ccccc2)c1=O]

In one embodiment the compound of formula (I) is 1-benzyl-N3-methyl-N5-((1S,2S)-2-methylcyclopropyl)-2-oxo-1,2-dihydropyridine-3,5-dicarboxamide or a salt thereof. In another embodiment the compound of formula (I) is 1-benzyl-N3-methyl-N5-((1S,2S)-2-methylcyclopropyl)-2-oxo-1,2-dihydropyridine-3,5-dicarboxamide or a pharmaceutically acceptable salt thereof. In a further embodiment the compound of formula (I) is 1-benzyl-N3-methyl-N5-((1S,2S)-2-methylcyclopropyl)-2-oxo-1,2-dihydropyridine-3,5-dicarboxamide.

In one embodiment the compound of formula (I) is

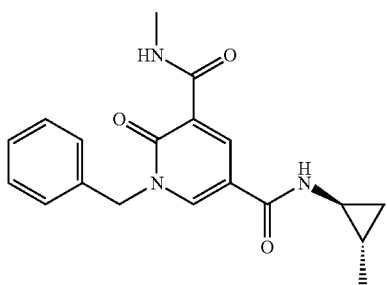 [SMILES: CNC(=O)c1cc(C(=O)N[C@H]2C[C@@H]2C)cn(Cc2ccccc2)c1=O]

or a salt thereof.

In another embodiment the compound of formula (I) is a pharmaceutically acceptable salt of

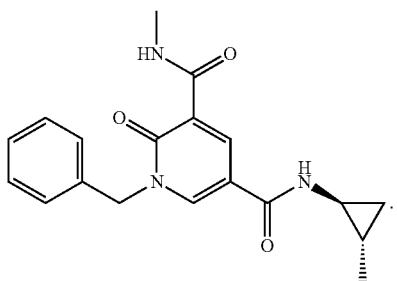

In a further embodiment the compound of formula (I) is

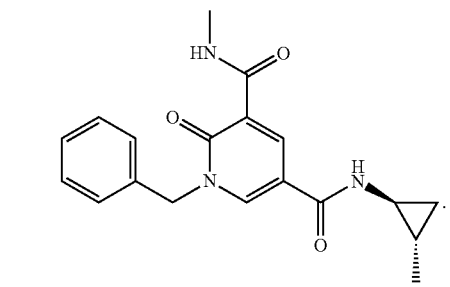 [SMILES: CNC(=O)c1cc(C(=O)N[C@H]2C[C@@H]2C)cn(Cc2ccccc2)c1=O]

In one embodiment the compound of formula (I) is

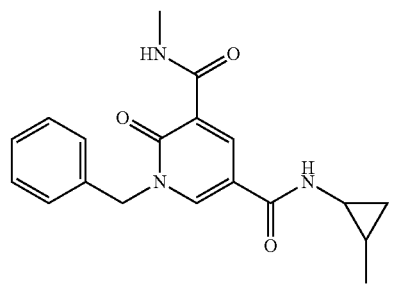 [SMILES: CNC(=O)c1cc(C(=O)NC2CC2C)cn(Cc2ccccc2)c1=O]

or a salt thereof.

In another embodiment the compound of formula (I) is a pharmaceutically acceptable salt of

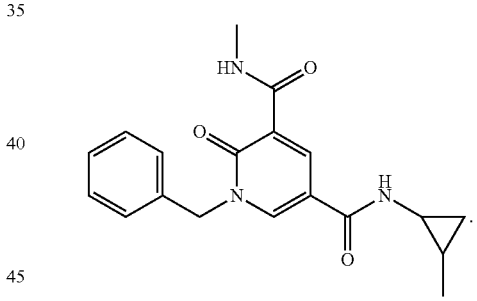

In a further embodiment the compound of formula (I) is

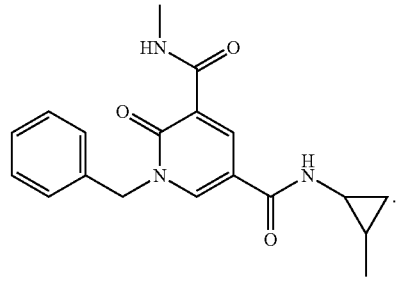 [SMILES: CNC(=O)c1cc(C(=O)NC2CC2C)cn(Cc2ccccc2)c1=O]

In one embodiment, the compound of formula (I) is 1-(3-(2-hydroxyethoxy)benzyl)-N3-methyl-N5-((1S,2S)-2-methylcyclopropyl)-2-oxo-1,2-dihydropyridine-3,5-dicarboxamide or a salt thereof. In another embodiment, the compound of formula (I) is 1-(3-(2-hydroxyethoxy)benzyl)-N3-methyl-N5-((1S,2S)-2-methylcyclopropyl)-2-oxo-1,2-dihydropyridine-3,5-dicarboxamide or a pharmaceutically acceptable salt thereof. In a further embodiment, the compound of formula (I) is 1-(3-(2-hydroxyethoxy)benzyl)-N3-methyl-N5-((1S,2S)-2-methylcyclopropyl)-2-oxo-1,2-dihydropyridine-3,5-dicarboxamide.

In one embodiment the compound of formula (I) is

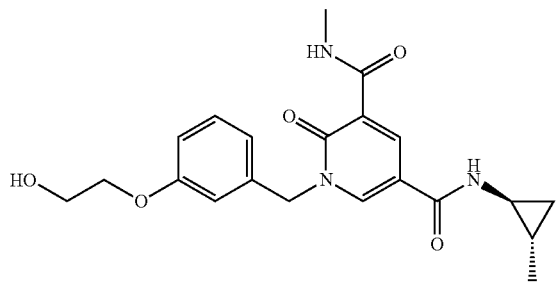 [SMILES: CNC(=O)c1cc(C(=O)N[C@H]2C[C@@H]2C)cn(Cc2cccc(OCCO)c2)c1=O]

or a salt thereof.

In another embodiment the compound of formula (I) is a pharmaceutically acceptable salt of

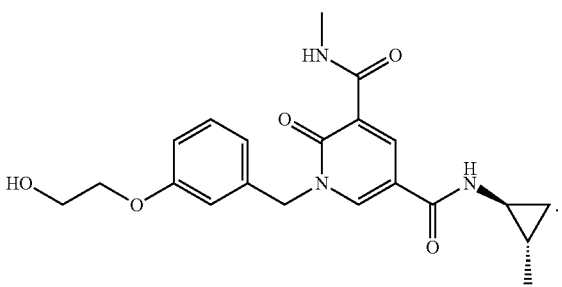 [SMILES: CNC(=O)c1cc(C(=O)N[C@H]2C[C@@H]2C)cn(Cc2cccc(OCCO)c2)c1=O]

In a further embodiment the compound of formula (I) is

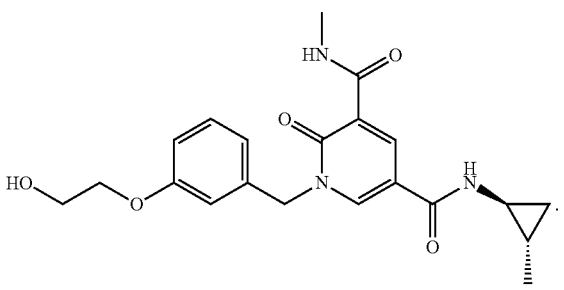 [SMILES: CNC(=O)c1cc(C(=O)N[C@H]2C[C@@H]2C)cn(Cc2cccc(OCCO)c2)c1=O]

In one embodiment the compound of formula (I) is

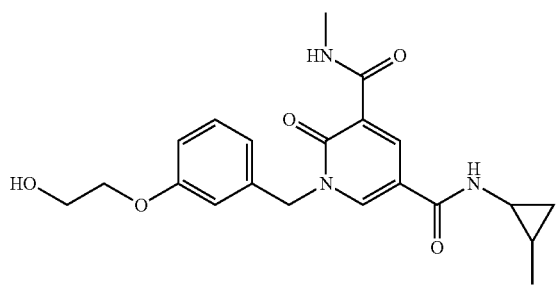 [SMILES: CNC(=O)c1cc(C(=O)NC2CC2C)cn(Cc2cccc(OCCO)c2)c1=O]

or a salt thereof.

In another embodiment the compound of formula (I) is a pharmaceutically acceptable salt of

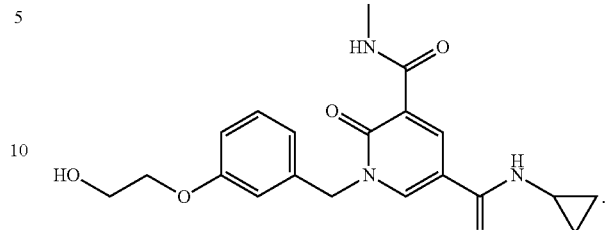

In a further embodiment the compound of formula (I) is

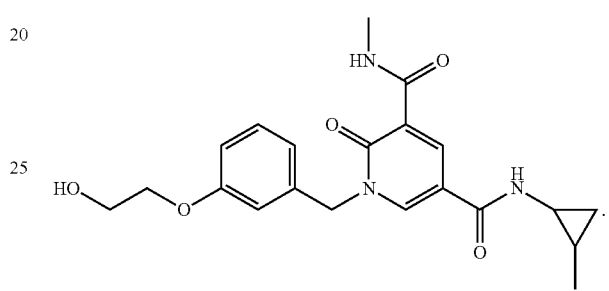

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

STATEMENT OF USE

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, renal fibrosis, post-operative stricture, keloid scar formation, scleroderma (including morphea) or cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colarectal cancer.

Bromodomain inhibitors may be useful in the treatment of diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain which comprises contacting the bromodomain with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages
Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subjectcompliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are desfibed in Cancer Principles and Practice of Oncology by V. T. Devita and S. Hellman (editors), $6^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

General Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

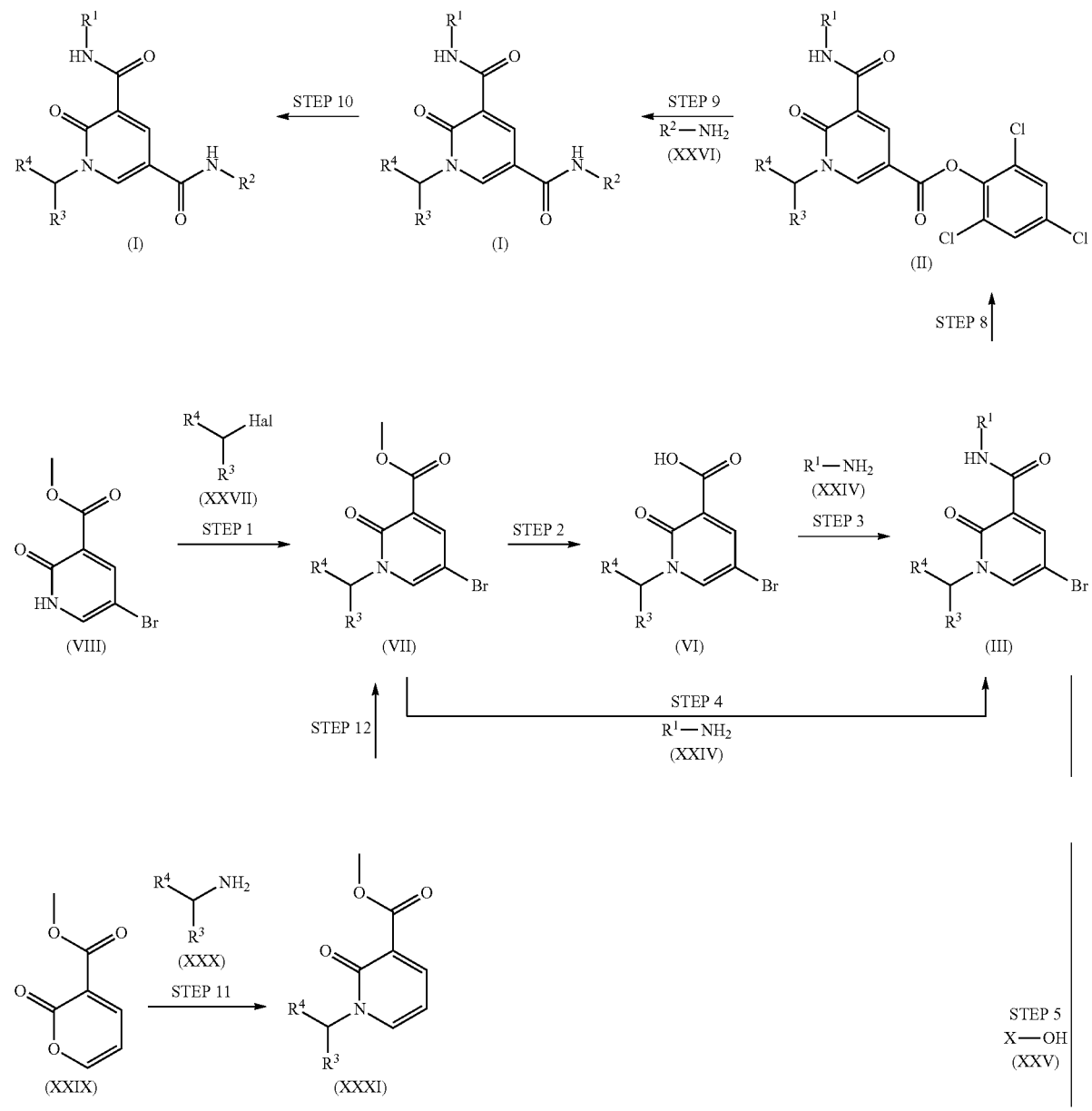

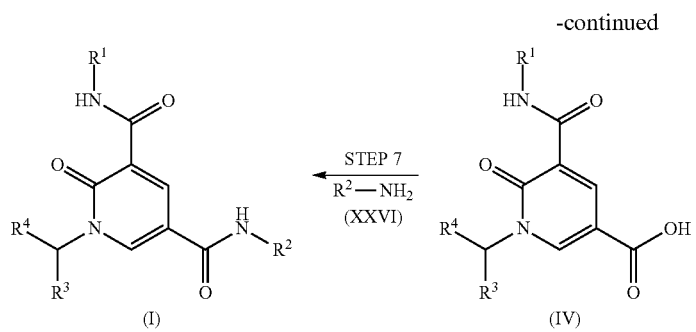
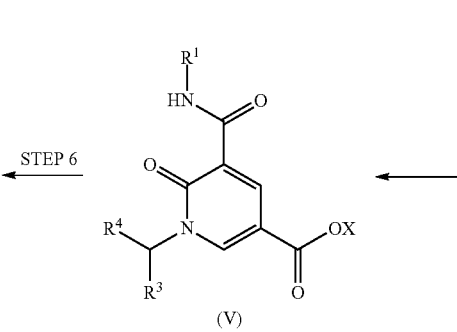

wherein $R^1$, $R^2$, $R^3$ and $R^4$ are as described above, Hal is chlorine or bromine and X is a $C_{1-6}$alkyl group.

In respect of the steps shown in Scheme 1 above the following reaction conditions may be utilised:

Step 1: is an alkylation and may be carried out using an alkyl or benzyl halide of formula $R^4CH(R^3)$Hal, such as an alkylbromide of formula $R^4CH(R^3)$Br, in the presence of an inorganic base, such as sodium hydride, in a suitable solvent, preferably an aprotic solvent, such as DMF, THF or 2-MeTHF, at a suitable temperature, such as 0° C.

Step 2: is base hydrolysis and may be carried out using any suitable inorganic base, such as LiOH, in a suitable solvent or solvent mixture, such as a mixture of methanol and THF, at a suitable temperature, such as room temperature.

Step 3: is an amide coupling reaction consisting of two steps. Step 3a, to produce the acid chloride, may be carried out using a chlorinating agent, such as oxalyl chloride, in the presence of a suitable catalyst, such as DMF, in a suitable solvent, such as DCM, at a suitable temperature, such as room temperature. Step 3b may be carried out using an amine reagent, $R^1$—$NH_2$, optionally in the presence of a tertiary amine, such as triethylamine, in a suitable solvent, such as THF, at a suitable temperature, such as 0° C.

Step 4: is an amine displacement reaction and may be carried out using an amine reagent, $R^1$—$NH_2$, in a suitable solvent or solvent mixture, such as a mixture of water and methanol, at a suitable temperature, such as 50° C.

Step 5: is a carbonylation reaction and may be carried out using an alcohol reagent, XOH (X is a $C_{1-6}$alkyl group), in the presence of a tertiary amine, such as triethylamine, in the presence of a palladium catalyst, such as palladium acetate, in the presence of a phosphine ligand, such as dppb, in the presence of carbon monoxide, in a suitable solvent, such as DMSO, at a suitable temperature, such as 100° C.

Step 6: is a hydrolysis step and may be carried out using an inorganic base, such as NaOH or LiOH, in a suitable solvent or solvent mixture, such as methanol and THF, at a suitable temperature, such as room temperature.

Step 7: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 8: is a carbonylation reaction and may be carried out using a metal carbonyl complex, such as dicobalt octacarbonyl, in the presence of a phosphine ligand, such as Xantphos, in the presence of a suitable palladium catalyst, such as palladium (II) acetate, in the presence of a nucleophilic catalyst, such as DMAP, in the presence of a suitable solvent, such as THF, at a suitable temperature, such as 80° C.

Step 9: is a displacement reaction and may be carried out using an amine reagent, $R^2$—$NH_2$, in the presence of a nucleophilic catalyst, such as DMAP, in the presence of a tertiary amine, such as triethylamine, in the presence of a suitable solvent, such as THF, at a suitable temperature, such as 45° C.

Step 10: is an optional deprotection step to remove a protecting group, such as BOC and may be carried out using an acid such as TFA, in the presence of a suitable solvent, such as DCM, at a suitable temperature, such as room temperature.

Step 11: is a pyridone formation and may be carried out using an alkyl or benzyl amine, such as $R^4CH(R^3)NH_2$, in a suitable solvent or solvent mixture, such as DMF and THF, with the addition of a suitable amide coupling reagent, such as EDC, a suitable nucleophilic catalyst, such as DMAP, and a suitable temperature, such as room temperature.

Step 12: is a bromination reaction and may be carried out using a suitable brominating reactant, such as NBS, in a suitable solvent, such as 2-MeTHF, at a suitable temperature, such as room temperature.

Scheme 2:

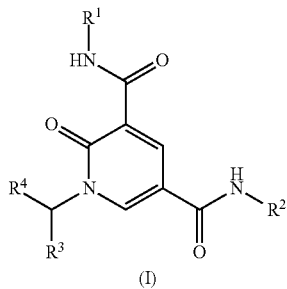

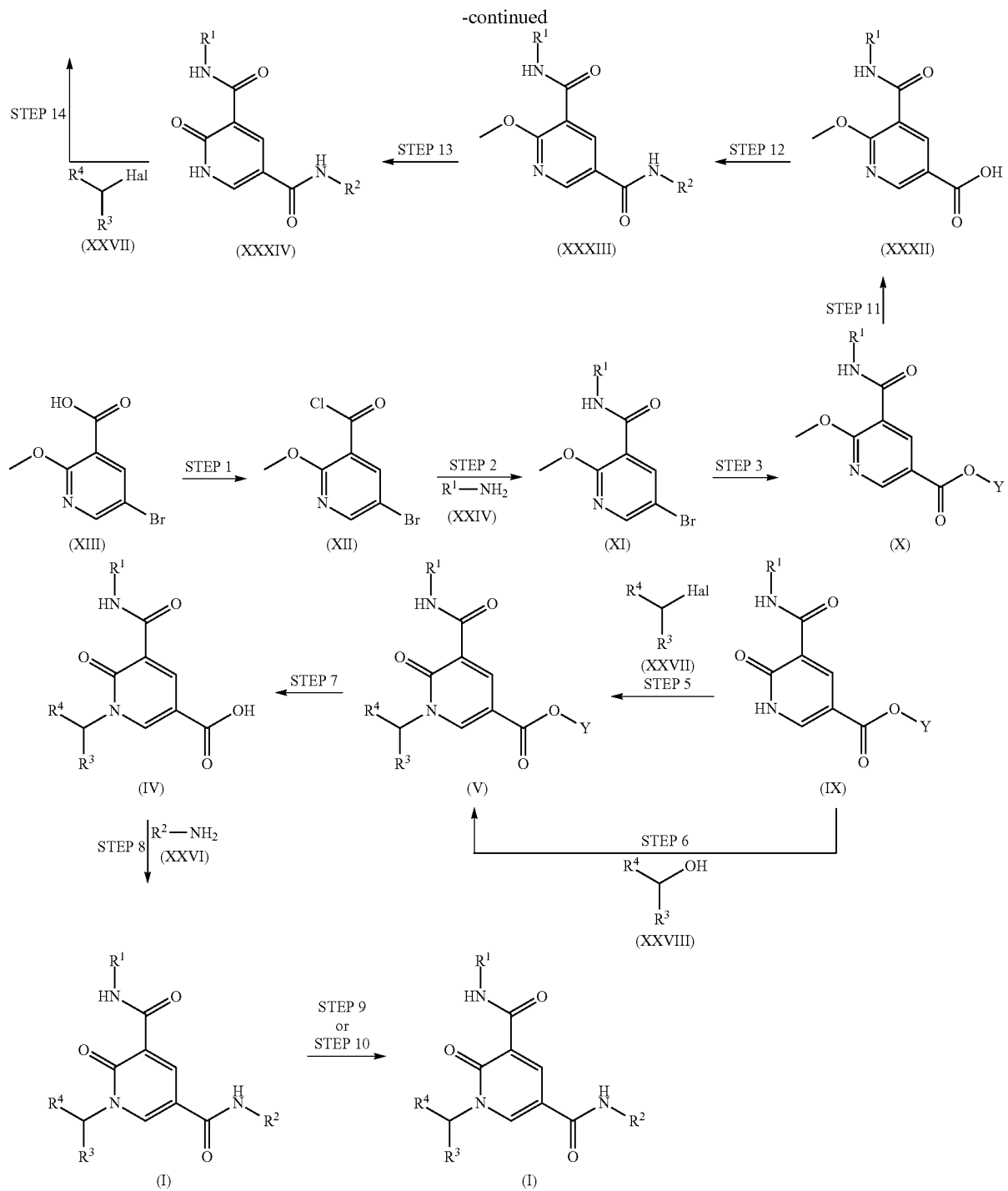

wherein $R^1$, $R^2$, $R^3$ and $R^4$ are as described above, Y is a $C_{1-6}$alkyl group and Hal is bromine or chlorine.

In respect of the steps shown in Scheme 2 above the following reaction conditions may be utilised:

Step 1: is an acid chloride formation, and may be carried out using a chlorinating agent, such as oxalyl chloride, in the presence of a suitable catalyst, such as DMF, in a suitable solvent, such as DCM, at a suitable temperature, such as room temperature.

Step 2: is an amine displacement reaction, and may be carried out using an amine reagent, $R^1$—$NH_2$, in the presence of a tertiary amine, such as triethylamine, in a suitable solvent, such as THF, at a suitable temperature, such as 0° C.

Step 3: is a carbonylation reaction and may be carried out using an alcohol reagent, YOH (Y is a $C_{1-6}$alkyl group), in the presence of a tertiary amine, such as triethylamine, in the presence of a palladium catalyst, such as palladium (II) acetate, in the presence of a phosphine ligand, such as dppb, in the presence of carbon monoxide, in a suitable solvent, such as DMSO, at a suitable temperature, such as 100° C.

Step 4: is a demethylation reaction and may be carried out using a demethylating agent, such as NaI with TMS-Cl, in a suitable solvent, such as acetonitrile, at a suitable temperature, such as room temperature.

Step 5: is an alkylation and may be carried out using an alkyl or benzyl halide such as a R⁴CH(R³)Br or R⁴CH(R³)Cl, in the presence of an inorganic base, such as potassium carbonate, in a suitable solvent, such as DMF, at a suitable temperature, such as 90° C.

Step 6: is a Mitsunobu reaction and may be carried out using an alcohol, such as R⁴CH(R³)OH, a Mitsunobu reagent, such as DIAD in the presence of a phosphine, such as triphenyl phosphine, or 2-(tributylphosphoranylidene)acetonitrile, in a suitable solvent, such as toluene, at a suitable temperature, such as room temperature or 120° C.

Step 7: is a hydrolysis step and may be carried out using an inorganic base, such as NaOH or LiOH, in a suitable solvent or solvent mixture, such as methanol and THF or 1,4-dioxane and water, at a suitable temperature, such as room temperature.

Step 8: is an amide coupling reaction and may be carried out using an amine reagent, R²—NH₂, in the presence of a suitable tertiary amine, such as triethylamine or DIPEA, in the presence of an amide coupling reactant, such as HATU, in a suitable solvent, such as DCM or DMF, at a suitable temperature, such as room temperature.

Step 9: is an optional deprotection step to remove a protecting group, such as BOC and may be carried out using an acid such as TFA, in the presence of a suitable solvent, such as DCM, at a suitable temperature, such as room temperature.

Step 10: is an optional chiral separation, using a suitable chiral HPLC column and a suitable solvent system.

Step 11: is a hydrolysis step and may be carried out using an inorganic base, such as NaOH or LiOH, in a suitable solvent or solvent mixture, such as methanol and THF or 1,4-dioxane and water, at a suitable temperature, such as room temperature.

Step 12: is an amide coupling reaction and may be carried out using an amine reagent, R²—NH₂, in the presence of a suitable tertiary amine, such as triethylamine or DIPEA, in the presence of an amide coupling reactant, such as HATU, in a suitable solvent, such as DCM or DMF, at a suitable temperature, such as room temperature.

Step 13: is a demethylation reaction and may be carried out using a demethylating agent, such as NaI with TMS-Cl, in a suitable solvent, such as acetonitrile, at a suitable temperature, such as room temperature.

Step 14: is an alkylation and may be carried out using an alkyl or benzyl halide such as a R⁴CH(R³)Br or R⁴CH(R³)Cl, in the presence of an inorganic base, such as potassium carbonate, in a suitable solvent, such as DMF, at a suitable temperature, such as 90° C.

Scheme 3:

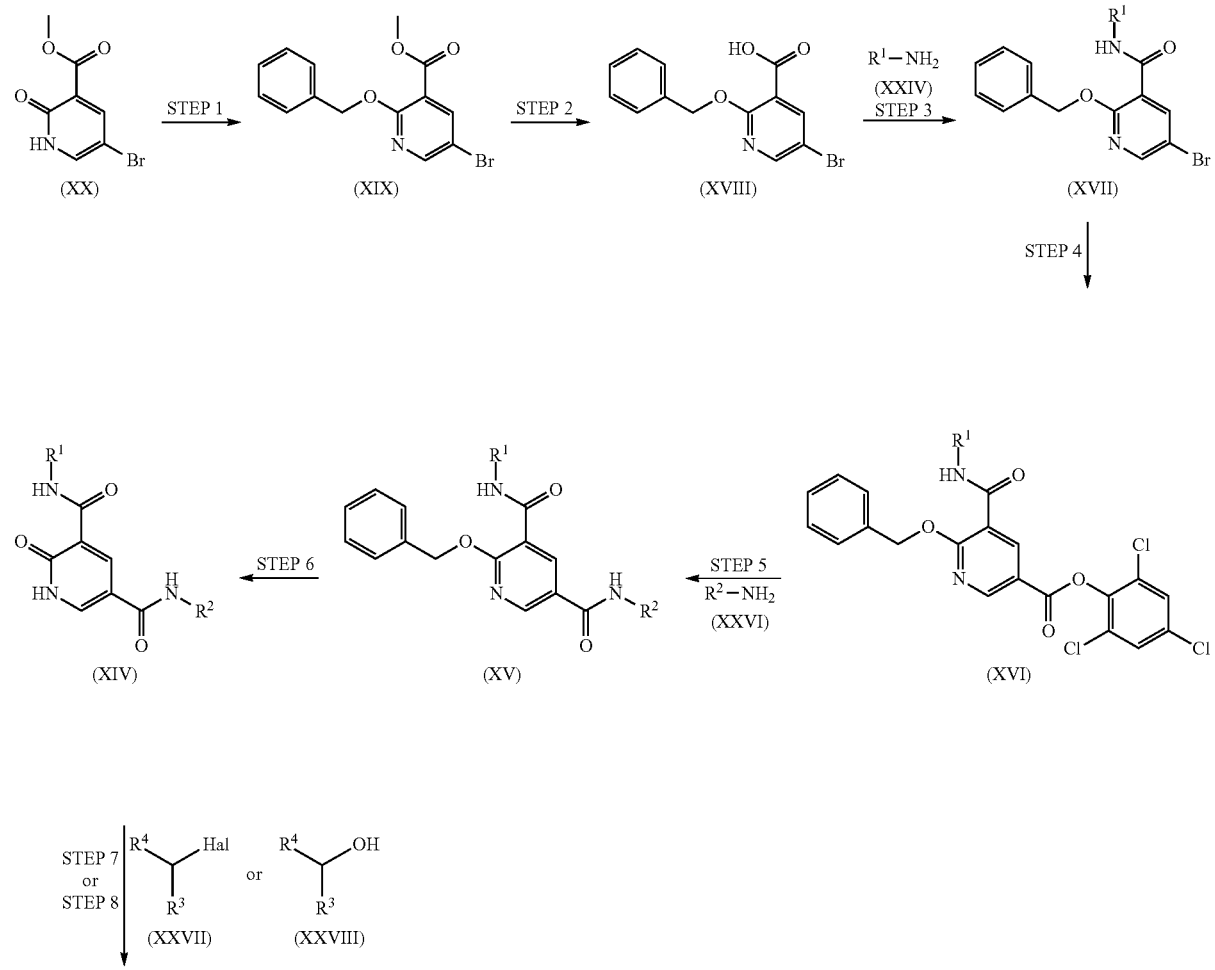

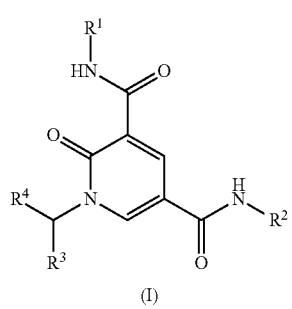

(I)

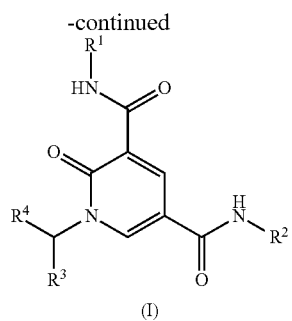

-continued (I)

wherein $R^1$, $R^2$, $R^3$ and $R^4$ are as described above and Hal is bromine or chlorine.

In respect of the steps shown in Scheme 3 above the following reaction conditions may be utilised:

Step 1: is an benzylation and may be carried out using a suitable silver salt, such as silver carbonate, a benzyl halide such as benzyl bromide, a suitable solvent, such as chloroform and heated for example, under reflux.

Step 2: is a hydrolysis step and may be carried out using an inorganic base, such as NaOH or LiOH, in a suitable solvent or solvent mixture, such as methanol and THF or 1,4-dioxane and water, at a suitable temperature, such as room temperature.

Step 3: is an amide coupling reaction consisting of two steps. Step 3a, to produce the acid chloride, may be carried out using a chlorinating agent, such as oxalyl chloride, in the presence of a suitable catalyst, such as DMF, in a suitable solvent, such as DCM, at a suitable temperature, such as room temperature. Step 3b may be carried out using an amine reagent, $R^1$—$NH_2$, in a suitable solvent, such as THF, at a suitable temperature, such as 0° C.

Step 4: is a carbonylation reaction and may be carried out using 2,4,6-trichlorophenyl formate, in the presence of a phosphine ligand, such as Xantphos, in the presence of a suitable palladium catalyst, such as palladium (II) acetate, in the presence of a tertiary amine, such as triethylamine, in the presence of a suitable solvent, such as toluene, at a suitable temperature, such as 80° C.

Step 5: is a displacement reaction and may be carried out using an amine reagent, $R^2$—$NH_2$, in the presence of a nucleophilic catalyst, such as DMAP, in the presence of a tertiary amine, such as triethylamine, in the presence of a suitable solvent, such as THF, at a suitable temperature, such as 45° C.

Step 6: is a debenzylation and may be carried out using a suitable acid, such as TFA, at a suitable temperature, such as 80° C.

Step 7: is a Mitsunobu reaction and may be carried out using an alcohol, such as $R^4CH(R^3)OH$, a Mitsunobu reagent, such as DIAD in the presence of a phosphine, such as triphenyl phosphine, or 2-(tributylphosphoranylidene)acetonitrile, in a suitable solvent, such as toluene, at a suitable temperature, such as room temperature or 120° C.

Step 8: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as DMF, at a suitable temperature, such as 90° C.

Step 9: is an optional deprotection step to remove a protecting group, such as BOC and may be carried out using an acid such as TFA, in the presence of a suitable solvent, such as DCM, at a suitable temperature, such as room temperature.

Step 10: is an optional deprotection step to cleave a sulfonamide group, such as tosyl and may be carried out using an inorganic base, such as cesium carbonate, in the presence of a suitable solvent or solvent mixture, such as methanol and THF, at a suitable temperature, such as 70° C.

Scheme 4:

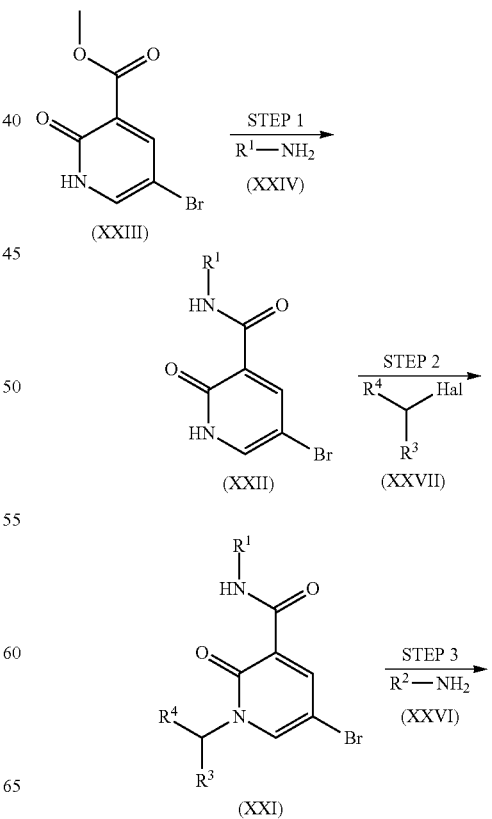

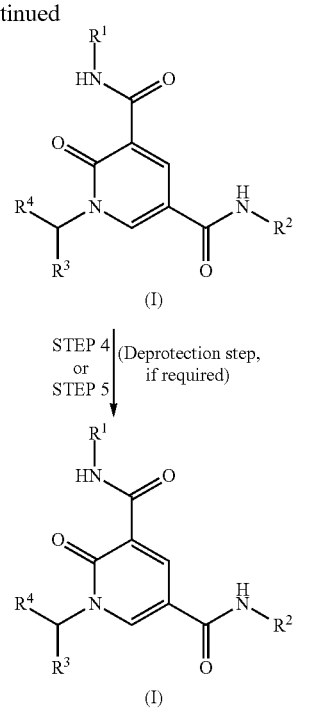

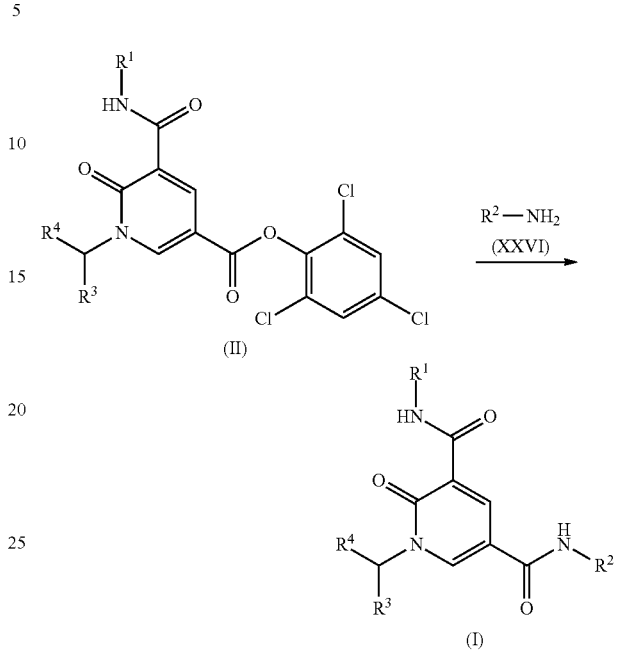

Accordingly, in one embodiment there is provided a process for the preparation of a compound of formula (I) by the reaction of a compound of formula (II) with an amine of formula (XXVI)

wherein $R^1$, $R^2$, $R^3$ and $R^4$ are as described above and Hal is chorine or bromine.

In respect of the steps shown in Scheme 4 above the following reaction conditions may be utilised:

Step 1: is an amine displacement reaction and may be carried out using an amine reagent, $R^1$—$NH_2$, in a suitable solvent, such as THF, at a suitable temperature, such as under reflux.

Step 2: is an alkylation and may be carried out using an alkyl or benzyl halide such as a $R^4CH(R^3)Br$ or $R^4CH(R^3)Cl$, in the presence of an inorganic base, such as potassium carbonate, in a suitable solvent, such as methanol or DMF, at a suitable temperature, such as 65° C. or 90° C.

Step 3: is an amino carbonylation reaction and may be carried out using an amine reagent such as $R^2$—$NH_2$, a metal carbonyl complex, such as dicobalt octacarbonyl, in the presence of a phosphine ligand, such as Xantphos or Catacxium A, in the presence of a suitable palladium catalyst, such as palladium (II) acetate, in the presence of a suitable nucleophilic catalyst, such as DMAP, in the presence of a suitable solvent, such as 1,4 dioxane or THF, at a suitable temperature, such as 80° C.

Step 4: is an optional deprotection step to cleave a sulfonamide group, such as tosyl and may be carried out using an inorganic base such as cesium carbonate, in the presence of a suitable solvent or solvent mixture, such as methanol and THF, at a suitable temperature, such as 70° C.

Step 5: is an optional deprotection step to remove a protecting group, such as BOC and may be carried out using a suitable acid, such as TFA, in the presence of a suitable solvent, such as DCM, at a suitable temperature, such as room temperature.

Compounds of Formulae (VIII), (XIII), (XX), (XXIII) and (XXIX) are commercially available from, for example, Sigma Aldrich, Fluorochem, Apollo Scientific or Combi-Blocks. Compounds of formulae $R^1$—$NH_2$, XOH, $R^2$—$NH_2 R^4CH(R^3)OH$, $R^3CH(R^3)NH_2$ and $R^4CH(R^3)Hal$ are either commercially available from the suppliers mentioned above or can by made by methods well known in the art or described herein.

wherein $R^1$, $R^2$, $R^3$ and $R^4$ are as hereinbefore defined; in the presence of a nucleophilic catalyst, such as DMAP, in the presence of a tertiary amine, such as triethylamine, in the presence of a suitable solvent, such as THF, at a suitable temperature, such as 45° C. This step may be followed by removal of any protecting group, if required, followed by preparation of a salt, if required.

In a second embodiment there is provided a process for the preparation of a compound of formula (I) by the reaction of a compound of formula (III) with an amine of formula (XXVI)

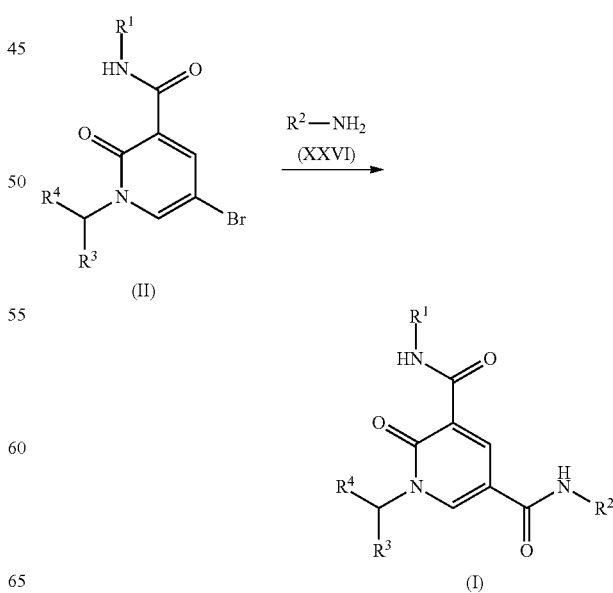

wherein $R^1$, $R^2$, $R^3$ and $R^4$ are as hereinbefore defined; in the presence of a metal carbonyl complex, such as dicobalt octacarbonyl, in the presence of a phosphine ligand, such as Xantphos or Catacxium A, in the presence of a suitable nucleophilic catalyst, such as DMAP, in the presence of a suitable solvent, such as 1,4 dioxane or THF, at a suitable temperature, such as 80° C. This step may be followed by removal of any protecting group, if required, followed by preparation of a salt, if required.

In a third embodiment there is provided a process for the preparation of a compound of formula (I) by the reaction of a compound of formula (IV) with an amine of formula (XXVI)

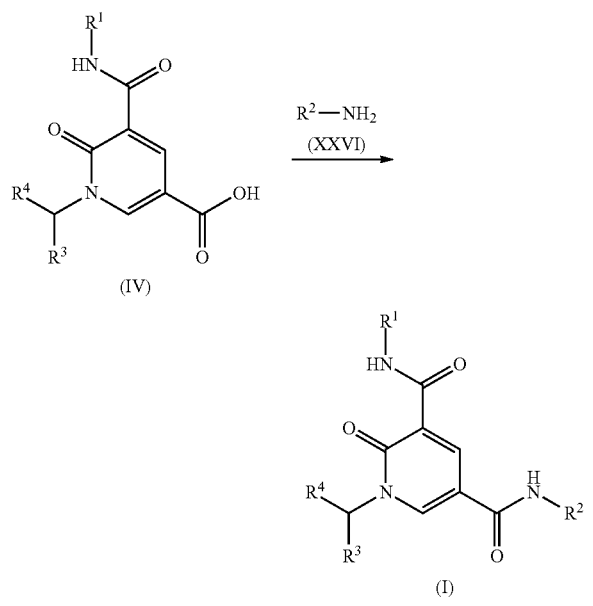

wherein $R^1$, $R^2$, $R^3$ and $R^4$ are as hereinbefore defined; in the presence of an amide coupling reagent, such as HATU, a tertiary amine, such as triethylamine or DIPEA, in the presence of a suitable solvent, such as DCM or DMF, at a suitable temperature, such as room temperature. This step may be followed by removal of any protecting group, if required, followed by preparation of a salt, if required.

In a fourth embodiment there is provided a process for the preparation of a compound of formula (I) by the reaction of a compound of formula (XIV) with a compound of formula (XXVII)

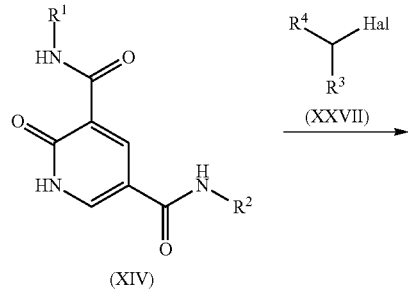

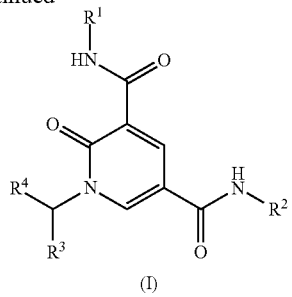

wherein $R^1$, $R^2$, $R^3$ and $R^4$ are as hereinbefore defined and Hal is chlorine or bromine; in the presence of an inorganic base, such as potassium carbonate, in a suitable solvent, such as DMF, at a suitable temperature, such as 90° C. This step may be followed by removal of any protecting group, if required, followed by preparation of a salt, if required.

In a fifth embodiment there is provided a process for the preparation of a compound of formula (I) by the reaction of a compound of formula (XIV) with a compound of formula (XXVIII)

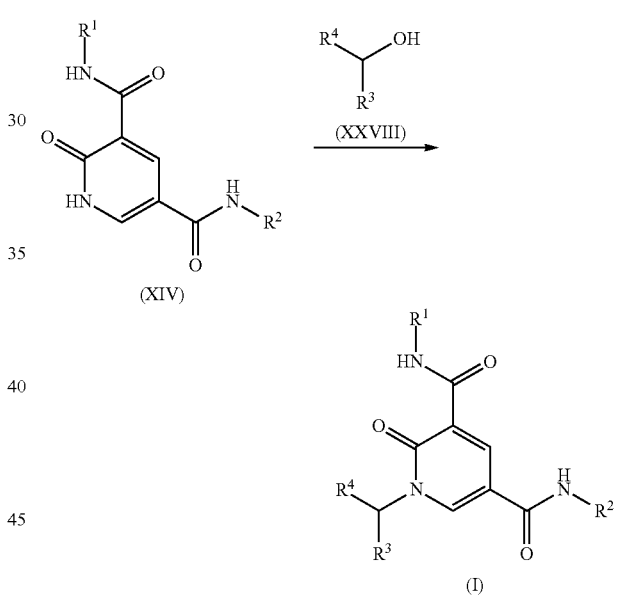

$R^1$, $R^2$, $R^3$ and $R^4$ are as hereinbefore defined; in the presence of a Mitsunobu reagent, such as 2-(tributylphosphoranylidene)acetonitrile or DIAD in the presence of a phosphine, such as triphenyl phosphine, in a suitable solvent, such as toluene, at a suitable temperature, such as 120° C. or room temperature. This step may be followed by removal of any protecting group, if required, followed by preparation of a salt, if required.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

EXAMPLES

General Methods
General Experimental Details
All temperatures referred to are in ° C.
As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations

AcOH acetic acid
BBr$_3$ boron tribromide
BOC/Boc tert-butyloxycarbonyl
BuLi butyllithium
Cs$_2$CO$_3$ cesium carbonate
CHCl$_3$ chloroform
Cobalt carbonyl dicobalt octacarbonyl
CV column volume
DMSO-d$_6$ deuterated dimethylsulfoxide
DCM dichloromethane
DIAD diisopropyl azodicarboxylate
DIBAL-H diisobutylaluminium hydride
DIPEA diisopropylethylamine
DMAP 4-dimethylaminopyridine
DMF dimethylformamide
DMSO dimethylsulfoxide
DPPA diphenylphosphoryl azide
dppb 1,4-bis(diphenylphosphino)butane
EDC 1-ethyl-3-(3-dimethylaminopropyl)carbodiimide
Et$_3$N triethylamine
EtOAc ethyl acetate
h hour(s)
HATU O-(7-azabenzotriazol-1-yl)-N,N,N',N'-tetramethyluronium hexafluorophosphate
HCl hydrochloric acid
HCO$_2$H formic acid
IPA isopropyl alcohol
Isolera Biotage Flash purification system
K$_2$CO$_3$ potassium carbonate
KOH potassium hydroxide
LCMS liquid chromatography-mass spectrometry
LiOH lithium hydroxide
M molar (concentration)
MDAP mass directed autoprep
MeCN acetonitrile
MeI methyl iodide
MeOH methanol
2-MeTHF 2-methyl tetrahydrofuran
MgSO$_4$ magnesium sulphate
min minute(s)
MTBE methyl tert-butyl ether
N normal (concentration)
N$_2$ nitrogen
Na$_2$CO$_3$ sodium carbonate
NaI sodium iodide
NaH sodium hydride
NaOH sodium hydroxide
Na(OAc)$_3$BH sodium triacetoxy borohydride
Na$_2$SO$_4$ sodium sulphate
NBS N-bromosuccinimide
NEt$_3$ triethylamine
NMP N-methyl-2-pyrrolidone
NUT nuclear protein in testis
Pd/C palladium on carbon
PPh$_3$ triphenylphosphine
RBF round bottomed flask
Rt retention time
rt room temperature
sat saturated
SCX Isolute strong cation exchange sorbent SPE
SiO$_2$ silicon dioxide
SNAP Biotage (silica) flash chromatography cartridge
SP4 Biotage Flash purification system
SPE solid phase extraction
TBME tert-butyl methyl ether
Tf$_2$O trifluoromethanesulfonic anhydride
TFA trifluoroacetic acid
THF tetrahydrofuran
TMSCl/TMS-Cl trimethylsilyl chloride
TLC Thin layer chromatography
Ts tosyl
UPLC ultra performance liquid chromatograpy
XantPhos 1,1'-(9,9-dimethyl-9H-xanthene-4,5-diyl)bis[1,1-diphenylphosphine The names of the following compounds have been obtained using the compound naming programme "ACD Name Pro 6.02" or using the naming functionality of ChemDraw Ultra 12.0.

LCMS Methodology
Formic Method
LC Conditions

The UPLC analysis was conducted on an Acquity UPLC CSH C18 column (50 mm×2.1 mm, i.d. 1.7 µm packing diameter) at 40° C.

The solvents employed were:

A=0.1% v/v solution of formic acid in water
B=0.1% v/v solution of formic acid in acetonitrile The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions The UPLC analysis was conducted on an Acquity UPLC CSH C18 column (50 mm×2.1 mm, i.d. 1.7 µm packing diameter) at 40° C.

The solvents employed were:

A=10 mM ammonium hydrogen carbonate in water adjusted to pH10 with ammonia solution
B=acetonitrile The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions The UPLC analysis was conducted on an Acquity UPLC CSH C18 column (50 mm×2.1 mm, i.d. 1.7 µm packing diameter) at 40° C.

The solvents employed were:

A=0.1% v/v solution of trifluoroacetic acid in water
B=0.1% v/v solution of trifluoroacetic acid in acetonitrile The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.

MS Conditions
MS Waters ZQ
Ionisation mode Alternate-scan positive and negative electrospray
Scan range 100 to 1000 AMU
Scan time 0.27 sec
Inter scan delay: 0.10 sec
General MDAP Purification Methods Listed below are examples of mass-directed autopreparative chromatography (MDAP) methods that have been used or may be used in compound purification.

MDAP (High pH).

The HPLC analysis was conducted on an Xselect CSH C18 column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic).

The HPLC analysis was conducted on an Xselect CSH C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA).

The HPLC analysis was conducted on an Xselect CSH C18 column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at either 302 K or at 392-393 K for VT spectra.

Intermediate 1: tert-Butyl 4-(hydroxymethyl)-1H-benzo[d]imidazole-1-carboxylate

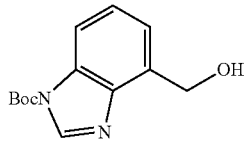 [SMILES: CC(C)(C)OC(=O)n1cnc2c(CO)cccc21]

To a solution of (1H-benzo[d]imidazol-7-yl)methanol (200 mg, 1.350 mmol, commercially available from, for example, Apollo Scientific) in acetonitrile (10.799 mL) and water (2.70 mL) was added sodium bicarbonate (227 mg, 2.70 mmol) and Boc$_2$O (0.431 mL, 1.856 mmol). The mixture was stirred for 4 h at rt. The reaction mixture was diluted with ethyl acetate (70 mL) and washed with 10% aqueous citric acid (3×25 mL). LCMS revealed the acid washes contained some product and the aqueous phase was concentrated in vacuo before extracting with ethyl acetate (3×15 mL). The combined ethyl acetate portions were washed with water (25 mL) and brine (25 mL) before drying through a hydrophobic frit and evaporating in vacuo to yield the crude product. The product was loaded in dichloromethane onto a 50 g SNAP silica cartridge and purified via Biotage SP4 chromatography eluting from 15-60% ethyl acetate/cyclohexane. The relevant fractions were evaporated in vacuo to yield a yellow gum. The flask was sonicated with ether and evaporated once more. The product was further dried in vacuo to yield the purified product—tert-butyl 4-(hydroxymethyl)-1H-benzo[d]imidazole-1-carboxylate (262 mg, 1.055 mmol, 78% yield) as a yellow gum.

LCMS (2 min Formic): Rt=0.91 min, [MH]$^+$=249.0.

Intermediate 2: Methyl 1-tosyl-1H-indole-4-carboxylate

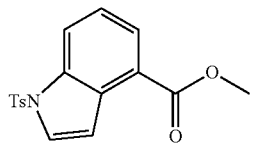 [SMILES: COC(=O)c1cccc2c1ccn2S(=O)(=O)c1ccc(C)cc1]

Methyl 1H-indole-4-carboxylate (750 mg, 4.28 mmol, commercially available from, for example, Sigma-Aldrich) was dissolved in DMF (13.591 mL) at 0° C. under nitrogen. Sodium hydride (205 mg, 5.14 mmol, 60% dispersion in mineral oil) was added in portions. The reaction was stirred at 0° C. for 10 min before warming to rt and stirring for 30 min. Tosyl-Cl (979 mg, 5.14 mmol) was added and the reaction mixture was stirred at rt for 10 min. The reaction was cooled to 0° C. and quenched by the dropwise addition of water (3.86 mL, 214 mmol), before pouring onto saturated aqueous lithium chloride (140 mL). The product was extracted with ethyl acetate (3×30 mL) and the combined organic portions were dried through a hydrophobic frit and evaporated in vacuo to yield the crude product (2056 mg). The residue was dry loaded onto a 50 g SNAP silica cartridge and purified via Biotage SP4 flash chromaotography, eluting from 0-25% ethyl acetate/cyclohexane. The relevant fractions were combined and evaporated in vacuo to yield the pure product—methyl 1-tosyl-1H-indole-4-carboxylate (1039 mg, 3.15 mmol, 73.7% yield) as a white solid.

LCMS (2 min Formic): Rt=1.29 min, [MH]$^+$=330.0.

Intermediate 3: (1-Tosyl-1H-indol-4-yl)methanol

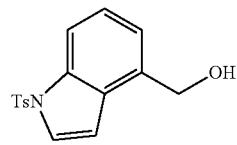 [SMILES: Cc1ccc(S(=O)(=O)n2ccc3c(CO)cccc32)cc1]

A solution of methyl 1-tosyl-1H-indole-4-carboxylate (1016 mg, 3.08 mmol) in DCM (30.361 mL) was cooled to −78° C. and DIBAL-H (1M in toluene, 13.57 mL, 13.57 mmol) was added dropwise over 1 h. The reaction mixture was stirred for a further 1.5 h, followed by a further 40 min. The reaction was quenched with methanol (0.125 mL, 3.08 mmol) when still at −78° C. and then allowed to warm to ambient temperature. The reaction was diluted with saturated Rochelle's salt solution (60 mL) and stirred for 16 h. The layers were separated, and the aqueous phase was extracted with dichloromethane (2×50 mL). The combined organic layers were dried through a hydrophobic frit and evaporated in vacuo to yield the crude product (913 mg). The residue was loaded in dichloromethane onto a 50 g SNAP cartridge and purified via Biotage SP4, eluting from 15-75% ethyl acetate/cyclohexane. The relevant fractions were combined and evaporated in vacuo to yield the pure product—(1-tosyl-1H-indol-4-yl)methanol (901 mg, 2.84 mmol, 92% yield) as a white solid.

LCMS (2 min Formic): Rt=1.07 min, [M+Na]$^+$=324.0.

Intermediate 4: 4-(Bromomethyl)-1-tosyl-1H-indole

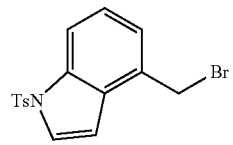 [SMILES: Cc1ccc(S(=O)(=O)n2ccc3c(CBr)cccc32)cc1]

(1-Tosyl-1H-indol-4-yl)methanol (500 mg, 1.659 mmol) and HBr (3995 μL, 48% in water, 33.2 mmol) were heated at 80° C. monitoring by LCMS. Initial LCMS indicated formation of product and the reaction was heated for a further 4 h. The reaction mixture was poured onto water (10 mL) and the product was extracted with dichloromethane (3×20 mL). The combined organic portions were dried through a hydrophobic frit and evaporated in vacuo to yield the crude product—4-(bromomethyl)-1-tosyl-1H-indole (564 mg, 1.316 mmol, 79% yield) as a purple solid which was used without further purification.

LCMS (2 min Formic): Rt=1.35 min, [M−H]$^-$=362.0, 364.0.

Intermediate 5: Methyl 1-tosyl-1H-indole-7-carboxylate

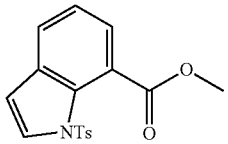 [SMILES: COC(=O)c1cccc2ccn(S(=O)(=O)c3ccc(C)cc3)c12]

Methyl 1H-indole-7-carboxylate (1 g, 5.71 mmol, commercially available from, for example, Apollo Scientific) was dissolved in DMF (18.12 mL) at 0° C. under nitrogen. Sodium hydride (0.251 g, 60% dispersion in mineral oil, 6.28 mmol) was added in portions. The reaction was stirred at 0° C. for 10 min before warming to rt and stirring for 30 min. Tosyl-Cl (1.197 g, 6.28 mmol) was added and the reaction mixture was stirred for 2 hr. The reaction was cooled back down to 0° C. and a further portion of sodium hydride (0.114 g, 60% dispersion in mineral oil, 2.85 mmol) was added portionwise. The reaction mixture was stirred for 10 min before warming to rt and stirring for 30 min. An additional portion of tosyl-Cl (0.544 g, 2.85 mmol) was added at this point. The reaction was stirred for a further 1.5 h. The reaction was quenched by the dropwise addition of water (5.14 mL, 285 mmol). The reaction was poured onto saturated aqueous lithium chloride (100 mL) and the product was extracted with ethyl acetate (3×30 mL). The combined organic portions were dried through a hydrophobic frit and evaporated in vacuo to yield the crude product (2158 mg). The residue was dry loaded onto a 50 g SNAP silica cartridge and purified via Biotage SP4 flash chromatography, eluting from 0-25% ethyl acetate/cyclohexane. The relevant fractions were combined and evaporated in vacuo to yield the pure product—methyl 1-tosyl-1H-indole-7-carboxylate (1159 mg, 3.52 mmol, 61.6% yield) as a yellow solid.

LCMS (2 min Formic): Rt=1.18 min, $[MH]^+$=330.0.

Intermediate 6: (1-Tosyl-1H-indol-7-yl)methanol

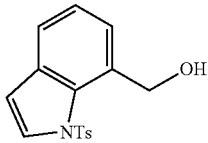 [SMILES: Cc1ccc(S(=O)(=O)n2ccc3cccc(CO)c32)cc1]

A solution of methyl 1-tosyl-1H-indole-7-carboxylate (1117 mg, 3.39 mmol) in DCM (33.913 mL) was cooled to −78° C. and DIBAL-H (14.92 mL, 1M in toluene, 14.92 mmol) was added dropwise over 15 min. The reaction mixture was stirred for 1.5 h more. The reaction was quenched with methanol (6.04 mL, 149 mmol) when still at −78° C. and then allowed to warm to ambient temperature. The reaction was diluted with Rochelle's salt solution (60 mL) and stirred for 16 h. The layers were separated, and the aqueous phase was extracted with dichloromethane (2×50 mL). The combined organic layers were dried through a hydrophobic frit and evaporated in vacuo to yield the crude product (1065 mg). The residue was loaded in dichloromethane and purified via Biotage SP4, eluting from 10-50% ethyl acetate/cyclohexane. The relevant fractions were combined and evaporated in vacuo to yield a clear oil. The product was air dried to yield—(1-tosyl-1H-indol-7-yl)methanol (901 mg, 2.84 mmol, 84% yield).

LCMS (2 min Formic): Rt=1.07 min, $[M-H]^-$=300.1.

Intermediate 7: 7-(Bromomethyl)-1-tosyl-1H-indole

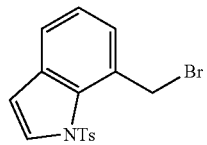 [SMILES: Cc1ccc(S(=O)(=O)n2ccc3cccc(CBr)c32)cc1]

(1-Tosyl-1H-indol-7-yl)methanol (500 mg, 1.659 mmol) and HBr (3995 μL, 48% in water, 33.2 mmol) were heated at 80° C. for 1 h. The reaction mixture was filtered through a sinter funnel and washed with water. The collected precipitate was dissolved in dichloromethane (100 mL), dried through a hydrophobic frit and evaporated in vacuo to yield the crude product—7-(bromomethyl)-1-tosyl-1H-indole (602 mg, 1.322 mmol, 80% yield) as a deep red oil which was used without further purification.

LCMS (2 min Formic): Rt=1.34 min, $[MH]^+$=364.0, 366.0.

Intermediate 8: (1,2,3,4-Tetrahydroquinolin-8-yl)methanol

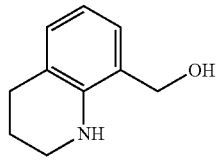 [SMILES: OCc1cccc2c1NCCC2]

To 1,2,3,4-tetrahydroquinoline-8-carboxylic acid (500 mg, 2.82 mmol, commercially available from, for example, Fluorochem), borane tetrahydrofuran complex (8.47 mL, 1M in THF, 8.47 mmol) was added and the reaction stirred at rt for 18 h. A further portion of borane tetrahydrofuran complex (2.82 mL, 1M in THF, 2.82 mmol) was added and stirring was continued for a further 3 h. The reaction was quenched with methanol (10 mL, 247 mmol) and hydrochloric acid (10 mL, 1M, 10.00 mmol) and stirred for 2 h at rt. The reaction was concentrated in vacuo and taken up in EtOAc (20 mL) and washed with $NaHCO_3$ (30 mL). The aqueous layer was extracted with EtOAc (3×20 mL), the organic layers were washed with brine (10 mL), dried over a hydrophobic frit and concentrated to give the crude product (ca. 450 mg) as an orange oil. The product was loaded in dichloromethane onto a 25 g SNAP silica cartridge and purified via Biotage SP4 flash chromatography, eluting from 15-75% ethyl acetate/cyclohexane. The relevant fractions were combined and evaporated in vacuo to yield the desired product—(1,2,3,4-tetrahydroquinolin-8-yl)methanol (185 mg, 1.077 mmol, 38.2% yield).

LCMS (2 min Formic): Rt=0.40 min, $[MH]^+$=164.1.

Intermediate 9: 5-(Bromomethyl)quinoxaline

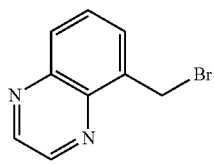

5-Methylquinoxaline (0.180 mL, 1.387 mmol, commercially available from, for example, Sigma-Aldrich), NBS (289 mg, 1.624 mmol), benzoyl peroxide (37 mg, 0.153 mmol) and 1,2-dichloroethane (4 mL) was stirred at 110° C. for 2 h. Further portions of NBS (260 mg, 1.461 mmol) and benzoyl peroxide (31 mg, 0.128 mmol) were added and the reaction refluxed for a further 2 h. The solution was concentrated to give 1.1 g of a brown solid which was purified by chromatography on $SiO_2$ (Biotage SNAP 50 g cartridge, eluting with 0-100% diethylether/cyclohexane). The desired fractions were concentrated to give 5-(bromomethyl)quinoxaline (310 mg, 0.882 mmol, 63.6% yield) as a yellow oil.

LCMS (2 min Formic): Rt=0.91 min, $[MH]^+$=223, 225.

Intermediate 10: 4-(Bromomethyl)-1H-indazole, hydrobromide

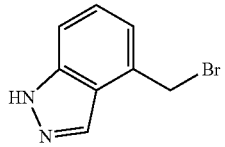

1H-Indazol-4-yl)methanol (202 mg, 1.363 mmol, commercially available from, for example, Apollo Scientific) and HBr (3.3 mL, 48% in water, 27.4 mmol) were heated at 80° C. for 2 h. The resulting suspension was allowed to cool to rt, filtered under vacuum, washed with cold water and dried in a vacuum oven to give 4-(bromomethyl)-1H-indazole, hydrobromide (213 mg, 0.657 mmol, 48.2% yield) as an off white solid.

LCMS (2 min Formic): Rt=0.85 min, $[MH]^+$=211, 213.

Intermediate 11: 7-(Bromomethyl)-1H-indazole, hydrobromide

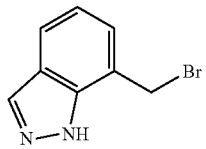 [SMILES: BrCc1cccc2cn[nH]c12]

(1H-Indazol-7-yl)methanol (250 mg, 1.687 mmol, commercially available from, for example Fluorochem) and HBr (4 mL, 48% in water, 33.2 mmol) were heated at 80° C. for 1 h. The suspension was allowed to cool to rt, filtered under vacuum, washed with cold water and dried in a vacuum oven to give 7-(bromomethyl)-1H-indazole, hydrobromide (449 mg, 1.307 mmol, 77% yield) as a white solid.

LCMS (2 min Formic): Rt=0.84 min, $[MH]^+$=211, 213.

Intermediate 12: Methyl methyl 3-methyl-1H-indole-4-carboxylate

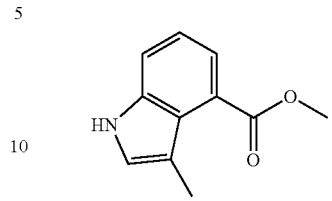

To 3-methyl-1H-indole-4-carboxylic acid (400 mg, 2.283 mmol, commercially available from, for example, Apollo Scientific) in methanol (20.757 mL) was added sulfuric acid (0.127 mL, 2.260 mmol) and the reaction was heated under reflux (65° C.) for 6 h. The reaction was cooled to ambient temperature and left to stand for 5 days. The reaction mixture was evaporated in vacuo and taken up in ethyl acetate (100 mL) and washed with water (2×10 mL), saturated sodium bicarbonate (10 mL) and brine (10 mL). The organic layer was dried through a hydrophobic frit and evaporated in vacuo to yield the crude product as an orange oil (434 mg). The sample was loaded in DCM onto a 25 g SNAP cartridge and purified via Biotage SP4 flash chromatography, eluting from 0-50% diethyl ether/cyclohexane. The relevant fractions were combined and evaporated in vacuo to isolate the pure product. The desired product methyl 3-methyl-1H-indole-4-carboxylate (279 mg, 1.401 mmol, 61.4% yield) was obtained as a light green solid.

LCMS (2 min Formic): Rt=0.92 min, $[MH]^+$=190.1.

Intermediate 13: Methyl 3-methyl-1-tosyl-1H-indole-4-carboxylate

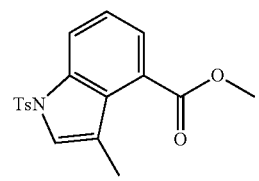 [SMILES: COC(=O)c1cccc2c1c(C)cn2S(=O)(=O)c1ccc(C)cc1]

Methyl 3-methyl-1H-indole-4-carboxylate (266 mg, 1.406 mmol) was dissolved in DMF (3.515 mL) at 0° C. under nitrogen. Sodium hydride (60% dispersion in mineral oil) (73.1 mg, 1.828 mmol) was added in portions. The reaction was stirred at 0° C. for 10 min before warming to rt and stirring for 30 min. Tosyl-Cl (322 mg, 1.687 mmol) was added and the reaction mixture was stirred at rt for 15 min. The reaction was cooled to 0° C. and quenched by the careful addition of water (1 mL, 55.5 mmol). Precipitation of the product was noted and the reaction mixture was filtered, washing with water to retrieve a light green solid. The solid was dried in vacuo to yield the desired product— methyl 3-methyl-1-tosyl-1H-indole-4-carboxylate (444 mg, 1.228 mmol, 87% yield) as a light green solid.

LCMS (2 min Formic): Rt=1.31 min, $[MH]^+$=344.0.

Intermediate 14: (3-Methyl-1-tosyl-1H-indol-4-yl)methanol

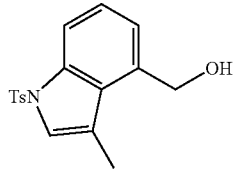 [SMILES: Cc1ccc(S(=O)(=O)n2cc(C)c3c(CO)cccc32)cc1]

A solution of methyl 3-methyl-1-tosyl-1H-indole-4-carboxylate (430 mg, 1.252 mmol) in DCM (6.261 mL) under nitrogen, was cooled to −78° C. and DIBAL-H (2355 µL, 5.51 mmol, 2.34 M in toluene) was added drop-wise over 30 min and the reaction was stirred at −78° C. for 2 h. The reaction was quenched with methanol (1520 µL, 37.6 mmol) when still at −78° C. and after allowed to warm to ambient temperature. The reaction was diluted with Rochelle's Salt solution (20 mL) and stirred for 16 h. The layers were separated, and the aqueous phase was extracted with DCM (3×20 mL). The combined organic layers were dried through a hydrophobic frit, then evaporated in vacuo to yield the crude product (481 mg). The sample was loaded in DCM onto a SNAP cartridge (25 g) and purified via Biotage SP4 flash chromatography, eluting from 10-62% ethyl acetate/cyclohexane. The fractions were combined and evaporated in vacuo to yield the desired product (3-methyl-1-tosyl-1H-indol-4-yl)methanol (311 mg, 0.966 mmol, 77% yield) as a white solid.

LCMS (2 min Formic): Rt=1.12 min, Does not ionise at correct [MH]+.

Intermediate 15: tert-Butyl 7-(hydroxymethyl)-4,5-dihydro-1H-benzo[d]azepine-3(2H)-carboxylate

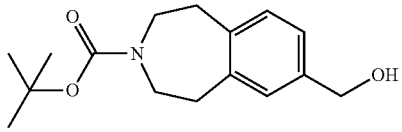 [SMILES: CC(C)(C)OC(=O)N1CCc2ccc(CO)cc2CC1]

To 3-(tert-butoxycarbonyl)-2,3,4,5-tetrahydro-1H-benzo[d]azepine-7-carboxylic acid (200 mg, 0.686 mmol, commerically available from, for example, Pharmablock), borane tetrahydrofuran complex (2.1 mL, 1M in THF, 2.100 mmol) was added and the reaction stirred at rt under N₂ for 1 h. The reaction mixture was diluted with EtOAc (10 mL) and washed with NaHCO₃ (10 mL). The aqueous layer was extracted with EtOAc (2×10 mL) and the combined organic layers were dried over a hydrophobic frit and concentrated to give tert-butyl 7-(hydroxymethyl)-4,5-dihydro-1H-benzo[d]azepine-3(2H)-carboxylate (184 mg, 0.597 mmol, 87% yield) as a colourless oil.

LCMS (2 min Formic): Rt=1.03 min, [M+Na]+=300.1.

Intermediate 16: (+/−)-1-(1-Bromoethyl)-3-methylbenzene

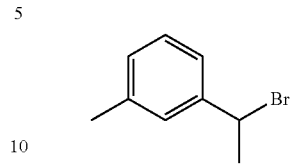

1-(m-Tolyl)ethanol (200 mg, 1.469 mmol, commercially available from, for example, Alfa Aesar) was dissolved in DCM (5.9 mL) and stirred at 0° C. under N₂. PBr₃ (0.06 mL, 0.636 mmol) was added dropwise and the reaction stirred for 30 min at 0° C., then allowed to slowly warm to rt. The solution was quenched with sat. aq. sodium bicarbonate (20 mL), the aqueous layer was extracted with DCM (3×20 mL) and the combined organic layers were dried over a hydrophobic frit and concentrated to give (+/−)-1-(1-bromoethyl)-3-methylbenzene (250 mg, 1.130 mmol, 77% yield) as a colourless oil.

¹H NMR (400 MHz, DMSO-d₆) δ ppm 7.20-7.34 (m, 3H) 7.11 (d, J=7.3 Hz, 1H) 5.44 (q, J=6.8 Hz, 1H) 2.31 (s, 3H) 1.97 (d, J=6.8 Hz, 3H).

Intermediate 17: (+/−)-1-(1-Bromoethyl)-2-methylbenzene

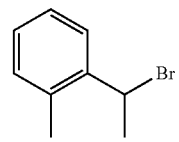

1-(o-Tolyl)ethanol (513 mg, 3.77 mmol, commercially available from, for example, Alfa Aesar) was dissolved in DCM (5 mL) and stirred at 0° C. under N₂. PBr₃ (0.142 mL, 1.507 mmol) was added dropwise and the reaction stirred for 30 min at 0° C., then allowed to slowly warm to rt. A further portion of PBr₃ (0.355 mL, 3.77 mmol) was added dropwise at rt and the reaction stirred for 1.5 h. The solution was quenched with sat. aq. sodium bicarbonate (20 mL), the aqueous layer was extracted with DCM (3×20 mL) and the combined organic layers were dried over a hydrophobic frit and concentrated to give (+/−)-1-(1-bromoethyl)-2-methylbenzene (670 mg, 2.69 mmol, 71.5% yield) as a colourless oil.

¹H NMR (400 MHz, DMSO-d₆) δ ppm 7.54-7.60 (m, 1H) 7.15-7.27 (m, 3H) 5.62 (q, J=6.8 Hz, 1H) 2.37 (s, 3H) 2.03 (d, J=6.8 Hz, 3H)

Intermediate 18: tert-Butyl 5-(hydroxymethyl)-3,4-dihydroisoquinoline-2(1H)-carboxylate

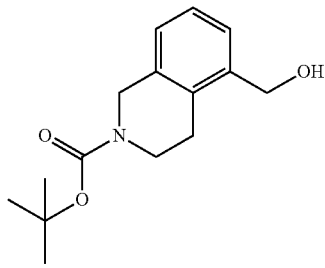 [SMILES: CC(C)(C)OC(=O)N1CCc2c(CO)cccc2C1]

To a solution of 2-(tert-butoxycarbonyl)-1,2,3,4-tetrahydroisoquinoline-5-carboxylic acid (113 mg, 0.407 mmol, commercially available from, for example, ASW MedChem) in THF (1 mL), borane tetrahydrofuran complex (1.2 mL, 1M in THF, 1.200 mmol) was added and the reaction stirred at rt for 1.5 h. The reaction was diluted with EtOAc (10 mL) and washed with NaHCO$_3$ (10 mL). The aqueous layer was extracted with EtOAc (2×10 mL) and the organic layers were dried over a hydrophobic frit and concentrated to give 600 mg of a colourless oil. This was purified by chromatography on SiO$_2$ (Biotage SNAP 50 g cartridge, eluting with 0-100% EtOAc/cyclohexane). The appropriate fractions were concentrated to give tert-butyl 5-(hydroxymethyl)-3,4-dihydroisoquinoline-2(1H)-carboxylate (110 mg, 0.376 mmol, 92% yield) as a colourless oil.

LCMS (2 min Formic): Rt=0.99 min, [MH-tBu]$^+$=208.

Intermediate 19: 6-(Bromomethyl)-1H-benzo[d]imidazole

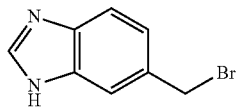 [SMILES: BrCc1ccc2nc[nH]c2c1]

1H-Benzo[d]imidazol-6-yl)methanol (205 mg, 1.384 mmol, commercially available from, for example, Fluorochem) and HBr (3.4 mL, 48% in water, 28.2 mmol) were heated at 80° C. for 30 min. The pH of the solution was adjusted to pH 9 with sodium bicarbonate solution and extracted with EtOAc (2×20 mL). The combined organic layers were dried over a hydrophobic frit and concentrated to give 6-(bromomethyl)-1H-benzo[d]imidazole (90 mg, 0.341 mmol, 24.66% yield) as a colourless oil.

$^1$H NMR (400 MHz, MeOH-d$_4$) δ ppm 8.24 (s, 1H) 7.55-7.67 (m, 2H) 7.30 (dd, J=8.3, 1.2 Hz, 1H) 4.73 (s, 2H).

Intermediate 20: tert-Butyl 4-(hydroxymethyl)indoline-1-carboxylate

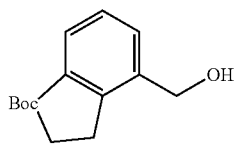

Indolin-4-ylmethanol (301 mg, 2.018 mmol, commercially available from, for example, Fluorochem) was dissolved in DCM (5 mL), Boc-anhydride (660 mg, 3.03 mmol) was added and the reaction stirred at rt under N$_2$ for 2 h. The reaction was diluted with sat. aq. sodium bicarbonate (10 mL), extracted with DCM (2×10 mL), dried over a hydrophobic frit and concentrated to give an orange oil (776 mg). This was purified by chromatography on SiO$_2$ (Biotage SNAP 50 g cartridge, eluting with 0-50% EtOAc/cyclohexane). The appropriate fractions were concentrated to give tert-butyl 4-(hydroxymethyl)indoline-1-carboxylate (472 mg, 1.704 mmol, 84% yield) as a colourless oil.

LCMS (2 min Formic): Rt=1.00 min, [MH]$^+$=194.1.

$^1$H NMR (400 MHz, DMSO-d$_6$) δ ppm 7.52 (br. s., 1H) 7.12 (t, J=7.7 Hz, 1H) 6.95 (d, J=7.6 Hz, 1H) 5.05 (t, J=5.5 Hz, 1H) 4.42 (d, J=5.4 Hz, 2H) 3.91 (t, J=8.7 Hz, 2H) 3.00 (t, J=8.7 Hz, 2H) 1.50 (s, 9H).

Intermediate 21: Methyl 2-methyl-1H-benzo[d]imidazole-7-carboxylate

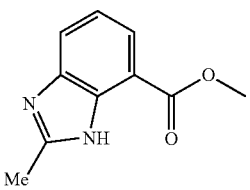

To 2-methyl-1H-benzo[d]imidazole-7-carboxylic acid (500 mg, 2.84 mmol, commercially available from, for example Fluorochem) in methanol (30 mL), sulfuric acid (2.84 mL, 53.3 mmol) was added and the reaction stirred at 65° C. for 4 h. The reaction was then left to sit at rt for 3 days. The reaction mixture was basified with aqueous ammonia at 65° C. The reaction mixture was extracted with DCM and concentrated under vacuum to give the title compound (410 mg, 2.156 mmol, 76% yield) as a yellow solid.

LCMS (2 min Formic): Rt=0.35 min, [MH]$^+$=191.2.

Intermediate 22: (2-Methyl-1H-benzo[d]imidazol-7-yl)methanol

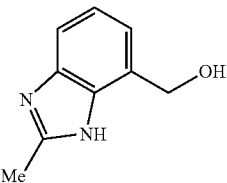 [SMILES: Cc1nc2cccc(CO)c2[nH]1]

Under nitrogen, lithium borohydride (85 mg, 3.88 mmol) and methanol (4 mL, 99 mmol) were dissolved in THF (20 mL). Then, methyl 2-methyl-1H-benzo[d]imidazole-7-carboxylate (410 mg, 2.156 mmol) in THF (5 mL) was added to the mixture. The reaction was then stirred overnight at 50° C. under an inert atmosphere. The reaction mixture was quenched with water and 2M hydrochloric acid. The reaction mixture was then partitioned between water (50 mL) and ethyl acetate (50 mL). The aqueous layer was then extracted with ethyl acetate (2×50 mL). The combined organic layers were passed through a hydriphobic frit and the solvent was removed under vacuum to give mainly unreacted SM. DIBAL-H (1.812 mL, 25% in toluene, 2.69 mmol) was added dropwise to the crude recovered sample (500 mg) in a solution of anhydrous DCM (20 mL) cooled to 0° C. The reaction was allowed to stir at 0° C. for 1 h under nitrogen. Further DIBAL-H (1.812 mL, 25% in toluene, 2.69 mmol) was added to the solution and the reaction mixture was allowed to stir overnight. Methanol (4 mL, 99 mmol) was added slowly to the solution, followed by Rochelle's salt solution (40 mL) and the mixture allowed to stir for 40 min. The organic layer was separated and the aqueous layer extracted with DCM (2×20 mL). The combined organics were washed with water (40 mL) followed by brine (40 mL). The organic layer was passed through a hydrophobic frit and concentrated under vacuum to give the title compound (250 mg, 1.541 mmol, 71.5%) as a white solid.

LCMS (2 min High pH): Rt=0.48 min, [MH]$^+$=163.1.

Intermediate 23: tert-Butyl 7-(hydroxymethyl)-2-methyl-1H-benzo[d]imidazole-1-carboxylate

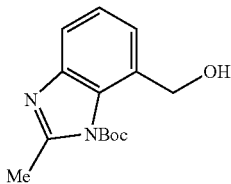

To a solution of (2-methyl-1H-benzo[d]imidazol-7-yl)methanol (250 mg, 1.541 mmol) in acetonitrile (11 mL) and water (2.75 mL) was added Boc$_2$O (0.501 mL, 2.158 mmol) and sodium bicarbonate (259 mg, 3.08 mmol). The mixture was stirred overnight at rt. The reaction mixture was diluted with ethyl acetate (70 mL) and washed with 10% aqueous citric acid (3×25 mL). The aqueous layer was extracted with ethyl acetate (3×25 mL). The combined ethyl acetate portions were washed with water (25 mL) and brine (25 mL) before drying through a hydrophobic frit and evaporating in vacuo to yield the crude product. The product was loaded in dichloromethane onto a SNAP cartridge (25 g) and purified via Biotage SP4 flash chromatography eluting from 0-100% ethyl acetate/cyclohexane. The relevant fractions were evaporated in vacuo to yield the title compound (128 mg, 0.488 mmol, 31.7% yield) as a white solid.

LCMS (2 min Formic): Rt=0.90 min, [MH]$^+$=263.1.

Intermediate 24: Benzofuran-4-ylmethanol

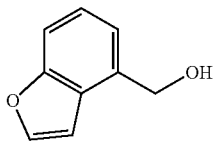 [SMILES: OCc1cccc2occc12]

To benzofuran-4-carboxylic acid (50 mg, 0.308 mmol, commercially available from, for example, J&W PharmLab) in THF (1 mL), borane tetrahydrofuran complex (0.47 mL, 1M in THF, 0.470 mmol) was added and the reaction stirred at rt for 1 h. The reaction was quenched with NaHCO$_3$ (20 mL) and extracted with EtOAc (3×10 mL). The organic layers were dried over a hydrophobic frit and concentrated to give 50 mg of a colourless oil. This was purified by chromatography on SiO$_2$ (Biotage SNAP 10 g cartridge, eluting with 0-50% EtOAc/cyclohexane), the appropriate fractions were concentrated to give benzofuran-4-ylmethanol (37 mg, 0.225 mmol, 72.9% yield) as a white solid.

LCMS (2 min Formic): Rt=0.72 min, [M–OH]$^+$=131.1.

Intermediate 25: 4-(Bromomethyl)benzofuran

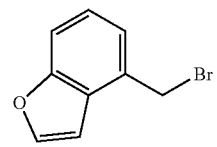 [SMILES: BrCc1cccc2occc12]

Benzofuran-4-ylmethanol (35 mg, 0.236 mmol) was dissolved in diethyl ether (1 mL) and DCM (1 mL) at 0° C. under N$_2$. PBr$_3$ (0.04 mL, 0.424 mmol) was added dropwise and the reaction was stirred at rt under N$_2$. After 30 min, TLC (eluting with 50:50 EtOAc:water) showed complete conversion to a non polar product. The solution was quenched with water (10 mL) and extracted with diethyl ether (3×20 mL), dried over a hydrophobic frit and concentrated to give 4-(bromomethyl)benzofuran (41 mg, 0.117 mmol, 49.3% yield) as a white solid.

LCMS (2 min Formic): Rt=1.15 min, product does not ionise at correct [MH]$^+$.

Intermediate 26: 1-(1-Tosyl-1H-indol-4-yl)ethanone

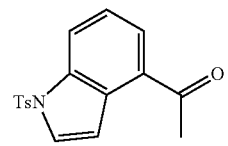 [SMILES: CC(=O)c1cccc2c1ccn2S(=O)(=O)c1ccc(C)cc1]

1-(1H-Indol-4-yl)ethanone (505 mg, 3.17 mmol, commercially available from, for example, Activate Scientific) was dissolved in DMF (5 mL) at 0° C. under N$_2$. Sodium hydride (167 mg, 4.18 mmol, 60% in mineral oil) was added in portions. The reaction was stirred at 0° C. for 10 min before warming to rt and stirring for 30 min. Tosyl-Cl (726 mg, 3.81 mmol) was added and the reaction mixture was stirred at rt for 30 min. Further sodium hydride (140 mg, 3.50 mmol, 60% in mineral oil) was added and the reaction stirred for 10 min, then tosyl-Cl (721 mg, 3.78 mmol) was added and the reaction stirred for 20 min. The reaction was quenched with water (20 mL) and left to stand overnight. This was extracted with EtOAc (2×20 mL), dried over a hydrophobic frit and concentrated to give 1.33 g of a brown solid. This was purified by chromatography on SiO$_2$ (Biotage SNAP 25 g cartridge, eluting with 0-50% EtOAc/cyclohexane). The appropriate fractions were concentrated to give 1-(1-tosyl-1H-indol-4-yl)ethanone (899 mg, 2.58 mmol, 81% yield) as a yellow solid.

LCMS (2 min Formic): Rt=1.23 min, [MH]$^+$=314.0.

Intermediate 27: (+/−)-1-(1-Tosyl-1H-indol-4-yl)ethanol

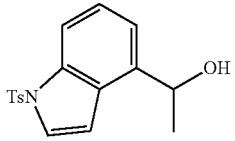

1-(1-Tosyl-1H-indol-4-yl)ethanone (899 mg, 2.87 mmol) was dissolved in methanol (9 mL) at 0° C. under N₂. Sodium borohydride (170 mg, 4.49 mmol) was added and the reaction allowed to warm to rt. After stirring for 1.5 h, further sodium borohydride (121 mg, 3.20 mmol) was added and the reaction was stirred overnight. The solution was concentrated to give an orange solid. This was partitioned between EtOAc (20 mL) and water (20 mL), extracted with EtOAc (2×20 mL), dried over a hydrophobic frit and concentrated to give 1.05 g crude product as an orange oil. This was purified by chromatography on SiO₂ (Biotage SNAP 25 g cartridge, eluting with 0-50% EtOAc/cyclohexane). The appropriate fractions were concentrated to give 1-(1-tosyl-1H-indol-4-yl)ethanol (862 mg, 2.460 mmol, 86% yield) as a yellow oil.

LCMS (2 min Formic): Rt=1.12 min, [M−H]⁻=314.1.

Intermediate 28: (+/−)-4-(1-Bromoethyl)-1-tosyl-1H-indole

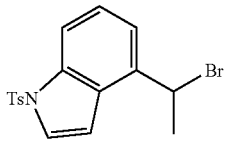

1-(1-Tosyl-1H-indol-4-yl)ethanol (160 mg, 0.507 mmol) was dissolved in diethyl ether (1 mL) and DCM (1 mL) at 0° C. under N₂. PBr₃ (0.07 mL, 0.742 mmol) was added dropwise and the reaction was stirred at rt under N₂ for 2 h. Further PBr₃ (0.07 mL, 0.742 mmol) was added and the reaction stirred for 3 h. Further PBr₃ (0.07 mL, 0.742 mmol) was added and the reaction stirred for 2 h. The reaction was quenched with water (20 mL), extracted with Et₂O (2×20 mL), dried over a hydrophobic frit and concentrated to give 4-(1-bromoethyl)-1-tosyl-1H-indole (275 mg, 0.509 mmol, 100% yield) as a pink solid which was used crude in further synthesis.

LCMS (2 min Formic): Rt=1.32 min, product does not ionise at correct [MH]⁺.

Intermediate 29: 5-(Bromomethyl)-2-methoxypyridine

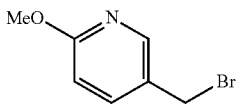

(6-Methoxypyridin-3-yl)methanol (250 mg, 1.797 mmol, commercially available from, for example, Fluorochem) was dissolved in chloroform (20 mL) in a 50 mL round-bottomed flask, open to the atmosphere and phosphorus tribromide (0.188 mL, 1.989 mmol) was added slowly at 0° C. The reaction mixture was stirred at rt for 1 h. The aqueous layer was extracted with DCM (3×30 mL) and the organic layers were combined, washed with brine (30 mL), passed through a hydrophobic frit and evaporated under vacuum. The resulting oil was loaded in DCM and purified by Biotage Isolera SNAP 25 g silica chromatography using a gradient of 0-40% cyclohexane/ethyl acetate. The product containing fractions were combined to give the title compound (160 mg, 0.792 mmol, 44.1% yield) as a colourless oil.

LCMS (2 min Formic): Rt=0.93 min, [MH]⁺=202.

Intermediate 30: 2,4,6-Trichlorophenyl Formate

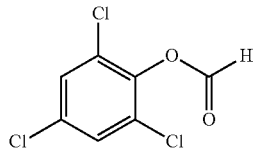 [SMILES: O=COc1c(Cl)cc(Cl)cc1Cl]

Formic acid (57.3 mL, 1519 mmol) and acetic anhydride (115 mL, 1216 mmol) were stirred and heated to 60° C. for 1.5 h then allowed to cool to ambient temperature. The resulting solution was poured into a flask containing 2,4,6-trichlorophenol (30 g, 152 mmol, commercially available from, for example, Sigma-Aldrich) and sodium acetate (12.46 g, 152 mmol). The mixture was stirred for 3.5 h, diluted with toluene (300 mL), washed with water (2×200 mL), dried with sodium sulphate, filtered and evaporated to dryness in vacuo to afford white needle-like crystals (32.45 g).

LCMS (2 min Formic): Rt=1.15 min, [M+Na]⁺=249.8.

Intermediate 31: tert-Butyl ((1S,2S)-2-methylcyclopropyl)carbamate

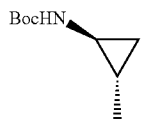

(1S,2S)-2-Methylcyclopropanecarboxylic acid (200 mg, 1.998 mmol, commercially available from, for example, Enamine) and triethylamine (0.9 mL, 6.46 mmol) were dissolved in tert-butanol (4 mL). Diphenyl phosphorylazide (0.47 mL, 2.181 mmol) was added and the reaction was heated at 90° C. The reaction was followed by TLC (eluting with 50:50 EtOAc:cyclohexane, visualising with Ninhydrin). After 2 h, TLC showed the formation of a less polar product as well as residual SM. The reaction was stirred for 3 days. The solution was partitioned between EtOAc (10 mL), and sodium bicarbonate solution. (10 mL), extracted with EtOAc (2×20 mL), dried over a hydrophobic frit and concentrated to give 1.08 g of a yellow solid. This was purified by chromatography on SiO₂ (Biotage SNAP 25 g cartridge, eluting with 0-50% EtOAc/cyclohexane). The appropriate fractions were concentrated to give tert-butyl ((1S,2S)-2-methylcyclopropyl)carbamate (223 mg, 1.172 mmol, 58.7% yield) as a white crystalline solid.

¹H NMR (400 MHz, MeOH-d₄) δ ppm 2.05-2.14 (m, 1H) 1.43 (br. s., 9H) 1.04 (d, J=5.9 Hz, 3H) 0.78 (m, J=8.9, 6.0, 6.0, 3.1 Hz, 1H) 0.59 (dt, J=8.9, 4.3 Hz, 1H) 0.39 (q, J=6.0 Hz, 1H).

Intermediate 32:
(1S,2S)-2-Methylcyclopropanamine hydrochloride

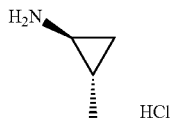

tert-Butyl ((1S,2S)-2-methylcyclopropyl)carbamate (215 mg, 1.256 mmol) was stirred in 4 M HCl in dioxane (16 mL, 64.0 mmol). The reaction was followed by TLC (50:50 EtOAc:cyclohexane, visualising with Ninhydrin). After 30 min, the solution was concentrated to give (1S,2S)-2-methylcyclopropanamine hydrochloride (151 mg, 1.123 mmol, 89% yield) as an off white solid.

¹H NMR (400 MHz, DMSO-d₆) δ ppm 8.27 (br. s., 3H) 2.25 (br. s., 1H) 1.06-1.18 (m, 1H) 0.99 (d, J=6.1 Hz, 3H) 0.85 (ddd, J=9.4, 5.6, 3.8 Hz, 1H) 0.48 (dt, J=7.5, 5.9 Hz, 1H).

Intermediate 33: Methyl 1-benzyl-5-bromo-2-oxo-1,2-dihydropyridine-3-carboxylate

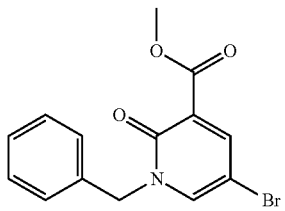 [SMILES: COC(=O)c1cc(Br)cn(Cc2ccccc2)c1=O]

Sodium hydride (5.17 g, 60% dispersion in mineral oil, 129 mmol) was added to a solution of methyl 5-bromo-2-oxo-1,2-dihydro-3-pyridinecarboxylate (25 g, 108 mmol, commercially available from, for example, Fluorochem) in DMF (200 mL) and THF (200 mL) at 0° C. and the mixture was stirred for 30 min, giving a dense suspension. Benzyl bromide (14.10 mL, 119 mmol) was added and the mixture stirred for a further 2 h, allowing to warm to rt, then the resulting clear brown solution was added to water (400 mL) and extracted with EtOAc (2×300 mL). The combined organics were washed with water (2×200 mL), dried and evaporated in vacuo to give methyl 1-benzyl-5-bromo-2-oxo-1,2-dihydropyridine-3-carboxylate (31 g, 96 mmol, 89% yield) as a beige solid. This material was carried through to the next step without purification.

LCMS (2 min High pH): Rt=0.98 min, [MH]⁺=322.0 & 324.1.

¹H NMR (400 MHz, CHCl₃-d) δ ppm 8.16 (d, J=2.9 Hz, 1H) 7.62 (d, J=2.9 Hz, 1H) 7.30-7.43 (m, 5H) 5.15 (s, 2H) 3.92 (s, 3H).

Intermediate 34: 1-Benzyl-5-bromo-2-oxo-1,2-dihydropyridine-3-carboxylic acid

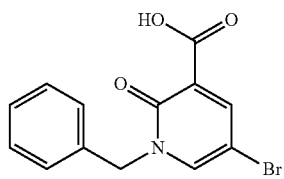 [SMILES: O=C(O)c1cc(Br)cn(Cc2ccccc2)c1=O]

Lithium hydroxide (6.91 g, 289 mmol) in water (200 mL) was added to a mixture of methyl 1-benzyl-5-bromo-2-oxo-1,2-dihydropyridine-3-carboxylate (31 g, 96 mmol), THF (200 mL) and methanol (200 mL) and the mixture was stirred at rt for 2 h, then evaporated in vacuo to about half volume, giving a dense suspension. This was diluted with water (200 mL) and acidified with acetic acid to pH 5, then extracted with EtOAc (2×300 mL). The combined organics were dried over sodium sulphate and evaporated in vacuo to give an off-white solid. The product was suspended in ether (200 mL), sonicated, diluted with cyclohexane (100 mL) and collected by filtration to give 1-benzyl-5-bromo-2-oxo-1,2-dihydropyridine-3-carboxylic acid (23 g, 74.6 mmol, 78% yield).

LCMS (2 min Formic): Rt=1.01 min, [MH]⁺=308.0 & 310.1.

¹H NMR (400 MHz, CHCl₃-d) δ ppm 14.02 (br. s., 1H) 8.55 (d, J=2.7 Hz, 1H) 7.73 (d, J=2.7 Hz, 1H) 7.40-7.47 (m, 3H) 7.31-7.37 (m, 2H) 5.25 (s, 2H).

Intermediate 35: 1-Benzyl-5-bromo-N-methyl-2-oxo-1,2-dihydropyridine-3-carboxamide

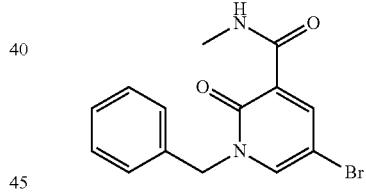

1-Benzyl-5-bromo-2-oxo-1,2-dihydropyridine-3-carboxylic acid (28 g, 91 mmol) was suspended in DCM (300 mL) and oxalyl chloride (23.86 mL, 273 mmol) and DMF (0.352 mL, 4.54 mmol) were added, then the mixture was stirred for 2 h at rt. The solvent was evaporated in vacuo to give a brown residue, which was then dissolved in THF (300 mL) and Et₃N (12.67 mL, 91 mmol) was added. The mixture was cooled in an ice bath, then methanamine (91 mL, 2M in THF, 182 mmol) was added dropwise over 30 min and the mixture stirred for a further 1 h at 0° C. The solvent was evaporated in vacuo and the solid residue was partitioned between water (300 mL) and DCM (300 mL), the organic layer was washed with brine, dried and evaporated in vacuo to give 1-benzyl-5-bromo-N-methyl-2-oxo-1,2-dihydropyridine-3-carboxamide (27.6 g, 86 mmol, 95% yield) as a brown solid.

LCMS (2 min Formic): Rt=0.97 min, [MH]⁺=321.0 & 323.1.

¹H NMR (400 MHz, CHCl₃-d) δ ppm 9.57 (br. s., 1H) 8.60 (d, J=2.9 Hz, 1H) 7.62 (d, J=2.9 Hz, 1H) 7.34-7.48 (m, 3H) 7.29-7.33 (m, 2H) 5.20 (s, 2H) 3.00 (d, J=4.9 Hz, 3H).

Intermediate 36: Ethyl 1-benzyl-5-(methylcarbamoyl)-6-oxo-1,6-dihydropyridine-3-carboxylate

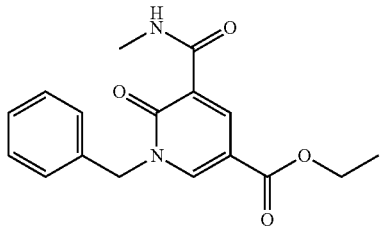 [SMILES: CCOC(=O)c1cc(C(=O)NC)c(=O)n(Cc2ccccc2)c1]

1-Benzyl-5-bromo-N-methyl-2-oxo-1,2-dihydropyridine-3-carboxamide (23 g, 71.6 mmol), DMSO (60 mL), ethanol (70 g, 1519 mmol), Et$_3$N (19.96 mL, 143 mmol), dppb (3.05 g, 7.16 mmol) and palladium acetate (1.608 g, 7.16 mmol) were placed in a steel Parr vessel, which was then purged with carbon monoxide by filling to 50 psi, then releasing the pressure, then refilled to 50 psi and heated overnight at 100° C. The mixture was diluted with water (200 mL) and extracted with EtOAc (2×300 mL), the organic layer washed with water (2×300 mL), then dried and evaporated in vacuo and the residue was triturated with ether (200 mL) and the solid collected by filtration to give ethyl 1-benzyl-5-(methylcarbamoyl)-6-oxo-1,6-dihydropyridine-3-carboxylate (21.2 g, 67.4 mmol, 94% yield).

LCMS (2 min Formic): Rt=0.99 min, [MH]$^+$=315.2.

$^1$H NMR (400 MHz, CHCl$_3$-d) δ ppm 9.37 (br. s., 1H) 9.03 (d, J=2.4 Hz, 1H) 8.38 (d, J=2.7 Hz, 1H) 7.34-7.42 (m, 3H) 7.28-7.34 (m, 2H) 5.25 (s, 2H) 4.35 (q, J=7.1 Hz, 2H) 2.99 (d, J=4.9 Hz, 3H) 1.37 (t, J=7.2 Hz, 3H).

Intermediate 37: 1-Benzyl-5-(methylcarbamoyl)-6-oxo-1,6-dihydropyridine-3-carboxylic acid

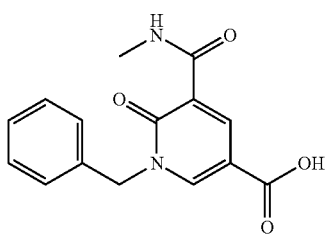 [SMILES: CNC(=O)c1cc(C(=O)O)cn(Cc2ccccc2)c1=O]

Sodium hydroxide (99 mL, 199 mmol) was added to a solution of ethyl 1-benzyl-5-(methylcarbamoyl)-6-oxo-1,6-dihydropyridine-3-carboxylate (20.8 g, 66.2 mmol) in a mixture of methanol (100 mL) and THF (100 mL) and the resulting solution was stirred for 2 h at rt, then evaporated in vacuo to approximately 100 mL volume. The mixture was diluted with water (200 mL), then filtered to remove a dark grey solid, the filtrate was washed with MTBE (200 mL), then acidified to pH 4 with 2M HCl and the resulting suspension stirred for 2 h, then filtered and the product washed with water, then dried in the vacuum oven to give 1-benzyl-5-(methylcarbamoyl)-6-oxo-1,6-dihydropyridine-3-carboxylic acid (15.2 g, 53.1 mmol, 80% yield).

LCMS (2 min High pH): Rt=0.58 min, [MH]$^+$=287.2.

$^1$H NMR (400 MHz, DMSO-d$_6$) δ ppm 13.19 (br. s., 1H) 9.14-9.34 (m, 1H) 8.88 (d, J=2.7 Hz, 1H) 8.70 (d, J=2.7 Hz, 1H) 7.25-7.42 (m, 5H) 5.33 (s, 2H) 2.82 (d, J=4.6 Hz, 3H).

Intermediate 38: Methyl 2-(benzyloxy)-5-bromonicotinate

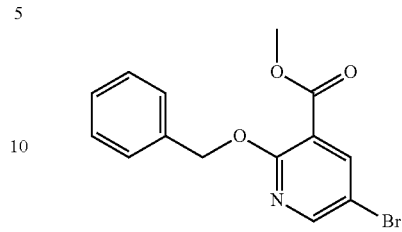

Methyl 5-bromo-2-oxo-1,2-dihydropyridine-3-carboxylate (5 g, 21.55 mmol, commercially available from, for example, Sigma-Aldrich) was dissolved in chloroform (100 mL), then silver carbonate (11.88 g, 43.1 mmol) and benzyl bromide (3.33 mL, 28.0 mmol) were added and the mixture heated at reflux overnight. The mixture was filtered and the filtrate evaporated in vacuo to give a pale yellow liquid. This was dissolved in DCM (5 mL) and loaded onto a 50 g silica column, then eluted with 0-50% EtOAc/cyclohexane and the product-containing fractions evaporated in vacuo to give methyl 2-(benzyloxy)-5-bromonicotinate (4.65 g, 14.43 mmol, 67.0% yield) as a colourless solid LCMS (2 min High pH): Rt=1.37 min, [MH]$^+$=322.1, 324.1.

$^1$H NMR (400 MHz, CHCl$_3$-d) δ ppm 8.35 (d, J=2.7 Hz, 1H) 8.29 (d, J=2.4 Hz, 1H) 7.51 (d, J=7.6 Hz, 2H) 7.38 (t, J=7.5 Hz, 2H) 7.28-7.34 (m, 1H) 5.51 (s, 2H) 3.93 (s, 3H).

Intermediate 39: (R)-Methyl 2-oxo-1-(1-phenylethyl)-1,2-dihydropyridine-3-carboxylate

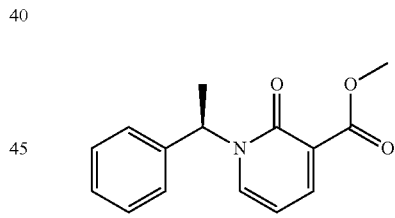

(R)-1-Phenylethanamine (8.93 mL, 70.2 mmol) was added to a stirred solution of methyl 2-oxo-2H-pyran-3-carboxylate (10.3 g, 66.8 mmol, commercially available from, for example, Sigma-Aldrich) in a mixture of dry DMF (43 mL) and dry THF (173 mL). The resulting dark red solution was stirred for 30 min, under N$_2$. EDC (16.66 g, 87 mmol) and DMAP (0.506 g, 4.14 mmol) were added and the resulting suspension stirred over the weekend. The reaction mixture was evaporated in vacuo to a brown slurry. The residue was partitioned between EtOAc and water and the aqueous layer removed. The organic layer was washed (3×2 M aq. HCl, 1× brine), dried over MgSO$_4$ and filtered through silica eluting with EtOAc. The filtrate was evaporated in vacuo to give the product as a brown oil (12.94 g).

LCMS (2 min TFA): Rt=0.84 min, [MH]$^+$=258.1.

Intermediate 40: (R)-Methyl 5-bromo-2-oxo-1-(1-phenylethyl)-1,2-dihydropyridine-3-carboxylate

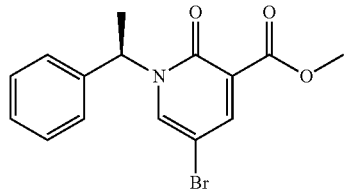 [SMILES: COC(=O)c1cc(Br)cn([C@H](C)c2ccccc2)c1=O]

NBS (10.74 g, 60.4 mmol) was added in one portion to a dark brown solution of (R)-methyl 2-oxo-1-(1-phenylethyl)-1,2-dihydropyridine-3-carboxylate (12.94 g, 50.3 mmol) in 2-MeTHF (150 mL). The initial suspension became a light brown solution and was stirred for 15 min whereupon it was a dark brown solution. The reaction mixture was washed [3× sat. aq. NaHCO$_3$ (40 mL), 1× aq. 10% sodium thiosulfate (20 mL), 1× brine (10 mL)], dried over MgSO$_4$ and evaporated in vacuo to a black oil. The residue was dissolved in toluene (40 mL), filtered through celite, washing with toluene (80 mL) and evaporated in vacuo to give the product (19.62 g) as a black oil.

LCMS (2 min TFA): Rt=1.02 min, [MH]$^+$=336.0 & 337.9.

Intermediate 41: (R)-5-Bromo-N-methyl-2-oxo-1-(1-phenylethyl)-1,2-dihydropyridine-3-carboxamide

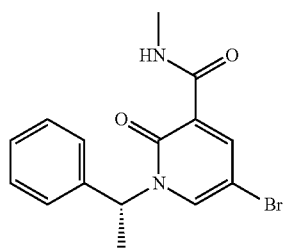

Methylamine solution (74 mL, 40% aq., 855 mmol) was added to a solution of (R)-methyl 5-bromo-2-oxo-1-(1-phenylethyl)-1,2-dihydropyridine-3-carboxylate (19.2 g, 40.0 mmol) in methanol (133 mL). The resulting solution was heated to 50° C. with a balloon fitted to the top of a condensor. The reaction mixture was stirred for 90 min. The reaction mixture was evaporated in vacuo to a black gum that was suspended in EtOAc. The suspension was filtered through silica eluting with EtOAc and the filtrate evaporated to give the product (13.1 g) as a brown gum.

LCMS (2 min TFA): Rt=1.01 min, [MH]$^+$=335.1 & 337.1

Intermediate 42: (R)-Methyl 5-(methylcarbamoyl)-6-oxo-1-(1-phenylethyl)-1,6-dihydropyridine-3-carboxylate

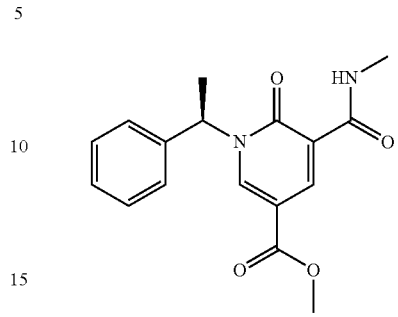

Xantphos (1.65 g, 2.85 mmol) and palladium(II) acetate (0.877 g, 3.91 mmol) were added to a solution of (R)-5-bromo-N-methyl-2-oxo-1-(1-phenylethyl)-1,2-dihydropyridine-3-carboxamide (13.1 g, 39.1 mmol), triethylamine (16.34 mL, 117 mmol) and methanol (15.81 mL, 391 mmol) in DMF (220 mL). Carbon monoxide was sparged through the mixture until a brown suspension formed. The reaction was held under a balloon of carbon monoxide and heated to 60° C. for 4 h. The reaction mixture was cooled to rt and sparged with N$_2$ to remove any residual carbon monoxide. The reaction mixture was filtered through celite, rinsing with EtOAc and the filtrate evaporated in vacuo to a black slurry. The residue was partitioned between EtOAc (350 mL) and water (100 mL). The aqueous layer was removed, the organic layer washed (2× water [50 mL], 1× brine [50 mL]), dried over MgSO$_4$ and evaporated in vacuo to a black gum. The gum was dissolved in toluene (60 mL) and loaded on to a Biotage 340 g silica column. The column was eluted with cyclohexane:EtOAc (20→66%). The product containing fractions were evaporated to give the product (7.43 g) as a brown gum.

LCMS (2 min TFA): Rt=0.94 min, [MH]$^+$=315.2.

Intermediate 43: (R)-5-(Methylcarbamoyl)-6-oxo-1-(1-phenylethyl)-1,6-dihydropyridine-3-carboxylic acid

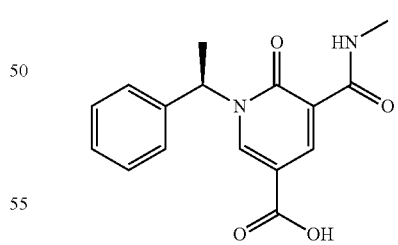

Sodium hydroxide (1.891 g, 47.3 mmol) was added to a solution of (R)-methyl 5-(methylcarbamoyl)-6-oxo-1-(1-phenylethyl)-1,6-dihydropyridine-3-carboxylate (7.43 g, 23.64 mmol) in methanol (70 mL). Water was added to the stirred suspension and the resulting solution stirred overnight. The reaction mixture was evaporated in vacuo to a pale brown solid and acidified with 2M aq. HCl (100 mL). Acetone (10 mL) was added and the suspension stirred for 15 min and filtered. The filtercake was washed [water:

acetone (1:1, 20 mL), acetone (20 mL)] and dried in vacuo to give the product (6.40 g) as a beige solid.

LCMS (2 min TFA): Rt=0.82 min, [MH]⁺=301.0.

Intermediate 44: (S*)-Methyl 5-(methylcarbamoyl)-6-oxo-1-(1-(m-tolyl)ethyl)-1,6-dihydropyridine-3-carboxylate

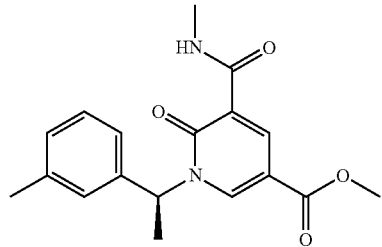

Methyl 5-(methylcarbamoyl)-6-oxo-1,6-dihydropyridine-3-carboxylate (700 mg, 3.33 mmol), 1-(1-bromoethyl)-3-methylbenzene (800 mg, 4.02 mmol), potassium carbonate (1310 mg, 9.48 mmol) and DMF (5 mL) were stirred at 90° C. for 1 h. The suspension was concentrated, partitioned between EtOAc (20 mL) and water (20 mL), the aqueous phase was extracted with EtOAc (2×20 mL), dried over a hydrophobic frit and concentrated to give 1.2 g of an orange oil. This was purified by chromatography on SiO₂ (Biotage SNAP 50 g cartridge, eluting with 0-100% (25% EtOH in EtOAc)/cyclohexane). The appropriate fractions were concentrated to give (+/−)-methyl 5-(methylcarbamoyl)-6-oxo-1-(1-(m-tolyl)ethyl)-1,6-dihydropyridine-3-carboxylate (710 mg, 1.946 mmol, 58.4% yield) as a white solid. 677 mg of the racemate was submitted for chiral separation:

Analytical Method:

The racemate (~0.5 mg) was dissolved in 50% EtOH/Heptane (1 mL). 20 µL was injected on the column. (Column: 4.6 mmid×25 cm Chiralpak IA, Lot No. IA00CE-MC024). This was eluted with 50% EtOH/Heptane, f=1.0 mL/min, detector wavelength 215 nm, 4. Ref 550,100

Prep Method:

The racemate (~80 mg) was dissolved in DCM (1 mL) and EtOH (2 mL). 3 mL of the solution was injected onto the column. (Column: 30 mm×25 cm Chirapak IA (5 µm), Lot No IA11157-01). This was eluted with 50% EtOH/Heptane, f=30 mL/min, detector wavelength=215 nm, 4. Ref 550,100

There were a total of 14 injections. Fractions from 7-8 min were bulked and labelled peak 1, fractions from 8-9 min were bulked and labelled mix, fractions from 9-12 min were bulked and labelled peak 2. The bulked mix fractions were vac'ed down and reprocessed using the the prep method above. The bulked fractions were vac'ed down using a rotary evaporator and then transferred to a weighed flask for final analysis as described by the analytical method above.

First eluting isomer: (9S)-methyl 5-(methylcarbamoyl)-6-oxo-1-(1-(m-tolyl)ethyl)-1,6-dihydropyridine-3-carboxylate (289 mg, 0.792 mmol, 23.78% yield) was obtained as a colourless oil.

LCMS (2 min Formic): Rt=1.05 min, [M−H]⁻=329.1.

Intermediate 45: (S*)-5-(Methylcarbamoyl)-6-oxo-1-(1-(m-tolyl)ethyl)-1,6-dihydropyridine-3-carboxylic acid

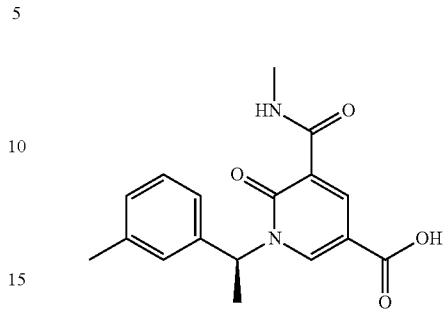

(S*)-Methyl 5-(methylcarbamoyl)-6-oxo-1-(1-(m-tolyl)ethyl)-1,6-dihydropyridine-3-carboxylate (289 mg, 0.880 mmol), lithium hydroxide (66 mg, 2.76 mmol), 1,4-dioxane (3 mL) and water (3 mL) were stirred at rt for 30 min. The solution was acidified to pH 4 with acetic acid (0.050 mL, 0.880 mmol), then partitioned between EtOAc (20 mL) and water (20 mL), extracted with EtOAc (20 mL), dried over a hydrophobic frit and concentrated to give (*)-5-(methylcarbamoyl)-6-oxo-1-(1-(m-tolyl)ethyl)-1,6-dihydropyridine-3-carboxylic acid (277 mg, 0.705 mmol, 80% yield).

LCMS (2 min Formic): Rt=0.94 min, [M−H]⁻=313.2.

Intermediate 46: Methyl 5-bromo-2-oxo-1-(1-phenylethyl)-1,2-dihydropyridine-3-carboxylate

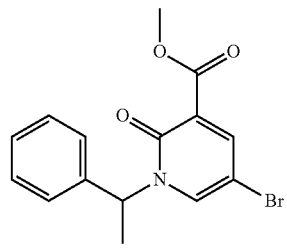 [SMILES: COC(=O)c1cc(Br)cn(C(C)c2ccccc2)c1=O]

(1-Bromoethyl)benzene (0.706 mL, 5.17 mmol) was added to a stirred suspension of methyl 5-bromo-2-oxo-1,2-dihydropyridine-3-carboxylate (1.0 g, 4.31 mmol) and potassium carbonate (0.715 g, 5.17 mmol) in DMF (10 mL). The white suspension was stirred overnight. The reaction mixture was partitioned between EtOAc and water. The aqueous layer was removed, the organic layer washed (2× water), dried over MgSO₄ and evaporated in vacuo to a colourless oil. The residue was dissolved in DCM, loaded on to a 25 g Biotage silica SNAP column and eluted with cyclohexane:EtOAc (5→40%). The product containing fractions were evaporated in vacuo to give the product (824 mg) as a colourless oil.

LCMS (2 min TFA): Rt=1.02 min, [MH]⁺=335.9 & 337.9.

Intermediate 47: 5-Bromo-N-methyl-2-oxo-1-(1-phenylethyl)-1,2-dihydropyridine-3-carboxamide

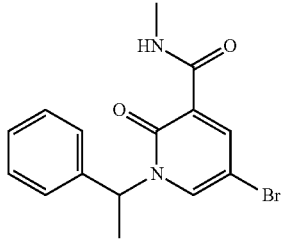 [SMILES: CNC(=O)c1cc(Br)cn(C(C)c2ccccc2)c1=O]

Methylamine solution (3.167 mL, 40% aq., 36.6 mmol) was added to a solution of methyl 5-bromo-2-oxo-1-(1-phenylethyl)-1,2-dihydropyridine-3-carboxylate (820 mg, 2.439 mmol) in methanol (8 mL). The resulting solution was heated to 50° C. in a sealed system with a balloon fitted for 4 h. The reaction mixture was evaporated in vacuo to give the product (793 mg) as a colourless gum.

LCMS (2 min TFA): Rt=1.01 min, [MH]$^+$=335.0 & 337.0.

Intermediate 48: 2-(Benzyloxy)-5-bromonicotinic acid

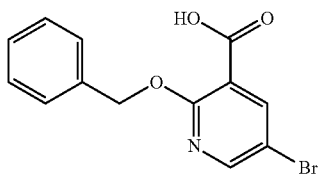 [SMILES: O=C(O)c1cc(Br)cnc1OCc1ccccc1]

Methyl 2-(benzyloxy)-5-bromonicotinate (4.6 g, 14.28 mmol) was dissolved in THF (50 mL) and methanol (50 mL), then LiOH (1.368 g, 57.1 mmol) in water (50 mL) was added and the mixture stirred for 2 h at rt. The solvent was evaporated in vacuo and the residue was suspended in water (100 mL) and acidified with 2M HCl to pH 4, then extracted with 10% MeOH/DCM (3×100 mL, poor solubility) and the organic layer washed with water, dried and evaporated in vacuo to give 2-(benzyloxy)-5-bromonicotinic acid (4.15 g, 13.47 mmol, 94% yield) as a colourless solid.

LCMS (2 min High pH): Rt=0.68 min, [MH]$^+$=308.2, 310.0.

$^1$H NMR (400 MHz, DMSO-$d_6$) δ ppm 8.43 (d, J=2.4 Hz, 1H) 8.18 (d, J=2.7 Hz, 1H) 7.47 (d, J=7.1 Hz, 2H) 7.37 (t, J=7.3 Hz, 2H) 7.27-7.33 (m, 1H) 5.43 (s, 2H).

Intermediate 49: 2-(Benzyloxy)-5-bromo-N-methylnicotinamide

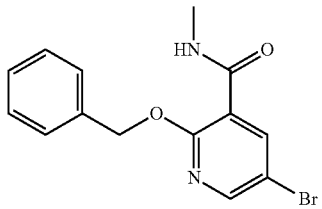 [SMILES: CNC(=O)c1cc(Br)cnc1OCc1ccccc1]

2-(Benzyloxy)-5-bromonicotinic acid (4.2 g, 13.63 mmol) was suspended in DCM (50 mL) and oxalyl chloride (2.386 mL, 27.3 mmol) was added, followed by DMF (0.053 mL, 0.682 mmol) and the reaction mixture was stirred for 2 h at rt, then evaporated in vacuo. The residue was dissolved in THF (50 mL), then methanamine (13.63 mL, 2M in THF, 27.3 mmol) was added and the resulting suspension stirred for 2 h at rt, then evaporated in vacuo. The residue was dissolved in THF (50 mL) and methanamine (13.63 mL, 2M in THF, 27.3 mmol) was added, then the resulting mixture stirred for 2 h, then evaporated in vacuo. The residue was partitioned between EtOAc (100 mL) and water (100 mL), the aq. layer was extracted with further EtOAc (100 mL) and the combined organics washed with brine, dried and evaporated in vacuo to give a yellow gummy solid. This was dissolved in a mixture of DCM (20 mL) and methanol (5 mL) with difficulty, then loaded onto a 50 g silica column, which was then sucked dry using a vacuum line. The column was eluted with 0-100% EtOAc/cyclohexane to give 2-(benzyloxy)-5-bromo-N-methylnicotinamide (2.35 g, 7.32 mmol, 53.7% yield)

LCMS (2 min High pH): Rt=1.19 min, [MH]$^+$=321.1, 323.1.

$^1$H NMR (400 MHz, CHCl$_3$-d) δ ppm 8.65 (d, J=2.4 Hz, 1H) 8.31 (d, J=2.4 Hz, 1H) 7.87 (br. s., 1H) 7.33-7.48 (m, 5H) 5.53 (s, 2H) 2.94 (d, J=4.9 Hz, 3H).

Intermediate 50: 2,4,6-Trichlorophenyl 6-(benzyloxy)-5-(methylcarbamoyl)nicotinate

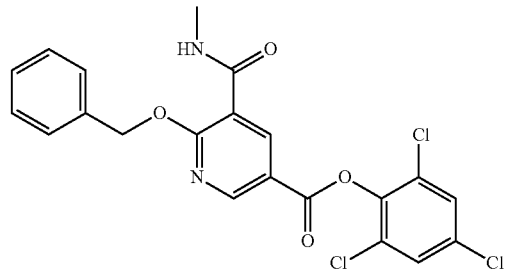 [SMILES: CNC(=O)c1cc(C(=O)Oc2c(Cl)cc(Cl)cc2Cl)cnc1OCc1ccccc1]

2-(Benzyloxy)-5-bromo-N-methylnicotinamide (2 g, 6.23 mmol), Xantphos (0.721 g, 1.245 mmol), palladium acetate (0.140 g, 0.623 mmol) and Et$_3$N (1.302 mL, 9.34 mmol) were combined in a three necked flask equipped with a dropping funnel and a condensor with a nitrogen bubbler on the top. Toluene (30 mL) was added and the mixture was heated at 80° C. under nitrogen for 20 min, then a solution of 2,4,6-trichlorophenyl formate (2.106 g, 9.34 mmol) in toluene (20 mL) was added dropwise over 30 min and heating continued for 18 h.

Separately, 2-(benzyloxy)-5-bromo-N-methylnicotinamide (0.6 g, 1.868 mmol), Xantphos (0.216 g, 0.374 mmol), palladium acetate (0.042 g, 0.187 mmol) and Et$_3$N (0.391 mL, 2.80 mmol) were combined in a three necked flask equipped with a dropping funnel and a condensor with a nitrogen bubbler on the top. Toluene (30 mL) was added and the mixture was heated at 80° C. under nitrogen for 20 min, then a solution of 2,4,6-trichlorophenyl formate (0.632 g, 2.80 mmol) in toluene (20 mL) was added dropwise over 30 min and heating continued for 2 h.

The two separate reactions were combined and diluted with EtOAc (100 mL) and washed with water (50 mL) and brine (50 mL), dried and evaporated in vacuo to give an orange oil. This was dissolved in DCM (10 mL) and loaded onto a 50 g silica column, then eluted with 0-50% EtOAc/cyclohexane and the product-containing fractions evaporated in vacuo to give a beige solid. The product was columned again on a 50 g silica cartridge eluting with 0-50% EtOAc/cyclohexane, and the pure fractions collected and evaporated in vacuo to give 2,4,6-trichlorophenyl 6-(benzyloxy)-5-(methylcarbamoyl)nicotinate (1.65 g, 3.54 mmol, 56.9% yield).

LCMS (2 min High pH): Rt=1.52 min, [MH]$^+$=465.3.

$^1$H NMR (400 MHz, CHCl$_3$-d) δ ppm 9.31 (d, J=2.4 Hz, 1H) 9.10 (d, J=2.4 Hz, 1H) 7.80 (d, J=3.7 Hz, 1H) 7.38-7.53 (m, 7H) 5.68 (s, 2H) 2.98 (d, J=4.6 Hz, 3H).

Intermediate 51: 2-(Benzyloxy)-N5-cyclobutyl-N3-methyl pyridine-3,5-dicarboxamide

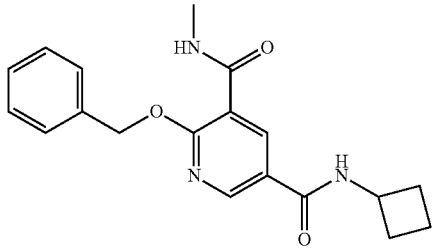 [SMILES: CNC(=O)c1cc(C(=O)NC2CCC2)cnc1OCc1ccccc1]

2,4,6-Trichlorophenyl 6-(benzyloxy)-5-(methylcarbamoyl)nicotinate (1.65 g, 3.54 mmol) was dissolved in THF (20 mL) and Et$_3$N (0.988 mL, 7.09 mmol) was added. Cyclobutanamine (0.605 mL, 7.09 mmol) and DMAP (0.022 g, 0.177 mmol) were added and the reaction mixture heated at 45° C. for 15 min. The reaction was heated for a further 30 min, then allowed to cool and concentrated in vacuo. The crude colourless oil was then partitioned between ethyl acetate (30 mL) and water (30 mL). The product was extracted with ethyl acetate (2×30 mL) and the combined ethyl acetate layers were dried (Na$_2$SO$_4$) and evaporated in vacuo. The crude residue was loaded in dichloromethane and purified via Biotage SP4 flash chromatography eluting from 20-100% ethyl acetate/cyclohexane. The relevant fractions were combined and evaporated in vacuo to yield the product—2-(benzyloxy)-N5-cyclobutyl-N3-methylpyridine-3,5-dicarboxamide (1.025 g, 3.02 mmol, 85% yield) as a white solid.

LCMS (2 min Formic): Rt=1.01 min, [MH]$^+$=340.0.

Intermediate 52: N5-Cyclobutyl-N3-methyl-2-oxo-1,2-dihydropyridine-3,5-dicarboxamide

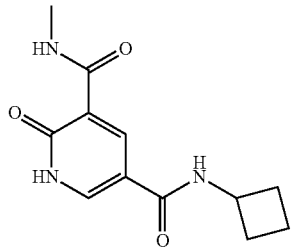 [SMILES: CNC(=O)c1cc(C(=O)NC2CCC2)c[nH]c1=O]

TFA (2 mL, 26.0 mmol) was added to 2-(benzyloxy)-N5-cyclobutyl-N3-methylpyridine-3,5-dicarboxamide (1.18 g, 3.48 mmol) and the mixture was heated at 80° C. for 1 h and then a further 20 min and then allowed to cool and evaporated in vacuo to give a grey solid. The crude product was triturated with ether (5 mL) and the product collected by filtration to give N5-cyclobutyl-N3-methyl-2-oxo-1,2-dihydropyridine-3,5-dicarboxamide (718 mg, 2.88 mmol, 83% yield) as a white solid.

LCMS (2 min Formic): Rt=0.55 min, [MH]$^+$=250.0.

Intermediate 53: 2-(Benzyloxy)-N5-cyclopropyl-N3-methylpyridine-3,5-dicarboxamide

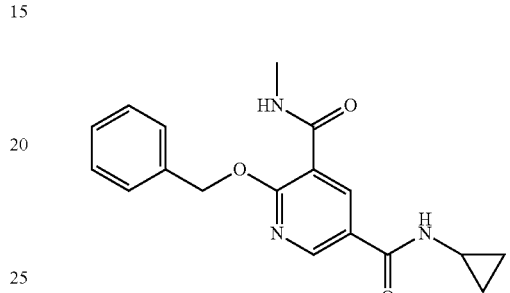

The reactants, 2,4,6-trichlorophenyl 6-(benzyloxy)-5-(methylcarbamoyl)nicotinate (771 mg, 1.656 mmol), cyclopropanamine (327 mg, 5.73 mmol), Et$_3$N (461 μL, 3.31 mmol) and DMAP (10.11 mg, 0.083 mmol) were combined in 2-methyltetrahydrofuran (20 mL) and heated to 45° C. overnight and the reaction was then cooled and concentrated in vacuo. The crude product was applied to a 50 g SNAP silica cartridge in the minimum of DCM and eluted with 5-50% (3:1 EtOAc:EtOH) in cyclohexane. The appropriate fractions were concentrated in vacuo to give 2-(benzyloxy)-N5-cyclopropyl-N3-methylpyridine-3,5-dicarboxamide (485.2 mg, 1.417 mmol, 86% yield) as a cream solid.

LCMS (2 min Formic): Rt=0.90 min, [MH]$^+$=326.3.

$^1$H NMR (400 MHz, CHCl$_3$-d) δ ppm 8.88 (d, J=2.7 Hz, 1H) 8.72 (d, J=2.4 Hz, 1H) 7.88 (br. s., 1H) 7.32-7.50 (m, 5H) 6.40 (br. s., 1H) 5.62 (s, 2H) 2.87-2.99 (m, 4H) 0.82-0.95 (m, 2H) 0.57-0.70 (m, 2H).

Intermediate 54: N5-Cyclopropyl-N3-methyl-2-oxo-1,2-dihydropyridine-3,5-dicarboxamide

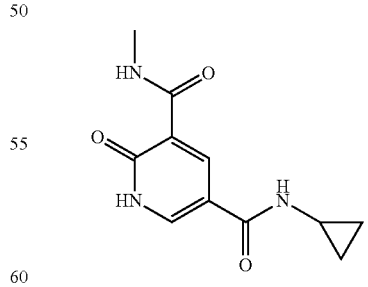

2-(Benzyloxy)-N5-cyclopropyl-N3-methylpyridine-3,5-dicarboxamide (485 mg, 1.491 mmol) was taken up in TFA (5 mL, 64.9 mmol) and heated to 90° C. for 3 h and the reaction was concentrated in vacuo. The residue was stirred in Et$_2$O (20 mL) for 30 min and then left to stand over the weekend. The resulting precipitate was collected by filtration to give N5-cyclopropyl-N3-methyl-2-oxo-1,2-dihydropyridine-3,5-dicarboxamide (364.9 mg, 1.474 mmol, 99% yield) as a cream solid.

LCMS (2 min Formic): Rt=0.45 min, [MH]⁺=236.2.

¹H NMR (400 MHz, DMSO-d₆) δ ppm 12.79 (br. s., 1H) 9.41 (d, J=4.9 Hz, 1H) 8.76 (d, J=2.7 Hz, 1H) 8.44 (d, J=3.7 Hz, 1H) 8.19 (d, J=2.7 Hz, 1H) 2.76-2.87 (m, 4H) 0.64-0.71 (m, 2H) 0.51-0.57 (m, 2H).

Intermediate 55: tert-Butyl 4-((5-(cyclopropylcarbamoyl)-3-(methylcarbamoyl)-2-oxopyridin-1(2H)-yl)methyl)-1H-benzo[d]imidazole-1-carboxylate

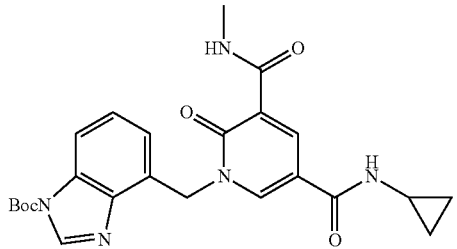 [SMILES: CNC(=O)c1cc(C(=O)NC2CC2)cn(Cc2cccc3c2ncn3C(=O)OC(C)(C)C)c1=O]

N5-Cyclopropyl-N3-methyl-2-oxo-1,2-dihydropyridine-3,5-dicarboxamide (192 mg, 0.815 mmol), tert-butyl 4-(hydroxymethyl)-1H-benzo[d]imidazole-1-carboxylate (184 mg, 0.741 mmol) and 2-(tributylphosphoranylidene)acetonitrile (612 µL, 2.334 mmol) were combined in toluene (3.7 mL) and the reaction mixture heated in a 5 mL microwave vial in a Biotage initiator microwave at 120° C. for 30 min. The vial was returned to the microwave for a further 30 min at 120° C. An additional portion of 2-(tributylphosphoranylidene)acetonitrile (428 µL, 1.630 mmol) was added, and the reaction was returned to the microwave for 30 min at 120° C. The reaction mixture was poured onto water (30 mL) and extracted with ethyl acetate (3×15 mL). The combined organic portions were washed with brine, dried through a hydrophobic frit and evaporated in vacuo to yield the crude product. The residue was loaded in dichloromethane onto a 50 g SNAP silica cartridge and was purified via Biotage SP4 flash chromatography, eluting from 10-70% (3:1 ethyl acetate:ethanol)/cyclohexane. The relevant fractions were combined and evaporated in vacuo to yield the product—tert-butyl 4-((5-(cyclopropylcarbamoyl)-3-(methylcarbamoyl)-2-oxopyridin-1(2H)-yl)methyl)-1H-benzo[d]imidazole-1-carboxylate (91 mg, 0.195 mmol, 26.4% yield) as a brown glass which was used without further purification in the subsequent reaction.

LCMS (2 min Formic): Rt=1.03 min, [MH]⁺=466.2.

Intermediate 56: tert-Butyl 4-((5-(cyclobutylcarbamoyl)-3-(methylcarbamoyl)-2-oxopyridin-1(2H)-yl)methyl)-1H-benzo[d]imidazole-1-carboxylate

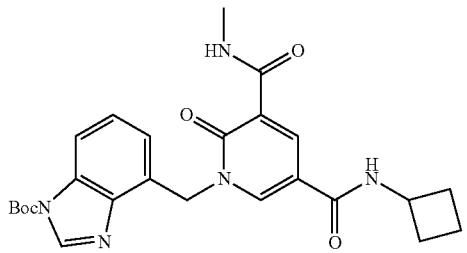 [SMILES: CNC(=O)c1cc(C(=O)NC2CCC2)cn(Cc2cccc3c2ncn3C(=O)OC(C)(C)C)c1=O]

N5-Cyclobutyl-N3-methyl-2-oxo-1,2-dihydropyridine-3,5-dicarboxamide (55 mg, 0.221 mmol), tert-butyl 4-(hydroxymethyl)-1H-benzo[d]imidazole-1-carboxylate (69 mg, 0.278 mmol) and 2-(tributylphosphoranylidene)acetonitrile (0.182 mL, 0.695 mmol) were combined in toluene (1.5 mL) and the reaction mixture heated in a 5 mL microwave vial in a Biotage initiator at 120° C. for 30 min. The reaction was returned to the microwave at 120° C. for 20 min. The reaction mixture was poured onto water (20 mL) and extracted with ethyl acetate (3×10 mL). The combined organic portions were washed with brine, dried through a hydrophobic frit and evaporated in vacuo to yield the crude product. The residue was loaded in dichloromethane onto a 25 g SNAP silica cartridge and purified via Biotage SP4 flash chromatography, eluting from 10-50% (3:1 ethyl acetate:ethanol)/cyclohexane. The relevant fractions were combined and evaporated in vacuo to yield the product tert-butyl 4-((5-(cyclobutylcarbamoyl)-3-(methylcarbamoyl)-2-oxopyridin-1(2H)-yl)methyl)-1H-benzo[d]imidazole-1-carboxylate (54 mg, 0.113 mmol, 51.0% yield) as a brown glass, which was used without further purification.

LCMS (2 min Formic): Rt=1.12 min, [MH]⁺=480.2.

Intermediate 57: 2,4,6-Trichlorophenyl 1-benzyl-5-(methylcarbamoyl)-6-oxo-1,6-dihydropyridine-3-carboxylate

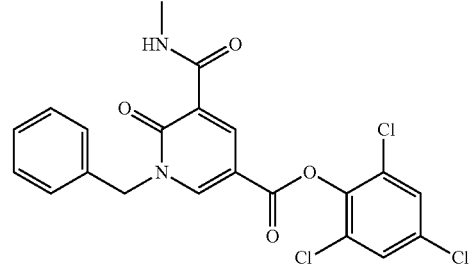 [SMILES: CNC(=O)c1cc(C(=O)Oc2c(Cl)cc(Cl)cc2Cl)cn(Cc2ccccc2)c1=O]

1-Benzyl-5-bromo-N-methyl-2-oxo-1,2-dihydropyridine-3-carboxamide (2 g, 6.23 mmol), Xantphos (0.360 g, 0.623 mmol), palladium acetate (0.070 g, 0.311 mmol) and Et₃N (1.302 mL, 9.34 mmol) were combined in a three necked flask equipped with a dropping funnel and a condensor with a nitrogen bubbler on the top. Toluene (30 mL) was added and the mixture was heated at 80° C. under nitrogen for 20 min, then a solution of 2,4,6-trichlorophenyl formate (2.106 g, 9.34 mmol) in toluene (20 mL) was added dropwise over 30 min and heating continued for 2 h. The reaction mixture was diluted with EtOAc (50 mL) and washed with water (50 mL) and brine (50 mL), dried and evaporated in vacuo to give an orange oil. This was dissolved in DCM (10 mL) and loaded onto a 50 g silica column, then eluted with 0-50% EtOAc/cyclohexane and the product-containing fractions evaporated in vacuo to give 2,4,6-trichlorophenyl 1-benzyl-5-(methylcarbamoyl)-6-oxo-1,6-dihydropyridine-3-carboxylate (2.52 g, 5.41 mmol, 87% yield) as a beige solid LCMS (2 min Formic): Rt=1.36 min, [MH]⁺=465, 467.

¹H NMR (400 MHz, CHCl₃-d) δ ppm 9.32 (br. d, J=4.4 Hz, 1H) 9.20 (d, J=2.7 Hz, 1H) 8.58 (d, J=2.7 Hz, 1H) 7.30-7.50 (m, 7H) 5.29 (s, 2H) 3.01 (d, J=4.9 Hz, 3H).

Intermediate 58: 5-Bromo-2-methoxynicotinoyl chloride

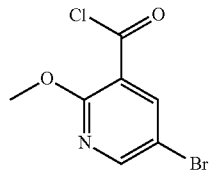

5-Bromo-2-methoxynicotinic acid (15 g, 64.6 mmol, commercially available from, for example Apollo Scientific) was suspended in DCM (100 mL) and then oxalyl chloride (16.98 mL, 194 mmol) was added, followed by DMF (5.01 mL, 64.6 mmol) and the mixture was stirred for 18 h at rt. The solvent was evaporated in vacuo and the residue was redissolved in DCM (100 mL) and evaporated to dryness to give 5-bromo-2-methoxynicotinoyl chloride (16.33 g, 65.2 mmol, 101% yield) which was used in the next step immediately.

$^1$H NMR (400 MHz, CHCl$_3$-d) δ ppm 8.49 (d, J=2.7 Hz, 1H) 8.44 (d, J=2.4 Hz, 1H) 4.06 (s, 3H).

Intermediate 59: 5-Bromo-2-methoxy-N-methylnicotinamide

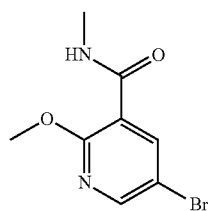

5-Bromo-2-methoxynicotinoyl chloride (16 g, 63.9 mmol) was dissolved in 2-methyltetrahydrofuran (100 mL) and Et$_3$N (8.90 mL, 63.9 mmol) was added, followed by methanamine (31.9 mL, 2M in THF, 63.9 mmol) and the mixture was stirred for 3 h at rt, then added to water (200 mL) and extracted with EtOAc (200 mL). The organic layer was washed with brine (200 mL), dried and evaporated in vacuo to give 5-bromo-2-methoxy-N-methylnicotinamide (14.8 g, 60.4 mmol, 95% yield) as a pale yellow solid.

LCMS (2 min High pH): Rt=0.83 min, [MH]$^+$=245.1, 247.1.

$^1$H NMR (400 MHz, CHCl$_3$-d) δ ppm 8.62 (d, J=2.4 Hz, 1H) 8.29 (d, J=2.4 Hz, 1H) 7.80 (br. s., 1H) 4.09 (s, 3H) 3.02 (d, J=4.9 Hz, 3H).

Intermediate 60: Butyl 6-methoxy-5-(methylcarbamoyl)nicotinate

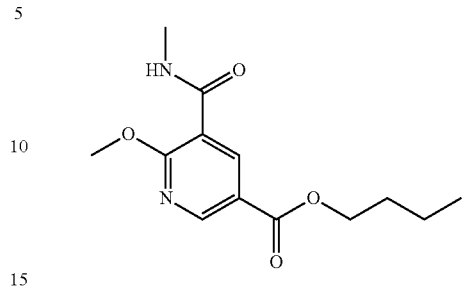

(9,9-Dimethyl-9H-xanthene-4,5-diyl)bis(diphenylphosphine) (2.479 g, 4.28 mmol), triethylamine (18.58 g, 184 mmol), diacetoxypalladium (0.962 g, 4.28 mmol) and 5-bromo-2-methoxy-N-methylnicotinamide (15 g, 61.2 mmol) were combined in a 500 mL RBF, then DMF (100 mL) and 1-butanol (28.0 mL, 306 mmol) were added and the mixture was purged with carbon monoxide for 10 min, then a balloon containing around 1.5 litre of CO was added and the mixture was heated overnight at 90° C. The mixture was then cooled, diluted with water (500 mL) and extracted with EtOAc (2×500 mL). The organics were washed with water (200 mL), dried and evaporated in vacuo and the resulting black oil was purified by chromatography on a 340 g silica column eluting with 0-100% EtOAc/cyclohexane to give butyl 6-methoxy-5-(methylcarbamoyl)nicotinate (11 g, 41.3 mmol, 67.5% yield) as a pale yellow crystalline solid.

LCMS (2 min High pH): Rt=1.04 min, [MH]$^+$=267.2.

Intermediate 61: Methyl 6-methoxy-5-(methylcarbamoyl)nicotinate

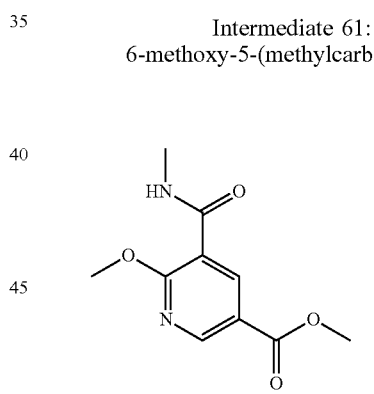

Carbon monoxide was gently bubbled through a mixture of 5-bromo-2-methoxy-N-methylnicotinamide (10.6 g, 43.3 mmol), xantphos (1.502 g, 2.60 mmol), triethylamine (12.06 mL, 87 mmol), palladium(II) acetate (0.486 g, 2.163 mmol) and methanol (17.50 mL, 433 mmol) in DMF (150 mL) until a yellow/green suspension resulted. The suspension was held under a balloon of carbon monoxide and heated to 60° C. for 5 h. LCMS showed significant SM, so the reaction was left overnight (16 h). The reaction mixture was then allowed to cool to rt. The solution was diluted with water (300 mL) and extracted with EtOAc (3×300 mL), and the combined organics back extracted with brine (3×100 mL). The combined organics were then dried (Na$_2$SO$_4$) and evaporated in vacuo to a brown solid. The residue was dissolved in DCM, loaded on to a 340 g Biotage silica SNAP column and eluted with 20→80% EtOAc/cyclohexane. The product containing fractions were evaporated in vacuo to a yellow solid—methyl 6-methoxy-5-(methylcarbamoyl) nicotinate (4 g, 17.84 mmol, 41.2% yield)

As the yield was lower than expected, the retained aqueous layer was analysed by LCMS and found to contain further product. This was therefore further extracted with DCM (3×100 mL), the combined organics were dried (Na$_2$SO$_4$) and concentrated in vacuo (for a prolonged period to remove DMF). The aqueous layer was re-analysed by LCMS and found to no longer contain product. The crude product from the organic phase, a yellow solid was taken up in DCM and added to a SNAP silica cartridge (100 g) and eluted with 20→80% EtOAc/cyclohexane The product containing fractions were evaporated in vacuo to a yellow solid—methyl 6-methoxy-5-(methylcarbamoyl)nicotinate (1.9 g, 8.47 mmol, 19.59% yield)

LCMS (2 min Formic): Rt=0.67 min, [MH]+=225.1.

$^1$H NMR (400 MHz, DMSO-d$_6$) δ ppm 8.82 (d, J=2.2 Hz, 1H) 8.55 (d, J=2.4 Hz, 1H) 8.30 (br. d, J=3.9 Hz, 1H) 4.05 (s, 3H) 3.87 (s, 3H) 2.82 (d, J=4.6 Hz, 3H).

Intermediate 62: Methyl 5-(methylcarbamoyl)-6-oxo-1,6-dihydropyridine-3-carboxylate

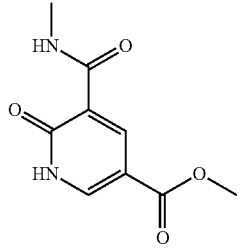

Sodium iodide (4.88 g, 32.6 mmol) was added to a solution of methyl 6-methoxy-5-(methylcarbamoyl)nicotinate (3.65 g, 16.28 mmol) in acetonitrile (100 mL) and this solution was stirred for 10 min under nitrogen. TMS-Cl (10.40 mL, 81 mmol) was added dropwise, and the reaction mixture was stirred at rt for 1 h. The reaction was quenched with water (100 mL) and the mixture was extracted five times with a mix of DCM/MeOH and the combined organic phase was dried over a hydrophobic frit and evaporated under vacuum. The crude material was dissolved in DCM and loaded onto a 100 g SNAP silica cartridge and eluted with 0-100% ethanol in EtOAc. The appropriate fractions were evaporated under vacuum, and the desired product was obtained—methyl 5-(methylcarbamoyl)-6-oxo-1,6-dihydropyridine-3-carboxylate (1.5 g, 7.14 mmol, 43.8% yield).

LCMS (2 min Formic): Rt=0.47 min, [MH]+=211.1.

$^1$H NMR (400 MHz, DMSO-d$_6$) δ ppm 10.25 (br. s, 1H) 9.55 (br. d, J=4.4 Hz, 1H) 8.63 (d, J=2.7 Hz, 1H) 8.32 (d, J=2.7 Hz, 1H) 3.80 (s, 3H) 2.82 (d, J=4.9 Hz, 3H).

Intermediate 63: Butyl 5-(methylcarbamoyl)-6-oxo-1,6-dihydropyridine-3-carboxylate

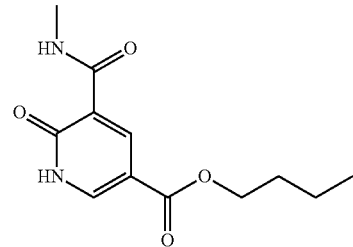 [SMILES: CCCCOC(=O)c1c[nH]c(=O)c(C(=O)NC)c1]

TMSCl (15.84 mL, 124 mmol) and sodium iodide (18.58 g, 124 mmol) were added to a solution of butyl 6-methoxy-5-(methylcarbamoyl)nicotinate (11 g, 41.3 mmol) in acetonitrile (200 mL) at rt, and the mixture was stirred for 1 h, then evaporated in vacuo and the residue partitioned between EtOAc (200 mL) and saturated sodium thiosulphate solution (200 mL). The organic layer was washed with brine, dried and evaporated in vacuo to give butyl 5-(methylcarbamoyl)-6-oxo-1,6-dihydropyridine-3-carboxylate (6.5 g, 25.8 mmol, 62.4% yield) as a pale yellow solid.

LCMS (2 min High pH): Rt=0.66 min, [MH]$^+$=253.2.

Intermediate 64: Methyl 1-(3-methoxybenzyl)-5-(methylcarbamoyl)-6-oxo-1,6-dihydropyridine-3-carboxylate

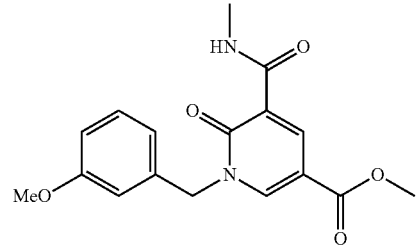 [SMILES: CNC(=O)c1cc(C(=O)OC)cn(Cc2cccc(OC)c2)c1=O]

Methyl 5-(methylcarbamoyl)-6-oxo-1,6-dihydropyridine-3-carboxylate (580 mg, 2.76 mmol), 1-(bromomethyl)-3-methoxybenzene (0.580 mL, 4.14 mmol), potassium carbonate (770 mg, 5.57 mmol) and DMF (5 mL) were stirred at 90° C. for 1 h. This was washed with LiCl (20 mL), partitioned between EtOAc (40 mL) and water (40 mL), the aqueous phase was extracted with EtOAc (2×40 mL), dried over a hydrophobic frit and concentrated to give a colourless oil. This was purified by chromatography on SiO$_2$ (Biotage SNAP 100 g cartridge, eluting with 0-100% EtOAc/cyclohexane). The appropriate fractions were concentrated to give methyl 1-(3-methoxybenzyl)-5-(methylcarbamoyl)-6-oxo-1,6-dihydropyridine-3-carboxylate (683 mg, 1.861 mmol, 67.4% yield) as a white solid.

LCMS (2 min Formic): Rt=0.91 min, [MH]+=331.0.

$^1$H NMR (400 MHz, DMSO-d$_6$) δ ppm 9.22 (br. d, J=4.6 Hz, 1H) 8.93 (d, J=2.7 Hz, 1H) 8.70 (d, J=2.7 Hz, 1H) 7.27 (t, J=7.9 Hz, 1H) 6.92 (m, J=1.7 Hz, 1H) 6.84-6.90 (m, 2H) 5.30 (s, 2H) 3.84 (s, 3H) 3.73 (s, 3H) 2.83 (s, 3H).

Intermediate 65: 1-(3-Methoxybenzyl)-5-(methylcarbamoyl)-6-oxo-1,6-dihydropyridine-3-carboxylic acid

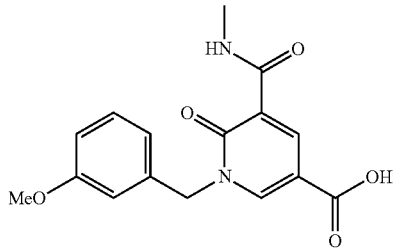 [SMILES: CNC(=O)c1cc(C(=O)O)cn(Cc2cccc(OC)c2)c1=O]

Methyl 1-(3-methoxybenzyl)-5-(methylcarbamoyl)-6-oxo-1,6-dihydropyridine-3-carboxylate (670 mg, 2.028 mmol), lithium hydroxide (146 mg, 6.08 mmol), 1,4-dioxane (3 mL) and water (3 mL) were stirred at rt for 30 min. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-methoxybenzyl)-5-(methylcarbamoyl)-6-oxo-1,6-dihydropyridine-3-carboxylic acid (641 mg, 1.824 mmol, 90% yield) as a white solid.

LCMS (2 min Formic): Rt=0.81 min, [MH]+=317.0.

$^1$H NMR (400 MHz, DMSO-$d_6$) δ ppm 13.09 (br. s, 1H) 9.26 (br. q, J=4.4, 4.4, 4.4 Hz, 1H) 8.84 (d, J=2.7 Hz, 1H) 8.70 (d, J=2.4 Hz, 1H) 7.27 (t, J=7.9 Hz, 1H) 6.91-6.94 (m, 1H) 6.84-6.90 (m, 2H) 5.29 (s, 2H) 3.73 (s, 3H) 2.82 (d, J=4.9 Hz, 3H).

Intermediate 66: Butyl 5-(methylcarbamoyl)-6-oxo-1-((1-tosyl-1H-indol-4-yl)methyl-1,6-dihydropyridine-3-carboxylate

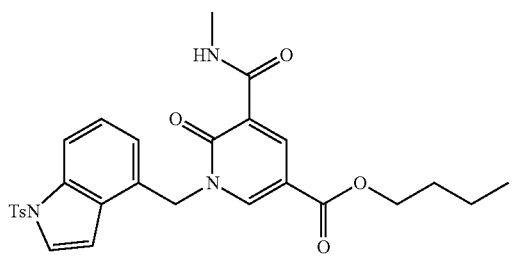 [SMILES: CCCCOC(=O)c1cc(C(=O)NC)c(=O)n(Cc2cccc3c2ccn3S(=O)(=O)c2ccc(C)cc2)c1]

To a solution of butyl 5-(methylcarbamoyl)-6-oxo-1,6-dihydropyridine-3-carboxylate (447 mg, 1.772 mmol) in DMF (11.8 mL) was added potassium carbonate (490 mg, 3.54 mmol) and 4-(bromomethyl)-1-tosyl-1H-indole (1033 mg, 2.84 mmol). The mixture was stirred at rt for 2 h. The reaction was quenched with water (1.596 mL, 89 mmol) and poured onto water (100 mL) and saturated aqueous lithium chloride (20 mL). The aqueous phase was extracted with ethyl acetate (3×30 mL) and the combined organics were washed with brine (10 mL), dried through a hydrophobic frit and evaporated in vacuo to yield the crude product (1.74 g). The residue was loaded in dichloromethane onto a 50 g SNAP silica cartridge and purified via Biotage SP4 flash chromatography, eluting from 20-100% ethyl acetate/cyclohexane. The relevant fractions were combined and evaporated in vacuo to yield the pure product—butyl 5-(methylcarbamoyl)-6-oxo-1-((1-tosyl-1H-indol-4-yl)methyl)-1,6-dihydropyridine-3-carboxylate (907 mg, 1.609 mmol, 91% yield) as a white solid.

LCMS (2 min Formic): Rt=1.34 min, [MH]+=536.1.

Intermediate 67: 1-((1H-Indol-4-yl)methyl)-5-(methylcarbamoyl)-6-oxo-1,6-dihydropyridine-3-carboxylic acid

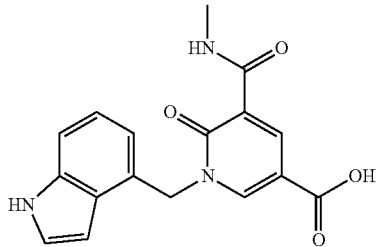 [SMILES: CNC(=O)c1cc(C(=O)O)cn(Cc2cccc3[nH]ccc23)c1=O]

To a solution of butyl 5-(methylcarbamoyl)-6-oxo-1-((1-tosyl-1H-indol-4-yl)methyl)-1,6-dihydropyridine-3-carboxylate (821 mg, 1.533 mmol) in methanol (1.703 mL) and THF (3.406 mL) stirred under nitrogen at rt was added solid cesium carbonate (3995 mg, 12.26 mmol) in one charge. The reaction mixture was stirred at 70° C. for 3 h. The reaction mixture was concentrated in vacuo, before diluting with 1,4-dioxane (1.703 mL) and water (1.703 mL). The mixture was stirred at 70° C. for 4.5 h. The reaction mixture was poured onto saturated sodium bicarbonate (30 mL) and extracted with ethyl acetate (3×10 mL). The aqueous phase was acidified with 2M HCl and extracted with ethyl acetate (8×30 mL). Following extraction, a solid precipitate remained in the organic phase which was filtered off to give some desired crude product (251 mg). The filtrate from workup was dried through a hydrophobic frit and evaporated in vacuo to yield a brown solid. The solid was triturated with ether (30 mL) and filtered to give further product (539 mg). This residue was suspended in water (20 mL) and brought to pH 4 with 2M HCl. The suspension was filtered, washed with water (2×5 mL) and diethyl ether (2×10 mL). The collected solid (213 mg) was suspended in dichloromethane (10 mL) and combined with the previous batch of crude product. The combined suspension was sonicated and blown down under a stream of nitrogen and dried in vacuo to give the final product 1-((1H-indol-4-yl)methyl)-5-(methylcarbamoyl)-6-oxo-1,6-dihydropyridine-3-carboxylic acid (432 mg, 1.222 mmol, 80% yield).

LCMS (2 min Formic): Rt=0.77 min, [MH]+=326.2.

Intermediate 68: Butyl 1-(2-fluoro-3-methyl benzyl)-5-(methylcarbamoyl)-6-oxo-1,6-dihydropyridine-3-carboxylate

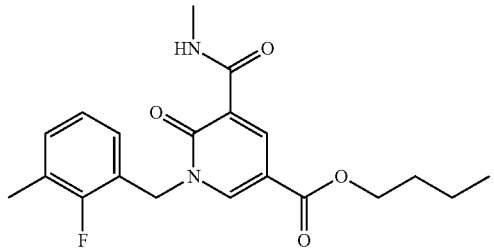 [SMILES: CCCCOC(=O)c1cc(C(=O)NC)c(=O)n(Cc2cccc(C)c2F)c1]

A stirred suspension of butyl 5-(methylcarbamoyl)-6-oxo-1,6-dihydropyridine-3-carboxylate (695.9 mg, 2.76 mmol) and potassium carbonate (769.4 mg, 5.57 mmol) in DMF (4 mL) at rt had a solution of 1-(bromomethyl)-2-fluoro-3-methylbenzene (607.4 mg, 2.99 mmol) in DMF (6 mL) added to it. The mixture was stirred at rt under nitrogen for 73 h before being partitioned between water (20 mL) and ethyl acetate (25 mL). The organic phase was washed with further water (20 mL) and the combined aqueous phases back-extracted with ethyl acetate (25 mL). The combined organic phases were dried by filtering through a cartridge fitted with a hydrophobic frit and the solvent was evaporated in vacuo to give a pale yellow oil which crystallised upon standing overnight to a pale yellow solid. The solid was purified by being re-dissolved in dichloromethane (ca. 5 mL) and applied to a 50 g SNAP silica cartridge which was eluted with a gradient of 20-60% ethyl acetate in cyclohexane. The required fractions were combined and evaporated in vacuo to give the desired product as a white solid (958.7 mg).

LCMS (2 min Formic): Rt=1.26 min, [MH]$^+$=375.2.

Intermediate 69: 1-(2-Fluoro-3-methylbenzyl)-5-(methylcarbamoyl)-6-oxo-1,6-dihydropyridine-3-carboxylic acid

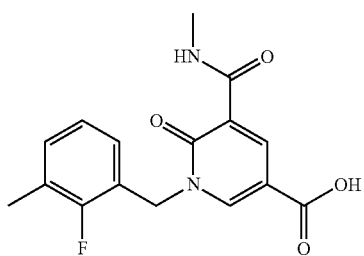 [SMILES: CNC(=O)c1cc(C(=O)O)cn(Cc2cccc(C)c2F)c1=O]

To a stirred solution of butyl 1-(2-fluoro-3-methylbenzyl)-5-(methylcarbamoyl)-6-oxo-1,6-dihydropyridine-3-carboxylate (953.7 mg, 2.55 mmol) in acetonitrile (10 mL) and THF (10 mL) under nitrogen was added lithium hydroxide (1.0 M aqueous solution) (5.1 mL, 5.10 mmol) and the mixture was stirred at rt for 2.5 h. The volatiles were evaporated from the mixture in vacuo and the residue dried in vacuo before being partitioned between 2 M aqueous hydrochloric acid (20 mL) and ethyl acetate (150 mL) [solid was poorly soluble in both phases]. The aqueous phase was extracted with further ethyl acetate (75 mL) and the combined organic phases washed with water (20 mL) and saturated brine solution (30 mL). The organic phase was dried by filtering through a cartridge fitted with a hydrophobic frit and the solvent evaporated in vacuo. The solid residue was triturated twice with methanol (10 mL+5 mL) and the solid dried in vacuo to give the desired product as a white solid (621.7 mg).

LCMS (2 min Formic): Rt=0.90 min, [MH]$^+$=319.1.

Intermediate 70: Methyl 1-(3-hydroxybenzyl)-5-(methylcarbamoyl)-6-oxo-1,6-dihydropyridine-3-carboxylate

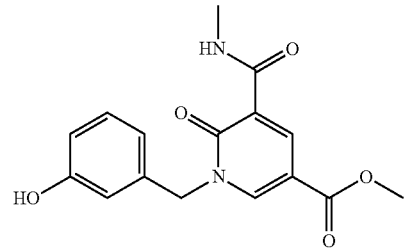 [SMILES: CNC(=O)c1cc(C(=O)OC)cn(Cc2cccc(O)c2)c1=O]

Methyl 1-(3-methoxybenzyl)-5-(methylcarbamoyl)-6-oxo-1,6-dihydropyridine-3-carboxylate (0.990 g, 3.00 mmol) in DCM (5 mL) was cooled to 0° C. under N$_2$ and BBr$_3$ (15 mL, 1 M in DCM, 15 mmol) was added dropwise and the reaction stirred for 1.5 h. The reaction was quenched with water (30 mL), extracted with DCM (2×30 mL), the aqueous layer was then extracted with EtOAc (2×30 mL). The combined organic layers were dried over a hydrophobic frit and concentrated to give 675 mg of a yellow solid. This was purified by chromatography on SiO$_2$ (Biotage SNAP 50 g cartridge, eluting with 40-100% EtOAc/cyclohexane). The appropriate fractions were concentrated to give methyl 1-(3-hydroxybenzyl)-5-(methylcarbamoyl)-6-oxo-1,6-dihydropyridine-3-carboxylate (473 mg, 1.346 mmol, 44.9% yield) as a white solid.

LCMS (2 min Formic): Rt=0.74 min, [MH]+=317.0.

$^1$H NMR (400 MHz, DMSO-d$_6$) δ ppm 9.46 (br. s, 1H) 9.23 (br. d, J=4.6 Hz, 1H) 8.90 (d, J=2.7 Hz, 1H) 8.70 (d, J=2.7 Hz, 1H) 7.05-7.20 (m, 1H) 6.65-6.76 (m, 3H) 5.26 (s, 2H) 3.78-3.90 (m, 3H) 2.82 (d, J=4.9 Hz, 3H).

Intermediate 71: Methyl 1-(3-(2-hydroxyethoxy)benzyl)-5-(methylcarbamoyl)-6-oxo-1,6-dihydropyridine-3-carboxylate

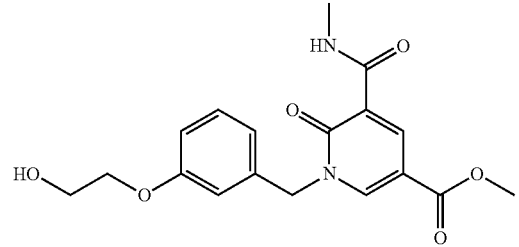 [SMILES: CNC(=O)c1cc(C(=O)OC)cn(Cc2cccc(OCCO)c2)c1=O]

Methyl 1-(3-hydroxybenzyl)-5-(methylcarbamoyl)-6-oxo-1,6-dihydropyridine-3-carboxylate (450 mg, 1.423 mmol), 1,3-dioxolan-2-one (475 mg, 5.39 mmol), potassium carbonate (600 mg, 4.34 mmol) and DMF (10 mL) were heated at 90° C. for 5 h. The solution was partitioned between EtOAc (40 mL) and LiCl soln. (40 mL), the aqueous phase was extracted with EtOAc (2×40 mL), dried over a hydrophobic frit and concentrated to give 900 mg of a yellow oil. This was purified by chromatography on SiO$_2$ (Biotage SNAP 10 g cartridge, eluting with 0-100% (25% EtOH in EtOAc)/cyclohexane). The appropriate fractions were concentrated to give methyl 1-(3-(2-hydroxyethoxy)

benzyl)-5-(methylcarbamoyl)-6-oxo-1,6-dihydropyridine-3-carboxylate (446 mg, 1.114 mmol, 78% yield) as a colourless oil.

LCMS (2 min Formic): Rt=0.74 min, [MH]+=361.1.

$^1$H NMR (400 MHz, DMSO-$d_6$) δ ppm 9.22 (br. q, J=4.9, 4.9, 4.9 Hz, 1H) 8.94 (d, J=2.7 Hz, 1H) 8.70 (d, J=2.4 Hz, 1H) 7.25 (t, J=7.8 Hz, 1H) 6.82-6.94 (m, 3H) 5.30 (s, 2H) 4.81 (t, J=5.6 Hz, 1H) 3.95 (t, J=5.0 Hz, 2H) 3.84 (s, 3H) 3.69 (q, J=5.3 Hz, 2H) 2.82 (d, J=4.6 Hz, 3H).

Intermediate 72: 1-(3-(2-Hydroxyethoxy)benzyl)-5-(methylcarbamoyl)-6-oxo-1,6-dihydropyridine-3-carboxylic acid

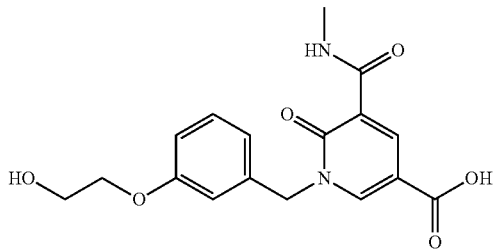 [SMILES: CNC(=O)c1cc(C(=O)O)cn(Cc2cccc(OCCO)c2)c1=O]

Methyl 1-(3-(2-hydroxyethoxy)benzyl)-5-(methylcarbamoyl)-6-oxo-1,6-dihydropyridine-3-carboxylate (440 mg, 1.221 mmol), lithium hydroxide (86 mg, 3.59 mmol), 1,4-dioxane (3 mL) and water (3 mL) were stirred at rt for 1 h. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give 1-(3-(2-hydroxyethoxy)benzyl)-5-(methylcarbamoyl)-6-oxo-1,6-dihydropyridine-3-carboxylic acid (343 mg, 0.891 mmol, 73.0% yield) as a white solid.

LCMS (2 min Formic): Rt=0.66 min, [MH]+=347.0.

$^1$H NMR (400 MHz, DMSO-$d_6$) δ ppm 9.27 (br. q, J=4.2, 4.2, 4.2 Hz, 1H) 8.85 (d, J=2.4 Hz, 1H) 8.71 (d, J=2.4 Hz, 1H) 7.27 (t, J=7.8 Hz, 1H) 6.80-6.99 (m, 3H) 5.30 (s, 2H) 4.82 (t, J=5.5 Hz, 1H) 3.96 (app. t, J=5.0 Hz, 2H) 3.70 (ABq, J=5.1 Hz, 2H) 2.83 (d, J=4.9 Hz, 3H).

Intermediate 73: Methyl 1-(3-methylbenzyl)-5-(methylcarbamoyl)-6-oxo-1,6-dihydropyridine-3-carboxylate

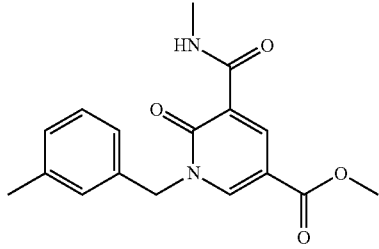

Methyl 5-(methylcarbamoyl)-6-oxo-1,6-dihydropyridine-3-carboxylate (500.2 mg, 2.380 mmol), 1-(bromomethyl)-3-methylbenzene (0.354 mL, 2.62 mmol) and potassium carbonate (140 mg, 1.013 mmol) were stirred in anhydrous DMF (10 mL) at rt under nitrogen for 4 h. The reaction mixture was concentrated in vacuo before being partitioned between water (20 mL) and ethyl acetate (20 mL). The aqueous phase was extracted with further ethyl acetate (2×20 mL) and the combined organic phases were dried by filtering through a cartridge fitted with a hydrophobic frit. The solvent was evaporated and dried in vacuo to give the desired product, as a pale yellow gum (588.2 mg). The product was used in the subsequent reaction without further purification.

LCMS (2 min Formic): Rt=1.00 min, [MH]+=315.2.

Intermediate 74: 1-(3-Methylbenzyl)-5-(methylcarbamoyl)-6-oxo-1,6-dihydropyridine-3-carboxylic acid

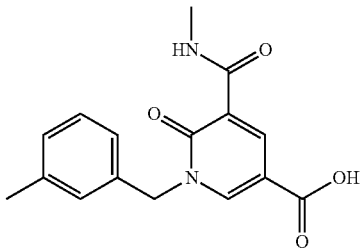 [SMILES: CNC(=O)c1cc(C(=O)O)cn(Cc2cccc(C)c2)c1=O]

A mixture of methyl 1-(3-methylbenzyl)-5-(methylcarbamoyl)-6-oxo-1,6-dihydropyridine-3-carboxylate (583.9 mg, 1.858 mmol) and lithium hydroxide (92.4 mg, 3.86 mmol) in THF (10 mL) and water (5.00 mL) was stirred at rt under nitrogen for 16.75 h. The mixture was then acidified to pH 0 with a 2M solution of hydrochloric acid (2 mL). Water (30 mL) was added and the resulting precipitate extracted with ethyl acetate (20 mL). The layers were separated and the aqueous layer further extracted with ethyl acetate (2×20 mL). The organic layers were combined and filtered through a cartridge containing a hydrophobic frit before being concentrated in vacuo. The residue was applied to a 25 g SNAP silica cartridge as a suspension in ethyl acetate. The precipitate remaining on the top of the cartridge was removed and retained as a portion of the desired product. The cartridge was eluted with a gradient of 0-7.5% ethanol (with 0.3% acetic acid) in ethyl acetate. The required fractions were combined with the previously obtained solid, evaporated and dried in vacuo to give the desired product as a white solid (355.4 mg).

LCMS (2 min Formic): Rt=0.88 min, [MH]$^+$=301.2.

Intermediate 75: Methyl 1-(2-fluoro-5-methyl benzyl)-5-(methylcarbamoyl)-6-oxo-1,6-dihydropyridine-3-carboxylate

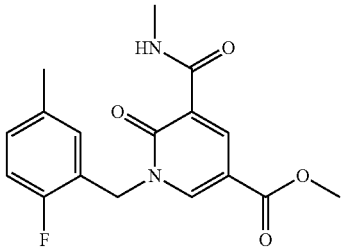 [SMILES: CNC(=O)c1cc(C(=O)OC)cn(Cc2cc(C)ccc2F)c1=O]

2-(Bromomethyl)-1-fluoro-4-methylbenzene (412 mg, 2.027 mmol) was added to a solution of methyl 5-(methylcarbamoyl)-6-oxo-1,6-dihydropyridine-3-carboxylate (426 mg, 2.027 mmol) and potassium carbonate (560 mg, 4.05 mmol) in DMF (15 mL). The reaction mixture was left to stir at rt for 2 h. The reaction mixture was concentrated under vacuum and partitioned between DCM (20 mL) and water (20 mL). The organic layer was concentrated under vacuum, loaded in DCM (3 mL) and purified by Biotage Isolera SNAP 25 g silica chromatography using a gradient of 0-60% cyclohexane/ethyl acetate. The appropriate fractions were combined and concentrated under vacuum to give the product (310 mg) as a white solid.

LCMS (2 min Formic): Rt=1.00 min, [MH]$^+$=333.0.

Intermediate 76: 1-(2-Fluoro-5-methylbenzyl)-5-(methylcarbamoyl)-6-oxo-1,6-dihydropyridine-3-carboxylic acid

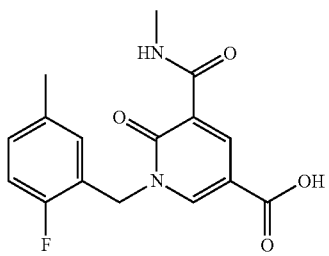 [SMILES: CNC(=O)c1cc(C(=O)O)cn(Cc2cc(C)ccc2F)c1=O]

Methyl 1-(2-fluoro-5-methylbenzyl)-5-(methylcarbamoyl)-6-oxo-1,6-dihydropyridine-3-carboxylate (310 mg, 0.933 mmol) was taken up in THF (4 mL) and water (4 mL). Lithium hydroxide (44.7 mg, 1.866 mmol) was added to the solution and the reaction stirred overnight at rt. 2M aq. HCl (1.399 mL, 2.80 mmol) was added and resulting solid was washed with water to give the product (290 mg) as a white solid.

LCMS (2 min Formic): Rt=0.89 min, [MH]$^+$=319.0.

Intermediate 77: 5-Bromo-N-methyl-1-(4-methylbenzyl)-2-oxo-1,2-dihydropyridine-3-carboxamide

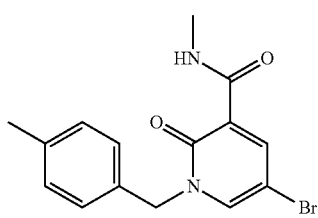 [SMILES: CNC(=O)c1cc(Br)cn(Cc2ccc(C)cc2)c1=O]

To a solution of 5-bromo-N-methyl-2-oxo-1,2-dihydropyridine-3-carboxamide (136 mg, 0.589 mmol) in methanol (1 mL) was added potassium carbonate (285 mg, 2.060 mmol) and 1-(bromomethyl)-4-methylbenzene (327 mg, 1.766 mmol). The mixture was heated to 65° C. for 3 h. The reaction was quenched with water (530 µL, 29.4 mmol), and poured onto water (10 mL). The product was extracted with ethyl acetate (4×10 mL). The combined organics were washed with brine (10 mL), dried through a hydrophobic frit and evaporated in vacuo to yield the crude product (414 mg). The residue was loaded in dichloromethane and purified via Biotage SP4 flash chromatography, eluting from 15-75% ethyl acetate/cyclohexane. The relevant fractions were combined and evaporated in vacuo to yield the pure product—5-bromo-N-methyl-1-(4-methylbenzyl)-2-oxo-1,2-dihydropyridine-3-carboxamide (120 mg, 0.358 mmol, 60.8% yield) as a white solid.

LCMS (2 min Formic): Rt=1.04 min, [MH]$^+$=335.0, 337.0.

Intermediate 78: 5-Bromo-N-methyl-1-(3-methylbenzyl)-2-oxo-1,2-dihydropyridine-3-carboxamide

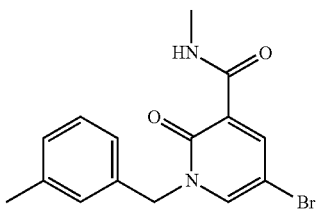 [SMILES: CNC(=O)c1cc(Br)cn(Cc2cccc(C)c2)c1=O]

1-(Bromomethyl)-3-methylbenzene (0.263 mL, 1.948 mmol) was added to a suspension of 5-bromo-N-methyl-2-oxo-1,2-dihydropyridine-3-carboxamide (300 mg, 1.298 mmol) and potassium carbonate (359 mg, 2.60 mmol) in methanol (4 mL). The reaction mixture was heated to 65° C. for 2 h, after which further 1-(bromomethyl)-3-methylbenzene (0.263 mL, 1.948 mmol) and potassium carbonate (359 mg, 2.60 mmol) were added and the reaction mixture was heated to 65° C. for a further 1 h. The reaction mixture was partitioned between ethyl acetate (20 mL) and water (20 mL) and the organic layer washed with water (2×20 mL). This was passed through a hydrophobic frit and the solvent removed under reduced pressure. The resulting yellow oil was dissolved in DCM and purified by flash chromatography on a 25 g Biotage SNAP silica column using a gradient of 0-70% cyclohexane/ethyl acetate. The product-containing fractions were combined and the solvent removed under reduced pressure. The product was left to dry in vacuo overnight to give 5-bromo-N-methyl-1-(3-methylbenzyl)-2-oxo-1,2-dihydropyridine-3-carboxamide (205.8 mg, 0.614 mmol, 47.3% yield) as a white solid.

LCMS (2 min Formic): Rt=1.05 min, [MH]$^+$=335.0 & 337.0.

Intermediate 79: 5-Bromo-N-methyl-2-oxo-1-((1-tosyl-1H-indol-7-yl)methyl)-1,2-dihydropyridine-3-carboxamide

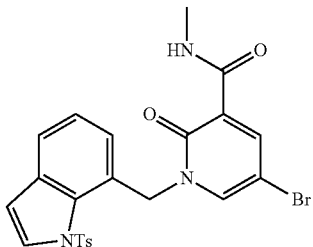 [SMILES: CNC(=O)c1cc(Br)cn(Cc2cccc3ccn(S(=O)(=O)c4ccc(C)cc4)c23)c1=O]

To a solution of 5-bromo-N-methyl-2-oxo-1,2-dihydropyridine-3-carboxamide (300 mg, 1.298 mmol) in methanol (2.164 mL) was added potassium carbonate (359 mg, 2.60 mmol) and 7-(bromomethyl)-1-tosyl-1H-indole (568 mg, 1.558 mmol). The mixture was heated to 65° C. for 5 h in total. The reaction was quenched with water (1.170 mL, 64.9 mmol) and taken up in dichloromethane (30 mL). The solution was washed with water (20 mL), and the aqueous phase was back extracted with dichloromethane (2×10 mL). The combined organic portions were dried through a hydrophobic frit and evaporated in vacuo to yield the crude product (700 mg). The residue was loaded in dichloromethane onto a 25 g SNAP silica cartridge and purified via Biotage SP4 flash chromatography, eluting from 15-65% ethyl acetate/cyclohexane. The relevant fractions were combined and evaporated in vacuo to yield an orange oil. The residue was further dried in vacuo to yield—5-bromo-N-methyl-2-oxo-1-((1-tosyl-1H-indol-7-yl)methyl)-1,2-dihydropyridine-3-carboxamide (326 mg, 0.570 mmol, 43.9% yield) as an orange solid.

LCMS (2 min Formic): Rt=1.22 min, [MH]$^+$=513.9, 515.9.

Intermediate 80: N5-Cyclopropyl-N3-methyl-2-oxo-1-((1-tosyl-1H-indol-7-yl)methyl)-1,2-dihydropyridine-3,5-dicarboxamide

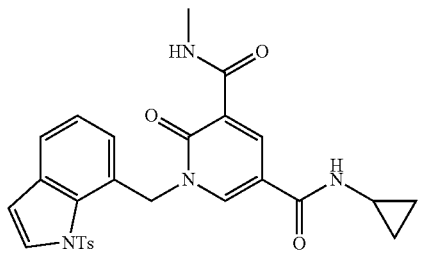 [SMILES: CNC(=O)c1cc(C(=O)NC2CC2)cn(Cc2cccc3ccn(S(=O)(=O)c4ccc(C)cc4)c23)c1=O]

To a dry microwave vial, 5-bromo-N-methyl-2-oxo-1-((1-tosyl-1H-indol-7-yl)methyl)-1,2-dihydropyridine-3-carboxamide (297 mg, 0.577 mmol) and Pd(OAc)$_2$ (12.96 mg, 0.058 mmol) were added and taken up in in dry 1,4-dioxane (3.849 mL). Xantphos (33.4 mg, 0.058 mmol), DMAP (141 mg, 1.155 mmol) and cyclopropylamine (81 μL, 1.155 mmol) were added followed by dicobalt octacarbonyl (59.2 mg, 0.173 mmol). The vial was sealed immediately and heated under microwave irradiation for 40 min at 80° C. The reaction mixture was filtered through celite, concentrated in vacuo, taken up in dichloromethane (30 mL) and washed with 2M HCl (30 mL). The acid layer was extracted with dichloromethane (2×10 mL). The combined organic portions were dried through a hydrophobic frit and evaporated in vacuo. The crude residue (396 mg) was loaded in dichloromethane onto a 25 g SNAP silica cartridge and purified via Biotage SP4 flash chromatography, eluting from 10-50% (3:1 ethyl acetate:ethanol)/cyclohexane. The relevant fractions were combined and evaporated in vacuo to yield—N5-cyclopropyl-N3-methyl-2-oxo-1-((1-tosyl-1H-indol-7-yl)methyl)-1,2-dihydropyridine-3,5-dicarboxamide (251 mg, 0.290 mmol, 50.3% yield) as an orange solid which was used without further purification in subsequent chemistry.

LCMS (2 min Formic): Rt=1.09 min, [MH]$^+$=519.0.

Intermediate 81: Methyl 1-((1H-indazol-7-yl)methyl)-5-(methylcarbamoyl)-6-oxo-1,6-dihydropyridine-3-carboxylate

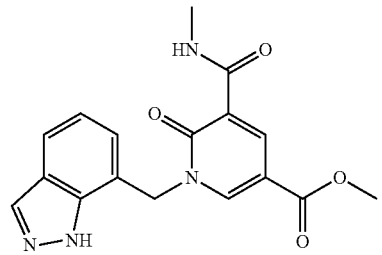 [SMILES: CNC(=O)c1cc(C(=O)OC)cn(Cc2cccc3cn[nH]c23)c1=O]

DIAD (0.185 mL, 0.952 mmol) was added to a suspension of methyl 5-(methylcarbamoyl)-6-oxo-1,6-dihydropyridine-3-carboxylate (100 mg, 0.476 mmol), (1H-indazol-7-yl)methanol (106 mg, 0.714 mmol, commercially available from, for example, Fluorochem) and triphenylphosphine (250 mg, 0.952 mmol) in toluene (4 mL). The reaction was stirred at rt under N$_2$ for 1.5 h. Further portions of (1H-indazol-7-yl)methanol (106 mg, 0.715 mmol), DIAD (0.185 mL, 0.950 mmol) and triphenylphosphine (250 mg, 0.953 mmol) were added and reaction mixture continued to stir at rt overnight. The reaction mixture was concentrated to give ~1.2 g of crude product as an orange oil. This was purified by chromatography on SiO$_2$ (Biotage SNAP 25 g cartridge, eluting with 0-100% ethyl acetate/cyclohexane) to give methyl 1-((1H-indazol-7-yl)methyl)-5-(methylcarbamoyl)-6-oxo-1,6-dihydropyridine-3-carboxylate (76 mg, 0.167 mmol, 35.2% yield) as a pale yellow oil.

LCMS (2 min Formic): Rt=0.80 min, [MH]$^+$=341.1.

Intermediate 82: 1-((1H-Indazol-7-yl)methyl)-5-(methylcarbamoyl)-6-oxo-1,6-dihydropyridine-3-carboxylic acid

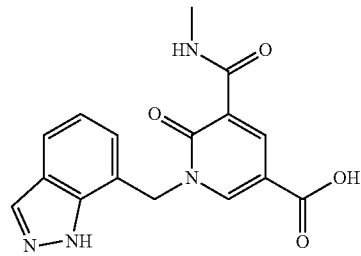 [SMILES: CNC(=O)c1cc(C(=O)O)cn(Cc2cccc3cn[nH]c23)c1=O]

Methyl 1-((1H-indazol-7-yl)methyl)-5-(methylcarbamoyl)-6-oxo-1,6-dihydropyridine-3-carboxylate (76 mg, 0.223 mmol) was dissolved in 1,4-dioxane (2 mL). Water (2 mL) was added, followed by LiOH (11 mg, 0.459 mmol) and the reaction mixture stirred at rt for 1.5 h. The dioxane was removed in vacuo and the residue partitioned between ethyl acetate and sat. NaHCO$_3$ solution. The aqueous layer was separated. The aqueous layer was acidified to pH 5 with acetic acid (4 mL, 69.9 mmol) and extracted with ethyl acetate (5×30 mL). The combined organic layers were dried (Na$_2$SO$_4$) and conc. to give 640 mg of a white solid. This was re-dissolved in water (5 mL) and the pH adjusted to pH 5 with 2M HCl solution. This was then extracted with ethyl acetate and the combined organic layers were dried (Na$_2$SO$_4$) and conc. to give 544 mg of a white solid. This was dissolved in water (with a small amount of DMSO and MeOH added to solubilise all the material) and loaded onto a reverse phase 30 g C18 column. This was eluted with 0-95% MeCN/water with 0.1% formic acid over 10 column volumes and the fractions containing the desired product were concentrated in vacuo to give 1-((1H-indazol-7-yl) methyl)-5-(methylcarbamoyl)-6-oxo-1,6-dihydropyridine-3-carboxylic acid (17 mg, 0.047 mmol, 21% yield) as a white solid.

LCMS (2 min Formic): Rt=0.72 min, [MH]+=327.1.

Intermediate 83: 5-Bromo-N-methyl-2-oxo-1,2-dihydropyridine-3-carboxamide

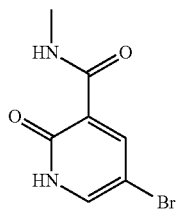

Methyl 5-bromo-2-oxo-1,2-dihydropyridine-3-carboxylate (2 g, 8.62 mmol, commercially available from, for example, CombiBlocks) and 2M methylamine in THF (13 mL, 26.0 mmol) were refluxed under N$_2$. After 4 h a white precipitate had formed. THF (15 mL) was added and the solution was refluxed for 1 h. 2M methylamine in THF (13 mL, 26.0 mmol) was added and the reaction refluxed for 2 h. Further 2M methylamine in THF (22 mL, 44.0 mmol) was added and the reaction refluxed overnight. The solution was concentrated to give a yellow solid. This was transferred to 2×20 mL microwave vials with 2M methylamine in THF (15 mL, 30.0 mmol) and THF (15 mL) and both were heated at 80° C. for 1 h. The suspension from the first microwave vial was concentrated, and triturated from diethyl ether to give 5-bromo-N-methyl-2-oxo-1,2-dihydropyridine-3-carboxamide (880 mg). The suspension from the second microwave vial was concentrated and triturated from diethyl ether to give further 5-bromo-N-methyl-2-oxo-1,2-dihydropyridine-3-carboxamide (880 mg)

LCMS (2 min Formic): Rt=0.50 min, [MH]+=231.0, 233.0.

Intermediate 84: 5-Bromo-N-methyl-2-oxo-1-((1-tosyl-1H-indol-4-yl)methyl)-1,2-dihydropyridine-3-carboxamide

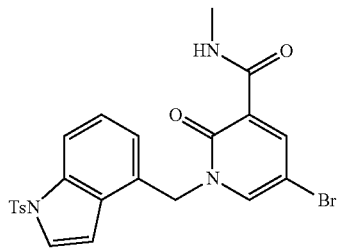 [SMILES: CNC(=O)c1cc(Br)cn(Cc2cccc3c2ccn3S(=O)(=O)c2ccc(C)cc2)c1=O]

To a solution of 5-bromo-N-methyl-2-oxo-1,2-dihydropyridine-3-carboxamide (300 mg, 1.298 mmol) in methanol (2.164 mL) was added potassium carbonate (359 mg, 2.60 mmol) and 4-(bromomethyl)-1-tosyl-1H-indole (568 mg, 1.559 mmol). The mixture was heated to 65° C. for 2 h. The reaction was quenched with water (1.170 mL, 64.9 mmol) and taken up in dichloromethane (30 mL). The solution was washed with water (20 mL), and the aqueous phase was back extracted with dichloromethane (2×10 mL). The combined organic portions were dried through a hydrophobic frit and evaporated in vacuo to yield the crude product (607 mg). The residue was loaded in dichloromethane onto a 25 g SNAP silica cartridge and purified via Biotage SP4 flash chromatography, eluting from 20-100% ethyl acetate/cyclohexane. The relevant fractions were combined and evaporated in vacuo to yield—5-bromo-N-methyl-2-oxo-1-((1-tosyl-1H-indol-4-yl)methyl)-1,2-dihydropyridine-3-carboxamide (312 mg, 0.546 mmol, 42.0% yield) as a white solid.

LCMS (2 min Formic): Rt=1.24 min, [MH]+=513.9, 515.9.

Intermediate 85: N5-Cyclopropyl-N3-methyl-2-oxo-1-((1-tosyl-1H-indol-4-yl)methyl)-1,2-dihydropyridine-3,5-dicarboxamide

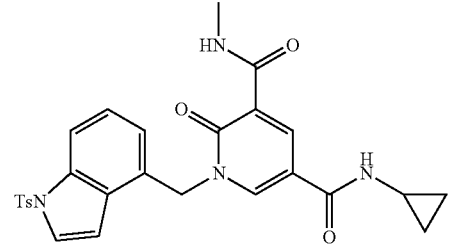 [SMILES: CNC(=O)c1cc(C(=O)NC2CC2)cn(Cc2cccc3c2ccn3S(=O)(=O)c2ccc(C)cc2)c1=O]

To a dry microwave vial, 5-bromo-N-methyl-2-oxo-1-((1-tosyl-1H-indol-4-yl)methyl)-1,2-dihydropyridine-3-carboxamide (301 mg, 0.585 mmol) and Pd(OAc)$_2$ (13.14 mg, 0.059 mmol) were added and taken up in dry 1,4-dioxane (2.5 mL). Xantphos (33.9 mg, 0.059 mmol), DMAP (143 mg, 1.170 mmol) and cyclopropylamine (82 µL, 1.170 mmol) were added followed by dicobalt octacarbonyl (60.0 mg, 0.176 mmol). The vial was sealed immediately and heated under microwave irradiation for 40 min at 80° C. The reaction mixture was filtered through celite, concentrated in vacuo, taken up in dichloromethane (30 mL) and washed with 2M HCl (30 mL). The acid layer was extracted with dichloromethane (2×10 mL). The combined organic portions were dried through a hydrophobic frit and evaporated in vacuo. The crude residue (361 mg) was loaded in dichloromethane onto a 25 g SNAP silica cartridge and purified via Biotage SP4 flash chromatography, eluting from 10-50% (3:1 ethyl acetate:ethanol)/cyclohexane. The relevant fractions were combined and evaporated in vacuo to yield a yellow solid—N5-cyclopropyl-N3-methyl-2-oxo-1-((1-tosyl-1H-indol-4-yl)methyl)-1,2-dihydropyridine-3,5-dicarboxamide (255 mg, 0.320 mmol, 54.6% yield).

LCMS (2 min Formic): Rt=1.10 min, [MH]+=519.1.

Intermediate 86: N5-Cyclopropyl-N3-methyl-1-((3-methyl-1-tosyl-1H-indol-4-yl)methyl)-2-oxo-1,2-dihydropyridine-3,5-dicarboxamide

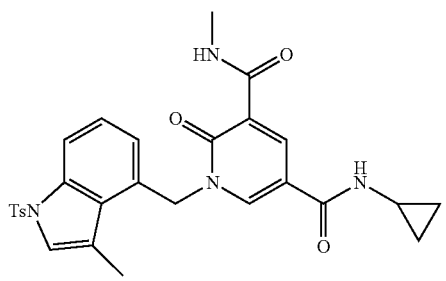 [SMILES: CNC(=O)c1cc(C(=O)NC2CC2)cn(Cc2cccc3c2c(C)cn3S(=O)(=O)c2ccc(C)cc2)c1=O]

To a solution of N5-cyclopropyl-N3-methyl-2-oxo-1,2-dihydropyridine-3,5-dicarboxamide (80 mg, 0.340 mmol) and (3-methyl-1-tosyl-1H-indol-4-yl)methanol (161 mg, 0.510 mmol) in toluene (2.267 mL) was added triphenylphosphine (268 mg, 1.020 mmol) and DIAD (198 µL, 1.020 mmol). The reaction was stirred at rt under nitrogen. A further portion of (3-methyl-1-tosyl-1H-indol-4-yl)methanol (90 mg, 0.285 mmol) was added as a suspension in toluene (1 mL). The reaction was stirred for 4 days. Further portions of triphenylphosphine (89 mg, 0.340 mmol) and DIAD (66 µL, 0.340 mmol) were added and the reaction stirred for 1.5 h. The reaction mixture was poured onto water (30 mL). The aqueous phase was extracted with ethyl acetate (3×15 mL) and the combined organics were washed with brine (10 mL), dried through a hydrophobic frit and evaporated in vacuo to yield the crude product as a yellow oil (1.376 g). The oil was loaded in dichloromethane onto a SNAP cartridge (50 g) and this was purified via Biotage SP4 flash chromatography, eluting from 0-50% (3:1 ethyl acetate:ethanol)/cyclohexane. The relevant fractions were combined and evaporated in vacuo to give N5-cyclopropyl-N3-methyl-1-((3-methyl-1-tosyl-1H-indol-4-yl)methyl)-2-oxo-1,2-dihydropyridine-3,5-dicarboxamide (61 mg, 0.097 mmol, 28.6% yield) as a white solid.

LCMS (2 min Formic): Rt=1.15 min, [MH]$^+$=533.3.

Intermediate 87: tert-Butyl 4-((5-(cyclopropylcarbamoyl)-3-(methylcarbamoyl)-2-oxopyridin-1(2H)-yl)methyl)indoline-1-carboxylate

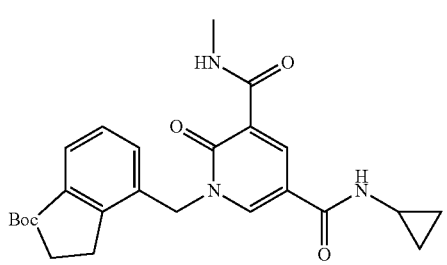

DIAD (0.09 mL, 0.463 mmol) was added to a suspension of N5-cyclopropyl-N3-methyl-2-oxo-1,2-dihydropyridine-3,5-dicarboxamide (50 mg, 0.213 mmol), tert-butyl 4-(hydroxymethyl)indoline-1-carboxylate (79 mg, 0.319 mmol) and triphenylphosphine (117 mg, 0.446 mmol) in toluene (2 mL). The reaction was stirred at rt under N$_2$ for 2 h. tert-Butyl 4-(hydroxymethyl)indoline-1-carboxylate (79 mg, 0.319 mmol), DIAD (0.09 mL, 0.463 mmol) and triphenylphosphine (122 mg, 0.465 mmol) were added and the reaction stirred for 2 h. The reaction was stirred overnight. The reaction was concentrated to give an orange oil (926 mg). This was purified by chromatography on SiO$_2$ (Biotage SNAP 100 g cartridge, eluting with 0-100% EtOAc/cyclohexane). The appropriate fractions were concentrated to give tert-butyl 4-((5-(cyclopropylcarbamoyl)-3-(methylcarbamoyl)-2-oxopyridin-1(2H)-yl)methyl)indoline-1-carboxylate (41 mg, 0.075 mmol, 35.1% yield) as a colourless oil LCMS (2 min Formic): Rt=1.08 min, [MH]$^+$=467.2.

$^1$H NMR (400 MHz, MeOH-d$_4$) δ ppm 8.83 (d, J=2.7 Hz, 1H) 8.47 (d, J=2.7 Hz, 1H) 7.60-7.71 (m, 1H) 7.14 (t, J=7.9 Hz, 1H) 6.73 (d, J=7.6 Hz, 1H) 5.24 (s, 2H) 4.00 (t, J=8.7 Hz, 2H) 3.14 (t, J=8.7 Hz, 2H) 2.93 (s, 3H) 2.80 (tt, J=7.3, 3.7 Hz, 1H) 1.56 (s, 9H) 0.74-0.82 (m, 2H) 0.58-0.65 (m, 2H).

Intermediate 88: (+/−)-N5-Cyclopropyl-N3-methyl-2-oxo-1-(1-(1-tosyl-1H-indol-4-yl)ethyl)-1,2-dihydropyridine-3,5-dicarboxamide

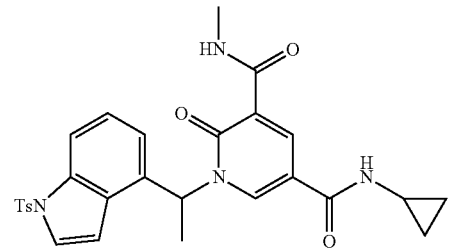 [SMILES: CNC(=O)c1cc(C(=O)NC2CC2)cn(C(C)c2cccc3c2ccn3S(=O)(=O)c2ccc(C)cc2)c1=O]

N5-Cyclopropyl-N3-methyl-2-oxo-1,2-dihydropyridine-3,5-dicarboxamide (53 mg, 0.225 mmol), 4-(1-bromoethyl)-1-tosyl-1H-indole (102 mg, 0.270 mmol), potassium carbonate (52 mg, 0.376 mmol) and DMF (2 mL) were stirred at 90° C. for 5 h and then overnight. Separately, N5-cyclopropyl-N3-methyl-2-oxo-1,2-dihydropyridine-3,5-dicarboxamide (42 mg, 0.179 mmol), 4-(1-bromoethyl)-1-tosyl-1H-indole (102 mg, 0.270 mmol), potassium carbonate (45.0 mg, 0.326 mmol) and DMF (1.5 mL) were stirred at 90° C. for 8 h. The resultant suspensions were combined, partitioned between EtOAc (20 mL) and water (20 mL), extracted with EtOAc (20 mL), dried over a hydrophobic frit and concentrated to give an orange oil. This was purified by chromatography on SiO$_2$ (Biotage SNAP 50 g cartridge, eluting with 0-100% EtOAc/cyclohexane). The appropriate fractions were concentrated to give the desired product (66 mg) as a yellow oil. This was purified by MDAP (High pH, injected in 1 mL, 1:1 DMSO:MeOH). The appropriate fractions were concentrated to give (+/−)-N5-cyclopropyl-N3-methyl-2-oxo-1-(1-(1-tosyl-1H-indol-4-yl)ethyl)-1,2-dihydropyridine-3,5-dicarboxamide (42 mg, 0.071 mmol, 31.5% yield).

LCMS (2 min Formic): Rt=1.15 min, [MH]$^+$=533.1.

Intermediate 89: tert-Butyl 7-((5-(cyclopropylcarbamoyl)-3-(methylcarbamoyl)-2-oxopyridin-1(2H)-yl)methyl)-2-methyl-1H-benzo[d]imidazole-1-carboxylate

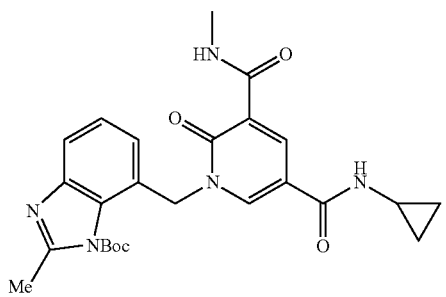 [SMILES: CNC(=O)c1cc(C(=O)NC2CC2)cn(Cc2cccc3nc(C)n(C(=O)OC(C)(C)C)c23)c1=O]

DIAD (0.087 mL, 0.446 mmol) was added to a suspension of N5-cyclopropyl-N3-methyl-2-oxo-1,2-dihydropyridine-3,5-dicarboxamide (50 mg, 0.213 mmol), tert-butyl 4-(hydroxymethyl)-2-methyl-1H-benzo[d]imidazole-1-carboxylate (66.9 mg, 0.255 mmol) and triphenylphosphine (117 mg, 0.446 mmol) in toluene (2 mL). The reaction was stirred at rt under $N_2$ overnight. Further DIAD (0.087 mL, 0.446 mmol) and triphenylphosphine (117 mg, 0.446 mmol) were added and the reaction stirred for 3 h. The reaction was concentrated, loaded in DCM and purified by chromatography on $SiO_2$ (Biotage SNAP 10 g cartridge, eluting with 0-100% EtOAc/cyclohexane). The appropriate fractions were concentrated to give the crude product. This was purified further by MDAP (High pH). The appropriate fractions were combined to give the title compound (14 mg, 0.029 mmol, 13.7% yield)

LCMS (2 min Formic): Rt=1.07 min, [MH]$^+$=480.2.

Intermediate 90: Butyl 5-(methylcarbamoyl)-6-oxo-1-((1,2,3,4-tetrahydroquinolin-8-yl)methyl)-1,6-dihydropyridine-3-carboxylate

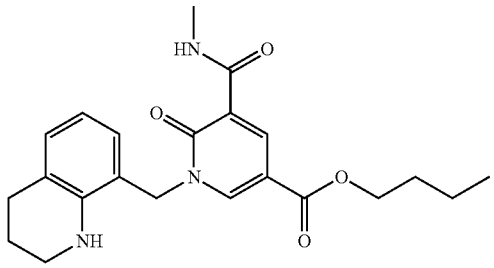 [SMILES: CCCCOC(=O)c1cc(C(=O)NC)c(=O)n(Cc2cccc3c2NCCC3)c1]

DIAD (324 µl, 1.665 mmol) was added to a suspension of butyl 5-(methylcarbamoyl)-6-oxo-1,6-dihydropyridine-3-carboxylate (140 mg, 0.555 mmol), (1,2,3,4-tetrahydroquinolin-8-yl)methanol (136 mg, 0.832 mmol) and triphenylphosphine (437 mg, 1.665 mmol) in toluene (3.7 mL). The reaction was stirred at rt under nitrogen for 1 h. The reaction mixture was poured onto water (30 mL) and the aqueous phase was extracted with ethyl acetate (3×15 mL). The combined organics were washed with brine (10 mL), dried through a hydrophobic frit and evaporated in vacuo to yield the crude product as a yellow oil (1.3704 g). The oil was loaded in dichloromethane onto a 25 g SNAP silica cartridge and purified via Biotage SP4 flash chromatography eluting from 15-75% ethyl acetate/cyclohexane. The relevant fractions were combined and evaporated in vacuo to yield the purified product—butyl 5-(methylcarbamoyl)-6-oxo-1-((1,2,3,4-tetrahydroquinolin-8-yl)methyl)-1,6-dihydropyridine-3-carboxylate (112 mg, 0.248 mmol, 44.7% yield) as a yellow glass.

LCMS (2 min Formic): Rt=1.27 min, [MH]$^+$=398.3.

Intermediate 91: 5-(Methylcarbamoyl)-6-oxo-1-((1,2,3,4-tetrahydroquinolin-8-yl)methyl)-1,6-dihydropyridine-3-carboxylic acid

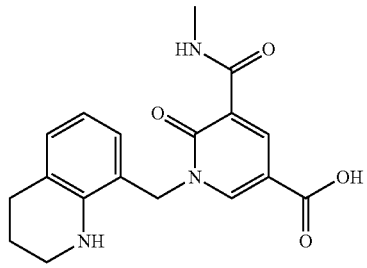 [SMILES: CNC(=O)c1cc(C(=O)O)cn(Cc2cccc3c2NCCC3)c1=O]

Butyl 5-(methylcarbamoyl)-6-oxo-1-((1,2,3,4-tetrahydroquinolin-8-yl)methyl)-1,6-dihydropyridine-3-carboxylate (104 mg, 0.262 mmol) was suspended in 1,4-dioxane (534 µL). Water (534 µL) was added followed by lithium hydroxide (15 mg, 0.626 mmol) and the reaction mixture stirred at rt for 2.5 h. HCl (2M, 0.313 mL) was added and the solvents were evaporated in vacuo to yield the required product 5-(methylcarbamoyl)-6-oxo-1-((1,2,3,4-tetrahydroquinolin-8-yl)methyl)-1,6-dihydropyridine-3-carboxylic acid (134 mg) as a yellow glass. However the sample contained LiCl from work up. Purity estimated at 66%, based on weight, assuming quantitative yield.

LCMS (2 min Formic): Rt=0.84 min, [MH]$^+$=342.1.

Intermediate 92: 6-Methoxy-5-(methylcarbamoyl)nicotinic acid

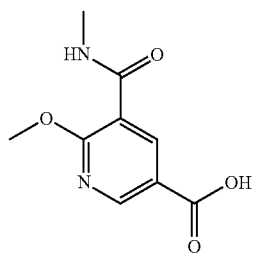

Methyl 6-methoxy-5-(methylcarbamoyl)nicotinate (1.9 g, 8.47 mmol) was taken up in THF (16 mL) and water (16 mL). Lithium hydroxide (0.223 g, 9.32 mmol) was added and the reaction stirred for 16 h at rt. 2M HCl(aq) (4.66 mL, 9.32 mmol) was added and a white precipitate formed, this was filtered and washed with further THF/water (40 mL, 1:1). Both the residue and the filtrate were analysed by LCMS and found to contain product, therefore these were recombined (washing with MeOH) and concentrated in vacuo to afford the desired product as a white solid—6-methoxy-5-(methylcarbamoyl)nicotinic acid (2.84 g). The sample is assumed ~60% purity with the remaining mass due to inorganic impurity (LiCl). This material was used crude in the subsequent reactions.

LCMS (2 min Formic): Rt=0.54 min, [MH]⁺=211.1.

Intermediate 93: 2-Methoxy-N3-methyl-N5-((1S, 2S)-2-methylcyclopropyl)pyridine-3,5-dicarboxamide AND Intermediate 94: 2-Methoxy-N3-methyl-N5-((1R, 2R)-2-methylcyclopropyl)pyridine-3,5-dicarboxamide

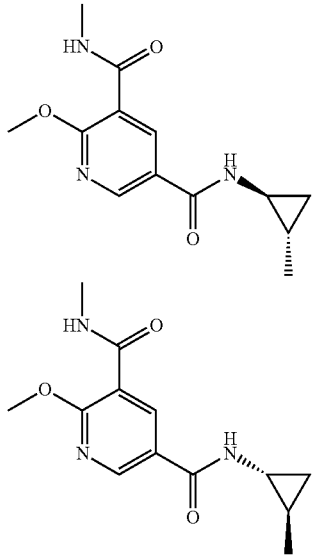

A solution of 6-methoxy-5-(methylcarbamoyl)nicotinic acid (710 mg, 2.027 mmol), HATU (1002 mg, 2.63 mmol) and DIPEA (0.708 mL, 4.05 mmol) in DMF (6 mL) was stirred for 5 min before (+/−)-(trans)-2-methylcyclopropanamine (159 mg, 2.229 mmol) was added. The reaction was stirred for 1 h at rt. The reaction was diluted with EtOAc (30 mL) and water (30 mL) then added and the layers separated. The aqueous layer was further extracted with EtOAc (4×20 mL) and the aqueous layer analysed and found to have only a small amount of product. The combined organics were back-extracted with water (2×10 mL) and brine (10 mL) and the organic phase then dried (Na₂SO₄) and concentrated in vacuo to afford the crude product. This was taken up in DCM and added to a SNAP silica cartridge (25 g) and purified by SP4 flash chromatography, eluting with 0-60% (25% EtOH/EtOAc)/cyclohexane. The appropriate fractions were collected and concentrated in vacuo to afford the crude product as a yellow oil—(+/−)-2-methoxy-N3-methyl-N5-((trans)-2-methylcyclopropyl)pyridine-3,5-dicarboxamide (695 mg, 1.980 mmol, 98% yield). The bulk solid was submitted for chiral separation Analytical Method:
Column: Chiralpak AD-H (250×4.6 mm)
Flow Rate: 1 mL/min
Detection: UV Diode Array at 280 nm (Band width 140 nm, reference 400 nm bandwidth 100 nm)
Mobile Phase A: Heptane
Mobile Phase B: Propan-2-ol
Isocratic method—90:10 Mobile phase A:Mobile phase B
Runtime—30 min Preparative Method:
Sample preparation—Total sample dissolved in 30 mL ethanol with sonication.
Column: Chiralpak AD-H (250×30 mm, 5 micron)
Flow Rate: 42.5 mL/min (pressure 85 bar)
Detection: UV Diode Array at 280 nm (Band width 140 nm, reference 400 nm bandwidth 100 nm)
Mobile Phase A: Heptane
Mobile Phase B: Propan-2-ol
Isocratic method—90:10 mobile phase A:mobile phase B
Runtime—30 min
0.3 mL manual injections via Rheodyne valve.

Fractions containing the first eluting isomer were collected in a 1 L Duran bottle between 12 min and 13 min. Fractions containing the second eluting isomer were collected in a 1 L Duran bottle between 14 min and 16 min. The isomer fractions were evaporated to dryness (Rotavapor, 30° C. bath temperature) and then taken up in ethanol (3×4 mL) and transferred to a tared 20 mL glass vial. A 50 μL sample was taken for final chiral hplc analysis and the bulk sample blown down to dyness under a stream of nitrogen gas. Final chiral HPLC analysis showed the first eluting isomer to be 99.3% chirally pure by UV—2-methoxy-N3-methyl-N5-((1R,2R)-2-methylcyclopropyl)pyridine-3,5-dicarboxamide (190 mg, 0.722 mmol, 35.6% yield).

LCMS (2 min Formic): Rt=0.66 min, [MH]⁺=264.1.

Chiral HPLC analysis of the second eluting isomer showed the presence of 3.1% (by UV) of the first eluting isomer, a shoulder was evident on the major isomer peak thus the exact proportion of the first eluting isomer in the sample could not be accurately assessed—2-methoxy-N3-methyl-N5-((1S,2S)-2-methylcyclopropyl)pyridine-3,5-dicarboxamide (216 mg, 0.820 mmol, 40.5% yield)

LCMS (2 min Formic): Rt=0.66 min, [MH]⁺=264.1.

Intermediate 95: N3-Methyl-N5-((1S,2S)-2-methylcyclopropyl)-2-oxo-1,2-dihydropyridine-3,5-dicarboxamide

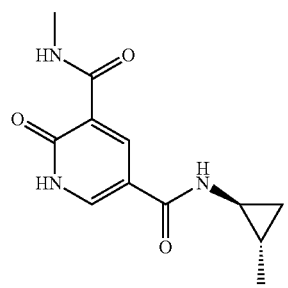 [SMILES: CNC(=O)c1cc(C(=O)N[C@H]2C[C@@H]2C)c[nH]c1=O]

Sodium iodide (166 mg, 1.109 mmol) was added to a solution of 2-methoxy-N3-methyl-N5-((1S,2S)-2-methylcyclopropyl)pyridine-3,5-dicarboxamide (146 mg, 0.555 mmol) and TMS-Cl (0.354 mL, 2.77 mmol) in acetonitrile (3 mL) and the reaction mixture was stirred at rt for 1 h. The reaction mixture was concentrated in vacuo and taken up in DCM (as a suspension) and added to a SNAP silica (25 g) cartridge which was eluted with 0-50% (20% MeOH/DCM)/DCM. The desired fractions were combined and concentrated in vacuo to afford the desired product as a brown solid—N3-methyl-N5-((1S,2S)-2-methylcyclopropyl)-2-oxo-1,2-dihydropyridine-3,5-dicarboxamide (187 mg, 0.548 mmol, 99% yield)

LCMS (2 min Formic): Rt=0.54 min, [MH]⁺=250.1.

Intermediate 96: N3-Methyl-N5-((1R,2R)-2-methyl-cyclopropyl)-2-oxo-1,2-dihydropyridine-3,5-dicarboxamide

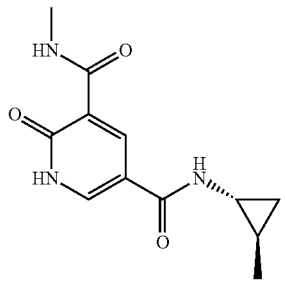 [SMILES: CNC(=O)c1cc(C(=O)N[C@@H]2C[C@H]2C)c[nH]c1=O]

Sodium iodide (56.9 mg, 0.380 mmol) was added to a solution of 2-methoxy-N3-methyl-N5-((1R,2R)-2-methyl-cyclopropyl)pyridine-3,5-dicarboxamide (50 mg, 0.190 mmol) and TMS-Cl (0.121 mL, 0.950 mmol) in acetonitrile (1 mL) and the reaction mixture was stirred at rt for 1 h. The reaction mixture was concentrated in vacuo and taken up in DCM (as a suspension) and added to a SNAP silica 10 g cartridge which was eluted with 0-50% (20% MeOH/DCM)/DCM. The desired fractions were combined and concentrated in vacuo to afford the desired product as a yellow solid—N3-methyl-N5-((1R,2R)-2-methylcyclopropyl)-2-oxo-1,2-dihydropyridine-3,5-dicarboxamide (60 mg). Due to the additional mass, the product is assumed to be contaminated with inorganic impurities, assume 79% purity.

LCMS (2 min Formic): Rt=0.54 min, [MH]⁺=250.1.

Intermediate 97: 5-Bromo-1-(3-fluorobenzyl)-N-methyl-2-oxo-1,2-dihydropyridine-3-carboxamide

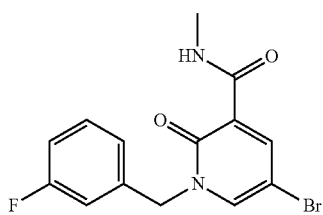

To a solution of 5-bromo-N-methyl-2-oxo-1,2-dihydropyridine-3-carboxamide (150 mg, 0.649 mmol) in methanol (1 mL) was added potassium carbonate (179 mg, 1.298 mmol) and 1-(bromomethyl)-3-fluorobenzene (116 µL, 0.946 mmol). The mixture was heated to 65° C. for 6 h. A further portion of potassium carbonate (90 mg, 0.649 mmol) and 1-(bromomethyl)-3-fluorobenzene (119 µL, 0.974 mmol) were added, and the stirring was continued for a further 2.7 h. The reaction was quenched with water (585 µL, 32.5 mmol), concentrated in vacuo and poured onto water (15 mL). The product was extracted with ethyl acetate (10 mL) and dichloromethane (3×10 mL, due to insolubility in ethyl acetate). The ethyl acetate layer was washed with brine (10 mL), dried through a hydrophobic frit and evaporated in vacuo. To the residue was added the (frit dried) DCM portions, before evaporating again in vacuo to yield the crude product (286 mg). The residue was dry loaded in dichloromethane onto a 25 g SNAP silica cartridge and purified via Biotage SP4 flash chromatography, eluting from 15-75% ethyl acetate/cyclohexane. The relevant fractions were combined and evaporated in vacuo to yield the pure product—5-bromo-1-(3-fluorobenzyl)-N-methyl-2-oxo-1,2-dihydropyridine-3-carboxamide (135 mg, 0.398 mmol, 61.3% yield) as a white solid.

LCMS (2 min Formic): Rt=0.96 min, [MH]⁺=338.9, 340.9.

Intermediate 98: 5-Bromo-1-((6-methoxypyridin-3-yl)methyl)-N-methyl-2-oxo-1,2-dihydropyridine-3-carboxamide

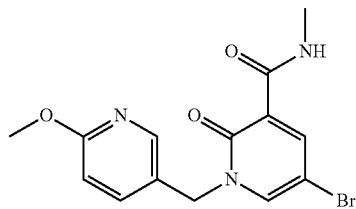 [SMILES: CNC(=O)c1cc(Br)cn(Cc2ccc(OC)nc2)c1=O]

5-(Bromomethyl)-2-methoxypyridine (144 mg, 0.714 mmol) was added to a solution of 5-bromo-N-methyl-2-oxo-1,2-dihydropyridine-3-carboxamide (165 mg, 0.714 mmol) and potassium carbonate (197 mg, 1.428 mmol), in DMF (5 mL). The reaction mixture was left to stir at rt overnight. The reaction mixture was concentrated under vacuum and partitioned between DCM (20 mL) and water (20 mL). The organic solution was concentrated under vacuum, loaded in DCM (3 mL) and purified by Biotage Isolera SNAP 25 g silica flash chromatography using a gradient of 0-100% cyclohexane/ethyl acetate. The appropriate fractions were combined and concentrated under vacuum to give the product (152 mg) as a white solid.

LCMS (2 min Formic): Rt=0.83 min, [MH]⁺=352.0 & 353.9.

Intermediate 99: Methyl 1-(3-acetylbenzyl)-5-(methylcarbamoyl)-6-oxo-1,6-dihydropyridine-3-carboxylate

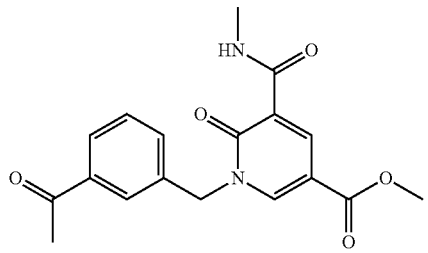 [SMILES: CNC(=O)c1cc(C(=O)OC)cn(Cc2cccc(C(C)=O)c2)c1=O]

To a solution of methyl 5-(methylcarbamoyl)-6-oxo-1,6-dihydropyridine-3-carboxylate (350 mg, 1.665 mmol) in DMF (8.326 mL) was added potassium carbonate (460 mg, 3.33 mmol) and 1-(3-(chloromethyl)phenyl)ethanone (371 µL, 2.498 mmol). The mixture was stirred at rt for 1.3 h. A further portion of 1-(3-(chloromethyl)phenyl)ethanone (124 µL, 0.833 mmol) was added and the reaction stirring was continued for 3.75 h. The reaction was poured onto saturated aqueous lithium chloride (100 mL). The aqueous phase was extracted with ethyl acetate (4×20 mL). The combined organics were washed with brine (10 mL), dried through a hydrophobic frit and evaporated in vacuo to yield the crude product as an orange gum. The residue was loaded in dichloromethane onto a 25 g SNAP silica cartridge and purified via Biotage SP4 flash chromatography, eluting from 15-75% (3:1 ethyl acetate:ethanol)/cyclohexane. The relevant fractions were combined and evaporated in vacuo to yield the product (431 mg) as a colourless gum. This was dissolved in ethyl acetate (60 mL) and washed with water (2×20 mL) and brine (20 mL). The aqueous layer was back extracted with diethyl ether (2×20 mL). The combined organic layers were dried through a hydrophobic frit and evaporated in vacuo to yield—methyl 1-(3-acetylbenzyl)-5-(methylcarbamoyl)-6-oxo-1,6-dihydropyridine-3-carboxylate (420 mg, 1.165 mmol, 70.0% yield) as a white solid.

LCMS (2 min Formic): Rt=0.82 min, [MH]$^+$=343.1.

Intermediate 100: 1-(3-Acetylbenzyl)-5-(methylcarbamoyl)-6-oxo-1,6-dihydropyridine-3-carboxylic acid

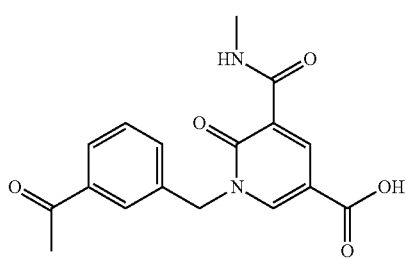 [SMILES: CNC(=O)c1cc(C(=O)O)cn(Cc2cccc(C(C)=O)c2)c1=O]

Methyl 1-(3-acetylbenzyl)-5-(methylcarbamoyl)-6-oxo-1,6-dihydropyridine-3-carboxylate (355 mg, 1.037 mmol) was suspended in 1,4-dioxane (3.116 mL). Water (2.116 mL) was added followed by lithium hydroxide (62.1 mg, 2.59 mmol) and the reaction mixture stirred at rt for 1 h. HCl (2M, 1.295 mL) was added and the solvents were evaporated in vacuo to yield the required product—1-(3-acetylbenzyl)-5-(methylcarbamoyl)-6-oxo-1,6-dihydropyridine-3-carboxylic acid (503 mg) as a white solid. However the sample contained LiCl from work up. Purity estimated at 67%, based on weight, assuming quantitative yield.

LCMS (2 min Formic): Rt=0.72 min, [MH]$^+$=329.1.

Intermediate 101: rac-Butyl 5-(methylcarbamoyl)-6-oxo-1-(1-(m-tolyl)ethyl)-1,6-dihydropyridine-3-carboxylate

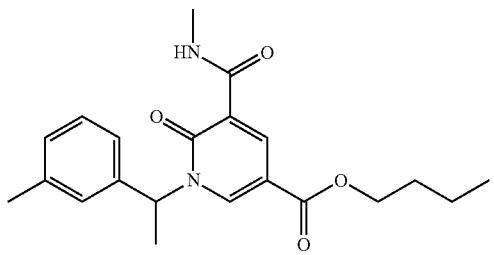 [SMILES: CCCCOC(=O)c1cc(C(=O)NC)c(=O)n(C(C)c2cccc(C)c2)c1]

Butyl 5-(methylcarbamoyl)-6-oxo-1,6-dihydropyridine-3-carboxylate (158 mg, 0.626 mmol), 1-(1-bromoethyl)-3-methylbenzene (197 mg, 0.990 mmol), potassium carbonate (172 mg, 1.245 mmol) and DMF (1.4 mL) were stirred at 90° C. for 1 h. LiCl solution (20 mL) was added and reaction mixture was partitioned between EtOAc (40 mL) and water (40 mL). The aqueous phase was extracted with EtOAc (2×40 mL) and the combined organic layers were dried over a hydrophobic frit and concentrated to give 299 mg of a yellow oil. This was purified by chromatography on SiO$_2$ (Biotage SNAP 25 g cartridge, eluting with 0-50% EtOAc/cyclohexane). The appropriate fractions were concentrated to give rac-butyl 5-(methylcarbamoyl)-6-oxo-1-(1-(m-tolyl)ethyl)-1,6-dihydropyridine-3-carboxylate (193 mg, 0.469 mmol, 74.9% yield) as a white solid.

LCMS (2 min Formic): Rt=1.28 min, [MH]+=371.

Intermediate 102: rac-5-(Methylcarbamoyl)-6-oxo-1-(1-(m-tolyl)ethyl)-1,6-dihydropyridine-3-carboxylic acid

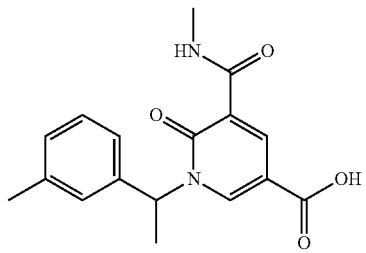 [SMILES: CNC(=O)c1cc(C(=O)O)cn(C(C)c2cccc(C)c2)c1=O]

Butyl 5-(methylcarbamoyl)-6-oxo-1-(1-(m-tolyl)ethyl)-1,6-dihydropyridine-3-carboxylate (200 mg, 0.540 mmol), lithium hydroxide (39 mg, 1.629 mmol), 1,4-dioxane (2 mL) and water (2 mL) were stirred at rt for 1 h. Acetic acid (1 mL, 17.47 mmol) was added and the solution was partitioned between EtOAc (20 mL) and water (20 mL), the aqueous phase was extracted with EtOAc (2×20 mL), dried over a hydrophobic frit and concentrated to give rac-5-(methylcarbamoyl)-6-oxo-1-(1-(m-tolyl)ethyl)-1,6-dihydropyridine-3-carboxylic acid (188 mg, 0.538 mmol, 100% yield) as a white solid.

LCMS (2 min Formic): Rt=0.94 min, [MH]+=315.

Intermediate 103: rac-Butyl 5-(methylcarbamoyl)-6-oxo-1-(1-(o-tolyl)ethyl)-1,6-dihydropyridine-3-carboxylate

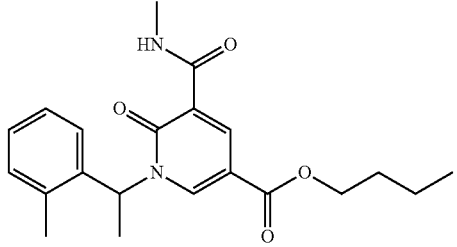 [SMILES: CCCCOC(=O)c1cc(C(=O)NC)c(=O)n(C(C)c2ccccc2C)c1]

Butyl 5-(methylcarbamoyl)-6-oxo-1,6-dihydropyridine-3-carboxylate (300 mg, 1.189 mmol), 1-(1-bromoethyl)-2-methylbenzene (670 mg, 3.37 mmol), potassium carbonate (329 mg, 2.378 mmol) and DMF (4 mL) were stirred at 90° C. for 1 h. The reaction mixture was washed with LiCl solution (20 mL) and partitioned between EtOAc (20 mL) and water (20 mL). The aqueous phase was extracted with EtOAc (2×20 mL) and the combined organic layers were dried over a hydrophobic frit and concentrated to give 790 mg of an orange oil. This was purified by chromatography on SiO₂ (Biotage SNAP 100 g cartridge, eluting with 0-100% EtOAc/cyclohexane). The appropriate fractions were concentrated to give rac-butyl 5-(methylcarbamoyl)-6-oxo-1-(1-(o-tolyl)ethyl)-1,6-dihydropyridine-3-carboxylate (410 mg, 0.996 mmol, 84% yield) as a colourless oil.

LCMS (2 min Formic): Rt=1.28 min, [MH]+=371.

Intermediate 104: rac-5-(Methylcarbamoyl)-6-oxo-1-(1-(o-tolyl)ethyl)-1,6-dihydropyridine-3-carboxylic acid

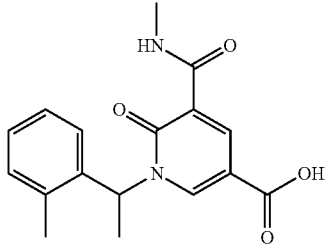 [SMILES: CNC(=O)c1cc(C(=O)O)cn(C(C)c2ccccc2C)c1=O]

Butyl 5-(methylcarbamoyl)-6-oxo-1-(1-(o-tolyl)ethyl)-1,6-dihydropyridine-3-carboxylate (410 mg, 1.107 mmol), lithium hydroxide (82 mg, 3.42 mmol), 1,4-dioxane (3 mL) and water (3 mL) were stirred at rt for 1 h. Acetic acid (1 mL, 17.47 mmol) was added and the solution was partitioned between EtOAc (20 mL) and water (20 mL), the aqueous phase was extracted with EtOAc (2×20 mL) and the combined organic layers were dried over a hydrophobic frit and concentrated to give rac-5-(methylcarbamoyl)-6-oxo-1-(1-(o-tolyl)ethyl)-1,6-dihydropyridine-3-carboxylic acid (438 mg, 1.254 mmol, 113% yield) as a colourless oil.

LCMS (2 min Formic): Rt=0.92 min, [MH]+=315.

Intermediate 105: Butyl 1-(3-methoxybenzyl)-5-(methylcarbamoyl)-6-oxo-1,6-dihydropyridine-3-carboxylate

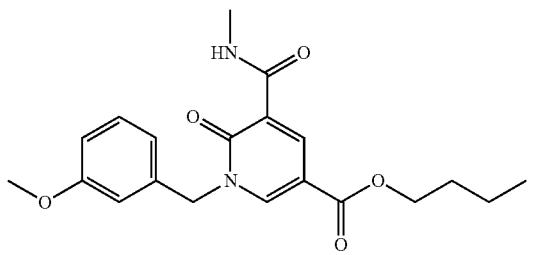 [SMILES: CCCCOC(=O)c1cc(C(=O)NC)c(=O)n(Cc2cccc(OC)c2)c1]

Butyl 5-(methylcarbamoyl)-6-oxo-1,6-dihydropyridine-3-carboxylate (198 mg, 0.785 mmol), 1-(bromomethyl)-3-methoxybenzene (0.165 mL, 1.177 mmol), potassium carbonate (220 mg, 1.592 mmol) and DMF (2 mL) were stirred at 90° C. for 1 h. The reaction mixture was washed with LiCl solution (20 mL), partitioned between EtOAc (40 mL) and water (40 mL) and the aqueous phase was extracted with EtOAc (2×40 mL). The combined organic layers were dried over a hydrophobic frit and concentrated to give 680 mg of an orange oil. This was purified by chromatography on SiO₂ (Biotage SNAP 100 g cartridge, eluting with 0-80% EtOAc/cyclohexane). The appropriate fractions were concentrated to give butyl 1-(3-methoxybenzyl)-5-(methylcarbamoyl)-6-oxo-1,6-dihydropyridine-3-carboxylate (266 mg, 0.643 mmol, 82% yield) as a white solid.

LCMS (2 min Formic): Rt=1.15 min, [MH]+=373.

Intermediate 106: 1-(3-Hydroxybenzyl)-5-(methylcarbamoyl)-6-oxo-1,6-dihydropyridine-3-carboxylic acid

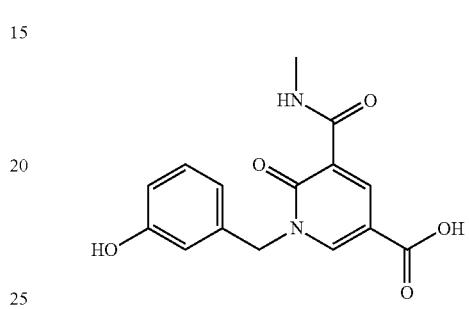

Butyl 1-(3-methoxybenzyl)-5-(methylcarbamoyl)-6-oxo-1,6-dihydropyridine-3-carboxylate (135 mg, 0.362 mmol) in DCM (0.6 mL) was cooled to 0° C. under N₂ and BBr₃ (1.8 mL, 1M in DCM, 1.800 mmol) was added dropwise. After 2 h the reaction was warmed to rt and more BBr₃ (1.8 mL, 1M in DCM, 1.800 mmol) was added. After stirring for a further 2 h, the reaction was quenched with methanol (20 mL) and concentrated. This was repeated three times to give crude 1-(3-hydroxybenzyl)-5-(methylcarbamoyl)-6-oxo-1,6-dihydropyridine-3-carboxylic acid (157 mg, 0.390 mmol, 107% yield) as an orange solid.

LCMS (2 min Formic): Rt=0.66 min, [MH]+=303.

Intermediate 107: N5-Cyclopropyl-1-(3-hydroxybenzyl)-N3-methyl-2-oxo-1,2-dihydropyridine-3,5-dicarboxamide

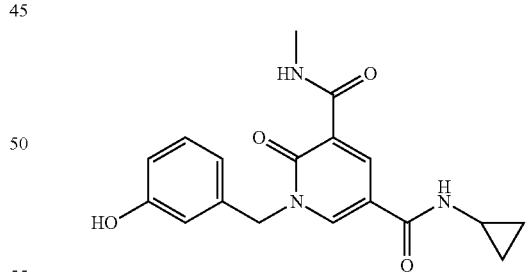

1-(3-Hydroxybenzyl)-5-(methylcarbamoyl)-6-oxo-1,6-dihydropyridine-3-carboxylic acid (158 mg, 0.392 mmol), HATU (222 mg, 0.584 mmol), DIPEA (0.28 mL, 1.603 mmol), cyclopropanamine (0.054 mL, 0.784 mmol) and DMF (2 mL) were stirred at rt under N₂ for 1 h. LiCl solution (20 mL) was added and the reaction mixture was partitioned between EtOAc (20 mL) and water (20 mL), the aqueous phase was extracted with EtOAc (2×20 mL) and the combined organic layers dried over a hydrophobic frit and concentrated to give 476 mg of a yellow oil. This was purified by chromatography on SiO₂ (Biotage SNAP 50 g cartridge, eluting with 0-100% (25% EtOH in EtOAc)/cyclohexane). The appropriate fractions were concentrated to give 147 mg of a white solid. This was further purified by MDAP (Formic). The appropriate fractions were concentrated to give N5-cyclopropyl-1-(3-hydroxybenzyl)-N3-methyl-2-oxo-1,2-dihydropyridine-3,5-dicarboxamide (46 mg, 0.121 mmol, 30.9% yield) as the desired product.

LCMS (2 min Formic): Rt=0.69 min, [MH]+=342.

Intermediate 108: 5-Bromo-1-(3-chlorobenzyl)-N-methyl-2-oxo-1,2-dihydropyridine-3-carboxamide

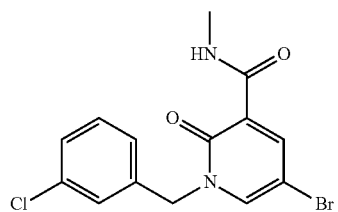 [SMILES: CNC(=O)c1cc(Br)cn(Cc2cccc(Cl)c2)c1=O]

1-(Bromomethyl)-3-chlorobenzene (0.097 mL, 0.736 mmol) was added to a suspension of 5-bromo-N-methyl-2-oxo-1,2-dihydropyridine-3-carboxamide (170 mg, 0.736 mmol) and potassium carbonate (203 mg, 1.472 mmol) in DMF (5 mL). The reaction mixture was left to stir at rt for 2 h. The reaction mixture was concentrated under vacuum and partitioned between DCM (20 mL) and water (20 mL). The organic layer was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (220 mg) as a white solid.

LCMS (2 min Formic): Rt=1.06 min, [MH]+=354.9 & 356.9.

Intermediate 109: 5-Bromo-1-(4-fluorobenzyl)-N-methyl-2-oxo-1,2-dihydropyridine-3-carboxamide

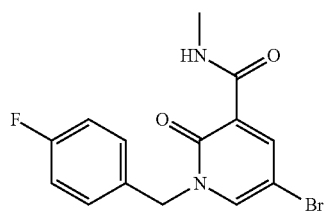 [SMILES: CNC(=O)c1cc(Br)cn(Cc2ccc(F)cc2)c1=O]

To a solution of 5-bromo-N-methyl-2-oxo-1,2-dihydropyridine-3-carboxamide (150 mg, 0.649 mmol) in methanol (3 mL) was added potassium carbonate (179 mg, 1.298 mmol) and 1-(bromomethyl)-4-fluorobenzene (118 µL, 0.947 mmol). The mixture was heated to 65° C. for 10.5 h. Heating was suspended over the weekend. Following this, a further portion of 1-(bromomethyl)-4-fluorobenzene (81 µL, 0.649 mmol) and potassium carbonate (90 mg, 0.649 mmol) were added and heating was continued for a further 5 h. A further portion of 1-(bromomethyl)-4-fluorobenzene (81 µL, 0.649 mmol) was added and the reaction was continued for 2.5 h. The reaction was quenched with water (585 µL, 32.5 mmol), concentrated in vacuo and poured onto water (20 mL). The product was extracted with ethyl acetate (4×10 mL). The combined organics were washed with brine, dried through a hydrophobic frit and evaporated in vacuo to yield the crude product (336 mg). The residue was loaded in dichloromethane and purified via Biotage SP4 flash chromatography, eluting from 15-75% ethyl acetate/cyclohexane. The relevant fractions were combined and evaporated in vacuo to yield the pure product—5-bromo-1-(4-fluorobenzyl)-N-methyl-2-oxo-1,2-dihydropyridine-3-carboxamide (127 mg, 0.374 mmol, 57.7% yield) as a white solid.

LCMS (2 min Formic): Rt=0.96 min, [MH]+=339.0, 341.0.

Intermediate 110: 5-Bromo-1-(3-(bromomethyl)benzyl)-N-methyl-2-oxo-1,2-dihydropyridine-3-carboxamide

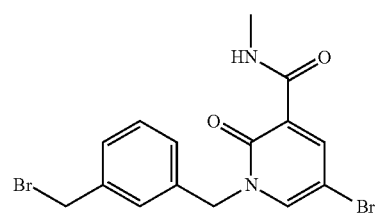 [SMILES: CNC(=O)c1cc(Br)cn(Cc2cccc(CBr)c2)c1=O]

5-Bromo-N-methyl-2-oxo-1,2-dihydropyridine-3-carboxamide (118 mg, 0.511 mmol), 1,3-bis(bromomethyl)benzene (162 mg, 0.613 mmol) and potassium carbonate (106 mg, 0.766 mmol) were suspended in acetonitrile (2 mL) and the reaction mixture stirred at 65° C. under $N_2$ for 2 h. The reaction was heated further at 80° C. overnight. The reaction mixture was used crude in subsequent reactions with no further purification.

LCMS (2 min Formic): Rt=1.07 min, [MH]+=415.0.

Intermediate 111: 5-Bromo-N-methyl-1-(3-(morpholinomethyl)benzyl)-2-oxo-1,2-dihydropyridine-3-carboxamide

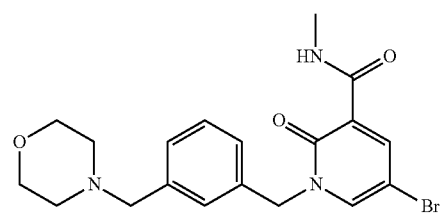 [SMILES: CNC(=O)c1cc(Br)cn(Cc2cccc(CN3CCOCC3)c2)c1=O]

A crude solution of 5-bromo-1-(3-(bromomethyl)benzyl)-N-methyl-2-oxo-1,2-dihydropyridine-3-carboxamide (118 mg, 0.285 mmol) (assumed input mass from estimated purity of preceding step, containing unreacted SM and other impurities) in acetonitrile (2 mL) and morpholine (124 mg, 1.425 mmol) was added. The reaction mixture was heated at 70° C. under $N_2$. The reaction mixture was concentrated and suspended in MeOH. This was loaded onto a 2 g SCX cartridge (pre-eluted with MeOH) and eluted with MeOH (40 mL) followed by 2M $NH_3$ in MeOH (40 mL). All fractions were combined and concentrated to give 318 mg of crude pale yellow solid. This was purified by chromatography on $SiO_2$ (Biotage SNAP 25 g cartridge, eluting with 0-100% (25% ethanol/ethyl acetate)/cyclohexane over 330 mL). The fractions containing the desired product were combined and concentrated in vacuo to give 5-bromo-N-methyl-1-(3-(morpholinomethyl)benzyl)-2-oxo-1,2-dihydropyridine-3-carboxamide (79 mg, 0.188 mmol, 66.0% yield) as a colourless oil.

LCMS (2 min Formic): Rt=0.45 min, [MH]⁺=420, 422.

Intermediate 112: 5-Bromo-N-methyl-2-oxo-1-(quinoxalin-5-ylmethyl)-1,2-dihydropyridine-3-carboxamide

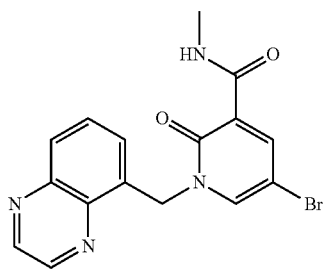 [SMILES: CNC(=O)c1cc(Br)cn(Cc2cccc3nccnc23)c1=O]

5-Bromo-N-methyl-2-oxo-1,2-dihydropyridine-3-carboxamide (213 mg, 0.922 mmol), 5-(bromomethyl)quinoxaline (308 mg, 1.383 mmol), potassium carbonate (254 mg, 1.838 mmol) and methanol (2 mL) were stirred at 65° C. for 1 h. The resulting solution was concentrated to give 815 mg of an orange solid. This was partitioned between EtOAc (10 mL) and water (10 mL). The aqueous phase was extracted with EtOAc (2×20 mL), dried over a hydrophobic frit and concentrated to give 400 mg of a brown oil. This was purified by chromatography on SiO₂ (Biotage SNAP 50 g cartridge, eluting with 0-100% ethyl acetate/cyclohexane). The appropriate fractions were concentrated to give 5-bromo-N-methyl-2-oxo-1-(quinoxalin-5-ylmethyl)-1,2-dihydropyridine-3-carboxamide (127 mg, 0.306 mmol, 33.2% yield) as an orange solid.

LCMS (2 min Formic): Rt=0.87 min, [MH]⁺=373, 375.

Intermediate 113: 5-Bromo-1-(4-methoxybenzyl)-N-methyl-2-oxo-1,2-dihydropyridine-3-carboxamide

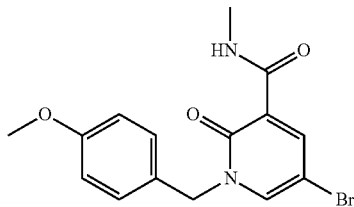 [SMILES: CNC(=O)c1cc(Br)cn(Cc2ccc(OC)cc2)c1=O]

5-Bromo-N-methyl-2-oxo-1,2-dihydropyridine-3-carboxamide (205 mg, 0.887 mmol), 1-(bromomethyl)-4-methoxybenzene (274 mg, 1.363 mmol), potassium carbonate (250 mg, 1.809 mmol) and methanol (2 mL) were stirred at 65° C. under N₂ for 1.5 h. A further portion of 1-(bromomethyl)-4-methoxybenzene (324 mg, 1.611 mmol) was added and reaction mixture was stirred overnight. The resulting solution was concentrated to give an orange solid. This was partitioned between EtOAc (10 mL) and water (10 mL), the aqueous phase was extracted with EtOAc (2×20 mL), dried over a hydrophobic frit and concentrated to give 650 mg of an orange oil. This was purified by chromatography on SiO₂ (Biotage SNAP 50 g cartridge, eluting with 0-100% diethylether/cyclohexane). The appropriate fractions were concentrated to give 5-bromo-1-(4-methoxybenzyl)-N-methyl-2-oxo-1,2-dihydropyridine-3-carboxamide (85 mg, 0.218 mmol, 24.55% yield) as a white solid LCMS (2 min Formic): Rt=0.97 min, [MH]⁺=351, 353.

Intermediate 114: 1-((1H-Indazol-4-yl)methyl)-5-bromo-N-methyl-2-oxo-1,2-dihydropyridine-3-carboxamide

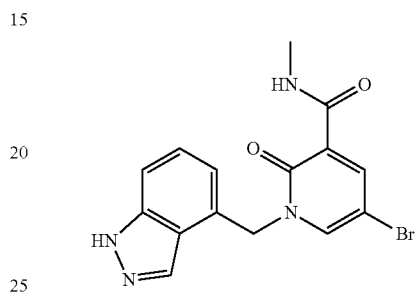

5-Bromo-N-methyl-2-oxo-1,2-dihydropyridine-3-carboxamide (130 mg, 0.563 mmol), 4-(bromomethyl)-1H-indazole, hydrobromide (214 mg, 0.731 mmol), potassium carbonate (223 mg, 1.614 mmol) and DMF (4 mL) were stirred at 90° C. for 2 h. LiCl solution (20 mL) was added and reaction mixture was partitioned between EtOAc (20 mL) and water (20 mL). The aqueous phase was extracted with EtOAc (2×20 mL), dried over a hydrophobic frit and concentrated to give 430 mg of an orange oil. This was purified by chromatography on SiO₂ (Biotage SNAP 50 g cartridge, eluting with 0-100% (25% EtOH in EtOAc)/cyclohexane). The appropriate fractions were concentrated to give 1-((1H-indazol-4-yl)methyl)-5-bromo-N-methyl-2-oxo-1,2-dihydropyridine-3-carboxamide (234 mg, 0.453 mmol, 81% yield) as a colourless oil.

LCMS (2 min Formic): Rt=0.78 min, [MH]⁺=361, 363.

Intermediate 115: 1-((1H-Indazol-7-yl)methyl)-5-bromo-N-methyl-2-oxo-1,2-dihydropyridine-3-carboxamide

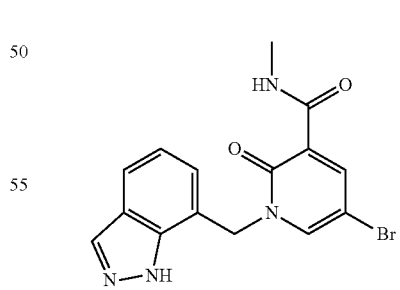

5-Bromo-N-methyl-2-oxo-1,2-dihydropyridine-3-carboxamide (312 mg, 1.350 mmol), 7-(bromomethyl)-1H-indazole, hydrobromide (415 mg, 1.421 mmol), potassium carbonate (558 mg, 4.04 mmol) and DMF (5 mL) were stirred at 90° C. for 1 h. LiCl solution (20 mL) was added and the reaction mixture was partitioned between EtOAc (20 mL) and water (20 mL), the aqueous phase was extracted with EtOAc (2×20 mL), dried over a hydrophobic frit and concentrated to give a cream solid. This was purified by chromatography on SiO₂ (Biotage SNAP 50 g cartridge, eluting with 0-60% (25% EtOH in EtOAc)/cyclohexane). The appropriate fractions were concentrated to give 1-((1H-indazol-7-yl)methyl)-5-bromo-N-methyl-2-oxo-1,2-dihydropyridine-3-carboxamide (396 mg, 0.877 mmol, 65.0% yield) as an off white solid.

LCMS (2 min Formic): Rt=0.86 min, [MH]⁺=361, 363.

Intermediate 116: 1-Benzyl-5-bromo-N-cyclopropyl-2-oxo-1,2-dihydropyridine-3-carboxamide

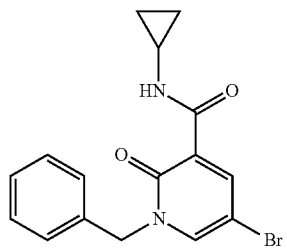 [SMILES: O=C(NC1CC1)c1cc(Br)cn(Cc2ccccc2)c1=O]

1-Benzyl-5-bromo-2-oxo-1,2-dihydropyridine-3-carboxylic acid (1.09 g, 3.54 mmol) was dissolved in DCM (10 mL) and oxalyl chloride (0.929 mL, 10.61 mmol) and DMF (0.014 mL, 0.177 mmol) were added, then the mixture stirred at rt for 1 h. The solution was concentrated under vacuum and dissolved in THF (10 mL), cyclopropanamine (0.735 mL, 10.61 mmol) was added to the solution. The mixture was stirred for 2 h, then evaporated in vacuo and the residue partitioned between DCM (50 mL) and saturated sodium bicarbonate solution. The organic layer was washed with brine, dried and evaporated in vacuo to give the product (1.07 g) as an orange solid.

LCMS (2 min Formic): Rt=1.07 min, MH+=346.9 & 348.9.

Intermediate 117: 5-Bromo-1-(4-fluoro-3-methylbenzyl)-N-methyl-2-oxo-1,2-dihydropyridine-3-carboxamide

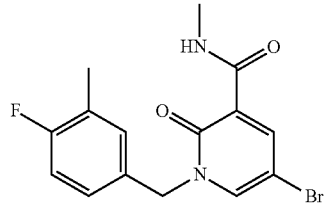 [SMILES: CNC(=O)c1cc(Br)cn(Cc2ccc(F)c(C)c2)c1=O]

5-Bromo-N-methyl-2-oxo-1,2-dihydropyridine-3-carboxamide (195 mg, 0.844 mmol), potassium carbonate (233 mg, 1.688 mmol) in a solution of DMF (5 mL) were stirred at rt and 4-(bromomethyl)-1-fluoro-2-methylbenzene (257 mg, 1.266 mmol) was added dropwise. The reaction mixture was allowed to stir at rt for 3 h. The reaction mixture was concentrated under vacuum, redissolved in ethyl acetate (30 mL) and washed with water (30 mL). The solution was concentrated under vacuum, loaded in DCM and purified by Biotage Isolera SNAP 25 g silica flash chromatography using a gradient of 0-55% cyclohexane/ethyl acetate. The appropriate fractions were combined and concentrated under vacuum to give the product (188 mg).

LCMS (2 min Formic): Rt=1.07 min, [MH]⁺=353.0 & 355.0.

Intermediate 118: 5-Bromo-1-(2-fluoro-3-methylbenzyl)-N-methyl-2-oxo-1,2-dihydropyridine-3-carboxamide

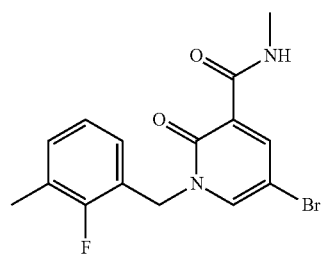 [SMILES: CNC(=O)c1cc(Br)cn(Cc2cccc(C)c2F)c1=O]

1-(Bromomethyl)-2-fluoro-3-methylbenzene (176 mg, 0.866 mmol) was added to a suspension of 5-bromo-N-methyl-2-oxo-1,2-dihydropyridine-3-carboxamide (200 mg, 0.866 mmol) and potassium carbonate (239 mg, 1.731 mmol), in DMF (5 mL). The reaction mixture was left to stir at rt for 2 h. The reaction mixture was concentrated under vacuum and partitioned between DCM (20 mL) and water (20 mL). The organic solution was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (200 mg).

LCMS (2 min Formic): Rt=1.08 min, MH+=353.0 & 354.9.

Intermediate 119: 5-Bromo-1-(3,5-dimethylbenzyl)-N-methyl-2-oxo-1,2-dihydropyridine-3-carboxamide

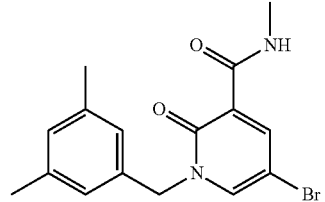 [SMILES: CNC(=O)c1cc(Br)cn(Cc2cc(C)cc(C)c2)c1=O]

1-(Bromomethyl)-3,5-dimethylbenzene (155 mg, 0.779 mmol) was added to a solution of 5-bromo-N-methyl-2-oxo-1,2-dihydropyridine-3-carboxamide (180 mg, 0.779 mmol) and potassium carbonate (215 mg, 1.558 mmol), in DMF (5 mL). The reaction mixture was left to stir at rt for 2 h. The reaction mixture was concentrated under vacuum and partitioned between DCM (20 mL) and water (20 mL). The organic solution was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (160 mg) as a solid.

LCMS (2 min formic): Rt=1.14 min, [MH]⁺=349.0 & 351.0.

Intermediate 120: 5-Bromo-1-(2-fluoro-5-methyl-benzyl)-N-methyl-2-oxo-1,2-dihydropyridine-3-carboxamide

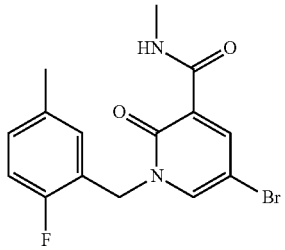 [SMILES: CNC(=O)c1cc(Br)cn(Cc2cc(C)ccc2F)c1=O]

2-(Bromomethyl)-1-fluoro-4-methylbenzene (0.264 mL, 1.948 mmol) was added to a suspension of 5-bromo-N-methyl-2-oxo-1,2-dihydropyridine-3-carboxamide (300 mg, 1.298 mmol) and potassium carbonate (359 mg, 2.60 mmol) in DMF (5 mL). The reaction mixture was stirred under nitrogen for 1 h. The reaction mixture was partitioned between ethyl acetate and water and the organic layer washed with 2× water. The organic layer was passed through a hydrophobic frit and the solvent removed under reduced pressure. The yellow oil was dissolved in DCM and loaded onto a 25 g Biotage SNAP column which was eluted in cyclohexane:ethyl acetate (0-75%). The product containing fractions were combined and the solvent removed under reduced pressure to give the product (330 mg) as a pale yellow solid.

LCMS (2 min Formic): Rt=1.07 min, [MH]⁺=352.9 & 354.9

Intermediate 121: 5-Bromo-N-methyl-2-oxo-1-(quinolin-8-ylmethyl)-1,2-dihydropyridine-3-carboxamide

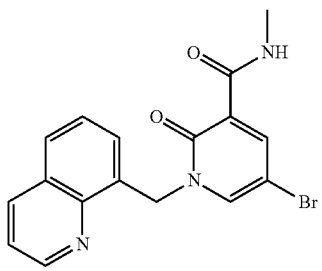 [SMILES: CNC(=O)c1cc(Br)cn(Cc2cccc3cccnc23)c1=O]

8-(Bromomethyl)quinoline (288 mg, 1.298 mmol) was added to a solution of 5-bromo-N-methyl-2-oxo-1,2-dihydropyridine-3-carboxamide (200 mg, 0.866 mmol) and potassium carbonate (239 mg, 1.731 mmol), in DMF (5 mL). The reaction mixture was left to stir at rt overnight. The reaction mixture was concentrated under vacuum and partitioned between DCM (20 mL) and water (20 mL). The organic layer was concentrated under vacuum, loaded in DCM (3 mL) and purified by Biotage Isolera SNAP 25 g silica flash chromatography using a gradient of 0-80% cyclohexane/ethyl acetate. The appropriate fractions were combined and concentrated under vacuum to give the product (220 mg).

LCMS (2 min Formic): Rt=1.01 min, [MH]⁺=372.1 & 374.1.

Intermediate 122: tert-Butyl 5-((5-(methoxycarbonyl)-3-(methylcarbamoyl)-2-oxopyridin-1(2H)-yl)methyl)-3,4-dihydroisoquinoline-2(1H)-carboxylate

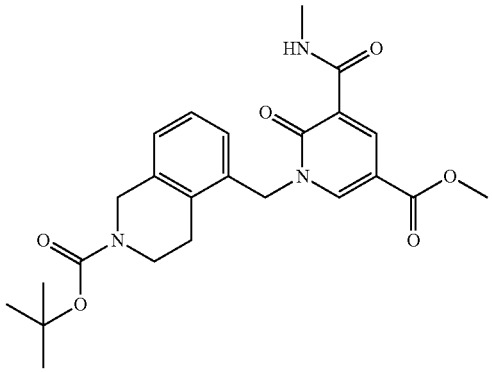 [SMILES: CNC(=O)c1cc(C(=O)OC)cn(Cc2cccc3c2CCN(C(=O)OC(C)(C)C)C3)c1=O]

DIAD (0.11 mL, 0.566 mmol) was added to a suspension of methyl 5-(methylcarbamoyl)-6-oxo-1,6-dihydropyridine-3-carboxylate (60 mg, 0.285 mmol), tert-butyl 5-(hydroxymethyl)-3,4-dihydroisoquinoline-2(1H)-carboxylate (110 mg, 0.418 mmol) and triphenylphosphine (152 mg, 0.580 mmol) in toluene (2 mL). The reaction was stirred at rt under N₂ for 1 h. Further portions of DIAD (0.11 mL, 0.566 mmol) and triphenylphosphine (150 mg, 0.571 mmol) were added and the reaction mixture stirred for a further 1 h. Further portions of DIAD (0.11 mL, 0.566 mmol) and triphenylphosphine (150 mg, 0.571 mmol) were added and reaction mixture was stirred for a further 1 h. The reaction was partitioned between EtOAc (20 mL) and water (20 mL), the aqueous layer was extracted with EtOAc (2×20 mL) and the combined organic layers were dried over a hydrophobic frit and concentrated to give 1.3 g of an orange oil. This was purified by chromatography on SiO₂ (Biotage SNAP 100 g cartridge, eluting with 0-100% ethyl acetate/cyclohexane). The appropriate fractions were concentrated to give tert-butyl 5-((5-(methoxycarbonyl)-3-(methylcarbamoyl)-2-oxopyridin-1(2H)-yl)methyl)-3,4-dihydroisoquinoline-2 (1H)-carboxylate (522 mg, 0.236 mmol, 83% yield) as a white solid.

LCMS (2 min Formic): Rt=1.13 min, [MH]+=456.3.

Intermediate 123: 1-((2-(tert-Butoxycarbonyl)-1,2,3,4-tetrahydroisoquinolin-5-yl)methyl)-5-(methylcarbamoyl)-6-oxo-1,6-dihydropyridine-3-carboxylic acid

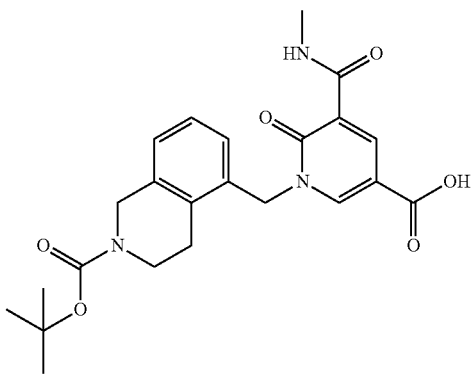 [SMILES: CNC(=O)c1cc(C(=O)O)cn(Cc2cccc3c2CCN(C(=O)OC(C)(C)C)C3)c1=O]

tert-Butyl 5-((5-(methoxycarbonyl)-3-(methylcarbamoyl)-2-oxopyridin-1(2H)-yl)methyl)-3,4-dihydroisoquinoline-2(1H)-carboxylate (522 mg, 0.241 mmol), lithium hydroxide (25 mg, 1.044 mmol), 1,4-dioxane (3 mL) and water (3 mL) were stirred at rt for 1 h. The solution was diluted with sat. aq. sodium bicarbonate (20 mL) and extracted with EtOAc (2×20 mL), the aqueous layer was then acidified to pH 4 with acetic acid and was then extracted with EtOAc (3×20 mL). The combined organic layers were dried over a hydrophobic frit and concentrated to give 1-((2-(tert-butoxycarbonyl)-1,2,3,4-tetrahydroisoquinolin-5-yl)methyl)-5-(methylcarbamoyl)-6-oxo-1,6-dihydropyridine-3-carboxylic acid (71 mg, 0.145 mmol, 60.1% yield) LCMS (2 min Formic): Rt=1.03 min, [MH]+=442.

Intermediate 124: tert-Butyl 5-((5-(cyclopropylcarbamoyl)-3-(methylcarbamoyl)-2-oxopyridin-1(2H)-yl)methyl)-3,4-dihydroisoquinoline-2(1H)-carboxylate

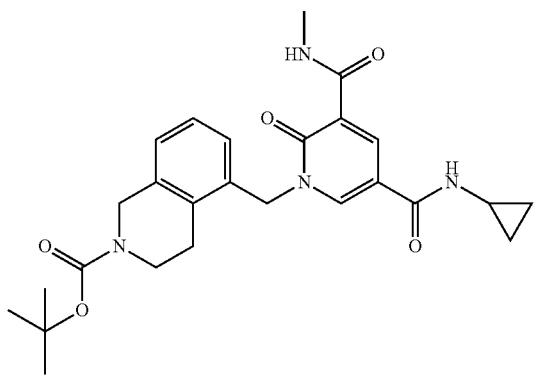 [SMILES: CNC(=O)c1cc(C(=O)NC2CC2)cn(Cc2cccc3c2CCN(C(=O)OC(C)(C)C)C3)c1=O]

1-((2-(tert-Butoxycarbonyl)-1,2,3,4-tetrahydroisoquinolin-5-yl)methyl)-5-(methylcarbamoyl)-6-oxo-1,6-dihydropyridine-3-carboxylic acid (67 mg, 0.152 mmol), HATU (88 mg, 0.231 mmol), DIPEA (0.08 mL, 0.458 mmol), cyclopropanamine (0.03 mL, 0.433 mmol) and DMF (1 mL) were stirred at rt under N$_2$ for 2 h. Further portions of HATU (92 mg, 0.242 mmol), DIPEA (0.08 mL, 0.458 mmol) and cyclopropanamine (0.03 mL, 0.433 mmol) were added and the reaction was stirred for a further 3 h at rt. Further portions of HATU (84 mg, 0.221 mmol), DIPEA (0.08 mL, 0.458 mmol) and cyclopropanamine (0.03 mL, 0.426 mmol) were added and the reaction mixture stirred for a further 1 h at rt. The reaction mixture was washed with water (20 mL), partitioned between EtOAc (20 mL) and water (20 mL), the aqueous phase was extracted with EtOAc (2×20 mL) and the combined organic layers were dried over a hydrophobic frit and concentrated to give an orange oil. This was purified by chromatography on SiO$_2$ (Biotage SNAP 25 g cartridge, eluting with 0-100% EtOAc/cyclohexane followed by 25% EtOH in EtOAc). The appropriate fractions were concentrated to give 31 mg of a colourless oil. This was further purified by MDAP (Formic). The appropriate fractions were concentrated to give tert-butyl 5-((5-(cyclopropylcarbamoyl)-3-(methylcarbamoyl)-2-oxopyridin-1(2H)-yl)methyl)-3,4-dihydroisoquinoline-2(1H)-carboxylate (4.2 mg, 7.87 μmol, 5.18% yield) as a colourless oil.
LCMS (2 min Formic): Rt=1.04 min, [MH]+=481.

Intermediate 125: tert-Butyl (6-(1-benzyl-5-(methylcarbamoyl)-6-oxo-1,6-dihydropyridine-3-carboxamido)spiro[3.3]heptan-2-yl)carbamate

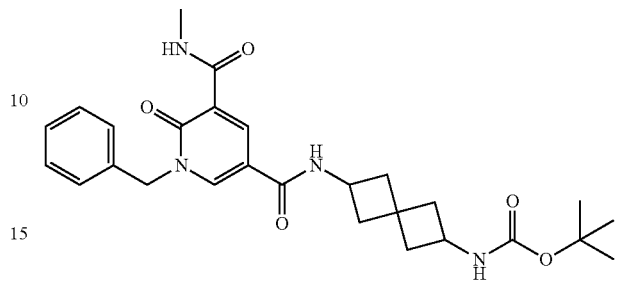

2,4,6-Trichlorophenyl 1-benzyl-5-(methylcarbamoyl)-6-oxo-1,6-dihydropyridine-3-carboxylate (80 mg, 0.172 mmol), N,N-dimethylpyridin-4-amine (5 mg, 0.041 mmol), tert-butyl (6-aminospiro[3.3]heptan-2-yl)carbamate (78 mg, 0.344 mmol), triethylamine (0.08 mL, 0.574 mmol) and THF (1 mL) were stirred at 45° C. under N$_2$ for 3 h. The reaction mixture was concentrated to give 200 mg of an off white solid which was purified by chromatography on SiO$_2$ (Biotage SNAP 10 g cartridge, eluting with 0-60% (25% EtOH in EtOAc)/cyclohexane). The desired fractions were concentrated to give tert-butyl (6-(1-benzyl-5-(methylcarbamoyl)-6-oxo-1,6-dihydropyridine-3-carboxamido)spiro[3.3]heptan-2-yl)carbamate (86 mg, 0.148 mmol, 86% yield) as a colourless oil.
LCMS (2 min Formic): Rt=1.09 min, [MH]+=495.

Intermediate 126: tert-Butyl 7-((5-bromo-3-(methylcarbamoyl)-2-oxopyridin-1(2H)-yl)methyl)-4,5-dihydro-1H-benzo[d]azepine-3(2H)-carboxylate

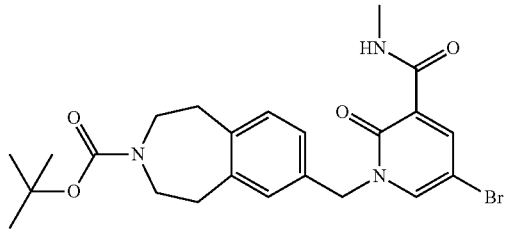 [SMILES: CNC(=O)c1cc(Br)cn(Cc2ccc3c(c2)CCN(C(=O)OC(C)(C)C)CC3)c1=O]

DIAD (0.1 mL, 0.514 mmol) was added to a suspension of 5-bromo-N-methyl-2-oxo-1,2-dihydropyridine-3-carboxamide (100 mg, 0.433 mmol), tert-butyl 7-(hydroxymethyl)-4,5-dihydro-1H-benzo[d]azepine-3(2H)-carboxylate (180 mg, 0.649 mmol) and triphenylphosphine (134 mg, 0.511 mmol) in toluene (3 mL). The reaction was stirred at rt under N$_2$ for 1 h. Further portions of DIAD (0.1 mL, 0.514 mmol) and triphenylphosphine (136 mg, 0.519 mmol) were added and the reaction mixture was stirred for a further 1 h. The reaction mixture was partitioned between EtOAc (20 mL) and water (20 mL), the aqueous layer was extracted with more EtOAc (2×20 mL) and the combined organic layers were dried over a hydrophobic frit and concentrated to give 1.06 g of a yellow oil. This was purified by chromatography on SiO$_2$ (Biotage SNAP 100 g cartridge, eluting with 0-100% ethylacetate/cyclohexane). The appropriate fractions were concentrated to give tert-butyl 7-((5-bromo-3-

(methylcarbamoyl)-2-oxopyridin-1(2H)-yl)methyl)-4,5-dihydro-H-benzo[d]azepine-3(2H)-carboxylate (193 mg, 0.354 mmol, 82% yield) as a colourless oil LCMS (2 min Formic): Rt=1.22 min, [MH]$^+$=490, 492.

Intermediate 127: tert-Butyl 7-((5-(cyclopropylcarbamoyl)-3-(methylcarbamoyl)-2-oxopyridin-1(2H)-yl)methyl)-4,5-dihydro-1H-benzo[d]azepine-3(2H)-carboxylate

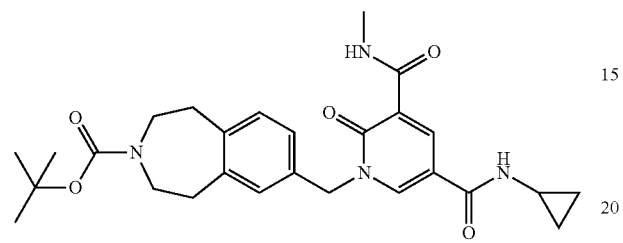

tert-Butyl 7-((5-bromo-3-(methylcarbamoyl)-2-oxopyridin-(2H)-yl)methyl)-4,5-dihydro-1H-benzo[d]azepine-3 (2H)-carboxylate (190 mg, 0.387 mmol), cobalt carbonyl (40 mg, 0.117 mmol), cyclopropanamine (0.054 mL, 0.775 mmol), DMAP (97 mg, 0.794 mmol), palladium acetate (5 mg, 0.022 mmol) and xantphos (13 mg, 0.022 mmol) were combined in a microwave vial and de-gassed, 1,4-Dioxane (3.5 mL) was added and the vial was heated at 80° C. for 40 min. The reaction mixture was filtered through celite and partitioned between water and EtOAc, washed with 2M HCl and extracted with EtOAc (2×30 mL). The organic layers were combined and dried over a hydrophobic frit and concentrated to give 240 mg of a green oil. This was purified by chromatography on SiO$_2$ (Biotage SNAP 25 g cartridge, eluting with 0-50% (25% EtOH in EtOAc)/cyclohexane). The appropriate fractions were concentrated to give 175 mg of a yellow oil. This was further purified by MDAP (Formic). The appropriate fractions were concentrated to give tert-butyl 7-((5-(cyclopropylcarbamoyl)-3-(methylcarbamoyl)-2-oxopyridin-1(2H)-yl)methyl)-4,5-dihydro-1H-benzo[d]azepine-3(2H)-carboxylate (99 mg, 0.160 mmol, 41.3% yield) as a colourless oil.

LCMS (2 min Formic): Rt=1.06 min, [MH]$^+$=495.

Intermediate 128: Butyl 1-(4-fluoro-3-methylbenzyl)-5-(methylcarbamoyl)-6-oxo-1,6-dihydropyridine-3-carboxylate

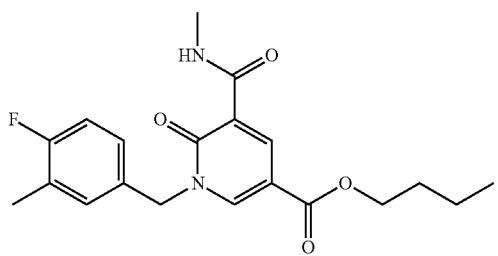 [SMILES: CCCCOC(=O)c1cc(C(=O)NC)c(=O)n(Cc2ccc(F)c(C)c2)c1]

4-(Bromomethyl)-1-fluoro-2-methylbenzene (0.805 g, 3.96 mmol) was added to a solution of butyl 5-(methylcarbamoyl)-6-oxo-1,6-dihydropyridine-3-carboxylate (1 g, 3.96 mmol) and potassium carbonate (1.096 g, 7.93 mmol) in DMF (20 mL). The reaction mixture was left to stir at rt for 2 h. The reaction mixture was concentrated under vacuum and partitioned between DCM (20 mL) and water (20 mL). The organic layer was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (900 mg) as a white solid.

LCMS (2 min Formic): Rt=1.24 min, [MH]$^+$=375.1.

Intermediate 129: 1-(4-Fluoro-3-methylbenzyl)-5-(methylcarbamoyl)-6-oxo-1,6-dihydropyridine-3-carboxylic acid

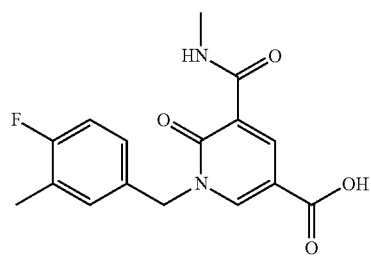 [SMILES: CNC(=O)c1cc(C(=O)O)cn(Cc2ccc(F)c(C)c2)c1=O]

Butyl 1-(4-fluoro-3-methylbenzyl)-5-(methylcarbamoyl)-6-oxo-1,6-dihydropyridine-3-carboxylate (900 mg, 2.404 mmol) was taken up in THF (10 mL) and water (10 mL). Lithium hydroxide (115 mg, 4.81 mmol) was added to the solution and the reaction stirred overnight at rt. 2M aq. HCl (3.61 mL, 7.21 mmol) was added and the resulting solid was washed with water to give the product (1 g) as a white solid.

LCMS (2 min Formic): Rt=0.91 min, [MH]$^+$=319.0.

Intermediate 130: Butyl 1-(3-fluorobenzyl)-5-(methylcarbamoyl)-6-oxo-1,6-dihydropyridine-3-carboxylate

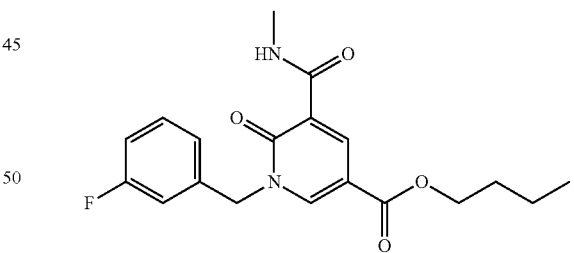

1-(Bromomethyl)-3-fluorobenzene (0.729 mL, 5.95 mmol) was added to a stirred suspension of butyl 5-(methylcarbamoyl)-6-oxo-1,6-dihydropyridine-3-carboxylate (1 g, 3.96 mmol) and potassium carbonate (1.096 g, 7.93 mmol) in DMF (20 mL). The reaction mixture was stirred at rt for 1 h and partitioned between ethyl acetate (40 mL) and water (40 mL). The organic layer was washed with water (2×40 mL). This was passed through a hydrophobic frit and the solvent removed under reduced pressure. The resulting yellow oil was dissolved in DCM and purified by 100 g Biotage SNAP silica column using a gradient of 0-75% ethyl acetate/cyclohexane. The clean, product-containing fractions were combined and the solvent removed under reduced pressure. The product was left to dry in vacuo for 2 h to give butyl 1-(3-fluorobenzyl)-5-(methylcarbamoyl)-6-oxo-1,6-dihydropyridine-3-carboxylate (1.23 g, 3.41 mmol, 86% yield) as a white solid.

LCMS (2 min Formic): Rt=1.16 min, [MH]$^+$=361.1.

Intermediate 131: 1-(3-Fluorobenzyl)-5-(methylcarbamoyl)-6-oxo-1,6-dihydropyridine-3-carboxylic acid

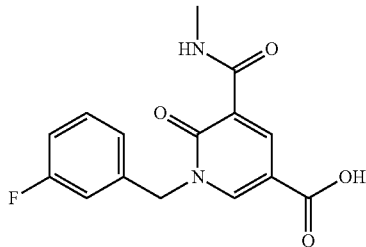 [SMILES: CNC(=O)c1cc(C(=O)O)cn(Cc2cccc(F)c2)c1=O]

Sodium hydroxide (3.41 mL, 2.5 M, 8.53 mmol) in water was added to a stirred solution of butyl 1-(3-fluorobenzyl)-5-(methylcarbamoyl)-6-oxo-1,6-dihydropyridine-3-carboxylate (1.23 g, 3.41 mmol) in methanol (10 mL) and THF (10 mL). The reaction mixture was stirred at rt for 1 h and left to stand overnight. The reaction mixture was neutralised to pH 7 with 2M HCl and the solvent removed under reduced pressure. This was partitioned between ethyl acetate (40 mL) and water (40 mL) and the organic layer extracted with water (2×40 mL); the aqueous layer was placed in a round-bottomed flask and the solvent removed under reduced pressure. The solid was left to dry in vacuo for 3 h to give 1-(3-fluorobenzyl)-5-(methylcarbamoyl)-6-oxo-1,6-dihydropyridine-3-carboxylic acid (1.252 g, 3.29 mmol, 96% yield) as a white solid with 12 mol % NaCl impurity. Impurity carried forward in further synthesis.

LCMS (2 min Formic): Rt=0.82 min, [MH]$^+$=305.0.

Intermediate 132: 5-Bromo-1-(2-fluorobenzyl)-N-methyl-2-oxo-1,2-dihydropyridine-3-carboxamide

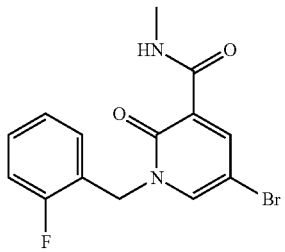 [SMILES: CNC(=O)c1cc(Br)cn(Cc2ccccc2F)c1=O]

1-(Bromomethyl)-2-fluorobenzene (0.392 mL, 3.25 mmol) was added to a suspension of 5-bromo-N-methyl-2-oxo-1,2-dihydropyridine-3-carboxamide (500 mg, 2.164 mmol) and potassium carbonate (598 mg, 4.33 mmol) in DMF (8 mL). The reaction mixture was stirred at rt under nitrogen for 2 h, partitioned between ethyl acetate and water and the organic layer washed with 2× water. The organic layer was passed through a hydrophobic frit and the solvent removed under reduced pressure. The yellow oil was dissolved in DCM and loaded onto a 50 g Biotage SNAP column which was eluted in cyclohexane:ethyl acetate (0-75%). The product-containing fractions were combined and the solvent removed under reduced pressure. The product was left to dry in vacuo overnight to give the product (536.3 mg) as a pale yellow solid.

LCMS (2 min Formic): Rt=0.98 min, [MH]$^+$=338.9 & 340.9

Intermediate 133: Methyl 1-(4-fluorobenzyl)-5-(methylcarbamoyl)-6-oxo-1,6-dihydropyridine-3-carboxylate

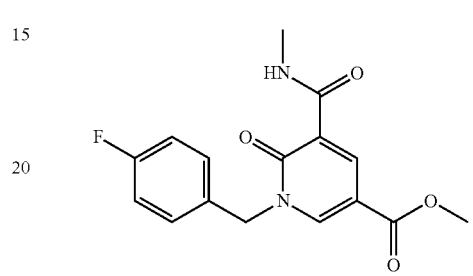

1-(Bromomethyl)-4-fluorobenzene (0.207 mL, 1.665 mmol) was added to a solution of methyl 5-(methylcarbamoyl)-6-oxo-1,6-dihydropyridine-3-carboxylate (350 mg, 1.665 mmol) and potassium carbonate (460 mg, 3.33 mmol), in DMF (15 mL). The reaction mixture was left to stir at rt for 2 h. The reaction mixture was concentrated under vacuum and separated between DCM (20 mL) and water (20 mL). The organic solution was concentrated under vacuum, loaded in DCM (3 mL) and purified by Biotage Isolera SNAP 25 g silica flash chromatography using a gradient of 0-60% cyclohexane/ethyl acetate. The appropriate fractions were combined and concentrated under vacuum to give the product (428 mg) as a white solid.

LCMS (2 min Formic): Rt=0.92 min, [MH]$^+$=319.0.

Intermediate 134: 1-(4-Fluorobenzyl)-5-(methylcarbamoyl)-6-oxo-1,6-dihydropyridine-3-carboxylic acid

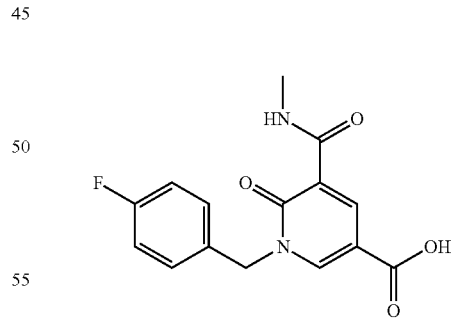

Methyl 1-(4-fluorobenzyl)-5-(methylcarbamoyl)-6-oxo-1,6-dihydropyridine-3-carboxylate (330 mg, 1.037 mmol) was taken up in THF (4 mL) and water (4.00 mL). Lithium hydroxide (49.7 mg, 2.074 mmol) was added to the solution and the reaction stirred overnight at rt. 2M aq. HCl (1.555 mL, 3.11 mmol) was added and the reaction mixture partitioned between water (10 mL) and 10% MeOH/DCM (10 mL). The aqueous layer was washed further with 10% MeOH/DCM (2×10 mL). The organic layers were combined, passed through a hydrophobic frit and concentrated under vacuum to give the product (123.5 mg) as a white solid.

LCMS (2 min Formic): Rt=0.82 min, [MH]$^+$=305.0.

Intermediate 135: N5-Cyclopropyl-1-(3-formylbenzyl)-N3-methyl-2-oxo-1,2-dihydropyridine-3,5-dicarboxamide

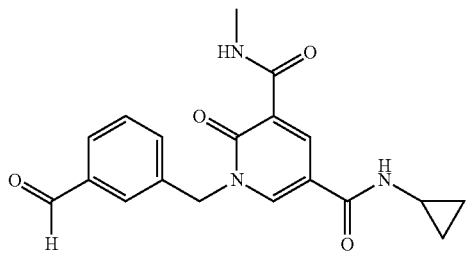 [SMILES: CNC(=O)c1cc(C(=O)NC2CC2)cn(Cc2cccc(C=O)c2)c1=O]

To a stirred solution of N5-cyclopropyl-N3-methyl-2-oxo-1,2-dihydropyridine-3,5-dicarboxamide (300 mg, 1.275 mmol) and potassium carbonate (353 mg, 2.55 mmol) in DMF (5.101 mL) under nitrogen at rt, was added 3-(bromomethyl)benzaldehyde (381 mg, 1.913 mmol) and the reaction stirred for 2 h. The reaction mixture was poured onto saturated aqueous lithium chloride (60 mL) at which point the product precipitated. The suspension was extracted with ethyl acetate (150 mL, then 2×50 mL) to dissolve the poorly soluble precipitate. The combined organics were washed with brine (2×20 mL), dried through a hydrophobic frit and evaporated in vacuo to yield the crude product as a yellow oil (588 mg). The oil was dry loaded onto a SNAP cartridge (25 g) and purified via Biotage SP4 flash chromatography, eluting from 15-75% (3:1 ethyl acetate:ethanol)/cyclohexane. The relevant fractions were combined and evaporated in vacuo to yield the desired product—N5-cyclopropyl-1-(3-formylbenzyl)-N3-methyl-2-oxo-1,2-dihydropyridine-3,5-dicarboxamide (369 mg, 0.992 mmol, 78% yield).

LCMS (2 min Formic): Rt=0.72 min, [MH]$^+$=354.1.

Intermediate 136: (+/−)-(trans)-Methyl 2-(2-(tert-butoxy)-2-oxoethyl)cyclopropanecarboxylate

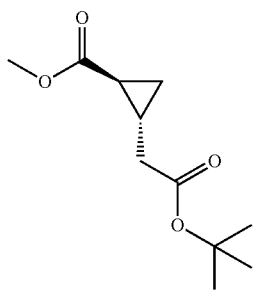

A solution of diisopropylamine (5.70 mL, 40 mmol) in THF (25 mL) under nitrogen was treated at −78° C. with n-butyllithium (25 mL, 40.0 mmol, 1.6M in hexanes). The resulting mixture was stirred for 5 min then stirred at 0° C. for 30 min before being cooled again to −78° C. The solution was treated with the dropwise addition of tert-butyl acetate (5.37 mL, 40.0 mmol) in THF (10 mL) and the resulting mixture was stirred at this temperature for 30 min before being treated with (E)-methyl 4-bromobut-2-enoate (7.16 g, 40 mmol, commercially available from, for example, Sigma-Aldrich) in THF (15 mL). The mixture was stirred for 1 h (orange solution) and an aliquot then taken which was diluted with DCM, washed with water, dried using a phase separator and concentrated in vacuo. After, overall 1.5 h, the reaction mixture was treated with a saturated NH$_4$Cl aqueous solution and warmed to rt. The mixture was partitioned between water and AcOEt and the layers were separated. The aqueous layer was extracted with AcOEt and the combined organics were washed with brine, dried over MgSO$_4$ and concentrated in vacuo to give (+/−)-(trans)-methyl 2-(2-(tert-butoxy)-2-oxoethyl)cyclopropanecarboxylate (8.30 g, 38.7 mmol, 97% yield) as a yellow oil.

A solution of (+/−)-(trans)-methyl 2-(2-(tert-butoxy)-2-oxoethyl)cyclopropanecarboxylate (8.30 g, 38.7 mmol) contaminated with (E)-methyl 4-bromobut-2-enoate (25% by NMR) in methanol (140 mL) was treated with palladium on carbon (1.5 g, 1.41 mmol, 50% wet, 10% w/w) and the resulting mixture was stirred under hydrogen (1 bar) for 4 h. The palladium was then filtered off and rinsed with AcOEt. Triethylamine (2.70 mL, 19.37 mmol) was added and the mixture was concentrated in vacuo. The residue was partitioned between AcOEt and water and the layers were separated. The aqueous phase was extracted with AcOEt and the combined organics were washed with brine, dried over MgSO$_4$ and concentrated in vacuo to give (+/−)-(trans)-methyl 2-(2-(tert-butoxy)-2-oxoethyl)cyclopropanecarboxylate (7 g, 32.7 mmol, 84% yield) as an orange/red oil which was used directly in the next reaction.

$^1$H NMR (400 MHz, CDCl$_3$) δ ppm 3.68 (s, 3H) 2.23 (d, J=7.1 Hz, 2H) 1.67 (dqd, J=8.9, 6.8, 6.8, 6.8, 4.2 Hz, 1H) 1.43-1.53 (m, 10H) 1.23-1.29 (m, 1H) 0.81 (ddd, J=8.3, 6.3, 4.5 Hz, 1H)

Intermediate 137: (+/−)-(trans)-2-(2-(tert-Butoxy)-2-oxoethyl)cyclopropanecarboxylic acid

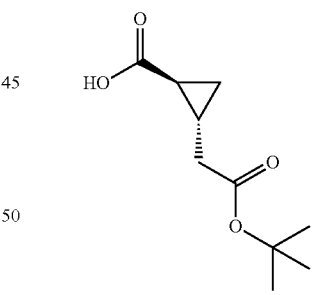

A solution of (+/−)-(trans)-methyl 2-(2-(tert-butoxy)-2-oxoethyl)cyclopropanecarboxylate (1071 mg, 5 mmol) in THF (15 mL) at rt was treated with NaOH (5 mL, 10.00 mmol, 2M aq.) and the resulting mixture stirred for 3 h. As it remained a biphasic mixture, MeOH (5 mL) was added and the reaction stirred o/n. The solvent was then concentrated in vacuo. The residue was dissolved in water and treated with HCl (2N aq.) and then extracted with AcOEt twice. The combined organics were washed with brine, dried over MgSO$_4$ and concentrated in vacuo to give, after trituration with Et$_2$O, (+/−)-(trans)-2-(2-(tert-butoxy)-2-oxoethyl)cyclopropanecarboxylic acid (720 mg, 3.60 mmol, 72% yield) as a white solid.

¹H NMR (400 MHz, CDCl₃) δ ppm 2.26 (ABq, J=7.1, 5.6 Hz, 2H) 1.70-1.83 (m, 1H) 1.43-1.57 (m, 10H) 1.29-1.39 (m, 1H) 0.87-0.95 (m, 1H). Exchangeable proton not observed Intermediate 138: (+/−)-tert-Butyl 2-((trans)-2-(((benzyloxy)carbonyl)amino)cyclopropyl)acetate

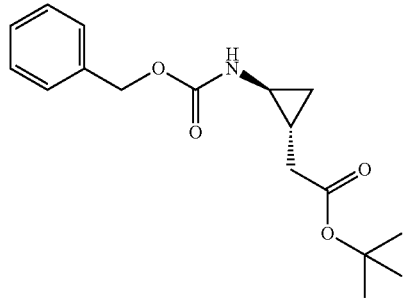 [SMILES: CC(C)(C)OC(=O)C[C@H]1C[C@@H]1NC(=O)OCc1ccccc1]

A solution of (+/−)-(trans)-2-(2-(tert-butoxy)-2-oxoethyl)cyclopropanecarboxylic acid (720 mg, 3.60 mmol) in toluene (12 mL) was treated with triethylamine (1.50 mL, 10.79 mmol) then diphenyl phosphorazidate (0.930 mL, 4.32 mmol), followed 2 min later by benzyl alcohol (0.748 mL, 7.19 mmol). The resulting mixture was stirred at 110° C. and followed by LCMS. Bubbling occurred extremely rapidly. After 4 h, the mixture was cooled to rt and concentrated in vacuo. The residue was partitioned between EtOAc and a saturated NaHCO₃ aqueous solution, and the layers were separated. The aqueous phase was then extracted with EtOAc and the combined organics were washed with brine, dried over MgSO₄ and concentrated in vacuo. Purification of the crude product (ca. 1.6 g) was undertaken by flash chromatography on a Biotage SP4 (50 g silica column, 30% EtOAc/hexanes) to give (+/−)-tert-butyl 2-((trans)-2-(((benzyloxy)carbonyl)amino)cyclopropyl)acetate (660 mg, 2.16 mmol, 60% yield) as a yellow oil which was used without further purification.

LCMS (2 min formic): Rt=1.20 min, [M+Na]⁺=328.2.

Intermediate 139: (+/−)-tert-Butyl 2-((trans)-2-aminocyclopropyl)acetate

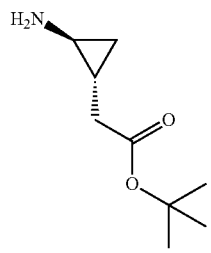

A solution of (+/−)-tert-butyl 2-((trans)-2-(((benzyloxy)carbonyl)amino)cyclopropyl)acetate (660 mg, 2.16 mmol) in methanol (40 mL) at rt was treated with palladium on carbon (150 mg, 0.14 mmol) (50% wet, 10% w/w) and the resulting mixture was stirred under an atmosphere of hydrogen (1 bar) for 5 h. The catalyst was removed through a pad of celite and rinsed with methanol. The combined organics were concentrated in vacuo to give (+/−)-tert-butyl 2-((trans)-2-aminocyclopropyl)acetate (380 mg, 2.219 mmol, 103% yield) as a pale yellow oil. Further experiments showed that this product was contaminated with the linear chain amine (in a 2:1 ratio in favour of the desired product). This mixture was used crude in the subsequent reaction ¹H NMR (400 MHz, CDCl₃) δ ppm 2.08-2.17 (m, 2H) 1.42-1.55 (m, 10H) 0.92-1.05 (m, 1H) 0.54-0.62 (m, 1H) 0.34-0.42 (m, 1H). Exchangeable protons not observed.

Intermediate 140: 2-((1S,2S)-2-(Hydroxymethyl)cyclopropyl)isoindoline-1,3-dione

Intermediate 141: 2-((1R,2R)-2-(Hydroxymethyl)cyclopropyl)isoindoline-1,3-dione

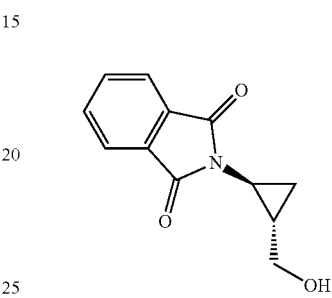

2-((trans)-2-(Hydroxymethyl)cyclopropyl)isoindoline-1,3-dione (3.2 g) was purified by chiral HPLC. The racemate (300 mg) was dissolved in EtOH (2 mL) with heat. Injection: 2 mL of the solution was injected onto the column (50% EtOH/heptane, flow rate=30 mL/min, detection wavelength=215 nm, 4. Ref 550, 100, Column 30 mm×25 cm Chiralpak AD-H (5 μm), lot no. ADH12143-01). Total number of injections=11. Fractions from 11-15.5 min were bulked and labelled peak 1. Fractions from 18-28 min were bulked and labelled peak 2. The bulked fractions were concentrated in vacuo and then transferred to weighed flasks. Final compounds were recovered from DCM and heptane in order to obtain a solid.

The fractions corresponding to peak 1 were collected to afford intermediate 140 (1.38 g)

LCMS (2 min formic): Rt=0.65 min, [M−OH]⁺=200.2.

The fractions corresponding to peak 2 were collected to afford intermediate 141 (1.36 g)

LCMS (2 min formic): Rt=0.65 min, [M−OH]⁺=200.2.

Intermediate 142: 2-((1S,2S)-2-(Methoxymethyl)cyclopropyl)isoindoline-1,3-dione

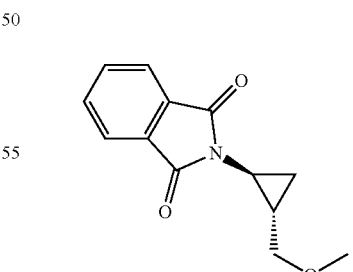

2-((1S,2S)-2-(Hydroxymethyl)cyclopropyl)isoindoline-1,3-dione (200 mg, 0.92 mmol) and N¹,N¹,N⁸,N⁸-tetramethylnaphthalene-1,8-diamine (592 mg, 2.76 mmol) were dissolved in DCM (8 mL). Trimethyloxonium tetrafluoroborate (409 mg, 2.76 mmol) was added slowly and the reaction mixture was stirred under nitrogen for 1 h. The reaction mixture was partitioned between DCM and water, the aqueous layer was then extracted with DCM (2×20 mL), and the organic layer washed with water (20 mL) and sat. sodium bicarbonate solution (20 mL). This was passed through a hydrophobic frit and concentrated to ~5 mL. The solution was purified by flash chromatography using a Biotage SNAP column (25 g) using a gradient of 0-100% ethyl acetate/cyclohexane. The product-containing fractions were concentrated and the solvent removed in vacuo. The product was dried under a stream of nitrogen to give 2-((1S,2S)-2-(methoxymethyl)cyclopropyl)isoindoline-1,3-dione (193 mg, 0.709 mmol, 77% yield) as a yellow solid.

LCMS (2 min formic): Rt=0.84 min, [MH]⁺=232.4.

Intermediate 143:
(1S,2S)-2-(Methoxymethyl)cyclopropanamine, hydrochloride

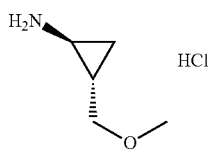

Hydrazine hydrate (0.023 mL, 0.745 mmol) was added slowly to a suspension of 2-((1S,2S)-2-(methoxymethyl)cyclopropyl)isoindoline-1,3-dione (193 mg, 0.71 mmol) in ethanol (7 mL). The reaction mixture was heated to 40° C. under nitrogen for 2 days after which further hydrazine hydrate (0.023 mL, 0.75 mmol) was added. The reaction mixture was heated to 50° C. under nitrogen overnight and further hydrazine hydrate (0.023 mL, 0.75 mmol) was added. Heating was continued under nitrogen for 4 h. The suspension was cooled in an ice bath, filtered, and washed with ethanol. The filtrate was acidified to pH 1 with 2M HCl and the solvent concentrated to ~10 mL. The white precipitate was filtered off and washed with DCM. The filtrate was placed in a round-bottomed flask and the solvent concentrated to ~3 mL. Some white precipitate was noticed so ethyl acetate was added and the suspension was passed through a hydrophobic frit to filter off the remaining solid. The product was left to dry under a stream of nitrogen to give crude (1S,2S)-2-(methoxymethyl)cyclopropanamine, HCl salt (106 mg, 0.51 mmol, 71% yield) as an orange oil.

¹H NMR (400 MHz, CDCl₃) δ ppm 3.37-3.43 (m, 1H) 3.33 (s, 3H) 3.28 (dd, J=10.4, 6.5 Hz, 1H) 2.57-2.65 (m, 1H) 1.75-1.85 (m, 1H) 1.27-1.35 (m, 1H) 0.81-0.89 (m, 1H). No exchangeable protons observed.

Intermediate 144: (1S,2S)-2-(1,3-Dioxoisoindolin-2-yl)cyclopropanecarbaldehyde

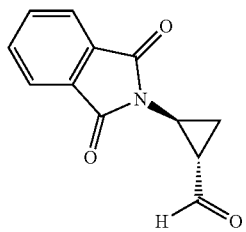 [SMILES: O=C[C@H]1C[C@@H]1N1C(=O)c2ccccc2C1=O]

2-((1S,2S)-2-(Hydroxymethyl)cyclopropyl)isoindoline-1,3-dione (287 mg, 1.32 mmol) was stirred in DCM (10 mL) and Dess-Martin periodinane (616 mg, 1.45 mmol) was added slowly under nitrogen. The reaction mixture was stirred at rt under nitrogen for 90 min. The reaction mixture was quenched with sodium thiosulfate solution (10% in water, 50 mL) and partitioned between DCM and sat. sodium bicarbonate solution. The organic layer was washed with sat. sodium bicarbonate solution. (20 mL) and brine (20 mL) and passed through a hydrophobic frit. The solvent was concentrated to ~5 mL in vacuo and the resulting oil was purified by flash chromatography using a 25 g Biotage SNAP column and a gradient of 0-70% ethyl acetate/cyclohexane. The product containing fraction was concentrated and the product was left to dry under a stream of nitrogen to give (1S,2S)-2-(1,3-dioxoisoindolin-2-yl)cyclopropanecarbaldehyde (235 mg, 1.092 mmol, 83% yield) as a white solid.

LCMS (2 min formic): Rt=0.75 min, [MH]⁺=216.4.

Intermediate 145: 2-((1S,2R)-2-((Dimethylamino)methyl)cyclopropyl)isoindoline-1,3-dione

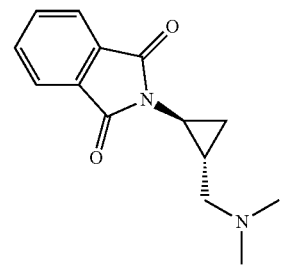 [SMILES: CN(C)C[C@H]1C[C@@H]1N1C(=O)c2ccccc2C1=O]

Sodium triacetoxyborohydride (370 mg, 1.75 mmol) was added to a solution of (1S,2S)-2-(1,3-dioxoisoindolin-2-yl)cyclopropanecarbaldehyde (235 mg, 1.09 mmol) and dimethylamine (2M in THF, 0.573 mL, 1.15 mmol) in DCM (6 mL). The reaction mixture was stirred at rt under nitrogen for 90 min. The reaction mixture was quenched with sat. sodium bicarbonate solution. and extracted with DCM (2×20 mL). The organic layer was passed through a hydrophobic frit and concentrated to ~5 mL. This was purified by flash chromatography using a 25 g Biotage SNAP column and a gradient of 0-75% (20% methanolic ammonia in DCM)/DCM. The product-containing fractions were combined and the solvent removed in vacuo. The product was left to dry under a stream of nitrogen to give 2-((1S,2R)-2-((dimethylamino)methyl)cyclopropyl)isoindoline-1,3-dione (76.1 mg, 0.31 mmol, 29% yield) as a yellow oil.

LCMS (2 min High pH): Rt=0.81 min, [MH]⁺=245.3.

Intermediate 146:
(1S,2R)-2-((Dimethylamino)methyl)cyclopropanamine, hydrochloride

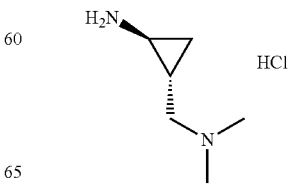

Hydrazine hydrate (15 μL, 0.478 mmol) was added to a solution of 2-((1S,2R)-2-((dimethylamino)methyl)cyclopropyl)isoindoline-1,3-dione (76 mg, 0.31 mmol) in ethanol (5 mL). The reaction mixture was heated to 50° C. under nitrogen for 90 min, after which further hydrazine hydrate (15 μL, 0.48 mmol) was added and heating was continued under nitrogen overnight. The suspension was cooled in an ice bath, filtered, and washed with ethanol. The filtrate was acidified to pH 1 with 2M HCl and this was concentrated to ~10 mL. The resulting white precipitate was removed by filtration and washed with ethanol, and the filtrate concentrated to ~5 mL. This was passed through a hydrophobic frit and left to dry under a stream of nitrogen to give impure (1S,2R)-2-((dimethylamino)methyl)cyclopropanamine hydrochloride (95.8 mg, 0.19 mmol, 61% yield) as a yellow solid. The crude product was of ~30% purity and was used without further purification in further synthesis.

Intermediate 147: 2-((1R,2R)-2-(Ethoxymethyl)cyclopropyl)isoindoline-1,3-dione

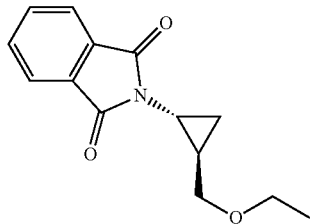 [SMILES: CCOC[C@@H]1C[C@H]1N1C(=O)c2ccccc2C1=O]

Meerwein's reagent (525 mg, 2.76 mmol) was added slowly to a suspension of 2-((1R,2R)-2-(hydroxymethyl)cyclopropyl)isoindoline-1,3-dione (200 mg, 0.921 mmol) and $N^1,N^1,N^8,N^8$-tetramethylnaphthalene-1,8-diamine (592 mg, 2.76 mmol) in DCM (5 mL). The reaction mixture was stirred for 90 min. The reaction mixture was then partitioned between DCM (20 mL) and water (20 mL) and the aqueous layer was extracted with DCM (20 mL). The organic layer was washed with sat. sodium bicarbonate solution. (10 mL) and passed through a hydrophobic frit. The solvent was removed in vacuo and the resulting oil dissolved in DCM. This was purified by flash chromatography using a 10 g Biotage SNAP column and a gradient of 0-100% cyclohexane/ethyl acetate. The product-containing fractions were combined and the solvent removed in vacuo. The resulting oil was purified by MDAP (Formic) and the product-containing fractions were concentrated. The product was dried under a stream of nitrogen to give 2-((1R,2R)-2-(ethoxymethyl)cyclopropyl)isoindoline-1,3-dione (145 mg, 0.59 mmol, 64% yield) as a white solid.

LCMS (2 min formic): Rt=0.94 min, [MH]$^+$=246.4.

Intermediate 148: (1R,2R)-2-(Ethoxymethyl)cyclopropanamine, hydrochloride

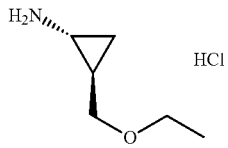

Hydrazine monohydrate (0.029 mL, 0.59 mmol) was added to a solution of 2-((1R,2R)-2-(ethoxymethyl)cyclopropyl)isoindoline-1,3-dione (145 mg, 0.59 mmol) in ethanol (8 mL). The reaction mixture was heated to 40° C. under nitrogen overnight, after which further hydrazine monohydrate (0.029 mL, 0.59 mmol) was added and the temperature was increased to 50° C. Heating was continued for 4 h. The reaction mixture was then cooled to rt, filtered, and washed with ethanol. The filtrate was acidified to pH 1 with 2M HCl and the solvent concentrated to ~10 mL. The resulting white precipitate was filtered off and washed with DCM. Further white precipitate formed in the filtrate so this was passed through a hydrophobic frit and the solvent removed in vacuo. The product was left to dry under a stream of nitrogen to give (1R,2R)-2-(ethoxymethyl)cyclopropanamine hydrochloride salt (160 mg, 0.42 mmol, 71% yield) as an off-white solid.

$^1$H NMR (400 MHz, CDCl$_3$) δ ppm 3.70 (dd, J=10.3, 6.1 Hz, 1H) 3.55-3.63 (m, 2H) 3.40 (dd, J=10.5, 6.8 Hz, 1H) 2.67 (dt, J=7.6, 3.8 Hz, 1H) 1.70-1.81 (m, 1H) 1.23-1.32 (m, 4H) 1.04-1.11 (m, 1H). No exchangeable protons observed.

Intermediate 149: 2-((1S,2S)-2-(Ethoxymethyl)cyclopropyl)isoindoline-1,3-dione

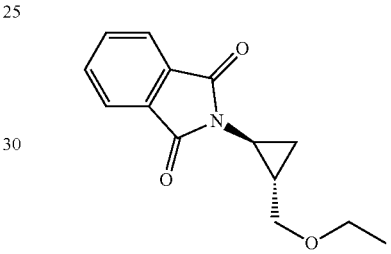

Meerwein's reagent (350 mg, 1.84 mmol) was added slowly to a solution of 2-((1S,2S)-2-(hydroxymethyl)cyclopropyl)isoindoline-1,3-dione (200 mg, 0.92 mmol) and $N^1,N^1,N^8,N^8$-tetramethylnaphthalene-1,8-diamine (395 mg, 1.84 mmol) in DCM (5 mL). The reaction mixture was stirred at rt under nitrogen for 1 h. The reaction mixture was then partitioned between DCM (30 mL) and water (30 mL). The organic layer was washed with water (20 mL) and sat. sodium bicarbonate solution. (20 mL), passed through a hydrophobic frit, and the solvent concentrated to ~10 mL. This was purified by flash chromatography using a 25 g Biotage SNAP column and a gradient of 0-100% ethyl acetate/cyclohexane. The product-containing fractions were combined and the solvent removed in vacuo. The product was left to dry under a stream of nitrogen overnight to give 2-((1S,2S)-2-(ethoxymethyl)cyclopropyl)isoindoline-1,3-dione (188 mg, 0.74 mmol, 80% yield) as a pale yellow solid.

LCMS (2 min formic): Rt=0.94 min, [MH]$^+$=246.2.

Intermediate 150: (1S,2S)-2-(Ethoxymethyl)cyclopropanamine hydrochloride

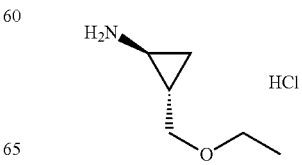

Hydrazine hydrate (0.072 mL, 0.81 mmol) was added to a suspension of 2-((1S,2S)-2-(ethoxymethyl)cyclopropyl)isoindoline-1,3-dione (188 mg, 0.77 mmol) in ethanol (7 mL). The reaction mixture was heated to 40° C. under nitrogen for 6 h. The reaction mixture was then cooled in an ice bath, filtered, and washed with cold ethanol. The filtrate was acidified to pH 1 with 2M HCl and the solvent concentrated to ~5 mL. The remaining white precipitate was filtered off and washed with DCM, and the filtrate was placed in a round-bottomed flask. The solvent was removed in vacuo and significant amounts of white precipitate were observed. This was filtered off and washed with DCM, and the solvent of the filtrate was removed in vacuo. The product was left to dry under a stream of nitrogen for 2 h to give (1R,2R)-2-(ethoxymethyl)cyclopropanamine, hydrochloride salt (21 mg, 0.04 mmol, 5% yield) as a yellow oil.

$^1$H NMR (400 MHz, CDCl$_3$) δ ppm 3.70 (dd, J=10.5, 5.9 Hz, 1H) 3.55-3.64 (m, 2H) 3.40 (dd, J=10.5, 6.6 Hz, 1H) 2.67 (dt, J=7.6, 3.8 Hz, 1H) 1.70-1.80 (m, 1H) 1.22-1.32 (m, 4H) 1.04-1.11 (m, 1H). No exchangeable protons observed.

Intermediate 151: (±)-2-((trans)-2-(Methoxymethyl)cyclopropyl)isoindoline-1,3-dione

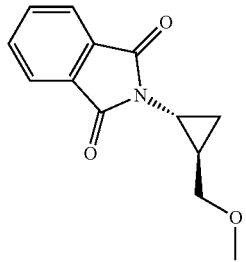 [SMILES: COC[C@@H]1C[C@H]1N1C(=O)c2ccccc2C1=O]

(±)-2-((trans)-2-(Hydroxymethyl)cyclopropyl)isoindoline-1,3-dione (150 mg, 0.69 mmol) and N$^1$,N$^1$,N$^8$,N$^8$-tetramethylnaphthalene-1,8-diamine (443 mg, 2.07 mmol) were dissolved in DCM (7 mL) and trimethyloxonium tetrafluoroborate (320 mg, 2.16 mmol) was added slowly, the reaction was stirred under N$_2$ at rt. After 30 min the suspension was partitioned between DCM (20 mL) and water (20 mL), extracted with DCM (2×20 mL), dried over a hydrophobic frit and concentrated to give 520 mg of a yellow solid. This was purified by chromatography on SiO$_2$ (Biotage SNAP 50 g cartridge, eluting with 0-50% ethyl acetate/cyclohexane). The desired fractions were concentrated to give (±)-2-((trans)-2-(methoxymethyl)cyclopropyl)isoindoline-1,3-dione (62 mg, 0.24 mmol, 35% yield).

LCMS (2 min Formic): Rt=0.84 min, [MH]$^+$=232.2.

Intermediate 152: (±)-(trans)-2-(Methoxymethyl)cyclopropanamine hydrochloride

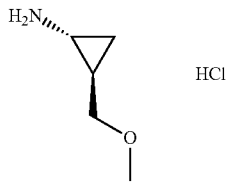

(±)-2-((trans)-2-(Methoxymethyl)cyclopropyl)isoindoline-1,3-dione (68 mg, 0.29 mmol) was added to methylamine (33% in ethanol, 0.5 mL, 4.02 mmol) and the solution was then heated at 120° C. in a microwave for 1 h. A white precipitate had formed, this was filtered under vacuum. The filtrate was evaporated in vacuo (250 mbar, rt). 4 M HCl in dioxane (1.25 mL, 5.00 mmol) was added, this was concentrated to give (±)-(trans)-2-(methoxymethyl)cyclopropanamine, hydrochloride (147 mg, 0.267 mmol, 91% yield) as a white crystalline solid.

$^1$H NMR (400 MHz, DMSO-d$_6$) δ ppm 8.35 (br. s., 3H) 3.27-3.33 (m, 1H) 3.24 (s, 3H) 3.13 (dd, J=10.5, 7.1 Hz, 1H) 2.41-2.47 (m, 1H) 1.44 (td, J=6.6, 3.7 Hz, 1H) 0.93 (ddd, J=9.8, 5.7, 4.0 Hz, 1H) 0.66 (dt, J=7.6, 6.0 Hz, 1H)

Intermediate 153: 2-((1R,2R)-2-(Methoxymethyl)cyclopropyl)isoindoline-1,3-dione

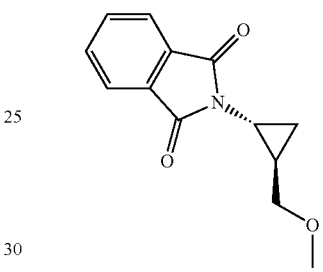

2-((1R,2R)-2-(Hydroxymethyl)cyclopropyl)isoindoline-1,3-dione (205 mg, 0.94 mmol) and N$^1$,N$^1$,N$^8$,N$^8$-tetramethylnaphthalene-1,8-diamine (602 mg, 2.81 mmol) were dissolved in DCM (10 mL) and trimethyloxonium tetrafluoroborate (410 mg, 2.77 mmol) was added slowly, the reaction was stirred under N$_2$ at rt. After 1.5 h, the suspension was partitioned between DCM (20 mL) and water (20 mL), extracted with DCM (2×20 mL), dried over a hydrophobic frit and concentrated to give the crude product (863 mg) as a yellow solid. This was purified by chromatography on SiO$_2$ (Biotage SNAP 50 g cartridge, eluting with 0-50% ethyl acetate/cyclohexane). The desired fractions were concentrated to give 2-((1R,2R)-2-(methoxymethyl)cyclopropyl)isoindoline-1,3-dione (193 mg, 0.75 mmol, 80% yield) as a white solid.

LCMS (2 min Formic): Rt=0.84 min, [MH]$^+$=232.4.

Intermediate 154: (1R,2R)-2-(Methoxymethyl)cyclopropanamine, hydrochloride

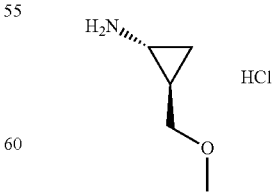

Hydrazine hydrate (0.043 mL, 0.88 mmol) was added slowly to a suspension of 2-((1R,2R)-2-(methoxymethyl)cyclopropyl)isoindoline-1,3-dione (194 mg, 0.84 mmol) in ethanol (7 mL). The reaction mixture was heated to 50° C.

under N₂ overnight. The white precipitate was filtered under vacuum. The filtrate was acidified to pH 1 with 4M HCl in dioxane (5 mL, 20.00 mmol) and concentrated to give (1R,2R)-2-(methoxymethyl)cyclopropanamine, hydrochloride (240 mg, 0.84 mmol, 100% yield) as a white solid.

¹H NMR (400 MHz, DMSO-d₆) δ ppm 8.33 (br. s., 3H) 3.30 (dd, J=10.5, 6.1 Hz, 1H) 3.24 (s, 3H) 3.13 (dd, J=10.6, 7.2 Hz, 1H) 2.45 (dd, J=8.1, 3.7 Hz, 1H) 1.44 (dt, J=6.4, 3.4 Hz, 1H) 0.92 (ddd, J=9.8, 5.7, 4.0 Hz, 1H) 0.67 (dt, J=7.6, 6.1 Hz, 1H)

Intermediate 155: (+/−)-2-((trans)-2-(Methoxycarbonyl)cyclopropyl)acetic acid

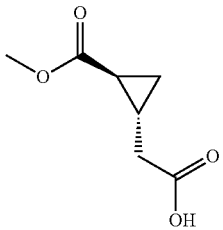

A solution of (+/−)-(trans)-methyl 2-(2-(tert-butoxy)-2-oxoethyl)cyclopropanecarboxylate (321 mg, 1.50 mmol) in DCM (2 mL) at 0° C. was treated with TFA (2 mL) dropwise and the resulting mixture was stirred at this temperature for 1.5 h. An aliquot was concentrated in vacuo and showed complete conversion. The remaining solution was concentrated in vacuo and co-evaporated with Et₂O then DCM to give (+/−)-2-((trans)-2-(methoxycarbonyl)cyclopropyl)acetic acid (200 mg, 1.27 mmol, 84% yield) as a very pale brown oil.

¹H NMR (400 MHz, CDCl₃) δ ppm 3.72 (s, 3H) 2.40-2.46 (m, 2H) 1.71-1.81 (m, 1H) 1.55-1.61 (m, 1H) 1.31-1.37 (m, 1H) 0.85-0.92 (m, 1H). No exchangeable proton observed.

Intermediate 156: (+/−)-(trans)-Methyl 2-(2-hydroxyethyl)cyclopropanecarboxylate

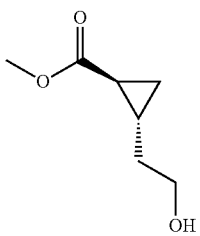

A solution of (+/−)-2-((trans)-2-(methoxycarbonyl)cyclopropyl)acetic acid (967 mg, 6.11 mmol) in THF (20 mL) at 0° C. was treated with borane tetrahydrofuran complex (1M in THF, 15.29 mL, 15.29 mmol) and the resulting mixture was stirred at this temperature for 1.5 h. After overall 2 h, the resulting mixture was treated with methanol (4.95 mL, 122.0 mmol) and after 5 min, concentrated in vacuo. Purification of this residue by SP4 flash chromatography was undertaken, using a 50 g silica column and eluting with a 50% GLOBAL gradient (AcOEt in hexanes) to give after concentration in vacuo—(+/−)-(trans)-methyl 2-(2-hydroxyethyl)cyclopropanecarboxylate (1.6 g, 11.10 mmol, 60% yield) as a colourless oil then a further batch of (+/−)-(trans)-methyl 2-(2-hydroxyethyl)cyclopropanecarboxylate (404 mg, 2.80 mmol, 15% yield)

¹H NMR (400 MHz, CDCl₃) δ ppm 3.74 (t, J=6.5 Hz, 2H) 3.65-3.69 (m, 3H) 1.51-1.67 (m, 2H) 1.40-1.50 (m, 2H) 1.17-1.24 (m, 1H) 0.73-0.81 (m, 1H). No exchangeable proton observed.

Intermediate 157: (+/−)-(trans)-Methyl 2-(2-((tert-butyldimethylsilyl)oxy)ethyl)cyclopropanecarboxylate

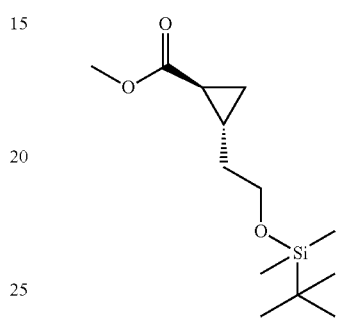

A solution of (+/−)-(trans)-methyl 2-(2-hydroxyethyl)cyclopropanecarboxylate (404 mg, 2.80 mmol) in DCM (15 mL) at rt was treated with imidazole (286 mg, 4.20 mmol) then TBDMS-Cl (507 mg, 3.36 mmol) then DMAP (34.2 mg, 0.28 mmol) and the resulting mixture was stirred at this temperature for 16 h. A white precipitate formed very quickly. The mixture was diluted with DCM and water and the layers were separated. The aqueous phase was extracted with DCM and the combined organics were dried using a phase separator then were concentrated in vacuo to give (+/−)-(trans)-methyl 2-(2-((tert-butyldimethylsilyl)oxy)ethyl)cyclopropanecarboxylate (724 mg, 2.80 mmol, 100% yield) as a colourless oil.

¹H NMR (400 MHz, CDCl₃) δ ppm 3.65-3.71 (m, 5H) 1.39-1.59 (m, 4H) 1.14-1.21 (m, 1H) 0.90 (s, 9H) 0.71-0.77 (m, 1H) 0.05 (s, 6H)

Intermediate 158: (+/−)-(trans)-2-(2-((tert-Butyldimethylsilyl)oxy)ethyl)cyclopropanecarboxylic acid

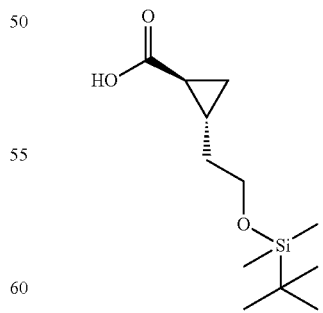

A solution of (+/−)-(trans)-methyl 2-(2-((tert-butyldimethylsilyl)oxy)ethyl)cyclopropanecarboxylate (724 mg, 2.80 mmol) in methanol (8 mL) at rt was treated with NaOH (2.80 mL, 5.60 mmol, 2N in water) and the resulting mixture was stirred at this temperature for 16 h before being concentrated in vacuo. The residue was partitioned between AcOEt and water and the mixture was treated with HCl (2.80 mL, 5.60 mmol, 2M aq.). The layers were separated and the aqueous phase was extracted with EtOAc. The combined organics were dried over MgSO₄ and concentrated in vacuo to give (+/−)-(trans)-2-(2-((tert-butyldimethylsilyl)oxy)ethyl)cyclopropanecarboxylic acid (549 mg, 2.25 mmol, 80% yield) as a pale yellow solid.

$^1$H NMR (400 MHz, CDCl$_3$) δ ppm 3.66-3.72 (m, 2H) 1.51-1.56 (m, 3H) 1.42 (ddd, J=8.2, 4.6, 3.5 Hz, 1H) 1.21-1.29 (m, 1H) 0.90 (s, 9H) 0.81-0.86 (m, 1H) 0.06 (s, 6H). No exchangeable proton observed.

Intermediate 159: (+/−)-Benzyl ((trans)-2-(2-((tert-butyldimethylsilyl)oxy)ethyl)cyclopropyl)carbamate

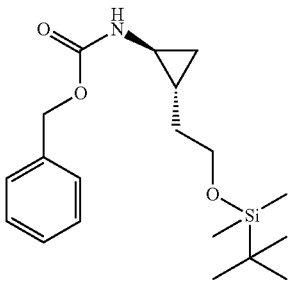 [SMILES: CC(C)(C)[Si](C)(C)OCC[C@H]1C[C@@H]1NC(=O)OCc1ccccc1]

A solution of (+/−)-(trans)-2-(2-((tert-butyldimethylsilyl)oxy)ethyl)cyclopropanecarboxylic acid (2.31 g, 9.45 mmol) in toluene (40 mL) was treated with triethylamine (3.95 mL, 28.4 mmol) then diphenyl phosphorazidate (2.444 mL, 11.34 mmol), followed 2 min later by benzyl alcohol (1.966 mL, 18.90 mmol). The resulting mixture was stirred at 110° C. After 6 h, the mixture was cooled to rt and concentrated in vacuo. The residue was partitioned between EtOAc and water, and the layers were separated. The aqueous phase was extracted with EtOAc and the combined organics were washed with brine, dried over MgSO₄ and concentrated in vacuo. Purification of the crude (ca. 4 g) by SP4 flash chromatography was underaken, using a 100 g silica column, and eluting with a 50% GLOBAL gradient (EtOAc in hexanes) to give after concentration in vacuo, (+/−)-benzyl ((trans)-2-(2-((tert-butyldimethylsilyl)oxy)ethyl)cyclopropyl)carbamate (1.57 g, 4.49 mmol, 48% yield) as a yellow oil.

LCMS (2 min High pH): Rt=1.55 min, [MH]$^+$=350.3.

Intermediate 160: (+/−)-(trans)-2-(2-((tert-Butyldimethylsilyl)oxy)ethyl)cyclopropanamine

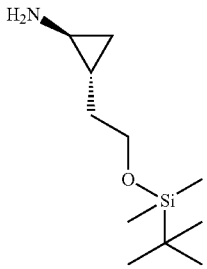

A solution of (+/−)-benzyl ((trans)-2-(2-((tert-butyldimethylsilyl)oxy)ethyl)cyclopropyl)carbamate (1.4 g, 4.01 mmol) in methanol (30 mL) at rt was treated with palladium on carbon (300 mg, 0.28 mmol, 10% w/w, 50% wet) and the resulting suspension was stirred at this temperature under an atmosphere of hydrogen (1 bar) for 16 h. The catalyst was filtered off and rinsed with methanol. The combined organics were concentrated in vacuo to give (+/−)-(trans)-2-(2-((tert-butyldimethylsilyl)oxy)ethyl)cyclopropanamine (920 mg, 4.27 mmol, 107% yield) as a colourless oil.

$^1$H NMR (400 MHz, CDCl$_3$) δ ppm 3.64-3.67 (m, 2H) 1.40-1.55 (m, 2H) 1.33 (dt, J=13.6, 6.8 Hz, 1H) 0.91 (s, 9H) 0.70-0.77 (m, 1H) 0.45-0.51 (m, 1H) 0.29 (dt, J=6.8, 5.3 Hz, 1H) 0.07 (s, 6H). No exchangeable protons observed.

Intermediate 161:
(1H-Pyrrolo[3,2-c]pyridin-4-yl)methanol, hydrochloride

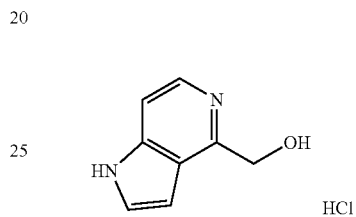

To a solution of 1H-pyrrolo[3,2-c]pyridine-4-carboxylic acid (400 mg, 2.47 mmol, commercially available from, for example, Sigma-Aldrich) in THF (16 mL), was added borane tetrahydrofuran complex (1 M in THF, 4.93 mL, 4.93 mmol) at rt. The reaction was stirred at rt for 3 h. The reaction was then quenched with methanol (0.998 mL, 24.67 mmol) and hydrochloric acid (1M, 3.08 mL, 6.17 mmol) and stirred for 1 h at rt. The reaction mixture was left to stand overnight. A precipitate was noted in the reaction mixture which was filtered off to yield (1H-pyrrolo[3,2-c]pyridin-4-yl)methanol, hydrochloride (306 mg, 1.33 mmol, 54% yield) as an off-white solid which was used without further purification.

LCMS (2 min High pH): Rt=0.43 min, [MH]$^+$=149.1.

Intermediate 162: Methyl 2-methyl-1H-indole-4-carboxylate

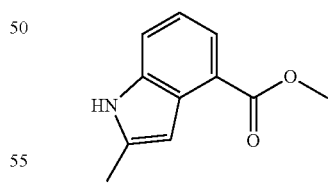

To sulfuric acid (0.127 mL, 2.26 mmol) in methanol (20.8 mL) was added 2-methyl-1H-indole-4-carboxylic acid (400 mg, 2.28 mmol, commercially available from, for example, Apollo Scientific) and the reaction was heated under reflux (65° C.) for 18 h. The reaction mixture was then neutralized with sodium bicarbonate, evaporated in vacuo and taken up in dichloromethane (40 mL). The organic layer was washed with water (20 mL) and the aqueous layer was back extracted with dichloromethane (2×20 mL). The organic layer was dried through a hydrophobic frit and evaporated in vacuo to yield the desired product as an orange solid—methyl 2-methyl-1H-indole-4-carboxylate (430 mg, 2.16 mmol, 95% yield).

LCMS (2 min formic): Rt=0.94 min, [MH]⁺=190.2.

Intermediate 163: Methyl 2-methyl-1-tosyl-1H-indole-4-carboxylate

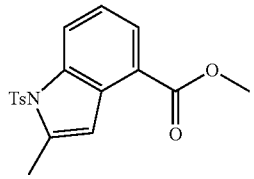

Methyl 2-methyl-1H-indole-4-carboxylate (430 mg, 2.273 mmol) was dissolved in DMF (5.7 mL) at 0° C. under nitrogen. Sodium hydride (60% dispersion in mineral oil, 136 mg, 3.41 mmol) was added in portions. The reaction was stirred at 0° C. for 10 min before warming to rt and stirring for 30 min. Tosyl-Cl (563 mg, 2.95 mmol) was added and the reaction mixture was stirred at rt. Upon completion, the reaction was cooled to 0° C. and quenched with water (8 mL). A precipitate was noted in the reaction mixture which was filtered off and washed with water (2×10 mL). The solid was dried in vacuo to yield methyl 2-methyl-1-tosyl-H-indole-4-carboxylate (680 mg, 1.88 mmol, 83% yield) as a brown solid.

LCMS (2 min formic): Rt=1.36 min, [MH]⁺=344.1.

Intermediate 164: (2-Methyl-1-tosyl-1H-indol-4-yl)methanol

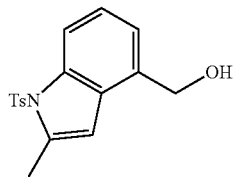 [SMILES: Cc1ccc(S(=O)(=O)n2c(C)cc3c(CO)cccc32)cc1]

A solution of methyl 2-methyl-1-tosyl-1H-indole-4-carboxylate (675 mg, 1.97 mmol) in DCM (9.8 mL) under nitrogen was cooled to −78° C. and DIBAL-H (2.34 M in toluene, 3.70 mL, 8.65 mmol) was added dropwise over 30 min and the reaction was stirred at −78° C. for 2 h. The reaction was then quenched with methanol (795 μL, 19.66 mmol) when still at −78° C. and then allowed to warm to ambient temperature. The reaction was diluted with Rochelle's salt solution (50 mL) and stirred for 16 h. The layers were separated and the aqueous layer was extracted with dichloromethane (3×20 mL). The combined organics were dried through a hydrophobic frit and evaporated in vacuo to yield the crude product as a brown oil (692 mg). The sample was loaded in dichloromethane onto a 25 g SNAP cartridge and purified via Biotage SP4 flash chromatography eluting with 15-65% ethyl acetate/cyclohexane. The relevant fractions were combined and evaporated in vacuo to yield the desired product (2-methyl-1-tosyl-1H-indol-4-yl)methanol (535 mg, 1.61 mmol, 82% yield) as a colourless gum.

LCMS (2 min formic): Rt=1.12 min, [MH]⁺=316.1.

Intermediate 165: 4-(Bromomethyl)-2-methyl-1-tosyl-1H-indole

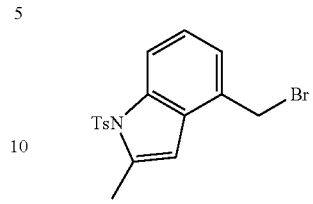

(2-Methyl-1-tosyl-1H-indol-4-yl)methanol (254 mg, 0.81 mmol) was dissolved in DCM (1611 μL) and stirred at 0° C. under N₂. PBr₃ (114 μL, 1.21 mmol) was added dropwise and the reaction stirred at 0° C. for 1 h. The reaction was then quenched with aqueous sodium bicarbonate (1 mL), poured onto water (25 mL) and extracted with dichloromethane (3×25 mL). The combined organics were dried through a hydrophobic frit and evaporated in vacuo to yield the crude product 4-(bromomethyl)-2-methyl-1-tosyl-1H-indole (351 mg, 0.56 mmol, 69.1% yield) as a purple gum.

LCMS (2 min formic): Rt=1.40 min, [MH]⁺=378.1, 380.0.

Intermediate 166: Quinolin-7-ylmethanol

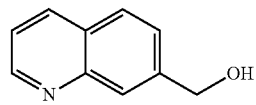 [SMILES: OCc1ccc2cccnc2c1]

To quinoline-7-carboxylic acid (200 mg, 1.16 mmol, commercially available from, for example, Fluorochem) in THF (1 mL), borane tetrahydrofuran complex (1M in THF, 3.46 mL, 3.46 mmol) was added and the reaction stirred at rt for 1 h. The reaction was then diluted with EtOAc (10 mL), washed with NaHCO₃ solution (10 mL), the aqueous layer was extracted with EtOAc (2×10 mL), the organic layers were dried over a hydrophobic frit and concentrated to give 271 mg of a yellow oil. This was purified by flash chromatography on SiO₂ (Biotage SNAP 25 g cartridge, eluting with 0-100% EtOAc/cyclohexane), the appropriate fractions were concentrated to give quinolin-7-ylmethanol (140 mg, 0.79 mmol, 69% yield) as a yellow solid.

LCMS (2 min formic): Rt=0.71 min, [MH]⁺=160.1.

Intermediate 167: 7-(Bromomethyl)quinoline

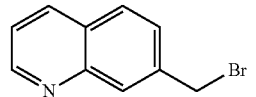 [SMILES: BrCc1ccc2cccnc2c1]

A solution of quinolin-7-ylmethanol (63 mg, 0.40 mmol) in HBr (48% in water, 1 mL, 8.84 mmol) was heated to 80° C. for 2.5 h. The reaction mixture was then evaporated in vacuo to yield the crude product 7-(bromomethyl)quinoline (115 mg, 0.26 mmol, 65% yield, 50% purity) as a brown solid. This was used crude in the next reaction.

LCMS (2 min formic): Rt=0.60 min, [MH]⁺=222.1, 224.1.

Intermediate 168: 1-(1-Bromoethyl)-3-methoxybenzene

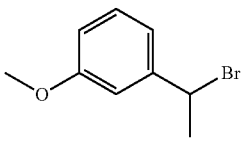

1-(3-Methoxyphenyl)ethanol (1000 mg, 6.57 mmol, commercially available from, for example, Enamine) was dissolved in DCM (6.6 mL) and stirred at 0° C. under N₂. PBr₃ (273 μL, 2.89 mmol) was added dropwise and the reaction stirred at 0° C. for 1.5 h. A further portion of PBr₃ (62.0 μL, 0.657 mmol) was added and the reaction warmed to rt and stirred overnight. The reaction was cooled back down to 0° C. and a further portion of PBr₃ (186 μL, 1.971 mmol) was added. After 18.5 h the reaction was quenched with water (3 mL), neutralized with sodium bicarbonate and diluted up to 50 mL with water. The aqueous layer was extracted with DCM (3×20 mL), dried through a hydrophobic frit and evaporated in vacuo to give 1-(1-bromoethyl)-3-methoxybenzene (1384 mg, 5.79 mmol, 88% yield) as a colourless oil.

LCMS (2 min formic): Rt=1.18 min, does not ionise at correct [MH]⁺

Intermediate 169: 2-(3-(Bromomethyl)phenyl)ethanol

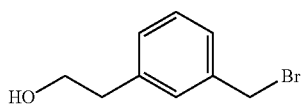 [SMILES: OCCc1cccc(CBr)c1]

Borane tetrahydrofuran complex (1M in THF, 4.37 mL, 4.37 mmol) was added dropwise to a THF (20 mL) solution of 2-(3-(bromomethyl)phenyl)acetic acid (500 mg, 2.18 mmol, commercially available from, for example, Fluorochem) at 0° C. The mixture was allowed to warm to rt and stirred for 2 h. Excess reagent was quenched by the slow addition of MeOH at 0° C. The reaction mixture was concentrated in vacuo, loaded in DCM and purified by Biotage Isolera flash chromatography, using a SNAP 25 g silica cartridge and eluting with a gradient of 0-100% EtOAc/cyclohexane to give after concentration in vacuo 2-(3-(bromomethyl)phenyl)ethanol (440 mg, 2.05 mmol, 94% yield) as a brown residue.

LCMS (2 min Formic): Rt=0.87 min, [MH]⁺=216

Intermediate 170: Methyl 1-tosyl-1H-pyrrolo[3,2-c]pyridine-4-carboxylate

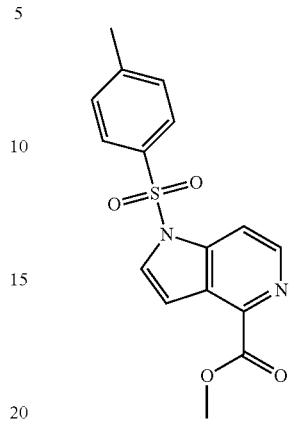

A solution of methyl 1H-pyrrolo[3,2-c]pyridine-4-carboxylate (501.7 mg, 2.85 mmol; commercially available from, for example, Matrix Scientific) in DMF (10 mL) was cooled to approx. 0° C. in an ice bath under nitrogen. To this stirring mixture was added sodium hydride (60% dispersion in mineral oil, 179.1 mg, 4.48 mmol) portionwise to afford a bright yellow solution. This was stirred at 0° C. for approx. 10 min, after which 4-toluenesulfonyl chloride (700.1 mg, 3.67 mmol) was added. The mixture was allowed to warm to rt while stirring and was stirred for a further 2.25 h. To the reaction mixture was added water (10 mL) and it was stirred for a further 5 min. To this mixture was added sat. aqueous lithium chloride (25 mL) and water (25 mL). The resulting cloudy yellow solution was extracted with ethyl acetate (3×50 mL). The organic phases were combined and filtered through a cartridge fitted with a hydrophobic frit. The filtrate was evaporated in vacuo to give a light yellow solid; methyl 1-tosyl-1H-pyrrolo[3,2-c]pyridine-4-carboxylate (837.9 mg, 2.54 mmol, 89% yield).

LCMS (2 min high pH) Rt=1.07 min, m/z=331 for [MH]⁺

¹H NMR (400 MHz, CDCl₃) δ ppm 8.62 (d, J=5.4 Hz, 1H) 8.09 (dd, J=5.6, 0.7 Hz, 1H) 7.79 (d, J=8.3 Hz, 2H) 7.73 (d, J=3.7 Hz, 1H) 7.42 (d, J=3.2 Hz, 1H) 7.24-7.31 (m, 2H) 4.04 (s, 3H) 2.37 (s, 3H)

Intermediate 171: (1-Tosyl-1H-pyrrolo[3,2-c]pyridin-4-yl)methanol

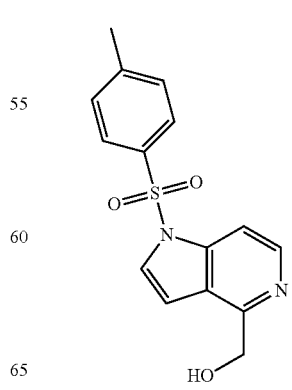

A mixture of methyl 1-tosyl-1H-pyrrolo[3,2-c]pyridine-4-carboxylate (836.7 mg, 2.53 mmol) and calcium chloride (560.1 mg, 5.05 mmol) in ethanol (10.0 mL) and 2-methyltetrahydrofuran (10.0 mL) was cooled to 0° C. in an ice bath while stirring under nitrogen. To this mixture was added sodium borohydride (148.1 mg, 3.91 mmol) portionwise, after which the mixture was removed from the ice bath and allowed to warm to rt. The mixture was stirred at rt for 28 h. The reaction mixture was warmed to 40° C. and stirred for a further 19 h before being allowed to cool to rt. To the mixture was added sat. aqueous ammonium chloride (10 mL) and the mixture stirred for 10 min. The resulting mixture was concentrated in vacuo to remove the organic solvents. To this was added brine (10 mL), water (25 mL) and ethyl acetate (30 mL) and the layers separated. The aqueous layer was extracted with ethyl acetate (2×30 mL) and the combined organic phases combined and washed with water (2×30 mL). The organic phase was filtered through a cartridge fitted with a hydrophobic frit and the cartridge washed with methanol (approx. 50 mL) and dichloromethane (approx. 30 mL). The filtrate was evaporated in vacuo to give a white solid which was suspended in methanol and directly applied to the top of a 20 g Isolute aminopropyl ion exchange column. The column was eluted with 6 column volumes of methanol. The required fractions were combined and evaporated under a stream of nitrogen to give a glassy orange solid; (1-tosyl-1H-pyrrolo[3,2-c]pyridin-4-yl)methanol (605.2 mg, 1.60 mmol, 63% yield).

LCMS (2 min high pH) Rt=0.94 min, m/z=303 for [MH]$^+$
$^1$H NMR (400 MHz, CDCl$_3$) δ ppm 8.42 (d, J=5.9 Hz, 1H) 7.84 (d, J=5.9 Hz, 1H) 7.80 (d, J=8.3 Hz, 2H) 7.62 (d, J=3.7 Hz, 1H) 7.26-7.31 (m, 2H) 6.71 (d, J=3.2 Hz, 1H) 4.95 (s, 2H) 4.23 (br. s., 1H) 2.38 (s, 3H)

Intermediate 172: tert-Butyl 3-formyl-1H-pyrrolo[2,3-b]pyridine-1-carboxylate

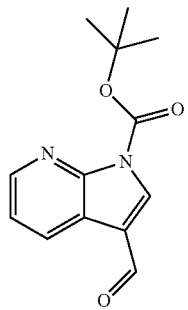 [SMILES: CC(C)(C)OC(=O)n1cc(C=O)c2cccnc21]

To a suspension of 1H-pyrrolo[2,3-b]pyridine-3-carbaldehyde (304 mg, 2.08 mmol; commercially available from, for example, Enamine) and di-tert-butyl dicarbonate (0.580 mL, 2.50 mmol) in acetonitrile (5 mL) was added DMAP (28 mg, 0.23 mmol) and the reaction mixture stirred at rt under nitrogen for 6.5 h before being left to stand overnight. The reaction mixture was concentrated in vacuo to give a brown solid which was dissolved in dichloromethane (3 mL) and loaded onto a 25 g SNAP silica cartridge and purified by flash chromatography eluting with a gradient of 30-50% ethyl acetate in cyclohexane. The required fractions were combined and concentrated in vacuo before the residue was dissolved in dichloromethane (6 mL), transferred to a tarred vial, concentrated under a stream of nitrogen and dried in vacuo to give a white solid; tert-butyl 3-formyl-1H-pyrrolo[2,3-b]pyridine-1-carboxylate (420.7 mg, 1.71 mmol, 82% yield).

LCMS (2 min high pH) Rt=0.97 min, m/z=247 for [MH]$^+$

Intermediate 173: tert-Butyl 3-(hydroxymethyl)-1H-pyrrolo[2,3-b]pyridine-1-carboxylate

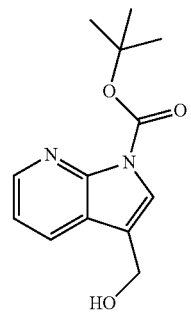 [SMILES: CC(C)(C)OC(=O)n1cc(CO)c2cccnc21]

A solution of tert-butyl 3-formyl-1H-pyrrolo[2,3-b]pyridine-1-carboxylate (420 mg, 1.71 mmol) in ethanol (10 mL) was cooled to 0° C. with stirring under nitrogen before sodium borohydride (126.6 mg, 3.35 mmol) was added. The reaction mixture was allowed to warm to rt and stirred for 1.25 h. An aqueous solution of hydrochloric acid (2 M, 4 drops) was added, followed immediately by a saturated solution of sodium bicarbonate (1 mL). The reaction mixture was concentrated in vacuo and the residue partitioned between saturated aqueous sodium bicarbonate solution (50 mL) and ethyl acetate (50 mL). The phases were separated and the aqueous phase further extracted with ethyl acetate (2×50 mL). The organic phases were combined, filtered through a cartridge containing a hydrophobic frit and the solvent evaporated in vacuo. The residue was dissolved in a 1:1 mixture of dichloromethane/methanol (10 mL), concentrated under a stream of nitrogen, and dried in vacuo to give a white solid which was dissolved in dichloromethane (5 mL) and loaded onto a 25 g SNAP silica cartridge which was purified by flash chromatography, eluting with a gradient of 50-100% ethyl acetate in cyclohexane. The required fractions were concentrated in vacuo before being dissolved in a 1:1 mixture of dichloromethane/methanol (10 mL), transferred to a tarred vial, concentrated under a stream of nitrogen and dried in vacuo to give a white solid; tert-butyl 3-(hydroxymethyl)-1H-pyrrolo[2,3-b]pyridine-1-carboxylate (199.7 mg, 0.80 mmol, 47% yield).

LCMS (2 min formic) Rt=0.72 min, m/z=249 for [MH]$^+$

Intermediate 174: 1-(2-((tert-Butyldimethylsilyl)oxy)ethyl)-1H-indole-3-carbaldehyde

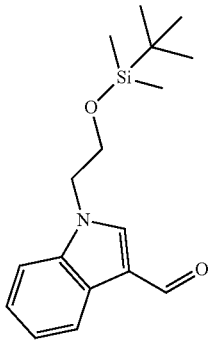 [SMILES: CC(C)(C)[Si](C)(C)OCCn1cc(C=O)c2ccccc21]

To a suspension of 1H-indole-3-carbaldehyde (49.7 mg, 0.34 mmol, commercially available from, for example, Sigma-Aldrich) and potassium carbonate (72.7 mg, 0.53 mmol) in DMF (2 mL) was added (2-bromoethoxy)(tert-butyl)dimethylsilane (0.088 mL, 0.41 mmol; commercially available from, for example, Sigma-Aldrich) and the reaction mixture was stirred at 80° C. under nitrogen for 20.5 h. The reaction mixture was left to cool to rt and left standing for 2 days. Saturated aqueous sodium bicarbonate (10 mL) was added and the mixture extracted with ethyl acetate (10 mL). The phases were separated and the aqueous phase further extracted with ethyl acetate (2×10 mL). The organic phases were combined, filtered through a cartridge containing a hydrophobic frit and concentrated in vacuo. The residue was dissolved in dichloromethane (5 mL), transferred to a tarred vial, concentrated under a stream of nitrogen and dried in vacuo to give an orange oil. The oil was dissolved in dichloromethane (3 mL) and loaded onto a 10 g SNAP silica cartridge which was eluted with a gradient of 20-70% ethyl acetate in cyclohexane. The required fractions were concentrated in vacuo before being dissolved in dichloromethane (6 mL), transferred to a tarred vial, concentrated under a stream of nitrogen and dried in vacuo to give a yellow oil; 1-(2-((tert-butyldimethylsilyl)oxy)ethyl)-1H-indole-3-carbaldehyde (98.8 mg, 0.33 mmol, 95% yield).

LCMS (2 min formic) Rt=1.38 min, m/z=304 for [MH]+

Intermediate 175: (1-(2-((tert-Butyldimethylsilyl)oxy)ethyl)-1H-indol-3-yl)methanol

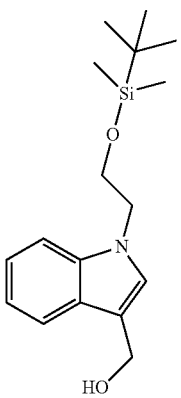 [SMILES: CC(C)(C)[Si](C)(C)OCCn1cc(CO)c2ccccc21]

A solution of 1-(2-((tert-butyldimethylsilyl)oxy)ethyl)-1H-indole-3-carbaldehyde (97.5 mg, 0.32 mmol) in ethanol (2 mL) was cooled to 0° C. with stirring under nitrogen before sodium borohydride (25 mg, 0.66 mmol) was added. The reaction mixture was allowed to warm to rt and stirred for 6 h. Water (3 mL) was added and the reaction mixture partitioned between aqueous saturated sodium bicarbonate solution (10 mL) and ethyl acetate (10 mL). The phases were separated and the aqueous phase extracted with further ethyl acetate (2×10 mL). The organic phases were combined, filtered through a cartridge containing a hydrophobic frit and concentrated in vacuo. The resulting oil was dissolved in a 1:1 mixture of dichloromethane/methanol (6 mL), transferred to a tarred vial, concentrated under a stream of nitrogen and dried in vacuo to give a yellow oil; (1-(2-((tert-butyldimethylsilyl)oxy)ethyl)-1H-indol-3-yl)methanol (88.5 mg, 0.29 mmol, 90% yield).

$^1$H NMR (400 MHz, CDCl$_3$) δ ppm 7.74 (d, J=8.1 Hz, 1H) 7.36 (d, J=8.1 Hz, 1H) 7.25 (dt, J=7.1 Hz, 1.2 Hz, 1H) 7.18 (s, 1H) 7.16 (dt, J=7.1 Hz, 1.0 Hz, 1H) 4.88 (d, J=4.9 Hz, 2H) 4.23 (t, J=5.6 Hz, 2H) 3.93 (t, J=5.6 Hz, 2H) 1.37 (br t, J=5.4 Hz 1H) 0.86 (s, 9H) −0.09 (2, 6H).

Intermediate 176:
5-Bromo-N-ethyl-2-methoxynicotinamide

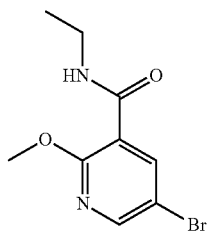

To a solution of 5-bromo-2-methoxynicotinic acid (15 g, 64.6 mmol, commercially available from, for example, Combiblocks) in DCM (100 mL) cooled to 0° C., was added oxalyl dichloride (16.98 mL, 194.0 mmol) followed by the slow addition of DMF (5.01 mL, 64.6 mmol) at 0° C. The reaction mixture was then stirred for 18 h at rt. A small aliquot of the reaction mixture was taken and quenched with MeOH, the TLC shows the complete conversion of SM. The reaction mixture was then concentrated and re-dissolved in DCM (150 mL) and treated with ethanamine hydrochloride (7.91 g, 97 mmol). The reaction mixture was stirred for 3 h at rt. After the reaction, water was added and the organics extracted with ethyl acetate (2×300 mL). The organic layer was separated, dried over Na$_2$SO$_4$, filtered and concentrated to obtain the crude product. The crude product was purified by column chromatography on a silica gel 100-200 column and was eluted with 16% EtOAc/n-hexane. The collected pure fractions were concentrated under reduced pressure to afford the desired product 5-bromo-N-ethyl-2-methoxynicotinamide (11 g, 41.0 mmol, 64% yield) as an off-white solid.

LCMS (10 min RND-FA-10-MIN): Rt=4.22 min, [MH]+=261.
LCMS Conditions: RND-FA-10-MIN:
Column: Acquity BEH C18 (100 mm×2.1 mm, 1.7 μm)
Mobile Phase: A: 0.05% formic acid in ACN; B: 0.05% formic acid in water
Time (min)/% B: 0/97, 0.4/97, 7.5/2, 9.5/2, 9.6/97, 10/97
Column Temp: 35° C., Flow Rate: 0.45 mL/min

Intermediate 177: Butyl 5-(ethylcarbamoyl)-6-methoxynicotinate

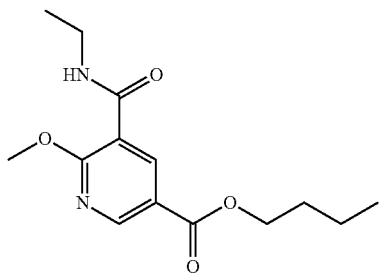 [SMILES: CCCCOC(=O)c1cnc(OC)c(C(=O)NCC)c1]

To a solution of 5-bromo-N-ethyl-2-methoxynicotinamide (11 g, 41.0 mmol) in DMF (100 mL) was added triethylamine (17.16 mL, 123 mmol), 1-butanol (11.98 mL, 205 mmol) and xantphos (1.662 g, 2.87 mmol) in a steel bomb. The reaction mixture was degassed for 10 min with argon. Then palladium(II) acetate (0.921 g, 4.10 mmol) was added and the reaction stirred under a carbon monoxide atmosphere at rt. Then the steel bomb was closed and the reaction was stirred under a carbon monoxide atmosphere (100 psi) at 110° C. for 18 h. After cooling, the reaction mixture was filtered through a Celite pad and washed with ethyl acetate. The filtrate was partitioned between ethyl acetate & cold water. The organic phase was washed with saturated brine, dried over $Na_2SO_4$ and concentrated under vacuum to afford the crude product. The crude product was purified by column chromatography on a silica gel 100-200 column which was eluted with 25% EtOAc/n-hexane. The collected pure fractions were concentrated under reduced pressure to give the desired product—butyl 5-(ethylcarbamoyl)-6-methoxynicotinate (4.4 g, 12.57 mmol, 30.6% yield).

LCMS (10 min RND-ABC-10-MIN-V): Rt=4.70 min, $[MH]^+$=281.1.

LCMS Conditions: RND-ABC-10-MIN-V
Column: Xbridge C18 (50 mm×4.6 mm, 2.5 μm),
Mobile Phase: A: 5 mM ammonium bicarbonate in water (pH 10); B: ACN
Time (min)/% ACN: 0/5, 0.5/5, 1/15, 6/98, 9/98, 9.5/5, 10/5
Column temp: 35° C., Flow Rate: 1.3 mL

Intermediate 178: 5-(Ethylcarbamoyl)-6-methoxynicotinic acid

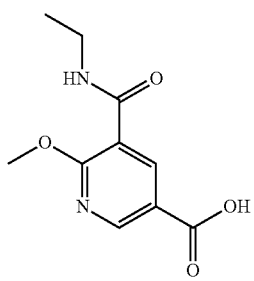 [SMILES: CCNC(=O)c1cc(C(=O)O)cnc1OC]

To a solution of butyl 5-(ethylcarbamoyl)-6-methoxynicotinate (4.4 g, 12.56 mmol) in THF (40 mL), acetonitrile (40 mL) and water (40 mL), was added LiOH (0.601 g, 25.1 mmol) at rt. The reaction mixture was stirred at rt for 16 h. After the reaction, the solvent was evaporated in vacuum, water was added and the reaction acidified with 1N HCl, (until pH=2) and then extracted with ethyl acetate (2×200 mL). The organic phase was separated, dried over $Na_2SO_4$ and concentrated under vacuum to afford the crude product, which was washed with n-pentane (2×10 mL) to afford the pure product—5-(ethylcarbamoyl)-6-methoxynicotinic acid (3 g, 12.13 mmol, 97% yield) as a white solid.

LCMS (10 min RND-FA-10-MIN): Rt=2.83 min, $[MH]^+$=225.1.

LCMS Conditions: RND-FA-10-MIN:
Column: Acquity BEH C18 (100 mm×2.1 mm, 1.7 μm)
Mobile Phase: A: 0.05% formic acid in ACN; B: 0.05% formic acid in water
Time (min)/% B: 0/97, 0.4/97, 7.5/2, 9.5/2, 9.6/97, 10/97
Column Temp: 35° C., Flow Rate: 0.45 mL/min

Intermediate 179: (+/−)-$N^3$-Ethyl-2-methoxy-$N^5$-((trans)-2-methylcyclopropyl)pyridine-3,5-dicarboxamide

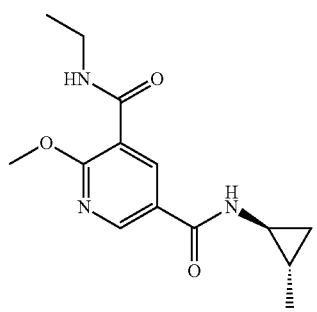 [SMILES: CCNC(=O)c1cc(C(=O)N[C@H]2C[C@@H]2C)cnc1OC]

To a solution of 5-(ethylcarbamoyl)-6-methoxynicotinic acid (2.8 g, 11.24 mmol) in DMF (24 mL) stirred under nitrogen at 0° C., was added DIPEA (5.89 mL, 33.7 mmol) and HATU (8.55 g, 22.48 mmol) and the reaction stirred for 30 min at rt. (+/−)-(trans)-2-Methylcyclopropanamine (0.959 g, 13.49 mmol, commercially available from, for example, ChemBridge corporation) was added to the reaction mixture at 0° C. and the reaction stirred for 16 h at rt. After completion of the reaction, the reaction mixture was diluted with water (50 mL) and extracted with EtOAc (2×250 mL). The combined organic layer was dried over anhydrous $Na_2SO_4$, filtered and the filtrate was concentrated to give (+/−)-$N^3$-ethyl-2-methoxy-$N^5$-((trans)-2-methylcyclopropyl)pyridine-3,5-dicarboxamide (6 g, 8.22 mmol, 73% yield). This was taken on to the next step without purification.

LCMS (10 min RND-FA-10-MIN): Rt=3.36 min, $[MH]^+$=278.1.

LCMS Conditions: RND-FA-10-MIN:
Column: Acquity BEH C18 (100 mm×2.1 mm, 1.7 μm)
Mobile Phase: A: 0.05% formic acid in ACN; B: 0.05% formic acid in water
Time (min)/% B: 0/97, 0.4/97, 7.5/2, 9.5/2, 9.6/97, 10/97
Column Temp: 35° C., Flow Rate: 0.45 mL/min

Intermediate 180: (+/−)-N³-Ethyl-N⁵-((trans)-2-methylcyclopropyl)-2-oxo-1,2-dihydropyridine-3,5-dicarboxamide

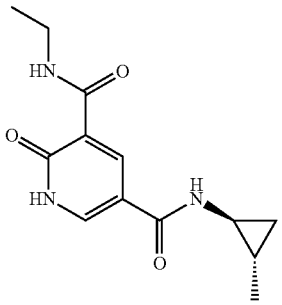 [SMILES: CCNC(=O)c1cc(C(=O)N[C@H]2C[C@@H]2C)c[nH]c1=O]

A solution of (+/−)-N³-ethyl-2-methoxy-N⁵-((trans)-2-methylcyclopropyl)pyridine-3,5-dicarboxamide (6 g, 8.22 mmol), TMSCl (3.15 mL, 24.66 mmol) and sodium iodide (3.70 g, 24.66 mmol) in acetonitrile (30 mL) was stirred under nitrogen at rt for 1 h. After completion of the reaction, the reaction mixture was diluted with EtOAc (300 mL) and washed with sodium thiosulphate solution (50 mL). The combined organic layer was dried over anhydrous Na₂SO₄, filtered and the filtrate was concentrated to afford the crude product. The crude product was purified by flash chromatography using a 100-200 mesh silica gel column eluting with 0-10% MeOH in DCM. The pure fractions were collected, concentrated and dried to afford (+/−)-N³-ethyl-N⁵-((trans)-2-methylcyclopropyl)-2-oxo-1,2-dihydropyridine-3,5-dicarboxamide (2 g, 7.22 mmol, 88% yield) as an off white solid.

LCMS (4.5 min RND-FA-4.5-MIN): Rt=1.37 min, [MH]⁺=264.3.
LCMS Conditions: RND-FA-4.5-MIN
Column: Acquity BEH C18 (50 mm×2.1 mm, 1.7 µm)
Mobile Phase: A: 0.05% formic acid in water; B: 0.05% formic acid in ACN
Time (min)/% B: 0/3, 0.4/3, 3.2/98, 3.8/98, 4.2/3, 4.5/3
Column Temp: 35° C., Flow Rate: 0.6 mL/min

Intermediate 181: 2-(Benzyloxy)-N³-methyl-N⁵-((1S,2S)-2-methylcyclopropyl)pyridine-3,5-dicarboxamide

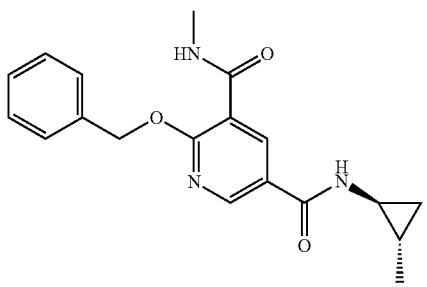 [SMILES: CNC(=O)c1cc(C(=O)N[C@H]2C[C@@H]2C)cnc1OCc1ccccc1]

2,4,6-Trichlorophenyl 6-(benzyloxy)-5-(methylcarbamoyl)nicotinate (1022 mg, 2.19 mmol), (1S,2S)-2-methylcyclopropanamine hydrochloride (260 mg, 2.42 mmol), DMAP (39 mg, 0.319 mmol), triethylamine (0.92 mL, 6.60 mmol) and THF (10 mL) were stirred at 45° C. under N₂. After stirring for 4 h, DMAP (22 mg, 0.18 mmol) and triethylamine (0.3 mL, 2.15 mmol) were added and the reaction stirred overnight. The suspension was then partitioned between EtOAc (20 mL) and sodium bicarbonate solution. (20 mL), extracted with EtOAc (20 mL), dried over a hydrophobic frit and concentrated to give the crude product (1.57 g) as a cream solid. This was purified by chromatography on SiO₂ (Biotage SNAP 100 g cartridge, eluting with 0-100% EtOAc/cyclohexane). The desired fractions were concentrated to give 2-(benzyloxy)-N³-methyl-N⁵-((1S,2S)-2-methylcyclopropyl)pyridine-3,5-dicarboxamide (321 mg, 0.85 mmol, 39% yield).

LCMS (2 min Formic): Rt=0.98 min, [MH]⁺=340.2.

¹H NMR (400 MHz, DMSO-d₆) δ ppm 8.67 (d, J=2.4 Hz, 1H) 8.53 (br. d, J=3.9 Hz, 1H) 8.46 (d, J=2.4 Hz, 1H) 8.24-8.32 (m, 1H) 7.44-7.50 (m, 2H) 7.38 (t, J=7.2 Hz, 2H) 7.28-7.34 (m, 1H) 5.55 (s, 2H) 2.80 (d, J=4.6 Hz, 3H) 2.51-2.57 (m, 1H) 1.06 (d, J=6.1 Hz, 3H) 0.87-0.98 (m, 1H) 0.74 (dt, J=8.6, 4.6 Hz, 1H) 0.48 (dt, J=7.3, 5.5 Hz, 1H)

Intermediate 182: N³-Methyl-N⁵-((1S,2S)-2-methylcyclopropyl)-2-oxo-1,2-dihydropyridine-3,5-dicarboxamide

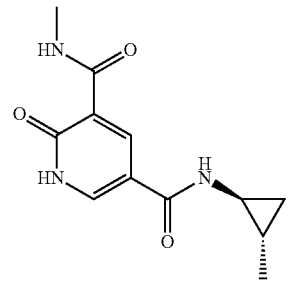 [SMILES: CNC(=O)c1cc(C(=O)N[C@H]2C[C@@H]2C)c[nH]c1=O]

2-(Benzyloxy)-N³-methyl-N⁵-((1S,2S)-2-methylcyclopropyl)pyridine-3,5-dicarboxamide (320 mg, 0.94 mmol) was stirred in TFA (3 mL, 38.9 mmol) at 90° C. After 1 h the sample was concentrated to give the crude product (633 mg) as a red oil. This was purified by chromatography on SiO₂ (Biotage SNAP 50 g cartridge, eluting with 0-50% (25% EtOH in EtOAc)/EtOAc). The desired fractions were concentrated and dried in vacuo to give N³-methyl-N⁵-((1S,2S)-2-methylcyclopropyl)-2-oxo-1,2-dihydropyridine-3,5-dicarboxamide (297 mg, 0.94 mmol, 100% yield) as a cream solid.

LCMS (2 min Formic): Rt=0.54 min, [MH]⁺=250.1.

¹H NMR (400 MHz, DMSO-d₆) δ ppm 12.77 (br. d, J=5.9 Hz, 1H) 9.37-9.45 (m, 1H) 8.76 (d, J=2.9 Hz, 1H) 8.42 (d, J=3.9 Hz, 1H) 8.18 (dd, J=6.8, 2.7 Hz, 1H) 2.83 (d, J=4.6 Hz, 3H) 2.47-2.53 (obs, 1H) 1.04 (d, J=6.1 Hz, 3H) 0.84-0.95 (m, 1H) 0.71 (dt, J=8.9, 4.5 Hz, 1H) 0.46 (dt, J=7.3, 5.5 Hz, 1H)

Intermediate 183: (S*)-Butyl 1-(1-(3-methoxyphenyl)ethyl)-5-(methylcarbamoyl)-6-oxo-1,6-dihydropyridine-3-carboxylate

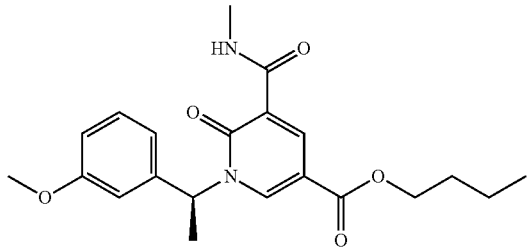 [SMILES: CCCCOC(=O)c1cc(C(=O)NC)c(=O)n([C@@H](C)c2cccc(OC)c2)c1]

Butyl 5-(methylcarbamoyl)-6-oxo-1,6-dihydropyridine-3-carboxylate (200 mg, 0.79 mmol) and potassium carbonate (219 mg, 1.59 mmol) were stirred in DMF (4.0 mL) under nitrogen at rt, before the addition of 1-(1-bromoethyl)-3-methoxybenzene (286 mg, 1.33 mmol). The reaction was stirred at rt for 24 h. The reaction mixture was poured onto 3:1 brine:water (50 mL) and the aqueous layer was extracted with ethyl acetate (3×20 mL). The combined organics were washed with brine, dried through a hydrophobic frit and evaporated in vacuo to yield the crude product as an orange solvate in DMF. The residue was loaded in dichloromethane onto a 25 g SNAP cartridge and purified via Biotage SP4 flash chromatography, eluting from 15-75% ethyl acetate/cyclohexane. The relevant fractions were combined and evaporated in vacuo to yield the desired product (+/−)-butyl 1-(1-(3-methoxyphenyl)ethyl)-5-(methylcarbamoyl)-6-oxo-1,6-dihydropyridine-3-carboxylate (268 mg, 0.66 mmol, 83% yield) as an orange gum.

The racemate (257 mg) was dissolved in EtOH (~8-10 mL) with heat. Injection: 0.3 mL manual injections were made via a Rheodyne valve onto the column (10% EtOH (with 0.2% v/v isopropylamine)/heptane (with 0.2% v/v isopropylamine), flow rate=42.5 mL/min (pressure: 83 bar), detection: UV Diode Array at 280 nm (Band width 1 40 nm, reference 400 nm, bandwidth 100 nm), Column Chiralpak AD-H (250×30 mm, 5 µm). Fractions from 19-21 min were bulked and labelled peak 1. Fractions from 22-24 min were bulked and labelled peak 2. The bulked fractions were concentrated in vacuo, then taken up in EtOH and transferred to weighed flasks which were blown down to dyness under a stream of nitrogen gas.

The fractions corresponding to peak 1 were collected to afford intermediate 183 (102 mg, 0.25 mmol, 32%)

LCMS (2 min formic): Rt=1.22 min, [MH]$^+$=387.2.

The fractions corresponding to peak 2 were also collected to afford the undesired enantiomer (115 mg, 0.28 mmol, 36% yield)

Intermediate 184: (S*)-1-(1-(3-Methoxyphenyl)ethyl)-5-(methylcarbamoyl)-6-oxo-1,6-dihydropyridine-3-carboxylic acid

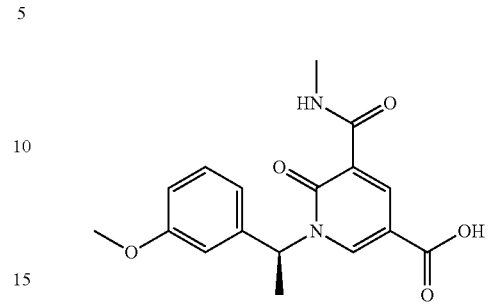

(S*)-Butyl 1-(1-(3-methoxyphenyl)ethyl)-5-(methylcarbamoyl)-6-oxo-1,6-dihydropyridine-3-carboxylate (100 mg, 0.26 mmol) was suspended in 1,4-dioxane (863 µL). Water (863 µL) was added, followed by lithium hydroxide (17 mg, 0.71 mmol) and the reaction mixture was stirred at rt for 1.5 h. The reaction mixture was then neutralized with 2M HCl and evaporated in vacuo to yield (S*)-1-(1-(3-methoxyphenyl)ethyl)-5-(methylcarbamoyl)-6-oxo-1,6-dihydropyridine-3-carboxylic acid (121 mg, 0.22 mmol, 85% yield) as a white solid. The purity was estimated at 60% based on the projected quantity of NaCl in residue.

LCMS (2 min formic): Rt=0.87 min, [MH]$^+$=331.1.

Intermediate 185: Butyl 1-(3-methoxybenzyl)-5-(methylcarbamoyl)-6-oxo-1,6-dihydropyridine-3-carboxylate

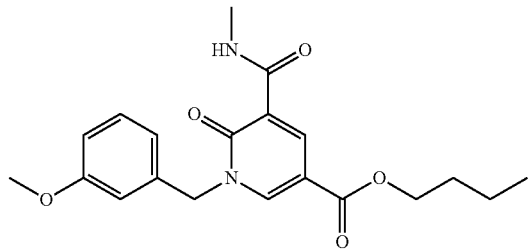 [SMILES: CCCCOC(=O)c1cc(C(=O)NC)c(=O)n(Cc2cccc(OC)c2)c1]

Butyl 5-(methylcarbamoyl)-6-oxo-1,6-dihydropyridine-3-carboxylate (2 g, 7.93 mmol), 1-(bromomethyl)-3-methoxybenzene (1.6 mL, 11.43 mmol), potassium carbonate (2.2 g, 15.92 mmol) and DMF (10 mL) were stirred at 90° C. for 1 h. The reaction mixture was then washed with LiCl (20 mL) and partitioned between EtOAc (40 mL) and water (40 mL). The aqueous phase was extracted with EtOAc (2×40 mL) and the combined organics dried over a hydrophobic frit and concentrated to give the crude product (~2.49 g) as an orange solid. This was purified by chromatography on SiO$_2$ (Biotage SNAP 100 g cartridge, eluting with 10-75% EtOAc/cyclohexane). The appropriate fractions were concentrated to give butyl 1-(3-methoxybenzyl)-5-(methylcarbamoyl)-6-oxo-1,6-dihydropyridine-3-carboxylate (2.01 g, 4.86 mmol, 61% yield) as an off white solid.

LCMS (2 min Formic): Rt=1.16 min, [MH]$^+$=373.2.

Intermediate 186: Butyl 1-(3-hydroxybenzyl)-5-(methylcarbamoyl)-6-oxo-1,6-dihydropyridine-3-carboxylate

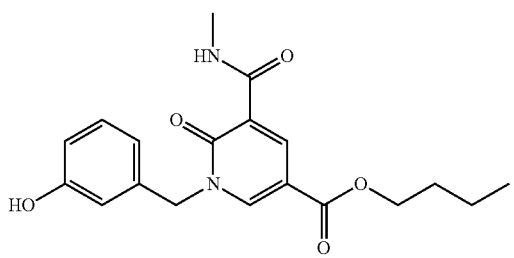 [SMILES: CCCCOC(=O)c1cc(C(=O)NC)c(=O)n(Cc2cccc(O)c2)c1]

Butyl 1-(3-methoxybenzyl)-5-(methylcarbamoyl)-6-oxo-1,6-dihydropyridine-3-carboxylate (500 mg, 1.34 mmol) in DCM (8 mL) was cooled to 0° C. under $N_2$ and $BBr_3$ (1M in DCM, 6.71 mL, 6.71 mmol) was added dropwise. After 10 min, the reaction was quenched with water (40 mL) and extracted with DCM (3×20 mL). The organic extract was then washed with sat. $NaHCO_3$ solution, dried ($Na_2SO_4$) and concentrated to give butyl 1-(3-hydroxybenzyl)-5-(methylcarbamoyl)-6-oxo-1,6-dihydropyridine-3-carboxylate (328 mg, 0.82 mmol, 61% yield) as an off-white solid.

LCMS (2 min Formic): Rt=1.00 min, $[MH]^+$=359.2.

Intermediate 187: (S)-Butyl 1-(3-(2-hydroxypropoxy)benzyl)-5-(methylcarbamoyl)-6-oxo-1,6-dihydropyridine-3-carboxylate

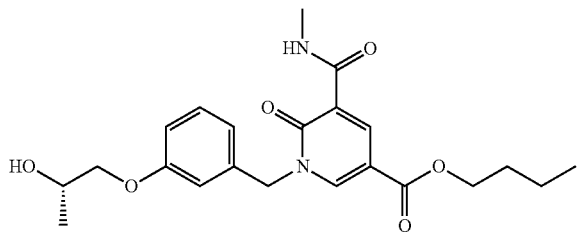 [SMILES: CCCCOC(=O)c1cc(C(=O)NC)c(=O)n(Cc2cccc(OC[C@H](C)O)c2)c1]

A mixture of butyl 1-(3-hydroxybenzyl)-5-(methylcarbamoyl)-6-oxo-1,6-dihydropyridine-3-carboxylate (100 mg, 0.28 mmol), (S)-2-methyloxirane (0.098 mL, 1.40 mmol, commercially available from, for example, Alfa Aesar) and $Et_3N$ (0.078 mL, 0.56 mmol) were dissolved in DMF (1 mL) and the reaction mixture was heated at 150° C. for 30 min in a 2 mL microwave vial.

Separately, a mixture of butyl 1-(3-hydroxybenzyl)-5-(methylcarbamoyl)-6-oxo-1,6-dihydropyridine-3-carboxylate (35 mg, 0.10 mmol), (S)-2-methyloxirane (0.034 mL, 0.49 mmol) and $Et_3N$ (0.027 mL, 0.20 mmol) were dissolved in DMF (0.5 mL) and the reaction mixture was heated at 150° C. for 30 min in a 2 mL microwave vial.

Both reaction mixtures were combined and partitioned between ethyl acetate and water. The organic layer was separated and the aqueous layer further extracted with ethyl acetate (2×20 mL). The combined organic layers were dried ($Na_2SO_4$) and concentrated to give the crude product (148 mg) as a pale yellow oil. This was purified by chromatography on $SiO_2$ (Biotage SNAP 10 g cartridge, eluting with 0-100% EtOAc/cyclohexane). The appropriate fractions were concentrated to give (S)-butyl 1-(3-(2-hydroxypropoxy)benzyl)-5-(methylcarbamoyl)-6-oxo-1,6-dihydropyridine-3-carboxylate (115 mg, 0.25 mmol, 89% yield) as a colourless oil.

$^1$H NMR (400 MHz, MeOH-$d_4$) δ ppm 8.84 (d, J=2.4 Hz, 1H) 8.64 (d, J=2.7 Hz, 1H) 7.26 (t, J=7.9 Hz, 1H) 6.86-6.97 (m, 3H) 5.27 (s, 2H) 4.28 (t, J=6.6 Hz, 2H) 4.01-4.13 (m, 1H) 3.79-3.89 (m, 2H) 2.93 (s, 3H) 1.66-1.77 (m, 2H) 1.37-1.50 (m, 2H) 1.24 (d, J=6.6 Hz, 3H) 0.96 (t, J=7.5 Hz, 3H). Exchangeable protons not observed.

Intermediate 188: (S)-1-(3-(2-Hydroxypropoxy)benzyl)-5-(methylcarbamoyl)-6-oxo-1,6-dihydropyridine-3-carboxylic acid

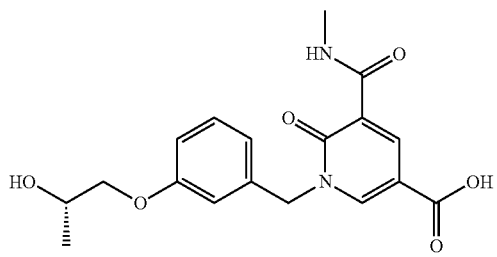 [SMILES: CNC(=O)c1cc(C(=O)O)cn(Cc2cccc(OC[C@H](C)O)c2)c1=O]

(S)-Butyl 1-(3-(2-hydroxypropoxy)benzyl)-5-(methylcarbamoyl)-6-oxo-1,6-dihydropyridine-3-carboxylate (115 mg, 0.28 mmol) was dissolved in 1,4-dioxane (3 mL). Water (3 mL) was added, followed by LiOH (14 mg, 0.59 mmol) and the reaction mixture stirred at rt for 2 h. The dioxane was removed in vacuo and acetic acid (0.032 mL, 0.55 mmol) was added. The reaction mixture was partitioned between ethyl acetate and water. The organic layer was separated and the aqueous layer extracted with further ethyl acetate (4×20 mL). The combined organic layers were dried ($Na_2SO_4$) and concentrated to give (S)-1-(3-(2-hydroxypropoxy)benzyl)-5-(methylcarbamoyl)-6-oxo-1,6-dihydropyridine-3-carboxylic acid (106 mg, 0.27 mmol, 96% yield) as a colourless oil.

LCMS (2 min Formic): Rt=0.72 min, $[MH]^+$=361.2.

Intermediate 189: 1-((1-(tert-Butoxycarbonyl)indolin-4-yl)methyl)-5-(methylcarbamoyl)-6-oxo-1,6-dihydropyridine-3-carboxylic acid

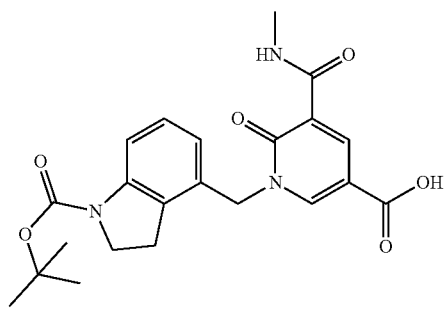 [SMILES: CNC(=O)c1cc(C(=O)O)cn(Cc2cccc3c2CCN3C(=O)OC(C)(C)C)c1=O]

tert-Butyl 4-((5-(butoxycarbonyl)-3-(methylcarbamoyl)-2-oxopyridin-1(2H)-yl)methyl)indoline-1-carboxylate (380 mg, 0.79 mmol) was taken up in THF (3 mL) and water (3 mL). LiOH (37.6 mg, 1.57 mmol) was added to the solution and the reaction stirred overnight at rt. HCl (2M, aq.) was added to acidify the solution to ~pH 5. The reaction mixture was then extracted using DCM. The organic layers were combined, passed through a hydrophobic frit and concentrated in vacuo to give 1-((1-(tert-butoxycarbonyl)indolin-4-yl)methyl)-5-(methylcarbamoyl)-6-oxo-1,6-dihydropyridine-3-carboxylic acid (312 mg, 0.73 mmol, 93% yield).

LCMS (2 min Formic): Rt=1.07 min, [MH]$^+$=428

Intermediate 190: $N^5$-Cyclopropyl-$N^3$-methyl-1-((2-methyl-1-tosyl-1H-indol-4-yl)methyl)-2-oxo-1,2-dihydropyridine-3,5-dicarboxamide

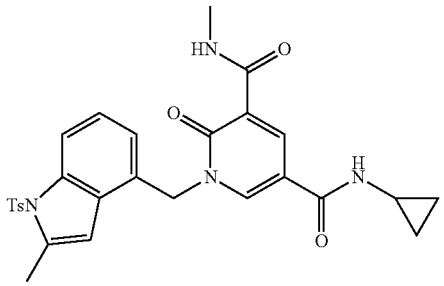 [SMILES: CNC(=O)c1cc(C(=O)NC2CC2)cn(Cc2cccc3c2cc(C)n3S(=O)(=O)c2ccc(C)cc2)c1=O]

To a stirred solution of $N^5$-cyclopropyl-$N^3$-methyl-2-oxo-1,2-dihydropyridine-3,5-dicarboxamide (60 mg, 0.26 mmol) and potassium carbonate (106 mg, 0.77 mmol) in DMF (2.3 mL) under nitrogen at rt, was added 4-(bromomethyl)-2-methyl-1-tosyl-1H-indole (322 mg, 0.51 mmol, 60% wt) as a solution in DMF (2.3 mL) and the reaction stirred for 3 h. A further portion of potassium carbonate (70.5 mg, 0.51 mmol) was added. The reaction was stirred for 19 h. Further portions of $N^5$-cyclopropyl-$N^3$-methyl-2-oxo-1,2-dihydropyridine-3,5-dicarboxamide (20 mg, 0.09 mmol) and potassium carbonate (35.3 mg, 0.26 mmol) were added. After 22.5 h a further portion of $N^5$-cyclopropyl-$N^3$-methyl-2-oxo-1,2-dihydropyridine-3,5-dicarboxamide (30 mg, 0.13 mmol) was added. After 24 h the reaction mixture was poured onto sat. aqueous LiCl (25 mL) and extracted with ethyl acetate (20 mL, then 2×10 mL). The combined ethyl acetate portions were washed with brine, dried through a hydrophobic frit and evaporated in vacuo to yield the crude product (379 mg). The sample was loaded in dichloromethane onto a 50 g SNAP cartridge and purified via Biotage SP4 flash chromatography, eluting with 0-50% (3:1 ethyl acetate: ethanol)/cyclohexane. The relevant fractions were combined and evaporated in vacuo. The residue was sonicated with diethyl ether and evaporated in vacuo again to yield $N^5$-cyclopropyl-$N^3$-methyl-1-((2-methyl-1-tosyl-1H-indol-4-yl)methyl)-2-oxo-1,2-dihydropyridine-3,5-dicarboxamide (78 mg, 0.14 mmol, 30% yield) as a white solid.

LCMS (2 min formic): Rt=1.17 min, [MH]$^+$=533.4.

Intermediate 191: (+/−)-$N^3$-Ethyl-$N^5$-((trans)-2-methylcyclopropyl)-2-oxo-1-((1-tosyl-1H-indol-4-yl)methyl)-1,2-dihydropyridine-3,5-dicarboxamide

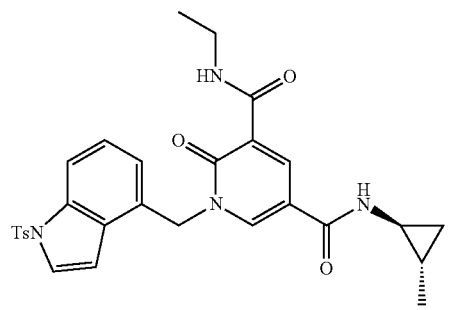 [SMILES: CCNC(=O)c1cc(C(=O)N[C@H]2C[C@@H]2C)cn(Cc2cccc3c2ccn3S(=O)(=O)c2ccc(C)cc2)c1=O]

A solution of (+/−)-$N^3$-ethyl-$N^5$-((trans)-2-methylcyclopropyl)-2-oxo-1,2-dihydropyridine-3,5-dicarboxamide (100 mg, 0.36 mmol), 4-(bromomethyl)-1-tosyl-1H-indole (201 mg, 0.54 mmol) and $K_2CO_3$ (100 mg, 0.72 mmol) in DMF (2 mL) was stirred under nitrogen at 90° C. for 2 h. After 16 h, the reaction mixture was cooled to rt, diluted with water (50 mL) and extracted with EtOAc (2×50 mL). The combined organic layer was dried over anhydrous $Na_2SO_4$, filtered and the filtrate was concentrated to afford the crude product. This was purified by flash chromatography using a 100-200 mesh silica gel column eluting with 0-5% MeOH in DCM. The pure fractions were collected, concentrated and dried to afford (+/−)-$N^3$-ethyl-$N^5$-((trans)-2-methylcyclopropyl)-2-oxo-1-((1-tosyl-1H-indol-4-yl)methyl)-1,2-dihydropyridine-3,5-dicarboxamide (150 mg, 0.24 mmol, 67% yield) as a yellow solid.

LCMS (5.5 min RND-FA-5-5-MIN-50): Rt=3.10 min, [MH]$^+$=547.3.
LCMS Conditions: RND-FA-5-5-MIN-50
Column: Acquity BEH C18 (50 mm×2.1 mm, 1.7 μm)
Mobile Phase: B: 0.05% formic acid in ACN; A: 0.05% formic acid in water
Time (min)/% A: 0/97, 0.4/97, 4.0/2, 4.5/2, 5/97, 5.5/97
Column Temp: 35° C., Flow Rate: 0.45 mL/min Intermediate 192: (+/−)-tert-Butyl 4-((3-(ethylcarbamoyl)-5-(((trans)-2-methylcyclopropyl)carbamoyl)-2-oxopyridin-1(2H)-yl)methyl)indoline-1-carboxylate

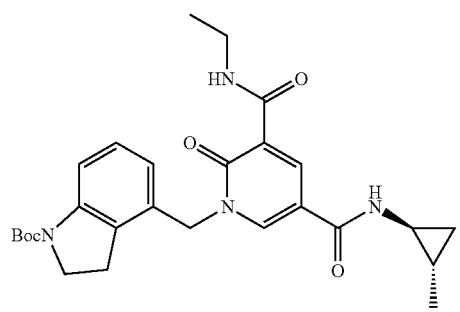 [SMILES: CCNC(=O)c1cc(C(=O)N[C@H]2C[C@@H]2C)cn(Cc2cccc3c2CCN3C(=O)OC(C)(C)C)c1=O]

To a solution of (+/−)-$N^3$-ethyl-$N^5$-((trans)-2-methylcyclopropyl)-2-oxo-1,2-dihydropyridine-3,5-dicarboxamide (150 mg, 0.541 mmol), triphenylphosphine (426 mg, 1.624 mmol) and DIAD (0.316 mL, 1.624 mmol) in toluene (5 mL) stirred under nitrogen at rt, was added tert-butyl 4-(hydroxymethyl)indoline-1-carboxylate (215 mg, 0.812 mmol). The reaction mixture was stirred at rt for 16 h. The reaction mixture was quenched with water and extracted with DCM (2×100 mL). The organic phase was washed with saturated brine (25 mL), dried over sodium sulphate, filtered and evaporated in vacuo to give (+/−)-tert-butyl 4-((3-(ethylcarbamoyl)-5-(((trans)-2-methylcyclopropyl)carbamoyl)-2-oxopyridin-1(2H)-yl)methyl)indoline-1-carboxylate (400 mg, 0.259 mmol, 47.8% yield) as a brown solid. The compound was used crude in the next reaction LCMS (5.5 min RND-FA-5-5-MIN-50): Rt=3.06 min, [MH]⁺=395.2.
LCMS Conditions: RND-FA-5-5-MIN-50
Column: Acquity BEH C18 (50 mm×2.1 mm, 1.7 µm)
Mobile Phase: B: 0.05% formic acid in ACN; A: 0.05% formic acid in water
Time (min)/% A: 0/97, 0.4/97, 4.0/2, 4.5/2, 5/97, 5.5/97
Column Temp: 35° C., Flow Rate: 0.45 mL/min Intermediate 193: (+/−)-N³-Ethyl-1-(3-methoxybenzyl)-N⁵-((trans)-2-methylcyclopropyl)-2-oxo-1,2-dihydropyridine-3,5-dicarboxamide

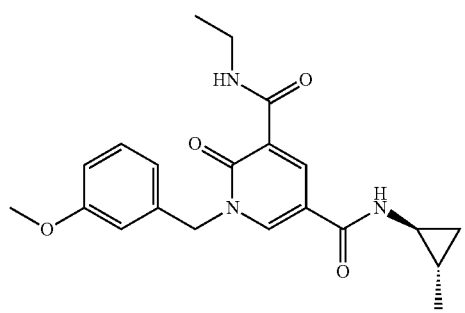 [SMILES: CCNC(=O)c1cc(C(=O)N[C@H]2C[C@@H]2C)cn(Cc2cccc(OC)c2)c1=O]

A solution of (+/−)-N³-ethyl-N⁵-((trans)-2-methylcyclopropyl)-2-oxo-1,2-dihydropyridine-3,5-dicarboxamide (300 mg, 1.08 mmol), 1-(bromomethyl)-3-methoxybenzene (326 mg, 1.62 mmol) and K₂CO₃ (299 mg, 2.17 mmol) in DMF (2 mL) was stirred under nitrogen at 60° C. for 1 h. The reaction mixture was then diluted with EtOAc (100 mL) and washed with water (50 mL). The combined organic layer was dried over anhydrous Na₂SO₄, filtered and the filtrate was concentrated to afford the crude product. This was purified by flash chromatography using a 100-200 mesh silica gel column and eluting with 0-10% MeOH in DCM. The pure fractions were collected, concentrated and dried to obtain (+/−)-N³-ethyl-1-(3-methoxybenzyl)-N5-((trans)-2-methylcyclopropyl)-2-oxo-1,2-dihydropyridine-3,5-dicarboxamide (320 mg, 0.69 mmol, 64% yield) as an off white solid.

LCMS (5.5 min RND-FA-5-5-MIN-50): Rt=2.54 min, [MH]⁺=384.1.
LCMS Conditions: RND-FA-5-5-MIN-50
Column: Acquity BEH C18 (50 mm×2.1 mm, 1.7 µm)
Mobile Phase: B: 0.05% formic acid in ACN; A: 0.05% formic acid in water
Time (min)/% A: 0/97, 0.4/97, 4.0/2, 4.5/2, 5/97, 5.5/97
Column Temp: 35° C., Flow Rate: 0.45 mL/min Intermediate 194: (+/−)-N³-Ethyl-1-(3-hydroxybenzyl)-N⁵-((trans)-2-methylcyclopropyl)-2-oxo-1,2-dihydropyridine-3,5-dicarboxamide

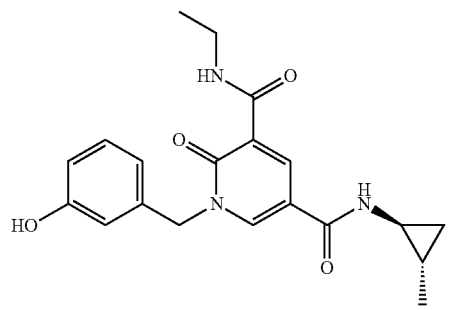 [SMILES: CCNC(=O)c1cc(C(=O)N[C@H]2C[C@@H]2C)cn(Cc2cccc(O)c2)c1=O]

To a solution of (+/−)-N³-ethyl-1-(3-methoxybenzyl)-N⁵-((trans)-2-methylcyclopropyl)-2-oxo-1,2-dihydropyridine-3,5-dicarboxamide (320 mg, 0.69 mmol) in DCM (2 mL) stirred under nitrogen at −10° C., was added BBr₃ (1.385 mL, 1.39 mmol, 1M in DCM). The reaction mixture was stirred at 0° C. for 30 min. The reaction mixture was then quenched with water and extracted with DCM (2×100 mL). The organic phase was washed with saturated brine (25 mL), dried over sodium sulphate, filtered and evaporated in vacuo to afford the crude product. This was purified by flash chromatography, using a 100-200 mesh silica gel column and eluting with 0-10% MeOH in DCM. The pure fractions were collected, concentrated and dried to obtain (+/−)-N³-ethyl-1-(3-hydroxybenzyl)-N⁵-((trans)-2-methylcyclopropyl)-2-oxo-1,2-dihydropyridine-3,5-dicarboxamide (150 mg, 0.40 mmol, 57% yield) as an off white solid.

LCMS (5.5 min RND-FA-5-5-MIN-50): Rt=2.19 min, [MH]⁺=370.1.
LCMS Conditions: RND-FA-5-5-MIN-50
Column: Acquity BEH C18 (50 mm×2.1 mm, 1.7 µm)
Mobile Phase: B: 0.05% formic acid in ACN; A: 0.05% formic acid in water
Time (min)/% A: 0/97, 0.4/97, 4.0/2, 4.5/2, 5/97, 5.5/97
Column Temp: 35° C., Flow Rate: 0.45 mL/min Intermediate 195: (+/−)-1-(3-(2-Hydroxyethoxy)benzyl)-N⁵-((trans)-2-hydroxymethyl)cyclopropyl)-N³-methyl-2-oxo-1,2-dihydropyridine-3,5-dicarboxamide

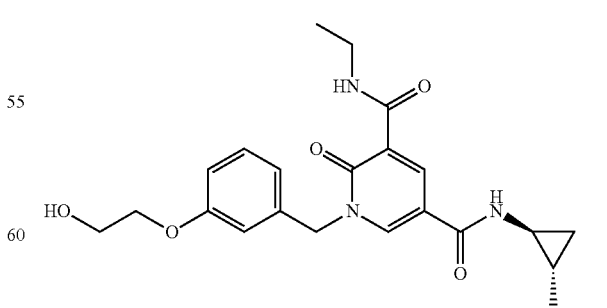

1-(3-(2-Hydroxyethoxy)benzyl)-5-(methylcarbamoyl)-6-oxo-1,6-dihydropyridine-3-carboxylic acid (120 mg, 0.35 mmol) was taken up in DMF (5 mL) and HATU (145 mg, 0.38 mmol) followed by DIPEA (0.121 mL, 0.69 mmol) were added. The reaction mixture was allowed to stir for 5 min, then (+/−)-((trans)-2-aminocyclopropyl)methanol (30.2 mg, 0.35 mmol) was added and the reaction allowed to stir overnight. The reaction mixture was concentrated in vacuo and purified by MDAP (High pH). The appropriate fractions were combined and concentrated in vacuo to give (+/−)-1-(3-(2-hydroxyethoxy)benzyl)-N$^5$-((trans)-2-(hydroxymethyl)cyclopropyl)-N$^3$-methyl-2-oxo-1,2-dihydropyridine-3,5-dicarboxamide (51 mg, 0.12 mmol, 35% yield) as an orange solid.

LCMS (2 min Formic): Rt=0.62 min, [MH]+=416

Intermediate 196: (+/−)-N$^5$-((trans)-2-Ethoxycyclopropyl)-1-(3-(2-hydroxyethoxy)benzyl)-N$^3$-methyl-2-oxo-1,2-dihydropyridine-3,5-dicarboxamide

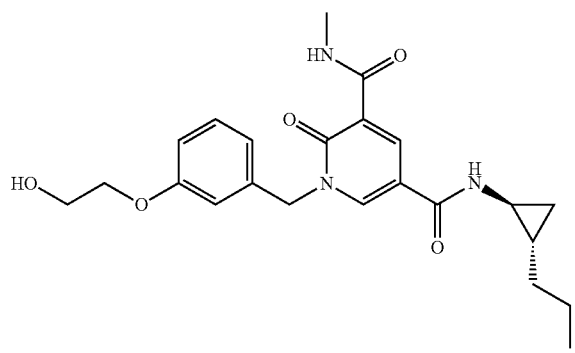 [SMILES: CCC[C@H]1C[C@@H]1NC(=O)c1cc(C(=O)NC)c(=O)n(Cc2cccc(OCCO)c2)c1]

1-(3-(2-Hydroxyethoxy)benzyl)-5-(methylcarbamoyl)-6-oxo-1,6-dihydropyridine-3-carboxylic acid (150 mg, 0.43 mmol) was taken up in DMF (4 mL) and HATU (181 mg, 0.48 mmol) followed by DIPEA (0.151 mL, 0.87 mmol) were added. The reaction mixture was allowed to stir for 5 min, then (+/−)-(trans)-2-ethoxycyclopropanamine, hydrochloride (65.6 mg, 0.48 mmol) was added and the reaction allowed to stir overnight. The reaction mixture was purified by MDAP (High pH). The appropriate fractions were combined and concentrated in vacuo to give (+/−)-N$^5$-((trans)-2-ethoxycyclopropyl)-1-(3-(2-hydroxyethoxy)benzyl)-N$^3$-methyl-2-oxo-1,2-dihydropyridine-3,5-dicarboxamide (130 mg, 0.30 mmol, 70% yield) as a white solid.

LCMS (2 min Formic): Rt=0.74 min, [MH]+=430

Intermediate 197: N$^3$-Methyl-N5-((1S,2S)-2-methylcyclopropyl)-2-oxo-1-(3-(2-oxoethyl)benzyl)-1,2-dihydropyridine-3,5-dicarboxamide

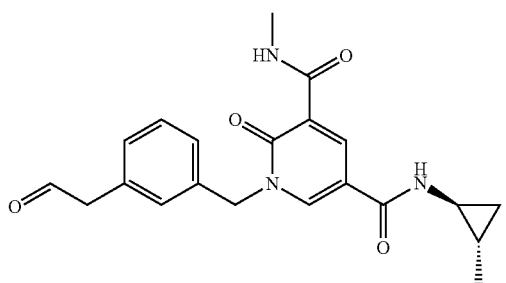

Dess-Martin Periodinane (237 mg, 0.56 mmol) was added to a solution of 1-(3-(2-hydroxyethyl)benzyl)-N$^3$-methyl-N$^5$-((1S,2S)-2-methylcyclopropyl)-2-oxo-1,2-dihydropyridine-3,5-dicarboxamide (165 mg, 0.43 mmol) in DCM (4 mL) at 0° C. The reaction mixture was allowed to warm to rt and stirred overnight. The reaction was quenched with sat. sodium bicarbonate solution and extracted with DCM. The organic layer was passed through a hydrophobic frit and concentrated in vacuo to give crude N$^3$-methyl-N$^5$-((1S,2S)-2-methylcyclopropyl)-2-oxo-1-(3-(2-oxoethyl)benzyl)-1,2-dihydropyridine-3,5-dicarboxamide (150 mg, 0.20 mmol, 46% yield) as a white solid.

LCMS (2 min Formic): Rt=0.78 min, [MH]+=382

Intermediate 198: N$^5$-Cyclopropyl-N$^3$-methyl-2-oxo-1-(3-(2-oxoethyl)benzyl)-1,2-dihydropyridine-3,5-dicarboxamide

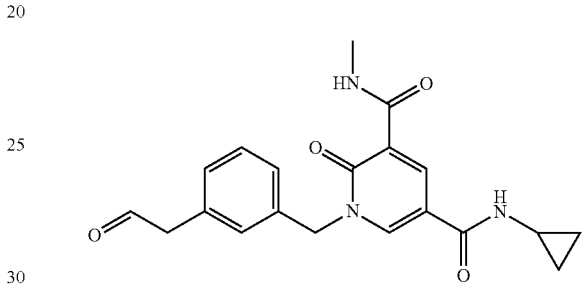

Dess-Martin periodinane (149 mg, 0.35 mmol) was added to a solution of N$^5$-cyclopropyl-1-(3-(2-hydroxyethyl)benzyl)-N$^3$-methyl-2-oxo-1,2-dihydropyridine-3,5-dicarboxamide (100 mg, 0.27 mmol) in DCM (2.5 mL) at 0° C. The reaction mixture was allowed to warm to rt and stirred for 48 h. The reaction was quenched with water and extracted with DCM. The organic layer was passed through a hydrophobic frit and concentrated in vacuo to give N$^5$-cyclopropyl-N$^3$-methyl-2-oxo-1-(3-(2-oxoethyl)benzyl)-1,2-dihydropyri-dine-3,5-dicarboxamide (100 mg, 0.27 mmol, 101% yield) as a white solid, which was used crude in the next step.

LCMS (2 min Formic): Rt=0.70 min, [MH]+=368

Intermediate 199: (+/−)-tert-Butyl 4-((5-(((trans)-2-ethylcycloropyl)carbamoyl-3-(methylcarbamoyl)-2-oxopyridin-1(2H)-yl)methyl)indoline-1-carboxylate

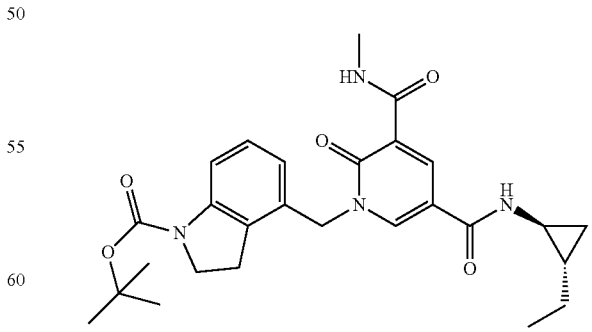

1-((1-(tert-Butoxycarbonyl)indolin-4-yl)methyl)-5-(methylcarbamoyl)-6-oxo-1,6-dihydropyridine-3-carboxylic acid (70 mg, 0.16 mmol) was taken up in DMF (1.5 mL) and HATU (68.5 mg, 0.18 mmol) followed by DIPEA (0.086 mL, 0.491 mmol) was added. The reaction mixture was allowed to stir for 5 min, then (+/−)-trans-2-ethylcyclopropanamine (15.34 mg, 0.18 mmol, commercially available from, for example, Enamine) was added and the reaction allowed to stir overnight. The reaction mixture was concentrated in vacuo and partitioned between EtOAc (15 mL) and citric acid solution (aq, 15 mL, 10% w/v). The EtOAc layer was then washed with sat. NaHCO₃ (aq), water and brine. The EtOAc layer was concentrated in vacuo, loaded in DCM and purified by Biotage Isolera flash chromatography using a SNAP 10 g silica cartridge and eluting with a gradient of 0-70% EtOAc/cyclohexane. The appropriate fractions were combined and concentrated in vacuo to give (+/−)-tert-butyl 4-((5-(((trans)-2-ethylcyclopropyl)carbamoyl)-3-(methylcarbamoyl)-2-oxopyridin-1(2H)-yl)methyl)indoline-1-carboxylate (54 mg, 0.11 mmol, 67% yield) as a colourless residue.

LCMS (2 min Formic): Rt=1.21 min, [MH]⁺=495

Intermediate 200: tert-Butyl (trans-4-(2-(1-benzyl-5-(methylcarbamoyl)-6-oxo-1,6-dihydropyridine-3-carboxamido)ethyl)cyclohexyl)carbamate

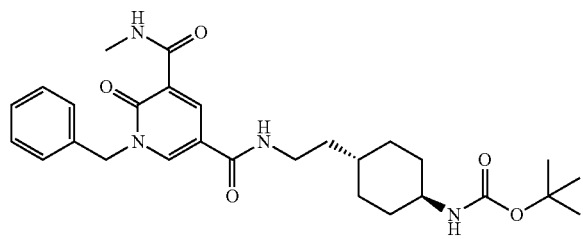 [SMILES: CNC(=O)c1cc(C(=O)NCC[C@H]2CC[C@H](NC(=O)OC(C)(C)C)CC2)cn(Cc2ccccc2)c1=O]

To a solution of 1-benzyl-5-(methylcarbamoyl)-6-oxo-1,6-dihydropyridine-3-carboxylic acid (50.4 mg, 0.18 mmol), HATU (87.3 mg, 0.23 mmol) and tert-butyl (trans-4-(2-aminoethyl)cyclohexyl)carbamate (52.3 mg, 0.22 mmol; commercially available from Matrix Scientific) in DMF (1 mL) was added N,N-diisopropylethylamine (0.061 mL, 0.35 mmol). The reaction mixture was stirred at rt for 1 h before being concentrated under a stream of nitrogen. The residue was made up to 2 mL with a 1:1 mixture of dimethylsulphoxide/methanol and directly purified by MDAP (2×1 mL injection; high pH). The required fractions from both injections were combined and concentrated in vacuo before being dissolved in a 1:1 mixture of dichloromethane/methanol (10 mL), concentrated under a stream of nitrogen and dried in vacuo to give a white solid; tert-butyl (trans-4-(2-(1-benzyl-5-(methylcarbamoyl)-6-oxo-1,6-dihydropyridine-3-carboxamido)ethyl)cyclohexyl)carbamate (78.4 mg, 0.15 mmol, 87% yield).

LCMS (2 min formic) Rt=1.16 min, m/z=511 for [MH]⁺

Intermediate 201: tert-Butyl (cis-4-(2-(1-benzyl-5-(methylcarbamoyl)-6-oxo-1,6-dihydropyridine-3-carboxamido)ethyl)cyclohexyl)carbamate

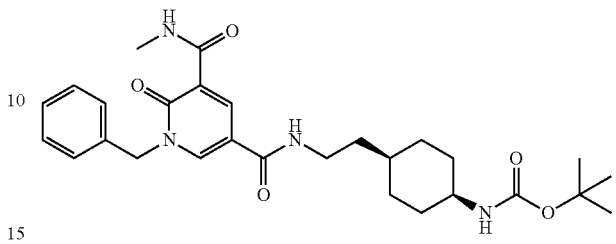

To a solution of 1-benzyl-5-(methylcarbamoyl)-6-oxo-1,6-dihydropyridine-3-carboxylic acid (51 mg, 0.18 mmol), HATU (89.2 mg, 0.24 mmol) and tert-butyl cis-4-(2-aminoethyl)cyclohexyl)carbamate (52.2 mg, 0.22 mmol, commercially available from, for example, Matrix Scientific) in DMF (1 mL) was added N,N-diisopropylethylamine (0.062 mL, 0.36 mmol). The reaction mixture was stirred at rt for 1 h before being concentrated under a stream of nitrogen. The residue was made up to 1 mL with dimethylsulphoxide and directly purified by MDAP (1 mL injection; high pH). The required fractions were combined and concentrated in vacuo before being dissolved in a 1:1 mixture of dichloromethane/methanol (10 mL), concentrated under a stream of nitrogen and dried in vacuo to give a white solid; tert-butyl (cis-4-(2-(1-benzyl-5-(methylcarbamoyl)-6-oxo-1,6-dihydropyridine-3-carboxamido)ethyl)cyclohexyl)carbamate (74.4 mg, 0.15 mmol, 82% yield).

LCMS (2 min formic) Rt=1.16 min, m/z=511 for [MH]⁺

Intermediate 202: N³-Methyl-N⁵-((1S,2S)-2-methylcyclopropyl)-2-oxo-1-((1-tosyl-1H-pyrrolo[3,2-c]pyridin-4-yl)methyl)-1,2-dihydropyridine-3,5-dicarboxamide

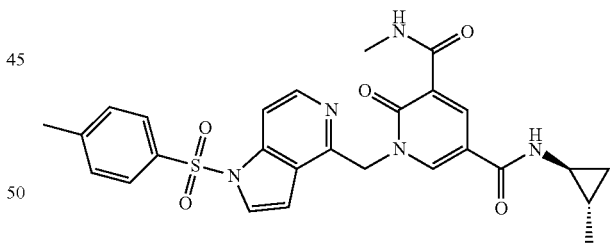

To a mixture of (1-tosyl-1H-pyrrolo[3,2-c]pyridin-4-yl)methanol (143.5 mg, 0.38 mmol) and N³-methyl-N⁵-((1S,2S)-2-methylcyclopropyl)-2-oxo-1,2-dihydropyridine-3,5-dicarboxamide (77.1 mg, 0.31 mmol) in toluene (1.5 mL) in a microwave vial was added 2-(tributylphosphoranylidene)acetonitrile (0.162 mL, 0.62 mmol). The vial was sealed and the mixture heated in a microwave reactor at 100° C. for a total of 40 min. The reaction mixture was evaporated under a stream of nitrogen to give a viscous black oil which was redissolved in dichloromethane (approx. 3 mL), directly applied to the top of a 25 g SNAP cartridge and purified by SP4 flash column chromatography. The column was eluted with a gradient of 0-40% ethyl acetate:ethanol (3:1) in cyclohexane. The required fractions were combined and evaporated in vacuo to give an orange gum which was redissolved in DMSO (approx. 1 mL) and further purified by MDAP (1 mL injection, high pH). The remaining sample in the injection vial (approx. 0.5 mL) was made up to 1 mL in DMSO and was also purified by MDAP (1 mL injection, high pH). The required fractions from both injections were combined and evaporated in vacuo to give a colourless gum; $N^3$-methyl-$N^5$-((1S,2S)-2-methylcyclopropyl)-2-oxo-1-((1-tosyl-1H-pyrrolo[3,2-c]pyridin-4-yl)methyl)-1,2-dihydropyridine-3,5-dicarboxamide (36.5 mg, 0.07 mmol, 22% yield).

LCMS (2 min high pH) Rt=1.09 min, m/z=534 for [MH]$^+$ $^1$H NMR (400 MHz, CDCl$_3$) δ ppm 9.48 (br. d, J=3.4 Hz, 1H) 8.84 (br. s., 1H) 8.64 (d, J=2.0 Hz, 1H) 8.36 (d, J=5.6 Hz, 1H) 7.74-7.92 (m, 3H) 7.63 (d, J=3.4 Hz, 1H) 7.28 (d, J=8.3 Hz, 2H) 6.99-7.19 (m, 1H) 6.89 (d, J=3.2 Hz, 1H) 5.54 (s, 2H) 2.90 (d, J=4.2 Hz, 3H) 2.48-2.57 (m, 1H) 2.37 (s, 3H) 1.10 (d, J=5.9 Hz, 3H) 0.86-1.00 (m, 1H) 0.68-0.79 (m, 1H) 0.54-0.65 (m, 1H)

Intermediate 203: Methyl 3-((5-(cyclopropylcarbamoyl)-3-(methylcarbamoyl)-2-oxopyridin-1(2H)-yl)methyl)benzoate

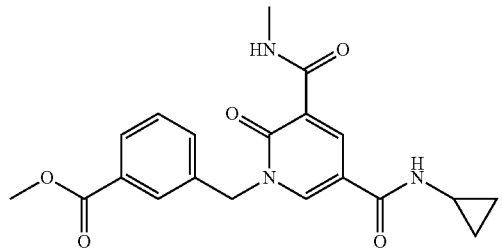 [SMILES: CNC(=O)c1cc(C(=O)NC2CC2)cn(Cc2cccc(C(=O)OC)c2)c1=O]

$N^5$-Cyclopropyl-$N^3$-methyl-2-oxo-1,2-dihydropyridine-3,5-dicarboxamide (42.1 mg, 0.18 mmol), methyl 3-(bromomethyl)benzoate (45.9 mg, 0.20 mmol; commercially available from, for example, Alfa Aesar) and potassium carbonate (52.1 mg, 0.38 mmol) were stirred in anhydrous DMF (1 mL) at rt under nitrogen for 2.5 h. The reaction mixture was partitioned between water (5 mL) and ethyl acetate (5 mL). The aqueous phase was extracted with further ethyl acetate (3×5 mL) and the combined organic phases were filtered through a cartridge fitted with a hydrophobic frit. The solvent was evaporated under a stream of nitrogen and the residue was dissolved in a 1:1 mixture of dichloromethane/methanol (6 mL), concentrated under a stream of nitrogen and dried in vacuo to give a white solid; methyl 3-((5-(cyclopropylcarbamoyl)-3-(methylcarbamoyl)-2-oxopyridin-1(2H)-yl)methyl)benzoate (65.5 mg, 0.17 mmol, 95% yield).

LCMS (2 min formic) Rt=0.82 min, m/z=384 for [MH]$^+$

Intermediate 204: tert-Butyl 3-((5-(cyclopropylcarbamoyl)-3-(methylcarbamoyl)-2-oxopyridin-1(2H)-yl)methyl)-1H-pyrrolo[2,3-b]pyridine-1-carboxylate

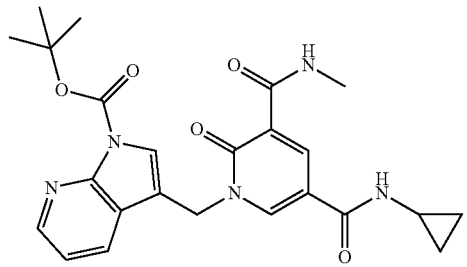 [SMILES: CNC(=O)c1cc(C(=O)NC2CC2)cn(Cc2cn(C(=O)OC(C)(C)C)c3ncccc23)c1=O]

To a suspension of $N^5$-cyclopropyl-$N^3$-methyl-2-oxo-1,2-dihydropyridine-3,5-dicarboxamide (53 mg, 0.23 mmol) and tert-butyl 3-(hydroxymethyl)-1H-pyrrolo[2,3-b]pyridine-1-carboxylate (69.2 mg, 0.28 mmol) in toluene (1.5 mL) in a microwave vial, was added 2-(tributylphosphoranylidene)acetonitrile (0.186 mL, 0.71 mmol; commercially available from, for example, TCI). The vial was sealed and heated in a microwave reactor at 80° C. for a total of 60 min. The reaction mixture was transferred to a vial using dichloromethane (2 mL) and concentrated under a stream of nitrogen to give a dark brown oil. This was made up to 3 mL with a 1:1 mixture of dimethylsulphoxide/methanol (3 mL) and directly purified by MDAP (3×1 mL injection, high pH). The required fractions were combined and concentrated in vacuo before being dissolved in a 1:1 mixture of dichloromethane/methanol (10 mL), concentrated under a stream of nitrogen and dried in vacuo to give a yellow solid; tert-butyl 3-((5-(cyclopropylcarbamoyl)-3-(methylcarbamoyl)-2-oxopyridin-1(2H)-yl)methyl)-1H-pyrrolo[2,3-b]pyridine-1-carboxylate (44.3 mg, 0.10 mmol, 42% yield).

LCMS (2 min formic) Rt=0.90 min, m/z=466 for [MH]$^+$

Intermediate 205: 1-((1-(2-((tert-Butyldimethylsilyl)oxy)ethyl)-1H-indol-3-yl)methyl)-$N^5$-cyclopropyl-$N^3$-methyl-2-oxo-1,2-dihydropyridine-3,5-dicarboxamide

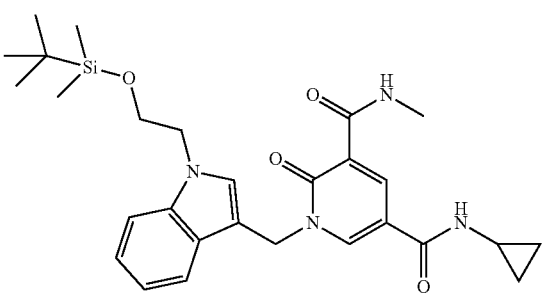 [SMILES: CNC(=O)c1cc(C(=O)NC2CC2)cn(Cc2cn(CCO[Si](C)(C)C(C)(C)C)c3ccccc23)c1=O]

To a suspension of $N^5$-cyclopropyl-$N^3$-methyl-2-oxo-1,2-dihydropyridine-3,5-dicarboxamide (57 mg, 0.24 mmol) and (1-(2-((tert-butyldimethylsilyl)oxy)ethyl)-1H-indol-3-yl)methanol (85.1 mg, 0.28 mmol) in toluene (1.5 mL) in a microwave vial, was added 2-(tributylphosphoranylidene) acetonitrile (0.200 mL, 0.76 mmol; commercially available from, for example, TCI). The vial was sealed and heated in a microwave reactor at 80° C. for 30 min and then for 30 min at 120° C. in a microwave reactor. The reaction mixture was transferred to a vial using dichloromethane (1 mL) and was concentrated under a stream of nitrogen to give a dark brown oil. This was made up to 3 mL with a 1:1 mixture of dimethylsulphoxide/methanol and directly purified by MDAP (1×3 mL injection: high pH). The required fractions were concentrated under a stream of nitrogen before being dissolved in a 1:1 mixture of dichloromethane/methanol (2×4 mL), combined, concentrated under a stream of nitrogen and dried in vacuo to give a pale brown solid; 1-((1-(2-((tert-butyldimethylsilyl)oxy)ethyl)-1H-indol-3-yl)methyl)-$N^5$-cyclopropyl-$N^3$-methyl-2-oxo-1,2-dihydropyridine-3,5-dicarboxamide (34.3 mg, 0.07 mmol, 27% yield).

LCMS (2 min high pH) Rt=1.37 min, m/z=521 for [M−H]⁻

Intermediate 206: (+/−)-1-((1H-Indol-4-yl)methyl)-$N^5$-((trans)-2-(2-((tert-butyldimethylsilyl)oxy)ethyl)cyclopropyl)-$N^3$-methyl-2-oxo-1,2-dihydropyridine-3,5-dicarboxamide

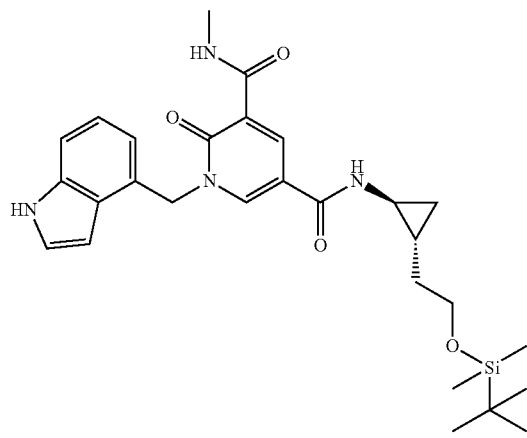 [SMILES: CNC(=O)c1cc(C(=O)N[C@H]2C[C@@H]2CCO[Si](C)(C)C(C)(C)C)cn(Cc2cccc3[nH]ccc23)c1=O]

1-((1H-Indol-4-yl)methyl)-5-(methylcarbamoyl)-6-oxo-1,6-dihydropyridine-3-carboxylic acid (400 mg, 1.230 mmol) was taken up in DMF (5 mL). DIPEA (0.644 mL, 3.69 mmol) then HATU (701 mg, 1.84 mmol) were added and the reaction stirred at rt for 10 min. (+/−)-(trans)-2-(2-((tert-Butyldimethylsilyl)oxy)ethyl)cyclopropanamine (318 mg, 1.48 mmol) was added and the reaction stirred at rt overnight. The reaction was concentrated in vacuo and the residue was partitioned between EtOAc and sat. NaHCO₃ (25 mL each). The aqueous layer was re-extracted with EtOAc (25 mL) and the combined organics were washed with brine, dried with Na₂SO₄, filtered through a hydrophobic frit and concentrated in vacuo to yield an orange oil. The crude product was applied to a 25 g ULTRA SNAP cartridge in the minimum of DCM and purified by flash chromatography, eluting with 10-60% (3:1 EtOAc:EtOH)/cyclohexane. The appropriate fractions were concentrated to give (+/−)-1-((1H-indol-4-yl)methyl)-$N^5$-((trans)-2-(2-((tert-butyldimethylsilyl)oxy)ethyl)cyclopropyl)-$N^3$-methyl-2-oxo-1,2-dihydropyridine-3,5-dicarboxamide (203.1 mg, 0.35 mmol, 28% yield) as a cream solid.

LCMS (2 min High pH): Rt=1.33 min, [MH]⁺=523.4.

Intermediate 207: (+/−)-tert-Butyl (2-((2-((trans)-2-(1-((1H-indol-4-yl)methyl)-5-(methylcarbamoyl)-6-oxo-1,6-dihydropyridine-3-carboxamido)cyclopropyl)ethyl(methyl)amino)ethyl)carbamate

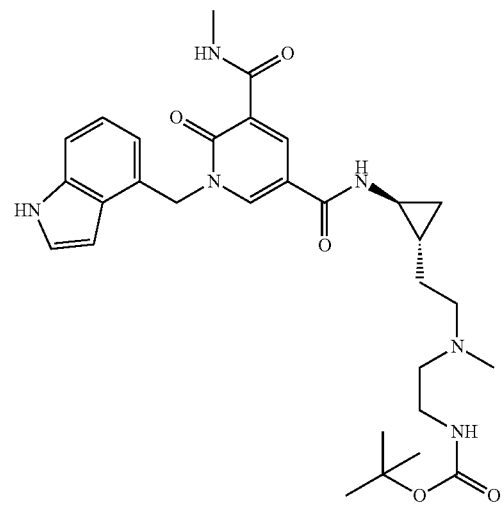 [SMILES: CNC(=O)c1cc(C(=O)N[C@H]2C[C@@H]2CCN(C)CCNC(=O)OC(C)(C)C)cn(Cc2cccc3[nH]ccc23)c1=O]

(+/−)-1-((1H-Indol-4-yl)methyl)-$N^5$-((trans)-2-(2-hydroxyethyl)cyclopropyl)-$N^3$-methyl-2-oxo-1,2-dihydropyridine-3,5-dicarboxamide (50 mg, 0.12 mmol) was suspended in DCM (5 mL) under nitrogen. Et₃N (0.034 mL, 0.25 mmol) then mesyl-Cl (10.49 µL, 0.14 mmol) were added and the reaction stirred at rt. After 45 min the reaction was diluted with DCM (5 mL) then washed with water (10 mL) then eluted through a hydrophobic frit and concentrated in vacuo to give a red oil. The oil was taken up in acetonitrile (5 mL). Et₃N (0.034 mL, 0.245 mmol) then tert-butyl (2-(methylamino)ethyl)carbamate (32.0 mg, 0.18 mmol) were added and the reaction heated to 80° C. overnight. An additional portion of Et₃N (0.034 mL, 0.245 mmol) and tert-butyl (2-(methylamino)ethyl)carbamate (32.0 mg, 0.18 mmol) were added and stirring at 80° C. continued over the weekend. The reaction had boiled dry so the residue was applied to a 10 g ULTRA SNAP cartridge in the minimum of DCM and purified by flash chromatography, eluting with 1-10% (2M NH₃ in methanol) in DCM. The appropriate fractions were concentrated in vacuo to give (+/−)-tert-butyl (2-((2-((1S,2S)-2-(1-((1H-indol-4-yl)methyl)-5-(methylcarbamoyl)-6-oxo-1,6-dihydropyridine-3-carboxamido)cyclopropyl)ethyl)(methyl)amino)ethyl)carbamate (44 mg, 0.07 mmol, 54% yield) as a brown oil.

LCMS (2 min High pH): Rt=1.03 min, [MH]⁺=565.5.

EXAMPLES

Example 1: 1-Benzyl-N5-cyclopropyl-N3-methyl-2-oxo-1,2-dihydropyridine-3,5-dicarboxamide

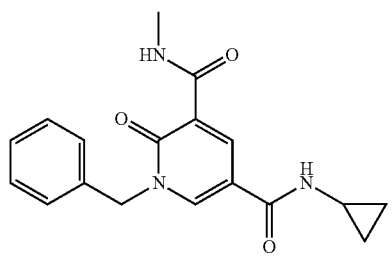 [SMILES: CNC(=O)c1cc(C(=O)NC2CC2)cn(Cc2ccccc2)c1=O]

1-Benzyl-5-(methylcarbamoyl)-6-oxo-1,6-dihydropyridine-3-carboxylic acid (5.5 g, 19.21 mmol) was suspended in DCM (100 mL) and Et$_3$N (3.21 mL, 23.05 mmol), HATU (9.50 g, 24.98 mmol) and cyclopropylamine (1.625 mL, 23.05 mmol) were added, then the mixture was stirred for 2 h at rt. The mixture was washed with water (100 mL), 0.5 M HCl (100 mL) and saturated sodium bicarbonate solution (100 mL) and the organic layer was dried and evaporated in vacuo to give a pale yellow solid. The solid was suspended in ether (20 mL) and sonicated, then filtered and the solid dried in the vacuum oven to give 1-benzyl-N5-cyclopropyl-N3-methyl-2-oxo-1,2-dihydropyridine-3,5-dicarboxamide (5.25 g, 16.14 mmol, 84% yield) as a colourless solid.

The product was combined with another batch, prepared by a similar method (2.4 g), the combined material was dissolved by refluxing in ethanol (200 mL) for 20 min, then Silicycle thiourea palladium scavenging resin (10 g) was added and the mixture heated for a further 30 min. The mixture was filtered into a Buchner flask and allowed to cool to rt over 1 h, then cooled in an ice bath for 1 h and the resulting solid collected by filtration and dried in the vacuum oven to give 1-benzyl-N5-cyclopropyl-N3-methyl-2-oxo-1,2-dihydropyridine-3,5-dicarboxamide (6.76 g, 20.78 mmol) as a colourless solid.

LCMS (2 min high pH): Rt=0.84 min, [MH]$^+$=326.

$^1$H NMR (400 MHz, DMSO-d$_6$) δ ppm 9.35 (d, J=4.9 Hz, 1H) 8.80 (d, J=2.7 Hz, 1H) 8.72 (d, J=2.7 Hz, 1H) 8.54 (d, J=3.9 Hz, 1H) 7.25-7.42 (m, 5H) 5.29 (s, 2H) 2.75-2.89 (m, 4H) 0.65-0.72 (m, 2H) 0.53-0.59 (m, 2H).

Example 2: 1-Benzyl-N5-cyclobutyl-N3-methyl-2-oxo-1,2-dihydropyridine-3,5-dicarboxamide

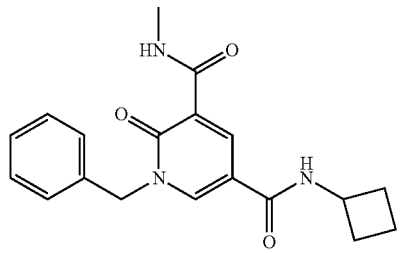 [SMILES: CNC(=O)c1cc(C(=O)NC2CCC2)cn(Cc2ccccc2)c1=O]

2,4,6-Trichlorophenyl 1-benzyl-5-(methylcarbamoyl)-6-oxo-1,6-dihydropyridine-3-carboxylate (401 mg, 0.861 mmol), cyclobutanamine (0.15 mL, 1.757 mmol), N,N-dimethylpyridin-4-amine (23 mg, 0.188 mmol), triethylamine (0.48 mL, 3.44 mmol) and THF (8 mL) were stirred at 45° C. under N$_2$ for 3 h. The reaction mixture was concentrated to give 600 mg of an off white solid which was purified by chromatography on SiO$_2$ (Biotage SNAP 50 g cartridge, eluting with 0-100% ethylacetate/cyclohexane). The desired fractions were concentrated to give 1-benzyl-N5-cyclobutyl-N3-methyl-2-oxo-1,2-dihydropyridine-3,5-dicarboxamide (295 mg, 0.782 mmol, 91% yield) as an off white solid LCMS (2 min Formic): Rt=0.91 min, [MH]$^+$=340.

Example 3: N5-Cyclopropyl-N3-methyl-2-oxo-1-(1-phenylethyl)-1,2-dihydropyridine-3,5-dicarboxamide

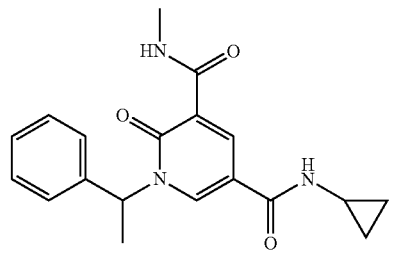

THF (1.5 mL) was added to a sealed microwave vial containing 5-bromo-N-methyl-2-oxo-1-(1-phenylethyl)-1,2-dihydropyridine-3-carboxamide (100 mg, 0.298 mmol), dicobalt octacarbonyl (28.3 mg, 0.075 mmol), DMAP (109 mg, 0.895 mmol), xantphos (10.36 mg, 0.018 mmol) and palladium (II) acetate (3.35 mg, 0.015 mmol) and flushed with N2. Cyclopropylamine (0.042 mL, 0.597 mmol) was added and the reaction mixture heated to 80° C. by microwave irradiation for 30 min. The reaction mixture was partitioned between EtOAc and water. The aqueous layer was removed, the organic layer washed (1× water, 2×2 M aq. HCl, 1× brine), dried over MgSO$_4$ and evaporated in vacuo to a yellow residue. The residue was dissolved in DCM, loaded onto a 10 g Biotage silica SNAP column and eluted with cyclohexane:EtOAc (50-100%). The product containing fractions were evaporated in vacuo to a brown gum. The gum was stirred with TBME and evaporated in vacuo to give the product (41 mg) as a white solid.

LCMS (2 min TFA): Rt=0.85 min, [MH]$^+$=340.1.

Example 4: rac-N5-Cyclopropyl-N3-methyl-2-oxo-1-(1-phenylpropyl)-1,2-dihydropyridine-3,5-dicarboxamide

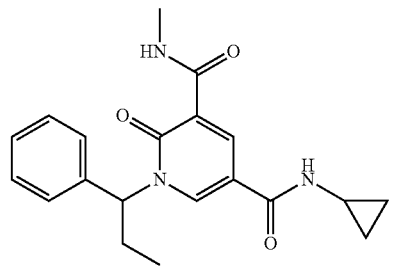 [SMILES: CCC(c1ccccc1)n1cc(C(=O)NC2CC2)cc(C(=O)NC)c1=O]

To a suspension of N5-cyclopropyl-N3-methyl-2-oxo-1,2-dihydropyridine-3,5-dicarboxamide (40 mg, 0.170 mmol), (1-bromopropyl)benzene (41 mg, 0.206 mmol) in DMF (1 mL), was added K$_2$CO$_3$ (29 mg, 0.210 mmol) and the reaction stirred under nitrogen at rt for 2 h. The reaction mixture was purified by MDAP (Formic) and the fractions containing desired product were concentrated to give rac-N5-cyclopropyl-N3-methyl-2-oxo-1-(1-phenylpropyl)-1,2-dihydropyridine-3,5-dicarboxamide (25 mg, 0.064 mmol, 37.4% yield) as a colourless oil.

LCMS (2 min Formic): Rt=0.97 min, [MH]$^+$=354.

Example 5: N5-Cyclobutyl-1-((2,3-dihydrobenzo[b][1,4]dioxin-5-yl)methyl)-N3-methyl-2-oxo-1,2-dihydropyridine-3,5-dicarboxamide

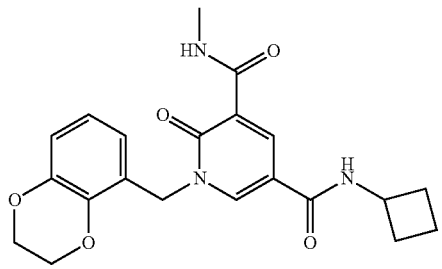 [SMILES: CNC(=O)c1cc(C(=O)NC2CCC2)cn(Cc2cccc3c2OCCO3)c1=O]

N5-Cyclobutyl-N3-methyl-2-oxo-1,2-dihydropyridine-3,5-dicarboxamide (50 mg, 0.201 mmol), (2,3-dihydrobenzo[b][1,4]dioxin-5-yl)methanol (50.0 mg, 0.301 mmol) and 2-(tributylphosphoranylidene)acetonitrile (0.166 mL, 0.632 mmol) were combined in toluene (1.5 mL) and the reaction mixture heated in a 5 mL microwave vial on a Biotage Initiator microwave at 120° C. for 30 min. The reaction mixture was poured onto water (20 mL), and extracted with ethyl acetate (3×10 mL). The combined organic portions were evaporated in vacuo to yield the crude product as a brown oil. The product was loaded in dichloromethane onto a 25 g SNAP silica cartridge and purified via Biotage SP4 flash chromatography, eluting from 50-100% ethyl acetate/cyclohexane. The relevant fractions were combined and evaporated in vacuo—yielding 76 mg of product. The sample was dissolved in MeOH/DMSO (1 mL, 1:1) and purified by MDAP (Formic). The solvent was evaporated in vacuo to give the required product—N5-cyclobutyl-1-((2,3-dihydrobenzo[b][1,4]dioxin-5-yl)methyl)-N3-methyl-2-oxo-1,2-dihydropyridine-3,5-dicarboxamide (40 mg, 0.096 mmol, 47.7% yield).

LCMS (2 min Formic): Rt=0.95 min, [MH]$^+$=398.1.

Example 6: N5-Cyclobutyl-N3-methyl-1-(3-(methylamino)benzyl)-2-oxo-1,2-dihydropyridine-3,5-dicarboxamide

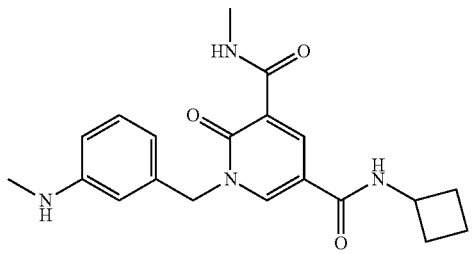 [SMILES: CNC(=O)c1cc(C(=O)NC2CCC2)cn(Cc2cccc(NC)c2)c1=O]

N5-Cyclobutyl-N3-methyl-2-oxo-1,2-dihydropyridine-3,5-dicarboxamide (25 mg, 0.100 mmol), (3-(methylamino)phenyl)methanol (20.64 mg, 0.150 mmol) and 2-(tributylphosphoranylidene)acetonitrile (0.083 mL, 0.316 mmol) were combined in toluene (0.75 mL) and the reaction mixture heated in a 5 mL microwave vial at 120° C. for 30 min. The reaction mixture was poured onto water (10 mL) and extracted with ethyl acetate (3×8 mL). The combined ethyl acetate layers were washed with brine (10 mL), dried through a hydrophobic frit and evaporated in vacuo to yield the crude product (170 mg). The residue was dissolved in MeOH/DMSO (1:1, 2×1 mL) and purified by MDAP (High pH). The solvent was dried under a stream of nitrogen to leave a white powder. The fractions were combined in dichloromethane, evaporated in vacuo, sonicated with diethyl ether and evaporated once more to yield the product—N5-cyclobutyl-N3-methyl-1-(3-(methylamino)benzyl)-2-oxo-1,2-dihydropyridine-3,5-dicarboxamide (17 mg, 0.046 mmol, 46.0% yield) as an off white solid.

LCMS (2 min Formic): Rt=0.72 min, [MH]$^+$=369.1.

Example 7: N5-Cyclobutyl-1-(3-(dimethylamino)benzyl)-N3-methyl-2-oxo-1,2-dihydropyridine-3,5-dicarboxamide

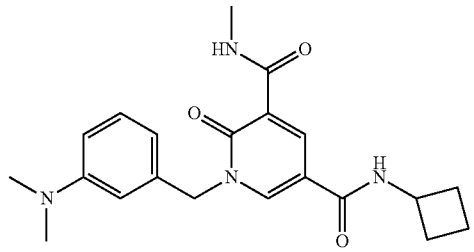 [SMILES: CNC(=O)c1cc(C(=O)NC2CCC2)cn(Cc2cccc(N(C)C)c2)c1=O]

N5-Cyclobutyl-N3-methyl-2-oxo-1,2-dihydropyridine-3,5-dicarboxamide (40 mg, 0.160 mmol), (3-(dimethylamino)phenyl)methanol (0.034 mL, 0.241 mmol) and 2-(tributylphosphoranylidene)acetonitrile (0.133 mL, 0.505 mmol) were combined in toluene (1.2 mL) and the reaction mixture heated in a 5 mL microwave vial at 120° C. for 30 min. The reaction was returned to the microwave for a further 30 min at 120° C. The reaction mixture was poured onto water (20 mL), and extracted with ethyl acetate (3×10 mL). The combined organic portions were evaporated in vacuo to yield the crude product as a brown oil. The sample was loaded in methanol and purified by SPE on sulphonic acid (SCX) 5 g using the sequential solvents: methanol, 2M ammonia/methanol. The appropriate fractions were combined and evaporated in vacuo to give the crude product (78 mg) as a brown glass. The sample was dissolved in MeOH/DMSO (1 mL, 1:1) and purified by MDAP (High pH). The solvent was evaporated in vacuo to give a pale yellow solid (8.1 mg). This was loaded in dichloromethane onto a 10 g SNAP silica cartridge and purified via Biotage SP4 flash chromatography eluting from 10-40% (3:1 ethyl acetate:ethanol)/cyclohexane. The relevant fractions were combined and evaporated in vacuo to yield N5-cyclobutyl-1-(3-(dimethylamino)benzyl)-N3-methyl-2-oxo-1,2-dihydropyridine-3,5-dicarboxamide (6.3 mg, 0.016 mmol, 10.27% yield) as a pale yellow solid.

LCMS (2 min Formic): Rt=0.77 min, [MH]$^+$=383.4.

Example 8: 1-Benzyl-N5-(3-fluorocyclobutyl)-N3-methyl-2-oxo-1,2-dihydropyridine-3,5-dicarboxamide

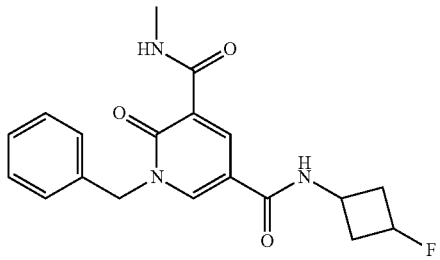 [SMILES: CNC(=O)c1cc(C(=O)NC2CC(F)C2)cn(Cc2ccccc2)c1=O]

2,4,6-Trichlorophenyl 1-benzyl-5-(methylcarbamoyl)-6-oxo-1,6-dihydropyridine-3-carboxylate (53 mg, 0.114 mmol), 3-fluorocyclobutanamine hydrochloride (29 mg, 0.231 mmol), N,N-dimethylpyridin-4-amine (3 mg, 0.025 mmol), triethylamine (0.063 mL, 0.455 mmol) and THF (1 mL) were heated at 45° C. overnight under $N_2$. The resulting off white suspension was concentrated to give 100 mg of an off white solid. This was purified by chromatography on $SiO_2$ (Biotage SNAP 10 g cartridge, eluting with 0-100% ethylacetate/cyclohexane). The desired fractions were concentrated to give 1-benzyl-N5-(3-fluorocyclobutyl)-N3-methyl-2-oxo-1,2-dihydropyridine-3,5-dicarboxamide (32 mg, 0.076 mmol, 66.9% yield) as a colourless oil.

LCMS (2 min Formic): Rt=0.90 min, $[MH]^+$=358.

Examples 9-18: Amide Array of N5-cyclobutyl-N3-methyl-2-oxo-1,2-dihydropyridine-3,5-dicarboxamide Monomers

| Ex No. | Reagent Name | Structure | MW | Reagent Mass (g) | Reagent Volume (mL) | mmol |
|---|---|---|---|---|---|---|
| 9 | 1-(Bromomethyl)-3,5-dimethylbenzene | 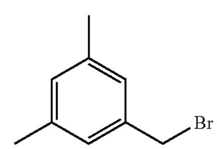 | 199.09 | 0.060 | — | 0.301 |
| 10 | 1-(Bromomethyl)-4-methoxybenzene | 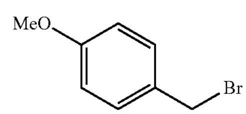 | 201.06 | 0.061 | — | 0.301 |
| 11 | 8-(Bromomethyl)quinoline | 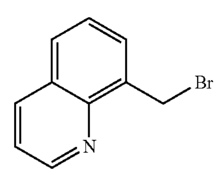 [SMILES: BrCc1cccc2cccnc12] | 222.08 | 0.067 | — | 0.301 |
| 12 | 1-(Bromomethyl)-2,3-dimethylbenzene | 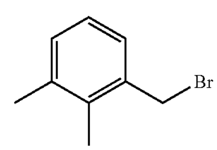 | 199.08 | 0.060 | — | 0.301 |
| 13 | 1-(Bromomethyl)-2-fluoro-3-methylbenzene | 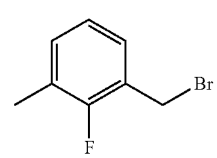 | 203.05 | 0.061 | — | 0.301 |
| 14 | 4-(Bromomethyl)-1-fluoro-2-methylbenzene | 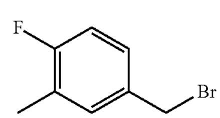 | 203.05 | 0.061 | — | 0.301 |
| 15 | 4-(Bromomethyl)-1-methoxy-2-methylbenzene | 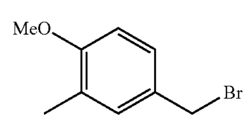 | 170.64 | 0.051 | — | 0.301 |

| Ex No. | Reagent Name | Structure | MW | Reagent Mass (g) | Reagent Volume (mL) | mmol |
|---|---|---|---|---|---|---|
| 16 | 1-(Bromomethyl)-3-fluoro-5-methylbenzene | 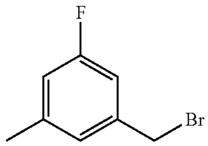 | 203.05 | 0.061 | — | 0.301 |
| 17 | 1-(Bromomethyl)-3-methylbenzene | 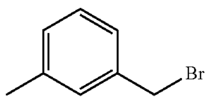 | 185.06 | 0.056 | — | 0.301 |
| 18 | 2-(Bromomethyl)-1-fluoro-4-methylbenzene | 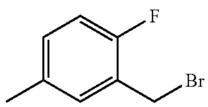 | 203.05 | 0.061 | — | 0.301 |

A stock solution of N5-cyclobutyl-N3-methyl-2-oxo-1,2-dihydropyridine-3,5-dicarboxamide (475 mg) dissolved in DMSO (11.4 mL) was made up. 0.6 mL of this solution was added to each of the listed bromide monomers (0.301 mmol). Potassium carbonate (41.6 mg, 0.301 mmol) was added to each of the reaction vessels and the reactions left stirring overnight. The samples were then filtered before purification. (N.B. Solubility issues in almost all samples. Issue resolved by first adding 50 μL of ammonia to each sample. For the samples where this failed to resolve the issue, a drop of formic acid was added and the solutions re-filtered.) The samples were then dissolved in DMSO (0.8 mL) and purified by MDAP (High pH). The solvent was dried under a stream of nitrogen to give the required products as listed in the subsequent table.

EXAMPLES

| Ex No. | Name | Structure | Mass (mg) | Yield (%) | [MH]+ | Rt (min)* |
|---|---|---|---|---|---|---|
| 9 | N5-Cyclobutyl-1-(3,5-dimethylbenzyl)-N3-methyl-2-oxo-1,2-dihydropyridine-3,5-dicarboxamide | 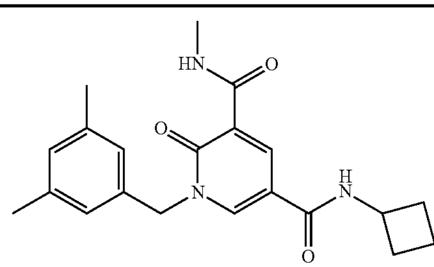 | 15 | 37 | 368 | 1.08 |
| 10 | N5-Cyclobutyl-1-(4-methoxybenzyl)-N3-methyl-2-oxo-1,2-dihydropyridine-3,5-dicarboxamide | 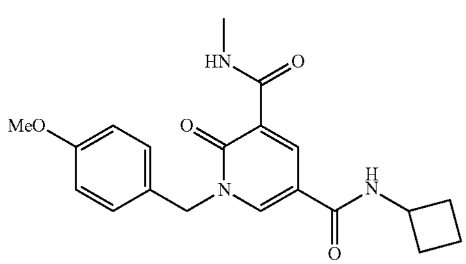 [SMILES: CNC(=O)c1cc(C(=O)NC2CCC2)cn(Cc2ccc(OC)cc2)c1=O] | 15 | 36 | 370 | 0.94 |
| 11 | N5-Cyclobutyl-N3-methyl-2-oxo-1-(quinolin-8-ylmethyl)-1,2-dihydropyridine-3,5-dicarboxamide | 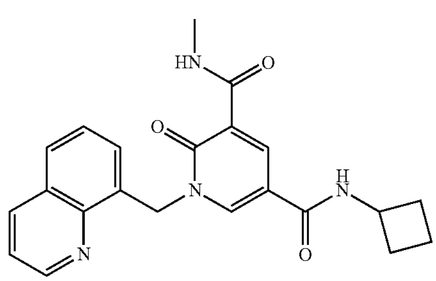 [SMILES: CNC(=O)c1cc(C(=O)NC2CCC2)cn(Cc2cccc3cccnc23)c1=O] | 12 | 27 | 391 | 0.97 |

| Ex No. | Name | Structure | Mass (mg) | Yield (%) | [MH]+ | Rt (min)* |
|---|---|---|---|---|---|---|
| 12 | N5-Cyclobutyl-1-(2,3-dimethylbenzyl)-N3-methyl-2-oxo-1,2-dihydropyridine-3,5-dicarboxamide | 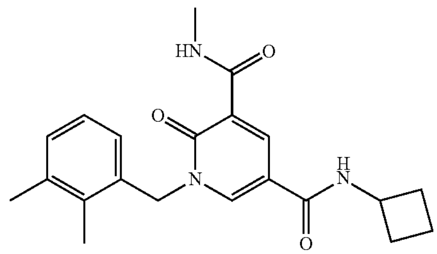 | 9 | 23 | 368 | 1.06 |
| 13 | N5-Cyclobutyl-1-(2-fluoro-3-methylbenzyl)-N3-methyl-2-oxo-1,2-dihydropyridine-3,5-dicarboxamide | 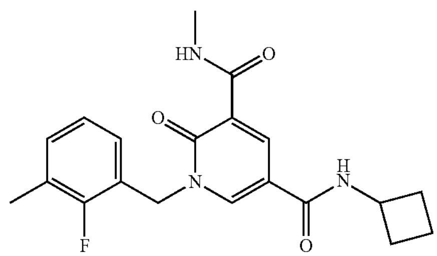 [SMILES: CNC(=O)c1cc(C(=O)NC2CCC2)cn(Cc2cccc(C)c2F)c1=O] | 8 | 19 | 372 | 1.02 |
| 14 | N5-Cyclobutyl-1-(4-fluoro-3-methylbenzyl)-N3-methyl-2-oxo-1,2-dihydropyridine-3,5-dicarboxamide | 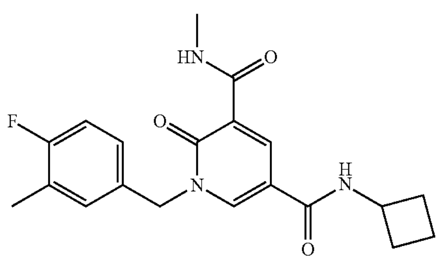 [SMILES: CNC(=O)c1cc(C(=O)NC2CCC2)cn(Cc2ccc(F)c(C)c2)c1=O] | 11 | 27 | 372 | 1.03 |
| 15 | N5-Cyclobutyl-1-(4-methoxy-3-methylbenzyl)-N3-methyl-2-oxo-1,2-dihydropyridine-3,5-dicarboxamide | 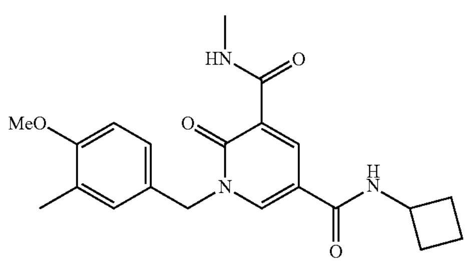 [SMILES: CNC(=O)c1cc(C(=O)NC2CCC2)cn(Cc2ccc(OC)c(C)c2)c1=O] | 22 | 50 | 383 | 1.03 |
| 16 | N5-cyclobutyl-1-(3-fluoro-5-methylbenzyl)-N3-methyl-2-oxo-1,2-dihydropyridine-3,5-dicarboxamide | 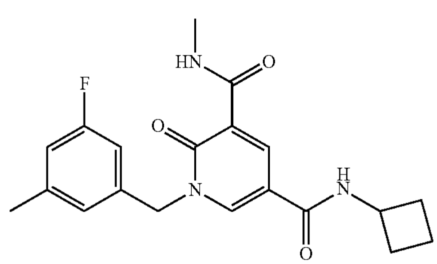 [SMILES: CNC(=O)c1cc(C(=O)NC2CCC2)cn(Cc2cc(C)cc(F)c2)c1=O] | 11 | 27 | 372 | 1.03 |

| Ex No. | Name | Structure | Mass (mg) | Yield (%) | [MH]+ | Rt (min)* |
|---|---|---|---|---|---|---|
| 17 | N5-Cyclobutyl-N3-methyl-1-(3-methylbenzyl)-2-oxo-1,2-dihydropyridine-3,5-dicarboxamide | 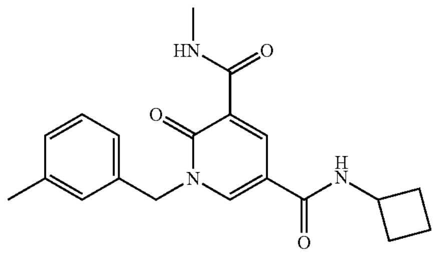 [SMILES: CNC(=O)c1cc(C(=O)NC2CCC2)cn(Cc2cccc(C)c2)c1=O] | 10 | 26 | 354 | 1.01 |
| 18 | N5-Cyclobutyl-1-(2-fluoro-5-methylbenzyl)-N3-methyl-2-oxo-1,2-dihydropyridine-3,5-dicarboxamide | 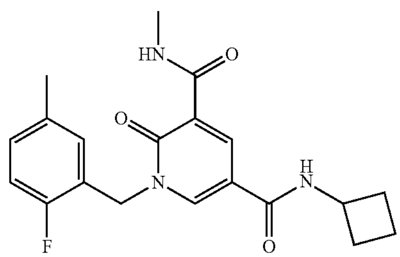 | 7 | 17 | 372 | 1.02 |

*All LCMS were conducted using 2 min High pH.

Example 19: 1-Benzyl-N3-methyl-2-oxo-N5-(3-phenylcyclobutyl)-1,2-dihydropyridine-3,5-dicarboxamide

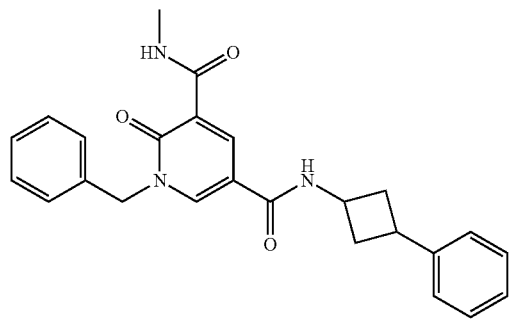 [SMILES: CNC(=O)c1cc(C(=O)NC2CC(c3ccccc3)C2)cn(Cc2ccccc2)c1=O]

2,4,6-Trichlorophenyl 1-benzyl-5-(methylcarbamoyl)-6-oxo-1,6-dihydropyridine-3-carboxylate (53 mg, 0.114 mmol), N,N-dimethylpyridin-4-amine (3 mg, 0.025 mmol), 3-phenylcyclobutanamine hydrochloride (39 mg, 0.212 mmol), triethylamine (0.06 mL, 0.430 mmol) and THF (1 mL) were stirred at 45° C. under $N_2$ for 3 h. The reaction mixture was concentrated to give 140 mg of an off white solid which was purified by chromatography on $SiO_2$ (Biotage SNAP 10 g cartridge, eluting with 0-100% ethylacetate/cyclohexane). The desired fractions were concentrated to give 1-benzyl-N3-methyl-2-oxo-N5-(3-phenylcyclobutyl)-1,2-dihydropyridine-3,5-dicarboxamide (40 mg, 0.087 mmol, 76% yield) as a white solid.

LCMS (2 min Formic): Rt=1.12 min, [MH]+=416.

Example 20: N5-(6-Aminospiro[3.3]heptan-2-yl)-1-benzyl-N3-methyl-2-oxo-1,2-dihydropyridine-3,5-dicarboxamide

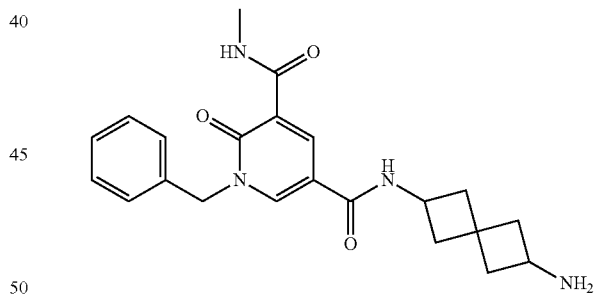

tert-Butyl (6-(1-benzyl-5-(methylcarbamoyl)-6-oxo-1,6-dihydropyridine-3-carboxamido)spiro[3.3]heptan-2-yl)carbamate (75 mg, 0.152 mmol) was dissolved in DCM (5 mL), TFA (1 mL, 12.98 mmol) was added and the reaction stirred at rt under $N_2$ for 30 min. The reaction mixture was concentrated and loaded onto a 2 g SCX cartridge (pre-conditioned with MeOH) and eluted with MeOH (40 mL) followed by 2M $NH_3$ in MeOH (40 mL). The ammonia fractions containing product were combined and concentrated to give N5-(6-aminospiro[3.3]heptan-2-yl)-1-benzyl-N3-methyl-2-oxo-1,2-dihydropyridine-3,5-dicarboxamide (49.6 mg, 0.113 mmol, 74.6% yield) as a colourless oil.

LCMS (2 min Formic): Rt=0.55 min, [MH]+=395.

Example 21: (+/−)-N5-Cyclobutyl-N3-methyl-2-oxo-1-(1-phenylethyl)-1,2-dihydropyridine-3,5-dicarboxamide

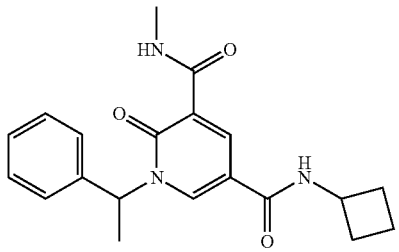 [SMILES: CNC(=O)c1cc(C(=O)NC2CCC2)cn(C(C)c2ccccc2)c1=O]

N5-Cyclobutyl-N3-methyl-2-oxo-1,2-dihydropyridine-3,5-dicarboxamide (50 mg, 0.201 mmol), 1-phenylethanol (0.036 mL, 0.301 mmol) and 2-(tributylphosphoranylidene) acetonitrile (0.166 mL, 0.632 mmol) were combined in toluene (1.5 mL) and the reaction mixture heated in a 5 mL microwave vial at 120° C. for 30 min in a Biotage Initiator microwave. The reaction mixture was poured onto water (20 mL), and extracted with ethyl acetate (3×10 mL). The combined organic portions were evaporated in vacuo to yield the crude product as a brown oil. The residue was loaded in dichloromethane onto a 25 g SNAP silica cartridge and purified via Biotage SP4 flash chromatography eluting from 10-40% (3:1 ethyl acetate:ethanol)/cyclohexane. The relevant fractions were combined and evaporated in vacuo. The residue was dissolved in MeOH/DMSO (2×1 mL, 1:1) and purified by MDAP (High pH, 2 injections). The relevant fractions were combined and evaporated in vacuo. The residue was loaded in dichloromethane onto a 10 g SNAP silica cartridge and purified via Biotage SP4 flash chromatography, eluting from 20-100% ethyl acetate/cyclohexane. The relevant fractions were combined and evaporated in vacuo to yield N5-cyclobutyl-N3-methyl-2-oxo-1-(1-phenylethyl)-1,2-dihydropyridine-3,5-dicarboxamide (16 mg, 0.045 mmol, 22.57% yield) as a white solid.

LCMS (2 min Formic): Rt=0.97 min, [MH]⁺=354.0.

Example 22: 1-Benzyl-N5-cyclobutyl-N3-cyclopropyl-2-oxo-1,2-dihydropyridine-3,5-dicarboxamide

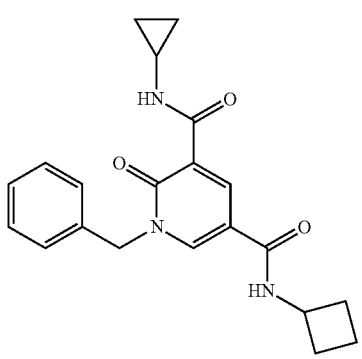 [SMILES: O=C(NC1CCC1)c1cc(C(=O)NC2CC2)c(=O)n(Cc2ccccc2)c1]

1-Benzyl-5-bromo-N-cyclopropyl-2-oxo-1,2-dihydropyridine-3-carboxamide (250 mg, 0.720 mmol), cobalt carbonyl (61.6 mg, 0.180 mmol), DMAP (176 mg, 1.440 mmol), palladium (II) acetate (8.08 mg, 0.036 mmol), cyclobutanamine (0.123 mL, 1.440 mmol) and xantphos (20.83 mg, 0.036 mmol) were added to a microwave vial. The vial was sealed and THF (3.3 mL) added and the reaction heated in a Biotage Initiator microwave at 80° C. for 40 min. The resulting mixture was diluted with water (20 mL) and extracted with ethyl acetate (20 mL). The organic layer was dried and concentrated under vacuum to give an orange residue. The residue was taken up in DCM and purified by Biotage Isolera SNAP 50 g silica flash chromatography using a gradient of 0-100% cyclohexane/ethyl acetate. The appropriate fractions were combined, concentrated under vacuum and purified by MDAP (High pH). The product containing fractions were combined and concentrated under vacuum to give the product (40 mg) as a white solid.

LCMS (2 min Formic): Rt=1.02 min, [MH]⁺=366.3.

Example 23: 1-((1H-Benzo[d]imidazol-4-yl)methyl)-N5-cyclobutyl-N3-methyl-2-oxo-1,2-dihydropyridine-3,5-dicarboxamide

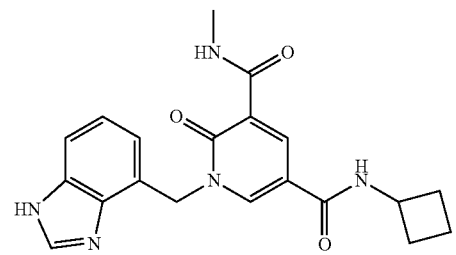 [SMILES: CNC(=O)c1cc(C(=O)NC2CCC2)cn(Cc2cccc3[nH]cnc23)c1=O]

tert-Butyl 4-((5-(cyclobutylcarbamoyl)-3-(methylcarbamoyl)-2-oxopyridin-1(2H)-yl)methyl)-1H-benzo[d]imidazole-1-carboxylate (54 mg, 0.113 mmol) was dissolved in DCM (2 mL) and trifluoroacetic acid (500 μL, 6.49 mmol) was added cautiously. The mixture was stirred at rt for 90 min. The reaction mixture was loaded onto an SCX column, washed with MeOH (2 CV) and then eluted with methanolic ammonia (2M) (4 CV). The appropriate fractions were combined and evaporated under reduced pressure to give a brown solid. The sample was dissolved in MeOH/DMSO (1 mL, 1:1) and purified by MDAP (High pH). The solvent was evaporated in vacuo to give the required product—1-((1H-benzo[d]imidazol-4-yl)methyl)-N5-cyclobutyl-N3-methyl-2-oxo-1,2-dihydropyridine-3,5-dicarboxamide (24 mg, 0.063 mmol, 56.2% yield) as a white solid.

LCMS (2 min Formic): Rt=0.97 min, [MH]⁺=354.0.

Example 24: 1-Benzyl-N5-(2-cyclopropylethyl)-N3-methyl-2-oxo-1,2-dihydropyridine-3,5-dicarboxamide

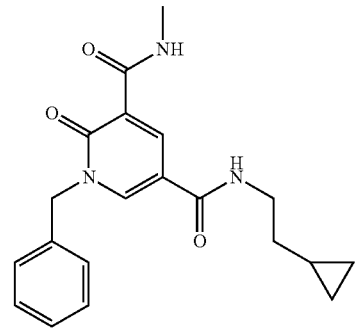 [SMILES: CNC(=O)c1cc(C(=O)NCCC2CC2)cn(Cc2ccccc2)c1=O]

Triethylamine (0.060 mL, 0.429 mmol), DMAP (6.56 mg, 0.054 mmol), 2,4,6-trichlorophenyl 1-benzyl-5-(methylcarbamoyl)-6-oxo-1,6-dihydropyridine-3-carboxylate (50 mg, 0.107 mmol) and 2-cyclopropylethanamine (18.28 mg, 0.215 mmol) were dissolved in THF (1.5 mL) and stirred at 45° C. under nitrogen for 1 h. The reaction mixture was then concentrated under vacuum, loaded in DCM and purified by Biotage Isolera SNAP 25 g silica flash chromatography using a gradient of 0-100% cyclohexane/ethyl acetate. The product containing fractions were combined and concentrated under vacuum to give the product (35 mg) as a white solid.

LCMS (2 min Formic): Rt=0.97 min, MH+=354.0.

Example 25: Methyl 3-((5-(cyclobutylcarbamoyl)-3-(methylcarbamoyl)-2-oxopyridin-1(2H)-yl)methyl)benzoate

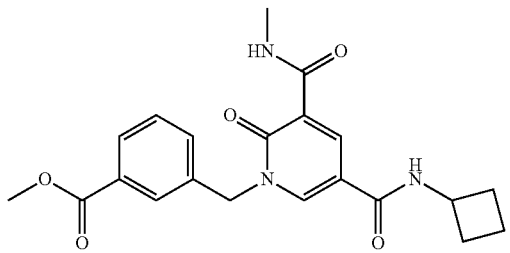 [SMILES: CNC(=O)c1cc(C(=O)NC2CCC2)cn(Cc2cccc(C(=O)OC)c2)c1=O]

N5-Cyclobutyl-N3-methyl-2-oxo-1,2-dihydropyridine-3,5-dicarboxamide (100 mg, 0.401 mmol), methyl 3-(hydroxymethyl)benzoate (100 mg, 0.602 mmol) and 2-(tributylphosphoranylidene)acetonitrile (0.416 mL, 1.586 mmol) were combined in toluene (3 mL) and the reaction mixture heated in a microwave vial at 120° C. for 30 min. The reaction mixture was poured onto water (20 mL) and extracted with ethyl acetate (3×10 mL). The combined organic portions were washed with brine, dried through a hydrophobic frit and evaporated in vacuo to yield the crude product. The residue was loaded in dichloromethane onto a 25 g SNAP silica cartridge and purified via Biotage SP4 flash chromatography, eluting from 10-50% (3:1 ethyl acetate:ethanol)/cyclohexane. The relevant fractions were combined and evaporated in vacuo to yield a light brown solid (91 mg). The residue was dissolved in MeOH/DMSO (1 mL, 1:1) and purified by MDAP (High pH). The solvent was evaporated in vacuo to give the required product—methyl 3-((5-(cyclobutylcarbamoyl)-3-(methylcarbamoyl)-2-oxopyridin-1(2H)-yl)methyl)benzoate (44 mg, 0.111 mmol, 27.6% yield) as a white solid.

LCMS (2 min Formic): Rt=0.91 min, [MH]⁺=398.0.

Example 26: N5-Cyclobutyl-1-(3-(hydroxymethyl)benzyl)-N3-methyl-2-oxo-1,2-dihydropyridine-3,5-dicarboxamide

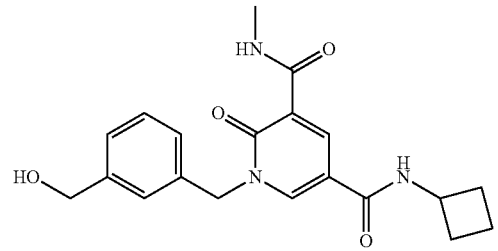 [SMILES: CNC(=O)c1cc(C(=O)NC2CCC2)cn(Cc2cccc(CO)c2)c1=O]

A solution of methyl 3-((5-(cyclobutylcarbamoyl)-3-(methylcarbamoyl)-2-oxopyridin-1(2H)-yl)methyl)benzoate (35 mg, 0.088 mmol) in DCM (881 µL) was cooled to −78° C. and DIBAL-H (1M in toluene, 299 µL, 0.299 mmol) was added dropwise over 1 h. After an additional 1 h at −78° C. a supplementary portion of DIBAL-H (1M in toluene, 88 µL, 0.088 mmol) was added dropwise over 20 min. The reaction mixture was stirred for 70 min more. The reaction was quenched with methanol (157 µL, 3.87 mmol) when still at −78° C. and then allowed to warm to ambient temperature. The reaction was diluted with dichloromethane (3 mL) and Rochelle's salt solution (3 mL) and stirred overnight. The layers were separated, and the aqueous phase was extracted with dichloromethane (2×5 mL). The combined organic layers were dried through a hydrophobic frit and evaporated in vacuo to yield the crude product (38 mg). The residue was loaded in dichloromethane onto a 10 g SNAP silica cartridge and purified via Biotage SP4 flash chromatography, eluting from 15-75% (3:1 ethyl acetate:ethanol)/cyclohexane. The relevant fractions were combined and evaporated in vacuo to yield—N5-cyclobutyl-1-(3-(hydroxymethyl)benzyl)-N3-methyl-2-oxo-1,2-dihydropyridine-3,5-dicarboxamide (7 mg, 0.019 mmol, 21.52% yield) as a white solid.

LCMS (2 min Formic): Rt=0.75 min, [MH]⁺=370.3.

Example 27: N5-Cyclobutyl-1-(3-methoxybenzyl)-N3-methyl-2-oxo-1,2-dihydropyridine-3,5-dicarboxamide

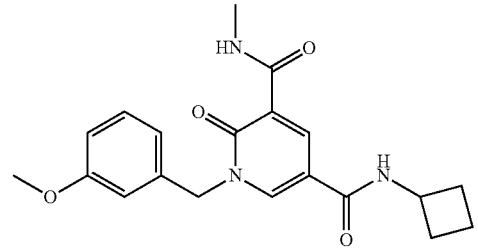 [SMILES: CNC(=O)c1cc(C(=O)NC2CCC2)cn(Cc2cccc(OC)c2)c1=O]

To a solution of N5-cyclobutyl-N3-methyl-2-oxo-1,2-dihydropyridine-3,5-dicarboxamide (100 mg, 0.401 mmol) in methanol (535 µL) was added potassium carbonate (111 mg, 0.802 mmol) and 1-(bromomethyl)-3-methoxybenzene (84 µL, 0.602 mmol). The mixture was heated to 65° C. for 3 h. The reaction flask was left to stand overnight, during which time the solvent evaporated. The residue was diluted with H₂O (10 mL) and extracted with EtOAc (4×10 mL). The combined organics were washed with brine, dried through a hydrophobic frit and evaporated in vacuo to yield the crude product (188 mg). The residue was loaded in dichloromethane and purified via Biotage SP4, eluting from 15-75% (3:1 ethyl acetate:ethanol)/cyclohexane. The relevant fractions were recombined and evaporated in vacuo. The residue N5-cyclobutyl-1-(3-methoxybenzyl)-N3-methyl-2-oxo-1,2-dihydropyridine-3,5-dicarboxamide (142 mg, 0.384 mmol, 96% yield) was obtained as an off white solid.

LCMS (2 min Formic): Rt=0.93 min, [MH]⁺=370.3.

Example 28: N5-Cyclobutyl-1-(3-hydroxybenzyl)-N3-methyl-2-oxo-1,2-dihydropyridine-3,5-dicarboxamide

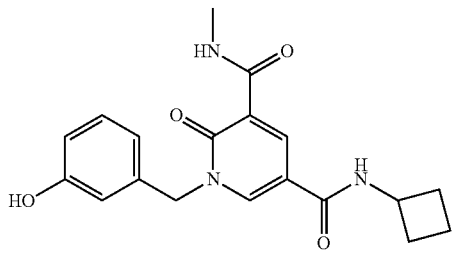 [SMILES: CNC(=O)c1cc(C(=O)NC2CCC2)cn(Cc2cccc(O)c2)c1=O]

To a solution of N5-cyclobutyl-1-(3-methoxybenzyl)-N3-methyl-2-oxo-1,2-dihydropyridine-3,5-dicarboxamide (75 mg, 0.134 mmol) in dry dichloromethane at 0° C. was slowly added BBr₃ (1M in dichloromethane, 402 µL, 0.402 mmol) under a nitrogen atmosphere. The mixture was stirred overnight while warming to rt. A further portion of BBr₃ (1M in dichloromethane, 402 µL, 0.402 mmol) was added and the reaction was stirred for a further 3 h. The reaction was quenched by the careful addition of brine, and neutralized with sodium bicarbonate. The mixture was diluted with water (10 mL) and the aqueous layer was extracted with dichloromethane (12×10 mL). A thick emulsion formed during extraction and LCMS indicated the presence of product in the aqueous phase. The aqueous phase was further extracted with ethyl acetate (3×15 mL). The combined dichloromethane fractions were dried through a hydrophobic frit and evaporated in vacuo. The combined ethyl acetate portions were washed with brine, dried through a hydrophobic frit, added to the residue from the dichloromethane fractions and evaporated in vacuo. The crude residue (86 mg) was dry loaded in methanol onto a 10 g SNAP silica cartridge and this was purified via Biotage SP4 flash chromatography, eluting from 10-50% (3:1 ethyl acetate:ethanol)/cyclohexane. The relevant fractions were combined and evaporated in vacuo to yield N5-cyclobutyl-1-(3-hydroxybenzyl)-N3-methyl-2-oxo-1,2-dihydropyridine-3,5-dicarboxamide (41 mg, 0.115 mmol, 86% yield) as a white solid.

LCMS (2 min Formic): Rt=0.76 min, [MH]⁺=356.2.

Example 29: N5-Cyclobutyl-1-(3-(2-hydroxyethoxy)benzyl)-N3-methyl-2-oxo-1,2-dihydropyridine-3,5-dicarboxamide

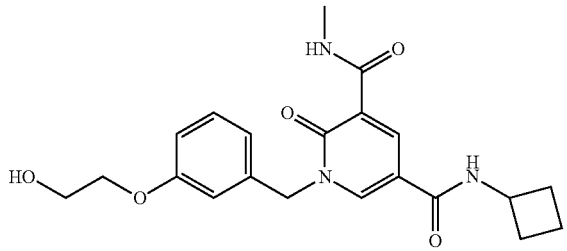 [SMILES: CNC(=O)c1cc(C(=O)NC2CCC2)cn(Cc2cccc(OCCO)c2)c1=O]

A solution of 1,3-dioxolan-2-one (28.6 mg, 0.325 mmol), potassium carbonate (40.8 mg, 0.295 mmol) and N5-cyclobutyl-1-(3-hydroxybenzyl)-N3-methyl-2-oxo-1,2-dihydropyridine-3,5-dicarboxamide (35 mg, 0.098 mmol), in DMF (0.985 mL) was stirred at 135° C. for 6 h. The reaction solution was partitioned between water (30 mL) and ethyl acetate (10 mL). The aqueous phase was extracted further with ethyl acetate (3×10 mL), and the combined organic portions were dried through a hydrophobic frit and evaporated in vacuo. The sample was dissolved in DMSO (1 mL) and purified by MDAP (High pH). The solvent was dried under a stream of nitrogen to give the required product—N5-cyclobutyl-1-(3-(2-hydroxyethoxy)benzyl)-N3-methyl-2-oxo-1,2-dihydropyridine-3,5-dicarboxamide (28 mg, 0.070 mmol, 71.2% yield) as a white solid.

LCMS (2 min Formic): Rt=0.77 min, [MH]⁺=400.2.

Example 30: 1-((1H-Benzo[d]imidazol-4-yl)methyl)-N5-cyclopropyl-N3-methyl-2-oxo-1,2-dihydropyridine-3,5-dicarboxamide

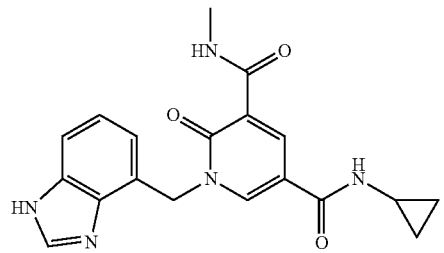 [SMILES: CNC(=O)c1cc(C(=O)NC2CC2)cn(Cc2cccc3[nH]cnc23)c1=O]

tert-Butyl 4-((5-(cyclopropylcarbamoyl)-3-(methylcarbamoyl)-2-oxopyridin-1(2H)-yl)methyl)-1H-benzo[d]imidazole-1-carboxylate (83 mg, 0.178 mmol) was dissolved in DCM (3.2 mL) and trifluoroacetic acid (783 µL, 10.16 mmol) was added cautiously. The mixture was stirred at rt for 90 min. The reaction mixture was loaded on an SCX column, washed with MeOH (2 CV) and eluted with methanolic ammonia (2M) (4 CV). The appropriate fractions were combined and evaporated under reduced pressure to give a brown solid—1-((1H-benzo[d]imidazol-4-yl)methyl)-N5-cyclopropyl-N3-methyl-2-oxo-1,2-dihydropyridine-3,5-dicarboxamide (60 mg, 0.164 mmol, 92% yield). 19 mg of the product was dissolved in methanol (1 mL) and purified via MDAP (High pH). The relevant fractions were blown down under a stream of nitrogen to give 1-((1H-benzo[d]imidazol- 4-yl)methyl)-N5-cyclopropyl-N3-methyl-2-oxo-1,2-dihydropyridine-3,5-dicarboxamide (9 mg, 0.025 mmol, 13.81% yield).

LCMS (2 min Formic): Rt=0.43 min, [MH]⁺=366.1.

Example 31:—(R)—N5-Cyclopropyl-N3-methyl-2-oxo-1-(1-phenylethyl)-1,2-dihydropyridine-3,5-dicarboxamide

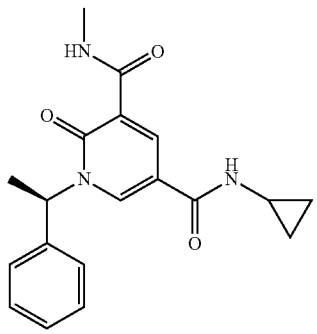 [SMILES: CNC(=O)c1cc(C(=O)NC2CC2)cn([C@H](C)c2ccccc2)c1=O]

HATU (95 mg, 0.250 mmol) was added to a solution of (R)-5-(methylcarbamoyl)-6-oxo-1-(1-phenylethyl)-1,6-dihydropyridine-3-carboxylic acid (50 mg, 0.166 mmol) and DIPEA (0.058 mL, 0.333 mmol) in DMF (0.5 mL). The solution was stirred for 5 min and cyclopropylamine (0.014 mL, 0.200 mmol) added. The resulting solution was stirred for 1 h. The reaction mixture was purified by MDAP (Formic). The product containing fraction was azeotroped in vacuo to dryness with EtOH to give a white solid (50 mg).

LCMS (2 min TFA): Rt=0.85 min, [MH]⁺=340.1.

Example 32: N5-Cyclopropyl-N3-methyl-1-((1-methyl-1H-benzo[d]imidazol-7-yl)methyl)-2-oxo-1,2-dihydropyridine-3,5-dicarboxamide

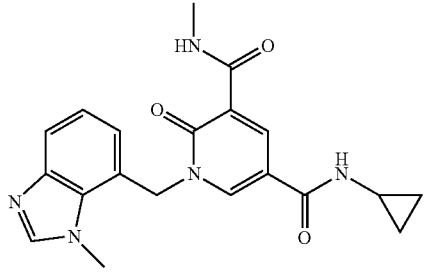 [SMILES: CNC(=O)c1cc(C(=O)NC2CC2)cn(Cc2cccc3ncn(C)c23)c1=O]

KOH (15.2 mg, 0.271 mmol) was added to a solution of 1-((1H-benzo[d]imidazol-4-yl)methyl)-N5-cyclopropyl-N3-methyl-2-oxo-1,2-dihydropyridine-3,5-dicarboxamide (42 mg, 0.115 mmol) in DCM (2.5 mL) at rt under nitrogen. Methyl iodide (7.91 µL, 0.126 mmol) was added dropwise with vigorous stirring. After 1 h a further portion of methyl iodide (7.19 µL, 0.115 mmol) and KOH (14.6 mg, 0.260 mmol) were added. The reaction was stirred for 23 h. The reaction was quenched with water (20.71 µL, 1.149 mmol), diluted with water (10 mL) and the products were extracted with dichloromethane (4×10 mL). The combined organic portions were dried through a hydrophobic frit and evaporated to dryness. The residue was dissolved in MeOH/DMSO (1 mL, 1:1) and purified by MDAP (High pH). The solvent was dried under a stream of nitrogen to give: N5-cyclopropyl-N3-methyl-1-((1-methyl-1H-benzo[d]imidazol-7-yl)methyl)-2-oxo-1,2-dihydropyridine-3,5-dicarboxamide (2.1 mg, 5.53 µmol, 4.82% yield) as a white solid.

LCMS (2 min Formic): Rt=0.40 min, [MH]⁺=380.2.

Example 33: (+/−)-1-Benzyl-N3-methyl-N5-((trans)-2-methylcyclopropyl)-2-oxo-1,2-dihydropyridine-3,5-dicarboxamide and Example 114: (+/−)-1-Benzyl-N3-methyl-N5-((cis)-2-methylcyclopropyl)-2-oxo-1,2-dihydropyridine-3,5-dicarboxamide

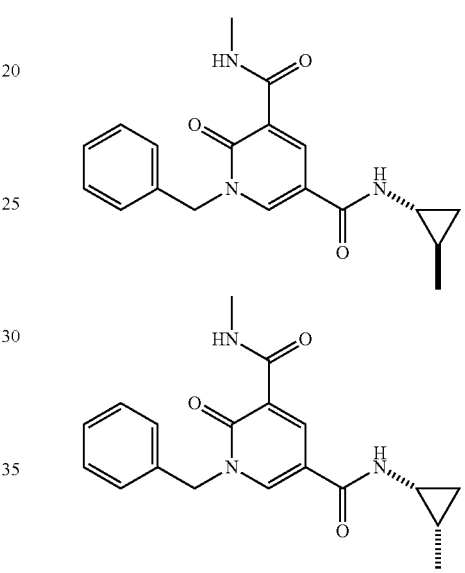

DIPEA (0.275 mL, 1.572 mmol) was added to a suspension of 1-benzyl-5-(methylcarbamoyl)-6-oxo-1,6-dihydropyridine-3-carboxylic acid (150 mg, 0.524 mmol), 2-methylcyclopropanamine (74.5 mg, 1.048 mmol, commercially available from, for example UkrOrgSyntez), and HATU (299 mg, 0.786 mmol) in DMF (4 mL). The reaction mixture was stirred at rt for 30 min, after which time further HATU (299 mg, 0.786 mmol) and DIPEA (0.275 mL, 1.572 mmol) were added. The reaction was stirred for a further 20 min. The reaction mixture was then partitioned between ethyl acetate and water and the organic layer washed with 2× water. This was passed through a hydrophobic frit and the solvent removed under reduced pressure. The resulting orange oil was dissolved in 1:1 DMSO:methanol and purified by MDAP. Two diastereomeric products were obtained from MDAP. The solvent was removed under reduced pressure and the products were left to dry in vacuo for 4 h to give:

(+/−)-1-benzyl-N3-methyl-N5-((cis)-2-methylcyclopropyl)-2-oxo-1,2-dihydropyridine-3,5-dicarboxamide (22.5 mg, 0.066 mmol, 12.65% yield) as a white solid LCMS (2 min Formic): Rt=0.87 min, [MH]⁺=340.1.

(+/−)-1-benzyl-N3-methyl-N5-((trans)-2-methylcyclopropyl)-2-oxo-1,2-dihydropyridine-3,5-dicarboxamide (120 mg, 0.354 mmol, 67.5% yield) as a pale yellow solid.

LCMS (2 min Formic): Rt=0.90 min, [MH]⁺=340.1.

Example 34: 1-Benzyl-N5-((trans)-4-hydroxycyclohexyl)-N3-methyl-2-oxo-1,2-dihydropyridine-3,5-dicarboxamide

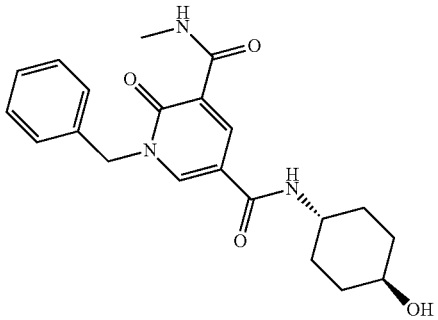 [SMILES: CNC(=O)c1cc(C(=O)N[C@H]2CC[C@H](O)CC2)cn(Cc2ccccc2)c1=O]

To a solution of 1-benzyl-5-(methylcarbamoyl)-6-oxo-1,6-dihydropyridine-3-carboxylic acid (48 mg, 0.168 mmol), 4-aminocyclohexanol (44.1 mg, 0.383 mmol) and 2-(3H-[1,2,3]triazolo[4,5-b]pyridin-3-yl)-1,1,3,3-tetramethylisouronium hexafluorophosphate (V) (HATU) (81 mg, 0.213 mmol) in DMF (1 mL) was added N,N-diisopropylethylamine (DIPEA) (0.059 mL, 0.335 mmol). The mixture was stirred at rt for 1.25 h before being concentrated under a stream of nitrogen. The solution was made up to 1 mL with methanol and directly purified by MDAP (formic). The required fraction was evaporated under a stream of nitrogen before being dissolved in a 1:1 mixture of dichloromethane/methanol (4 mL), concentrated under a stream of nitrogen and dried in vacuo to give the desired product as a pale yellow solid; 1-benzyl-N5-((trans)-4-hydroxycyclohexyl)-N3-methyl-2-oxo-1,2-dihydropyridine-3,5-dicarboxamide (61.8 mg, 0.161 mmol, 96% yield).

LCMS (2 min Formic): Rt=0.77 min, [MH]+=384.3.

Example 35: (+/−)-1-Benzyl-N5-(2-(hydroxymethyl)cyclopropyl)-N3-methyl-2-oxo-1,2-dihydropyridine-3,5-dicarboxamide

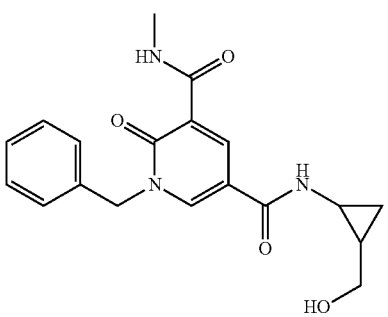 [SMILES: CNC(=O)c1cc(C(=O)NC2CC2CO)cn(Cc2ccccc2)c1=O]

DIPEA (0.092 mL, 0.524 mmol) was added to a suspension of 1-benzyl-5-(methylcarbamoyl)-6-oxo-1,6-dihydropyridine-3-carboxylic acid (50 mg, 0.175 mmol), (2-aminocyclopropyl)methanol (30.4 mg, 0.349 mmol, commercially available from, for example, Enamine), and HATU (100 mg, 0.262 mmol) in DMF (2 mL). The orange solution was stirred under nitrogen for 1 h and left to react overnight. Further (2-aminocyclopropyl)methanol (30.4 mg, 0.349 mmol), HATU (100 mg, 0.262 mmol), and DIPEA (0.092 mL, 0.524 mmol) were added and the reaction mixture was stirred under nitrogen for a further 2 h. The reaction mixture was partitioned between ethyl acetate and water: the aqueous layer was extracted with 2× ethyl acetate and the organic layer washed with 2× water and passed through a hydrophobic frit. The solvent was removed under reduced pressure and the resulting orange oil was dissolved in DCM. This was loaded onto a 10 g Biotage SNAP column, which was eluted in ethyl acetate:methanol (0-20%). The product-containing fractions were combined and the solvent removed under reduced pressure. The product was then left to dry in vacuo for 5 h to give 1-benzyl-N5-(2-(hydroxymethyl)cyclopropyl)-N3-methyl-2-oxo-1,2-dihydropyridine-3,5-dicarboxamide (19.4 mg, 0.055 mmol, 31.3% yield) as a yellow solid.

LCMS (2 min Formic): Rt=0.73 min, [MH]+=356.1.

Example 36: (+/−)-1-Benzyl-N5-(2-methoxycyclopropyl)-N3-methyl-2-oxo-1,2-dihydropyridine-3,5-dicarboxamide

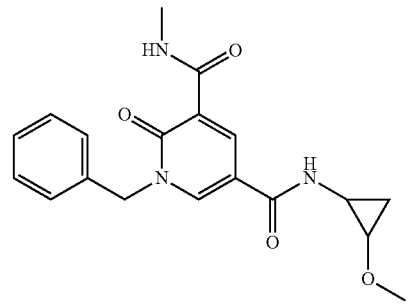 [SMILES: CNC(=O)c1cc(C(=O)NC2CC2OC)cn(Cc2ccccc2)c1=O]

2-Methoxycyclopropanamine, HCl salt (30.4 mg, 0.349 mmol, commercially available from, for example, ZereneX) in DMF (2 mL) was added to a mixture of 1-benzyl-5-(methylcarbamoyl)-6-oxo-1,6-dihydropyridine-3-carboxylic acid (50 mg, 0.175 mmol), HATU (100 mg, 0.262 mmol), and DIPEA (0.092 mL, 0.524 mmol). The resulting brown solution was stirred under nitrogen for 2 h. Further 2-methoxycyclopropanamine, HCl salt (30.4 mg, 0.349 mmol), HATU (100 mg, 0.262 mmol), and DIPEA (0.092 mL, 0.524 mmol) were added and the reaction mixture was stirred under nitrogen for a further 1 h and left to react overnight. The reaction mixture was partitioned between ethyl acetate and water and the aqueous layer was extracted with 2× ethyl acetate. The organic layer was washed with 2× water and 1× brine, passed through a hydrophobic frit, and the solvent removed under reduced pressure. The resulting orange oil was dissolved in DCM and loaded onto a 10 g Biotage SNAP column which was eluted with cyclohexane:ethyl acetate (50-100%). The product-containing fractions were combined and the solvent removed under reduced pressure. The solid was dissolved in DMSO:methanol (1:1) and purified by MDAP (Formic). The solvent was removed under reduced pressure and left to dry in vacuo for 2 days to give 1-benzyl-N5-(2-methoxycyclopropyl)-N3-methyl-2-oxo-1,2-dihydropyridine-3,5-dicarboxamide (13.6 mg, 0.038 mmol, 21.91% yield) as a pale yellow solid.

LCMS (2 min Formic): Rt=0.82 min, [MH]+=356.1.

Example 37: N5-Cyclopropyl-1-(3-fluorobenzyl)-N3-methyl-2-oxo-1,2-dihydropyridine-3,5-dicarboxamide

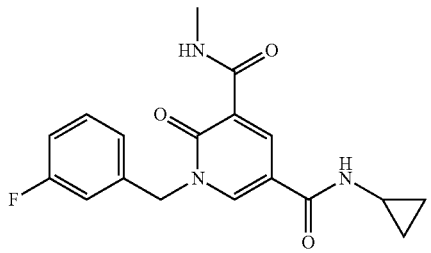 [SMILES: CNC(=O)c1cc(C(=O)NC2CC2)cn(Cc2cccc(F)c2)c1=O]

To a dry microwave vial, Pd(OAc)$_2$ (8 mg, 0.036 mmol), xantphos (14.5 mg, 0.025 mmol) and DMAP (88 mg, 0.719 mmol) were added followed by dicobalt octacarbonyl (36.9 mg, 0.108 mmol) and cyclopropylamine (50.7 µL, 0.719 mmol). The vial was sealed immediately and placed under nitrogen. 5-Bromo-1-(3-fluorobenzyl)-N-methyl-2-oxo-1,2-dihydropyridine-3-carboxamide (122 mg, 0.360 mmol) was added as a solution in 1,4-dioxane (2.5 mL) and the vial was heated under microwave irradiation for 40 min at 80° C. The reaction mixture was filtered through celite, concentrated in vacuo, taken up in ethyl acetate (30 mL) and washed with 2M HCl (10 mL). The acid layer was extracted with ethyl acetate (2×10 mL). The combined organic portions were washed with brine (10 mL), dried through a hydrophobic frit and evaporated in vacuo. The crude residue (163 mg) was loaded in dichloromethane onto a 25 g SNAP silica cartridge and purified via Biotage SP4 flash chromatography, eluting with 15-75% (3:1 ethyl acetate:ethanol)/cyclohexane. The relevant fractions were combined and evaporated in vacuo to yield a yellow glass. The sample was dissolved in DMSO (1 mL) and purified by MDAP (High pH). The solvent was dried under a stream of nitrogen to give—N5-cyclopropyl-1-(3-fluorobenzyl)-N3-methyl-2-oxo-1,2-dihydropyridine-3,5-dicarboxamide (38 mg, 0.105 mmol, 29.2% yield) as a white solid.

LCMS (2 min Formic): Rt=0.82 min, [MH]$^+$=344.1.

Example 38: (+/−)-1-Benzyl-N5-(1-cyanocyclopropyl)-N3-methyl-2-oxo-1,2-dihydropyridine-3,5-dicarboxamide

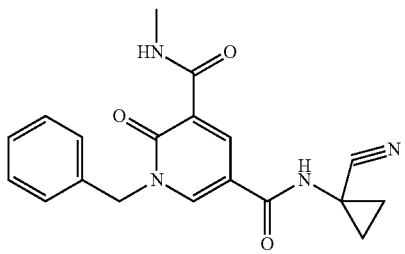 [SMILES: CNC(=O)c1cc(C(=O)NC2(C#N)CC2)cn(Cc2ccccc2)c1=O]

DIPEA (0.183 mL, 1.048 mmol) was added to a suspension of 1-benzyl-5-(methylcarbamoyl)-6-oxo-1,6-dihydropyridine-3-carboxylic acid (100 mg, 0.349 mmol), 1-aminocyclopropanecarbonitrile, HCl salt (57.4 mg, 0.699 mmol, commercially available from, for example, Sigma-Aldrich), and HATU (199 mg, 0.524 mmol) in DMF (2 mL). The reaction mixture was stirred under nitrogen for 2 h. This was then partitioned between ethyl acetate and water, the aqueous layer extracted with 2× ethyl acetate, and the organic layer washed with 2× water. This was then passed through a hydrophobic frit and the solvent removed under reduced pressure. The resulting brown-orange oil was dissolved in DCM and loaded onto a 10 g Biotage SNAP column which was eluted with cyclohexane:ethyl acetate (20-80%). The product-containing fractions were combined and the solvent removed under reduced pressure. The solid was left to dry in vacuo overnight to give 1-benzyl-N5-(1-cyanocyclopropyl)-N3-methyl-2-oxo-1,2-dihydropyridine-3,5-dicarboxamide (100 mg, 0.285 mmol, 82% yield) as a white solid.

LCMS (2 min Formic): Rt=0.83 min, [MH]$^+$=351.1.

Example 39: N5-Cyclopropyl-N3-methyl-2-oxo-1-(quinoxalin-5-ylmethyl)-1,2-dihydropyridine-3,5-dicarboxamide

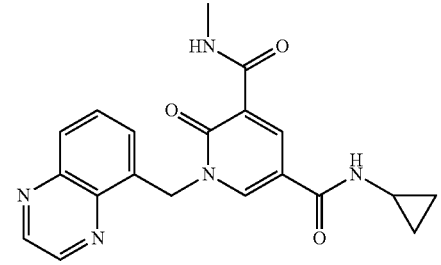 [SMILES: CNC(=O)c1cc(C(=O)NC2CC2)cn(Cc2cccc3nccnc23)c1=O]

5-Bromo-N-methyl-2-oxo-1-(quinoxalin-5-ylmethyl)-1,2-dihydropyridine-3-carboxamide (50 mg, 0.134 mmol), cobalt carbonyl (14 mg, 0.041 mmol), cyclopropanamine (0.019 mL, 0.268 mmol), DMAP (33 mg, 0.270 mmol), palladium acetate (2 mg, 8.91 µmol) and Catacxium A (3 mg, 8.37 µmol) were combined in a microwave vial and de-gassed. 1,4-Dioxane (1.5 mL) was added and the vial was heated at 80° C. for 40 min. The resulting solution was filtered through celite, partitioned between water and EtOAc, washed with 2M HCl, extracted with EtOAc (2×30 mL), dried over a hydrophobic frit and concentrated to give 70 mg of a green oil. This was purified by chromatography on SiO$_2$ (Biotage SNAP 50 g cartridge, eluting with 0-100% (25% ethanol in ethylacetate)/cyclohexane). The appropriate fractions were concentrated to give 10 mg of a yellow oil. This was further purified by MDAP (Formic) and the appropriate fractions were concentrated to give the title product, 4 mg as a white solid.

LCMS (2 min Formic): Rt=0.72 min, [MH]$^+$=376.

Example 40: (S*)-1-Benzyl-N5-(2,2-difluorocyclopropyl)-N3-methyl-2-oxo-1,2-dihydropyridine-3,5-dicarboxamide

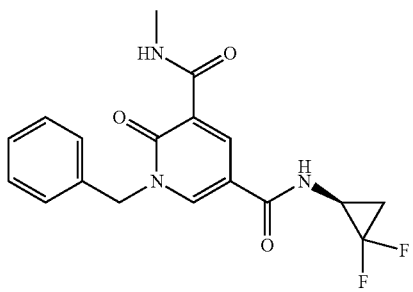 [SMILES: CNC(=O)c1cc(C(=O)N[C@H]2CC2(F)F)cn(Cc2ccccc2)c1=O]

DIPEA (0.183 mL, 1.048 mmol) was added to a solution of 1-benzyl-5-(methylcarbamoyl)-6-oxo-1,6-dihydropyridine-3-carboxylic acid (100 mg, 0.349 mmol), 2,2-difluorocyclopropanamine, HCl salt (65.0 mg, 0.699 mmol, commercially available from, for example, Manchester Organics), and HATU (199 mg, 0.524 mmol) in DMF (3 mL). The reaction mixture was stirred under nitrogen for 3 h. The solvent was removed under reduced pressure and the resulting orange oil was dissolved in DMSO/methanol (1:1). The solution was purified by MDAP (Formic) and the product-containing fractions were combined and the solvent removed under reduced pressure. The product was left to dry in vacuo overnight to give (+/−)-1-benzyl-N5-(2,2-difluorocyclopropyl)-N3-methyl-2-oxo-1,2-dihydropyridine-3,5-dicarboxamide (29 mg, 0.080 mmol, 22.98% yield) as a pale yellow solid. The racemic mixture was separated by achiral and chiral preparative HPLC:

Achiral Preparative Purification:

The sample was dissolved in DMSO (3 mL). 3000 µL injections were made onto a CSH C18 150×30 mm, 5 µm. column using the chromatographic conditions: Solvent A: 10 mM ammonium bicarbonate in water adjusted to pH 10 with ammonia solution, solvent B: acetonitrile, flow Rate: 40 mL/min. Gradient: as below:

| Time/min | % B | % A |
|---|---|---|
| 0 | 10 | 90 |
| 3.5 | 10 | 90 |
| 25 | 30 | 70 |
| 32 | 30 | 70 |
| 35 | 99 | 1 |

Fractionation was determined by mixture of diode array & mass spec signal: UV detection: a summed signal from wavelengths 210 nm to 350 nm. MS: Waters ZQ, Ionisation mode: Alt Pos/Neg Electrospray, Scan Range: 100 to 1000 AMU, Scan Time: 0.5 s, Inter scan Delay: 0.2 s. The flow and gradient was provided by a two pumps with a reduced flow passing through the injector during injection. The residual flow is introduced at the head of the column so the overall flow remains constant. The fractions were combined and dried under a stream of nitrogen blowdown at 40° C. and further purified by chiral purification.

Chiral Analytical Method:

Approx 0.5 mg of racemate was dissolved in 50% EtOH/Heptane (1 mL). Injection; 20 µL of the sample solution was injected onto the column (4.6 mm id×25 cm Chiralpak IC Lot No. IC00CE-OG021) eluting with 30% EtOH/heptane, at a rate of 1 mL/min and analysing at a wavelength of 215 nm.

Chiral Preparative Method:

Approx 30 mg of racemate was dissolved in EtOH (2 mL). Injection; 2 mL of the sample solution was injected onto the column (30 mm×25 cm Chiralpak IC Lot No. IC10028-01) eluting with 30% EtOH/heptane, at a rate of 30 mL/min and analysing at a wavelength of 215 nm. Fractions from 16-20 min were bulked and labelled peak 1. This gave the desired single (unknown) enantiomer as a white solid (6 mg).

LCMS (2 min Formic): Rt=0.88 min, [MH]+=362.1.

Example 41: tert-Butyl (3-(1-benzyl-5-(methylcarbamoyl)-6-oxo-1,6-dihydropyridine-3-carboxamido)cyclobutyl)carbamate

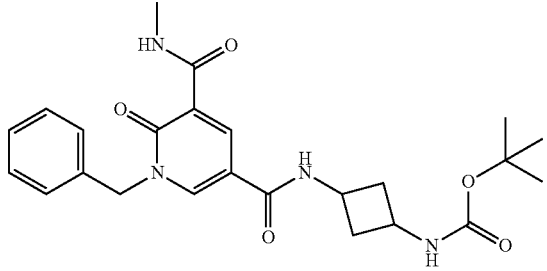 [SMILES: CNC(=O)c1cc(C(=O)NC2CC(NC(=O)OC(C)(C)C)C2)cn(Cc2ccccc2)c1=O]

1-Benzyl-5-(methylcarbamoyl)-6-oxo-1,6-dihydropyridine-3-carboxylic acid (400 mg, 1.397 mmol) was taken up in DMF (9 mL) and HATU (584 mg, 1.537 mmol) followed by DIPEA (0.488 mL, 2.79 mmol) were added. The reaction mixture was allowed to stir for 5 min, then tert-butyl (3-aminocyclobutyl)carbamate (260 mg, 1.397 mmol, commercially available from, for example, Fluorochem) was added and the reaction allowed to stir for 1 h. The reaction mixture was concentrated under vacuum, loaded in DCM and purified by Biotage Isolera flash chromatography using a SNAP 25 g silica cartridge, using a gradient of 0-100% ethyl acetate/cyclohexane. The appropriate fractions were combined and concentrated under vacuum. The solid obtained was dissolved in a minimum amount of DCM and purified by Biotage Isolera flash chromatography using a SNAP 25 g silica cartridge, using a gradient of 0-100% ethyl acetate/cyclohexane. The product containing fractions were combined and concentrated under vacuum to give the desired product (530 mg, 1.166 mmol, 83% yield) as a white solid.

LCMS (2 min Formic): Rt=1.00 min, [MH]+=455.2.

Example 42: N5-Cyclopropyl-1-(4-fluorobenzyl)-N3-methyl-2-oxo-1,2-dihydropyridine-3,5-dicarboxamide

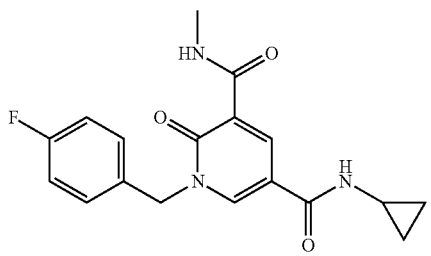 [SMILES: CNC(=O)c1cc(C(=O)NC2CC2)cn(Cc2ccc(F)cc2)c1=O]

To a dry microwave vial, 5-bromo-1-(4-fluorobenzyl)-N-methyl-2-oxo-1,2-dihydropyridine-3-carboxamide (123 mg, 0.363 mmol) and Pd(OAc)$_2$ (6.0 mg, 0.027 mmol) were added and taken up in dry 1,4-dioxane (2.5 mL). Xantphos (13.3 mg, 0.023 mmol), DMAP (89 mg, 0.725 mmol) and cyclopropylamine (51.1 µL, 0.725 mmol) were added, followed by dicobalt octacarbonyl (37.2 mg, 0.109 mmol). The vial was sealed immediately and heated under microwave irradiation for 40 min at 80° C. The reaction mixture was filtered through celite, concentrated in vacuo, taken up in ethyl acetate (30 mL) and washed with 2M HCl (10 mL). The acid layer was extracted with ethyl acetate (2×10 mL). The combined organic portions were washed with brine (10 mL), dried through a hydrophobic frit and evaporated in vacuo. The crude residue (195 mg) was loaded in dichloromethane onto a 25 g SNAP silica cartridge and purified via Biotage SP4 flash chromatography, eluting from 15-65% (3:1 ethyl acetate:ethanol)/cyclohexane. The relevant fractions were combined and evaporated in vacuo to yield a yellow glass. The sample was dissolved in DMSO (1 mL) and purified by MDAP (High pH). The solvent was dried under a stream of nitrogen to give a white solid. The solid was further dried in vacuo overnight to give—N5-cyclopropyl-1-(4-fluorobenzyl)-N3-methyl-2-oxo-1,2-dihydropyridine-3,5-dicarboxamide (47 mg, 0.130 mmol, 35.9% yield) as a white solid.

LCMS (2 min Formic): Rt=0.84 min, [MH]$^+$=344.2.

Example 43: N5-Cyclopropyl-1-(4-methoxybenzyl)-N3-methyl-2-oxo-1,2-dihydropyridine-3,5-dicarboxamide

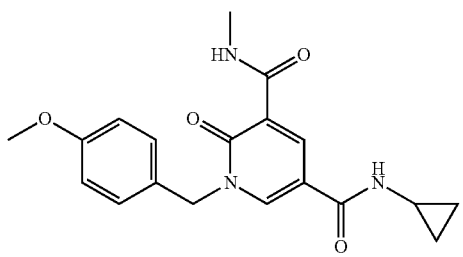 [SMILES: CNC(=O)c1cc(C(=O)NC2CC2)cn(Cc2ccc(OC)cc2)c1=O]

5-Bromo-1-(4-methoxybenzyl)-N-methyl-2-oxo-1,2-dihydropyridine-3-carboxamide (100 mg, 0.285 mmol), cobalt carbonyl (27 mg, 0.079 mmol), cyclopropanamine (0.04 mL, 0.577 mmol), DMAP (66 mg, 0.540 mmol), palladium acetate (3 mg, 0.013 mmol) and xantphos (8 mg, 0.014 mmol) were combined in a microwave vial and de-gassed. 1,4-Dioxane (3 mL) was added and the vial was heated at 80° C. for 40 min. The solution was filtered through celite, partitioned between water and EtOAc, washed with 2M HCl, extracted with EtOAc (2×30 mL), dried over a hydrophobic frit and concentrated to give 120 mg of a green oil. This was purified by chromatography on SiO$_2$ (Biotage SNAP 50 g cartridge, eluting with 0-100% (25% ethanol in ethylacetate)/cyclohexane). The appropriate fractions were concentrated to give 60 mg of a brown oil. This was purified by MDAP (Formic) and the appropriate fractions were concentrated to give N5-cyclopropyl-1-(4-methoxybenzyl)-N3-methyl-2-oxo-1,2-dihydropyridine-3,5-dicarboxamide (37 mg, 0.094 mmol, 32.9% yield) as a white solid.

LCMS (2 min Formic): Rt=0.82 min, [MH]$^+$=356.

Example 44: N5-Cyclopropyl-1-(3-methoxybenzyl)-N3-methyl-2-oxo-1,2-dihydropyridine-3,5-dicarboxamide

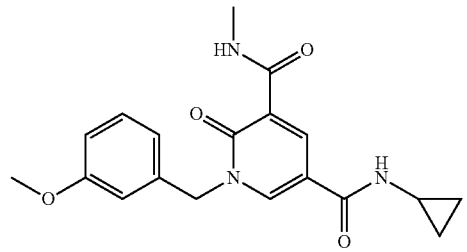 [SMILES: CNC(=O)c1cc(C(=O)NC2CC2)cn(Cc2cccc(OC)c2)c1=O]

To a solution of 1-(3-methoxybenzyl)-5-(methylcarbamoyl)-6-oxo-1,6-dihydropyridine-3-carboxylic acid (70 mg, 0.221 mmol) in DMF (2 mL) was added HATU (126 mg, 0.332 mmol) followed by cyclopropanamine (26 mg, 0.455 mmol) and DIPEA (0.155 mL, 0.885 mmol). The resulting reaction mixture was stirred at rt under N$_2$ for 7 h. The reaction mixture was concentrated to give 277 mg of a yellow oil and purified by chromatography on SiO$_2$ (Biotage SNAP 50 g cartridge, eluting with 40-100% EtOAc/cyclohexane). The appropriate fractions were concentrated to give N5-cyclopropyl-1-(3-methoxybenzyl)-N3-methyl-2-oxo-1,2-dihydropyridine-3,5-dicarboxamide (97 mg, 0.232 mmol, 100% yield) as a colourless oil.

LCMS (2 min Formic): Rt=0.84 min, [MH]$^+$=356.

Example 45: N5-Cyclopropyl-N3-methyl-1-(3-methylbenzyl)-2-oxo-1,2-dihydropyridine-3,5-dicarboxamide

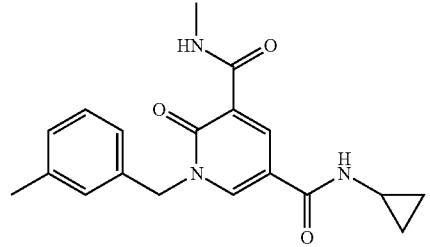 [SMILES: CNC(=O)c1cc(C(=O)NC2CC2)cn(Cc2cccc(C)c2)c1=O]

Cyclopropanamine (0.041 mL, 0.597 mmol) in THF (1.5 mL) was added to a sealed microwave vial containing 5-bromo-N-methyl-1-(3-methylbenzyl)-2-oxo-1,2-dihydropyridine-3-carboxamide (100 mg, 0.298 mmol), DMAP (109 mg, 0.895 mmol), xantphos (8.63 mg, 0.015 mmol), palladium acetate (3.34 mg, 0.015 mmol), and cobalt carbonyl (25.5 mg, 0.075 mmol). The resulting suspension was heated to 80° C. for 30 min by microwave irradiation. The blue reaction mixture was partitioned between ethyl acetate (20 mL) and water (20 mL), the aqueous layer extracted with ethyl acetate (2×20 mL) and the organic layer washed with water (2×20 mL) and brine (20 mL). This was dried over $MgSO_4$, filtered and the solvent removed under reduced pressure. The yellow solid was dissolved in DCM and purified by 10 g Biotage SNAP silica column using a gradient of 20-100% cyclohexane/ethyl acetate. The product-containing fractions were combined and the solvent removed under reduced pressure. The product was left to dry in vacuo overnight to give N5-cyclopropyl-N3-methyl-1-(3-methylbenzyl)-2-oxo-1,2-dihydropyridine-3,5-dicarboxamide (52.7 mg, 0.155 mmol, 52.0% yield) as a yellow solid.

LCMS (2 min Formic): Rt=0.90 min, [MH]$^+$=340.1.

Example 46: 1-Benzyl-N5-((1R*,2R*)-2-ethoxycyclopropyl)-N3-methyl-2-oxo-1,2-dihydropyridine-3,5-dicarboxamide and Example 47: 1-Benzyl-N5-((1S*,2S*)-2-ethoxycyclopropyl)-N3-methyl-2-oxo-1,2-dihydropyridine-3,5-dicarboxamide

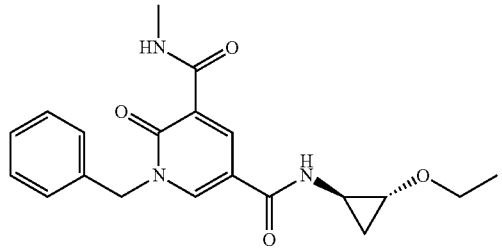 [SMILES: CCO[C@@H]1C[C@H]1NC(=O)c1cc(C(=O)NC)c(=O)n(Cc2ccccc2)c1]

DIPEA (0.549 mL, 3.14 mmol) was added to a suspension of 1-benzyl-5-(methylcarbamoyl)-6-oxo-1,6-dihydropyridine-3-carboxylic acid (300 mg, 1.048 mmol), 2-ethoxycyclopropanamine, HCl salt (212 mg, 2.096 mmol, commercially available from, for example, Enamine), and HATU (598 mg, 1.572 mmol) in DMF (5 mL). The resulting red solution was stirred under nitrogen for 1.5 h. The reaction mixture was partitioned between ethyl acetate and water, the aqueous layer was extracted with 2× ethyl acetate, and the organic layer washed with 2× water and 1× brine. This was passed through a hydrophobic frit and the solvent removed under reduced pressure. The resulting red oil was dissolved in DCM and loaded onto a 25 g Biotage SNAP silica column which was eluted with cyclohexane:ethyl acetate (30-100%). The product-containing fractions were combined and the solvent removed under reduced pressure. The product was left to dry in vacuo for 24 h to give (+/−)-(trans)-1-benzyl-N5-(2-ethoxycyclopropyl)-N3-methyl-2-oxo-1,2-dihydropyridine-3,5-dicarboxamide (213.4 mg, 0.578 mmol, 55.1% yield) as a pale yellow solid. This racemic mixture was purified by chiral HPLC:

Analytical Method:

Approx 0.5 mg of the diastereomer was dissolved in 50% EtOH/Heptane (1 mL). Injection; 20 μL of the sample solution was injected onto the column (4.6 mm id×25 cm Chiralpak IC Lot No. IC00CE-OG021) eluting with 30% EtOH/heptane, at a rate of 1 mL/min and analysing at a wavelength of 215 nm.

Preparative Method:

Approx 200 mg of the diastereomer was dissolved in EtOH (4 mL). Injection: 2 mL of the sample solution was injected onto the column (30 mm×25 cm Chiralpak IC Lot No. IC10028-01) eluting with 30% EtOH/heptane, at a rate of 30 mL/min and analysing at a wavelength of 215 nm. Fractions from 17-19 min were bulked and labelled peak 1. Fractions from 21-25 min were bulked and labelled peak 2.

This gave the single enantiomer 1 (example 46) as a white solid (87 mg).

LCMS (2 min Formic): Rt=0.88 min, [MH]$^+$=370.1.

This gave the single enantiomer 2 (example 47) as a white solid (71 mg).

LCMS (2 min Formic): Rt=0.88 min, [MH]$^+$=370.2.

Example 48: (+/−)-1-Benzyl-N5-((trans)-2-ethylcyclopropyl)-N3-methyl-2-oxo-1,2-dihydropyridine-3,5-dicarboxamide

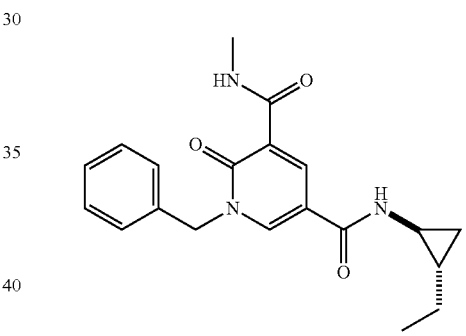

DIPEA (0.275 mL, 1.572 mmol) was added to a suspension of 1-benzyl-5-(methylcarbamoyl)-6-oxo-1,6-dihydropyridine-3-carboxylic acid (150 mg, 0.524 mmol), HATU (299 mg, 0.786 mmol), and (+/−)-(trans)-2-ethylcyclopropanamine (89 mg, 1.048 mmol, commercially available from, for example, Enamine) in DMF (3 mL). The reaction mixture was stirred for 20 min. The reaction mixture was partitioned between ethyl acetate and water and the organic layer washed with 2× water and 1× brine. This was passed through a hydrophobic frit and the solvent removed under reduced pressure. The oil was dissolved in 1:1 DMSO:methanol and purified by MDAP (TFA). The product-containing fractions were combined and the solvent removed under reduced pressure. The product was left to dry in vacuo for 4 h to give (+/−)-1-benzyl-N5-((trans)-2-ethylcyclopropyl)-N3-methyl-2-oxo-1,2-dihydropyridine-3,5-dicarboxamide (150.7 mg, 0.426 mmol, 81% yield) as a pale yellow solid.

LCMS (2 min Formic): Rt=0.99 min, [MH]$^+$=354.1.

Example 49: N5-Cyclopropyl-1-(4-fluoro-3-methyl-benzyl)-N3-methyl-2-oxo-1,2-dihydropyridine-3,5-dicarboxamide

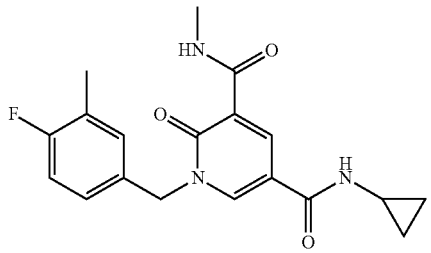 [SMILES: CNC(=O)c1cc(C(=O)NC2CC2)cn(Cc2ccc(F)c(C)c2)c1=O]

5-Bromo-1-(4-fluoro-3-methylbenzyl)-N-methyl-2-oxo-1,2-dihydropyridine-3-carboxamide (180 mg, 0.510 mmol), cobalt carbonyl (43.6 mg, 0.127 mmol), DMAP (125 mg, 1.019 mmol), palladium (II) acetate (5.72 mg, 0.025 mmol), cyclopropylamine (0.036 mL, 0.510 mmol) and xantphos (14.74 mg, 0.025 mmol) were added to a microwave vial. The vial was sealed and THF (3.3 mL) added and the reaction mixture then heated in a Biotage Initiator microwave at 90° C. for 30 min. The resulting mixture was diluted with water (20 mL) and extracted with ethyl acetate (20 mL). The organic layer was dried, concentrated under vacuum and purified by MDAP (High pH). The appropriate fractions were combined and concentrated under vacuum to give the desired product (70 mg).

LCMS (2 min Formic): Rt=0.92 min, MH+=358.1.

Example 50: N5-Cyclopropyl-N3-methyl-2-oxo-1-(quinolin-8-ylmethyl)-1,2-dihydropyridine-3,5-dicarboxamide

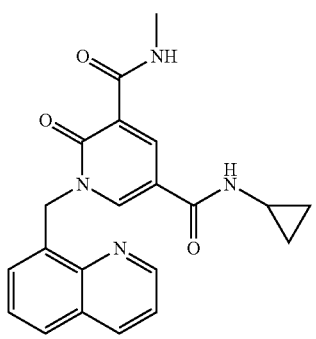 [SMILES: CNC(=O)c1cc(C(=O)NC2CC2)cn(Cc2cccc3cccnc23)c1=O]

5-Bromo-N-methyl-2-oxo-1-(quinolin-8-ylmethyl)-1,2-dihydropyridine-3-carboxamide (220 mg, 0.591 mmol), cobalt carbonyl (50.5 mg, 0.148 mmol), DMAP (144 mg, 1.182 mmol), palladium (II) acetate (6.63 mg, 0.030 mmol), cyclopropylamine (0.042 mL, 0.591 mmol) and xantphos (17.10 mg, 0.030 mmol) were added to a microwave vial. The vial was sealed and THF (3.3 mL) added and the reaction mixture was heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH). The appropriate fractions were combined to give the desired product (100 mg) as a white foam.

LCMS (2 min Formic): Rt=0.82 min, [MH]⁺=377.1.

Example 51: 1-((1H-Indazol-4-yl)methyl)-N5-cyclopropyl-N3-methyl-2-oxo-1,2-dihydropyridine-3,5-dicarboxamide

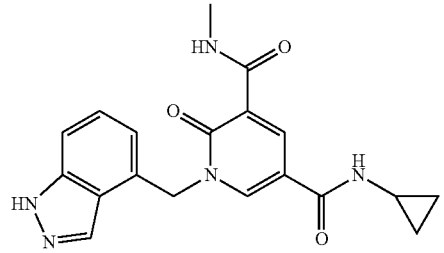 [SMILES: CNC(=O)c1cc(C(=O)NC2CC2)cn(Cc2cccc3[nH]ncc23)c1=O]

1-((1H-Indazol-4-yl)methyl)-5-bromo-N-methyl-2-oxo-1,2-dihydropyridine-3-carboxamide (140 mg, 0.388 mmol), cobalt carbonyl (39 mg, 0.114 mmol), cyclopropanamine (0.05 mL, 0.722 mmol), DMAP (93 mg, 0.761 mmol), palladium acetate (5 mg, 0.022 mmol) and xantphos (11 mg, 0.019 mmol) were combined in a microwave vial and de-gassed. 1,4-Dioxane (3 mL) was added and the vial was heated at 80° C. for 40 min. The solution was filtered through celite, partitioned between water and EtOAc, washed with 2M HCl, extracted with EtOAc (2×30 mL), dried over a hydrophobic frit and concentrated to give 560 mg of a green/blue oil. This was purified by chromatography on SiO₂ (Biotage SNAP 50 g cartridge, eluting with 0-100% (25% ethanol in ethylacetate)/cyclohexane). The appropriate fractions were concentrated to give 27 mg of a white solid. This was further purified by MDAP (Formic) and the appropriate fractions were concentrated to give 1-((1H-indazol-4-yl)methyl)-N5-cyclopropyl-N3-methyl-2-oxo-1,2-dihydropyridine-3,5-dicarboxamide (10 mg, 0.025 mmol, 6.35% yield) as a white solid.

LCMS (2 min Formic): Rt=0.67 min, [MH]⁺=366.

Example 52: 1-((1H-Indazol-7-yl)methyl)-N5-cyclopropyl-N3-methyl-2-oxo-1,2-dihydropyridine-3,5-dicarboxamide

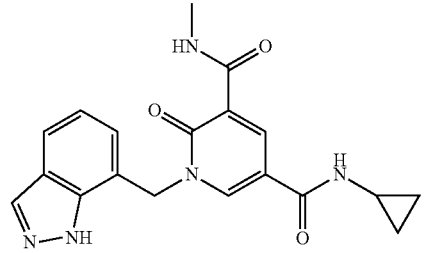 [SMILES: CNC(=O)c1cc(C(=O)NC2CC2)cn(Cc2cccc3cn[nH]c23)c1=O]

1-((1H-Indazol-7-yl)methyl)-5-bromo-N-methyl-2-oxo-1,2-dihydropyridine-3-carboxamide (204 mg, 0.565 mmol), cobalt carbonyl (54 mg, 0.158 mmol), cyclopropanamine (0.08 mL, 1.155 mmol), DMAP (147 mg, 1.203 mmol), palladium acetate (6 mg, 0.027 mmol) and xantphos (14 mg, 0.024 mmol) were combined in a microwave vial and de-gassed. 1,4-Dioxane (4 mL) was added and the vial was heated at 80° C. for 40 min. The solution was filtered through celite, partitioned between water and EtOAc, washed with 2M HCl, extracted with EtOAc (2×30 mL), dried over a hydrophobic frit and concentrated to give 250 mg of a green oil. This was purified by chromatography on SiO$_2$ (Biotage SNAP 50 g cartridge, eluting with 0-60% (25% ethanol in ethylacetate)/cyclohexane). The appropriate fractions were concentrated to give 114 mg of a yellow solid. This was further purified by MDAP (Formic) and the appropriate fractions were concentrated to give 1-((1H-indazol-7-yl)methyl)-N5-cyclopropyl-N3-methyl-2-oxo-1,2-dihydropyridine-3,5-dicarboxamide (38 mg, 0.094 mmol, 16.57% yield) as a white solid.

LCMS (2 min Formic): Rt=0.75 min, [MH]$^+$=366.

Example 53: N5-Cyclopropyl-N3-methyl-1-(4-methylbenzyl)-2-oxo-1,2-dihydropyridine-3,5-dicarboxamide

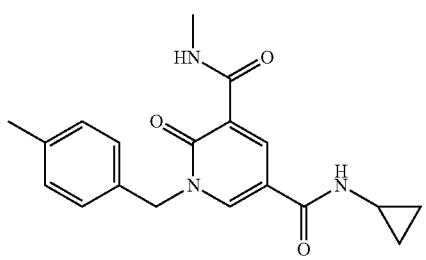 [SMILES: CNC(=O)c1cc(C(=O)NC2CC2)cn(Cc2ccc(C)cc2)c1=O]

To a dry microwave vial, 5-bromo-N-methyl-1-(4-methylbenzyl)-2-oxo-1,2-dihydropyridine-3-carboxamide (120 mg, 0.358 mmol) and Pd(OAc)$_2$ (4.5 mg, 0.020 mmol) were added and taken up in dry 1,4-dioxane (2.5 mL). Xantphos (15 mg, 0.026 mmol), DMAP (87 mg, 0.716 mmol) and cyclopropylamine (50.5 µL, 0.716 mmol) were added, followed by dicobalt octacarbonyl (36.7 mg, 0.107 mmol). The vial was sealed immediately and heated under microwave irradiation for 40 min at 80° C. The vial was returned to the microwave for a further 20 min. The reaction mixture was filtered through celite, concentrated in vacuo, taken up in ethyl acetate (30 mL) and washed with 2M HCl (10 mL). The acid layer was extracted with ethyl acetate (2×10 mL). The combined organic portions were washed with brine (10 mL), dried through a hydrophobic frit and evaporated in vacuo. The crude residue was loaded in dichloromethane onto a 25 g SNAP silica cartridge and purified via Biotage SP4 flash chromatography, eluting from 15-65% (3:1 ethyl acetate:ethanol)/cyclohexane. The relevant fractions were combined and evaporated in vacuo to yield a yellow glass. The sample was dissolved in DMSO (1 mL) and purified by MDAP (High pH). The solvent was dried under a stream of nitrogen to give a white solid (68 mg). The sample was submitted for achiral purification chromatography:

The sample was dissolved in 3 mL of DMSO. 1500 µL injections were made onto a CSH C18 150×30 mm, 5 µm column. Solvent A: 10 mM Ammonium Bicarbonate in water adjusted to pH 10 with Ammonia solution, solvent B: Acetonitrile, flow Rate: 40 mL/min. Gradient: as below:

| Time/min | % B | % A |
|---|---|---|
| 0 | 20 | 80 |
| 3 | 20 | 80 |
| 4 | 20 | 80 |
| 25 | 40 | 60 |
| 26 | 40 | 60 |

Fractionation was determined by mixture of diode array & mass spec signal: UV detection: a summed signal from wavelengths 210 nm to 350 nm. MS: Waters QDA, Ionisation mode: Positive Electrospray, Scan Range: 120 to 800 AMU, Scan Time: 0.5 s, Inter scan Delay: 0.1 s. The flow and gradient was provided by a two pumps with a reduced flow passing through the injector during injection. The residual flow is introduced at the head of the column so the overall flow remains constant. The fractions were combined and dried under a stream of nitrogen blowdown at 40° C. to afford N5-cyclopropyl-N3-methyl-1-(4-methylbenzyl)-2-oxo-1,2-dihydropyridine-3,5-dicarboxamide (51 mg, 0.150 mmol, 42.0% yield) as a white solid.

LCMS (2 min Formic): Rt=0.89 min, [MH]$^+$=340.1.

Example 54: N5-Cyclopropyl-1-(3,5-dimethylbenzyl)-N3-methyl-2-oxo-1,2-dihydropyridine-3,5-dicarboxamide

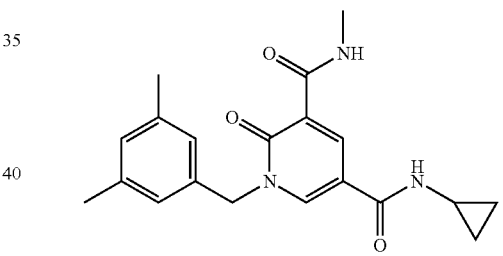

5-Bromo-1-(3,5-dimethylbenzyl)-N-methyl-2-oxo-1,2-dihydropyridine-3-carboxamide (160 mg, 0.458 mmol), cobalt carbonyl (39.2 mg, 0.115 mmol), DMAP (112 mg, 0.916 mmol), palladium (II) acetate (5.14 mg, 0.023 mmol), cyclopropylamine (0.032 mL, 0.458 mmol) and xantphos (13.26 mg, 0.023 mmol) were added to a microwave vial. The vial was sealed and THF (3.3 mL) added and the reaction mixture was heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH). The resulting product was loaded in DCM and purified by Biotage Isolera SNAP 10 g silica flash chromatography using a gradient of 0-60% cyclohexane/ethyl acetate. The product containing fractions were combined and concentrated under vacuum to give the desired product (49 mg) as a white solid.

LCMS (2 min Formic): Rt=0.98 min, [MH]$^+$=354.1.

Example 55: N5-Cyclopropyl-1-(2-fluoro-3-methyl-benzyl)-N3-methyl-2-oxo-1,2-dihydropyridine-3,5-dicarboxamide

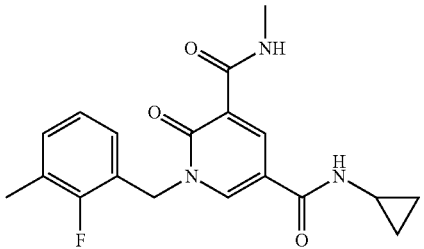 [SMILES: CNC(=O)c1cc(C(=O)NC2CC2)cn(Cc2cccc(C)c2F)c1=O]

5-Bromo-1-(2-fluoro-3-methylbenzyl)-N-methyl-2-oxo-1,2-dihydropyridine-3-carboxamide (200 mg, 0.566 mmol), cobalt carbonyl (48.4 mg, 0.142 mmol), DMAP (138 mg, 1.133 mmol), palladium (II) acetate (6.36 mg, 0.028 mmol), cyclopropylamine (0.040 mL, 0.566 mmol) and xantphos (16.38 mg, 0.028 mmol) were added to a microwave vial. The vial was sealed and THF (3.3 mL) added and the reaction mixture was then heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH), the appropriate fractions were combined and concentrated under vacuum. The resulting product was loaded in DCM and purified by purified by Biotage Isolera SNAP 10 g silica flash chromatography using a gradient of 0-60% cyclohexane/ethyl acetate. The product containing fractions were combined and concentrated under vacuum to give the desired product (50 mg) as a white solid.

LCMS (2 min Formic): Rt=0.91 min, [MH]$^+$=358.1.

Example 56: N5-Cyclopropyl-1-(2-fluorobenzyl)-N3-methyl-2-oxo-1,2-dihydropyridine-3,5-dicarbox-amide

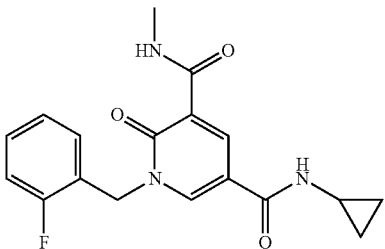 [SMILES: CNC(=O)c1cc(C(=O)NC2CC2)cn(Cc2ccccc2F)c1=O]

Cyclopropanamine (0.061 mL, 0.885 mmol) in THF (2 mL) was added to a sealed microwave vial containing 5-bromo-1-(2-fluorobenzyl)-N-methyl-2-oxo-1,2-dihydropyridine-3-carboxamide (150 mg, 0.442 mmol), cobalt carbonyl (42.0 mg, 0.111 mmol), xantphos (12.80 mg, 0.022 mmol), DMAP (162 mg, 1.327 mmol), and palladium acetate (4.95 mg, 0.022 mmol). The reaction mixture was heated to 80° C. for 30 min by microwave irradiation. The reaction mixture was heated to 80° C. for a further 15 min by microwave irradiation. This was then heated to 80° C. for a further 20 min by microwave irradiation. This was then partitioned between ethyl acetate (20 mL) and water (20 mL), the aqueous layer extracted with ethyl acetate (2×20 mL) and the combined organic layers then washed with water (2×20 mL). The organic layer was passed through a hydrophobic frit and the solvent removed under reduced pressure. The resulting orange oil was dissolved in DCM and purified by flash chromatography using a 25 g Biotage SNAP silica column and a gradient of 0-100% cyclohexane/ethyl acetate. The product-containing fractions were combined and the solvent removed under reduced pressure. The product was left to dry in vacuo for 2 days to give N5-cyclopropyl-1-(2-fluorobenzyl)-N3-methyl-2-oxo-1,2-dihydropyridine-3,5-dicarboxamide (59.6 mg, 0.174 mmol, 39.2% yield) as a pale yellow solid.

LCMS (2 min Formic): Rt=0.82 min, [MH]$^+$=344.1.

Example 57: N5-Cyclopropyl-1-(2-fluoro-5-methyl-benzyl)-N3-methyl-2-oxo-1,2-dihydropyridine-3,5-dicarboxamide

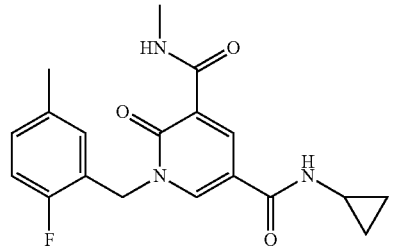 [SMILES: CNC(=O)c1cc(C(=O)NC2CC2)cn(Cc2cc(C)ccc2F)c1=O]

Cyclopropanamine (0.059 mL, 0.849 mmol) in THF (2 mL) was added to a sealed microwave vial containing 5-bromo-1-(2-fluoro-5-methylbenzyl)-N-methyl-2-oxo-1,2-dihydropyridine-3-carboxamide (150 mg, 0.425 mmol), cobalt carbonyl (40.3 mg, 0.106 mmol), xantphos (12.29 mg, 0.021 mmol), palladium acetate (4.76 mg, 0.021 mmol), and DMAP (156 mg, 1.274 mmol). The reaction mixture was heated to 80° C. for 30 min by microwave irradiation. This was heated to 80° C. for a further 30 min by microwave irradiation. The reaction mixture was partitioned between ethyl acetate (20 mL) and water (20 mL), the aqueous layer extracted with ethyl acetate (2×20 mL) and the organic layer washed with water (2×20 mL). This was passed through a hydrophobic frit and the solvent removed under reduced pressure. The brown oil was dissolved in DCM and purified by flash chromatography using a 25 g Biotage SNAP silica column and a gradient of 0-100% cyclohexane/ethyl acetate. The product-containing fractions were combined, the solvent removed under reduced pressure, and the solid dissolved in DMSO/methanol (1:1). This was purified by MDAP (Formic) and the solvent removed under reduced pressure. The product was left to dry in vacuo for 4 h to give N5-cyclopropyl-1-(2-fluoro-5-methylbenzyl)-N3-methyl-2-oxo-1,2-dihydropyridine-3,5-dicarboxamide (41.2 mg, 0.115 mmol, 27.1% yield) as a white solid.

LCMS (2 min Formic): Rt=0.91 min, [MH]$^+$=358.1.

Example 58: 1-((1H-Benzo[d]imidazol-6-yl)methyl)-N5-cyclopropyl-N3-methyl-2-oxo-1,2-dihydropyridine-3,5-dicarboxamide

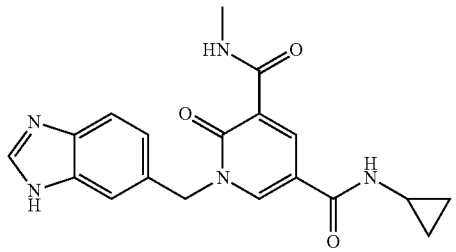 [SMILES: CNC(=O)c1cc(C(=O)NC2CC2)cn(Cc2ccc3nc[nH]c3c2)c1=O]

N5-Cyclopropyl-N3-methyl-2-oxo-1,2-dihydropyridine-3,5-dicarboxamide (60 mg, 0.255 mmol), 6-(bromomethyl)-1H-benzo[d]imidazole (88 mg, 0.417 mmol), potassium carbonate (75 mg, 0.543 mmol) and DMF (2 mL) were stirred at 90° C. under $N_2$ overnight followed by a further 3 h. The resulting suspension was concentrated and partitioned between EtOAc (20 mL) and water (20 mL). The aqueous phase was extracted with EtOAc (2×20 mL) and the combined organic layers were dried over a hydrophobic frit and concentrated to give 83 mg of a colourless oil. This was purified by chromatography on $SiO_2$ (Biotage SNAP 10 g cartridge, eluting with 0-100% (20% 2M $NH_3$ in MeOH in DCM)/DCM). The appropriate fractions were concentrated to give 12 mg of a white solid. This was further purified by MDAP (Formic). The appropriate fractions were concentrated to give 1-((1H-benzo[d]imidazol-6-yl)methyl)-N5-cyclopropyl-N3-methyl-2-oxo-1,2-dihydropyridine-3,5-dicarboxamide (7 mg, 0.017 mmol, 6.76% yield) as a white solid.

LCMS (2 min Formic): Rt=0.40 min, [MH]+=366.

Example 59: N5-Cyclopropyl-N3-methyl-1-(3-(morpholinomethyl)benzyl)-2-oxo-1,2-dihydropyridine-3,5-dicarboxamide, Formic Acid Salt

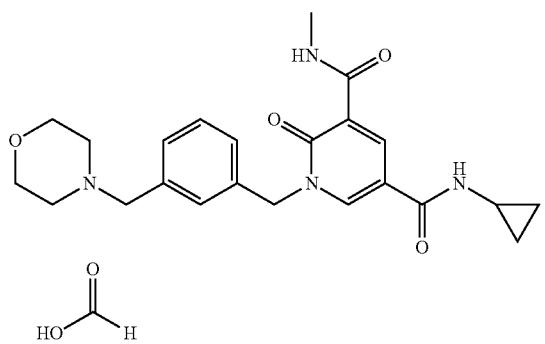

To a dry microwave vial, 5-bromo-N-methyl-1-(3-(morpholinomethyl)benzyl)-2-oxo-1,2-dihydropyridine-3-carboxamide (79 mg, 0.188 mmol) and N,N-dimethylpyridin-4-amine (46 mg, 0.377 mmol) were added and suspended in dry 1,4-dioxane (2 mL). Diacetoxypalladium (3 mg, 0.013 mmol), (9,9-dimethyl-9H-xanthene-4,5-diyl)bis(diphenylphosphine) (8 mg, 0.014 mmol) and cyclopropylamine (0.027 mL, 0.385 mmol) were added, followed by dicobalt octacarbonyl (20 mg, 0.058 mmol). The vial was sealed and heated under microwave irradiation for 40 min at 80° C. followed by heating at 80° C. for a further 30 min. The reaction mixture was filtered through a celite cartridge (2.5 g) and partitioned between ethyl acetate and water. The organic layer was separated, dried ($Na_2SO_4$) and concentrated to give ~82 mg of a crude yellow oil. This was purified by chromatography on $SiO_2$ (Biotage SNAP 10 g cartridge, eluting with 0-10% of 2M $NH_3$ in MeOH/DCM over 330 mL). Fractions containing product were concentrated in vacuo to give 10 mg of pale yellow oil. This was dissolved in MeOH (2 mL) and loaded onto a 2 g SCX cartridge (pre-eluted with MeOH) and eluted with MeOH (40 mL) followed by 2M $NH_3$ in MeOH (40 mL). The ammonia fractions containing the desired product were concentrated in vacuo to give 8 mg of pale yellow oil. This was further purified by MDAP (High pH) and the fractions containing the desired product were concentrated to give N5-cyclopropyl-N3-methyl-1-(3-(morpholinomethyl)benzyl)-2-oxo-1,2-dihydropyridine-3,5-dicarboxamide, formic acid salt (4 mg, 7.65 μmol, 4.07% yield) as a white solid.

LCMS (2 min High pH): Rt=0.80 min, [MH]+=425.

Example 60: 1-Benzyl-N5-((1S,2S)-2-(hydroxymethyl)cyclopropyl)-N3-methyl-2-oxo-1,2-dihydropyridine-3,5-dicarboxamide and

Example 84: 1-Benzyl-N5-((1R,2R)-2-(hydroxymethyl)cyclopropyl)-N3-methyl-2-oxo-1,2-dihydropyridine-3,5-dicarboxamide

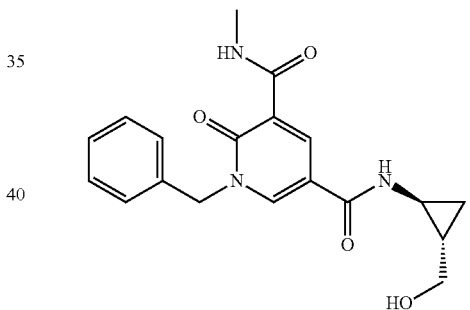

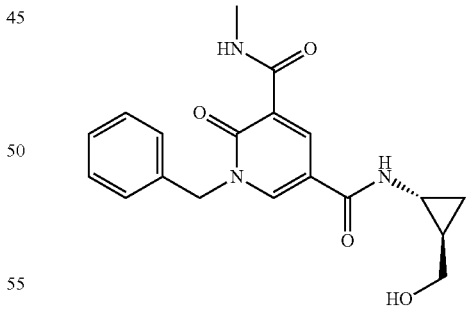

DIPEA (0.842 mL, 4.82 mmol) was added to a suspension of 1-benzyl-5-(methylcarbamoyl)-6-oxo-1,6-dihydropyridine-3-carboxylic acid (897 mg, 3.13 mmol), (2-aminocyclopropyl)methanol (210 mg, 2.410 mmol, commercially available from, for example, Enamine), and HATU (1283 mg, 3.37 mmol) in DMF (10 mL). The reaction mixture was stirred at rt for 90 min, after which further HATU (1283 mg, 3.37 mmol) and DIPEA (0.842 mL, 4.82 mmol) were added. The reaction was left to stand in solution for 2 days. The reaction mixture was partitioned between ethyl acetate and water and the aqueous layer extracted with 2x ethyl acetate. The organic layer was washed with 2x water and 1x brine and then passed through a hydrophobic frit. The solvent was removed under reduced pressure and the resulting red oil was dissolved in DCM. This was loaded onto a 25 g Biotage SNAP silica column which was eluted in cyclohexane/ethyl acetate (0-100%). No product was seen in the fractions so the column was flushed with ethyl acetate/methanol (0-20%). The product-containing fractions were combined and the solvent removed under reduced pressure. The resulting pale orange solid was dissolved in DMSO:methanol (1:1) and purified by MDAP (TFA). The product-containing fractions were combined and the solvent removed under reduced pressure. The product was left to dry in vacuo for 1 h and submitted for chiral separation.

Analytical Method:

Approx 0.5 mg racemate dissolved in 50% EtOH/Heptane (1 mL). Injection; 20 µL of the sample solution was injected onto column (4.6 mmidx25 cm Chiralpak IA Lot No. IA00CE-KL030) eluting with 40% EtOH/heptane, at a rate of 1 mL/min and analysing with a wavelength of 215 nm.

Preparative Method:

Approx 266 mg racemate dissolved in EtOH (4 mL)+heat. Injection; 2 mL of the sample solution was injected onto column (30 mm×25 cm Chiralpak IA Lot No. IA11321-01) eluting with 40% EtOH/heptane, at a rate of 30 mL/min and analysing with a wavelength of 215 nm. Fractions from 17-22 min were bulked and labelled peak 1. This isomer contained a related impurity which ran on the front of the isomer. Fractions from 25.5-38 min were bulked and labelled peak 2. The bulked fractions were vac'ed down using a rotary evaporator and then transferred to a weighed flask for final analysis as described by the analytical method above.

Peak 1: This gave the single enantiomer as a pale yellow solid (129 mg), but this was shown to be impure.

Peak 2: This gave the single enantiomer (Example 60) as a pale yellow solid (86 mg).

LCMS (2 min Formic): Rt=0.73 min, [MH]$^+$=356.1.

The sample corresponding to peak 1 was further purified by achiral preparative HPLC:

Achiral Purification

The sample was dissolved in DMSO (6 mL). 3000 µL injections were made onto a Xselect CSH C18 (150 mm×30 mm, 5 µm) column using the chromatographic conditions: Solvent A: 0.1% v/v solution of Formic Acid in Water, solvent B: 0.1% v/v solution of Formic Acid in Acetonitrile, flow Rate: 40 mL/min. Gradient: as below:

| Time/min | % B | % A |
| --- | --- | --- |
| 0 | 10 | 90 |
| 3.5 | 10 | 90 |
| 25 | 30 | 70 |
| 32 | 30 | 70 |
| 35 | 99 | 1 |

Fractionation was determined by mixture of diode array & mass spec signal: UV detection: a summed signal from wavelengths 210 nm to 350 nm. MS: Waters SQ, Ionisation mode: Alt Pos/Neg Electrospray, Scan Range: 100 to 1000 AMU, Scan Time: 0.5 s, Inter scan Delay: 0.2 s. The flow and gradient was provided by a two pumps with a reduced flow passing through the injector during injection. The residual flow is introduced at the head of the column so the overall flow remains constant. The fractions were combined and dried under a stream of nitrogen blowdown at 40° C. This gave the single enantiomer (Example 84) as a white solid (89 mg).

LCMS (2 min Formic): Rt=0.73 min, [MH]$^+$=356.1.

Example 61: (+/−)-1-(2-Fluorobenzyl)-N3-methyl-N5-((trans)-2-methylcyclopropyl)-2-oxo-1,2-dihydropyridine-3,5-dicarboxamide

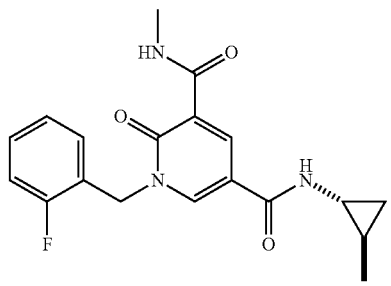

THF (2.5 mL) was added to a sealed microwave vial containing 5-bromo-1-(2-fluorobenzyl)-N-methyl-2-oxo-1,2-dihydropyridine-3-carboxamide (150 mg, 0.442 mmol), palladium acetate (4.95 mg, 0.022 mmol), cobalt carbonyl (42.0 mg, 0.111 mmol), (+/−)-(trans)-2-methylcyclopropanamine (62.9 mg, 0.885 mmol, commercially available from, for example, Fluorochem), xantphos (12.80 mg, 0.022 mmol), and DMAP (162 mg, 1.327 mmol). The reaction mixture was heated to 80° C. for 40 min by microwave irradiation. The reaction mixture was heated to 80° C. for a further 35 min by microwave irradiation. The reaction mixture was partitioned between ethyl acetate (20 mL) and water (20 mL), the aqueous layer was extracted with ethyl acetate (2×20 mL), and the organic layer washed with water (2×20 mL) and brine (20 mL). This was passed through a hydrophobic frit and the solvent removed under reduced pressure. The resulting orange oil was dissolved in DCM and purified by flash chromatography using a 25 g Biotage SNAP silica column and a gradient of 10-100% ethyl acetate/cyclohexane. The fractions were combined, the solvent removed in vacuo, and the product dissolved in DMSO:methanol (1:1) and purified by MDAP (Formic). The product-containing fractions were combined and the solvent removed under reduced pressure. The product was left to dry in vacuo for 2 h to give 1-(2-fluorobenzyl)-N3-methyl-N5-((trans)-2-methylcyclopropyl)-2-oxo-1,2-dihydropyridine-3,5-dicarboxamide (60.2 mg, 0.168 mmol, 38.1% yield) as a white solid.

LCMS (2 min Formic): Rt=0.91 min, [MH]$^+$=358.1.

Example 62: 5-Bromo-1-((6-methoxypyridin-3-yl)methyl)-N-methyl-2-oxo-1,2-dihydropyridine-3-carboxamide

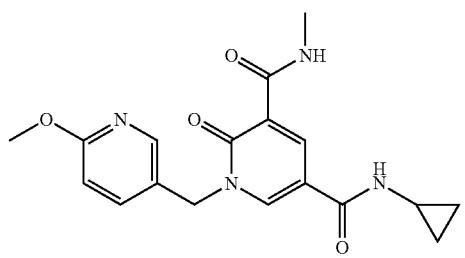 [SMILES: CNC(=O)c1cc(C(=O)NC2CC2)cn(Cc2ccc(OC)nc2)c1=O]

5-Bromo-1-((6-methoxypyridin-3-yl)methyl)-N-methyl-2-oxo-1,2-dihydropyridine-3-carboxamide (150 mg, 0.426 mmol), cobalt carbonyl (36.4 mg, 0.106 mmol), DMAP (104 mg, 0.852 mmol), palladium (II) acetate (4.78 mg, 0.021 mmol), cyclopropanamine (24.32 mg, 0.426 mmol) and xantphos (12.32 mg, 0.021 mmol) were added to a microwave vial. The vial was sealed, THF (3.3 mL) added and the reaction mixture was heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH), the appropriate fractions were combined and concentrated under vacuum. The resulting product was loaded in DCM and purified by Biotage Isolera SNAP 10 g silica flash chromatography using a gradient of 0-60% cyclohexane/ethyl acetate. The product containing fractions were combined and concentrated under vacuum to give the product (64 mg) as a white solid.

LCMS (2 min Formic): Rt=0.72 min, [MH]$^+$=357.1

Example 63: (+/−) 1-(2-Fluoro-5-methylbenzyl)-N3-methyl-N5-((trans)-2-methylcyclopropyl)-2-oxo-1,2-dihydropyridine-3,5-dicarboxamide

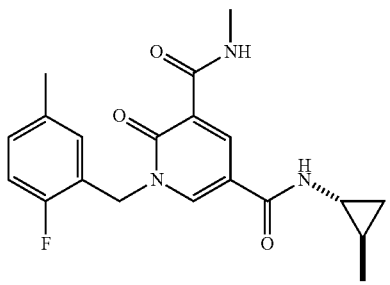

5-Bromo-1-(2-fluoro-5-methylbenzyl)-N-methyl-2-oxo-1,2-dihydropyridine-3-carboxamide (150 mg, 0.425 mmol), cobalt carbonyl (36.3 mg, 0.106 mmol), DMAP (104 mg, 0.849 mmol), palladium (II) acetate (4.77 mg, 0.021 mmol), (+/−)-(trans)-2-methylcyclopropanamine (30.2 mg, 0.425 mmol, commercially available from, for example, UkrOrgSynthesis Ltd.) and xantphos (12.29 mg, 0.021 mmol) were added to a microwave vial. The vial was sealed and THF (3.3 mL) added and the reaction mixture was heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH). The product containing fractions were combined and concentrated under vacuum to give the product (67 mg) as a brown solid.

LCMS (2 min Formic): Rt=0.99 min, MH+=372.1.

Example 64: 1-Benzyl-N5-((1R,2R)-2-ethylcyclopropyl)-N3-methyl-2-oxo-1,2-dihydropyridine-3,5-dicarboxamide and Example 65: 1-benzyl-N5-((1S,2S)-2-ethylcyclopropyl)-N3-methyl-2-oxo-1,2-dihydropyridine-3,5-dicarboxamide

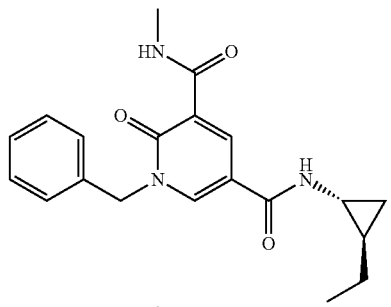

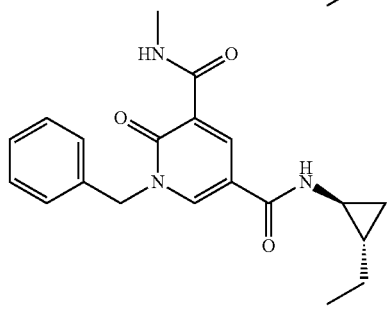

1-Benzyl-N5-(((+/−)-trans)-2-ethylcyclopropyl)-N3-methyl-2-oxo-1,2-dihydropyridine-3,5-dicarboxamide (for example, example 48, ~148 mg) was submitted for chiral separation:

Analytical Method:

Approx 0.5 mg racemate was dissolved in 50% EtOH/heptane (1 mL). Injection; 20 μL of the sample solution was injected onto the column (4.6 mmid×25 cm Chiralcel OJ-H Lot No. OJH0CE-QL055) eluting with 15% EtOH/heptane at a rate of 1 mL/min and analysing with a wavelength of 215 nm.

Preparative Method:

Approx 144 mg racemate was dissolved in EtOH (3 mL)+heat. Injection; 1.5 mL of the sample solution was injected onto the column (2 cm×25 cm Chiralcel OJ Lot No. OJ00CJ-PD002) eluting with 15% EtOH/heptane at a rate of 15 mL/min and analysing with a wavelength of 215 nm. Fractions from 8-11 min were bulked and labelled peak 1; fractions from 11-13 min were bulked and labelled mix; fractions from 13-20 min were bulked and labelled peak 2. The mix fractions were bulked, vac'ed down and reprocessed using the prep method above.

This gave the enantiomer 1 (example 64) as a pale yellow solid (67 mg).

LCMS (2 min Formic): Rt=0.99 min, [MH]$^+$=354.1.

This gave the enantiomer 2 (example 65) as a pale yellow solid (65 mg).

LCMS (2 min Formic): Rt=0.99 min, [MH]$^+$=354.1.

Example 66: 1-((1H-Indol-7-yl)methyl)-N5-cyclopropyl-N3-methyl-2-oxo-1,2-dihydropyridine-3,5-dicarboxamide

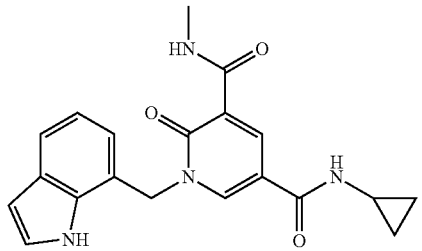 [SMILES: CNC(=O)c1cc(C(=O)NC2CC2)cn(Cc2cccc3cc[nH]c23)c1=O]

To a solution of N5-cyclopropyl-N3-methyl-2-oxo-1-((1-tosyl-1H-indol-7-yl)methyl)-1,2-dihydropyridine-3,5-dicarboxamide (124 mg, 0.120 mmol) in methanol (399 μL) and THF (797 μL) stirred under nitrogen at rt, was added solid cesium carbonate (117 mg, 0.359 mmol) in one charge. The reaction mixture was stirred at 70° C. for 1 h. The reaction mixture was concentrated in vacuo before being taken up in dichloromethane (20 mL) and water (15 mL). The aqueous phase was acidified with 2M HCl (1 mL) and extracted with dichloromethane (5×10 mL). The combined organics were dried through a hydrophobic frit and evaporated in vacuo to yield the crude product (99 mg). The sample was dissolved in MeOH/DMSO (1 mL, 1:1) and purified by MDAP (Formic). The solvent was dried under a stream of nitrogen to give a white solid (55 mg). The sample was dissolved in 9 mL of DMSO. 3000 μL injections were made onto a CSH C18 150×30 mm, 5 μm. column using the chromatographic conditions listed. Solvent A: 0.1% TFA acid in water, solvent B: 0.1% TFA in Acetonitrile, flow Rate: 40 mL/min. Gradient: as below:

| Time/min | % B | % A |
|---|---|---|
| 0 | 20 | 80 |
| 3.5 | 20 | 80 |
| 25 | 40 | 60 |
| 32 | 40 | 60 |
| 35 | 99 | 1 |

Fractionation was determined by mixture of diode array & mass spec signal: UV detection: a summed signal from wavelengths 210 nm to 350 nm. MS: Waters ZQ, Ionisation mode: Positive Electrospray, Scan Range: 100 to 1000 AMU, Scan Time: 0.5 s, Inter scan Delay: 0.2 s. The flow and gradient was provided by a two pumps with a reduced flow passing through the injector during injection. The residual flow is introduced at the head of the column so the overall flow remains constant. The fractions were combined and dried under a stream of nitrogen blowdown at 40° C. to provide two still impure sample.

Sample 1=11.8 mg (Purity: 80%), Sample 2=57 mg (Purity: 83%).

The impure samples were recombined and purified by chiral preparative HPLC:

Analytical Method:

Approx 0.5 mg sample was dissolved in 50% EtOH/Heptane (1 mL). 20 μL was injected onto column (Column 4.6 mmid×25 cm Chiralpak IC, Lot No. IC00CE-OG021) which was eluted with 40% EtOH (+0.2% isopropylamine)/Heptane, flow rate=1.0 mL/min, detection wavelength=215 nm, 4. Ref 550, 100

Preparative Method:

Approx 68 mg sample was dissolved in EtOH (4 mL). Injection; 2 mL of the solution was injected onto the column (Column: 30 mm×25 cm Chiralpak, Lot No IC10028-01) which was eluted with 40% EtOH (+0.2% isopropylamine)/Heptane (+0.2% isopropylamine), flow rate=30 mL/min, detection wavelength, 215 nm, 4. Ref 550, 100. Total number of injections=2. Fractions from 10-11 min were bulked and labelled peak 1. Fractions from 15-18 min were bulked and labelled peak 2. The bulked fractions were vac'ed down using a rotary evaporator and then transferred to a weighed flask for final analysis as described by the analytical method above. Peak 2 the desired product was further dried in vacuo to yield—1-((1H-indol-7-yl)methyl)-N5-cyclopropyl-N3-methyl-2-oxo-1,2-dihydropyridine-3,5-dicarboxamide (18.8 mg, 0.049 mmol, 41.0% yield) as a white solid.

LCMS (2 min Formic): Rt=0.90 min, [MH]$^+$=365.1.

Example 67: 1-((1H-Indol-4-yl)methyl)-N5-cyclopropyl-N3-methyl-2-oxo-1,2-dihydropyridine-3,5-dicarboxamide

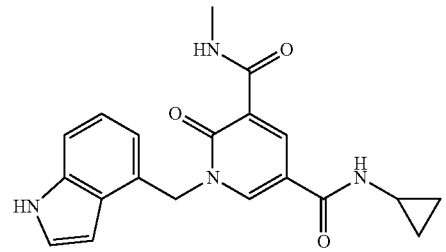 [SMILES: CNC(=O)c1cc(C(=O)NC2CC2)cn(Cc2cccc3[nH]ccc23)c1=O]

To a solution of N5-cyclopropyl-N3-methyl-2-oxo-1-((1-tosyl-1H-indol-4-yl)methyl)-1,2-dihydropyridine-3,5-dicarboxamide (208 mg, 0.160 mmol) in methanol (535 μL) and THF (1.070 mL) stirred under nitrogen at rt, was added solid cesium carbonate (157 mg, 0.481 mmol) in one charge. The reaction mixture was stirred at rt for 40 min. The temperature was increased to 70° C. and stirring continued for 1 h. The reaction mixture was concentrated in vacuo and the residue was taken up in water (15 mL) and dichloromethane (10 mL). The aqueous layer was extracted with dichloromethane (8×10 mL), and the combined organics were dried through a hydrophobic frit and evaporated in vacuo. LCMS revealed residual product in the aqueous phase, which was acidified with 2M HCl (1 mL) and extracted further with dichloromethane (3×10 mL). The combined organics were dried through a hydrophobic frit and evaporated in vacuo. The crude residue (136 mg) was submitted for chiral purification chromatography.

Analytical Method:

Approx 0.5 mg sample was dissolved in 50% EtOH/Heptane (1 mL). 20 μL was injected onto column (Column: 4.6 mm id×25 cm Chiralpak IC, Lot No. IC00CE-OG021) which was eluted with 40% EtOH (+0.2% isopropylamine)/heptane, flow rate=1.0 mL/min, detection wavelength=215 nm, 4. Ref 550, 100

Preparative Method:

Approx 135 mg sample was dissolved in EtOH (5 mL)+heat and centrifuge. Injection: 2.5 mL of the solution was injected onto the column (Column: 30 mm×25 cm Chiralpak, Lot No IC10028-01) which was eluted with 40% EtOH (+0.2% isopropylamine)/heptane (+0.2% isopropylamine), flow rate=30 mL/min, detection wavelength, 215 nm, 4. Ref 550, 100. Total number of injections=2. Fractions from 9.5-10.5 min were bulked and labelled peak 1. Fractions from 12.5-14 min were bulked and labelled peak 2. The bulked fractions were vac'ed down using a rotary evaporator and then transferred to a weighed flask for final analysis as described by the analytical method above. Peak 2 was the desired product and was dried in vacuo to afford—1-((1H-indol-4-yl)methyl)-N5-cyclopropyl-N3-methyl-2-oxo-1,2-dihydropyridine-3,5-dicarboxamide (52.8 mg, 0.138 mmol, 86% yield) as a white solid.

LCMS (2 min Formic): Rt=0.79 min, [MH]$^+$=365.1.

Example 68: 1-(3-Chlorobenzyl)-N5-cyclopropyl-N3-methyl-2-oxo-1,2-dihydropyridine-3,5-dicarboxamide

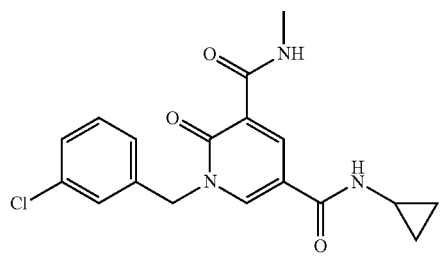 [SMILES: CNC(=O)c1cc(C(=O)NC2CC2)cn(Cc2cccc(Cl)c2)c1=O]

5-Bromo-1-(3-chlorobenzyl)-N-methyl-2-oxo-1,2-dihydropyridine-3-carboxamide (220 mg, 0.619 mmol), cobalt carbonyl (52.9 mg, 0.155 mmol), DMAP (151 mg, 1.237 mmol), palladium (II) acetate (6.94 mg, 0.031 mmol), cyclopropanamine (0.044 mL, 0.619 mmol) and xantphos (17.90 mg, 0.031 mmol) were added to a microwave vial. The vial was sealed and THF (3 mL) added and the reaction mixture was heated in a Biotage Initiator microwave at 80° C. for 30 min. The resulting mixture was diluted with water (20 mL) and extracted with ethyl acetate (20 mL). The organic layer was dried, concentrated under vacuum and purified by MDAP (High pH). The product containing fractions were combined and concentrated under vacuum to give the product (81 mg) as a white solid.

LCMS (2 min Formic): Rt=0.92 min, [MH]$^+$=360.0.

Examples 69-74: Amide Array of 1-(3-methylbenzyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 69 | rac-trans-2-methylcyclopropanamine | 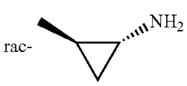 | 45.08 | 0.0085 | — | 0.120 |
| 70 | 2-cyclopropylethanamine | 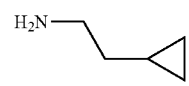 | 85.15 | 0.0102 | — | 0.120 |
| 71 | tert-butyl (6-aminospiro[3.3]heptan-2-yl)carbamate | 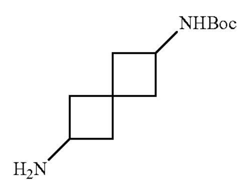 | 226.32 | 0.016 | — | 0.071 |
| 72 | 3-fluorocyclobutanamine hydrochloride | 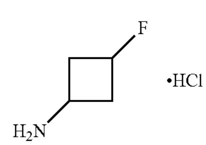 | 125.57 | 0.0151 | — | 0.120 |
| 73 | 2-(ethoxymethyl)cyclopropanamine | 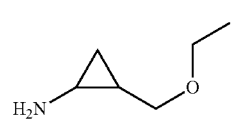 | 101.15 | 0.0121 | — | 0.120 |
| 74 | (2-aminocyclopropyl)methanol | 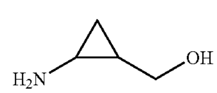 | 87.12 | 0.0105 | — | 0.120 |

To a stock solution of 1-(3-methylbenzyl)-5-(methylcarbamoyl)-6-oxo-1,6-dihydropyridine-3-carboxylic acid (300 mg, 1.0 mmol) and HATU (380 mg, 1.0 mmol) dissolved in DMF (5 mL) was added DIPEA (520 μL, 3.0 mmol). The mixture was shaken and sonicated to aid dispersion. An aliquot (0.5 mL) of this mixture was added to the appropriate amine (0.12 mmol) in a vial which was subsequently sealed. NOTE: to the reaction containing the monomer amine used to prepare example 72 was added additional DIPEA (50 μL, 0.286 mmol). Each vial was shaken before being allowed to stand at rt for 18 h. NOTE: to the reaction containing monomer amine used to prepare example 71 was added further HATU (0.038 g, 0.100 mmol) and DIPEA (0.052 mL, 0.300 mmol) before this mixture was left to stand at room temp for 1 h. The samples were injected as is and purified by MDAP (High pH). The solvent was dried under a stream of nitrogen in the plate blowdown apparatus to give the required products. The product derived from the monomer amine used to prepare example 69 was determined to still have impurities present and so was repurified by being dissolved in MeOH:DMSO (1 mL, 1:1) and purified by MDAP (High pH). The solvent was evaporated under a stream of nitrogen to give the required product. The product derived from the amine monomer used to prepare example 71 was dissolved in DCM (0.5 mL), TFA (0.5 mL) was added and the vial was capped and sonicated to aid dispersion. The mixture was left to stand at rt for 2 h and then the solvent was removed. The residue was redissolved in MeOH (0.5 mL) and applied to the top of a SCX-2 SPE cartridge (100 mg, preconditioned with MeOH (1 mL)). The cartridge was eluted with further MeOH (1 mL) followed by 2M $NH_3$/MeOH (1 mL). The solvent was dried under a stream of nitrogen in the plate blowdown apparatus to give the required products as shown in the table below.

EXAMPLES

| Ex No. | Name | Structure | Mass (mg) | Yield (%) | [MH]$^+$ | Rt (min)* |
|---|---|---|---|---|---|---|
| 69 | rac-N3-methyl-1-(3-methylbenzyl)-N5-((1R,2R)-2-methylcyclopropyl)-2-oxo-1,2-dihydropyridine-3,5-dicarboxamide | 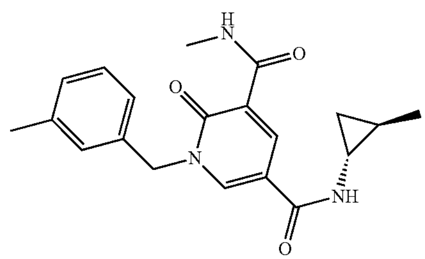 | 3.7 | 7.9 | 354 | 0.94 |
| 70 | N5-(2-cyclopropylethyl)-N3-methyl-1-(3-methylbenzyl)-2-oxo-1,2-dihydropyridine-3,5-dicarboxamide | 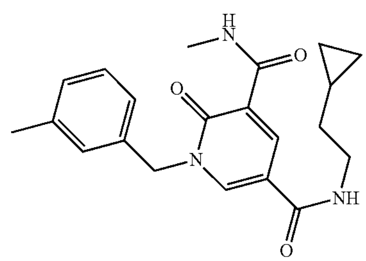 [SMILES: CNC(=O)c1cc(C(=O)NCCC2CC2)cn(Cc2cccc(C)c2)c1=O] | 13.6 | 28 | 368 | 1.00 |
| 71 | N5-(6-aminospiro[3.3]heptan-2-yl)-N3-methyl-1-(3-methylbenzyl)-2-oxo-1,2-dihydropyridine-3,5-dicarboxamide | 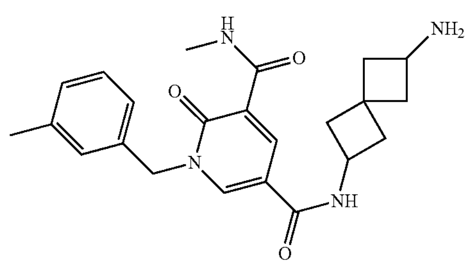 [SMILES: CNC(=O)c1cc(C(=O)NC2CC3(CC(N)C3)C2)cn(Cc2cccc(C)c2)c1=O] | 12.7 | 40 | 409 | 0.58 |
| 72 | N5-(3-fluorocyclobutyl)-N3-methyl-1-(3-methylbenzyl)-2-oxo-1,2-dihydropyridine-3,5-dicarboxamide | 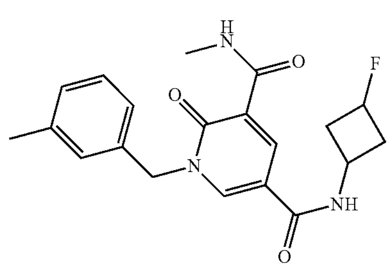 [SMILES: CNC(=O)c1cc(C(=O)NC2CC(F)C2)cn(Cc2cccc(C)c2)c1=O] | 20.8 | 42 | 372 | 0.92 |

-continued

| Ex No. | Name | Structure | Mass (mg) | Yield (%) | [MH]+ | Rt (min)* |
|---|---|---|---|---|---|---|
| 73 | N5-(2-ethoxycyclopropyl)-N3-methyl-1-(3-methylbenzyl)-2-oxo-1,2-dihydropyridine-3,5-dicarboxamide | 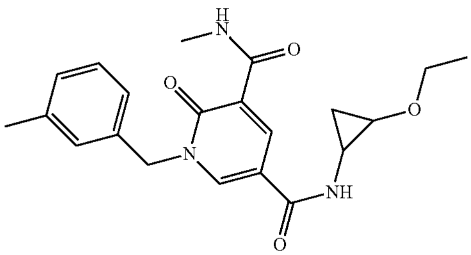 [SMILES: CCOC1CC1NC(=O)c1cc(C(=O)NC)c(=O)n(Cc2cccc(C)c2)c1] | 20.9 | 41 | 384 | 0.92 |
| 74 | N5-(2-(hydroxymethyl)cyclopropyl)-N3-methyl-1-(3-methylbenzyl)-2-oxo-1,2-dihydropyridine-3,5-dicarboxamide | 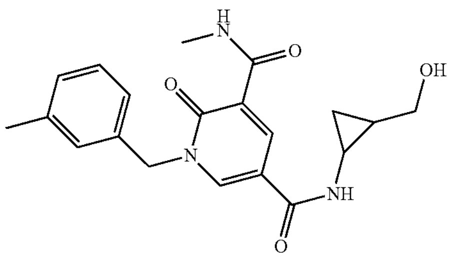 [SMILES: CNC(=O)c1cc(C(=O)NC2CC2CO)cn(Cc2cccc(C)c2)c1=O] | 11.5 | 28 | 370 | 0.77 |

*All LCMS were conducted using 2 min Formic.

Examples 75-79: Amide Array of (R)-5-(methylcarbamoyl)-6-oxo-1-(1-phenylethyl)-1,6-dihydropyridine-3-carboxylic acid To a stock solution of (R)-5-(methylcarbamoyl)-6-oxo-1-(1-phenylethyl)-1,6-dihydropyridine-3-carboxylic acid (30 mg, 0.1 mmol) and HATU (380 mg) in DMF (5 mL) was added DIPEA (520 µL). The mixture was shaken and sonicated to aid dispersion. The mixture was aliquoted (0.5 mL) to a set of preweighed amines (0.100 mmol) in micronic vials. These were capped and shaken and left to stand at rt for 18 h. The samples were purified by MDAP (High pH). The solvent was dried under a stream of nitrogen to give the required products. Example 75 had additional DIPEA (50 µL) added to the reaction mixture on addition of the DIPEA.

| Ex No. | Reagent Name | Structure | MW | Reagent Mass (g) | Reagent Volume (mL) | mmol |
|---|---|---|---|---|---|---|
| 75 | 3-fluorocyclobutanamine hydrochloride | 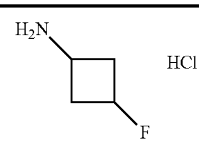 | 125.57 | 0.015 | — | 0.100 |
| 76 | 2-cyclopropylethanamine | 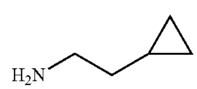 | 85.15 | 0.010 | — | 0.100 |
| 77 | rac-2-ethoxycyclopropanamine | 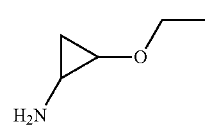 | 101.15 | 0.012 | — | 0.100 |
| 78 | rac-(2-aminocyclopropyl)methanol | 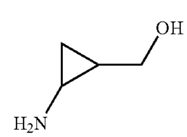 | 87.12 | 0.010 | — | 0.100 |

| Ex No. | Reagent Name | Structure | MW | Reagent Mass (g) | Reagent Volume (mL) | mmol |
|---|---|---|---|---|---|---|
| 79 | (+/−)-(trans)-2-methylcyclo-propanamine | 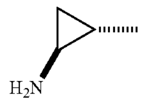 | 71.12 | 0.007 | | 0.100 |

| Ex no. | Name | Structure | Mass (mg) | Yield (%) | [MH]+ | Rt (min) |
|---|---|---|---|---|---|---|
| 75 | (R)-N5-(3-fluorocyclobutyl)-N3-methyl-2-oxo-1-(1-phenylethyl)-1,2-dihydropyridine-3,5-dicarboxamide | 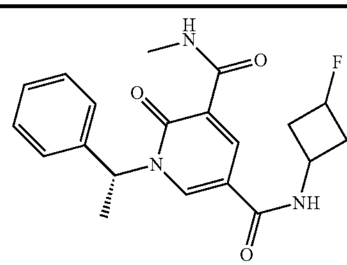 | 11 | 26.7 | 371.9 | 0.91 |
| 76 | (R)-N5-(2-cyclopropylethyl)-N3-methyl-2-oxo-1-(1-phenylethyl)-1,2-dihydropyridine-3,5-dicarboxamide | 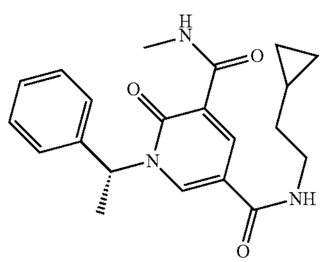 [SMILES: CNC(=O)c1cc(C(=O)NCCC2CC2)cn([C@H](C)c2ccccc2)c1=O] | 22.4 | 54.9 | 368.0 | 0.99 |
| 77 | N5-(2-ethoxycyclopropyl)-N3-methyl-2-oxo-1-((R)-1-phenylethyl)-1,2-dihydropyridine-3,5-dicarboxamide | 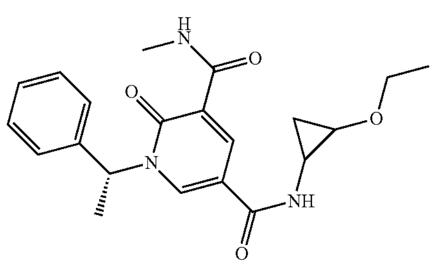 [SMILES: CCOC1CC1NC(=O)c1cc(C(=O)NC)c(=O)n([C@H](C)c2ccccc2)c1] | 20.8 | 48.8 | 383.9 | 0.90 |
| 78 | N5-(2-(hydroxymethyl)cyclopropyl)-N3-methyl-2-oxo-1-phenylethyl)-1,2-dihydropyridine-3,5-dicarboxamide | 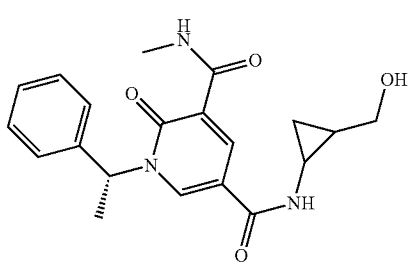 [SMILES: CNC(=O)c1cc(C(=O)NC2CC2CO)cn([C@H](C)c2ccccc2)c1=O] | 3.2 | 7.8 | 369.9 | 0.75 |

| Ex no. | Name | Structure | Mass (mg) | Yield (%) | [MH]+ | Rt (min) |
|---|---|---|---|---|---|---|
| 79 | N3-methyl-N5-((trans)-2-methylcyclopropyl)-2-oxo-1-((R)-1-phenylethyl)-1,2-dihydropyridine-3,5-dicarboxamide | 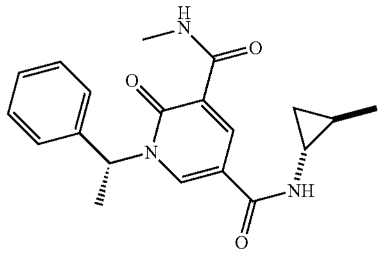 | 19.6 | 49.9 | 354.0 | 0.92 |

All LCMS were conducted using 2 min Formic method.

Example 80: N5-Cyclopropyl-N3-methyl-2-oxo-1-((2,3,4,5-tetrahydro-1H-benzo[d]azepin-7-yl)methyl)-1,2-dihydropyridine-3,5-dicarboxamide, hydrochloride

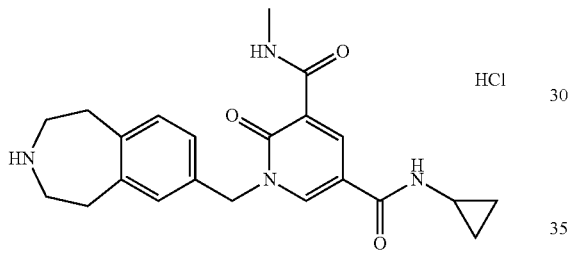

tert-Butyl 7-((5-(cyclopropylcarbamoyl)-3-(methylcarbamoyl)-2-oxopyridin-1(2H)-yl)methyl)-4,5-dihydro-1H-benzo[d]azepine-3(2H)-carboxylate (100 mg, 0.202 mmol) and TFA (1 mL, 12.98 mmol) were stirred at rt in DCM (4 mL) for 30 min. The reaction mixture was concentrated and loaded onto a 5 g SCX cartridge (pre-conditioned with MeOH) and eluted with MeOH (20 mL) followed by 2M $NH_3$ in MeOH (20 mL). Ammonia fractions containing product were combined and concentrated to give 79 mg of a colourless oil. This was further purified by MDAP (Formic). The appropriate fractions were partitioned between DCM (30 mL) and sat. sodium bicarbonate solution (30 mL), the aqueous layer was extracted with DCM (2×30 mL) and further extracted with 5% MeOH in DCM (3×30 mL), the combined organic layers were dried over a hydrophobic frit and concentrated to give 104 mg of a white solid. This was further purified by MDAP (High pH). The appropriate fractions were concentrated to give N5-cyclopropyl-N3-methyl-2-oxo-1-((2,3,4,5-tetrahydro-1H-benzo[d]azepin-7-yl)methyl)-1,2-dihydropyridine-3,5-dicarboxamide (44 mg, 0.100 mmol, 49.7% yield) as a colourless oil. This was dissolved in MeOH (1 mL) and 1M HCl in diethyl ether (0.11 mL, 0.110 mmol) was added and the sample blown down to give N5-cyclopropyl-N3-methyl-2-oxo-1-((2,3,4,5-tetrahydro-1H-benzo[d]azepin-7-yl)methyl)-1,2-dihydropyridine-3,5-dicarboxamide, hydrochloride (42 mg, 0.088 mmol, 43.4% yield) as an orange solid LCMS (2 min Formic): Rt=0.46 min, $[MH]^+$=395.

Example 81: 1-Benzyl-N5-(2-((cis)-4-hydroxycyclohexyl)ethyl)-N3-methyl-2-oxo-1,2-dihydropyridine-3,5-dicarboxamide and Example 85: 1-Benzyl-N5-(2-((trans)-4-hydroxycyclohexyl)ethyl)-N3-methyl-2-oxo-1,2-dihydropyridine-3,5-dicarboxamide

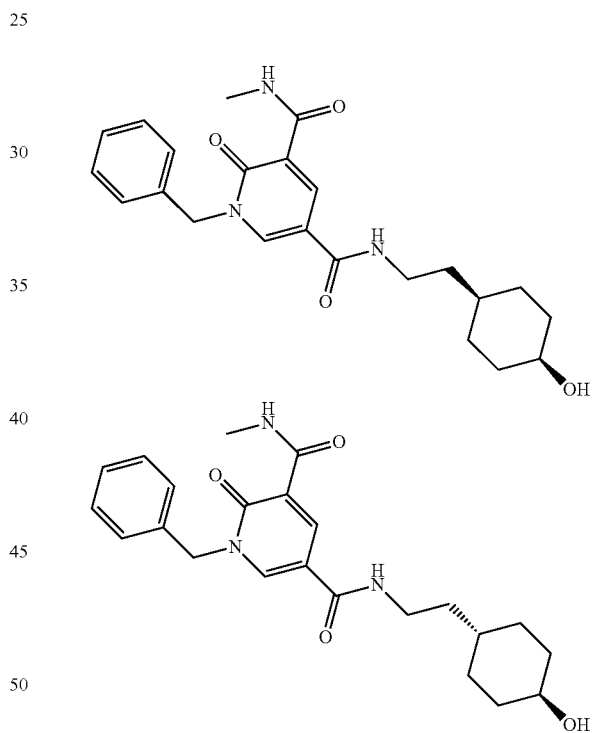

To a solution of 1-benzyl-5-(methylcarbamoyl)-6-oxo-1,6-dihydropyridine-3-carboxylic acid (50.1 mg, 0.175 mmol), 4-(2-aminoethyl)cyclohexanol (53.9 mg, 0.376 mmol, commercially available from, for example, TCI) and HATU (80.5 mg, 0.212 mmol) in DMF (1 mL) was added DIPEA (0.061 mL, 0.350 mmol). The mixture was stirred at rt for 1.25 h. Further HATU (43 mg, 0.113 mmol) and DIPEA (0.0305 mL, 0.175 mmol) were added and stirring continued for 1 h. The reaction mixture was then concentrated under a stream of nitrogen before being made up to 2 mL with a 2:1 mixture of DMSO/methanol and directly purified by MDAP (Formic). The required fractions for the two diastereomeric products were separately concentrated under a stream of nitrogen.

Cis-isomer: was further dried in vacuo to give a white solid 1-benzyl-N5-(2-((cis)-4-hydroxycyclohexyl)ethyl)-N3-methyl-2-oxo-1,2-dihydropyridine-3,5-dicarboxamide (33.9 mg, 0.082 mmol, 47.1% yield).

LCMS (2 min Formic): Rt=0.86 min, [MH]⁺=412.2.

Trans-isomer: was dissolved in DMSO (1 mL) and re-purified by MDAP (Formic). The required fraction was concentrated under a stream of nitrogen before being dissolved in a 1:1 mixture of dichloromethane/methanol, concentrated under a stream of nitrogen and dried in vacuo to give as a white solid, 1-benzyl-N5-(2-((trans)-4-hydroxycyclohexyl)ethyl)-N3-methyl-2-oxo-1,2-dihydropyridine-3,5-dicarboxamide (19.9 mg, 0.048 mmol, 27.6% yield).

LCMS (2 min formic): Rt=0.84 min, [MH]⁺=412.2.

Example 82: (+/−)-1-(4-Fluorobenzyl)-N3-methyl-N5-((trans)-2-methylcyclopropyl)-2-oxo-1,2-dihydropyridine-3,5-dicarboxamide

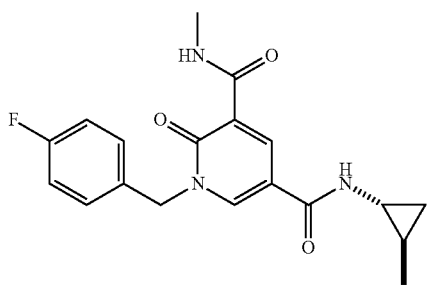

1-(4-Fluorobenzyl)-5-(methylcarbamoyl)-6-oxo-1,6-dihydropyridine-3-carboxylic acid (200 mg, 0.657 mmol) was taken up in DMF (5 mL) and HATU (275 mg, 0.723 mmol) was added followed by DIPEA (0.230 mL, 1.315 mmol). The reaction mixture was allowed to stir for 5 min, then (+/−)-(trans)-2-methylcyclopropanamine (46.7 mg, 0.657 mmol) was added and the reaction allowed to stir for 1 h. The reaction mixture was taken up in ethyl acetate (20 mL). The organic layer was washed with sat. aq. sodium bicarbonate (20 mL) and water (20 mL). The organic layers were combined and concentrated under vacuum. The solid was taken up in DCM and purified by Biotage Isolera flash chromatography using a SNAP 25 g silica cartridge, using a gradient of 0-60% EtOAc/cyclohexane. The appropriate fractions were combined and concentrated under vacuum to give the desired product (152 mg) as a white solid.

LCMS (2 min Formic): Rt=0.92 min, [MH]⁺=358.1.

Example 83: 1-(2-Fluorobenzyl)-N5-((1S*,2S*)-2-methoxycyclopropyl)-N3-methyl-2-oxo-1,2-dihydropyridine-3,5-dicarboxamide

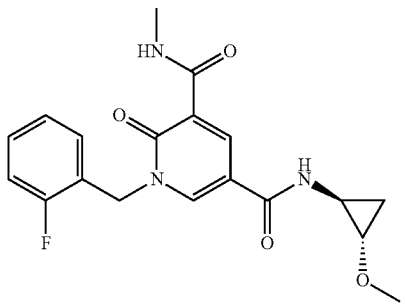 [SMILES: CNC(=O)c1cc(C(=O)N[C@H]2C[C@@H]2OC)cn(Cc2ccccc2F)c1=O]

THF (2.3 mL) was added to a sealed microwave vial containing 5-bromo-1-(2-fluorobenzyl)-N-methyl-2-oxo-1,2-dihydropyridine-3-carboxamide (120 mg, 0.354 mmol), 2-methoxycyclopropanamine, HCl salt (46.2 mg, 0.531 mmol, commercially available from, for example, ZereneX), palladium acetate (3.96 mg, 0.018 mmol), cobalt carbonyl (33.6 mg, 0.088 mmol), xantphos (10.24 mg, 0.018 mmol), and DMAP (130 mg, 1.061 mmol). The reaction mixture was heated to 80° C. for 35 min by microwave irradiation. The reaction mixture was then heated to 80° C. for 20 min by microwave irradiation, and heated to 80° C. for a further 20 min by microwave irradiation. The reaction mixture was partitioned between ethyl acetate (20 mL) and water (20 mL), the aqueous layer was extracted with ethyl acetate (2×20 mL), and the organic layer was washed with water (2×20 mL). This was passed through a hydrophobic frit and the solvent removed under reduced pressure. The resulting orange solid was dissolved in DMSO:methanol (1:1) and purified by MDAP (TFA). The product-containing fractions were placed in a round-bottomed flask and the solvent removed under reduced pressure. This was left to dry in vacuo for 4 h to give 1-(2-fluorobenzyl)-N5-(2-methoxycyclopropyl)-N3-methyl-2-oxo-1,2-dihydropyridine-3,5-dicarboxamide (23 mg, 0.062 mmol, 17.41% yield) as a pale orange solid which was purified by chiral preparative HPLC:

Analytical Method:

Approx 0.5 mg racemate was dissolved in 50% EtOH/Heptane (1 mL). Injection; 20 μL of the sample solution was injected onto the column (4.6 mmid×25 cm Chiralcel OJ-H Lot No. OJH0CE-RK007) eluting with 15% EtOH/heptane, at a rate of 1 mL/min and analysing with a wavelength of 215 nm.

Preparative Method:

Approx 20 mg racemate was dissolved in EtOH (2 mL). Injection: 2 mL of the sample solution was injected onto the column (30 mm×25 cm Chiralcel OJ-H Lot No. OJH10027-01) eluting with 15% EtOH/heptane, at a rate of 30 mL/min and analysing with a wavelength of 215 nm. Fractions from 23.5-26 min were bulked and labelled peak 2. This gave the single enantiomer (Example 83) as a pale yellow solid (9 mg).

LCMS (2 min Formic): Rt=0.83 min, [MH]⁺=374.1.

Example 86: 1-(4-Fluorobenzyl)-N5-(2-(hydroxymethyl)cyclopropyl)-N3-methyl-2-oxo-1,2-dihydropyridine-3,5-dicarboxamide

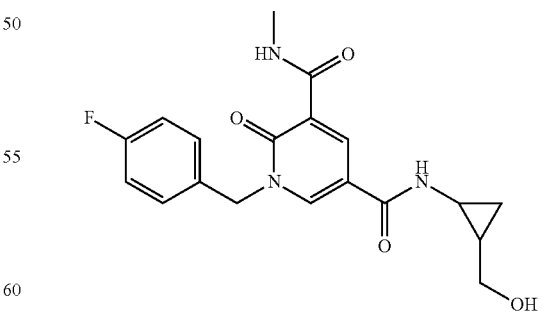

1-(4-Fluorobenzyl)-5-(methylcarbamoyl)-6-oxo-1,6-dihydropyridine-3-carboxylic acid (200 mg, 0.657 mmol) was taken up in DMF (5 mL) and HATU (275 mg, 0.723 mmol) followed by DIPEA (0.230 mL, 1.315 mmol) were added. The reaction mixture was allowed to stir for 5 min, then (2-aminocyclopropyl)methanol (57.3 mg, 0.657 mmol, commercially available from, for example, Enamine) was added and the reaction was allowed to stir for 1 h. The reaction mixture was concentrated under vacuum and purified by MDAP (High pH). The appropriate fractions were combined and concentrated under vacuum to give the product (152 mg) as a white solid.

LCMS (2 min Formic): Rt=0.75 min, [MH]⁺=374.1.

Example 87: N5-(2-Ethoxycyclopropyl)-1-(4-fluorobenzyl)-N3-methyl-2-oxo-1,2-dihydropyridine-3,5-dicarboxamide

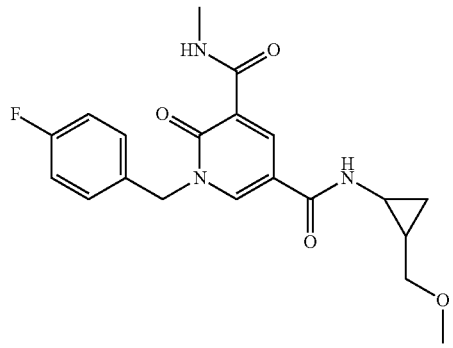 [SMILES: CNC(=O)c1cc(C(=O)NC2CC2COC)cn(Cc2ccc(F)cc2)c1=O]

1-(4-Fluorobenzyl)-5-(methylcarbamoyl)-6-oxo-1,6-dihydropyridine-3-carboxylic acid (200 mg, 0.657 mmol) was taken up in DMF (5 mL) and HATU (275 mg, 0.723 mmol) followed by DIPEA (0.230 mL, 1.315 mmol) were added. The reaction mixture was allowed to stir for 5 min, then 2-ethoxycyclopropanamine (66.5 mg, 0.657 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the product (102 mg), as a yellow solid.

LCMS (2 min Formic): Rt=0.90 min, [MH]⁺=388.1.

Example 88: rac-N5-Cyclopropyl-N3-methyl-2-oxo-1-(1-(m-tolyl)ethyl)-1,2-dihydropyridine-3,5-dicarboxamide

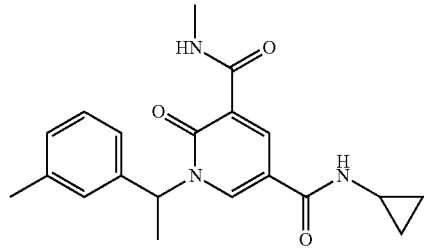 [SMILES: CNC(=O)c1cc(C(=O)NC2CC2)cn(C(C)c2cccc(C)c2)c1=O]

5-(Methylcarbamoyl)-6-oxo-1-(1-(m-tolyl)ethyl)-1,6-dihydropyridine-3-carboxylic acid (185 mg, 0.589 mmol), HATU (338 mg, 0.889 mmol), DIPEA (0.308 mL, 1.766 mmol), cyclopropanamine (0.082 mL, 1.177 mmol) and DMF (2 mL) were stirred at rt under N₂ for 1 h. LiCl solution (20 mL) was added and the reaction mixture was partitioned between EtOAc (20 mL) and water (20 mL), the aqueous phase was extracted with EtOAc (2×20 mL) and the combined organic layers were dried over a hydrophobic frit and concentrated to give 686 mg of a yellow oil. This was purified by chromatography on SiO₂ (Biotage SNAP 50 g cartridge, eluting with 0-100% EtOAc/cyclohexane). The appropriate fractions were concentrated to give 376 mg of an orange oil. This was further purified by MDAP (TFA) and the appropriate fractions were concentrated to give rac-N5-cyclopropyl-N3-methyl-2-oxo-1-(1-(m-tolyl)ethyl)-1,2-dihydropyridine-3,5-dicarboxamide (61 mg, 0.155 mmol, 26.4% yield) a colourless oil.

LCMS (2 min Formic): Rt=0.96 min, [MH]⁺=354.

Examples 89-94: Amide Array of 1-(3-methoxybenzyl)-5-(methylcarbamoyl)-6-oxo-1,6-dihydropyridine-3-carboxylic acid To a stock solution of 1-(3-methoxybenzyl)-5-(methylcarbamoyl)-6-oxo-1,6-dihydropyridine-3-carboxylic acid (316 mg, 1 mmol) and HATU (380 mg) in DMF (5 mL) was added DIPEA (520 µL). The mixture was shaken and sonicated to aid dispersion. The mixture was aliquoted (0.55 mL) to a set of preweighed amines (as shown in the table below). These were capped and shaken and left to stand at rt for 18 h. The samples were purified by MDAP (High pH). The solvent was dried under a stream of nitrogen to give the required products. Example 93 was dissolved in DCM (0.5 mL) and treated with TFA (0.5 mL) and the solution left to stand in a capped vial at rt for 2 h. The reaction mixture was evaporated and the residue dissolved in MeOH (0.5 mL). The solution was applied to a MeOH-preconditioned 100 mg SCX-2 cartridge which were then washed with MeOH (1 mL) followed by 2M ammonia in MeOH solution (1 mL). The basic washes were evaporated to dryness to give the final deprotected compound as the free base (as shown in the table below).

Monomers

| Ex No. | Reagent Name | Structure | MW | Reagent Mass (g) | Reagent Volume (mL) | mmol |
|---|---|---|---|---|---|---|
| 89 | 3-fluorocyclobutanamine hydrochloride | 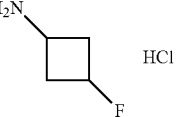 | 125.57 | 0.015 | — | 0.120 |

| Ex No. | Reagent Name | Structure | MW | Reagent Mass (g) | Reagent Volume (mL) | mmol |
|---|---|---|---|---|---|---|
| 90 | 2-cyclopropyl-ethanamine | 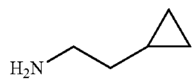 | 85.15 | 0.010 | — | 0.120 |
| 91 | rac-2-ethoxycyclo-propanamine | 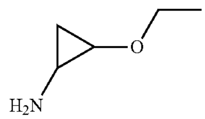 | 101.15 | 0.012 | — | 0.120 |
| 92 | rac-(2-aminocyclopropyl)methanol | 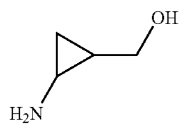 | 87.12 | 0.010 | — | 0.120 |
| 93 | tert-butyl (6-aminospiro[3.3]heptan-2-yl)carbamate | 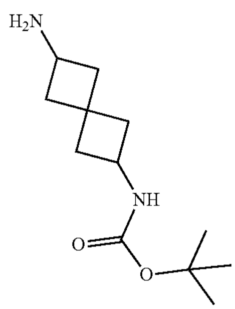 [SMILES: CC(C)(C)OC(=O)NC1CC2(CC(N)C2)C1] | 226.32 | 0.027 | — | 0.120 |
| 94 | rac-(trans)-2-methylcyclo-propanamine | 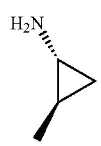 | 71.12 | 0.009 | — | 0.120 |

| Ex no. | Name | Structure | Mass (mg) | Yield (%) | [MH]+ | Rt (min) |
|---|---|---|---|---|---|---|
| 89 | N5-(3-fluorocyclobutyl)-1-(3-methoxybenzyl)-N3-methyl-2-oxo-1,2-dihydropyridine-3,5-dicarboxamide | 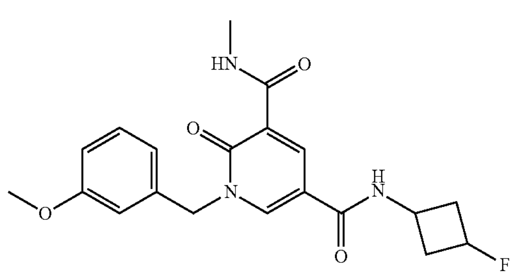 [SMILES: CNC(=O)c1cc(C(=O)NC2CC(F)C2)cn(Cc2cccc(OC)c2)c1=O] | 24.9 | 57.8 | 388 | 0.89 |

| Ex no. | Name | Structure | Mass (mg) | Yield (%) | [MH]+ | Rt (min) |
|---|---|---|---|---|---|---|
| 90 | N5-(2-cyclopropylethyl)-1-(3-methoxybenzyl)-N3-methyl-2-oxo-1,2-dihydropyridine-3,5-dicarboxamide | 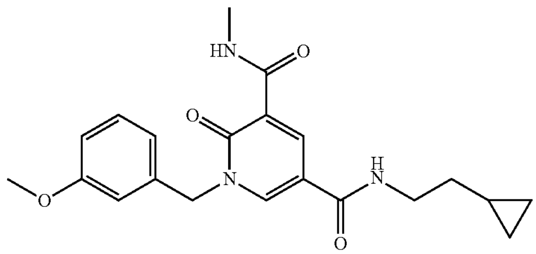 [SMILES: CNC(=O)c1cc(C(=O)NCCC2CC2)cn(Cc2cccc(OC)c2)c1=O] | 21.6 | 50.7 | 384 | 0.97 |
| 91 | rac-N5-(2-ethoxycyclopropyl)-1-(3-methoxybenzyl)-N3-methyl-2-oxo-1,2-dihydropyridine-3,5-dicarboxamide | 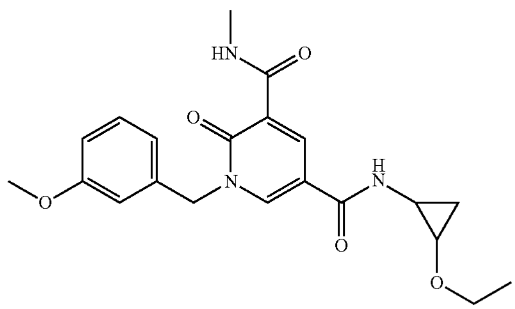 [SMILES: CCOC1CC1NC(=O)c1cc(C(=O)NC)c(=O)n(Cc2cccc(OC)c2)c1] | 20.1 | 45.3 | 400 | 0.89 |
| 92 | rac-N5-(2-(hydroxymethyl)cyclopropyl)-1-(3-methoxybenzyl)-N3-methyl-2-oxo-1,2-dihydropyridine-3,5-dicarboxamide | 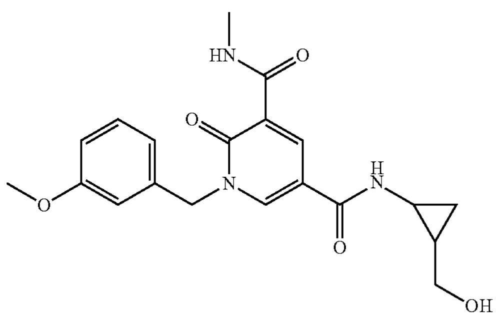 [SMILES: CNC(=O)c1cc(C(=O)NC2CC2CO)cn(Cc2cccc(OC)c2)c1=O] | 6 | 14.0 | 386 | 0.74 |
| 93 | N5-(6-Aminospiro[3.3]heptan-2-yl)-1-(3-methoxybenzyl)-N3-methyl-2-oxo-1,2-dihydropyridine-3,5-dicarboxamide | 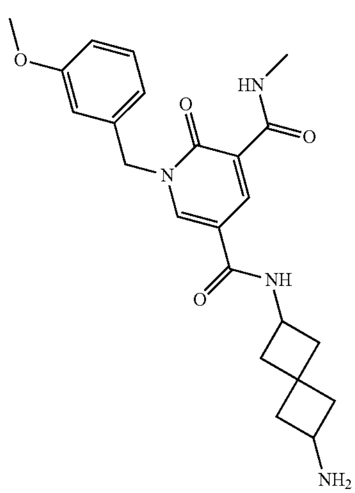 [SMILES: CNC(=O)c1cc(C(=O)NC2CC3(CC(N)C3)C2)cn(Cc2cccc(OC)c2)c1=O] | 11.7 | 24.8 | 425 | 0.56 |

| Ex no. | Name | Structure | Mass (mg) | Yield (%) | [MH]+ | Rt (min) |
|---|---|---|---|---|---|---|
| 94 | rac-1-(3-methoxybenzyl)-N3-methyl-N5-((trans)-2-methylcyclopropyl)-2-oxo-1,2-dihydropyridine-3,5-dicarboxamide | 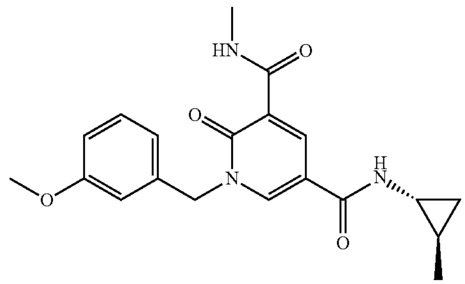 [SMILES: CNC(=O)c1cc(C(=O)N[C@@H]2C[C@H]2C)cn(Cc2cccc(OC)c2)c1=O] | 19.8 | 48.2 | 370 | 0.91 |

All LCMS were conducted using 2 min Formic method.

Example 95: 1-(3-Acetylbenzyl)-N5-cyclopropyl-N3-methyl-2-oxo-1,2-dihydropyridine-3,5-dicarboxamide

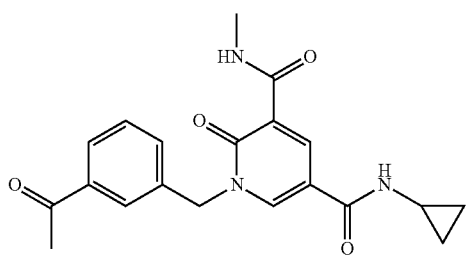 [SMILES: CNC(=O)c1cc(C(=O)NC2CC2)cn(Cc2cccc(C(C)=O)c2)c1=O]

To a solution of 1-(3-acetylbenzyl)-5-(methylcarbamoyl)-6-oxo-1,6-dihydropyridine-3-carboxylic acid (250 mg, 0.510 mmol), and HATU (291 mg, 0.765 mmol) in DMF (2041 µL) stirred at rt was added cyclopropylamine (71.9 µL, 1.020 mmol) and DIPEA (178 µL, 1.020 mmol). And the reaction stirred for ~18 h. A further portion of HATU (194 mg, 0.510 mmol) and the reaction stirred for a further 1 h. The reaction mixture was poured onto water (45 mL) and the aqueous layer was extracted with ethyl acetate (3×20 mL) and diethyl ether (2×20 mL). The combined organics were dried through a hydrophobic frit and evaporated in vacuo to yield the crude product as an orange oil (425 mg). The oil was loaded in dichloromethane/methanol onto a 25 g SNAP silica cartridge and purified via Biotage SP4 flash chromatography, eluting from 15-75% (3:1 ethyl acetate:ethanol)/cyclohexane. The pure fractions were combined and evaporated in vacuo to yield the desired product (203 mg) as a clear gum. The product was taken up in ethyl acetate (50 mL) and washed with water (10 mL) and brine (10 mL). The organic layer was dried through a hydrophobic frit and evaporated in vacuo to yield—1-(3-acetylbenzyl)-N5-cyclopropyl-N3-methyl-2-oxo-1,2-dihydropyridine-3,5-dicarboxamide (148 mg, 0.383 mmol, 75% yield). The mixed fractions from the SP4 chromatography were also combined and evaporated in vacuo to yield a clear gum which was taken up in ethyl acetate (50 mL) and washed with water (10 mL) and brine (10 mL). The organic layer was dried through a hydrophobic frit and evaporated in vacuo to yield further—1-(3-acetylbenzyl)-N5-cyclopropyl-N3-methyl-2-oxo-1,2-dihydropyridine-3,5-dicarboxamide (38 mg, 0.095 mmol, 18.65% yield) as a clear glass.

LCMS (2 min Formic): Rt=0.75 min, [MH]+=368.2.

Example 96: rac-N5-Cyclopropyl-N3-methyl-2-oxo-1-(1-(o-tolyl)ethyl)-1,2-dihydropyridine-3,5-dicarboxamide

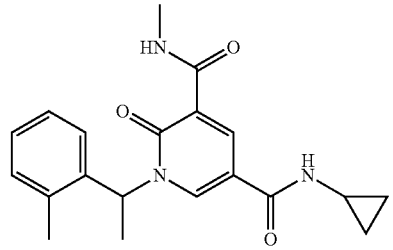

5-(Methylcarbamoyl)-6-oxo-1-(1-(o-tolyl)ethyl)-1,6-dihydropyridine-3-carboxylic acid (190 mg, 0.604 mmol), HATU (355 mg, 0.934 mmol), DIPEA (0.32 mL, 1.832 mmol), cyclopropanamine (0.084 mL, 1.209 mmol) and DMF (2 mL) were stirred at rt under $N_2$ for 2 h. The reaction mixture was washed with LiCl solution (20 mL) and partitioned between EtOAc (20 mL) and water (20 mL). The aqueous phase was extracted with EtOAc (2×20 mL) and the combined organic layers were dried over a hydrophobic frit and concentrated to give 449 mg of a red oil. This was purified by chromatography on $SiO_2$ (Biotage SNAP 50 g cartridge, eluting with 0-100% EtOAc/cyclohexane). The appropriate fractions were concentrated to give rac-N5-cyclopropyl-N3-methyl-2-oxo-1-(1-(o-tolyl)ethyl)-1,2-dihydropyridine-3,5-dicarboxamide (183 mg, 0.466 mmol, 77% yield).

LCMS (2 min Formic): Rt=0.93 min, [MH]+=354.

Example 97: 1-(4-Fluoro-3-methylbenzyl)-N5-(2-(hydroxymethyl)cyclopropyl)-N3-methyl-2-oxo-1,2-dihydropyridine-3,5-dicarboxamide

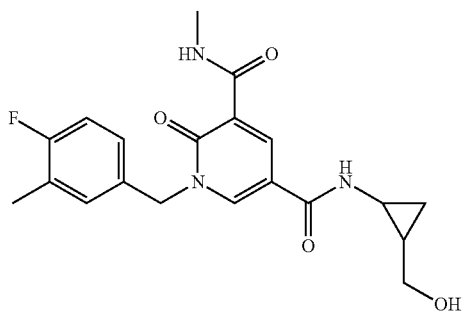 [SMILES: CNC(=O)c1cc(C(=O)NC2CC2CO)cn(Cc2ccc(F)c(C)c2)c1=O]

1-(4-Fluoro-3-methylbenzyl)-5-(methylcarbamoyl)-6-oxo-1,6-dihydropyridine-3-carboxylic acid (200 mg, 0.628 mmol) was taken up in DMF (5 mL) and HATU (263 mg, 0.691 mmol) followed by DIPEA (0.219 mL, 1.257 mmol) were added. The reaction mixture was allowed to stir for 5 min, then (2-aminocyclopropyl)methanol (54.7 mg, 0.628 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the crude product. This was further purified by MDAP (High pH). The product containing fractions were combined to give the product (140 mg) as a white solid.

LCMS (2 min Formic): Rt=0.83 min, [MH]⁺=388.1.

Example 98: N5-(2-Ethoxycyclopropyl-1-(4-fluoro-3-methylbenzyl)-N3-methyl-2-oxo-1,2-dihydropyridine-3,5-dicarboxamide

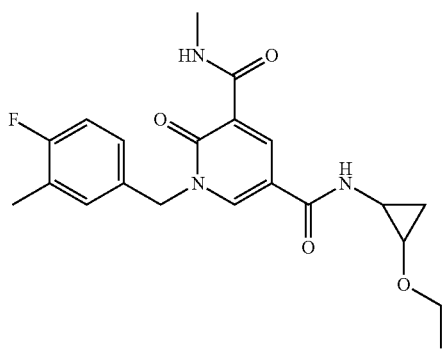 [SMILES: CCOC1CC1NC(=O)c1cc(C(=O)NC)c(=O)n(Cc2ccc(F)c(C)c2)c1]

1-(4-Fluoro-3-methylbenzyl)-5-(methylcarbamoyl)-6-oxo-1,6-dihydropyridine-3-carboxylic acid (200 mg, 0.628 mmol) was taken up in DMF (5 mL) and HATU (263 mg, 0.691 mmol), followed by DIPEA (0.219 mL, 1.257 mmol) were added. The reaction mixture was allowed to stir for 5 min, then 2-ethoxycyclopropanamine (63.6 mg, 0.628 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the desired product (141 mg, 0.351 mmol, 55.9% yield) as a white solid.

LCMS (2 min Formic): Rt=0.98 min, [MH]⁺=402.2.

Example 99: N5-Cyclopropyl-N3-methyl-2-oxo-1-((1,2,3,4-tetrahydroquinolin-8-yl)methyl)-1,2-dihydropyridine-3,5-dicarboxamide

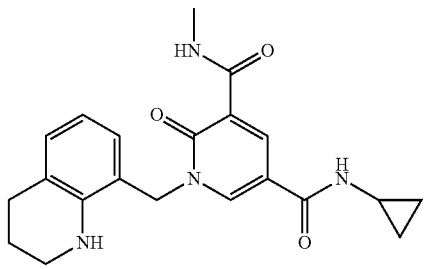 [SMILES: CNC(=O)c1cc(C(=O)NC2CC2)cn(Cc2cccc3c2NCCC3)c1=O]

To a solution of 5-(methylcarbamoyl)-6-oxo-1-((1,2,3,4-tetrahydroquinolin-8-yl)methyl)-1,6-dihydropyridine-3-carboxylic acid (132 mg, 0.255 mmol), and HATU (146 mg, 0.383 mmol) in DMF (1 mL) (stirred at rt) was added cyclopropylamine (54.0 μL, 0.766 mmol) and DIPEA (89 μL, 0.510 mmol). The reaction was stirred for 16 h. A further portion of HATU (48.5 mg, 0.128 mmol) was added and the reaction was continued for 17 h. A further portion of HATU (48.5 mg, 0.128 mmol) was added and the reaction was stirred for 20.5 h. The reaction mixture was poured onto saturated aqueous lithium chloride (15 mL) and the aqueous was extracted with ethyl acetate (4×10 mL). The combined organics were washed with brine, dried through a hydrophobic frit and evaporated in vacuo to yield the crude product as an orange oil (311 mg). The sample was loaded in dichloromethane onto a 25 g SNAP cartridge and purified via Biotage SP4 flash chromatography, eluting from 10-50% (3:1 ethyl acetate:ethanol)/cyclohexane. The relevant fractions were combined and evaporated in vacuo to yield a yellow solid (99 mg). The sample was dissolved in 1:1 MeOH:DMSO (2×1 mL) and was purified by MDAP (High pH). The solvent was evaporated in vacuo to give N5-cyclopropyl-N3-methyl-2-oxo-1-((1,2,3,4-tetrahydroquinolin-8-yl)methyl)-1,2-dihydropyridine-3,5-dicarboxamide (47 mg, 0.117 mmol, 46.0% yield) as a yellow solid.

LCMS (2 min Formic): Rt=0.86 min, [MH]⁺=381.2.

Example 100: (+/−)-1-(3-Fluorobenzyl)-N3-methyl-N5-((trans)-2-methylcyclopropyl)-2-oxo-1,2-dihydropyridine-3,5-dicarboxamide

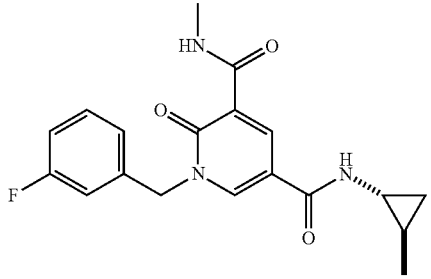

DIPEA (0.276 mL, 1.578 mmol) was added to a suspension of 1-(3-fluorobenzyl)-5-(methylcarbamoyl)-6-oxo-1,6-dihydropyridine-3-carboxylic acid (200 mg, 0.526 mmol), (+/−)-(trans)-2-methylcyclopropanamine (74.8 mg, 1.052 mmol, commercially available from, for example, Fluorochem), and HATU (300 mg, 0.789 mmol) in DMF (4 mL). The reaction mixture was stirred at rt for 4 h, after which further (+/−)-(trans)-2-methylcyclopropanamine (74.8 mg, 1.052 mmol), HATU (300 mg, 0.789 mmol), and DIPEA (0.276 mL, 1.578 mmol) were added. The reaction mixture was left to stand in solution overnight. The resulting orange oil was dissolved in 1:1 DMSO:methanol and purified by MDAP (TFA). The product-containing fractions were combined and the solvent removed under reduced pressure. The product was left to dry in vacuo for 2 h to give (+/−)-1-(3-fluorobenzyl)-N3-methyl-N5-((trans)-2-methylcyclopropyl)-2-oxo-1,2-dihydropyridine-3,5-dicarboxamide (72 mg, 0.201 mmol, 38.3% yield) as a dark orange solid.

LCMS (2 min Formic): Rt=0.93 min, [MH]⁺=358.2.

Example 101: 1-Benzyl-N3-methyl-N5-((1R,2R)-2-methylcyclopropyl)-2-oxo-1,2-dihydropyridine-3,5-dicarboxamide and Example 102: 1-Benzyl-N3-methyl-N5-((1S,2S)-2-methylcyclopropyl)-2-oxo-1,2-dihydropyridine-3,5-dicarboxamide

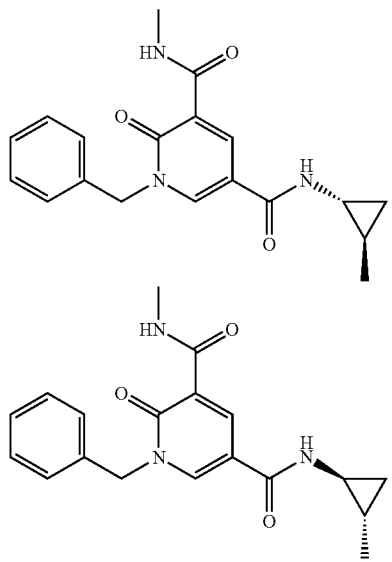

(+/−)-(trans)-2-Methylcyclopropanamine (149 mg, 2.096 mmol, commercially available from, for example, Fluorochem) was added to a suspension of 1-benzyl-5-(methylcarbamoyl)-6-oxo-1,6-dihydropyridine-3-carboxylic acid (300 mg, 1.048 mmol), HATU (598 mg, 1.572 mmol), and DIPEA (0.549 mL, 3.14 mmol) in DMF (6 mL). The reaction mixture was stirred for 1 h and left to react over the weekend. Further (+/−)-(trans)-2-methylcyclopropanamine (149 mg, 2.096 mmol), HATU (598 mg, 1.572 mmol), and DIPEA (0.549 mL, 3.14 mmol) were added and the reaction was stirred for 1 h. The reaction mixture was partitioned between ethyl acetate and water and the aqueous layer was extracted with 2× ethyl acetate. The organic layer was washed with 2× water and 1× brine and the solvent was removed under reduced pressure. The resulting orange oil was dissolved in DCM and loaded onto a 25 g Biotage SNAP silica column which was eluted with cyclohexane: ethyl acetate (0-80%). The product-containing fractions were combined and the solvent removed under reduced pressure. The product was left to dry in vacuo for 2 days. The product was further purified by MDAP (Formic) and the solvent was removed under reduced pressure. The clean product was left to dry in vacuo for 1 day to give (+/−)-1-benzyl-N3-methyl-N5-((trans)-2-methylcyclopropyl)-2-oxo-1,2-dihydropyridine-3,5-dicarboxamide (70 mg, 0.206 mmol, 19.68% yield) as a pale yellow solid. The racemic mixture was purified by chiral HPLC:

Analytical Method:

Approx 0.5 mg racemate was dissolved in 50% EtOH/Heptane (1 mL). Injection; 20 μL of the sample solution was injected onto the column (4.6 mm id×25 cm Chiralcel OJ-H Lot No. OJH0CE-QL055) eluting with 5% EtOH (+0.2% isopropylamine)/heptane, at a rate of 1 mL/min and analysing with a wavelength of 215 nm.

Preparative Method:

Approx. 70 mg racemate was dissolved in EtOH (0.5 mL). Injection: 0.5 mL of the sample solution was injected onto the column (30 mm×25 cm Chiralcel OJ-H Lot No. OJH10027-01) eluting with 5% EtOH (+0.2% isopropylamine)/heptane (+0.2% isopropylamine), at a rate of 30 mL/min and analysing with a wavelength of 215 nm.

Fractions from 34-41 min were bulked and labelled peak 1.

This gave the single enantiomer 1 (example 101) as a white solid (20 mg).

LCMS (2 min Formic): Rt=0.90 min, [MH]⁺=340.1.

Fractions from 44-54 min were bulked and labelled peak 2.

This gave the single enantiomer 2 (example 102) as a white solid (23 mg).

LCMS (2 min Formic): Rt=0.90 min, [MH]⁺=340.1.

¹H NMR (400 MHz, CHCl₃-d) δ ppm 9.52 (br. s., 1H) 8.66 (d, J=2.7 Hz, 1H) 8.46 (d, J=2.7 Hz, 1H) 7.29-7.41 (m, 5H) 6.39 (br. s., 1H) 5.25 (s, 2H) 2.99 (d, J=4.9 Hz, 3H) 2.55 (dd, J=7.1, 3.7 Hz, 1H) 1.14 (d, J=6.1 Hz, 3H) 0.97 (app. dquind, J=9.2, 6.0, 6.0, 6.0, 6.0, 3.3 Hz, 1H) 0.77 (ddd, J=9.3, 5.5, 3.8 Hz, 1H) 0.61-0.67 (m, 1H)

Alternative Process for the Preparation of Example 102

To a suspension of 1-benzyl-5-(methylcarbamoyl)-6-oxo-1,6-dihydropyridine-3-carboxylic acid (1.7 g) and (1S,2S)-2-methylcyclopropanamine, hydrochloride (0.639 g, 1 eq) in Dichloromethane (25.5 mL) was added triethylamine (2.48 mL, 3 eq). Propyl phosphonic anhydride (50% in ethyl acetate, 3.53 mL, 1.1 eq) was added dropwise with cooling to keep the temperature below 20° C. The mixture was then stirred for 1 h at rt. Once complete by HPLC, saturated sodium bicarbonate solution (10 mL) was added. After stirring for 10 min, the layers were separated and the aqueous phase was back extracted with DCM (5 vol). The combined DCM layers were washed with water (2×10 mL). The DCM layer was then dried over sodium sulphate and pumped through a 2 lenticle R55SP zeta carbon cuno cartridge at 120 mL/min. The cartridge was washed with DCM (17 mL) and the combined DCM solution was concentrated to dryness to give a yellow foam. The foam was dissolved in ethyl acetate (34 mL) after stirring for 30 min solid precipitated from solution and the slurry was cooled to 5±3° C. and aged for at least 2 h. The solid was then filtered off under vacuum and washed with cold ethyl acetate (3.4 mL). The product was then dried in vacuo at 40° C. to constant probe temperature. Yield: 52.6%.

Example 103: 1-(4-Fluoro-3-methylbenzyl)-N3-methyl-N5-(2-methylcyclopropyl)-2-oxo-1,2-dihydropyridine-3,5-dicarboxamide

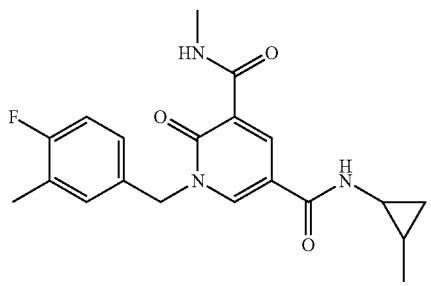 [SMILES: CNC(=O)c1cc(C(=O)NC2CC2C)cn(Cc2ccc(F)c(C)c2)c1=O]

1-(4-Fluoro-3-methylbenzyl)-5-(methylcarbamoyl)-6-oxo-1,6-dihydropyridine-3-carboxylic acid (200 mg, 0.628 mmol) was taken up in DMF (5 mL) and HATU (263 mg, 0.691 mmol) followed by DIPEA (0.219 mL, 1.257 mmol) were added. The reaction mixture was allowed to stir for 5 min, then 2-methylcyclopropanamine (44.7 mg, 0.628 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the desired product (166 mg, 0.447 mmol, 71.1% yield) as a white solid.

LCMS (2 min Formic): Rt=1.00 min, [MH]⁺=372.1.

Example 104: N5-Cyclopropyl-1-(3-(2-(dimethylamino)ethoxy)benzyl)-N3-methyl-2-oxo-1,2-dihydropyridine-3,5-dicarboxamide

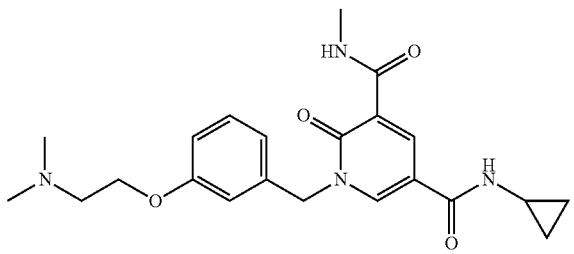 [SMILES: CNC(=O)c1cc(C(=O)NC2CC2)cn(Cc2cccc(OCCN(C)C)c2)c1=O]

2-Bromo-N,N-dimethylethanamine (23 mg, 0.151 mmol, commercially available from, for example, City Chemical LLC) was added to a suspension of N5-cyclopropyl-1-(3-hydroxybenzyl)-N3-methyl-2-oxo-1,2-dihydropyridine-3,5-dicarboxamide (46 mg, 0.135 mmol) and sodium hydride (11 mg, 60% dispersion in mineral oil, 0.275 mmol) in DMF (1 mL) at rt under N₂. After 1.5 h further portions of sodium hydride (10 mg, 60% dispersion in mineral oil, 0.25 mmol) and 2-bromo-N,N-dimethylethanamine (40 mg, 0.263 mmol) were added. After stirring for another 1 h, further portions of 2-bromo-N,N-dimethylethanamine (102 mg, 0.674 mmol) and sodium hydride (20 mg, 60% dispersion in mineral oil, 0.50 mmol) were added and the reaction mixture was stirred overnight. The reaction was quenched with water (20 mL), extracted with EtOAc (3×20 mL) and the combined organic layers dried over a hydrophobic frit and concentrated to give 193 mg of an of white solid. This was purified by chromatography on SiO₂ (Biotage SNAP 25 g cartridge, eluting with 0-50% (25% EtOH in EtOAc)/EtOAc) followed by 20% 2M NH₃ in MeOH in DCM and the appropriate fractions were collected to give N5-cyclopropyl-1-(3-(2-(dimethylamino)ethoxy)benzyl)-N3-methyl-2-oxo-1,2-dihydropyridine-3,5-dicarboxamide (6 mg, 0.012 mmol, 9.18% yield) as a colourless oil.

LCMS (2 min Formic): Rt=0.46 min, [MH]+=413.

Example 105: N5-(((+/−)-trans)-2-Ethoxycyclopropyl)-1-(3-fluorobenzyl)-N3-methyl-2-oxo-1,2-dihydropyridine-3,5-dicarboxamide

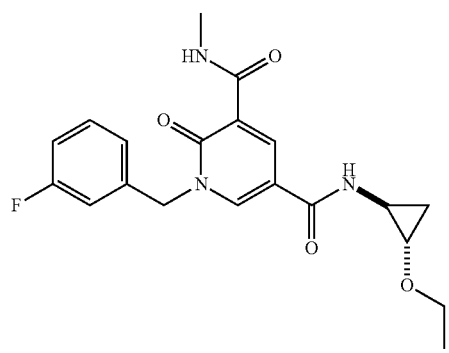

DIPEA (0.276 mL, 1.578 mmol) was added to a suspension of 1-(3-fluorobenzyl)-5-(methylcarbamoyl)-6-oxo-1,6-dihydropyridine-3-carboxylic acid (200 mg, 0.526 mmol), 2-ethoxycyclopropanamine, HCl salt (106 mg, 1.052 mmol, commercially available from, for example, Enamine), and HATU (300 mg, 0.789 mmol) in DMF (4 mL). The reaction mixture was stirred at rt for 90 min. The reaction mixture was partitioned between ethyl acetate (20 mL) and water (20 mL) and the organic layer washed with water (2×20 mL) and brine (20 mL). This was passed through a hydrophobic frit and the solvent removed under reduced pressure. The resulting orange oil was dissolved in DCM and purified by flash chromatography using a 25 g Biotage SNAP silica column and a gradient of 0-100% ethyl acetate/cyclohexane. The fractions were found to be impure so the product-containing fractions were combined, the solvent removed under reduced pressure, and the resulting orange oil dissolved in DMSO/methanol (1:1). This was then purified by MDAP (TFA)—the product-containing fractions were combined and the solvent removed under reduced pressure. The product was left to dry in vacuo for 2 days to give N5-(2-ethoxycyclopropyl)-1-(3-fluorobenzyl)-N3-methyl-2-oxo-1,2-dihydropyridine-3,5-dicarboxamide (200 mg, 0.516 mmol, 98% yield) as a pale orange solid, as a mixture of diastereomers, these were resolved by achiral HPLC:

The sample was dissolved in 9 mL of DMSO. 3000 μL injections were made onto a CSH C18 150×30 mm, 5 μm. column using the chromatographic conditions listed. Solvent A: 0.1% v/v solution of Formic Acid in Water, solvent B: 0.1% v/v solution of Formic Acid in Acetonitrile, flow Rate: 40 mL/min. Gradient: as below:

| Time/min | % B | % A |
|---|---|---|
| 0 | 20 | 80 |
| 3.5 | 20 | 80 |
| 25 | 40 | 60 |
| 32 | 40 | 60 |
| 35 | 99 | 1 |

Fractionation was determined by mixture of diode array & mass spec signal: UV detection: a summed signal from wavelengths 210 nm to 350 nm. MS: Waters SQ, Ionisation mode: Alt. Pos./Neg. Electrospray, Scan Range: 100 to 1000 AMU, Scan Time: 0.5 s, Inter scan Delay: 0.2 s. The flow and gradient was provided by a two pumps with a reduced flow passing through the injector during injection. The residual flow is introduced at the head of the column so the overall flow remains constant. The fractionation collected samples into multiple vessels and the suitable fractions were combined and dried using a Biotage V10 evaporator. This gave the trans-diastereomer (Example 105) as a white solid (106 mg).

LCMS (2 min Formic): Rt=0.90 min, [MH]⁺=388.1.

Example 106: (+/−)-1-((1H-Indol-4-yl)methyl)-N5-((trans)-2-ethylcyclopropyl)-N3-methyl-2-oxo-1,2-dihydropyridine-3,5-dicarboxamide

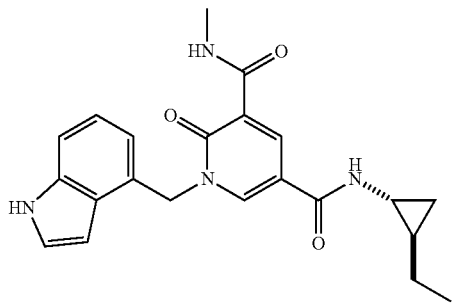

To a solution of 1-((1H-indol-4-yl)methyl)-5-(methylcarbamoyl)-6-oxo-1,6-dihydropyridine-3-carboxylic acid (25 mg, 0.077 mmol), and HATU (35.1 mg, 0.092 mmol) in DMF (500 µL) stirred at rt was added (+/−)-(trans)-2-ethylcyclopropanamine, hydrochloride (18.69 mg, 0.154 mmol, commercially available from, for example, Enamine) and DIPEA (26.8 µL, 0.154 mmol) and the reaction stirred for 30 min. The reaction mixture was diluted with DMSO (0.5 mL) and purified by MDAP (High pH). The solvent was evaporated in vacuo to yield the pure product (+/−)-1-((1H-indol-4-yl)methyl)-N5-((trans)-2-ethylcyclopropyl)-N3-methyl-2-oxo-1,2-dihydropyridine-3,5-dicarboxamide (15 mg, 0.036 mmol, 47.2% yield) as an off white solid.

LCMS (2 min Formic): Rt=0.93 min, [MH]⁺=393.2.

Examples 107-112: Amide Array of 1-(3-(2-hydroxyethoxy)benzyl)-5-(methylcarbamoyl)-6-oxo-1,6-dihydropyridine-3-carboxylic acid To a stock solution of 1-(3-(2-hydroxyethoxy)benzyl)-5-(methylcarbamoyl)-6-oxo-1,6-dihydropyridine-3-carboxylic acid (337 mg, 0.97 mmol) and HATU (374 mg) in DMF (5.5 mL) was added DIPEA (550 µL). The solution was shaken and sonicated to aid dispersion and aliquoted (0.55 mL) to a set of preweighed amines (as shown in table below). Additional DIPEA (55 µL) was added to example 107 reaction mixture to compensate for HCl salt of the amine monomer. After 18 h at rt, the samples were injected as is and purified by MDAP (High pH). The solvent was dried under a stream of nitrogen to give the required products. Example 111 was dissolved in DCM (0.5 mL) and treated with TFA (0.5 mL) and the solution left to stand in a capped vial at rt for 2 h. The reaction mixture was evaporated and example 111 was dissolved in MeOH (0.5 mL). The solution was applied to a MeOH-preconditioned 100 mg SCX-2 cartridge which was then washed with MeOH (1 mL) followed by 2 M ammonia in MeOH solution (1 mL). The basic washes were evaporated to dryness to give the final deprotected compound as the free base (as shown in table below). Example 111 was re-purified by MDAP (High pH). The solvent was dried under a stream of nitrogen to give the required product.

Monomers

| Ex No. | Reagent Name | Structure | MW | Reagent Mass (g) | Reagent Volume (mL) | mmol |
|---|---|---|---|---|---|---|
| 107 | 3-fluorocyclobutanamine hydrochloride | 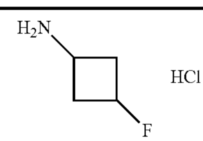 | 125.57 | 0.014 | — | 0.120 |
| 108 | 2-cyclopropylethanamine | 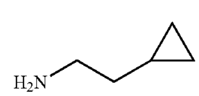 | 85.15 | 0.010 | — | 0.114 |
| 109 | rac-2-ethoxycyclopropanamine | 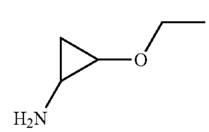 | 101.15 | 0.012 | — | 0.114 |
| 110 | rac-(2-aminocyclopropyl)methanol | 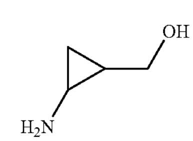 | 87.12 | 0.010 | — | 0.114 |

-continued

| Ex No. | Reagent Name | Structure | MW | Reagent Mass (g) | Reagent Volume (mL) | mmol |
|---|---|---|---|---|---|---|
| 111 | tert-butyl (6-aminospiro[3.3]heptan-2-yl)carbamate | 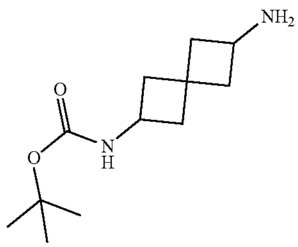 [SMILES: CC(C)(C)OC(=O)NC1CC2(CC(N)C2)C1] | 226.32 | 0.026 | — | 0.114 |
| 112 | rac-(trans)-2-methylcyclopropanamine | 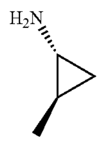 | 71.12 | 0.008 | — | 0.114 |

EXAMPLES

| Ex no. | Name | Structure | Mass (mg) | Yield (%) | [MH]+ | Rt (min) |
|---|---|---|---|---|---|---|
| 107 | N5-(3-fluorocyclobutyl)-1-(3-(2-hydroxyethoxy)benzyl)-N3-methyl-2-oxo-1,2-dihydropyridine-3,5-dicarboxamide | 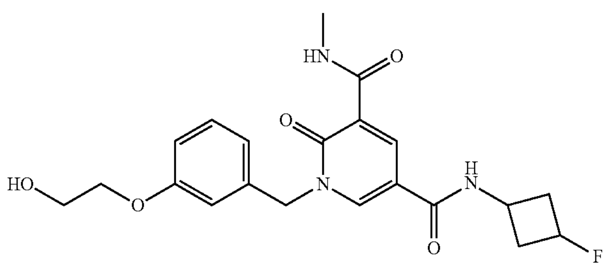 [SMILES: CNC(=O)c1cc(C(=O)NC2CC(F)C2)cn(Cc2cccc(OCCO)c2)c1=O] | 18.7 | 45.0 | 418 | 0.74 |
| 108 | N5-(2-cyclopropylethyl)-1-(3-(2-hydroxyethoxy)benzyl)-N3-methyl-2-oxo-1,2-dihydropyridine-3,5-dicarboxamide | 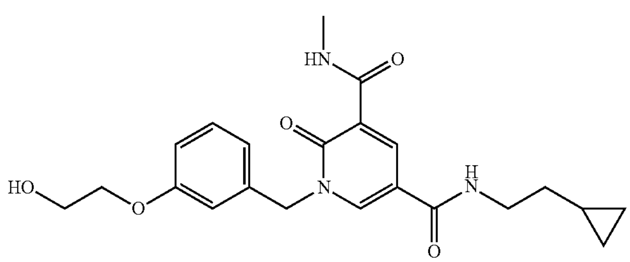 [SMILES: CNC(=O)c1cc(C(=O)NCCC2CC2)cn(Cc2cccc(OCCO)c2)c1=O] | 19.5 | 47.4 | 414 | 0.82 |
| 109 | rac-N5-(2-ethoxycyclopropyl)-1-(3-(2-hydroxyethoxy)benzyl)-N3-methyl-2-oxo-1,2-dihydropyridine-3,5-dicarboxamide | 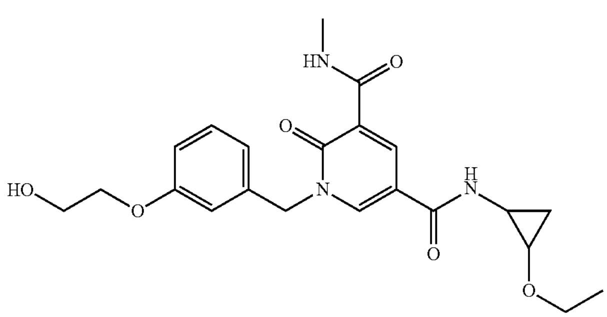 [SMILES: CCOC1CC1NC(=O)c1cc(C(=O)NC)c(=O)n(Cc2cccc(OCCO)c2)c1] | 17.3 | 40.5 | 430 | 0.74 |

| Ex no. | Name | Structure | Mass (mg) | Yield (%) | [MH]+ | Rt (min) |
|---|---|---|---|---|---|---|
| 110 | rac-1-(3-(2-hydroxyethoxy)benzyl)-N5-(2-(hydroxymethyl)cyclopropyl)-N3-methyl-2-oxo-1,2-dihydropyridine-3,5-dicarboxamide | 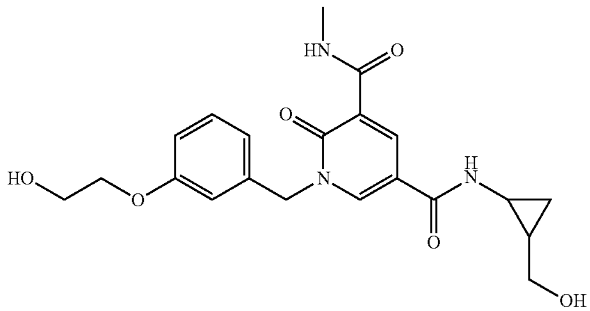 [SMILES: CNC(=O)c1cc(C(=O)NC2CC2CO)cn(Cc2cccc(OCCO)c2)c1=O] | 12.6 | 30.5 | 416 | 0.62 |
| 111 | N5-(6-Aminospiro[3.3]heptan-2-yl)-1-(3-(2-hydroxyethoxy)benzyl)-N3-methyl-2-oxo-1,2-dihydropyridine-3,5-dicarboxamide | 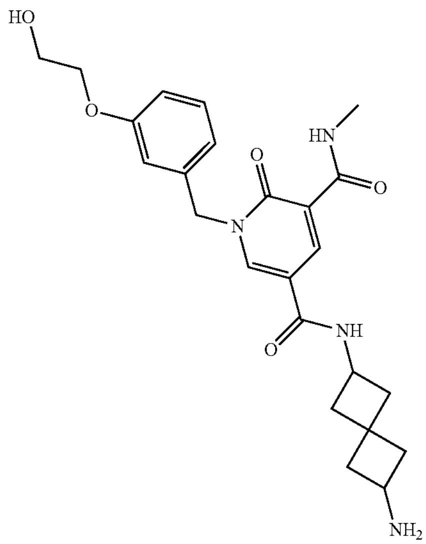 [SMILES: CNC(=O)c1cc(C(=O)NC2CC3(CC(N)C3)C2)cn(Cc2cccc(OCCO)c2)c1=O] | 5.9 | 13.1 | 455 | 0.47 |
| 112 | rac-1-(3-(2-hydroxyethoxy)benzyl)-N3-methyl-N5-((trans)-2-methylcyclopropyl)-2-oxo-1,2-dihydropyridine-3,5-dicarboxamide | 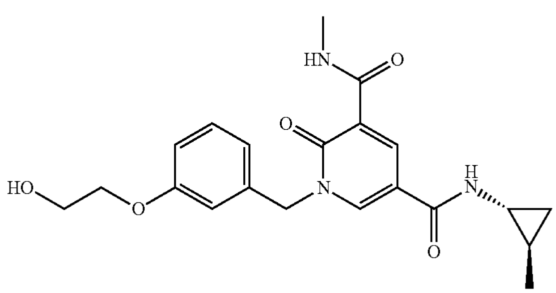 [SMILES: CNC(=O)c1cc(C(=O)N[C@@H]2C[C@H]2C)cn(Cc2cccc(OCCO)c2)c1=O] | 8.4 | 21.1 | 400 | 0.75 |

All LCMS were conducted using 2 min Formic method.

Example 113: (R*)—N5-Cyclopropyl-N3-methyl-2-oxo-1-(1-(m-tolyl)ethyl)-1,2-dihydropyridine-3,5-dicarboxamide—Enantiomer 1

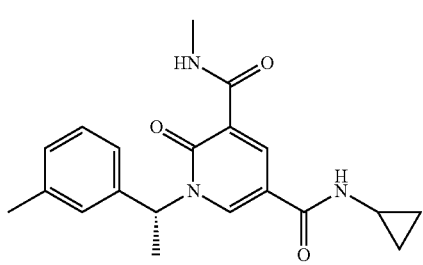 [SMILES: CNC(=O)c1cc(C(=O)NC2CC2)cn([C@H](C)c2cccc(C)c2)c1=O]

rac-N5-Cyclopropyl-N3-methyl-2-oxo-1-(1-(m-tolyl)ethyl)-1,2-dihydropyridine-3,5-dicarboxamide (for example, Example 88, 117 mg) was dissolved in EtOH (3 mL) and purified by chiral chromatography:

Analytical Method:

Approx 0.5 mg of racemate was dissolved in 50% EtOH/Heptane (1 mL). 20 µL was injected on the column (Column: 4.6 mmid×25 cm Chiralpak AD-H, Lot No. ADH0CE-PC014). This was eluted with 25% EtOH/Heptane, flow rate=1.0 mL/min, detection wavelength=215 nm, 4. Ref 550, 100

Preparative Method:

Approx 117 mg of racemate was dissolved in 3 mL EtOH. Injection; 1 mL of the solution was injected onto the column (Column: 30 mm×25 cm Chiralpak AD-H, Lot No. ADH12143-01). This was eluted with 25% EtOH/Heptane, flow rate=30 mL/min, detection wavelength=215 nm, 4. Ref 550, 100. Total number of injections: 3. Fractions from 10.5-13.5 min were bulked and labelled peak 1. Fractions from 15.5-24 min were bulked and labelled peak 2. The combined fractions for peak 1 were evaporated in vacuo to give pure enantiomer 1 as a white solid (51 mg), LCMS (2 min Formic): Rt=0.96 min, [MH]+=354.

Example 115: N5-(2-Ethoxycyclopropyl)-1-(2-fluoro-5-methylbenzyl)-N3-methyl-2-oxo-1,2-dihydropyridine-3,5-dicarboxamide

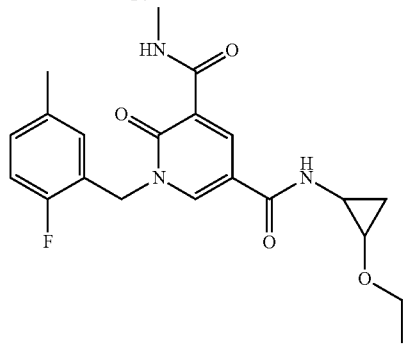 [SMILES: CCOC1CC1NC(=O)c1cc(C(=O)NC)c(=O)n(Cc2cc(C)ccc2F)c1]

1-(4-Fluoro-3-methylbenzyl)-5-(methylcarbamoyl)-6-oxo-1,6-dihydropyridine-3-carboxylic acid (200 mg, 0.628 mmol) was taken up in DMF (5 mL) and HATU (263 mg, 0.691 mmol) followed by DIPEA (0.219 mL, 1.257 mmol). The reaction mixture was allowed to stir for 5 min, then 2-ethoxycyclopropanamine (47.7 mg, 0.471 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the desired product (100 mg, 0.249 mmol, 52.9% yield) as a white solid.

LCMS (2 min Formic): Rt=0.97 min, [MH]$^+$=402.2.

Examples 116-118 and 130: Amide Array of 1-(2-fluoro-3-methylbenzyl)-5-(methylcarbamoyl)-6-oxo-1,6-dihydropyridine-3-carboxylic acid Monomers

| Ex No. | Reagent Name | Structure | MW | Reagent Mass (g) | Reagent Volume (mL) | mmol |
|---|---|---|---|---|---|---|
| 116 | 2-cyclopropylethanamine | 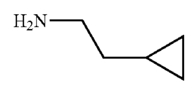 | 85.15 | 0.0102 | — | 0.120 |
| 117 | 2-(ethoxymethyl)cyclopropanamine | 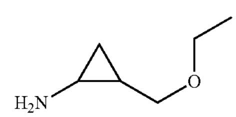 | 101.15 | 0.0121 | — | 0.120 |
| 118 | 3-fluorocyclobutanamine hydrochloride | 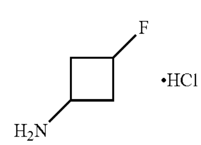 | 125.57 | 0.0107 | — | 0.085 |
| 130 | tert-butyl (6-aminospiro[3.3]heptan-2-yl)carbamate | 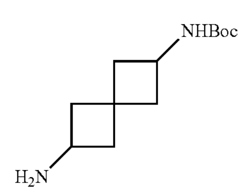 | 226.32 | 0.0272 | — | 0.120 |

To a stock solution of 1-(2-fluoro-3-methylbenzyl)-5-(methylcarbamoyl)-6-oxo-1,6-dihydropyridine-3-carboxylic acid (350 mg, 1.1 mmol) dissolved in DMF (5.5 mL) was added HATU (502 mg, 2.13 mmol) and DIPEA (570 μL, 3.3 mmol). The mixture was sonicated to aid dispersion and further DMF (5.5 mL) was added. An aliquot (1.0 mL) of this mixture was added to the appropriate amine (0.12 mmol) in DMF (0.3 mL) in a vial which was subsequently sealed, sonicated and left to stand at rt for 3 h. The samples were reduced to 1 mL, then injected as is and purified by MDAP (High pH). The solvent was removed using a plate dryer to give the required products as shown in the table.

DCM (0.5 mL) and TFA (0.5 mL) were added to the product derived from the amine monomer used to prepare example 130 and the vial was capped and left to stand at rt for 2 h. The solvent was removed using a plate dryer. The residue was redissolved in MeOH (0.5 mL) and applied to the top of a SCX-2 SPE cartridge (1 g, preconditioned with MeOH (1 mL)). The cartridge was eluted with further MeOH (1 mL) followed by 2M NH$_3$/MeOH (1 mL). The solvent was evaporated from the sample under a stream of nitrogen. The residue was dissolved in DCM (1 mL) and applied to a aminopropyl cartridge (100 mg), (preconditioned with CHCl$_3$), and this was eluted with further CHCl$_3$ (1 mL) and concentrated to provide the desired example 130.

EXAMPLES

| Ex No. | Name | Structure | Mass (mg) | Yield (%) | [MH]$^+$ | Rt (min)* |
|---|---|---|---|---|---|---|
| 116 | N5-(2-cyclopropylethyl)-1-(2-fluoro-3-methylbenzyl)-N3-methyl-2-oxo-1,2-dihydropyridine-3,5-dicarboxamide | 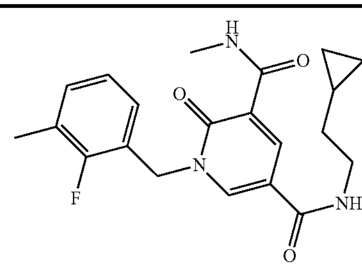 | 22.5 | 53 | 386 | 1.05 |
| 117 | N5-(2-ethoxycyclopropyl)-1-(2-fluoro-3-methylbenzyl)-N3-methyl-2-oxo-1,2-dihydropyridine-3,5-dicarboxamide | 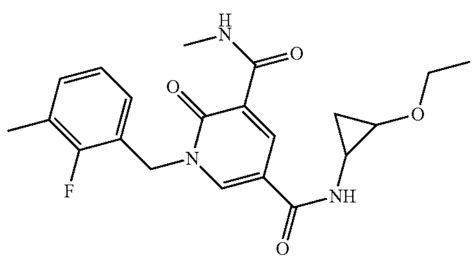 [SMILES: CCOC1CC1NC(=O)c1cc(C(=O)NC)c(=O)n(Cc2cccc(C)c2F)c1] | 26.6 | 50 | 402 | 0.96 |
| 118 | 1-(2-fluoro-3-methylbenzyl)-N5-(3-fluorocyclobutyl)-N3-methyl-2-oxo-1,2-dihydropyridine-3,5-dicarboxamide | 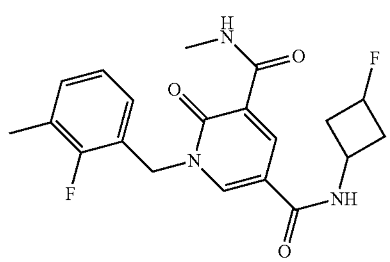 [SMILES: CNC(=O)c1cc(C(=O)NC2CC(F)C2)cn(Cc2cccc(C)c2F)c1=O] | 25.7 | 59 | 389 | 0.97 |
| 130 | N5-(6-aminospiro[3.3]heptan-2-yl)-1-(2-fluoro-3-methylbenzyl)-N3-methyl-2-oxo-1,2-dihydropyridine-3,5-dicarboxamide | 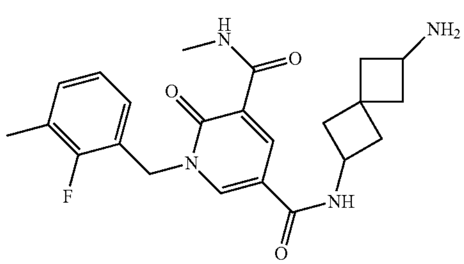 [SMILES: CNC(=O)c1cc(C(=O)NC2CC3(CC(N)C3)C2)cn(Cc2cccc(C)c2F)c1=O] | 3.4 | 6.0 | 346 | 0.90 |

Example 119: 1-(4-Fluorobenzyl)-N5-((1R*,2R*)-2-(hydroxymethyl)cyclopropyl)-N3-methyl-2-oxo-1,2-dihydropyridine-3,5-dicarboxamide—Enantiomer 1 and Example 120: 1-(4-Fluorobenzyl)-N5-((1S*,2S*)-2-(hydroxymethyl)cyclopropyl)-N3-methyl-2-oxo-1,2-dihydropyridine-3,5-dicarboxamide—Enantiomer 2

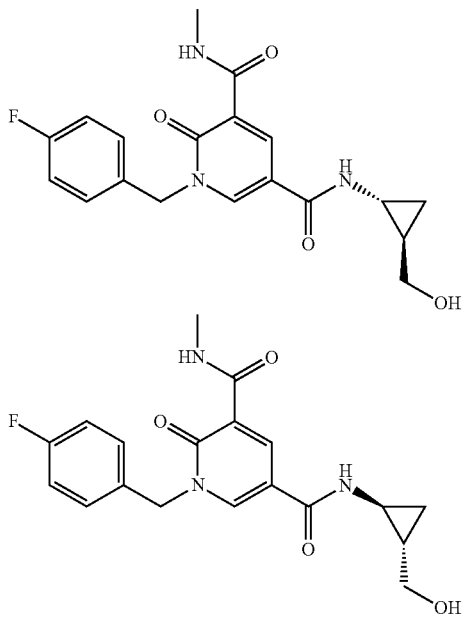

1-(4-Fluorobenzyl)-N5-(2-(hydroxymethyl)cyclopropyl)-N3-methyl-2-oxo-1,2-dihydropyridine-3,5-dicarboxamide (for example, Example 86, 145 mg) was dissolved in EtOH (9 mL) and purified by chiral chromatography:

Analytical Method:
Approx 0.5 mg racemate was dissolved in 50% EtOH/Heptane (1 mL). 20 µL of this was injected on the column (Column 4.6 mmid×25 cm Chiralpak AD-H, Lot No. ADH0CE-PC014) and eluted with 60% EtOH/Heptane, flow rate=1.0 mL/min, detection wavelength 215 nm, 4. Ref 550, 100.

Preparative Method:
Approx 145 mg racemate was dissolved in 9 mL EtOH+heat. Injection; 3 mL of the solution was injected onto the column (Column: 30 mm×25 cm Chiralpak AD-H, Lot No. ADH12143-01) and eluted with 60% EtOH/Heptane, flow rate=25 mL/min, detection wavelength 215 nm, 4. Ref 550,100. Total number of injections=3. Fractions from 14-19 min were bulked and labelled peak 1. Fractions from 22-31 min were bulked and labelled peak 2. The bulked fractions were vac'ed down using a rotary evaporator and then transferred to a weighed flask for final analysis as described by the analytical method above. The combined fractions from peak 1 were evaporated in vacuo to give pure enantiomer 1 as a colourless solid (72 mg).

HPLC-UV: RT~11.0 minutes, >99.5% isomeric purity by area HPLC @ 215 nm.
LCMS (2 min Formic): Rt=0.75 min, [MH]$^+$=374.1

The combined fractions from peak 2 were evaporated in vacuo to give pure enantiomer 2 as a colourless solid (65 mg).

HPLC-UV: RT~19.0 minutes, 98.3% isomeric purity by area HPLC @ 215 nm.
LCMS (2 min Formic): Rt=0.76 min, [MH]$^+$=374.2.

Example 121: 1-(4-Fluorobenzyl)-N3-methyl-N5-((1R,2R*)-2-methylcyclopropyl)-2-oxo-1,2-dihydropyridine-3,5-dicarboxamide—Enantiomer 1 and Example 122: 1-(4-Fluorobenzyl)-N3-methyl-N5-((1S*2S*)-2-methylcyclopropyl)-2-oxo-1,2-dihydropyridine-3,5-dicarboxamide—Enantiomer 2

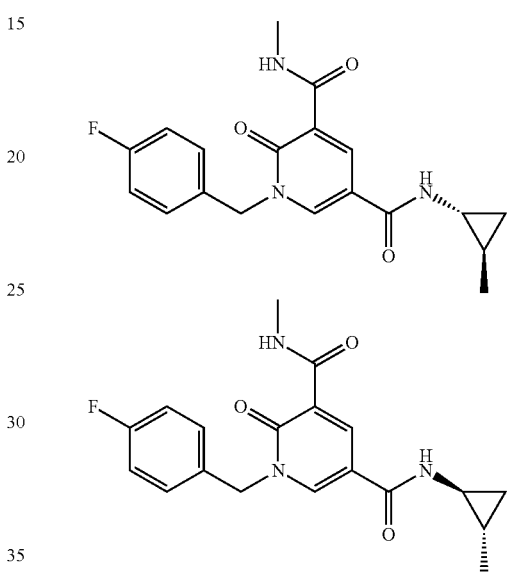

(+/−)-1-(4-Fluorobenzyl)-N3-methyl-N5-((trans)-2-methylcyclopropyl)-2-oxo-1,2-dihydropyridine-3,5-dicarboxamide (for example Example 82, 90 mg) was dissolved in EtOH (2 mL) and purified by chiral chromatography:

Analytical Method:
Approx 0.5 mg racemate was dissolved in 50% EtOH/Heptane (1 mL). 20 µL of the sample was injected on the column (Column: 4.6 mmid×25 cm Chiralcel OJ-H, Lot No. OJH0CE-QL055) and this was eluted with 5% EtOH (+0.2% isopropylamine)/Heptane, flow rate=1.0 mL/min, detection wavelength=215 nm, 4. Ref 550, 100.

Preparative Method:
Approx 90 mg of racemate was dissolved in 2 mL EtOH+heat. Injection: 1 mL of the solution was injected onto the column (Column: 30 mm×25 cm Chiralcel OJ-H, Lot No. OJH10027-01). This was eluted with 5% EtOH (+0.2% isopropylamine)/Heptane (+0.2% isopropylamine), flow rate=30 mL/min, detection wavelength=215 nm, 4. Ref 550, 100. Total number of injections=3. Fractions from 31-38 min were bulked and labelled peak 1. Fractions from 38-43 min were bulked and labelled mix. Fractions from 43-54 min were bulked and labelled peak 2. The mix fractions were bulked, vac'ed down and reprocessed using the prep method above. The bulked fractions were vac'ed down using a rotary evaporator and then transferred to a weighed flask for final analysis as described by the analytical method above. The combined fractions for peak 1 were evaporated in vacuo to give pure enantiomer 1 as a colourless solid (44 mg).

HPLC-UV: RT~30 minutes, >99.5% isomeric purity by area HPLC @ 215 nm.

LCMS (2 min Formic): Rt=0.92 min, [MH]⁺=358.2

The combined fractions for peak 2 were evaporated in vacuo to give pure enantiomer 2 as a colourless solid (43 mg).

HPLC-UV: RT~40 minutes, 97% isomeric purity by area HPLC @ 215 nm.

LCMS (2 min Formic): Rt=0.92 min, [MH]⁺=358.1.

Example 123: N5-((1R*,2R*)-2-ethoxycyclopropyl)-1-(4-fluorobenzyl)-N3-methyl-2-oxo-1,2-dihydropyridine-3,5-dicarboxamide—Enantiomer 1 and Example 124: N5-((1S,2S*)-2-ethoxycyclopropyl)-1-(4-fluorobenzyl)-N3-methyl-2-oxo-1,2-dihydropyridine-3,5-dicarboxamide—Enantiomer 1

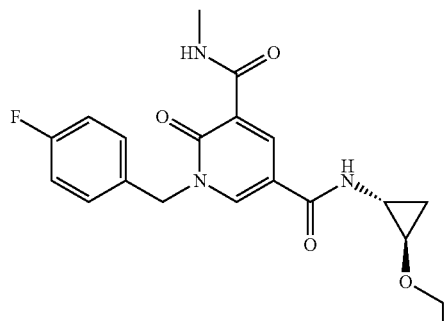

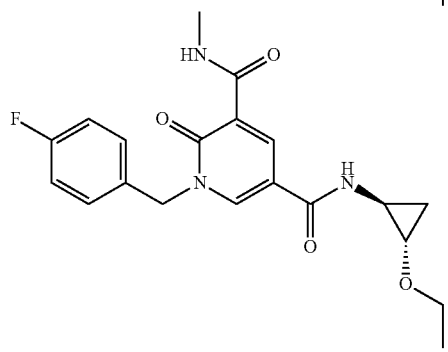

N5-(2-Ethoxycyclopropyl)-1-(4-fluorobenzyl)-N3-methyl-2-oxo-1,2-dihydropyridine-3,5-dicarboxamide (for example, Example 87, 98 mg) was dissolved in EtOH (2 mL) and purified by chiral chromatography:

Analytical Method:

Approx 0.5 mg racemate was dissolved in 50% EtOH/Heptane (1 mL). 20 μL of the sample was injected on the column (Column: 4.6 mmid×25 cm Chiralcel OJ-H, Lot No. OJH0CE-QL055). This was eluted with 40% EtOH/Heptane, flow rate=1.0 mL/min, detection wavelength=215 nm, 4. Ref 550, 100

Preparative Method:

Approx 98 mg racemate was dissolved in 2 mL EtOH+ heat. Injection: 2 mL of the solution was injected onto the column (Column: 30 mm×25 cm Chiralcel OJ-H, Lot No. OJH10027-01). This was eluted with 40% EtOH/Heptane, flow rate=30 mL/min, detection wavelength=215 nm, 4. Ref 550, 100. Total number of injections=1. Fractions from 7.5-11 min were bulked and labelled peak 1. Fractions from 13.5-21 min were bulked and labelled peak 2. The bulked fractions were vac'ed down using a rotary evaporator and then transferred to a weighed flask for final analysis as described by the analytical method above. The combined fractions from peak 1 were evaporated in vacuo to give pure enantiomer 1 as a colourless solid (45 mg).

HPLC-UV: RT~7.5 minutes, >99.5% isomeric purity by area HPLC @ 215 nm.

LCMS (2 min Formic): Rt=0.90 min, [MH]⁺=388.2

The combined fractions for peak 2 were evaporated in vacuo to give pure enantiomer 2 as a colourless solid (44 mg).

HPLC-UV: RT~13.5 minutes, >99.5% isomeric purity by area HPLC @ 215 nm.

LCMS (2 min Formic): Rt=0.92 min, [MH]⁺=358.1.

Example 125: N5-((1R*,2R*)-2-Ethoxycyclopropyl)-1-(4-fluoro-3-methylbenzyl)-N3-methyl-2-oxo-1,2-dihydropyridine-3,5-dicarboxamide—Enantiomer 1 and Example 126: N5-((1S*,2S*)-2-Ethoxycyclopropyl)-1-(4-fluoro-3-methylbenzyl)-N3-methyl-2-oxo-1,2-dihydropyridine-3,5-dicarboxamide—Enantiomer 2

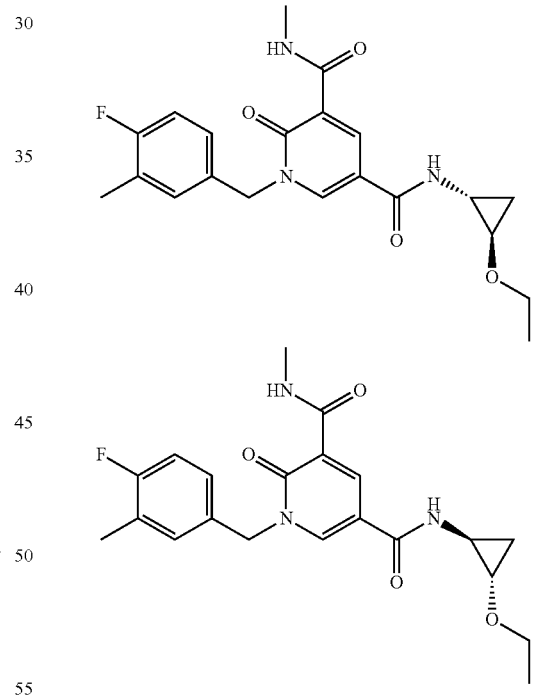

N5-(2-Ethoxycyclopropyl)-1-(4-fluoro-3-methylbenzyl)-N3-methyl-2-oxo-1,2-dihydropyridine-3,5-dicarboxamide (for example, Example 98, 144 mg) was dissolved in EtOH (2 mL) and purified by chiral chromatography:

Analytical Method:

Approx 0.5 mg racemate was dissolved in 50% EtOH/Heptane (1 mL). 20 μL of the sample was injected on the column (Column: 4.6 mm id×25 cm Chiralcel OJ-H, Lot No. OJH0CE-QL055). This was eluted with 25% EtOH/Heptane, flow rate=1.0 mL/min, detection wavelength=215 nm, 4. Ref 550, 100

Preparative Method:

Approx 144 mg racemate was dissolved in 2 mL EtOH+ heat. Injection; 1 mL of the solution was injected onto the column (Column: 30 mm×25 cm Chiralcel OJ-H, Lot No. OJH10027-01). This was eluted with 25% EtOH/Heptane, flow rate=30 mL/min, detection wavelength=215 nm, 4. Ref 550, 100. Total number of injections=2. Fractions from 8-9.5 min were bulked and labelled peak 1. Fractions from 12-17 min were bulked and labelled peak 2. The bulked fractions were vac'ed down using a rotary evaporator and then transferred to a weighed flask for final analysis as described by the analytical method above. The combined fractions for peak 1 were evaporated in vacuo to give pure enantiomer 1 as a colourless solid (56 mg).

HPLC-UV: RT~7.0 minutes, >99.5% isomeric purity by area HPLC @ 215 nm.

LCMS (2 min Formic): Rt=0.98 min, [MH]$^+$=402.2

The combined fractions for peak 2 were evaporated in vacuo to give pure enantiomer 2 as a colourless solid (66 mg).

HPLC-UV: RT~11.5 minutes, >99.5% isomeric purity by area HPLC @ 215 nm.

LCMS (2 min Formic): Rt=0.99 min, [MH]$^+$=402.3.

Example 127: N5-((1R*,2R*)-2-ethoxycyclopropyl)-1-(3-fluorobenzyl)-N3-methyl-2-oxo-1,2-dihydropyridine-3,5-dicarboxamide and Example 128: N5-((1S*,2S*)-2-ethoxycyclopropyl)-1-(3-fluorobenzyl-N3-methyl-2-oxo-1,2-dihydropyridine-3,5-dicarboxamide

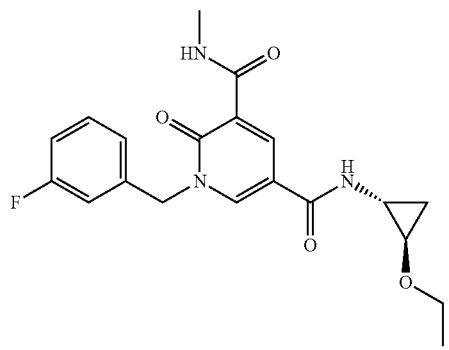

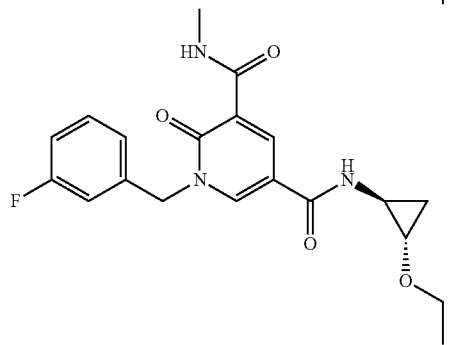

(+/−)-N5-((trans)-2-Ethoxycyclopropyl)-1-(3-fluorobenzyl)-N3-methyl-2-oxo-1,2-dihydropyridine-3,5-dicarboxamide (for example, example 105, ~100 mg) was submitted for chiral separation:

Analytical Method:

Approx 0.5 mg diastereomer was dissolved in 50% EtOH/heptane (1 mL). Injection: 20 µL of the sample solution was injected onto column (4.6 mm id×25 cm Chiralcel OJ-H Lot No. OJH0CE-QL055) eluting with 20% EtOH/heptane, at a rate of 1 mL/min and analysing with a wavelength of 215 nm.

Preparative Method:

Approx 100 mg diastereomer dissolved in EtOH (1 mL)+ heat. Injection: 1 mL of the sample solution was injected onto the column (30 mm×25 cm Chiralcel OJ-H Lot No. OJH10027-01) eluting with 20% EtOH/heptane at a rate of 30 mL/min and analysing with a wavelength of 215 nm. Fractions from 10-14 min were bulked and labelled peak 1. Fractions from 15.5-21 min were bulked and labelled peak 2.

Peak 1: This gave the single enantiomer (Example 127) as a white solid (40 mg).

LCMS (2 min Formic): Rt=0.90 min, [MH]$^+$=388.2.

Peak 2: This gave the single enantiomer (Example 128) as a white solid (40 mg).

LCMS (2 min Formic): Rt=0.90 min, [MH]$^+$=388.2.

Example 129: N5-Cyclopropyl-N3-methyl-2-oxo-1-((1,2,3,4-tetrahydroisoquinolin-5-yl)methyl)-1,2-dihydropyridine-3,5-dicarboxamide

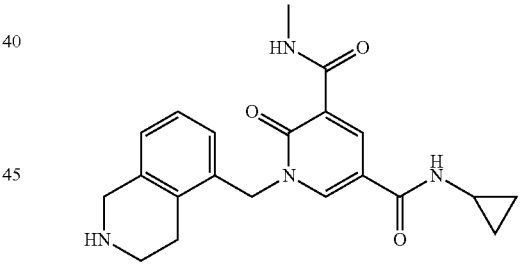

tert-Butyl 5-((5-(cyclopropylcarbamoyl)-3-(methylcarbamoyl)-2-oxopyridin-1(2H)-yl)methyl)-3,4-dihydroisoquinoline-2(1H)-carboxylate (5 mg, 10.40 µmol) and TFA (0.1 mL, 1298 µmol) were stirred at rt in DCM (0.4 mL) for 30 min. The reaction mixture was concentrated and loaded onto a 500 mg SCX cartridge (pre-conditioned with MeOH) and eluted with MeOH (5 mL) followed by 2M NH$_3$ in MeOH (5 mL). The ammonia fractions containing product were combined and concentrated to give N5-cyclopropyl-N3-methyl-2-oxo-1-((1,2,3,4-tetrahydroisoquinolin-5-yl)methyl)-1,2-dihydropyridine-3,5-dicarboxamide (4 mg, 9.46 µmol, 91% yield) as a colourless oil.

LCMS (2 min Formic): Rt=0.42 min, [MH]+=381.

Example 131: 1-(2-Fluoro-5-methylbenzyl)-N5-(2-(hydroxymethyl)cyclopropyl)-N3-methyl-2-oxo-1,2-dihydropyridine-3,5-dicarboxamide

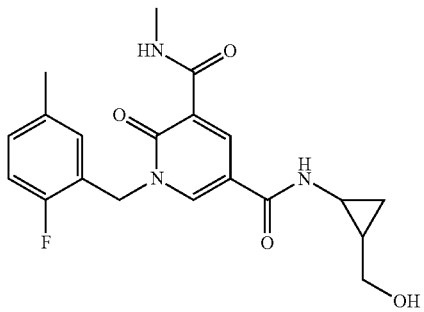 [SMILES: CNC(=O)c1cc(C(=O)NC2CC2CO)cn(Cc2cc(C)ccc2F)c1=O]

1-(2-Fluoro-5-methylbenzyl)-5-(methylcarbamoyl)-6-oxo-1,6-dihydropyridine-3-carboxylic acid (120 mg, 0.377 mmol) was taken up in DMF (3 mL) and HATU (158 mg, 0.415 mmol) followed by DIPEA (0.132 mL, 0.754 mmol) were added. The reaction mixture was allowed to stir for 5 min, then (2-aminocyclopropyl)methanol (32.8 mg, 0.377 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the title compound (90 mg, 0.232 mmol, 61.6% yield) as an orange-white solid.

LCMS (2 min Formic): Rt=0.81 min, [MH]$^+$=388.2.

Example 132: (+/−)-N5-((trans)-2-(Hydroxymethyl)cyclopropyl)-1-(3-methoxybenzyl)-N3-methyl-2-oxo-1,2-dihydropyridine-3,5-dicarboxamide

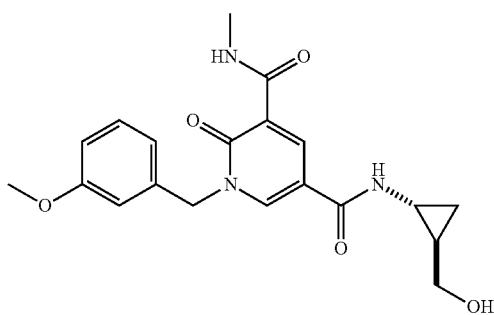

1-(3-Methoxybenzyl)-5-(methylcarbamoyl)-6-oxo-1,6-dihydropyridine-3-carboxylic acid (200 mg, 0.632 mmol) was taken up in DMF (3 mL) and HATU (264 mg, 0.696 mmol) followed by DIPEA (0.221 mL, 1.265 mmol) were added. The reaction mixture was allowed to stir for 5 min, then (2-aminocyclopropyl)methanol (55.1 mg, 0.632 mmol, commercially available from, for example, Enamine) was added and the reaction allowed to stir for 1 h. The reaction mixture was concentrated under vacuum and purified by MDAP (High pH). The appropriate fractions were combined and concentrated under vacuum to give the title compound (161 mg, 0.418 mmol, 66.1% yield) as a white solid.

LCMS (2 min Formic): Rt=0.74 min, [MH]$^+$=386.2.

$^1$H NMR (400 MHz, DMSO-d$_6$) δ ppm 9.35 (br. q, J=4.5, 4.5, 4.5 Hz, 1H) 8.80 (d, J=2.7 Hz, 1H) 8.69 (d, J=2.7 Hz, 1H) 8.56 (br. d, J=4.2 Hz, 1H) 7.27 (t, J=7.8 Hz, 1H) 6.82-6.92 (m, 3H) 5.25 (s, 2H) 4.48 (t, J=5.5 Hz, 1H) 3.73 (s, 3H) 3.30-3.42 (m, 2H) 2.82 (d, J=4.9 Hz, 3H) 2.71 (m, J=7.3, 3.4 Hz, 1H) 1.22 (dqd, J=9.1, 6.1, 6.1, 6.1, 3.4 Hz, 1H) 0.64-0.72 (m, 2H).

Example 133: 1-(2-Fluorobenzyl)-N3-methyl-N5-((1S*,2S*)-2-methylcyclopropyl)-2-oxo-1,2-dihydropyridine-3,5-dicarboxamide and

Example 134: 1-(2-Fluorobenzyl)-N3-methyl-N5-((1R*,2R*)-2-methylcyclopropyl)-2-oxo-1,2-dihydropyridine-3,5-dicarboxamide

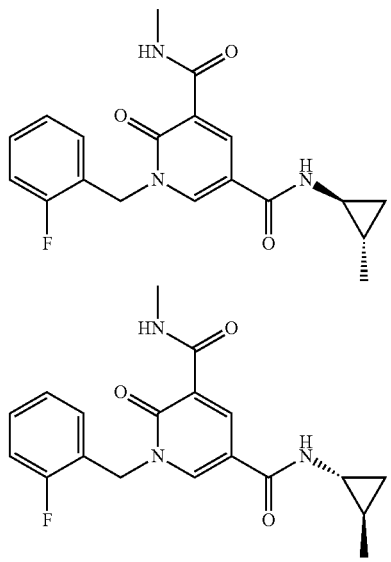

(+/−)-1-(2-Fluorobenzyl)-N3-methyl-N5-((trans)-2-methylcyclopropyl)-2-oxo-1,2-dihydropyridine-3,5-dicarboxamide (for example, example 61, ~30 mg) was submitted for chiral separation:

Analytical Method:
Approx 0.5 mg racemate dissolved in 50% EtOH/heptane (1 mL). Injection; 20 µL of the sample solution was injected onto a column (4.6 mm id×25 cm Chiralpak IA Lot No. IA00CE-MC024) eluting with 10% EtOH(+0.2% isopropylamine)/heptane, at a rate of 1 mL/min and analysing with a wavelength of 215 nm.

Preparative Method:
Approx 30 mg racemate dissolved in EtOH (2 mL). Injection: 0.5 mL of the sample solution was injected onto a column (2 cm×25 cm Chiralpak IA (5 µm) Lot No. IA00CJ-KF008) eluting with 10% EtOH (+0.2% isopropylamine)/heptane (+0.2% isopropylamine), at a rate of 20 mL/min and analysing with a wavelength of 215 nm. Fractions from 34-37 min were bulked and labelled peak 1; fractions from 37-40 min were bulked and labelled mix. Fractions from 40-50 min were bulked and labelled peak 2. The bulked mix fractions were vac'ed down and reprocessed using the the prep method above.

Peak 1: This gave the single enantiomer (Example 133) as a white solid (11 mg).
LCMS (2 min Formic): Rt=0.91 min, [MH]$^+$=358.2.
Peak 2: This gave the single enantiomer (Example 134) as a white solid (10 mg).
LCMS (2 min Formic): Rt=0.91 min, [MH]$^+$=358.2.

Examples 135-138: Amide Array of 1-((1H-Indol-4-yl)methyl)-5-(methylcarbamoyl)-6-oxo-1,6-dihydro-pyridine-3-carboxylic acid Monomers

| Ex No. | Reagent Name | Structure | MW | Reagent Mass (g) | Reagent Volume (mL) | mmol |
|---|---|---|---|---|---|---|
| 135 | 3-Fluorocyclobutanamine hydrochloride | 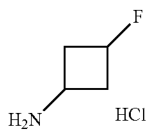 | 125.57 | 0.015 | — | 0.120 |
| 136 | 2-Cyclopropylethanamine | 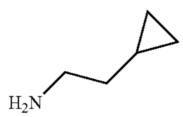 | 85.15 | 0.010 | — | 0.120 |
| 137 | 2-Ethoxycyclopropanamine | 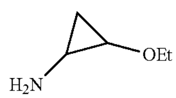 | 101.15 | 0.012 | — | 0.120 |
| 138 | (2-Aminocyclopropyl)methanol | 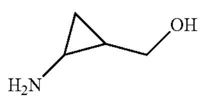 | 87.12 | 0.010 | — | 0.120 |

A stock solution of 1-((1H-indol-4-yl)methyl)-5-(methylcarbamoyl)-6-oxo-1,6-dihydropyridine-3-carboxylic acid (358 mg) was prepared in DMF (7.7 mL), along with HATU (502 mg), and DIPEA (0.57 mL), and was then capped and sonicated, before being aliquoted (0.7 mL) into vials containing the listed amine monomers (0.12 mmol). These were sealed and sonicated, then allowed to stand at rt for 18 h. The samples were then directly injected and purified by MDAP (High pH). The solvent was removed using a plate dryer to give the required products as indicated in the example table.

EXAMPLES

| Ex No. | Name | Structure | Mass (mg) | Yield (%) | [MH]+ | Rt (min)* |
|---|---|---|---|---|---|---|
| 135 | 1-((1H-Indol-4-yl)methyl)-N5-(3-fluorocyclobutyl)-N3-methyl-2-oxo-1,2-dihydropyridine-3,5-dicarboxamide | 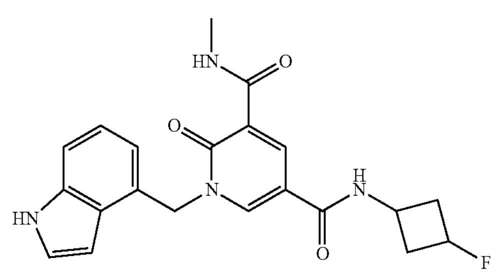 [SMILES: CNC(=O)c1cc(C(=O)NC2CC(F)C2)cn(Cc2cccc3[nH]ccc23)c1=O] | 24 | 55 | 397 | 0.85 |
| 136 | 1-((1H-Indol-4-yl)methyl)-N5-(2-cyclopropylethyl)-N3-methyl-2-oxo-1,2-dihydropyridine-3,5-dicarboxamide | 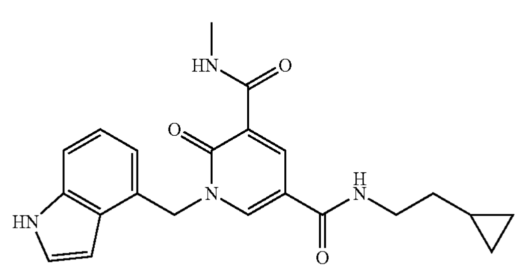 [SMILES: CNC(=O)c1cc(C(=O)NCCC2CC2)cn(Cc2cccc3[nH]ccc23)c1=O] | 26 | 61 | 393 | 0.93 |

| Ex No. | Name | Structure | Mass (mg) | Yield (%) | [MH]+ | Rt (min)* |
|---|---|---|---|---|---|---|
| 137 | (+/−)-1-((1H-Indol-4-yl)methyl)-N5-(2-ethoxycyclopropyl)-N3-methyl-2-oxo-1,2-dihydropyridine-3,5-dicarboxamide, single diastereomer with unknown relative stereochemistry | 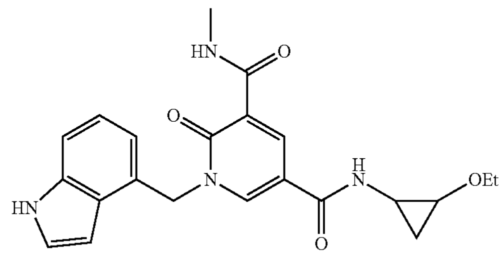 [SMILES: CCOC1CC1NC(=O)c1cc(C(=O)NC)c(=O)n(Cc2cccc3[nH]ccc23)c1] | 23 | 50 | 409 | 0.85 |
| 138 | (+/−)-1-((1H-Indol-4-yl)methyl)-N5-(2-(hydroxymethyl)cyclopropyl)-N3-methyl-2-oxo-1,2-dihydropyridine-3,5-dicarboxamide | 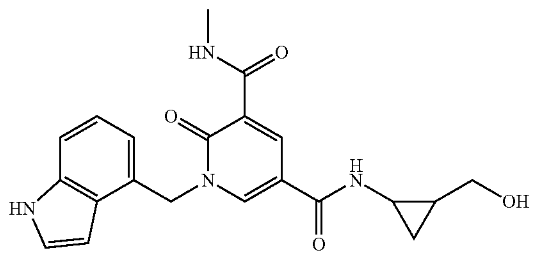 [SMILES: CNC(=O)c1cc(C(=O)NC2CC2CO)cn(Cc2cccc3[nH]ccc23)c1=O] | 27 | 62 | 395 | 0.71 |

*All LCMS were conducted using 2 min formic.

Example 139: (+/−)-1-((1H-Indol-4-yl)methyl)-N3-methyl-N5-((trans)-2-methylcyclopropyl)-2-oxo-1,2-dihydropyridine-3,5-dicarboxamide

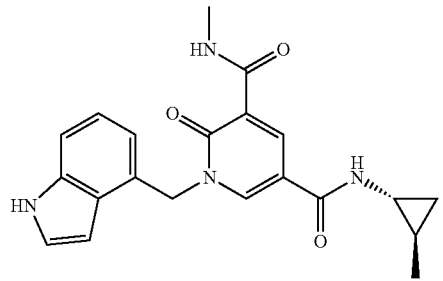 [SMILES: CNC(=O)c1cc(C(=O)N[C@@H]2C[C@H]2C)cn(Cc2cccc3[nH]ccc23)c1=O]

To a solution of 1-((1H-indol-4-yl)methyl)-5-(methylcarbamoyl)-6-oxo-1,6-dihydropyridine-3-carboxylic acid (150 mg, 0.304 mmol, 66% purity by wt), and HATU (174 mg, 0.456 mmol) in DMF (1.217 mL) stirred at rt was added (trans)-2-methylcyclopropanamine (43.3 mg, 0.609 mmol, commercially available from, for example, Enamine) and DIPEA (106 µL, 0.609 mmol). The reaction was stirred at rt for 3 h. The reaction mixture was poured onto water (30 mL) and extracted with ethyl acetate (4×30 mL). The combined organics were washed with brine, dried through a hydrophobic frit and evaporated in vacuo to yield the crude product as a yellow solid (223 mg). The solid was loaded in dichloromethane/methanol onto a 10 g SNAP cartridge and purified via Biotage SP4, eluting from 0-50% (3:1 ethyl acetate:ethanol)/cyclohexane. The relevant fractions were combined and evaporated in vacuo to yield the purified product (48 mg).

It was noted that the product had precipitated on silica and the column was flushed with 50% ethanol in ethyl acetate. The recovered fractions were combined and evaporated in vacuo to yield further product as a yellow solid (91 mg).

This sample was dissolved in MeOH:DMSO (1:1, 1 mL) and purified by MDAP (Formic). The solvent was combined with the initial batch of product (48 mg) and evaporated in vacuo to give (+/−)-1-((1H-indol-4-yl)methyl)-N3-methyl-N5-((trans)-2-methylcyclopropyl)-2-oxo-1,2-dihydropyridine-3,5-dicarboxamide (98 mg, 0.259 mmol, 85% yield).

LCMS (2 min Formic): Rt=0.86 min, [MH]+=379.2.

Example 140: (+/−)-N3-Methyl-1-(3-methylbenzyl)-N5-((cis)-2-methylcyclopropyl)-2-oxo-1,2-dihydropyridine-3,5-dicarboxamide

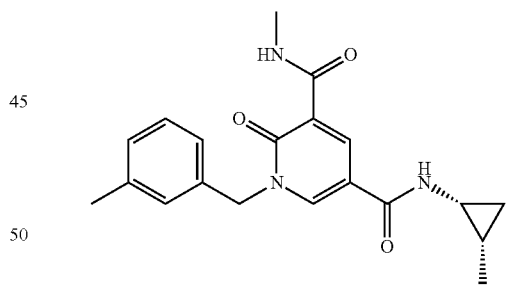

To a solution of 1-(3-methylbenzyl)-5-(methylcarbamoyl)-6-oxo-1,6-dihydropyridine-3-carboxylic acid (200.5 mg, 0.668 mmol) and HATU (310 mg, 0.815 mmol) in DMF (3 mL) was added 2-methylcyclopropanamine (94.1 mg, 1.323 mmol, commercially available from, for example, Fluorochem) and DIPEA (0.233 mL, 1.335 mmol). The mixture was stirred at rt for 1.5 h. Further HATU (129 mg, 0.339 mmol) and DIPEA (0.117 mL, 0.668 mmol) were added and stirring continued at rt for 0.5 h. The reaction mixture was concentrated under a stream of nitrogen before being made up to 3 mL with DMSO. This was then directly purified by MDAP (High pH). The appropriate fractions corresponding to the cis-diastereoisomer were concentrated under a stream of nitrogen before being dissolved in a mixture of dichloromethane/methanol (4 mL, 1:1), concentrated under a stream of nitrogen and dried in vacuo to give the product as a cream solid—(±)-N3-methyl-1-(3-methylbenzyl)-N5-((cis)-2-methylcyclopropyl)-2-oxo-1,2-dihydropyridine-3,5-dicarboxamide (11.3 mg, 0.032 mmol, 4.79% yield)

LCMS (2 min Formic): Rt=0.96 min, [MH]⁺=354.2.

The appropriate fractions corresponding to the trans-diastereoisomer were also combined and concentrated in vacuo before being dissolved in a mixture of dichloromethane/methanol (10 mL, 1:1), concentrated under a stream of nitrogen and dried in vacuo to give the product as a white solid, yield—(±)-N3-methyl-1-(3-methylbenzyl)-N5-((trans)-2-methylcyclopropyl)-2-oxo-1,2-dihydropyridine-3,5-dicarboxamide (172.6 mg, 0.488 mmol, 73.1% yield).

Example 141: (+/−)-N5-Cyclopropyl-1-(3-(1-hydroxyethyl)benzyl)-N3-methyl-2-oxo-1,2-dihydropyridine-3,5-dicarboxamide

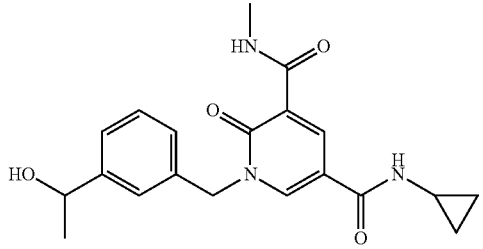 [SMILES: CNC(=O)c1cc(C(=O)NC2CC2)cn(Cc2cccc(C(C)O)c2)c1=O]

To a solution of N5-cyclopropyl-1-(3-formylbenzyl)-N3-methyl-2-oxo-1,2-dihydropyridine-3,5-dicarboxamide (183 mg, 0.518 mmol) in THF (10 mL) under nitrogen at −78° C. was added drop-wise a solution of methylmagnesium bromide (3M in diethyl ether) (0.690 mL, 2.071 mmol). The reaction was stirred at −78° C. for 45 min. The reaction was quenched with methanol while still at −78° C. The solution was warmed to ambient temperature and concentrated in vacuo. The residue was suspended in ethyl acetate (50 mL) and washed with water (50 mL). Some insoluble solid remained in the aqueous layer. The aqueous layer was back extracted with ethyl acetate (2×20 mL) and the combined organics were washed with brine (10 mL), dried through a hydrophobic frit and evaporated in vacuo to yield the crude product as a yellow glass (202 mg). The solid was loaded in the minimum volume of dichloromethane onto a SNAP cartridge (10 g) and purified via Biotage SP4 flash chromatography, eluting from 15-75% (3:1 ethyl acetate:ethanol)/cyclohexane. The relevant fractions were combined and evaporated in vacuo to yield a pale yellow gum (145 mg). The sample was dissolved in MeOH:DMSO (2×1 mL, 1:1) and purified by MDAP (High pH). The relevant fractions were combined and evaporated in vacuo to yield the desired product—N5-cyclopropyl-1-(3-(1-hydroxyethyl)benzyl)-N3-methyl-2-oxo-1,2-dihydropyridine-3,5-dicarboxamide (62 mg, 0.156 mmol, 30.1% yield) as a yellow solid. This product was combined with a second batch of the product prepared in an analogous manner, by sonicating together in diethyl ether and evaporating in vacuo to yield—N5-cyclopropyl-1-(3-(1-hydroxyethyl)benzyl)-N3-methyl-2-oxo-1,2-dihydropyridine-3,5-dicarboxamide (86.4 mg, 0.222 mmol, 42.9% yield) as a pale yellow solid.

LCMS (2 min Formic): Rt=0.69 min, [MH]⁺=370.2.

Example 142: N5-((1R,2R)-2-(Hydroxymethyl)cyclopropyl)-1-(3-methoxybenzyl)-N3-methyl-2-oxo-1,2-dihydropyridine-3,5-dicarboxamide

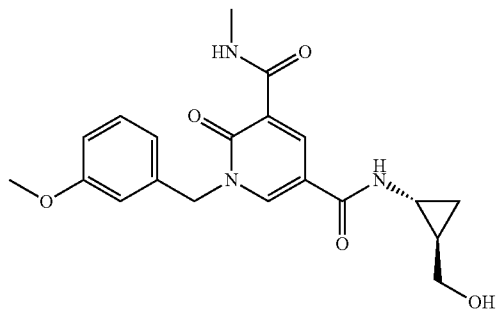 [SMILES: CNC(=O)c1cc(C(=O)N[C@@H]2C[C@H]2CO)cn(Cc2cccc(OC)c2)c1=O]

(+/−)-N5-((trans)-2-(Hydroxymethyl)cyclopropyl)-1-(3-methoxybenzyl)-N3-methyl-2-oxo-1,2-dihydropyridine-3,5-dicarboxamide (161 mg, 0.418 mmol, for example from example 132) was separated into its two enantiomers:

Analytical Method:

The racemate (~0.5 mg) was dissolved in 50% EtOH/Heptane (1 mL), 20 uL was injected onto the column. (Column: 4.6 mm id×25 cm Chiralpak IA, Lot No. IA00CE-KL030). This was eluted with 50% EtOH (+0.2% isopropylamine)/Heptane, f=1.0 mL/min, detector wavelength 230 nm, 4. Ref 550,100.

Preparative Method:

The racemate (~151 mg) was dissolved in DCM (2 mL) and EtOH (4 mL) with heating. Injection: 3 mL of the solution was injected onto the column (Column: 30 mm×25 cm Chiralpak IA (5 μm), Lot No. IA11157-01) This was eluted with 50% EtOH (+0.2% isopropylamine)/Heptane (+0.2% isopropylamine), flow rate=30 mL/min, detector wavelength=215 nm, 4. Ref 550, 100. Total number of injections: 2. Fractions from 18-23 min were bulked and labelled peak 1. Fractions from 26.5-36 min were bulked and labelled peak 2. The bulked fractions were vac'ed down using a rotary evaporator and then transferred to a weighed flask for final analysis as described by the analytical method above. The final material was recovered from DCM and heptane in order to obtain a solid.

Peak 1, Example 142, was collected as a white solid. (46 mg, 0.119 mmol, 28.6% yield)

LCMS (2 min Formic): Rt=0.75 min, [MH]⁺=386.1.

¹H NMR (400 MHz, DMSO-d₆) δ ppm 9.35 (br. q, J=4.2 Hz, 1H) 8.80 (d, J=2.7 Hz, 1H) 8.69 (d, J=2.7 Hz, 1H) 8.56 (br. d, J=4.4 Hz, 1H) 7.27 (t, J=7.8 Hz, 1H) 6.82-6.92 (m, 3H) 5.25 (s, 2H) 4.48 (t, J=5.5 Hz, 1H) 3.73 (s, 3H) 3.31-3.43 (m, 2H) 2.82 (d, J=4.9 Hz, 3H) 2.69-2.75 (m, 1H) 1.22 (dqd, J=9.1, 6.1, 6.1, 6.1, 3.4 Hz, 1H) 0.63-0.72 (m, 2H).

Example 143: N5-Cyclopropyl-1-(indolin-4-ylmethyl)-N3-methyl-2-oxo-1,2-dihydropyridine-3,5-dicarboxamide

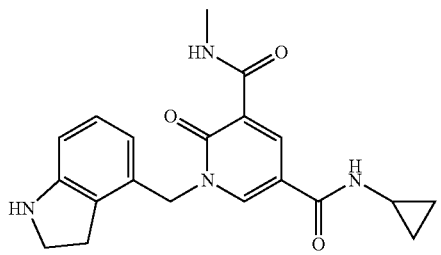

tert-Butyl 4-((5-(cyclopropylcarbamoyl)-3-(methylcarbamoyl)-2-oxopyridin-1(2H)-yl)methyl)indoline-1-carboxylate (43 mg, 0.092 mmol) and TFA (0.5 mL, 6.49 mmol) were stirred at rt in DCM for 30 min (2 mL). The reaction mixture was concentrated and loaded onto a SCX cartridge (5 g, pre-conditioned with MeOH) and eluted with MeOH (20 mL) followed by 2M $NH_3$ in MeOH (20 mL). The ammonia fractions containing product were combined and concentrated to give N5-cyclopropyl-1-(indolin-4-ylmethyl)-N3-methyl-2-oxo-1,2-dihydropyridine-3,5-dicarboxamide (30 mg, 0.074 mmol, 80% yield) as a yellow solid.

LCMS (2 min Formic): Rt=0.45 min, $[MH]^+$=367.2.

$^1$H NMR (400 MHz, MeOH-$d_4$) δ ppm 8.81 (d, J=2.7 Hz, 1H) 8.43 (d, J=2.7 Hz, 1H) 6.97 (t, J=7.8 Hz, 1H) 6.61 (d, J=7.8 Hz, 1H) 6.47 (d, J=7.6 Hz, 1H) 5.22 (s, 2H) 3.49 (t, J=8.4 Hz, 2H) 2.98 (t, J=8.4 Hz, 2H) 2.94 (s, 3H) 2.79 (tt, J=7.3, 3.8 Hz, 1H) 0.74-0.81 (m, 2H) 0.58-0.63 (m, 2H).

Example 144: N5-Cyclopropyl-N3-methyl-1-((1-methyl-1H-indol-4-yl)methyl)-2-oxo-1,2-dihydropyridine-3,5-dicarboxamide

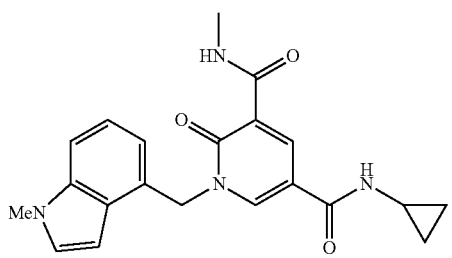 [SMILES: CNC(=O)c1cc(C(=O)NC2CC2)cn(Cc2cccc3c2ccn3C)c1=O]

To a solution of 1-((1H-indol-4-yl)methyl)-N5-cyclopropyl-N3-methyl-2-oxo-1,2-dihydropyridine-3,5-dicarboxamide (50 mg, 0.137 mmol, for example, Example 67) in DMF (900 μL) was added potassium carbonate (47.4 mg, 0.343 mmol) and iodomethane (17.16 μL, 0.274 mmol). The reaction was stirred at 80° C. for 2 h. A further portion of iodomethane (8.58 μL, 0.137 mmol) was added and stirring was continued for 19 h. A further portion of potassium carbonate (114 mg, 0.823 mmol) and iodomethane (42.9 μL, 0.686 mmol) were added. The reaction was continued for a further 24 h and was then concentrated in vacuo and filtered through cotton wool, however the filter became blocked. The filter was cleaned with methanol and the washings were combined and concentrated in vacuo. The residue was refiltered through cotton wool into a 1 mL vial, and diluted up to 1 mL with DMSO. The solution was purified by MDAP (Formic). The relevant fractions were dried under a stream of nitrogen to give the required product N5-cyclopropyl-N3-methyl-1-((1-methyl-1H-indol-4-yl)methyl)-2-oxo-1,2-dihydropyridine-3,5-dicarboxamide (12.3 mg, 0.031 mmol, 22.50% yield).

LCMS (2 min Formic): Rt=0.89 min, $[MH]^+$=379.3.

Example 145: N5-Cyclopropyl-N3-methyl-1-((2-methyl-1H-benzo[d]imidazol-4-yl)methyl)-2-oxo-1,2-dihydropyridine-3,5-dicarboxamide

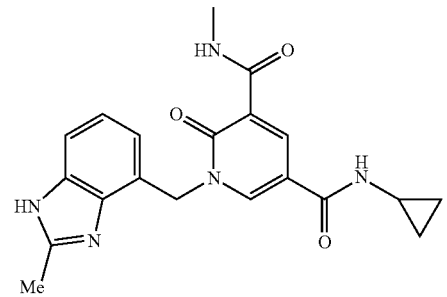 [SMILES: CNC(=O)c1cc(C(=O)NC2CC2)cn(Cc2cccc3[nH]c(C)nc23)c1=O]

tert-Butyl 7-((5-(cyclopropylcarbamoyl)-3-(methylcarbamoyl)-2-oxopyridin-1(2H)-yl)methyl)-2-methyl-1H-benzo[d]imidazole-1-carboxylate (10 mg, 0.021 mmol) was dissolved in HCl in IPA (0.634 μL, 0.021 mmol) and allowed to stir at rt over 3 days. The reaction mixture was concentrated under vacuum, dissolved in methanol and loaded onto a pre-conditioned SCX column (1 g). Methanol (10 mL) was then passed through the column followed by 2M methanolic ammonia. The methanolic ammonia fractions were combined and concentrated under vacuum to give the title compound (3.7 mg, 9.75 μmol, 46.8% yield).

LCMS (2 min Formic): Rt=0.42 min, $[MH]^+$=380.2.

Example 146: 1-(3-Methoxybenzyl)-N3-methyl-N5-((1S,2S)-2-methylcyclopropyl)-2-oxo-1,2-dihydropyridine-3,5-dicarboxamide

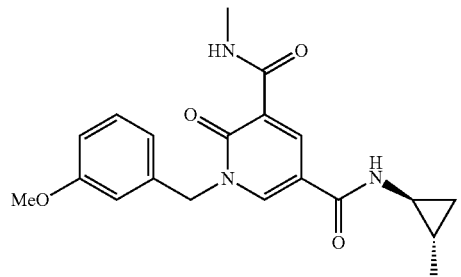

To a solution of N3-methyl-N5-((1S,2S)-2-methylcyclopropyl)-2-oxo-1,2-dihydropyridine-3,5-dicarboxamide (187 mg, 0.548 mmol) in DMF (3 mL) was added potassium carbonate (151 mg, 1.095 mmol) and 1-(bromomethyl)-3-methoxybenzene (165 mg, 0.821 mmol). The mixture was stirred at rt for 2 h. The reaction was quenched by the addition of water (30 mL) and EtOAc (30 mL) then added. The layers were separated and the aqueous layer further extracted with EtOAc (2×30 mL). The combined organics were then back-extracted with water (2×30 mL) and then brine (2×20 mL). The organic layer was dried (Na₂SO₄) and concentrated in vacuo to afford the crude product as a yellow oil. This was taken up in DCM and added to a SNAP (25 g) silica cartridge, this was purified by flash SP4 chromatography, eluting with 40→100% EtOAc/cyclohexane. The appropriate pure fractions were collected and concentrated in vacuo to afford the desired product as a colourless oil—1-(3-methoxybenzyl)-N3-methyl-N5-((1S,2S)-2-methylcyclopropyl)-2-oxo-1,2-dihydropyridine-3,5-dicarboxamide (115 mg, 0.311 mmol, 56.8% yield)

LCMS (2 min Formic): Rt=0.91 min, [MH]⁺=370.1.

Example 147: N5-Cyclopropyl-N3-methyl-1-((3-methyl-1H-indol-4-yl)methyl)-2-oxo-1,2-dihydropyridine-3,5-dicarboxamide

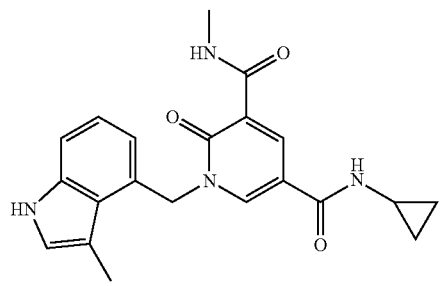 [SMILES: CNC(=O)c1cc(C(=O)NC2CC2)cn(Cc2cccc3[nH]cc(C)c23)c1=O]

To a solution of N5-cyclopropyl-N3-methyl-1-((3-methyl-1-tosyl-1H-indol-4-yl)methyl)-2-oxo-1,2-dihydropyridine-3,5-dicarboxamide (60 mg, 0.113 mmol) in methanol (376 μL) and THF (751 μL) stirred under nitrogen at rt was added solid cesium carbonate (147 mg, 0.451 mmol) in one charge. The reaction was heated to 70° C. for 2 h. The reaction mixture was concentrated in vacuo and taken up in ethyl acetate (30 mL) and water (10 mL). The aqueous layer was extracted with ethyl acetate (2×10 mL) and the combined organics were washed with brine (10 mL), dried through a hydrophobic frit and evaporated in vacuo to yield the crude product (38 mg). The sample was dissolved in MeOH:DMSO (1 mL, 1:1) and purified by MDAP (High pH). The solvent was dried under a stream of nitrogen to give N5-cyclopropyl-N3-methyl-1-((3-methyl-1H-indol-4-yl)methyl)-2-oxo-1,2-dihydropyridine-3,5-dicarboxamide (21 mg, 0.055 mmol, 49.3% yield) as an off white solid.

LCMS (2 min Formic): Rt=0.83 min, [MH]⁺=379.2.

Example 148: 1-((1H-Indazol-7-yl)methyl)-N3-methyl-N5-((1S,2S)-2-methylcyclopropyl)-2-oxo-1,2-dihydropyridine-3,5-dicarboxamide

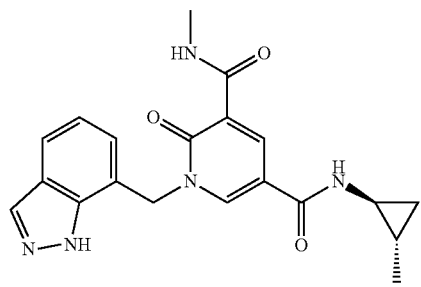 [SMILES: CNC(=O)c1cc(C(=O)N[C@H]2C[C@@H]2C)cn(Cc2cccc3cn[nH]c23)c1=O]

To a solution of 1-((1H-indazol-7-yl)methyl)-5-(methylcarbamoyl)-6-oxo-1,6-dihydropyridine-3-carboxylic acid (17 mg, 0.052 mmol) in DMF (2 mL) was added HATU (30 mg, 0.079 mmol) followed by (1S,2S)-2-methylcyclopropanamine, hydrochloride (8 mg, 0.074 mmol) and DIPEA (0.036 mL, 0.209 mmol). The resulting reaction mixture was stirred at rt under N₂ (formed a yellow solution) for 2.5 h. The crude reaction mixture was partitioned between ethyl acetate and a sat. solution of LiCl. The organic layer was separated and the aqueous layer further extracted with ethyl acetate. LCMS showed some product still in the aqueous layer so this was further extracted with DCM. The combined organic layers were dried (Na₂SO₄) and conc. to give ~5629 mg of a crude white solid contaminated with inorganics. This was purified by chromatography on SiO₂ (Biotage SNAP 10 g cartridge, eluting with 0-100% of ethyl acetate/cyclohexane) to give 1-((1H-indazol-7-yl)methyl)-N3-methyl-N5-((1S,2S)-2-methylcyclopropyl)-2-oxo-1,2-dihydropyridine-3,5-dicarboxamide (17 mg, 0.040 mmol, 77% yield) as a white solid.

LCMS (2 min Formic): Rt=0.82 min, [MH]⁺=380.0.

Example 149: (+/−)-N5-((trans)-2-Ethylcyclopropyl)-1-(3-(2-hydroxyethoxy)benzyl)-N3-methyl-2-oxo-1,2-dihydropyridine-3,5-dicarboxamide

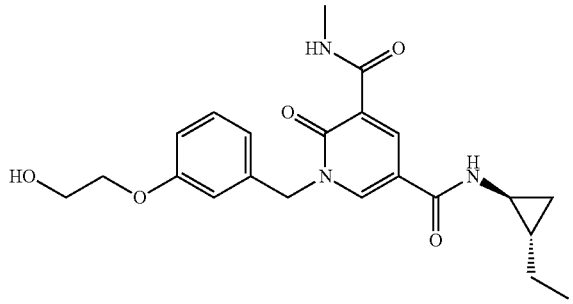 [SMILES: CC[C@H]1C[C@@H]1NC(=O)c1cc(C(=O)NC)c(=O)n(Cc2cccc(OCCO)c2)c1]

1-(3-(2-Hydroxyethoxy)benzyl)-5-(methylcarbamoyl)-6-oxo-1,6-dihydropyridine-3-carboxylic acid (150 mg, 0.433 mmol) was taken up in DMF (5 mL) and HATU (181 mg, 0.476 mmol), followed by DIPEA (0.076 mL, 0.433 mmol) were added. The reaction mixture was allowed to stir for 5 min, then (trans)-2-ethylcyclopropanamine, hydrochloride (57.9 mg, 0.476 mmol, commercially available from, for example, Enamine) was added and the reaction allowed to stir overnight. The reaction mixture was concentrated under vacuum and partitioned between ethyl acetate (20 mL) and citric acid solution (20 mL). The ethyl acetate layer was separated and washed with sodium bicarbonate solution (20 mL) and then washed with water (20 mL). The ethyl acetate layer was concentrated under vacuum and purified by MDAP (High pH). The appropriate fractions were combined and concentrated under vacuum to give the title compound (152 mg, 0.368 mmol, 85% yield) as a white solid. The solid was then dissolved in methanol and passed through a pre-prepared 2 g aminopropyl cartridge. The product containing fractions were combined to give the title compound (101 mg, 0.244 mmol, 56.4%) as a white solid.

LCMS (2 min Formic): Rt=0.84 min, [MH]⁺=414.2.

Example 150: 1-(Benzofuran-4-ylmethyl)-N5-cyclopropyl-N3-methyl-2-oxo-1,2-dihydropyridine-3,5-dicarboxamide

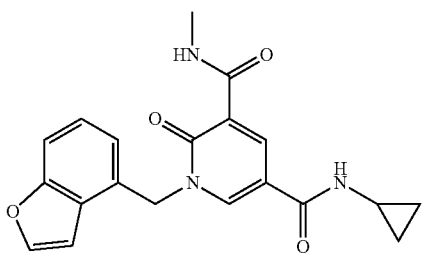 [SMILES: CNC(=O)c1cc(C(=O)NC2CC2)cn(Cc2cccc3occc23)c1=O]

N5-cyclopropyl-N3-methyl-2-oxo-1,2-dihydropyridine-3,5-dicarboxamide (44 mg, 0.187 mmol), 4-(bromomethyl)benzofuran (45 mg, 0.213 mmol), potassium carbonate (55 mg, 0.398 mmol) and DMF (1 mL) were stirred at 90° C. for 3 h. The suspension was partitioned between EtOAc (20 mL) and water (20 mL), extracted with EtOAc (20 mL), dried over a hydrophobic frit and concentrated to give 300 mg as a yellow oil. This was purified by chromatography on SiO$_2$ (Biotage SNAP 25 g cartridge, eluting with 0-100% EtOAc/cyclohexane). The appropriate fractions were concentrated to give 20 mg as a colourless oil. This was purified by MDAP (Formic, sample injected in 1 mL, 1:1 DMSO:MeOH). The appropriate fractions were concentrated to give 1-(benzofuran-4-ylmethyl)-N5-cyclopropyl-N3-methyl-2-oxo-1,2-dihydropyridine-3,5-dicarboxamide (13 mg, 0.032 mmol, 17.12% yield) as a colourless oil.

LCMS (2 min Formic): Rt=0.87 min, [MH]$^+$=366.1.

Example 151: N5-((trans)-2-(Hydroxymethyl)cyclopropyl)-N3-methyl-2-oxo-1-((S*)-1-(m-tolyl)ethyl)-1,2-dihydropyridine-3,5-dicarboxamide, 1:1 Mixture of Diastereomers at the cPr Stereocentres

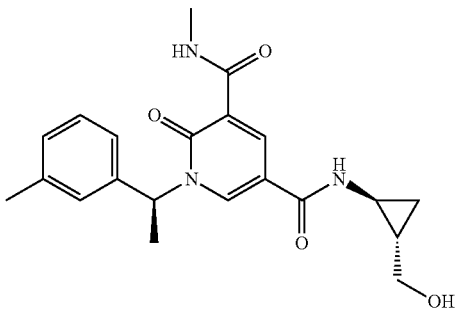 [SMILES: CNC(=O)c1cc(C(=O)N[C@H]2C[C@@H]2CO)cn([C@@H](C)c2cccc(C)c2)c1=O]

(S*)-5-(methylcarbamoyl)-6-oxo-1-(1-(m-tolyl)ethyl)-1,6-dihydropyridine-3-carboxylic acid (147 mg, 0.468 mmol), HATU (263 mg, 0.692 mmol), DIPEA (0.25 mL, 1.431 mmol), (+/−)-((trans)-2-aminocyclopropyl)methanol (85 mg, 0.976 mmol, commercially available from, for example, Enamine) and DMF (2 mL) were stirred at rt under N$_2$ for 1 h.

Further HATU (283 mg, 0.744 mmol), DIPEA (0.25 mL, 1.431 mmol) and (+/−)-((trans)-2-aminocyclopropyl)methanol (79 mg, 0.907 mmol) were added and the reaction stirred for 30 min. The solution was concentrated, partitioned between EtOAc (20 mL) and water (20 mL), extracted with EtOAc (2×20 mL), dried over a hydrophobic frit and concentrated to give 590 mg of a yellow oil. This was purified by chromatography on SiO$_2$ (Biotage SNAP 50 g cartridge, eluting with 0-50% (25% EtOAc in EtOH)/cyclohexane). The appropriate fractions were concentrated to give N5-((trans)-2-(hydroxymethyl)cyclopropyl)-N3-methyl-2-oxo-1-((S*))-1-(m-tolyl)ethyl)-1,2-dihydropyridine-3,5-dicarboxamide (204 mg, 0.468 mmol, 100% yield) as a mixture of diastereoisomers at the cPr stereocentres and as a colourless oil.

LCMS (2 min Formic): Rt=0.84 min, [MH]$^+$=384.2.

Example 152: (+/−)-1-(1-(1H-Indol-4-yl)ethyl)-N5-cyclopropyl-N3-methyl-2-oxo-1,2-dihydropyridine-3,5-dicarboxamide

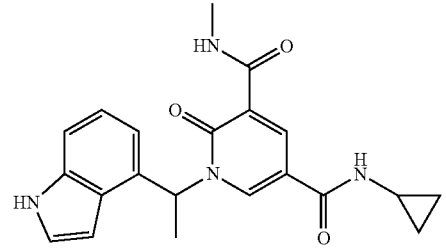 [SMILES: CNC(=O)c1cc(C(=O)NC2CC2)cn(C(C)c2cccc3[nH]ccc23)c1=O]

To a solution of N5-cyclopropyl-N3-methyl-2-oxo-1-(1-(1-tosyl-1H-indol-4-yl)ethyl)-1,2-dihydropyridine-3,5-dicarboxamide (40 mg, 0.075 mmol) in methanol (0.5 mL) and THF (1 mL) stirred under nitrogen at rt, cesium carbonate (186 mg, 0.571 mmol) was added and the reaction mixture was stirred at 70° C. for 1 h. The solution was partitioned between EtOAc (10 mL) and water (10 mL), extracted with EtOAc (2×20 mL), dried over a hydrophobic frit and concentrated to give 50 mg as an off white solid. This was purified by chromatography on SiO$_2$ (Biotage SNAP 25 g cartridge, eluting with 0-100% EtOAc/cyclohexane). The appropriate fractions were concentrated to give 1-(1-(1H-indol-4-yl)ethyl)-N5-cyclopropyl-N3-methyl-2-oxo-1,2-dihydropyridine-3,5-dicarboxamide (27 mg, 0.064 mmol, 86% yield) a colourless oil.

LCMS (2 min Formic): Rt=0.85 min, [MH]$^+$=379.2.

Example 153: 1-(3-(2-Hydroxyethoxy)benzyl)-N3-methyl-N5-((1S,2S)-2-methylcyclopropyl)-2-oxo-1,2-dihydropyridine-3,5-dicarboxamide

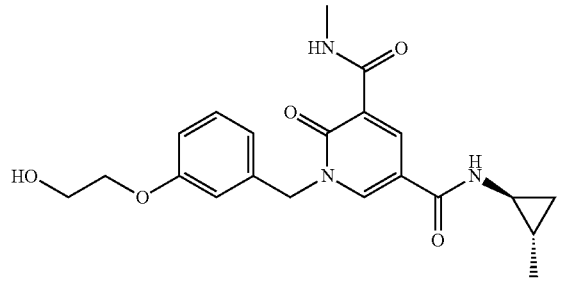 [SMILES: CNC(=O)c1cc(C(=O)N[C@H]2C[C@@H]2C)cn(Cc2cccc(OCCO)c2)c1=O]

1-(3-(2-Hydroxyethoxy)benzyl)-5-(methylcarbamoyl)-6-oxo-1,6-dihydropyridine-3-carboxylic acid (80 mg, 0.231 mmol) was taken up in DMF (2.5 mL) and HATU (97 mg, 0.254 mmol) followed by DIPEA (0.081 mL, 0.462 mmol) were added. The reaction mixture was allowed to stir for 5 min, then (1S,2S)-2-methylcyclopropanamine, hydrochloride (27.3 mg, 0.254 mmol) was added and the reaction allowed to stir overnight. The reaction mixture was concentrated under vacuum and partitioned between ethyl acetate (20 mL) and citric acid solution (20 mL). The ethyl acetate layer was separated and washed with sodium bicarbonate solution (20 mL) and then washed with water (20 mL). The ethyl acetate layer was concentrated under vacuum and purified by MDAP (High pH). The appropriate fractions were combined and concentrated under vacuum to give the title compound (8 mg, 0.020 mmol, 8.67% yield) as a white solid.

LCMS (2 min Formic): Rt=0.76 min, [MH]+=400.2.

$^1$H NMR (400 MHz, MeOH-d$_4$) δ ppm 8.81 (d, J=2.7 Hz, 1H) 8.52 (d, J=2.9 Hz, 1H) 7.27 (t, J=7.9 Hz, 1H) 6.84-7.00 (m, 3H) 5.27 (s, 2H) 4.03 (app. t, J=4.6 Hz, 2H) 3.85 (app. t, J=4.8 Hz, 2H) 2.94 (s, 3H) 2.48 (dt, J=7.3, 3.6 Hz, 1H) 1.11 (d, J=6.1 Hz, 3H) 0.91-1.03 (m, 1H) 0.78 (ddd, J=9.2, 5.3, 4.2 Hz, 1H) 0.52-0.59 (m, 1H).

Example 154: 1-((1H-Indol-4-yl)methyl)-N5-((1S*, 2S*)-2-(hydroxymethyl)cyclopropyl)-N3-methyl-2-oxo-1,2-dihydropyridine-3,5-dicarboxamide and Example 155: 1-((1H-Indol-4-yl)methyl)-N5-((1R*, 2R*)-2-(hydroxymethyl)cyclopropyl)-N3-methyl-2-oxo-1,2-dihydropyridine-3,5-dicarboxamide

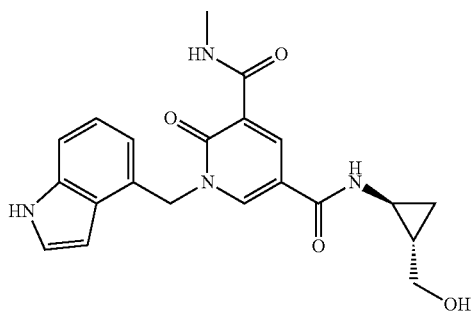

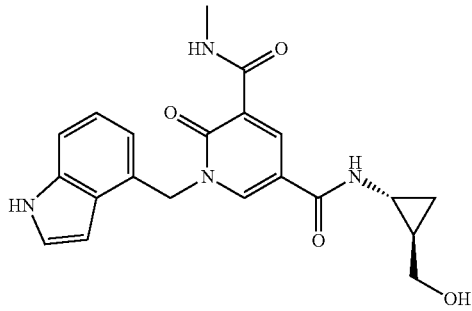

To a solution of 1-((1H-indol-4-yl)methyl)-5-(methylcarbamoyl)-6-oxo-1,6-dihydropyridine-3-carboxylic acid (150 mg, 0.304 mmol), and HATU (174 mg, 0.456 mmol) in DMF (1.217 mL) stirred at rt was added (+/−)-((trans)-2-aminocyclopropyl)methanol (53.0 mg, 0.609 mmol, commercially available from, for example, Enamine) and DIPEA (106 μl, 0.609 mmol). The reaction was stirred at rt for 2 h. The reaction mixture was poured onto water (30 mL) and extracted with ethyl acetate (4×30 mL). The combined organics were washed with brine, dried through a hydrophobic frit and evaporated in vacuo to yield the crude product as a yellow oil (214 mg). The oil was loaded in DCM/methanol onto a 25 g SNAP cartridge and purified via Biotage SP4 flash chromatography, eluting from 5-25% (80:20 DCM:methanol)/DCM. The relevant fractions were combined and evaporated in vacuo, sonicated with diethyl ether and evaporated again to yield the pure product 1-((1H-indol-4-yl)methyl)-N5-((trans)-2-(hydroxymethyl)cyclopropyl)-N3-methyl-2-oxo-1,2-dihydropyridine-3,5-dicarboxamide (109 mg, 0.263 mmol, 86% yield) as a white solid which was submitted for chiral purification chromatography.

Analytical Method:

The racemate (~0.5 mg) was dissolved in 50% EtOH/Heptane (1 mL). 20 uL was injected on column. (Column: 4.6 mmid×25 cm Chiralpak AD-H, Lot No. ADH0CE-PC014). This was eluted with 50% EtOH/Heptane, f=1.0 mL/min, detector wavelength=215 nm, 4. Ref 550,100

Prep Method:

The racemate (~107 mg) was dissolved in EtOH (1 mL). Injection: 1 mL of the solution was injected onto the column. (Column: 30 mm×25 cm Chiralpak AD-H (5 μm), Lot No. ADH13231-01). This was eluted with 50% EtOH/Heptane, f=30 mL/min, detector wavelength=215 nm, 4. Ref 550,100. Fraction Collection: Fractions from 17-26 min were bulked and labelled peak 1, fractions from 34-50 min were bulked and labelled peak 2. The bulked fractions were vac'ed down using a rotary evaporator and then transferred to a weighed flask for final analysis as described by the analytical method above.

The first eluting enantiomer—1-((1H-indol-4-yl)methyl)-N5-((1S*,2S*)-2-(hydroxymethyl)cyclopropyl)-N3-methyl-2-oxo-1,2-dihydropyridine-3,5-dicarboxamide (48 mg, 0.116 mmol, 38.0% yield).

LCMS (2 min Formic): Rt=0.69 min, [MH]+=395.2.

The second eluting enantiomer 1-((1H-indol-4-yl)methyl)-N5-((1R*,2R*)-2-(hydroxymethyl)cyclopropyl)-N3-methyl-2-oxo-1,2-dihydropyridine-3,5-dicarboxamide (49 mg, 0.118 mmol, 38.8% yield).

LCMS (2 min Formic): Rt=0.70 min, [MH]+=395.2.

Example 156: 1-(3-Methoxybenzyl)-N3-methyl-N5-((1R,2R)-2-methylcyclopropyl)-2-oxo-1,2-dihydropyridine-3,5-dicarboxamide

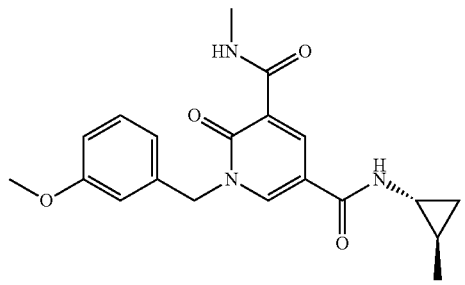 [SMILES: CNC(=O)c1cc(C(=O)N[C@@H]2C[C@H]2C)cn(Cc2cccc(OC)c2)c1=O]

To a solution of N3-methyl-N5-((1R,2R)-2-methylcyclopropyl)-2-oxo-1,2-dihydropyridine-3,5-dicarboxamide (60 mg, 0.190 mmol) in DMF (1 mL) was added potassium carbonate (52.6 mg, 0.380 mmol) and 1-(bromomethyl)-3-methoxybenzene (57.4 mg, 0.285 mmol). The mixture was stirred at rt for 2 h. The reaction was quenched by the addition of water (20 mL) and EtOAc (20 mL) then added. The layers were separated and the aqueous layer further extracted with EtOAc (2×20 mL). The combined organics were then back-extracted with water (20 mL) and then brine (2×20 mL). The organic layer was dried (Na$_2$SO$_4$) and concentrated in vacuo to afford the crude product as a yellow oil. This was taken up in DCM and added to a SNAP (10 g) silica cartridge, this was purified by flash SP4 chromatography, eluting with 40→100% EtOAc/cyclohexane. The appropriate fractions were collected and concentrated in vacuo to afford the desired product as a colourless oil (58 mg). The sample was taken up in DCM/MeOH and concentrated in vacuo at 45° C. (×3). The resultant colourless gum—1-(3-methoxybenzyl)-N3-methyl-N5-((1R,2R)-2-methylcyclopropyl)-2-oxo-1,2-dihydropyridine-3,5-dicarboxamide (46 mg, 0.125 mmol, 65.5% yield) was re-analysed.

LCMS (2 min Formic): Rt=0.91 min, [MH]$^+$=370.1.

Examples 157-268

Examples 157-268 were prepared in an analogous manner to the previous examples

| Ex No. | Name | Structure | [MH]$^+$ | Rt (min)* |
|---|---|---|---|---|
| 157 | N5-Cyclopropyl-1-(cyclopropyl(phenyl)methyl)-N3-methyl-2-oxo-1,2-dihydropyridine-3,5-dicarboxamide | 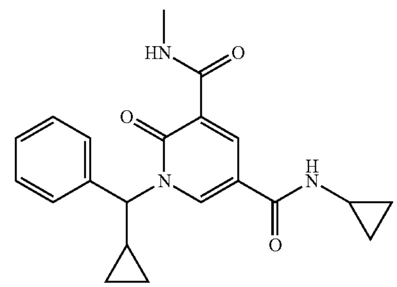 [SMILES: CNC(=O)c1cc(C(=O)NC2CC2)cn(C(c2ccccc2)C2CC2)c1=O] | 366.1 (formic) | 0.99 |
| 158 | 1-Benzyl-N5-(cyclobutylmethyl)-N3-methyl-2-oxo-1,2-dihydropyridine-3,5-dicarboxamide | 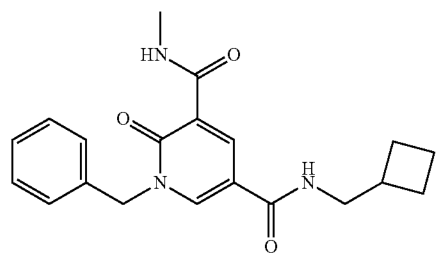 [SMILES: CNC(=O)c1cc(C(=O)NCC2CCC2)cn(Cc2ccccc2)c1=O] | 354.0 (formic) | 1.01 |
| 159 | N5-Cyclobutyl-N3-methyl-2-oxo-1-(pyridin-4-ylmethyl)-1,2-dihydropyridine-3,5-dicarboxamide | 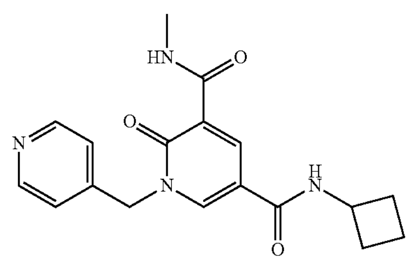 [SMILES: CNC(=O)c1cc(C(=O)NC2CCC2)cn(Cc2ccncc2)c1=O] | 341.0 (formic) | 0.46 |
| 160 | N5-Cyclobutyl-N3-methyl-2-oxo-1-(pyridin-2-ylmethyl)-1,2-dihydropyridine-3,5-dicarboxamide | 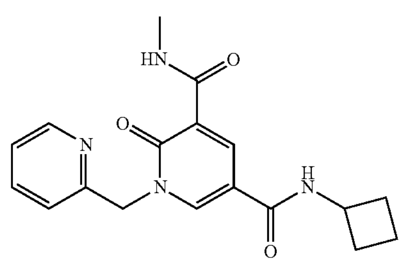 [SMILES: CNC(=O)c1cc(C(=O)NC2CCC2)cn(Cc2ccccn2)c1=O] | 341.0 (formic) | 0.71 |
| 161 | N5-Cyclobutyl-N3-methyl-2-oxo-1-(pyridin-3-ylmethyl)-1,2-dihydropyridine-3,5-dicarboxamide | 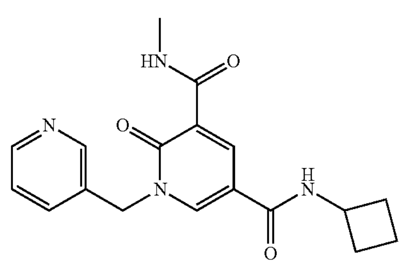 [SMILES: CNC(=O)c1cc(C(=O)NC2CCC2)cn(Cc2cccnc2)c1=O] | 341.0 (formic) | 0.51 |

| Ex No. | Name | Structure | [MH]+ | Rt (min)* |
|---|---|---|---|---|
| 162 | N5-Cyclobutyl-1-(2-fluorobenzyl)-N3-methyl-2-oxo-1,2-dihydropyridine-3,5-dicarboxamide | 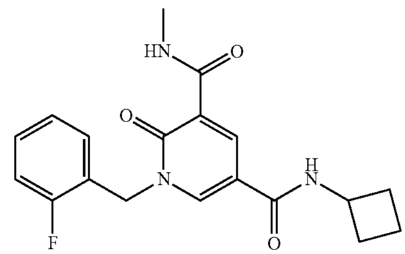 [SMILES: CNC(=O)c1cc(C(=O)NC2CCC2)cn(Cc2ccccc2F)c1=O] | 358.0 (formic) | 0.96 |
| 163 | N5-Cyclobutyl-N3-methyl-1-((1-methyl-1H-pyrazol-4-yl)methyl)-2-oxo-1,2-dihydropyridine-3,5-dicarboxamide | 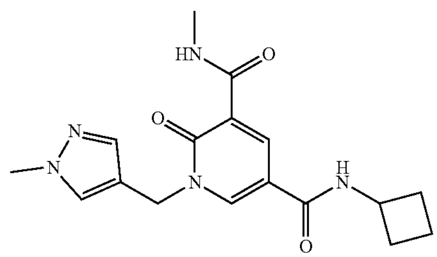 [SMILES: CNC(=O)c1cc(C(=O)NC2CCC2)cn(Cc2cnn(C)c2)c1=O] | 344.0 (formic) | 0.69 |
| 164 | N5-Cyclobutyl-1-(2,5-dimethylbenzyl)-N3-methyl-2-oxo-1,2-dihydropyridine-3,5-dicarboxamide | 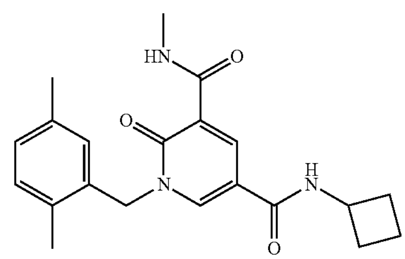 [SMILES: CNC(=O)c1cc(C(=O)NC2CCC2)cn(Cc2cc(C)ccc2C)c1=O] | 368.0 (formic) | 1.09 |
| 165 | 1-Benzyl-N5-((cis)-3-hydroxycyclobutyl)-N3-methyl-2-oxo-1,2-dihydropyridine-3,5-dicarboxamide | 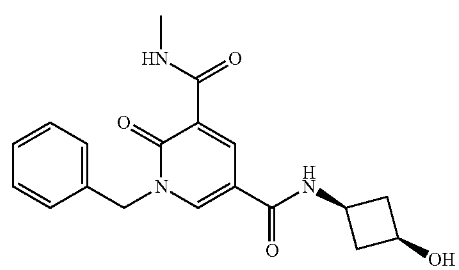 [SMILES: CNC(=O)c1cc(C(=O)N[C@H]2C[C@@H](O)C2)cn(Cc2ccccc2)c1=O] | 356.0 (formic) | 0.73 |
| 166 | 1-Benzyl-N5-(3,3-difluorocyclobutyl)-N3-methyl-2-oxo-1,2-dihydropyridine-3,5-dicarboxamide | 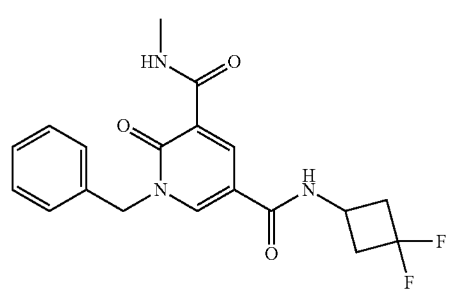 [SMILES: CNC(=O)c1cc(C(=O)NC2CC(F)(F)C2)cn(Cc2ccccc2)c1=O] | 376.0 (formic) | 0.94 |

| Ex No. | Name | Structure | [MH]+ | Rt (min)* |
|---|---|---|---|---|
| 167 | tert-Butyl (6-(1-benzyl-5-(methylcarbamoyl)-6-oxo-1,6-dihydropyridine-3-carboxamido)spiro[3.3]heptan-2-yl)carbamate | 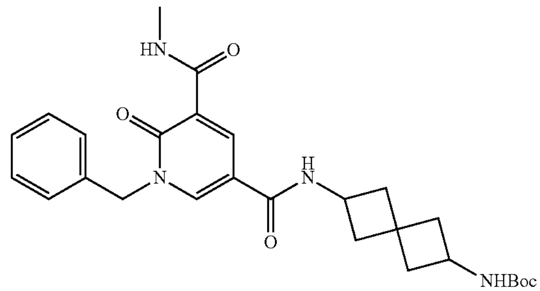 [SMILES: CNC(=O)c1cc(C(=O)NC2CC3(CC(NC(=O)OC(C)(C)C)C3)C2)cn(Cc2ccccc2)c1=O] | 495.2 (formic) | 1.09 |
| 168 | 1-Benzyl-N3-methyl-2-oxo-N5-(2-phenylcyclobutyl)-1,2-dihydropyridine-3,5-dicarboxamide | 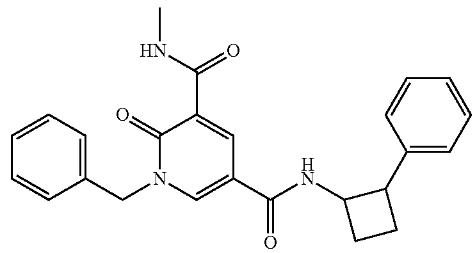 [SMILES: CNC(=O)c1cc(C(=O)NC2CCC2c2ccccc2)cn(Cc2ccccc2)c1=O] | 416.1 (formic) | 1.07 |
| 169 | (cis)-3-(1-Benzyl-5-(methylcarbamoyl)-6-oxo-1,6-dihydropyridine-3-carboxamido)cyclobutanecarboxylic acid | 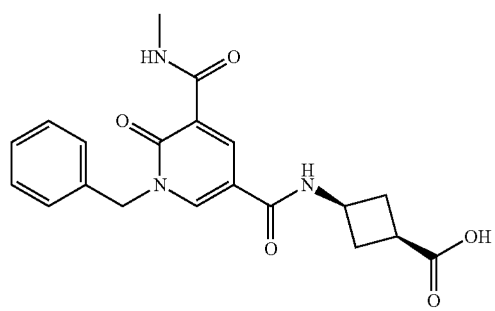 [SMILES: CNC(=O)c1cc(C(=O)N[C@H]2C[C@@H](C(=O)O)C2)cn(Cc2ccccc2)c1=O] | 384.0 (formic) | 0.78 |
| 170 | N5-Cyclobutyl-1-(isoquinolin-5-ylmethyl)-N3-methyl-2-oxo-1,2-dihydropyridine-3,5-dicarboxamide | 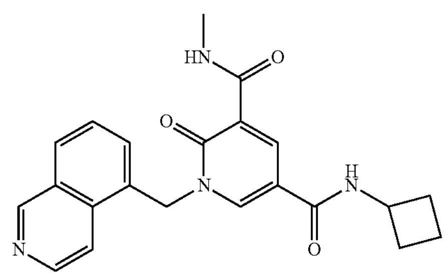 [SMILES: CNC(=O)c1cc(C(=O)NC2CCC2)cn(Cc2cccc3cnccc23)c1=O] | 391.0 (formic) | 0.55 |
| 171 | (S)-N5-Cyclobutyl-N3-methyl-2-oxo-1-(1-phenylethyl)-1,2-dihydropyridine-3,5-dicarboxamide | 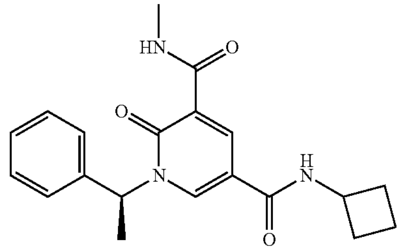 [SMILES: CNC(=O)c1cc(C(=O)NC2CCC2)cn([C@@H](C)c2ccccc2)c1=O] | 354.0 (formic) | 0.98 |

| Ex No. | Name | Structure | [MH]⁺ | Rt (min)* |
|---|---|---|---|---|
| 172 | 1-Benzyl-N5-cyclobutyl-N3-ethyl-2-oxo-1,2-dihydropyridine-3,5-dicarboxamide | 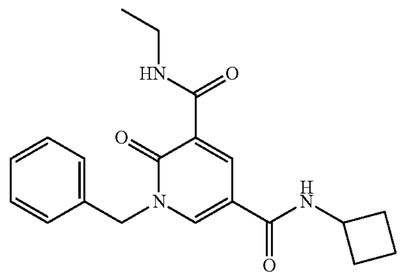 [SMILES: CCNC(=O)c1cc(C(=O)NC2CCC2)cn(Cc2ccccc2)c1=O] | 354.1 (formic) | 0.99 |
| 173 | 1-Benzyl-N5-(1-isobutylcyclopropyl)-N3-methyl-2-oxo-1,2-dihydropyridine-3,5-dicarboxamide | 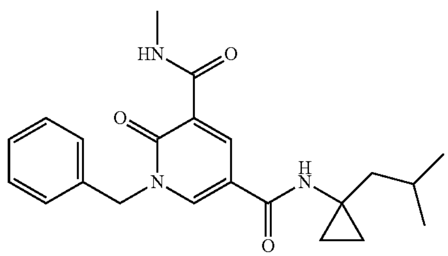 [SMILES: CNC(=O)c1cc(C(=O)NC2(CC(C)C)CC2)cn(Cc2ccccc2)c1=O] | 382.0 (formic) | 1.09 |
| 174 | 1-Benzyl-N5-(3-methoxy-2,2-dimethylcyclobutyl)-N3-methyl-2-oxo-1,2-dihydropyridine-3,5-dicarboxamide | 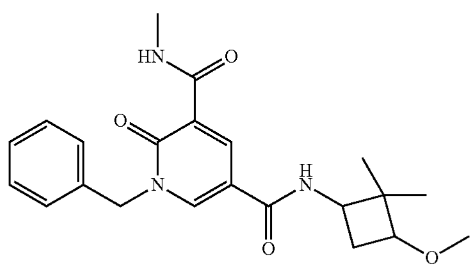 [SMILES: CNC(=O)c1cc(C(=O)NC2CC(OC)C2(C)C)cn(Cc2ccccc2)c1=O] | 398.1 (formic) | 0.96 |
| 175 | 1-Benzyl-N5-(3-ethoxycyclobutyl)-N3-methyl-2-oxo-1,2-dihydropyridine-3,5-dicarboxamide | 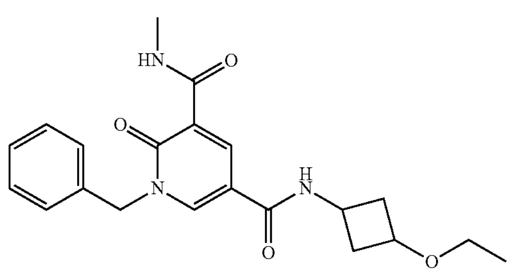 [SMILES: CCOC1CC(NC(=O)c2cc(C(=O)NC)c(=O)n(Cc3ccccc3)c2)C1] | 384.1 (formic) | 0.90 |
| 176 | 1-Benzyl-N3-methyl-N5-(3-methylcyclobutyl)-2-oxo-1,2-dihydropyridine-3,5-dicarboxamide | 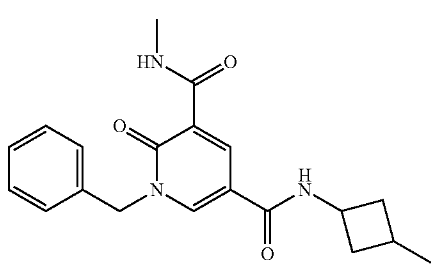 [SMILES: CNC(=O)c1cc(C(=O)NC2CC(C)C2)cn(Cc2ccccc2)c1=O] | 354.0 (formic) | 1.00 |

-continued

| Ex No. | Name | Structure | [MH]+ | Rt (min)* |
|---|---|---|---|---|
| 177 | 1-Benzyl-N5-(3-ethoxy-2-methoxycyclobutyl)-N3-methyl-2-oxo-1,2-dihydropyridine-3,5-dicarboxamide | 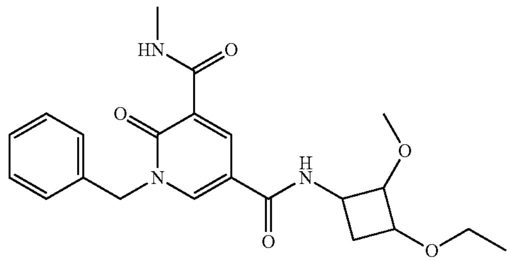 [SMILES: CCOC1CC(NC(=O)c2cc(C(=O)NC)c(=O)n(Cc3ccccc3)c2)C1OC] | 414.1 (formic) | 0.90 |
| 178 | 1-Benzyl-N3-methyl-2-oxo-N5-(1-propylcyclopropyl)-1,2-dihydropyridine-3,5-dicarboxamide | 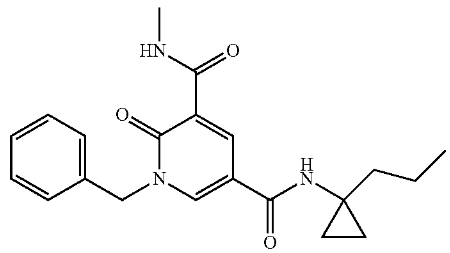 [SMILES: CCCC1(NC(=O)c2cc(C(=O)NC)c(=O)n(Cc3ccccc3)c2)CC1] | 368.1 (formic) | 1.02 |
| 179 | (S)-N5-Cyclopropyl-N3-methyl-2-oxo-1-(1-phenylethyl)-1,2-dihydropyridine-3,5-dicarboxamide | 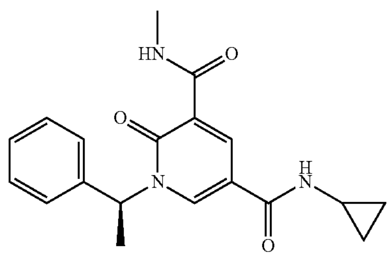 [SMILES: CNC(=O)c1cc(C(=O)NC2CC2)cn([C@@H](C)c2ccccc2)c1=O] | 340.0 (formic) | 0.88 |
| 180 | Methyl 4-((5-(cyclobutylcarbamoyl)-3-(methylcarbamoyl)-2-oxopyridin-1(2H)-yl)methyl)benzoate | 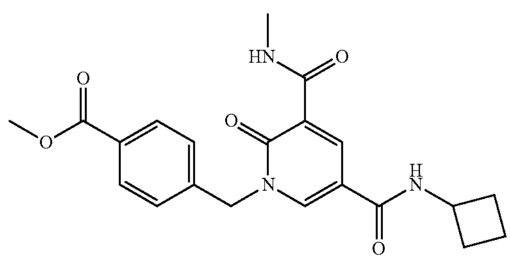 [SMILES: CNC(=O)c1cc(C(=O)NC2CCC2)cn(Cc2ccc(C(=O)OC)cc2)c1=O] | 398.0 (formic) | 0.90 |
| 181 | 1-Benzyl-N5-(2-ethoxycyclopropyl)-N3-methyl-2-oxo-1,2-dihydropyridine-3,5-dicarboxamide | 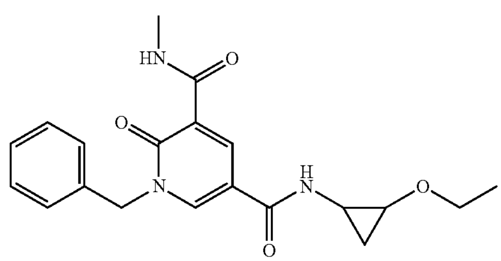 [SMILES: CCOC1CC1NC(=O)c1cc(C(=O)NC)c(=O)n(Cc2ccccc2)c1] | 370.2 (formic) | 0.88 |
| 182 | N5-Cyclobutyl-N3-methyl-2-oxo-1-(quinolin-5-ylmethyl)-1,2-dihydropyridine-3,5-dicarboxamide | 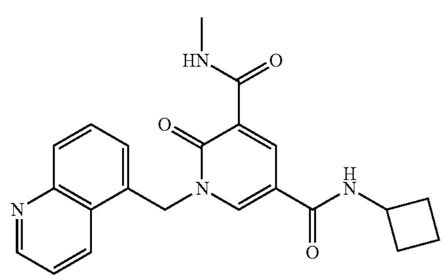 [SMILES: CNC(=O)c1cc(C(=O)NC2CCC2)cn(Cc2cccc3ncccc23)c1=O] | 391.2 (formic) | 0.62 |

| Ex No. | Name | Structure | [MH]+ | Rt (min)* |
|---|---|---|---|---|
| 183 | 1-Benzyl-N5-((1S,3R)-3-hydroxycyclopentyl)-N3-methyl-2-oxo-1,2-dihydropyridine-3,5-dicarboxamide | 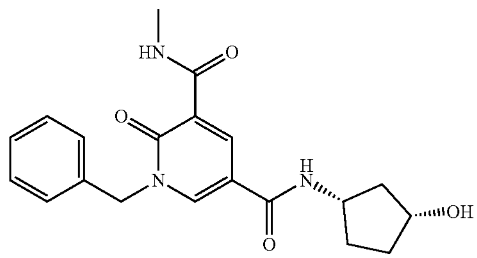 [SMILES: CNC(=O)c1cc(C(=O)N[C@H]2CC[C@@H](O)C2)cn(Cc2ccccc2)c1=O] | 370.3 (formic) | 0.77 |
| 184 | 1-(3-Cyanobenzyl)-N5-cyclopropyl-N3-methyl-2-oxo-1,2-dihydropyridine-3,5-dicarboxamide | 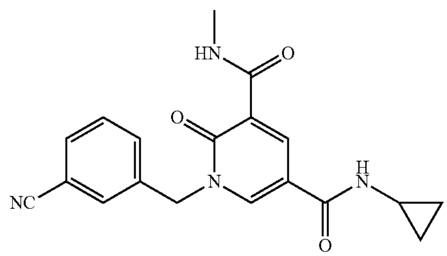 [SMILES: CNC(=O)c1cc(C(=O)NC2CC2)cn(Cc2cccc(C#N)c2)c1=O] | 351.1 (formic) | 0.76 |
| 185 | (+/−)-1-Benzyl-N5-((trans)-2-hydroxycyclohexyl)-N3-methyl-2-oxo-1,2-dihydropyridine-3,5-dicarboxamide | 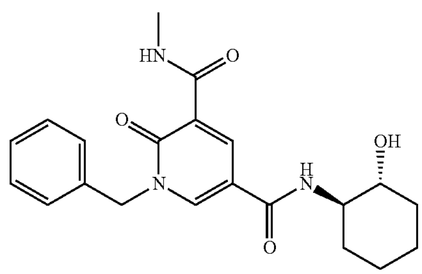 [SMILES: CNC(=O)c1cc(C(=O)N[C@@H]2CCCC[C@H]2O)cn(Cc2ccccc2)c1=O] | 384.3 (formic) | 0.84 |
| 186 | (+/−)-1-Benzyl-N5-((cis)-2-hydroxycyclohexyl)-N3-methyl-2-oxo-1,2-dihydropyridine-3,5-dicarboxamide | 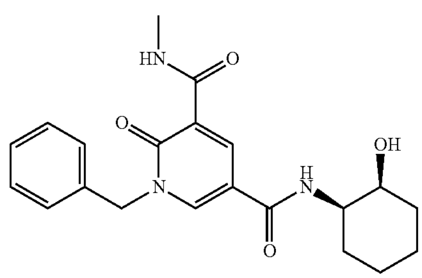 [SMILES: CNC(=O)c1cc(C(=O)N[C@@H]2CCCC[C@@H]2O)cn(Cc2ccccc2)c1=O] | 384.3 (formic) | 0.86 |
| 187 | N5-Cyclopropyl-N3-methyl-1-((6-methylpyridin-2-yl)methyl)-2-oxo-1,2-dihydropyridine-3,5-dicarboxamide | 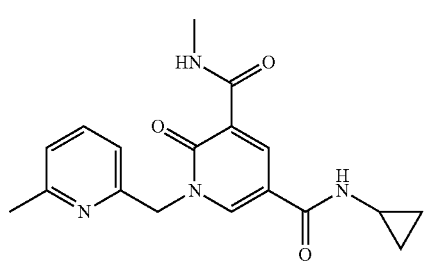 [SMILES: CNC(=O)c1cc(C(=O)NC2CC2)cn(Cc2cccc(C)n2)c1=O] | 341.1 (formic) | 0.55 |

-continued

| Ex No. | Name | Structure | [MH]+ | Rt (min)* |
|---|---|---|---|---|
| 188 | (R*)-1-Benzyl-N5-(2,2-difluorocyclopropyl)-N3-methyl-2-oxo-1,2-dihydropyridine-3,5-dicarboxamide | 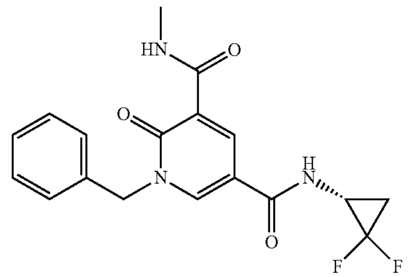 [SMILES: CNC(=O)c1cc(C(=O)N[C@@H]2CC2(F)F)cn(Cc2ccccc2)c1=O] | 362.1 (formic) | 0.88 |
| 189 | (+/−)-1-Benzyl-N5-(2-hydroxycyclopentyl)-N3-methyl-2-oxo-1,2-dihydropyridine-3,5-dicarboxamide, single diastereomer, unknown relative stereochemistry | 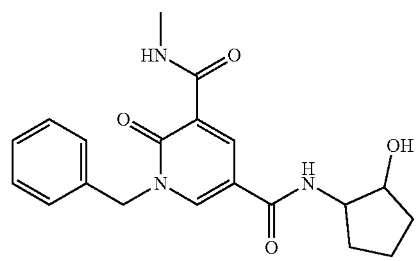 [SMILES: CNC(=O)c1cc(C(=O)NC2CCCC2O)cn(Cc2ccccc2)c1=O] | 370.3 (formic) | 0.80 |
| 190 | N5-Cyclopropyl-N3-methyl-2-oxo-1-(3-phenylpropyl)-1,2-dihydropyridine-3,5-dicarboxamide | 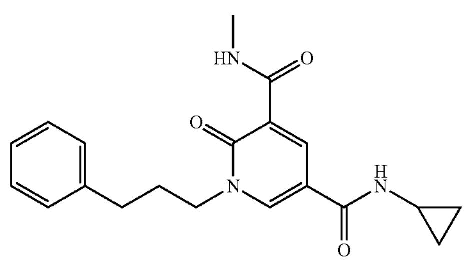 [SMILES: CNC(=O)c1cc(C(=O)NC2CC2)cn(CCCc2ccccc2)c1=O] | 354.1 (formic) | 0.93 |
| 191 | N5-Cyclopropyl-N3-methyl-2-oxo-1-phenethyl-1,2-dihydropyridine-3,5-dicarboxamide | 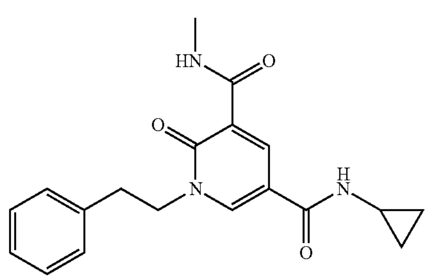 [SMILES: CNC(=O)c1cc(C(=O)NC2CC2)cn(CCc2ccccc2)c1=O] | 340.1 (formic) | 0.87 |
| 59b | N5-Cyclopropyl-N3-methyl-1-(3-(morpholinomethyl)benzyl)-2-oxo-1,2-dihydropyridine-3,5-dicarboxamide | 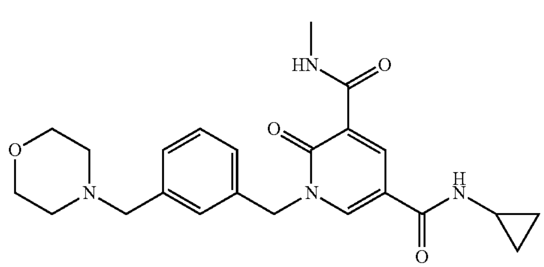 [SMILES: CNC(=O)c1cc(C(=O)NC2CC2)cn(Cc2cccc(CN3CCOCC3)c2)c1=O] | 425.3 (formic) | 0.42 |

-continued

| Ex No. | Name | Structure | [MH]+ | Rt (min)* |
|---|---|---|---|---|
| 192 | (+/−)-1-(2-fluorobenzyl)-N3-methyl-N5-((cis)-2-methylcyclopropyl)-2-oxo-1,2-dihydropyridine-3,5-dicarboxamide | 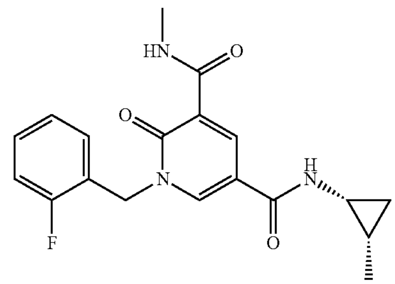 [SMILES: CNC(=O)c1cc(C(=O)N[C@@H]2C[C@@H]2C)cn(Cc2ccccc2F)c1=O] | 358.2 (formic) | 0.89 |
| 193 | (+/−)-1-(2-Fluorobenzyl)-N5-((trans)-2-methoxycyclopropyl)-N3-methyl-2-oxo-1,2-dihydropyridine-3,5-dicarboxamide | 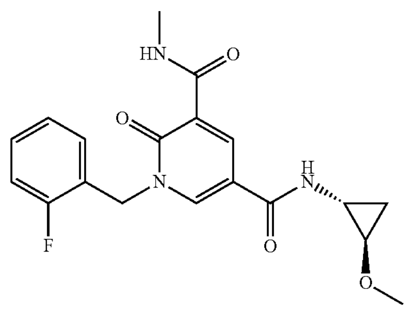 [SMILES: CNC(=O)c1cc(C(=O)N[C@@H]2C[C@H]2OC)cn(Cc2ccccc2F)c1=O] | 358.2 (formic) | 0.89 |
| 194 | 1-Benzyl-N5-((2-hydroxycyclohexyl)methyl)-N3-methyl-2-oxo-1,2-dihydropyridine-3,5-dicarboxamide | 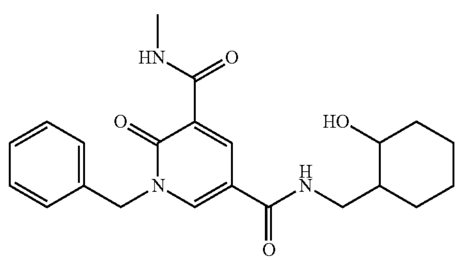 [SMILES: CNC(=O)c1cc(C(=O)NCC2CCCCC2O)cn(Cc2ccccc2)c1=O] | 398.3 (formic) | 0.92 |
| 195 | N5-Cyclopropyl-N3-methyl-2-oxo-1-((1,2,3,4-tetrahydroisoquinolin-7-yl)methyl)-1,2-dihydropyridine-3,5-dicarboxamide hydrochloride | 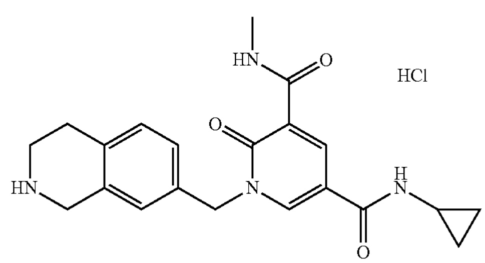 [SMILES: CNC(=O)c1cc(C(=O)NC2CC2)cn(Cc2ccc3c(c2)CNCC3)c1=O ; Cl] | 381.2 (formic) | 0.42 |
| 196 | (+/−)-1-Benzyl-N5-(((1R,2S)-2-hydroxycyclopentyl)methyl)-N3-methyl-2-oxo-1,2-dihydropyridine-3,5-dicarboxamide | 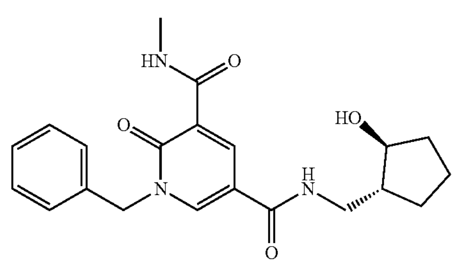 [SMILES: CNC(=O)c1cc(C(=O)NC[C@H]2CCC[C@@H]2O)cn(Cc2ccccc2)c1=O] | 384.3 (formic) | 0.83 |

-continued

| Ex No. | Name | Structure | [MH]+ | Rt (min)* |
|---|---|---|---|---|
| 197 | (+/−)-1-Benzyl-N5-(((cis)-2-hydroxycyclopentyl)methyl)-N3-methyl-2-oxo-1,2-dihydropyridine-3,5-dicarboxamide | 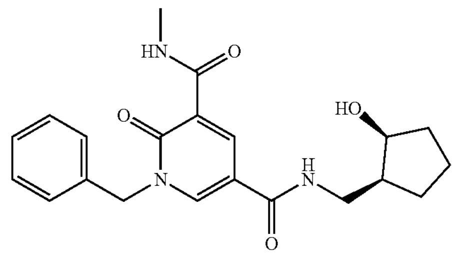 [SMILES: CNC(=O)c1cc(C(=O)NC[C@@H]2CCC[C@@H]2O)cn(Cc2ccccc2)c1=O] | 384.3 (formic) | 0.87 |
| 198 | (+/−)-1-Benzyl-N5-(((trans)-2-hydroxycyclopentyl)methyl)-N3-methyl-2-oxo-1,2-dihydropyridine-3,5-dicarboxamide | 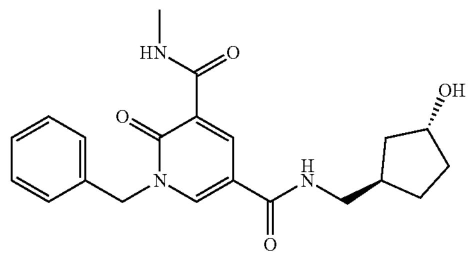 [SMILES: CNC(=O)c1cc(C(=O)NC[C@@H]2CC[C@@H](O)C2)cn(Cc2ccccc2)c1=O] | 384.3 (formic) | 0.78 |
| 199 | (+/−)-1-Benzyl-N5-(((cis)-3-hydroxycyclopentyl)methyl)-N3-methyl-2-oxo-1,2-dihydropyridine-3,5-dicarboxamide | 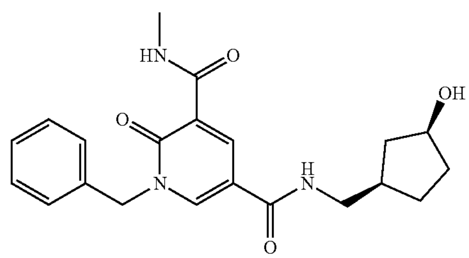 [SMILES: CNC(=O)c1cc(C(=O)NC[C@@H]2CC[C@H](O)C2)cn(Cc2ccccc2)c1=O] | 384.3 (formic) | 0.81 |
| 200 | 1-Benzyl-N5-(((trans)-4-hydroxycyclohexyl)methyl)-N3-methyl-2-oxo-1,2-dihydropyridine-3,5-dicarboxamide | 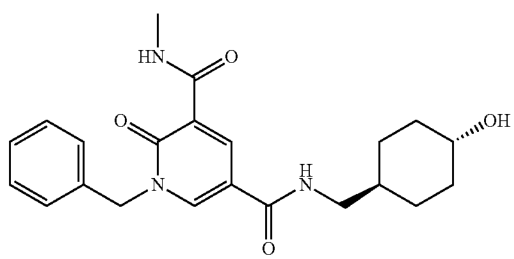 [SMILES: CNC(=O)c1cc(C(=O)NC[C@H]2CC[C@H](O)CC2)cn(Cc2ccccc2)c1=O] | 398.4 (formic) | 0.80 |
| 201 | 1-Benzyl-N5-(((cis)-4-hydroxycyclohexyl)methyl)-N3-methyl-2-oxo-1,2-dihydropyridine-3,5-dicarboxamide | 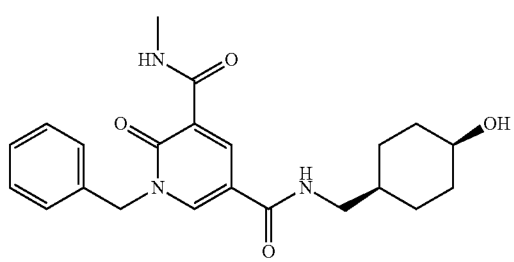 [SMILES: CNC(=O)c1cc(C(=O)NC[C@H]2CC[C@@H](O)CC2)cn(Cc2ccccc2)c1=O] | 398.4 (formic) | 0.82 |
| 202 | Methyl 4-((5-(cyclopropylcarbamoyl)-3-(methylcarbamoyl)-2-oxopyridin-1(2H)-yl)methyl)benzoate | 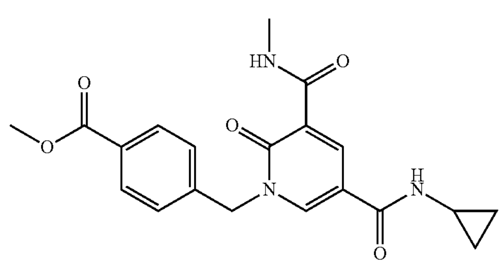 [SMILES: CNC(=O)c1cc(C(=O)NC2CC2)cn(Cc2ccc(C(=O)OC)cc2)c1=O] | 384.1 (formic) | 0.81 |

| Ex No. | Name | Structure | [MH]+ | Rt (min)* |
|---|---|---|---|---|
| 203 | N5-Cyclopropyl-1-(3-((dimethylamino)methyl)benzyl)-N3-methyl-2-oxo-1,2-dihydropyridine-3,5-dicarboxamide | 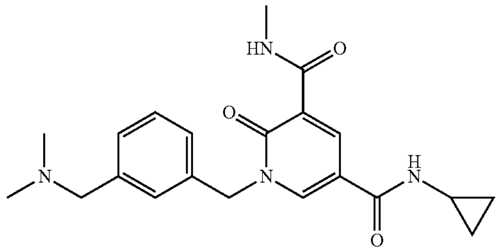 [SMILES: CNC(=O)c1cc(C(=O)NC2CC2)cn(Cc2cccc(CN(C)C)c2)c1=O] | 383.3 (High pH) | 0.83 |
| 204 | 1-(2-Fluorobenzyl)-N5-((1R*,2R*)-2-methoxycyclopropyl)-N3-methyl-2-oxo-1,2-dihydropyridine-3,5-dicarboxamide | 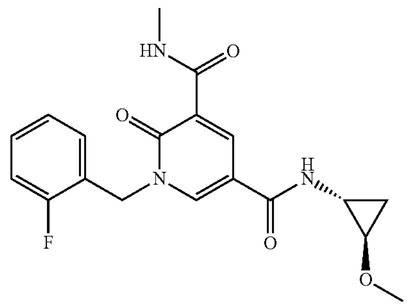 [SMILES: CNC(=O)c1cc(C(=O)N[C@@H]2C[C@H]2OC)cn(Cc2ccccc2F)c1=O] | 374.1 (formic) | 0.83 |
| 205 | (R)-N5-(6-Aminospiro[3.3]heptan-2-yl)-N3-methyl-2-oxo-1-(1-phenylethyl)-1,2-dihydropyridine-3,5-dicarboxamide | 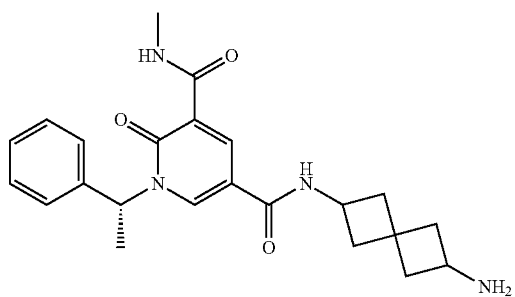 [SMILES: CNC(=O)c1cc(C(=O)NC2CC3(CC(N)C3)C2)cn([C@H](C)c2ccccc2)c1=O] | 409.0 (formic) | 0.58 |
| 206 | (+/−)-1-Benzyl-N5-(((1R,3S)-3-hydroxycyclohexyl)methyl)-N3-methyl-2-oxo-1,2-dihydropyridine-3,5-dicarboxamide | 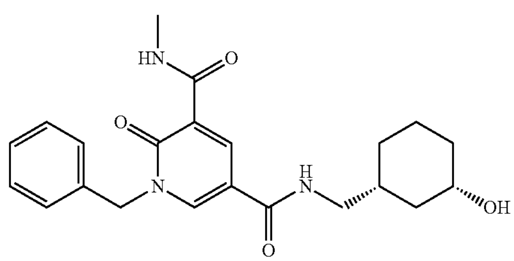 [SMILES: CNC(=O)c1cc(C(=O)NC[C@@H]2CCC[C@H](O)C2)cn(Cc2ccccc2)c1=O] | 398.2 (formic) | 0.82 |
| 207 | N5-Cyclopropyl-1-(4-methoxy-3-methylbenzyl)-N3-methyl-2-oxo-1,2-dihydropyridine-3,5-dicarboxamide | 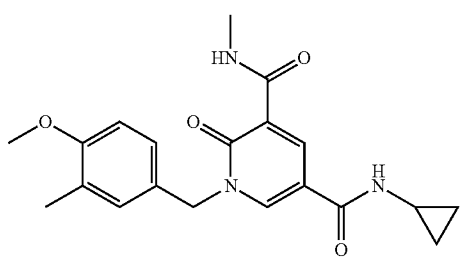 [SMILES: CNC(=O)c1cc(C(=O)NC2CC2)cn(Cc2ccc(OC)c(C)c2)c1=O] | 370.2 (formic) | 0.92 |

| Ex No. | Name | Structure | [MH]+ | Rt (min)* |
|---|---|---|---|---|
| 208 | (+/−)-N5-((cis)-2-ethoxycyclopropyl)-1-(3-fluorobenzyl)-N3-methyl-2-oxo-1,2-dihydropyridine-3,5-dicarboxamide | 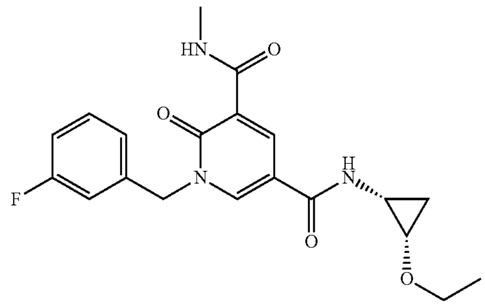 [SMILES: CCO[C@H]1C[C@H]1NC(=O)c1cc(C(=O)NC)c(=O)n(Cc2cccc(F)c2)c1] | 388.2 (formic) | 0.88 |
| 209 | 1-Benzyl-N5-((1R,2R)-2-hydroxycyclobutyl)-N3-methyl-2-oxo-1,2-dihydropyridine-3,5-dicarboxamide | 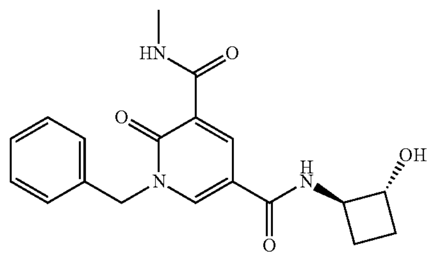 [SMILES: CNC(=O)c1cc(C(=O)N[C@@H]2CC[C@H]2O)cn(Cc2ccccc2)c1=O] | 356.1 (formic) | 0.76 |
| 210 | N5-Cyclopropyl-1-(4-(hydroxymethyl)benzyl)-N3-methyl-2-oxo-1,2-dihydropyridine-3,5-dicarboxamide | 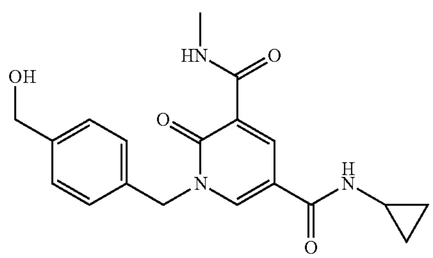 [SMILES: CNC(=O)c1cc(C(=O)NC2CC2)cn(Cc2ccc(CO)cc2)c1=O] | 356.2 (formic) | 0.64 |
| 211 | (S*)-N5-Cyclopropyl-N3-methyl-2-oxo-1-(1-(m-tolyl)ethyl)-1,2-dihydropyridine-3,5-dicarboxamide | 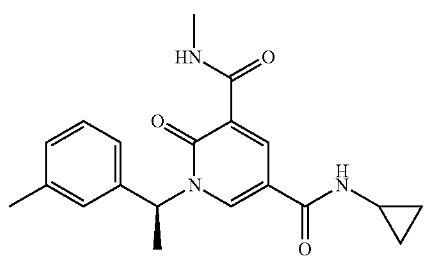 [SMILES: CNC(=O)c1cc(C(=O)NC2CC2)cn([C@@H](C)c2cccc(C)c2)c1=O] | 354.2 (formic) | 0.95 |
| 212 | (S*)-N5-Cyclopropyl-N3-methyl-2-oxo-1-(1-(o-tolyl)ethyl)-1,2-dihydropyridine-3,5-dicarboxamide | 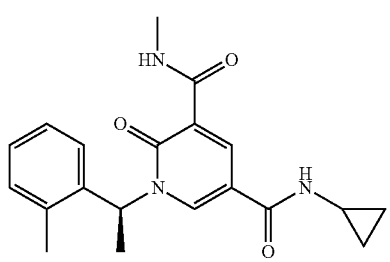 [SMILES: CNC(=O)c1cc(C(=O)NC2CC2)cn([C@@H](C)c2ccccc2C)c1=O] | 354.2 (formic) | 0.94 |

-continued

| Ex No. | Name | Structure | [MH]+ | Rt (min)* |
|---|---|---|---|---|
| 213 | (R*)-N5-Cyclopropyl-N3-methyl-2-oxo-1-(1-(o-tolyl)ethyl)-1,2-dihydropyridine-3,5-dicarboxamide | 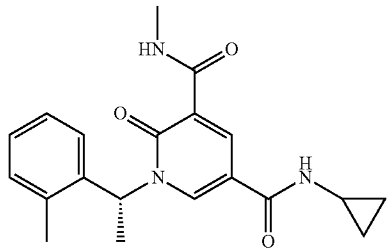 [SMILES: CNC(=O)c1cc(C(=O)NC2CC2)cn([C@H](C)c2ccccc2C)c1=O] | 354.2 (formic) | 0.94 |
| 214 | 1-(2-Fluoro-3-methylbenzyl)-N5-(2-(hydroxymethyl)cyclopropyl)-N3-methyl-2-oxo-1,2-dihydropyridine-3,5-dicarboxamide | 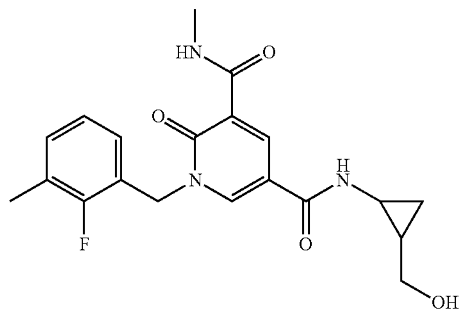 [SMILES: CNC(=O)c1cc(C(=O)NC2CC2CO)cn(Cc2cccc(C)c2F)c1=O] | 388.0 (formic) | 1.03 |
| 215 | (+/−)-1-(2-Fluoro-3-methylbenzyl)-N3-methyl-N5-((trans)-2-methylcyclopropyl)-2-oxo-1,2-dihydropyridine-3,5-dicarboxamide | 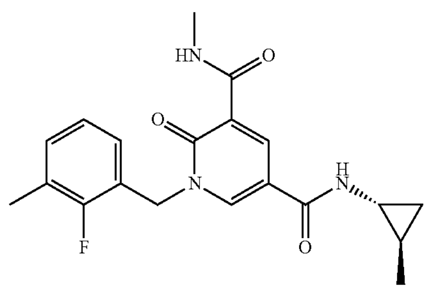 [SMILES: CNC(=O)c1cc(C(=O)N[C@@H]2C[C@H]2C)cn(Cc2cccc(C)c2F)c1=O] | 371.9 (formic) | 0.98 |
| 216 | 1-Benzyl-N5-((1S*,3S*)-3-hydroxycyclohexyl)-N3-methyl-2-oxo-1,2-dihydropyridine-3,5-dicarboxamide | 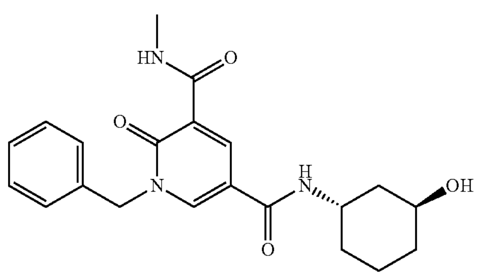 [SMILES: CNC(=O)c1cc(C(=O)N[C@H]2CCC[C@H](O)C2)cn(Cc2ccccc2)c1=O] | 384.3 (formic) | 0.81 |
| 217 | 1-Benzyl-N5-((1R*,3R*)-3-hydroxycyclohexyl)-N3-methyl-2-oxo-1,2-dihydropyridine-3,5-dicarboxamide | 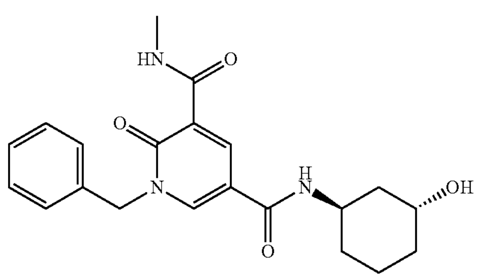 [SMILES: CNC(=O)c1cc(C(=O)N[C@@H]2CCC[C@@H](O)C2)cn(Cc2ccccc2)c1=O] | 384.3 (formic) | 0.81 |

| Ex No. | Name | Structure | [MH]+ | Rt (min)* |
|---|---|---|---|---|
| 218 | 1-Benzyl-N5-((1S*,3R*)-3-hydroxycyclohexyl)-N3-methyl-2-oxo-1,2-dihydropyridine-3,5-dicarboxamide | 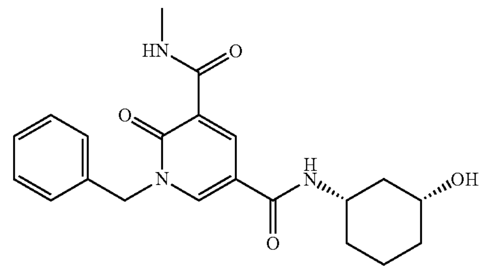 [SMILES: CNC(=O)c1cc(C(=O)N[C@H]2CCC[C@@H](O)C2)cn(Cc2ccccc2)c1=O] | 384.3 (formic) | 0.80 |
| 219 | 1-Benzyl-N5-((1R,3S)-3-hydroxycyclohexyl)-N3-methyl-2-oxo-1,2-dihydropyridine-3,5-dicarboxamide | 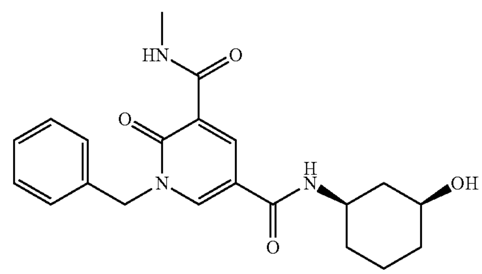 [SMILES: CNC(=O)c1cc(C(=O)N[C@@H]2CCC[C@H](O)C2)cn(Cc2ccccc2)c1=O] | 384.3 (formic) | 0.80 |
| 220 | N5-Cyclopropyl-N3-methyl-2-oxo-1-((1,2,3,4-tetrahydroisoquinolin-8-yl)methyl)-1,2-dihydropyridine-3,5-dicarboxamide | 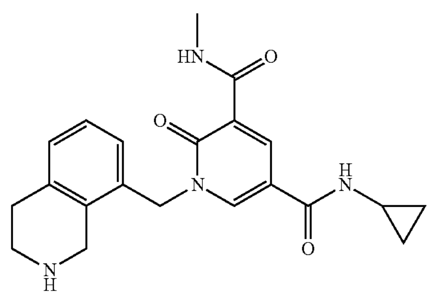 [SMILES: CNC(=O)c1cc(C(=O)NC2CC2)cn(Cc2cccc3c2CNCC3)c1=O] | 381.3 (formic) | 0.44 |
| 221 | 1-((1H-Indol-4-yl)methyl)-N5-(6-aminospiro[3.3]heptan-2-yl)-N3-methyl-2-oxo-1,2-dihydropyridine-3,5-dicarboxamide | 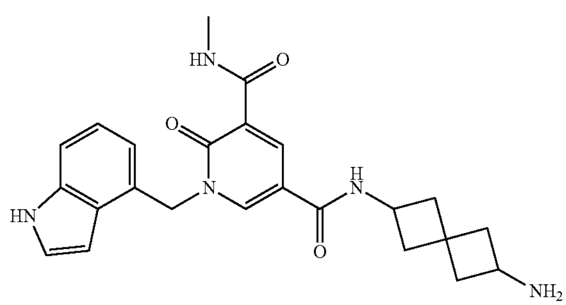 [SMILES: CNC(=O)c1cc(C(=O)NC2CC3(CC(N)C3)C2)cn(Cc2cccc3[nH]ccc23)c1=O] | 433.9 (formic) | 0.54 |
| 222 | (+/−)-N5-((cis)-2-ethoxycyclopropyl)-N3-methyl-1-(3-methylbenzyl)-2-oxo-1,2-dihydropyridine-3,5-dicarboxamide | 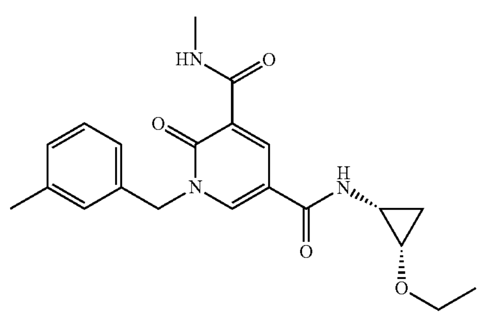 [SMILES: CCO[C@H]1C[C@H]1NC(=O)c1cc(C(=O)NC)c(=O)n(Cc2cccc(C)c2)c1] | 384.3 (formic) | 0.94 |

-continued

| Ex No. | Name | Structure | [MH]+ | Rt (min)* |
|---|---|---|---|---|
| 223 | (+/−)-N5-((trans)-2-ethoxycyclopropyl)-N3-methyl-1-(3-methylbenzyl)-2-oxo-1,2-dihydropyridine-3,5-dicarboxamide | 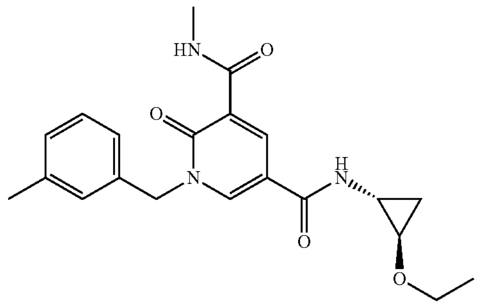 [SMILES: CCO[C@@H]1C[C@H]1NC(=O)c1cc(C(=O)NC)c(=O)n(Cc2cccc(C)c2)c1] | 384.3 (formic) | 0.96 |
| 224 | 1-Benzyl-N5-(2,2-dimethylcyclopropyl)-N3-methyl-2-oxo-1,2-dihydropyridine-3,5-dicarboxamide | 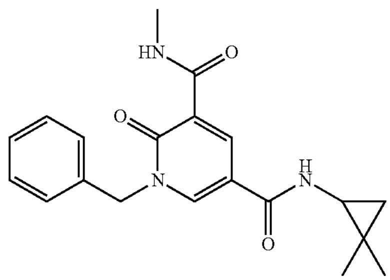 [SMILES: CNC(=O)c1cc(C(=O)NC2CC2(C)C)cn(Cc2ccccc2)c1=O] | 354.2 (formic) | 0.96 |
| 225 | 1-(2-Fluorobenzyl)-N5-((1R*,2R*)-2-(hydroxymethyl)cyclopropyl)-N3-methyl-2-oxo-1,2-dihydropyridine-3,5-dicarboxamide | 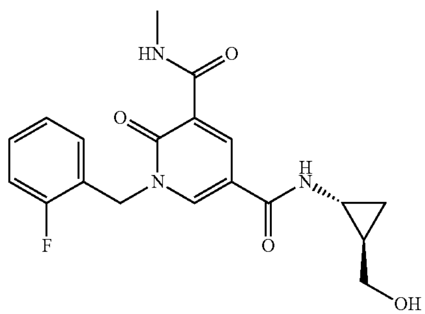 [SMILES: CNC(=O)c1cc(C(=O)N[C@@H]2C[C@H]2CO)cn(Cc2ccccc2F)c1=O] | 374.2 (formic) | 0.74 |
| 226 | 1-(2-Fluorobenzyl)-N5-((1S*,2S*)-2-(hydroxymethyl)cyclopropyl)-N3-methyl-2-oxo-1,2-dihydropyridine-3,5-dicarboxamide | 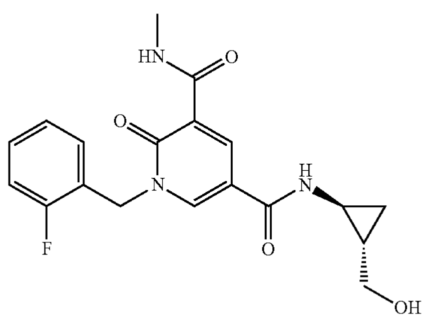 [SMILES: CNC(=O)c1cc(C(=O)N[C@H]2C[C@@H]2CO)cn(Cc2ccccc2F)c1=O] | 374.2 (formic) | 0.74 |
| 227 | N5-Cyclopropyl-1-(3-fluoro-5-methoxybenzyl)-N3-methyl-2-oxo-1,2-dihydropyridine-3,5-dicarboxamide | 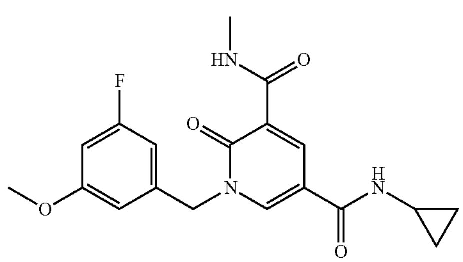 [SMILES: CNC(=O)c1cc(C(=O)NC2CC2)cn(Cc2cc(F)cc(OC)c2)c1=O] | 374.2 (formic) | 0.88 |

| Ex No. | Name | Structure | [MH]+ | Rt (min)* |
|---|---|---|---|---|
| 228 | N5-Cyclopropyl-N3-methyl-2-oxo-1-((1,2,3,4-tetrahydroquinolin-5-yl)methyl)-1,2-dihydropyridine-3,5-dicarboxamide | 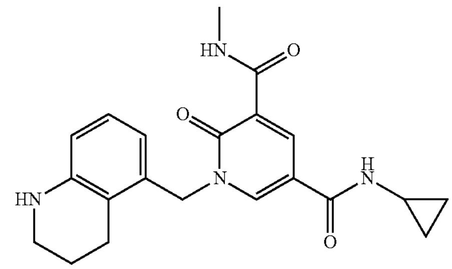 [SMILES: CNC(=O)c1cc(C(=O)NC2CC2)cn(Cc2cccc3c2CCCN3)c1=O] | 381.2 (formic) | 0.58 |
| 229 | 1-(2-Fluoro-5-methylbenzyl)-N5-((1S*,2S*)-2-(hydroxymethyl)cyclopropyl)-N3-methyl-2-oxo-1,2-dihydropyridine-3,5-dicarboxamide | 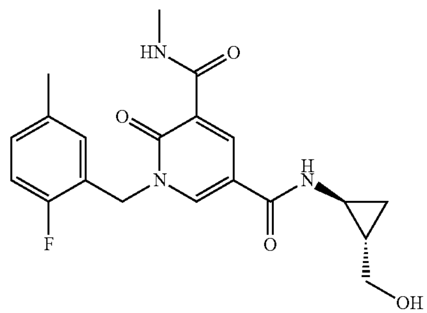 [SMILES: CNC(=O)c1cc(C(=O)N[C@H]2C[C@@H]2CO)cn(Cc2cc(C)ccc2F)c1=O] | 388.2 (formic) | 0.81 |
| 230 | 1-(2-Fluoro-5-methylbenzyl)-N5-((1R*,2R*)-2-(hydroxymethyl)cyclopropyl)-N3-methyl-2-oxo-1,2-dihydropyridine-3,5-dicarboxamide | 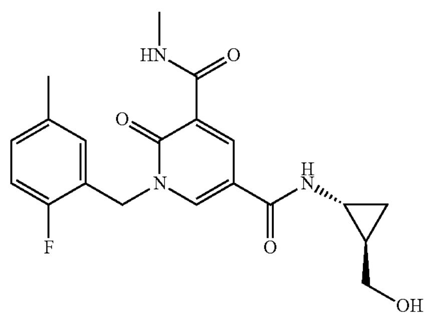 [SMILES: CNC(=O)c1cc(C(=O)N[C@@H]2C[C@H]2CO)cn(Cc2cc(C)ccc2F)c1=O] | 388.2 (formic) | 0.81 |
| 231 | N5-((1S*,2S*)-2-(Hydroxymethyl)cyclopropyl)-1-(3-methoxybenzyl)-N3-methyl-2-oxo-1,2-dihydropyridine-3,5-dicarboxamide | 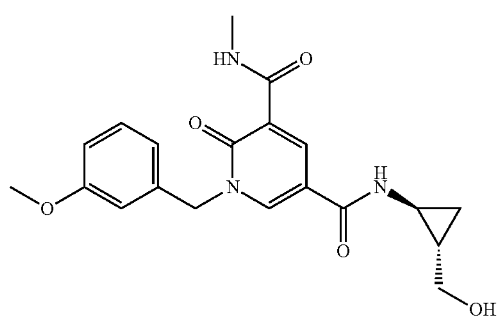 [SMILES: CNC(=O)c1cc(C(=O)N[C@H]2C[C@@H]2CO)cn(Cc2cccc(OC)c2)c1=O] | 386.2 (formic) | 0.75 |
| 232 | N5-((1R*,2R*)-2-ethoxycyclopropyl)-N3-methyl-1-(3-methylbenzyl)-2-oxo-1,2-dihydropyridine-3,5-dicarboxamide | 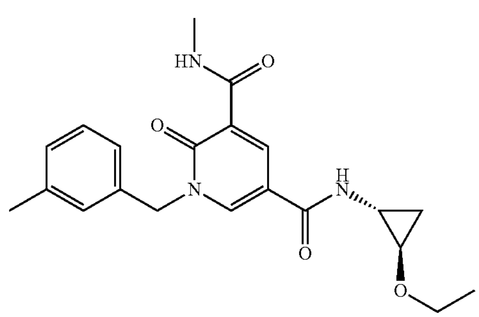 [SMILES: CCO[C@@H]1C[C@H]1NC(=O)c1cc(C(=O)NC)c(=O)n(Cc2cccc(C)c2)c1] | 384.2 (formic) | 0.96 |

-continued

| Ex No. | Name | Structure | [MH]+ | Rt (min)* |
|---|---|---|---|---|
| 233 | N5-((1S*,2S*)-2-Ethoxycyclopropyl)-N3-methyl-1-(3-methylbenzyl)-2-oxo-1,2-dihydropyridine-3,5-dicarboxamide | 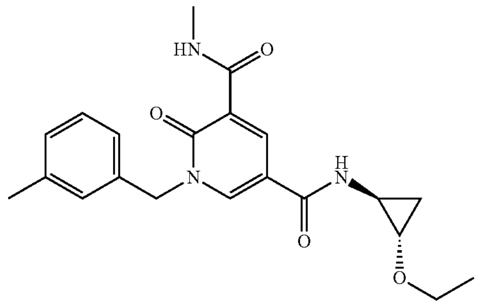 [SMILES: CCO[C@H]1C[C@@H]1NC(=O)c1cc(C(=O)NC)c(=O)n(Cc2cccc(C)c2)c1] | 384.2 (formic) | 0.96 |
| 234 | 1-(4-Fluoro-3-methylbenzyl)-N5-((1R*,2R)-2-(hydroxymethyl)cyclopropyl)-N3-methyl-2-oxo-1,2-dihydropyridine-3,5-dicarboxamide | 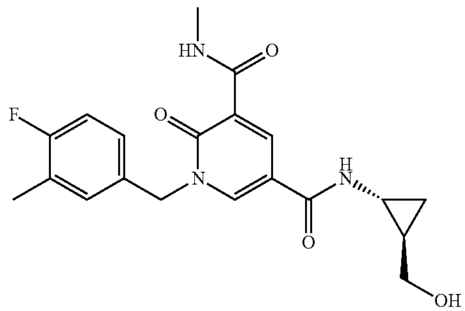 [SMILES: CNC(=O)c1cc(C(=O)N[C@@H]2C[C@H]2CO)cn(Cc2ccc(F)c(C)c2)c1=O] | 388.2 (formic) | 0.83 |
| 235 | 1-(4-Fluoro-3-methylbenzyl)-N5-((1S*,2S*)-2-(hydroxymethyl)cyclopropyl)-N3-methyl-2-oxo-1,2-dihydropyridine-3,5-dicarboxamide | 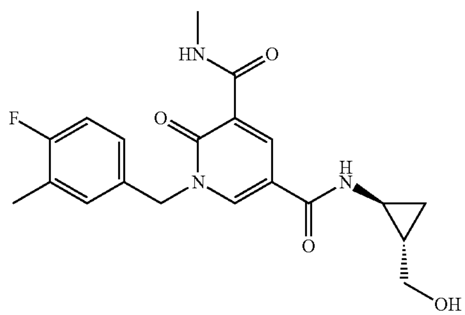 [SMILES: CNC(=O)c1cc(C(=O)N[C@H]2C[C@@H]2CO)cn(Cc2ccc(F)c(C)c2)c1=O] | 388.2 (formic) | 0.83 |
| 236 | 1-(3-Fluorobenzyl)-N5-((1S*,2S*)-2-(hydroxymethyl)cyclopropyl)-N3-methyl-2-oxo-1,2-dihydropyridine-3,5-dicarboxamide | 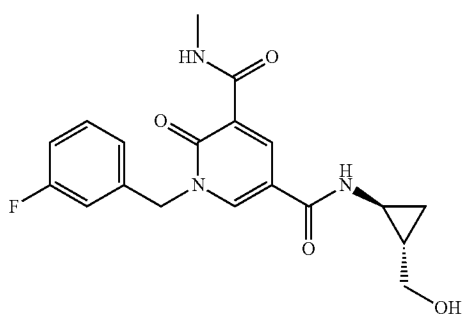 [SMILES: CNC(=O)c1cc(C(=O)N[C@H]2C[C@@H]2CO)cn(Cc2cccc(F)c2)c1=O] | 374.1 (formic) | 0.75 |
| 237 | 1-(3-Fluorobenzyl)-N5-((1R*,2R*)-2-(hydroxymethyl)cyclopropyl)-N3-methyl-2-oxo-1,2-dihydropyridine-3,5-dicarboxamide | 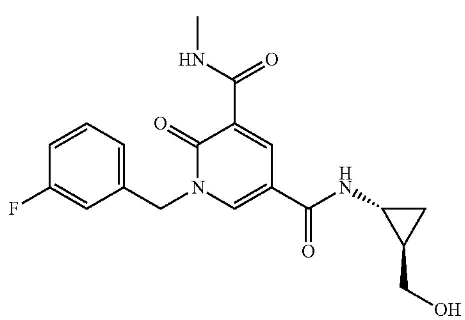 [SMILES: CNC(=O)c1cc(C(=O)N[C@@H]2C[C@H]2CO)cn(Cc2cccc(F)c2)c1=O] | 374.1 (formic) | 0.74 |

-continued

| Ex No. | Name | Structure | [MH]⁺ | Rt (min)* |
|---|---|---|---|---|
| 238 | (+/−)-N5-((trans)-2-ethoxycyclopropyl)-1-(2-fluoro-3-methylbenzyl)-N3-methyl-2-oxo-1,2-dihydropyridine-3,5-dicarboxamide | 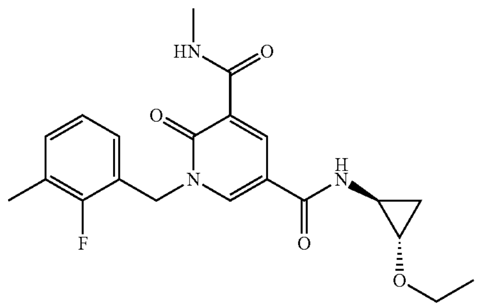 [SMILES: CCO[C@H]1C[C@@H]1NC(=O)c1cc(C(=O)NC)c(=O)n(Cc2cccc(C)c2F)c1] | 402.2 (formic) | 0.97 |
| 239 | N5-Cyclopropyl-1-(4-fluoro-3-methoxybenzyl)-N3-methyl-2-oxo-1,2-dihydropyridine-3,5-dicarboxamide | 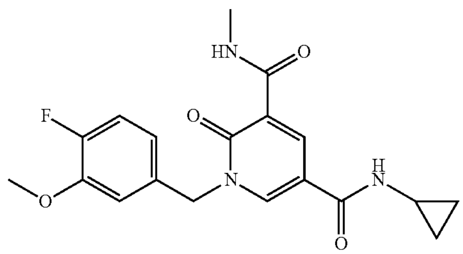 [SMILES: CNC(=O)c1cc(C(=O)NC2CC2)cn(Cc2ccc(F)c(OC)c2)c1=O] | 374.1 (formic) | 0.85 |
| 240 | 1-((1H-Indol-3-yl)methyl)-N5-cyclopropyl-N3-methyl-2-oxo-1,2-dihydropyridine-3,5-dicarboxamide | 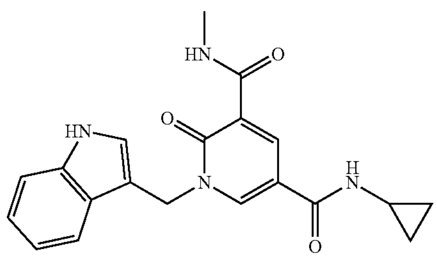 [SMILES: CNC(=O)c1cc(C(=O)NC2CC2)cn(Cc2c[nH]c3ccccc23)c1=O] | 365.2 (formic) | 0.83 |
| 241 | 1-(3-Fluorobenzyl)-N3-methyl-N5-((1R*,2R*)-2-methylcyclopropyl)-2-oxo-1,2-dihydropyridine-3,5-dicarboxamide | 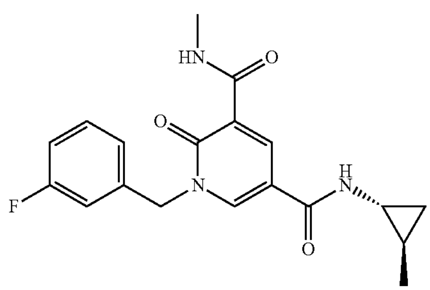 [SMILES: CNC(=O)c1cc(C(=O)N[C@@H]2C[C@H]2C)cn(Cc2cccc(F)c2)c1=O] | 358.1 (formic) | 0.92 |
| 242 | 1-(3-Fluorobenzyl)-N3-methyl-N5-((1S*,2S*)-2-methylcyclopropyl)-2-oxo-1,2-dihydropyridine-3,5-dicarboxamide | 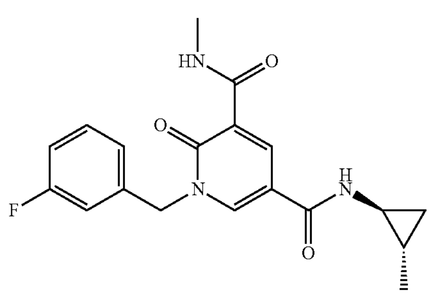 [SMILES: CNC(=O)c1cc(C(=O)N[C@H]2C[C@@H]2C)cn(Cc2cccc(F)c2)c1=O] | 358.2 (formic) | 0.92 |

| Ex No. | Name | Structure | [MH]+ | Rt (min)* |
|---|---|---|---|---|
| 243 | (+/−)-1-Benzyl-N5-((trans)-2-methoxycyclobutyl)-N3-methyl-2-oxo-1,2-dihydropyridine-3,5-dicarboxamide | 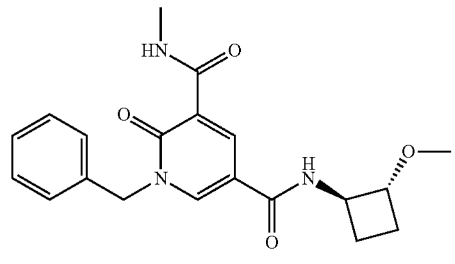 [SMILES: CNC(=O)c1cc(C(=O)N[C@@H]2CC[C@H]2OC)cn(Cc2ccccc2)c1=O] | 370.1 (formic) | 0.76 |
| 244 | N5-Cyclopropyl-1-(2-hydroxybenzyl)-N3-methyl-2-oxo-1,2-dihydropyridine-3,5-dicarboxamide | 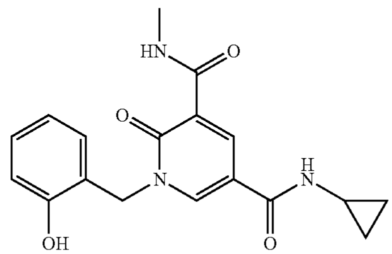 [SMILES: CNC(=O)c1cc(C(=O)NC2CC2)cn(Cc2ccccc2O)c1=O] | 342.2 (formic) | 0.76 |
| 245 | N5-Cyclopropyl-N3-methyl-1-((1-methyl-1H-benzo[d]imidazol-4-yl)methyl)-2-oxo-1,2-dihydropyridine-3,5-dicarboxamide | 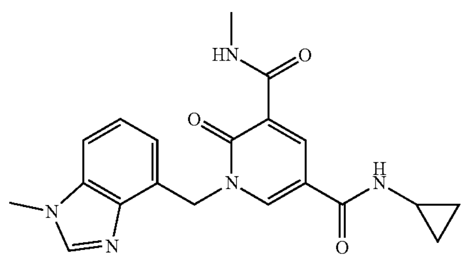 [SMILES: CNC(=O)c1cc(C(=O)NC2CC2)cn(Cc2cccc3c2ncn3C)c1=O] | 380.3 (formic) | 0.75 |
| 246 | N5-Cyclopropyl-1-(3-fluoro-5-methylbenzyl)-N3-methyl-2-oxo-1,2-dihydropyridine-3,5-dicarboxamide | 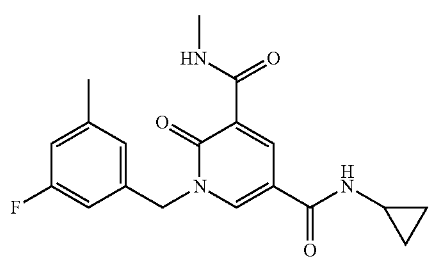 | 358.1 (formic) | 0.92 |
| 247 | (+/−)-N3-Methyl-N5-((trans)-2-methylcyclopropyl)-1-(3-(morpholinomethyl)benzyl)-2-oxo-1,2-dihydropyridine-3,5-dicarboxamide | 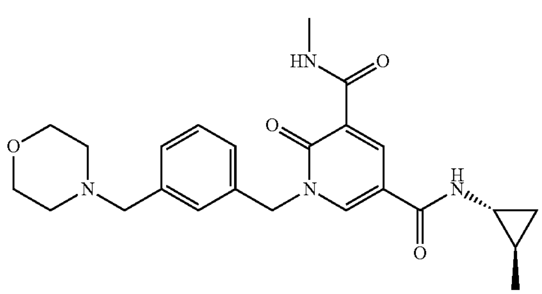 [SMILES: CNC(=O)c1cc(C(=O)N[C@@H]2C[C@H]2C)cn(Cc2cccc(CN3CCOCC3)c2)c1=O] | 439.2 (formic) | 0.48 |

-continued

| Ex No. | Name | Structure | [MH]+ | Rt (min)* |
|---|---|---|---|---|
| 248 | (R*)-1-Benzyl-N5-(2,2-dimethylcyclopropyl)-N3-methyl-2-oxo-1,2-dihydropyridine-3,5-dicarboxamide | 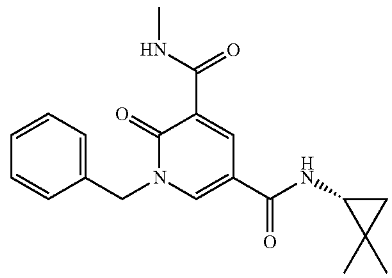 [SMILES: CNC(=O)c1cc(C(=O)N[C@@H]2CC2(C)C)cn(Cc2ccccc2)c1=O] | 354.1 (formic) | 0.96 |
| 249 | (S*)-1-Benzyl-N5-(2,2-dimethylcyclopropyl)-N3-methyl-2-oxo-1,2-dihydropyridine-3,5-dicarboxamide | 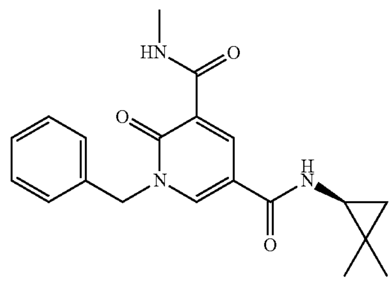 [SMILES: CNC(=O)c1cc(C(=O)N[C@H]2CC2(C)C)cn(Cc2ccccc2)c1=O] | 354.1 (formic) | 0.96 |
| 250 | (+/−)-N5-Cyclopropyl-N3-methyl-2-oxo-1-((4,5,6,7-tetrahydro-1H-benzo[d]imidazol-4-yl)methyl)-1,2-dihydropyridine-3,5-dicarboxamide | 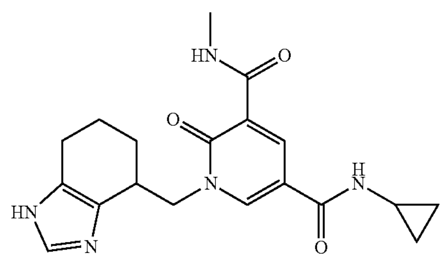 [SMILES: CNC(=O)c1cc(C(=O)NC2CC2)cn(CC2CCCc3[nH]cnc32)c1=O] | 370.2 (formic) | 0.46 |
| 251 | N3-Methyl-1-(3-methylbenzyl)-N5-((1R*,2R*)-2-methylcyclopropyl)-2-oxo-1,2-dihydropyridine-3,5-dicarboxamide | 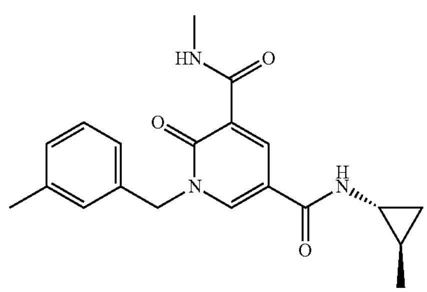 [SMILES: CNC(=O)c1cc(C(=O)N[C@@H]2C[C@H]2C)cn(Cc2cccc(C)c2)c1=O] | 354.2 (formic) | 0.98 |
| 252 | N3-Methyl-1-(3-methylbenzyl)-N5-((1S*,2S*)-2-methylcyclopropyl)-2-oxo-1,2-dihydropyridine-3,5-dicarboxamide | 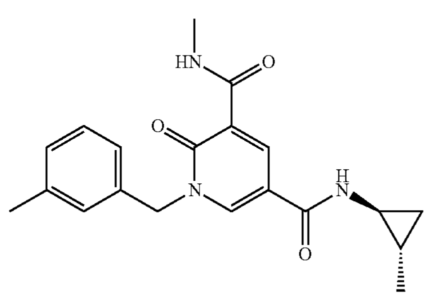 [SMILES: CNC(=O)c1cc(C(=O)N[C@H]2C[C@@H]2C)cn(Cc2cccc(C)c2)c1=O] | 354.2 (formic) | 0.98 |

-continued

| Ex No. | Name | Structure | [MH]+ | Rt (min)* |
|---|---|---|---|---|
| 253 | N5-((1R*,2R*)-2-Ethoxycyclopropyl)-1-(2-fluoro-5-methylbenzyl)-N3-methyl-2-oxo-1,2-dihydropyridine-3,5-dicarboxamide | 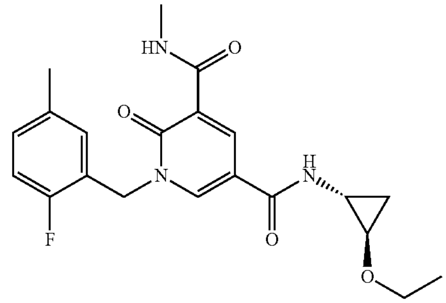 [SMILES: CCO[C@@H]1C[C@H]1NC(=O)c1cc(C(=O)NC)c(=O)n(Cc2cc(C)ccc2F)c1] | 402.2 (formic) | 0.96 |
| 254 | N5-((1S*,2S*)-2-Ethoxycyclopropyl)-1-(2-fluoro-5-methylbenzyl)-N3-methyl-2-oxo-1,2-dihydropyridine-3,5-dicarboxamide | 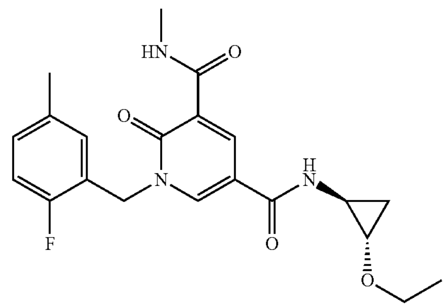 [SMILES: CCO[C@H]1C[C@@H]1NC(=O)c1cc(C(=O)NC)c(=O)n(Cc2cc(C)ccc2F)c1] | 402.2 (formic) | 0.96 |
| 255 | N5-((1R*,2R*)-2-Ethoxycyclopropyl)-1-(2-fluoro-3-methylbenzyl)-N3-methyl-2-oxo-1,2-dihydropyridine-3,5-dicarboxamide | 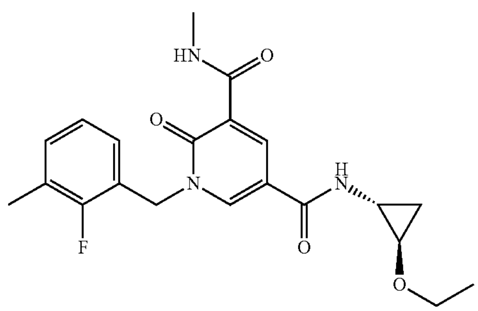 [SMILES: CCO[C@@H]1C[C@H]1NC(=O)c1cc(C(=O)NC)c(=O)n(Cc2cccc(C)c2F)c1] | 402.2 (formic) | 0.97 |
| 256 | N5-((1S*,2S*)-2-Ethoxycyclopropyl)-1-(2-fluoro-3-methylbenzyl)-N3-methyl-2-oxo-1,2-dihydropyridine-3,5-dicarboxamide | 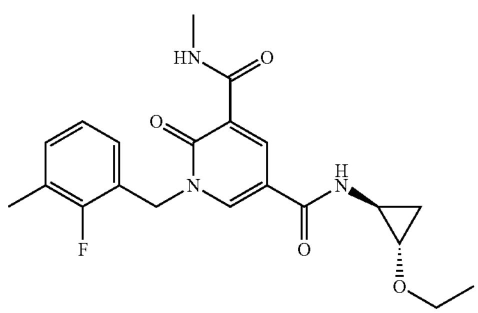 [SMILES: CCO[C@H]1C[C@@H]1NC(=O)c1cc(C(=O)NC)c(=O)n(Cc2cccc(C)c2F)c1] | 402.2 (formic) | 0.97 |
| 257 | 1-(4-Fluoro-3-methylbenzyl)-N3-methyl-N5-((1R*,2R*)-2-methylcyclopropyl)-2-oxo-1,2-dihydropyridine-3,5-dicarboxamide | 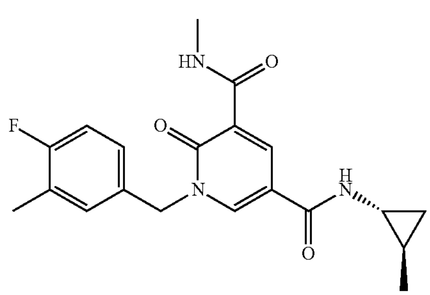 [SMILES: CNC(=O)c1cc(C(=O)N[C@@H]2C[C@H]2C)cn(Cc2ccc(F)c(C)c2)c1=O] | 372.2 (formic) | 1.00 |

| Ex No. | Name | Structure | [MH]+ | Rt (min)* |
|---|---|---|---|---|
| 258 | 1-(4-Fluoro-3-methylbenzyl)-N3-methyl-N5-((1S*,2S*)-2-methylcyclopropyl)-2-oxo-1,2-dihydropyridine-3,5-dicarboxamide | 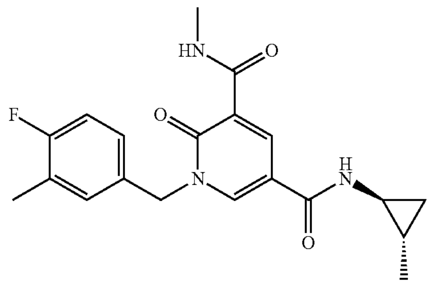 [SMILES: CNC(=O)c1cc(C(=O)N[C@H]2C[C@@H]2C)cn(Cc2ccc(F)c(C)c2)c1=O] | 372.2 (formic) | 1.00 |
| 259 | N3-Methyl-N5-((1R*,2R*)-2-methylcyclopropyl)-2-oxo-1-((R)-1-phenylethyl)-1,2-dihydropyridine-3,5-dicarboxamide | 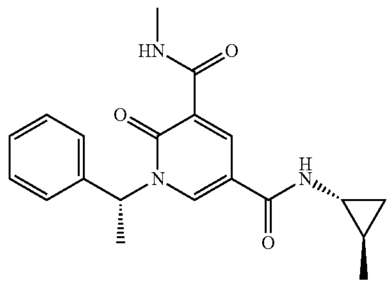 [SMILES: CNC(=O)c1cc(C(=O)N[C@@H]2C[C@H]2C)cn([C@H](C)c2ccccc2)c1=O] | 354.2 (formic) | 0.97 |
| 260 | N3-Methyl-N5-((1S*,2S*)-2-methylcyclopropyl)-2-oxo-1-((R)-1-phenylethyl)-1,2-dihydropyridine-3,5-dicarboxamide | 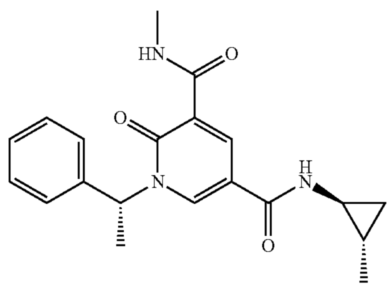 [SMILES: CNC(=O)c1cc(C(=O)N[C@H]2C[C@@H]2C)cn([C@H](C)c2ccccc2)c1=O] | 354.3 (formic) | 0.96 |
| 261 | N5-Cyclopropyl-1-(1-(3-methoxyphenyl)ethyl)-N3-methyl-2-oxo-1,2-dihydropyridine-3,5-dicarboxamide | 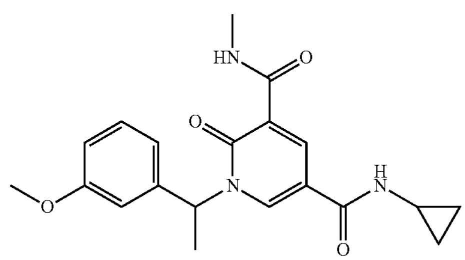 [SMILES: CNC(=O)c1cc(C(=O)NC2CC2)cn(C(C)c2cccc(OC)c2)c1=O] | 370.2 (formic) | 0.89 |
| 262 | (+/−)-1-(3-(2-Hydroxyethoxy)benzyl)-N5-((trans)-2-(hydroxymethyl)cyclopropyl)-N3-methyl-2-oxo-1,2-dihydropyridine-3,5-dicarboxamide | 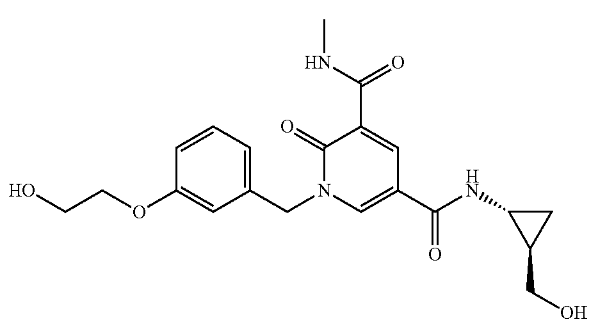 | 416.2 (formic) | 0.62 |

| Ex No. | Name | Structure | [MH]+ | Rt (min)* |
|---|---|---|---|---|
| 263 | 1-(Benzofuran-3-ylmethyl)-N5-cyclopropyl-N3-methyl-2-oxo-1,2-dihydropyridine-3,5-dicarboxamide | 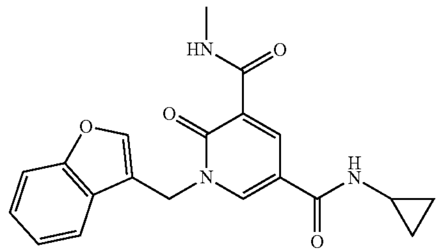 [SMILES: CNC(=O)c1cc(C(=O)NC2CC2)cn(Cc2coc3ccccc23)c1=O] | 366.1 (formic) | 0.91 |
| 264 | (+/−)-N5-((trans)-2-ethoxycyclopropyl)-1-(3-(2-hydroxyethoxy)benzyl)-N3-methyl-2-oxo-1,2-dihydropyridine-3,5-dicarboxamide | 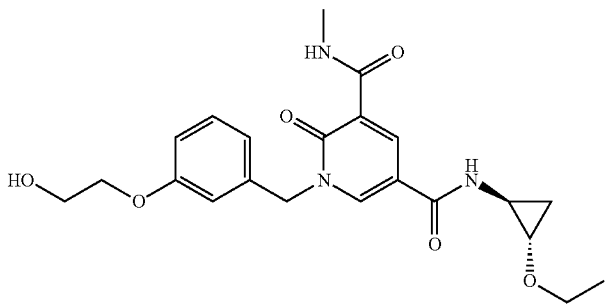 [SMILES: CCO[C@H]1C[C@@H]1NC(=O)c1cc(C(=O)NC)c(=O)n(Cc2cccc(OCCO)c2)c1] | 430.3 (formic) | 0.74 |
| 265 | (R*)-N5-Cyclopropyl-1-(3-(1-hydroxyethyl)benzyl)-N3-methyl-2-oxo-1,2-dihydropyridine-3,5-dicarboxamide | 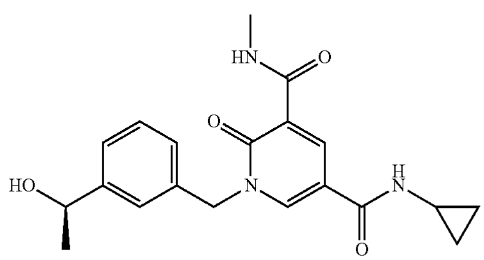 [SMILES: CNC(=O)c1cc(C(=O)NC2CC2)cn(Cc2cccc([C@@H](C)O)c2)c1=O] | 370.2 (formic) | 0.71 |
| 266 | (S*)-N5-Cyclopropyl-1-(3-(1-hydroxyethyl)benzyl)-N3-methyl-2-oxo-1,2-dihydropyridine-3,5-dicarboxamide | 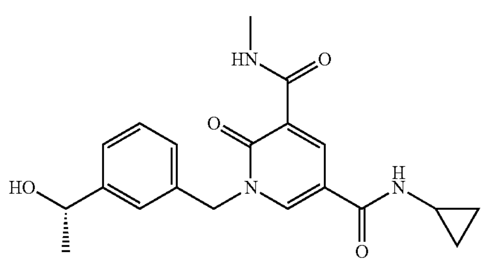 | 370.3 (formic) | 0.71 |

| Ex No. | Name | Structure | [MH]+ | Rt (min)* |
|---|---|---|---|---|
| 267 | N5-((trans)-2-(Hydroxymethyl)cyclopropyl)-N3-methyl-2-oxo-1-((S*)-1-(m-tolyl)ethyl)-1,2-dihydropyridine-3,5-dicarboxamide, 1:1 mix of trans-diastereomers at cPr stereocentres | 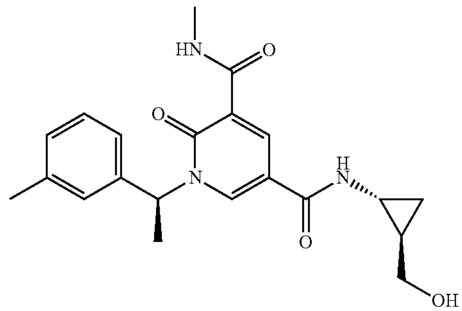 [SMILES: CNC(=O)c1cc(C(=O)N[C@@H]2C[C@H]2CO)cn([C@@H](C)c2cccc(C)c2)c1=O] | 384.2 (formic) | 0.85 |
| 268 | N5-Cyclopropyl-1-((2,3-dihydrobenzofuran-3-yl)methyl)-N3-methyl-2-oxo-1,2-dihydropyridine-3,5-dicarboxamide | 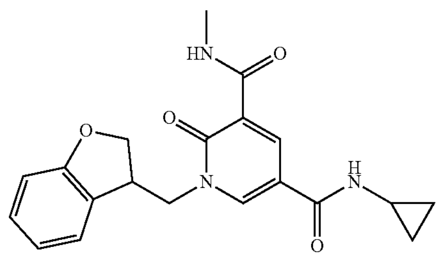 [SMILES: CNC(=O)c1cc(C(=O)NC2CC2)cn(CC2COc3ccccc32)c1=O] | 368.2 (formic) | 0.85 |

Example 269: 1-((1H-Indol-4yl)methyl-N³-methyl-N⁵-(1R*,2R*)-2-methylcyclopropyl)-2-oxo-1,2-dihydropyridine-3,5-dicarboxamide Example 270: 1-((1H-Indol-4-yl)methyl)-N³-methyl-N⁵-((1S*,2S*)-2-methylcyclopropyl)-2-oxo-1,2-dihydropyridine-3,5-dicarboxamide

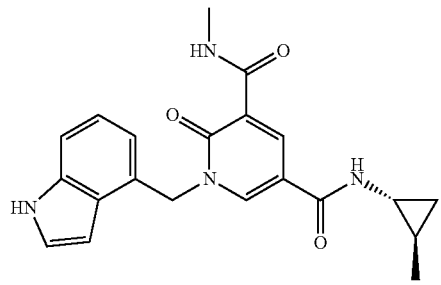

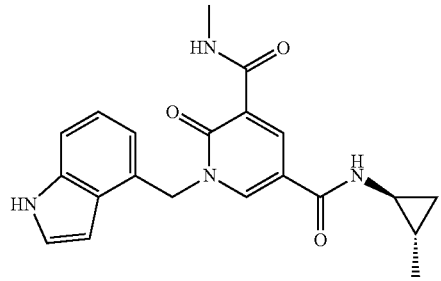

To a solution of 1-((1H-indol-4-yl)methyl)-5-(methylcarbamoyl)-6-oxo-1,6-dihydropyridine-3-carboxylic acid (150 mg, 0.30 mmol), and HATU (174 mg, 0.46 mmol) in DMF (1.2 mL) stirred at rt, was added (+/−)-(trans)-2-methylcyclopropanamine (43.3 mg, 0.61 mmol, commercially available from, for example, Enamine) and DIPEA (106 µL, 0.61 mmol). The reaction was stirred at rt for 3 h. The reaction mixture was poured onto water (30 mL) and extracted with ethyl acetate (4×30 mL). The combined organics were washed with brine, dried through a hydrophobic frit and evaporated in vacuo to yield the crude product as a yellow solid (223 mg). The solid was loaded in dichloromethane/methanol onto a 10 g SNAP cartridge and purified via Biotage SP4 flash chromatography, eluting from 0-50% (3:1 ethyl acetate:ethanol)/cyclohexane. The relevant fractions were combined and evaporated in vacuo to yield the purified product (48 mg). It was noted that the product had precipitated on silica and the column was flushed with 50% ethanol in ethyl acetate. The recovered fractions were combined and evaporated in vacuo to yield further impure product as a yellow solid (91 mg). The sample was dissolved in 1:1 MeOH:DMSO (1 mL) and purified by MDAP (Formic). The desired fractions was combined with the residue of the previous batch of product and evaporated in vacuo to give (+/−)-1-((1H-indol-4-yl)methyl)-N³-methyl-N⁵-((trans)-2-methylcyclopropyl)-2-oxo-1,2-dihydropyridine-3,5-dicarboxamide (98 mg, 0.26 mmol, 85% yield).

The racemate (98 mg) was dissolved in EtOH (~8-10 mL) with heat. Injection: 0.7 mL manual injections were made via a Rheodyne valve onto the column (15% iPrOH/heptane, flow rate=42.5 mL/min (pressure: 94 bar), detection: UV Diode Array at 280 nm (Band width 1 40 nm, reference 400 nm, bandwidth 100 nm), Column Chiralpak AD-H (250×30 mm, 5 µm). Fractions from 18-20.5 min were bulked and labelled peak 1. Fractions from 22-26 min were bulked and labelled peak 2. The bulked fractions were concentrated in vacuo, then taken up in EtOH and transferred to weighed flasks which were blown down to dyness under a stream of nitrogen gas.

The fractions corresponding to peak 1 were collected to afford Example 269 (34 mg, 0.09 mmol, 30% yield) as a white solid.

LCMS (2 min formic): Rt=0.86 min, [MH]⁺=379.2.

$^1$H NMR (400 MHz, DMSO-d$_6$) δ ppm 11.25 (br. s., 1H) 9.40-9.49 (m, 1H) 8.77-8.82 (m, 1H) 8.56 (d, J=2.7 Hz, 1H) 8.52 (d, J=3.9 Hz, 1H) 7.34-7.41 (m, 2H) 7.06 (t, J=7.7 Hz, 1H) 6.83 (d, J=7.1 Hz, 1H) 6.50 (t, J=2.0 Hz, 1H) 5.54 (s, 2H) 2.84 (d, J=4.6 Hz, 3H) 2.43-2.49 (m, 1H) 1.02 (d, J=6.1 Hz, 3H) 0.84-0.93 (m, 1H) 0.70 (dt, J=8.9, 4.5 Hz, 1H) 0.40-0.48 (m, 1H)

The fractions corresponding to peak 2 were collected to afford Example 270 (37 mg, 0.10 mmol, 32% yield) as a white solid.

LCMS (2 min formic): Rt=0.86 min, [MH]$^+$=379.2.

Example 271: 1-((1H-Pyrrolo[3,2-c]pyridin-4-yl)methyl)-N$^5$-cyclopropyl-N$^3$-methyl-2-oxo-1,2-dihydropyridine-3,5-dicarboxamide

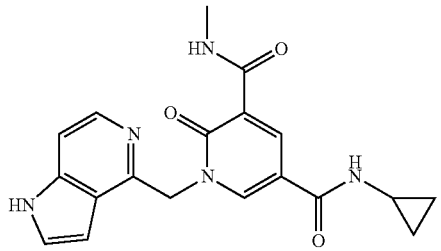 [SMILES: CNC(=O)c1cc(C(=O)NC2CC2)cn(Cc2nccc3[nH]ccc23)c1=O]

To a suspension of N$^5$-cyclopropyl-N$^3$-methyl-2-oxo-1,2-dihydropyridine-3,5-dicarboxamide (55 mg, 0.23 mmol) in acetonitrile (2.3 mL) was added triphenylphosphine (184 mg, 0.70 mmol), triethylamine (0.068 mL, 0.49 mmol) and DIAD (0.136 mL, 0.701 mmol). The reaction was stirred at rt under nitrogen for 5 h. Further portions of triphenylphosphine (184 mg, 0.70 mmol) and DIAD (0.136 mL, 0.70 mmol) were added. After 21 h, the reaction mixture was poured onto saturated aqueous sodium bicarbonate (10 mL) and extracted with ethyl acetate (3×15 mL). The combined organics were dried through a hydrophobic frit and evaporated in vacuo to yield the crude product (727 mg). The residue was dry loaded in methanol onto a 50 g SNAP cartridge and purified by Biotage SP4 flash chromatography, eluting from 18-88% (80:20 DCM:2M methanolic ammonia)/DCM. Poor separation was achieved and all fractions containing product were recombined and evaporated in vacuo to yield a clear glass (41 mg). The sample was dissolved in 1:1 MeOH:DMSO (1 mL) and purified by MDAP (High pH). The solvent was dried under a stream of nitrogen to give 1-((1H-pyrrolo[3,2-c]pyridin-4-yl)methyl)-N$^5$-cyclopropyl-N$^3$-methyl-2-oxo-1,2-dihydropyridine-3,5-dicarboxamide (3.2 mg, 8.32 μmol, 4% yield) as a white solid.

LCMS (2 min High pH): Rt=0.66 min, [MH]$^+$=366.4.

Example 272: N$^5$-Cyclopropyl-N$^3$-methyl-1-((2-methyl-1H-indol-4-yl)methyl)-2-oxo-1,2-dihydropyridine-3,5-dicarboxamide

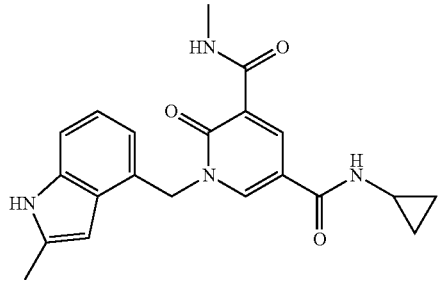 [SMILES: CNC(=O)c1cc(C(=O)NC2CC2)cn(Cc2cccc3[nH]c(C)cc23)c1=O]

To a solution of N$^5$-cyclopropyl-N$^3$-methyl-1-((2-methyl-1-tosyl-1H-indol-4-yl)methyl)-2-oxo-1,2-dihydropyridine-3,5-dicarboxamide (75 mg, 0.14 mmol) in methanol (469 μL) and THF (939 μL) stirred under nitrogen at rt was added solid cesium carbonate (144 mg, 0.44 mmol) in one charge. The reaction mixture was heated to 70° C. for 8 h on a timer then cooled to rt. The mixture was left to stand for 10 h before heating was resumed for a further 6 h. A further portion of cesium carbonate (92 mg, 0.28 mmol) was added and the mixture was heated for a further 18 h. The reaction mixture was then concentrated in vacuo and partitioned between water (50 mL) and ethyl acetate (20 mL). The layers were separated and the aqueous layer was extracted with ethyl acetate (2×10 mL). The combined organics were washed with brine (10 mL), dried through a hydrophobic frit and evaporated in vacuo to yield the crude product as a yellow solid (45 mg). The sample was loaded in dichloromethane onto a 10 g SNAP cartridge and purified via Biotage SP4 flash chromatography, eluting from 13-63% (3:1 ethyl acetate:ethanol)/cyclohexane. The relevant fractions were combined and evaporated in vacuo to yield the desired product N$^5$-cyclopropyl-N$^3$-methyl-1-((2-methyl-1H-indol-4-yl)methyl)-2-oxo-1,2-dihydropyridine-3,5-dicarboxamide (38 mg, 0.10 mmol, 68% yield) as a white solid.

LCMS (2 min High pH): Rt=0.84 min, [MH]$^+$=379.2.

Example 273: 1-(3-(Difluoromethoxy)benzyl)-N$^3$-methyl-N$^5$-((1S,2S)-2-methylcyclopropyl)-2-oxo-1,2-dihydropyridine-3,5-dicarboxamide

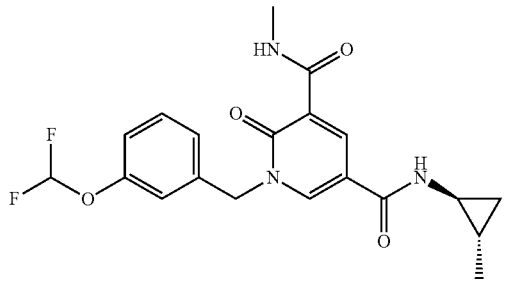 [SMILES: CNC(=O)c1cc(C(=O)N[C@H]2C[C@@H]2C)cn(Cc2cccc(OC(F)F)c2)c1=O]

N³-Methyl-N⁵-((1S,2S)-2-methylcyclopropyl)-2-oxo-1,2-dihydropyridine-3,5-dicarboxamide (55 mg, 0.22 mmol), 1-(bromomethyl)-3-(difluoromethoxy)benzene (62.8 mg, 0.27 mmol), potassium carbonate (69 mg, 0.50 mmol) and DMF (2 mL) were stirred at 90° C. After 1.5 h the suspension was partitioned between EtOAc (10 mL) and LiCl solution. (10 mL), extracted with EtOAc (2×10 mL), washed with brine, dried over a hydrophobic frit and concentrated to give the crude product (150 mg) as a colourless oil. This was purified by chromatography on SiO₂ (Biotage SNAP 25 g cartridge, eluting with 10-65% (25% EtOH in EtOAc)/cyclohexane). The desired fractions were concentrated to give 1-(3-(difluoromethoxy)benzyl)-N³-methyl-N⁵-((1S, 2S)-2-methylcyclopropyl)-2-oxo-1,2 dihydropyridine-3,5-dicarboxamide (39 mg, 0.087 mmol, 39.2% yield) as a colourless oil. This was further purified by MDAP (Formic). The appropriate fractions were concentrated to give 1-(3-(difluoromethoxy)benzyl)-N³-methyl-N⁵-((1S,2S)-2-methylcyclopropyl)-2-oxo-1,2-dihydropyridine-3,5-dicarboxamide (39 mg, 0.09 mmol, 39% yield) as a white solid.

LCMS (2 min Formic): Rt=0.97 min, [MH]⁺=406.2.

Example 274: N⁵-Cyclopropyl-1-(3-(difluoromethoxy)benzyl)-N³-methyl-2-oxo-1,2-dihydropyridine-3,5-dicarboxamide

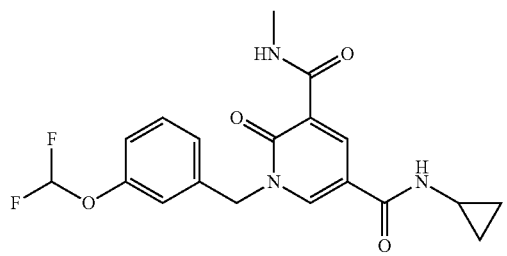 [SMILES: CNC(=O)c1cc(C(=O)NC2CC2)cn(Cc2cccc(OC(F)F)c2)c1=O]

N⁵-Cyclopropyl-N³-methyl-2-oxo-1,2-dihydropyridine-3,5-dicarboxamide (99 mg, 0.42 mmol), 1-(bromomethyl)-3-(difluoromethoxy)benzene (120 mg, 0.51 mmol), potassium carbonate (110 mg, 0.80 mmol) and DMF (4 mL) were stirred at 90° C. After 1 h the suspension was partitioned between EtOAc (10 mL) and LiCl solution. (10 mL), extracted with EtOAc (2×10 mL), washed with brine, dried over a hydrophobic frit and concentrated to give the crude product (200 mg) as a cream solid. This was purified by chromatography on SiO₂ (Biotage SNAP 25 g cartridge, eluting with 10-65% (25% EtOH in EtOAc)/cyclohexane). The desired fractions were concentrated to give 50 mg as a white solid. This was further purified by MDAP (Formic). The appropriate fractions were concentrated to give N⁵-cyclopropyl-1-(3-(difluoromethoxy)benzyl)-N³-methyl-2-oxo-1,2-dihydropyridine-3,5-dicarboxamide (37 mg, 0.09 mmol, 20% yield) as a colourless oil.

LCMS (2 min Formic): Rt=0.90 min, [MH]⁺=392.2.

Example 275: N⁵-cyclopropyl-N³-methyl-2-oxo-1-(quinolin-7-ylmethyl)-1,2-dihydropyridine-3,5-dicarboxamide

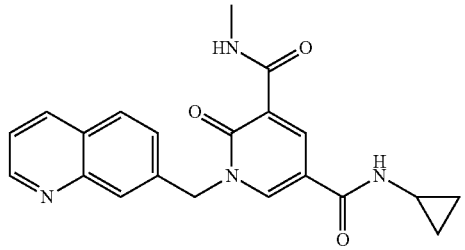 [SMILES: CNC(=O)c1cc(C(=O)NC2CC2)cn(Cc2ccc3cccnc3c2)c1=O]

To a stirred solution of N⁵-cyclopropyl-N³-methyl-2-oxo-1,2-dihydropyridine-3,5-dicarboxamide (40 mg, 0.17 mmol) and potassium carbonate (94 mg, 0.68 mmol) in DMF (850 µL) under nitrogen at rt, was added 7-(bromomethyl)quinoline (110 mg, 0.25 mmol) as a solution in DMF (850 µL). The reaction was stirred at rt for 18 h. The reaction mixture was then poured onto saturated aqueous lithium chloride (30 mL) and extracted with ethyl acetate (3×15 mL). The organics were concentrated to yield the crude product as an orange oil (64 mg). The sample was loaded in dichloromethane/methanol onto a 10 g SNAP cartridge and purified by Biotage SP4 flash chromatography, eluting from 10-50% 2M methanolic ammonia/DCM to yield a yellow solid (25 mg). The sample was dissolved in 1:1 MeOH:DMSO (1 mL) and purified by MDAP (High pH). The relevant fractions were evaporated in vacuo to yield the desired product N⁵-cyclopropyl-N³-methyl-2-oxo-1-(quinolin-7-ylmethyl)-1,2-dihydropyridine-3,5-dicarboxamide (14 mg, 0.04 mmol, 22% yield) as a white solid.

LCMS (2 min high pH): Rt=0.78 min, [MH]⁺=377.4.

Example 276: 1-((S*)-1-(3-Methoxyphenyl)ethyl)-N³-methyl-N⁵-((1S,2S)-2-methylcyclopropyl)-2-oxo-1,2-dihydropyridine-3,5-dicarboxamide

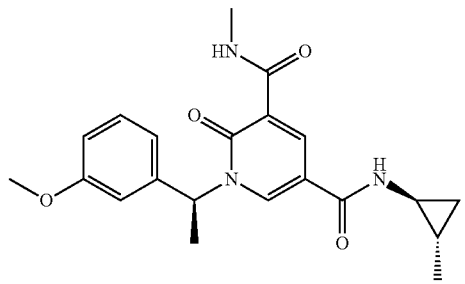 [SMILES: CNC(=O)c1cc(C(=O)N[C@H]2C[C@@H]2C)cn([C@@H](C)c2cccc(OC)c2)c1=O]

To a solution of (S*)-1-(1-(3-methoxyphenyl)ethyl)-5-(methylcarbamoyl)-6-oxo-1,6-dihydropyridine-3-carboxylic acid (116 mg, 0.21 mmol), and HATU (155 mg, 0.41 mmol) in DMF (2.1 mL) stirred at rt was added DIPEA (74 µL, 0.424 mmol) and (1S,2S)-2-methylcyclopropanamine hydrochloride (27 mg, 0.25 mmol) and the reaction stirred for 2 h. A further portion of (1S,2S)-2-methylcyclopropanamine hydrochloride (8 mg, 0.07 mmol) was added. After 21 h, the reaction mixture was poured onto saturated aqueous LiCl and extracted with ethyl acetate (1×15 mL, then 2×10 mL). The combined organics were washed with brine (10 mL), dried through a hydrophobic frit and evaporated in vacuo to yield the crude product as a yellow oil (176 mg). The oil was loaded in dichloromethane onto a 10 g SNAP cartridge and purified via Biotage SP4 flash chromatography, eluting from 8-38% (3:1 ethyl acetate:ethanol)/cyclohexane. The relevant fractions were combined and evaporated in vacuo to yield a clear gum (86 mg). The sample was dissolved in 1:1 MeOH:DMSO (1 mL) and purified by MDAP (Formic). The solvent was dried under a stream of nitrogen and the residue sonicated with diethyl ether and evaporated in vacuo to give 1-((S*)-1-(3-methoxyphenyl)ethyl)-N$^3$-methyl-N$^5$-((1S,2S)-2-methylcyclopropyl)-2-oxo-1,2-dihydropyridine-3,5-dicarboxamide (60 mg, 0.15 mmol, 71% yield) as a white solid.

LCMS (2 min formic): Rt=0.97 min, [MH]$^+$=384.2.

Example 277: 1-(3-(2-Hydroxyethoxy)benzyl)-N$^5$-((1R*,2R*)-2-(hydroxymethyl)cyclopropyl)-N$^3$-methyl-2-oxo-1,2-dihydrouridine-3,5-dicarboxamide Example 278 1-(3-(2-Hydroxyethoxy)benzyl)-N$^5$-((1S*,2S*)-2-(hydroxymethyl)cyclopropyl)-N$^3$-methyl-2-oxo-1,2-dihydropyridine-3,5-dicarboxamide

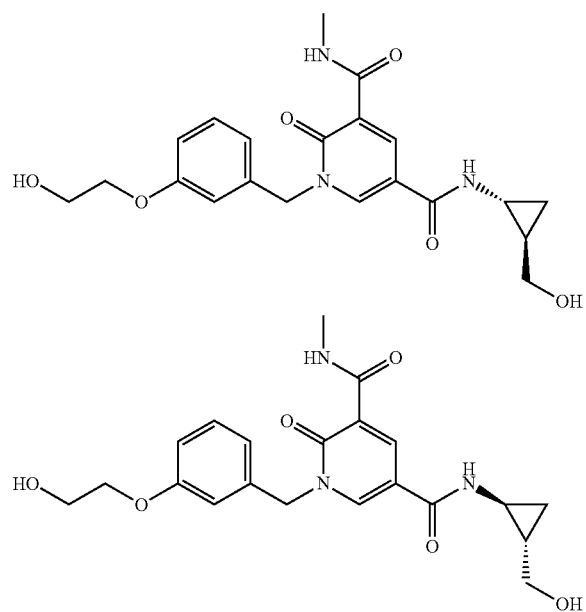

(+/−)-1-(3-(2-Hydroxyethoxy)benzyl)-N$^5$-((trans)-2-(hydroxymethyl)cyclopropyl)-N$^3$-methyl-2-oxo-1,2-dihydropyridine-3,5-dicarboxamide (50 mg) was submitted for chiral separation. The racemate (50 mg) was dissolved in EtOH (1 mL). Injection: 1 mL of the solution was injected onto the column (80% EtOH (+0.2% isopropylamine)/heptane (+0.2% isopropylamine), flow rate=20 mL/min, detection wavelength=215 nm, 4. Ref 550, 100, Column 30 mm×25 cm Chiralpak AD-H (5 μm), lot no. ADH12143-01). Total number of injections=1. Fractions from 18-23 min were bulked and labelled peak 1. Fractions from 36-55 min were bulked and labelled peak 2. The bulked fractions were concentrated in vacuo and then transferred to weighed flasks. Final compounds were recovered from DCM and heptane in order to obtain a solid.

The fractions corresponding to peak 1 were collected to afford—example 277—1-(3-(2-hydroxyethoxy)benzyl)-N$^5$-((1R*,2R*)-2-(hydroxymethyl)cyclopropyl)-N$^3$-methyl-2-oxo-1,2-dihydropyridine-3,5-dicarboxamide (18 mg, 36%) as a yellow solid.

LCMS (2 min Formic): Rt=0.62 min, [MH]$^+$=416

The fractions corresponding to peak 2 were collected to afford—example 278—1-(3-(2-hydroxyethoxy)benzyl)-N$^5$-((1S*,2S*)-2-(hydroxymethyl)cyclopropyl)-N$^3$-methyl-2-oxo-1,2-dihydropyridine-3,5-dicarboxamide (18 mg, 36%) as a yellow solid.

LCMS (2 min Formic): Rt=0.62 min, [MH]$^+$=416

Example 279: N$^5$-((1R*,2R*)-2-Ethylcyclopropyl)-1-(3-(2-hydroxyethoxy)benzyl)-N$^3$-methyl-2-oxo-1,2-dihydropyridine-3,5-dicarboxamide Example 280: N$^5$-((1S*,2S*)-2-Ethylcyclopropyl)-1-(3-(2-hydroxyethoxy)benzyl)-N$^3$-methyl-2-oxo-1,2-dihydropyridine-3,5-dicarboxamide

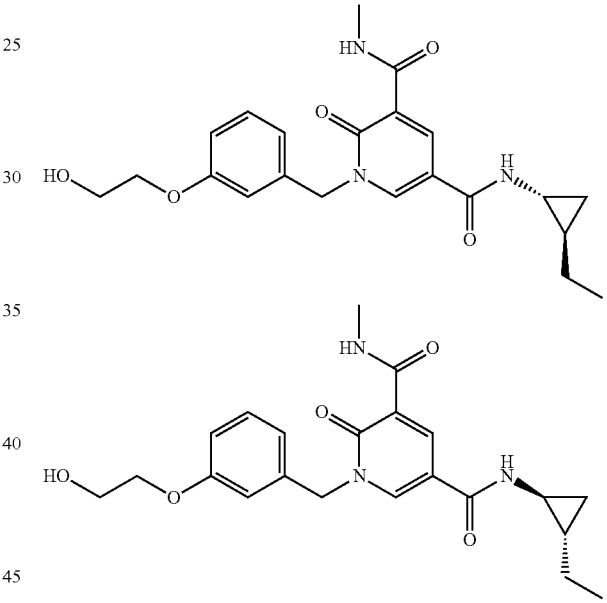

(+/−)-N$^5$-(-2-Ethylcyclopropyl)-1-(3-(2-hydroxyethoxy)benzyl)-N$^3$-methyl-2-oxo-1,2-dihydropyridine-3,5-dicarboxamide (102 mg) was submitted for chiral separation. The racemate (102 mg) was dissolved in EtOH (~10 mL) with heat. Injection: 0.5 mL manual injections via a Rheodyne valve were injected onto the column (80% iPrOH/heptane, flow rate=40 mL/min, detection: UV Diode Array at 280 nm (Band width 1 40 nm, reference 400 nm bandwidth 100 nm), Column 30 mm×25 cm Chiralpak AD-H (5 μm). Fractions from 16.5-18 min were bulked and labelled peak 1. Fractions from 20.5-22.5 min were bulked and labelled peak 2. The bulked fractions were concentrated in vacuo and then taken up in EtOH (3×4 mL) and transferred to weighed vials. The solvent was removed under a stream of nitrogen to afford the two products.

The fractions corresponding to peak 1 were collected to afford—example 279—N$^5$-((1R*,2R*)-2-ethylcyclopropyl)-1-(3-(2-hydroxyethoxy)benzyl)-N$^3$-methyl-2-oxo-1,2-dihydropyridine-3,5-dicarboxamide (40 mg, 40%).

LCMS (2 min Formic): Rt=0.84 min, [MH]$^+$=414

The fractions corresponding to peak 2 were collected to afford—example 280—$N^5$-((1S*,2S*)-2-ethylcyclopropyl)-1-(3-(2-hydroxyethoxy)benzyl)-$N^3$-methyl-2-oxo-1,2-dihydropyridine-3,5-dicarboxamide (41 mg, 41%).

LCMS (2 min Formic): Rt=0.84 min, [MH]$^+$=414

Example 281: $N^5$-((1R*,2R*)-2-Ethoxycyclopropyl)-1-(3-(2-hydroxyethoxy)benzyl)-$N^3$-methyl-2-oxo-1,2-dihydropyridine-3,5-dicarboxamide

Example 282: $N^5$-((1S*,2S*)-2-Ethoxycyclopropyl)-1-(3-(2-hydroxyethoxy)benzyl)-$N^3$-methyl-2-oxo-1,2-dihydropyridine-3,5-dicarboxamide

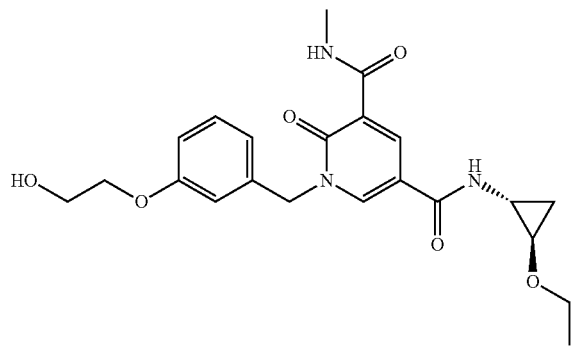

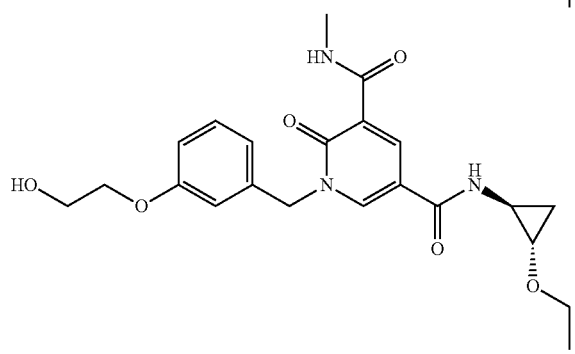

(+/−)-$N^5$-((trans)-2-Ethoxycyclopropyl)-1-(3-(2-hydroxyethoxy)benzyl)-$N^3$-methyl-2-oxo-1,2-dihydropyridine-3,5-dicarboxamide (126 mg) was submitted for chiral separation. The racemate (126 mg) was dissolved in EtOH (~10 mL) with heat. Injection: 0.6 mL manual injections via a Rheodyne valve were injected onto the column (80% iPrOH/heptane, flow rate=42.5 mL/min, detection: UV Diode Array at 280 nm (Band width 1 40 nm, reference 400 nm bandwidth 100 nm), Column 30 mm×25 cm Chiralpak AD-H (5 µm). Fractions from 23-26 min were bulked and labelled peak 1. Fractions from 29-33 min were bulked and labelled peak 2. The bulked fractions were concentrated in vacuo and then taken up in EtOH (3×4 mL) and transferred to weighed vials. The solvent was removed under a stream of nitrogen to afford the two products.

The fractions corresponding to peak 1 were collected to afford—example 281—$N^5$-((1R*,2R*)-2-ethoxycyclopropyl)-1-(3-(2-hydroxyethoxy)benzyl)-$N^3$-methyl-2-oxo-1,2-dihydropyridine-3,5-dicarboxamide (44 mg, 29%)

LCMS (2 min Formic): Rt=0.74 min, [MH]$^+$=430

The fractions corresponding to peak 2 were collected to afford—example 282—$N^5$-((1S*,2S*)-2-ethoxycyclopropyl)-1-(3-(2-hydroxyethoxy)benzyl)-N3-methyl-2-oxo-1,2-dihydropyridine-3,5-dicarboxamide (47 mg, 32%)

LCMS (2 min Formic): Rt=0.74 min, [MH]$^+$=430

Example 283: $N^5$-(2-((trans)-4-Aminocyclohexyl)ethyl)-1-benzyl-$N^3$-methyl-2-oxo-1,2-dihydropyridine-3,5-dicarboxamide hydrochloride

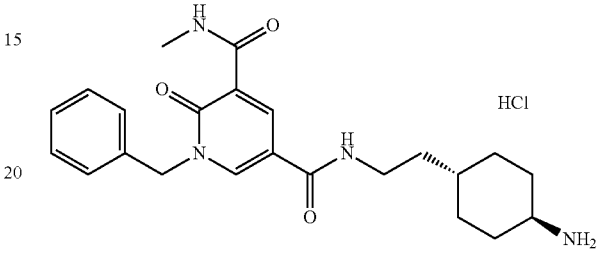

To a suspension of tert-butyl ((trans)-4-(2-(1-benzyl-5-(methylcarbamoyl)-6-oxo-1,6-dihydropyridine-3-carboxamido)ethyl)cyclohexyl)carbamate (75.5 mg, 0.15 mmol) in 1,4-dioxane (1 mL) was added hydrogen chloride (4M in 1,4-dioxane, 1.5 mL, 6.00 mmol) and the reaction mixture stirred at rt for 3.5 h. The reaction mixture was concentrated under a stream of nitrogen and dried in vacuo to give a white solid; $N^5$-(2-((trans)-4-aminocyclohexyl)ethyl)-1-benzyl-$N^3$-methyl-2-oxo-1,2-dihydropyridine-3,5-dicarboxamide hydrochloride (64.6 mg, 0.15 mmol, 98% yield).

LCMS (2 min formic) Rt=0.57 min, m/z=411 for [MH]$^+$

Example 284: $N^5$-(2-((cis)-4-Aminocyclohexyl)ethyl)-1-benzyl-$N^3$-methyl-2-oxo-1,2-dihydropyridine-3,5-dicarboxamide hydrochloride

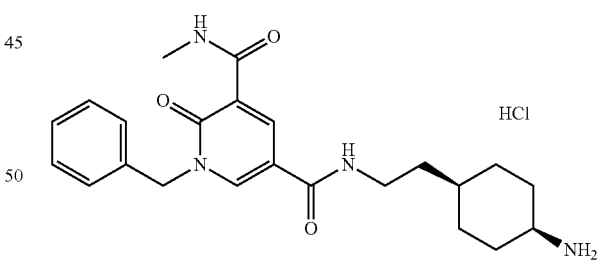

To a suspension of tert-butyl ((cis)-4-(2-(1-benzyl-5-(methylcarbamoyl)-6-oxo-1,6-dihydropyridine-3-carboxamido)ethyl)cyclohexyl)carbamate (70 mg, 0.14 mmol) in 1,4-dioxane (1 mL) was added hydrogen chloride (4M in 1,4-dioxane, 1.5 mL, 6.00 mmol) and the reaction mixture stirred at rt for 3.5 h. The reaction mixture was concentrated under a stream of nitrogen and dried in vacuo to give $N^5$-(2-((cis)-4-aminocyclohexyl)ethyl)-1-benzyl-$N^3$-methyl-2-oxo-1,2-dihydropyridine-3,5-dicarboxamide hydrochloride (66.4 mg, 0.15 mmol, 108% yield) (containing approx. 0.5 eq. 1,4-dioxane).

LCMS (2 min formic) Rt=0.62 min, m/z=411 for [MH]$^+$

Example 285: 1-((1H-Pyrrolo[3,2-c]pyridin-4-yl)methyl)-N³-methyl-N⁵-((1S,2S)-2-methylcyclopropyl)-2-oxo-1,2-dihydropyridine-3,5-dicarboxamide

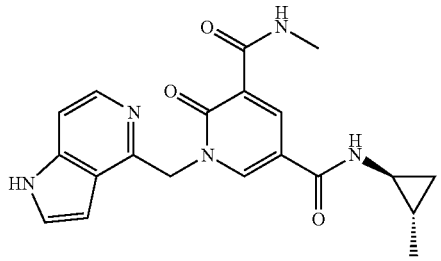 [SMILES: CNC(=O)c1cc(C(=O)N[C@H]2C[C@@H]2C)cn(Cc2nccc3[nH]ccc23)c1=O]

A solution of N³-methyl-N⁵-((1S,2S)-2-methylcyclopropyl)-2-oxo-1-((1-tosyl-1H-pyrrolo[3,2-c]pyridin-4-yl)methyl)-1,2-dihydropyridine-3,5-dicarboxamide (36.5 mg, 0.07 mmol) and potassium hydroxide (8.9 mg, 0.16 mmol) in methanol (1 mL) and water (0.25 mL) was stirred at 50° C. for 2 h under nitrogen. The volatiles were evaporated in vacuo and the residue suspended in water (3 mL) and dichloromethane (3 mL) and the layers separated. The aqueous layer was extracted with further dichloromethane (3×3 mL). The aqueous layer was diluted with further water (approx. 10 mL) and re-extracted with ethyl acetate (3×5 mL). To the aqueous layer was added brine (approx. 2 mL) and it was re-extracted with ethyl acetate (2×5 mL) and dichloromethane (2×5 mL). All organic phases were combined and filtered through a cartridge fitted with a hydrophobic frit. The filtrate was evaporated in vacuo to give a white solid; 1-((1H-pyrrolo[3,2-c]pyridin-4-yl)methyl)-N³-methyl-N⁵-((1S,2S)-2-methylcyclopropyl)-2-oxo-1,2-dihydropyridine-3,5-dicarboxamide (18.7 mg, 0.05 mmol, 72% yield).

LCMS (2 min high pH) Rt=0.74 min, m/z=380 for [MH]⁺

¹H NMR (400 MHz, DMSO-d₆) δ ppm 11.63 (br. s., 1H) 9.32 (q, J=4.6 Hz, 1H) 8.83 (d, J=2.7 Hz, 1H) 8.73 (d, J=2.7 Hz, 1H) 8.57 (d, J=4.2 Hz, 1H) 8.00 (d, J=5.9 Hz, 1H) 7.45-7.53 (m, 1H) 7.31 (d, J=5.9 Hz, 1H) 6.67 (d, J=2.9 Hz, 1H) 5.65 (s, 2H) 2.77 (d, J=4.9 Hz, 3H) 2.49-2.57 (obs, 1H) 1.05 (d, J=6.1 Hz, 3H) 0.87-0.98 (m, 1H) 0.74 (dt, J=8.6, 4.6 Hz, 1H) 0.48 (dt, J=7.3, 5.5 Hz, 1H)

Example 286: (±)-1-Benzyl-N⁵-((trans)-2-(methoxymethyl)cyclopropyl)-N³-methyl-2-oxo-1,2-dihydropyridine-3,5-dicarboxamide

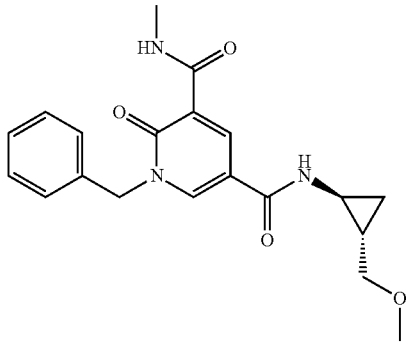 [SMILES: CNC(=O)c1cc(C(=O)N[C@H]2C[C@@H]2COC)cn(Cc2ccccc2)c1=O]

2,4,6-Trichlorophenyl 1-benzyl-5-(methylcarbamoyl)-6-oxo-1,6-dihydropyridine-3-carboxylate (189 mg, 0.41 mmol), (±)-(trans)-2-(methoxymethyl)cyclopropanamine hydrochloride (147 mg, 0.27 mmol), DMAP (8 mg, 0.07 mmol), triethylamine (0.11 mL, 0.79 mmol) and THF (2.5 mL) were stirred at 45° C. under N₂. After stirring for 1 h, 2,4,6-trichlorophenyl 1-benzyl-5-(methylcarbamoyl)-6-oxo-1,6-dihydropyridine-3-carboxylate (187 mg, 0.40 mmol) was added and the reaction stirred for 2 h. The suspension was partitioned between EtOAc (10 mL) and sodium bicarbonate solution. (10 mL), extracted with EtOAc (2×10 mL), dried over a hydrophobic frit and concentrated to give the crude product (560 mg) as a yellow solid. This was purified by chromatography on SiO₂ (Biotage SNAP 50 g, eluting with 0-100% (25% ethanol in ethyl acetate)/cyclohexane). The desired fractions were concentrated to give a white solid. This was purified by MDAP (TFA). The appropriate fractions were concentrated to give (±)-1-benzyl-N⁵-((trans)-2-(methoxymethyl)cyclopropyl)-N³-methyl-2-oxo-1,2-dihydropyridine-3,5-dicarboxamide (54 mg, 0.13 mmol, 49% yield) as a colourless oil.

LCMS (2 min Formic): Rt=0.82 min, [MH]⁺=370.2.

Example 287: N⁵-Cyclopropyl-1-(3-(2-hydroxyethyl)benzyl)-N³-methyl-2-oxo-1,2-dihydropyridine-3,5-dicarboxamide

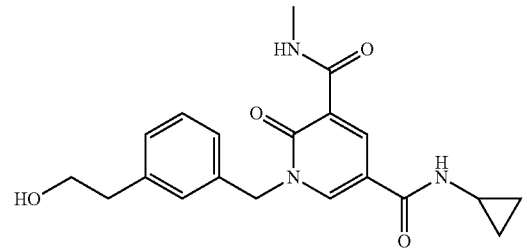 [SMILES: CNC(=O)c1cc(C(=O)NC2CC2)cn(Cc2cccc(CCO)c2)c1=O]

2-(3-(Bromomethyl)phenyl)ethanol (247 mg, 1.15 mmol) was added to a solution of N⁵-cyclopropyl-N³-methyl-2-oxo-1,2-dihydropyridine-3,5-dicarboxamide (270 mg, 1.15 mmol) and potassium carbonate (317 mg, 2.30 mmol) in THF (15 mL). The reaction mixture was left to stir at rt for 2 h. The reaction mixture was heated to 50° C. and left to stir under N₂ overnight. The reaction mixture was then concentrated in vacuo and separated between DCM and water. The organic solution was concentrated in vacuo, loaded in DCM and purified by Biotage Isolera flash chromatography using a SNAP 25 g silica cartridge and eluting with a gradient of 0-10% EtOH/EtOAc to give, after concentration in vacuo—N⁵-cyclopropyl-1-(3-(2-hydroxyethyl)benzyl)-N³-methyl-2-oxo-1,2-dihydropyridine-3,5-dicarboxamide (310 mg, 0.08 mmol, 23% yield) as a white solid.

LCMS (2 min Formic): Rt=0.69 min, [MH]⁺=370

Example 288: (+/−)-tert-Butyl 2-((trans)-2-(1-benzyl-5-(methylcarbamoyl)-6-oxo-1,6-dihydropyridine-3-carboxamido)cyclopropyl)acetate

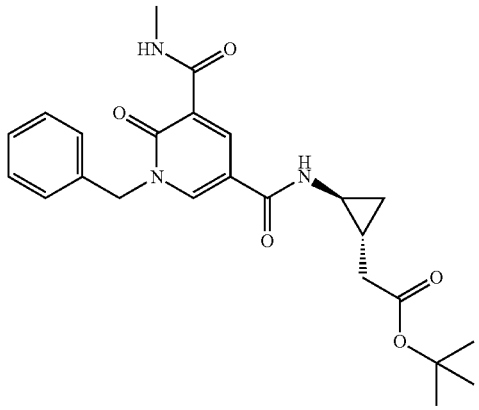 [SMILES: CNC(=O)c1cc(C(=O)N[C@H]2C[C@@H]2CC(=O)OC(C)(C)C)cn(Cc2ccccc2)c1=O]

A mixture of 2,4,6-trichlorophenyl 1-benzyl-5-(methylcarbamoyl)-6-oxo-1,6-dihydropyridine-3-carboxylate (1033 mg, 2.219 mmol) and triethylamine (0.619 mL, 4.44 mmol) in THF (15 mL) was treated with (+/−)-tert-butyl 2-((trans)-2-aminocyclopropyl)acetate (380 mg, 2.22 mmol) and DMAP (27.1 mg, 0.22 mmol) and the resulting mixture was stirred at 50° C. After 2 h the mixture was cooled to rt and concentrated in vacuo. The residue was partitioned between EtOAc and a saturated NaHCO$_3$ solution and the layers were separated. The aqueous phase was extracted with EtOAc and the combined organics were washed with brine, dried over MgSO$_4$ and concentrated in vacuo. Purification of the residue by Biotage SP4 flash chromatography on a 25 g silica column, eluting with a 50% GLOBAl gradient (AcOEt in hexanes) and concentration of the appropriate fractions provided a still impure product. 53 mg was purified by MDAP (Formic) to give tert-butyl 5-(1-benzyl-5-(methylcarbamoyl)-6-oxo-1,6-dihydropyridine-3-carboxamido)pentanoate (1 mg, 2.27 μmol, 0.1% yield). The remaining impure product (243 mg) was dissolved in DMSO (3 mL) and purified by preparative HPLC using the conditions below:

Preparative HPLC Method:
Injection: 3 mL
Column: CSH C18 column: 150×30 mm, 5 μm
Mobile Phase: B: acetonitrile; A: 10 mM ammonium bicarbonate in water, adjusted to pH 10 with ammonia solution
Time (min)/% A: 0/80, 3/80, 3.5/69, 25/58, 32/58, 35/1, 41/1
Temp: rt, Flow Rate: 40 mL/min
UV/MS Detection
UV detection: a summed signal from wavelength of 210 nm to 350 nm.
MS: Waters QDA
Ionisation mode: Positive Electrospray
Scan Range: 120 to 800 AMU
Scan Time: 0.5 s
Inter scan Delay: 0.1 s The fractions were combined and dried using a Biotage V10 evaporator to afford (+/−)-tert-butyl 2-((trans)-2-(1-benzyl-5-(methylcarbamoyl)-6-oxo-1,6-dihydropyridine-3-carboxamido)cyclopropyl)acetate (143 mg, 0.33 mmol, 15%) as a white solid.

LCMS (2 min formic): Rt=1.06 min, [MH]$^+$=440.3.

Example 289: N$^5$-Cyclopropyl-N$^3$-methyl-1-(3-(2-morpholinoethyl)benzyl)-2-oxo-1,2-dihydropyridine-3,5-dicarboxamide

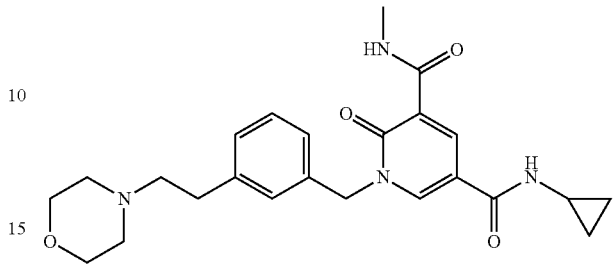

A mixture of N$^5$-cyclopropyl-N$^3$-methyl-2-oxo-1-(3-(2-oxoethyl)benzyl)-1,2-dihydropyridine-3,5-dicarboxamide (100 mg, 0.27 mmol), morpholine (0.047 mL, 0.54 mmol) and triethylamine (0.152 mL, 1.09 mmol) in DCM (3 mL) was stirred at rt for 45 min. Sodium triacetoxyborohydride (231 mg, 1.09 mmol) was added and the reaction was stirred at rt for 24 h. The reaction mixture was then left to stand for 9 days. Sat. NaHCO$_3$ (aq, 40 mL) was added and the mixture stirred at rt for 15 min. The organic phase was separated. The aqueous phase was extracted with DCM. The combined organics were passed through a hydrophobic frit and concentrated in vacuo. The resulting compound was then purified by MDAP (High pH). The appropriate fractions were combined and evaporated to give N$^5$-cyclopropyl-N$^3$-methyl-1-(3-(2-morpholinoethyl)benzyl)-2-oxo-1,2-dihydropyridine-3,5-dicarboxamide (30 mg, 0.07 mmol, 25% yield)

LCMS (2 min Formic): Rt=0.44 min, [MH]$^+$=439

Example 290: 3-((5-(Cyclopropylcarbamoyl)-3-(methylcarbamoyl)-2-oxopyridin-1(2H)-yl)methyl)benzoic acid

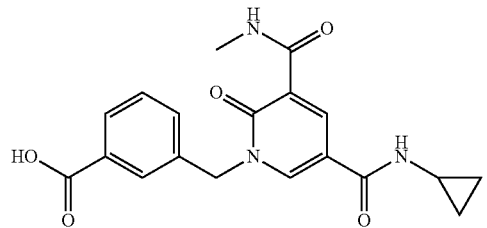 [SMILES: CNC(=O)c1cc(C(=O)NC2CC2)cn(Cc2cccc(C(=O)O)c2)c1=O]

A solution of methyl 3-((5-(cyclopropylcarbamoyl)-3-(methylcarbamoyl)-2-oxopyridin-1(2H)-yl)methyl)benzoate (62 mg, 0.16 mmol) and lithium hydroxide (9.4 mg, 0.39 mmol) in tetrahydrofuran (1.5 mL) and water (0.25 mL) was stirred at rt under nitrogen for 75 h. Further tetrahydrofuran (1.5 mL) and water (0.5 mL) were added (because the solvent had evaporated) and stirring was continued for 2 h. It was then left to stand for 16 h before being stirred for a further 5 h. The reaction mixture was diluted with water/acetonitrile (5:1) to a total volume of 2 mL and was purified by MDAP (2×1 mL injection, formic). The required fractions from both injections were evaporated under a stream of nitrogen, the residues were suspended in acetonitrile (ca. 2×5 mL), combined, evaporated under a stream of nitrogen

Example 291: 1-((1H-Pyrrolo[2,3-b]pyridin-3-yl)methyl)-$N^5$-cyclopropyl-$N^3$-methyl-2-oxo-1,2-dihydropyridine-3,5-dicarboxamide hydrochloride

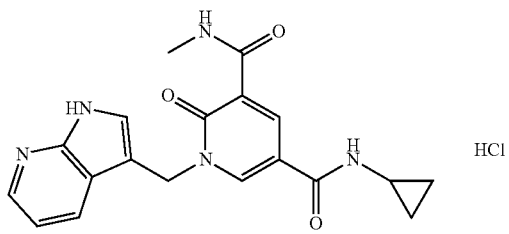 [SMILES: CNC(=O)c1cc(C(=O)NC2CC2)cn(Cc2c[nH]c3ncccc23)c1=O ; Cl]

To a suspension of tert-butyl 3-((5-(cyclopropylcarbamoyl)-3-(methylcarbamoyl)-2-oxopyridin-1(2H)-yl)methyl)-1H-pyrrolo[2,3-b]pyridine-1-carboxylate (44 mg, 0.10 mmol) in 1,4-dioxane (0.75 mL) was added hydrogen chloride (4M in 1,4-dioxane, 0.75 mL, 3.00 mmol) and the reaction mixture stirred at rt for 16.75 h. The reaction mixture was transferred to a tarred vial using a 1:1 mixture of dichloromethane/methanol (4 mL), concentrated under a stream of nitrogen and dried in vacuo to give a beige solid; 1-((1H-pyrrolo[2,3-b]pyridin-3-yl)methyl)-$N^5$-cyclopropyl-$N^3$-methyl-2-oxo-1,2-dihydropyridine-3,5-dicarboxamide, hydrochloride (38.5 mg, 0.10 mmol, 101% yield).

LCMS (2 min formic) Rt=0.57 min, m/z=366 for [MH]$^+$

Example 292: $N^5$-Cyclopropyl-1-(3-(2-(dimethylamino)ethyl)benzyl)-$N^3$-methyl-2-oxo-1,2-dihydropyridine-3,5-dicarboxamide

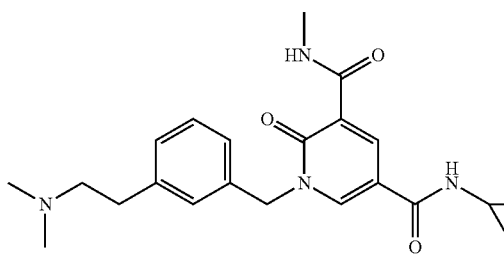

A mixture of $N^5$-cyclopropyl-$N^3$-methyl-2-oxo-1-(3-(2-oxoethyl)benzyl)-1,2-dihydropyridine-3,5-dicarboxamide (81 mg, 0.22 mmol), dimethylamine hydrochloride (19.78 mg, 0.24 mmol) and triethylamine (0.154 mL, 1.10 mmol) in DCM (3 mL) was stirred at rt for 45 min. Sodium triacetoxyborohydride (187 mg, 0.882 mmol) was added and the reaction was stirred at rt overnight. Sat. NaHCO$_3$ (aq, 40 mL) was added and the mixture was stirred at rt for 15 min. The organic phase was separated. The aqueous phase was extracted with DCM. The combined organics were passed through a hydrophobic frit and concentrated in vacuo. The resulting compound was then purified by MDAP (High pH). The appropriate fractions were combined and evaporated to give the crude product. This crude product was purified by Biotage Isolera flash chromatography using a SNAP 10 g silica cartridge and eluting with a gradient of 0-40% EtOAc/cyclohexane to give after concentration in vacuo—$N^5$-cyclopropyl-1-(3-(2-(dimethylamino)ethyl)benzyl)-$N^3$-methyl-2-oxo-1,2-dihydropyridine-3,5-dicarboxamide (10 mg, 0.03 mmol, 11% yield) as a white solid.

LCMS (2 min Formic): Rt=0.45 min, [MH]$^+$=397

Example 293: 1-(Indolin-4-ylmethyl)-$N^3$-methyl-$N^5$-((1S,2S)-2-methylcyclopropyl)-2-oxo-1,2-dihydropyridine-3,5-dicarboxamide

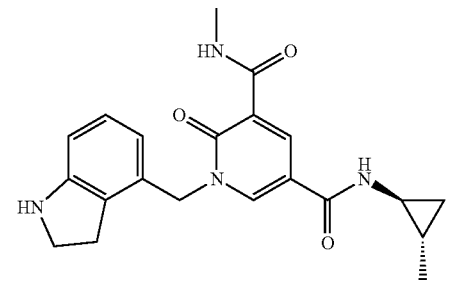 [SMILES: CNC(=O)c1cc(C(=O)N[C@H]2C[C@@H]2C)cn(Cc2cccc3c2CCN3)c1=O]

$N^3$-Methyl-$N^5$-((1S,2S)-2-methylcyclopropyl)-2-oxo-1,2-dihydropyridine-3,5-dicarboxamide (300 mg, 1.204 mmol), indolin-4-ylmethanol (269 mg, 1.81 mmol) and 2-(tributylphosphoranylidene)acetonitrile (0.995 mL, 3.79 mmol) were combined in toluene (12.0 mL) and the reaction mixture heated in a 5 mL microwave vial at 120° C. for 30 min. The reaction mixture was evaporated in vacuo, loaded in methanol and purified by SPE using a sulphonic acid (SCX) 10 g cartridge and eluting with sequential solvents: methanol, 2M ammonia/methanol. The appropriate fractions were combined and evaporated in vacuo to yield the crude product (711 mg) as an orange/brown gum. The residue was loaded in dichloromethane/methanol onto a 50 g SNAP cartridge and purified via Biotage SP4 flash chromatography, eluting from 15-75% (3:1 ethyl acetate:ethanol)/cyclohexane. The relevant fractions were combined and evaporated in vacuo to yield 1-(indolin-4-ylmethyl)-$N^3$-methyl-$N^5$-((1S,2S)-2-methylcyclopropyl)-2-oxo-1,2-dihydropyridine-3,5-dicarboxamide (284 mg, 0.64 mmol, 53% yield) as a yellow solid.

LCMS (2 min High pH): Rt=0.85 min, [MH]$^+$=381.3.

Example 294: 1-Benzyl-$N^5$-((1S,2S)-2-(methoxymethyl)cyclopropyl)-$N^3$-methyl-2-oxo-1,2-dihydropyridine-3,5-dicarboxamide

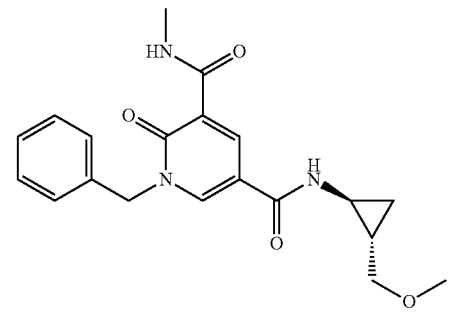 [SMILES: CNC(=O)c1cc(C(=O)N[C@H]2C[C@@H]2COC)cn(Cc2ccccc2)c1=O]

Triethylamine (0.228 mL, 1.64 mmol) was added to a suspension of 2,4,6-trichlorophenyl 1-benzyl-5-(methylcarbamoyl)-6-oxo-1,6-dihydropyridine-3-carboxylate (381 mg, 0.82 mmol), (1S,2S)-2-(methoxymethyl)cyclopropanamine, HCl salt (106 mg, 0.55 mmol), and DMAP (16.66 mg, 0.14 mmol) in THF (8 mL). The reaction mixture was heated to 45° C. under nitrogen overnight. The reaction mixture was partitioned between ethyl acetate and sat. sodium bicarbonate solution and the aqueous layer extracted with ethyl acetate (2×20 mL). The organic layer was passed through a hydrophobic frit and the solvent removed in vacuo. The resulting oil was dissolved in DCM and purified by flash chromatography using a 25 g Biotage SNAP column and a gradient of 0-100% ethyl acetate/cyclohexane followed by 0-20% methanol/ethyl acetate. The product-containing fractions were combined and the solvent removed in vacuo. The product was left to dry in vacuo overnight to give 1-benzyl-$N^5$-((1S,2S)-2-(methoxymethyl)cyclopropyl)-$N^3$-methyl-2-oxo-1,2-dihydropyridine-3,5-dicarboxamide (90 mg, 0.24 mmol, 45% yield) as a pale orange solid.

LCMS (2 min formic): Rt=0.82 min, [MH]$^+$=370.5.

Example 295: (+/−)-$N^5$-((trans)-2-Ethylcyclopropyl)-1-(indolin-4-ylmethyl)-N3-methyl-2-oxo-1,2-dihydropyridine-3,5-dicarboxamide

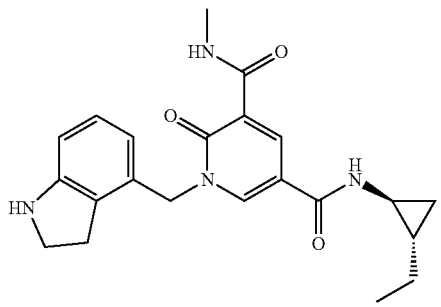 [SMILES: CC[C@H]1C[C@@H]1NC(=O)c1cc(C(=O)NC)c(=O)n(Cc2cccc3c2CCN3)c1]

(+/−)-tert-Butyl 4-((5-(((trans)-2-ethylcyclopropyl)carbamoyl)-3-(methylcarbamoyl)-2-oxopyridin-1(2H)-yl)methyl)indoline-1-carboxylate (54 mg, 0.11 mmol) was dissolved in HCl (5-6M in IPA, 2 mL, 11.00 mmol) and allowed to stir at rt for 3 days. The reaction mixture was concentrated in vacuo, dissolved in MeOH and loaded in a pre-conditioned SCX column (1 g). MeOH was then passed through the column followed by methanolic ammonia. The methanolic ammonia fractions were combined and concentrated in vacuo to give the crude product. The resulting solid was purified by MDAP (High pH) to give, after removal of the solvent—(+/−)-$N^5$-((trans)-2-ethylcyclopropyl)-1-(indolin-4-ylmethyl)-$N^3$-methyl-2-oxo-1,2-dihydropyridine-3,5-dicarboxamide (7 mg, 0.02 mmol, 16% yield) as a yellow solid.

LCMS (2 min Formic): Rt=0.61 min, [MH]$^+$=395

Example 296: 1-(3-(2-Hydroxyethyl)benzyl)-$N^3$-methyl-$N^5$-((1S,2S)-2-methylcyclopropyl)-2-oxo-1,2-dihydropyridine-3,5-dicarboxamide

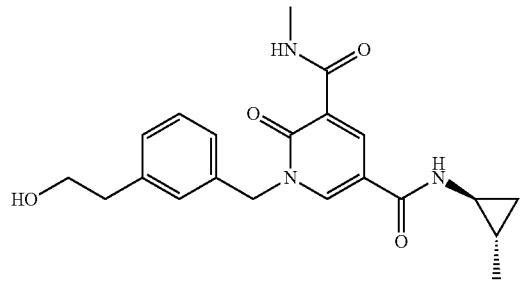 [SMILES: CNC(=O)c1cc(C(=O)N[C@H]2C[C@@H]2C)cn(Cc2cccc(CCO)c2)c1=O]

2-(3-(Bromomethyl)phenyl)ethanol (173 mg, 0.80 mmol) was added to a suspension of $N^3$-methyl-$N^5$-((1S,2S)-2-methylcyclopropyl)-2-oxo-1,2-dihydropyridine-3,5-dicarboxamide (200 mg, 0.80 mmol) and potassium carbonate (222 mg, 1.61 mmol) in DMF (6 mL). The reaction mixture was left to stir at rt for 5 h. The reaction mixture was concentrated in vacuo and separated between EtOAc and water. The organic solution was concentrated in vacuo, loaded in DCM and purified by Biotage Isolera flash chromatography using a SNAP 25 g silica chromatography eluting with a gradient of 30-100% EtOAc/cyclohexane. The appropriate fractions were combined and concentrated in vacuo to give 1-(3-(2-hydroxyethyl)benzyl)-$N^3$-methyl-$N^5$-((1S,2S)-2-methylcyclopropyl)-2-oxo-1,2-dihydropyridine-3,5-dicarboxamide (165 mg, 0.43 mmol, 54% yield) as a white solid.

LCMS (2 min Formic): Rt=0.77 min, [MH]$^+$=384

Example 297: 1-Benzyl-$N^5$-((1S,2R)-2-((dimethylamino)methyl)cyclopropyl)-$N^3$-methyl-2-oxo-1,2-dihydropyridine-3,5-dicarboxamide

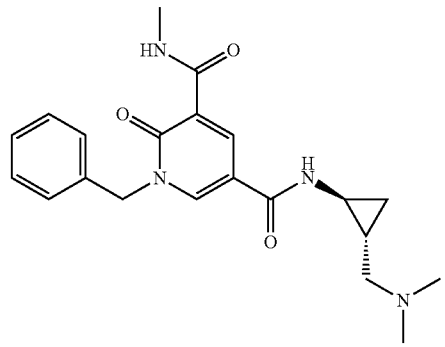 [SMILES: CNC(=O)c1cc(C(=O)N[C@H]2C[C@@H]2CN(C)C)cn(Cc2ccccc2)c1=O]

(1R,2S)-2-((Dimethylamino)methyl) cyclopropanamine, hydrochloride (95 mg, 0.22 mmol, 35% w/w) was added to a solution of 2,4,6-trichlorophenyl 1-benzyl-5-(methylcarbamoyl)-6-oxo-1,6-dihydropyridine-3-carboxylate (113 mg, 0.24 mmol), triethylamine (0.092 mL, 0.66 mmol), and DMAP (6.74 mg, 0.06 mmol) in THF (5 mL). The reaction mixture was heated to 45° C. under nitrogen overnight. The reaction mixture was partitioned between ethyl acetate and sat. sodium bicarbonate solution. and extracted with ethyl acetate (2×20 mL). The organic layer was passed through a hydrophobic frit and the solvent removed in vacuo. The resulting oil was dissolved in DCM and purified by flash chromatography using a 50 g Biotage SNAP silica column and eluting with a gradient of 0-100% (25% ethanol in ethyl acetate)/cyclohexane to remove the major starting material impurity, followed by a gradient of 0-100% (20% methanolic ammonia in DCM)/cyclohexane. The product-containing fraction was concentrated and the oil dissolved in 1:1 DMSO:methanol and purified by MDAP (Formic). The product-containing fractions were concentrated and the product left to dry under a stream of nitrogen overnight to give 1-benzyl-$N^5$-((1S,2R)-2-((dimethylamino)methyl)cyclopropyl)-$N^3$-methyl-2-oxo-1,2-dihydropyridine-3,5-dicarboxamide (2.2 mg, 5.75 μmol, 3% yield) as a yellow solid.

LCMS (2 min formic): Rt=0.52 min, [MH]$^+$=383.5.

Example 298: $N^3$-Methyl-$N^5$-((1S,2S)-2-methylcyclopropyl)-1-((6-methylpyridin-2-yl)methyl)-2-oxo-1,2-dihydropyridine-3,5-dicarboxamide

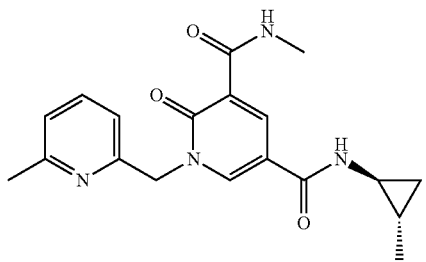 [SMILES: CNC(=O)c1cc(C(=O)N[C@H]2C[C@@H]2C)cn(Cc2cccc(C)n2)c1=O]

A mixture of $N^3$-methyl-$N^5$-((1S,2S)-2-methylcyclopropyl)-2-oxo-1,2-dihydropyridine-3,5-dicarboxamide (42.8 mg, 0.17 mmol), (6-methylpyridin-2-yl)methanol (26.9 mg, 0.22 mmol commercially available from, for example, Sigma-Aldrich) and 2-(tributylphosphoranylidene)acetonitrile (0.090 mL, 0.34 mmol; commercially available from, for example, TCI) in toluene (1 mL) in a sealed vial was heated at 100° C. for 0.5 h in a microwave reactor. The volatiles were evaporated from the mixture under a stream of nitrogen and the residue was redissolved in 3:1 methanol/DMSO (2 mL) and was purified by MDAP (2×1 mL injection, formic). The required fractions from both injections were combined, evaporated and dried in vacuo to give a dark brown oily residue. The residue was redissolved in 3:1 methanol/DMSO (1 mL) and was further purified by MDAP (1×1 mL injection, formic). The required fractions were combined, evaporated and dried in vacuo to give a pale yellow glass; $N^3$-methyl-$N^5$-((1S,2S)-2-methylcyclopropyl)-1-((6-methylpyridin-2-yl)methyl)-2-oxo-1,2-dihydropyridine-3,5-dicarboxamide (42.2 mg, 0.12 mmol, 69% yield).

LCMS (2 min formic) Rt=0.63 min, m/z=355 for [MH]$^+$

Example 299: (+/−)-1-Benzyl-$N^5$-((trans)-2-(2-hydroxyethyl)cyclopropyl)-$N^3$-methyl-2-oxo-1,2-dihydropyridine-3,5-dicarboxamide

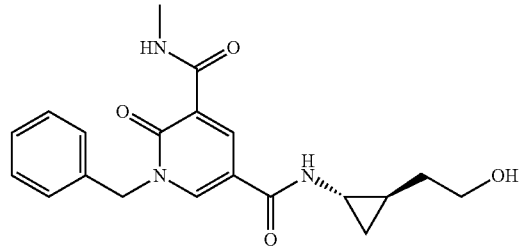 [SMILES: CNC(=O)c1cc(C(=O)N[C@H]2C[C@@H]2CCO)cn(Cc2ccccc2)c1=O]

(+/−)-2-((trans)-2-(1-Benzyl-5-(methylcarbamoyl)-6-oxo-1,6-dihydropyridine-3-carboxamido)cyclopropyl)acetic acid (100 mg, 0.26 mmol) was suspended in THF (5 mL) and Et$_3$N (0.073 mL, 0.52 mmol) was added, then the mixture was stirred for 10 min and isobutyl chloroformate (0.041 mL, 0.31 mmol) was added. The mixture was stirred for 1 h, then cooled in an ice bath and NaBH$_4$ (19.74 mg, 0.52 mmol) was added in one portion. The mixture was stirred for 1 h. Further NaBH$_4$ (20 mg) was added and the mixture was stirred for another 1 h at 0° C. The mixture was quenched by the addition of sat. NH$_4$Cl (aq, 10 mL), then extracted with EtOAc. The organic layer was dried and the crude product was dissolved in DCM and loaded onto a 10 g silica column, and purified by flash chromatography eluting with 0-25% EtOH/EtOAc. The product-containing fractions were evaporated in vacuo to give (+/−)-1-benzyl-$N^5$-(-2-((trans)-2-hydroxyethyl)cyclopropyl)-$N^3$-methyl-2-oxo-1,2-dihydropyridine-3,5-dicarboxamide (2.2 mg, 5.96 μmol, 2% yield)

LCMS (2 min High pH): Rt=0.83 min, [MH]$^+$=370

Example 300: $N^5$-Cyclopropyl-1-((1-(2-hydroxyethyl)-1H-indol-3-yl)methyl)-$N^3$-methyl-2-oxo-1,2-dihydropyridine-3,5-dicarboxamide

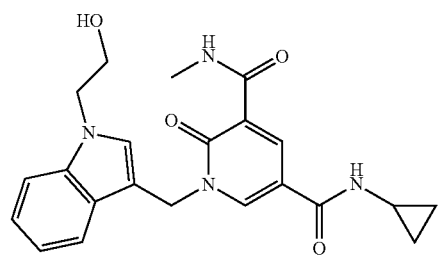 [SMILES: CNC(=O)c1cc(C(=O)NC2CC2)cn(Cc2cn(CCO)c3ccccc23)c1=O]

To a solution of 1-((1-(2-((tert-butyldimethylsilyl)oxy)ethyl)-1H-indol-3-yl)methyl)-$N^5$-cyclopropyl-$N^3$-methyl-2-oxo-1,2-dihydropyridine-3,5-dicarboxamide (34 mg, 0.07 mmol) in tetrahydrofuran (1 mL) was added TBAF (1M in THF, 0.13 mL, 0.13 mmol) and the reaction mixture stirred at rt for 1.5 h.

The solvent was evaporated under a stream of nitrogen to give a green/brown oil which was dissolved in dichloromethane (2 mL), loaded onto a 10 g SNAP silica cartridge and purified by flash chromatography eluting with a gradient of 0-10% ethanol in ethyl acetate. The required fractions were combined and concentrated in vacuo, before being dissolved in a 1:1 mixture of dichloromethane/methanol (10 mL), transferred to a tarred vial, concentrated under a stream of nitrogen and dried in vacuo to give a cream solid; $N^5$-cyclopropyl-1-((1-(2-hydroxyethyl)-1H-indol-3-yl)methyl)-$N^3$-methyl-2-oxo-1,2-dihydropyridine-3,5-dicarboxamide (12.1 mg, 0.03 mmol, 46% yield).

LCMS (2 min formic) Rt=0.79 min, m/z=409 for [MH]$^+$

Example 301: $N^3$-Methyl-$N^5$-((1S,2S)-2-methylcyclopropyl)-1-(3-(2-morpholinoethyl)benzyl)-2-oxo-1,2-dihydropyridine-3,5-dicarboxamide

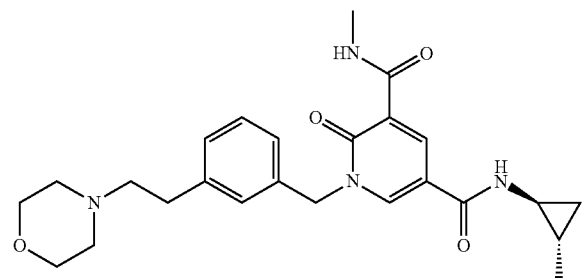

A mixture of $N^3$-methyl-$N^5$-((1S,2S)-2-methylcyclopropyl)-2-oxo-1-(3-(2-oxoethyl)benzyl)-1,2-dihydropyridine-3,5-dicarboxamide (150 mg, 0.39 mmol), morpholine (0.069 mL, 0.79 mmol) and triethylamine (0.219 mL, 1.57 mmol) in DCM (4 mL) was stirred at rt for 45 min. Sodium triacetoxyborohydride (333 mg, 1.57 mmol) was added and the reaction was stirred at rt for 24 h. Sat. NaHCO$_3$ (aq, 40 mL) was added and the mixture was stirred at rt for 1 h. The organic phase was separated. The aqueous phase was extracted with DCM. The combined organics were passed through a hydrophobic frit and concentrated in vacuo. The resulting compound was then purified by MDAP (High pH). The appropriate fractions were combined and evaporated. The solid was dissolved in MeOH and passed through a pre-prepared aminopropyl column (1 g). The appropriate fractions were combined and concentrated in vacuo to give $N^3$-methyl-$N^5$-((1S,2S)-2-methylcyclopropyl)-1-(3-(2-morpholinoethyl)benzyl)-2-oxo-1,2-dihydropyridine-3,5-dicarboxamide (31 mg, 0.07 mmol, 17% yield) as a white solid.

LCMS (2 min Formic): Rt=0.51 min, [MH]$^+$=453

Example 302: 1-Benzyl-$N^5$-((1R,2R)-2-(methoxymethyl)cyclopropyl)-$N^3$-methyl-2-oxo-1,2-dihydropyridine-3,5-dicarboxamide

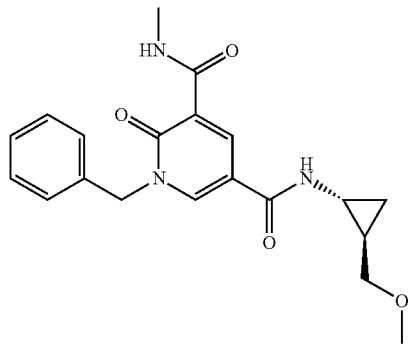 [SMILES: CNC(=O)c1cc(C(=O)N[C@@H]2C[C@H]2COC)cn(Cc2ccccc2)c1=O]

2,4,6-Trichlorophenyl 1-benzyl-5-(methylcarbamoyl)-6-oxo-1,6-dihydropyridine-3-carboxylate (135 mg, 0.29 mmol), (1R,2R)-2-(methoxymethyl)cyclopropanamine, hydrochloride (76 mg, 0.28 mmol), DMAP (3.54 mg, 0.03 mmol), triethylamine (0.121 mL, 0.87 mmol) and THF (3 mL) were stirred at rt under N$_2$. After stirring overnight this was concentrated to give the crude product (320 mg). This was purified by chromatography on SiO$_2$ (Biotage SNAP 50 g, eluting with 0-50% (25% ethanol in ethyl acetate)/ethyl acetate). The desired fractions were concentrated to give 1-benzyl-$N^5$-((1R,2R)-2-(methoxymethyl)cyclopropyl)-$N^3$-methyl-2-oxo-1,2-dihydropyridine-3,5-dicarboxamide (39 mg, 0.10 mmol, 33% yield) as a colourless oil.

LCMS (2 min Formic): Rt=0.82 min, [MH]$^+$=370.5.

Example 303: 1-Benzyl-$N^5$-((1R,2R)-2-(ethoxymethyl)cyclopropyl)-$N^3$-methyl-2-oxo-1,2-dihydropyridine-3,5-dicarboxamide

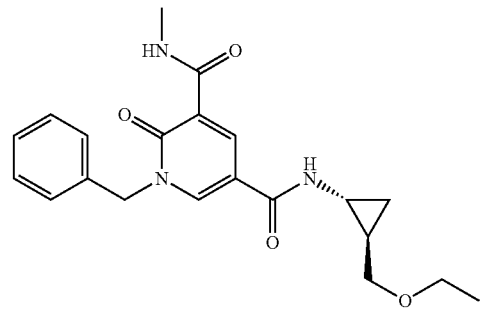 [SMILES: CCOC[C@@H]1C[C@H]1NC(=O)c1cc(C(=O)NC)c(=O)n(Cc2ccccc2)c1]

Triethylamine (0.116 mL, 0.83 mmol) was added to a solution containing 2,4,6-trichlorophenyl 1-benzyl-5-(methylcarbamoyl)-6-oxo-1,6-dihydropyridine-3-carboxylate (214 mg, 0.46 mmol), (1S,2S)-2-(ethoxymethyl)cyclopropanamine, HCl salt (160 mg, 0.42 mmol), and DMAP (12.73 mg, 0.10 mmol) in THF (5 mL). The reaction mixture was heated to 45° C. under nitrogen for 4 h. The reaction mixture was then diluted with sat. sodium bicarbonate solution. and extracted with ethyl acetate (2×20 mL). The organic layer was passed through a hydrophobic frit and the solvent removed in vacuo. The resulting oil was dissolved in DCM and purified by flash chromatography using a 25 g Biotage SNAP silica column and eluting with a gradient of 0-100% ethyl acetate/cyclohexane. The product-containing fractions were combined and the solvent removed in vacuo. The product was left to dry in vacuo overnight to give 1-benzyl-$N^5$-((1R,2R)-2-(ethoxymethyl)cyclopropyl)-$N^3$-methyl-2-oxo-1,2-dihydropyridine-3,5-dicarboxamide (31.3 mg, 0.08 mmol, 20% yield) as a pale yellow solid.

LCMS (2 min formic): Rt=0.88 min, [MH]$^+$=384.5.

Example 304: 1-(3-Hydroxybenzyl)-$N^3$-methyl-$N^5$-((1S,2S)-2-methylcyclopropyl)-2-oxo-1,2-dihydropyridine-3,5-dicarboxamide

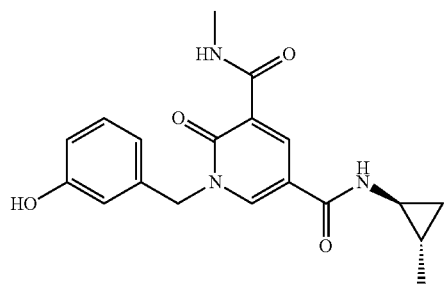 [SMILES: CNC(=O)c1cc(C(=O)N[C@H]2C[C@@H]2C)cn(Cc2cccc(O)c2)c1=O]

1-(3-Methoxybenzyl)-$N^3$-methyl-$N^5$-((1S,2S)-2-methylcyclopropyl)-2-oxo-1,2-dihydropyridine-3,5-dicarboxamide (520 mg, 1.41 mmol) in DCM (6 mL) was cooled to 0° C. under $N_2$ and $BBr_3$ (2.82 mL, 2.82 mmol, 1M in DCM) was added dropwise and allowed to stir under $N_2$ at rt for 6 h. The reaction was quenched with MeOH and concentrated in vacuo. The reaction mixture was dissolved in MeOH, loaded onto silica and purified by Biotage Isolera flash chromatography using a SNAP 50 g silica cartridge and eluting with a gradient of 20-100% EtOAc/cyclohexane to give the crude product which was further purified by MDAP (High pH). The appropriate fractions were combined and concentrated in vacuo to give 1-(3-hydroxybenzyl)-$N^3$-methyl-$N^5$-((1S,2S)-2-methylcyclopropyl)-2-oxo-1,2-dihydropyridine-3,5-dicarboxamide (75 mg, 0.21 mmol, 15% yield) as a white solid.

LCMS (2 min Formic): Rt=0.77 min, $[MH]^+$=356

Example 305: 1-Benzyl-$N^5$-((1S,2S)-2-(ethoxymethyl)cyclopropyl)-$N^3$-methyl-2-oxo-1,2-dihydropyridine-3,5-dicarboxamide

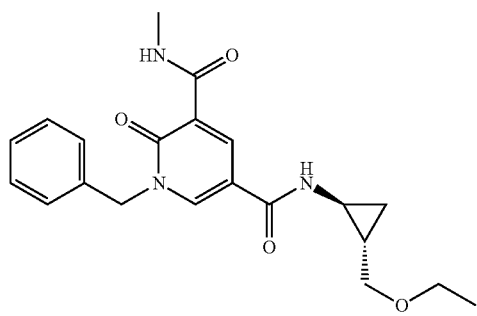 [SMILES: CCOC[C@H]1C[C@@H]1NC(=O)c1cc(C(=O)NC)c(=O)n(Cc2ccccc2)c1]

Triethylamine (0.020 mL, 0.146 mmol) was added to a solution of 2,4,6-trichlorophenyl 1-benzyl-5-(methylcarbamoyl)-6-oxo-1,6-dihydropyridine-3-carboxylate (37.4 mg, 0.08 mmol), (1R,2R)-2-(ethoxymethyl)cyclopropanamine, hydrochloride salt (21 mg, 0.07 mmol), and DMAP (2.2 mg, 0.02 mmol). The reaction mixture was heated to 45° C. under nitrogen for 5 h. The reaction mixture was then diluted with sat. sodium bicarbonate solution. (15 mL) and the organic layer extracted with ethyl acetate (2×15 mL). The organic layer was passed through a hydrophobic frit and the solvent removed in vacuo. The resulting oil was dissolved in DCM and purified by flash chromatography using a 10 g Biotage SNAP silica column and eluting with a gradient of 0-100% ethyl acetate/cyclohexane. The product was left to dry in vacuo for 4 h to give 1-benzyl-$N^5$-((1S,2S)-2-(ethoxymethyl)cyclopropyl)-$N^3$-methyl-2-oxo-1,2-dihydropyridine-3,5-dicarboxamide (1.8 mg, 4.69 μmol, 6% yield) as a pale yellow solid.

LCMS (2 min formic): Rt=0.88 min, $[MH]^+$=384.2.

Example 306: 1-(3-(2-Methoxyethoxy)benzyl)-$N^3$-meth-$N^5$-((1S,2S)-2-methylcyclopropyl)-2-oxo-1,2-dihydropyridine-3,5-dicarboxamide

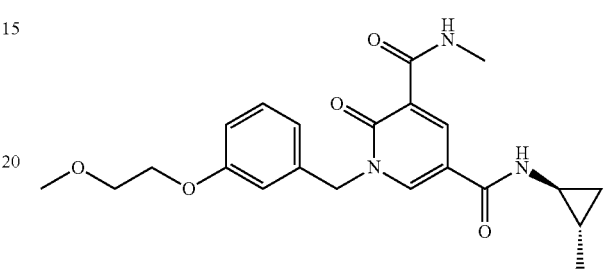

A mixture of 1-(3-hydroxybenzyl)-$N^3$-methyl-$N^5$-((1S,2S)-2-methylcyclopropyl)-2-oxo-1,2-dihydropyridine-3,5-dicarboxamide (55.8 mg, 0.16 mmol), 2-methoxyethanol (0.025 mL, 0.31 mmol) and 2-(tributylphosphoranylidene) acetonitrile (0.082 mL, 0.31 mmol; commercially available from, for example, TCI) in toluene (1.0 mL) in a sealed vial was heated at 100° C. for 30 min in a microwave reactor. The solvent was evaporated from the reaction mixture under a stream of nitrogen. The brown oily residue was re-dissolved in methanol (2 mL) and was purified by MDAP (2×1 mL injection, formic). The desired fractions from both injections were combined and evaporated in vacuo to give a pale yellow sticky solid; 1-(3-(2-methoxyethoxy)benzyl)-$N^3$-methyl-$N^5$-((1S,2S)-2-methylcyclopropyl)-2-oxo-1,2-dihydropyridine-3,5-dicarboxamide (62.2 mg, 0.15 mmol, 96% yield)

LCMS (2 min formic) Rt=0.89 min, m/z=414 for $[MH]^+$

Example 307: 1-(3-((S)-2-Hydroxypropoxy)benzyl)-$N^3$-methyl-$N^5$-((1S,2S)-2-methylcyclopropyl)-2-oxo-1,2-dihydropyridine-3,5-dicarboxamide

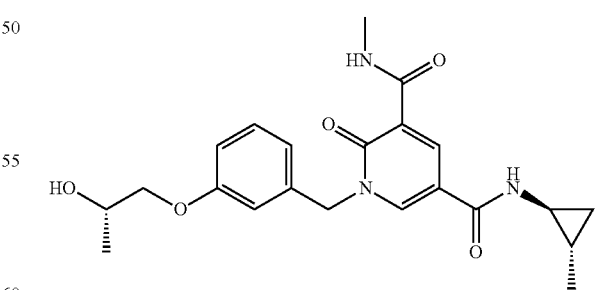

To a solution of (S)-1-(3-(2-hydroxypropoxy)benzyl)-5-(methylcarbamoyl)-6-oxo-1,6-dihydropyridine-3-carboxylic acid (102 mg, 0.28 mmol) in DMF (2 mL) was added HATU (161 mg, 0.43 mmol) followed by (1S,2S)-2-methylcyclopropanamine, hydrochloride (61 mg, 0.57 mmol) and DIPEA (0.247 mL, 1.415 mmol). The resulting reaction mixture was stirred at rt under $N_2$ (formed yellow solution) o/n. The reaction mixture was purified directly by MDAP (Formic). The fractions containing the desired product were partitioned between sat. $NaHCO_3$ solution and DCM. The organic layer was extracted (2×20 mL), dried ($Na_2SO_4$) and concentrated in vacuo to give 1-(3-((S)-2-hydroxypropoxy)benzyl)-$N^3$-methyl-$N^5$-((1S,2S)-2-methylcyclopropyl)-2-oxo-1,2-dihydropyridine-3,5-dicarboxamide (71 mg, 0.16 mmol, 55% yield) as a white solid.

LCMS (2 min Formic): Rt=0.82 min, $[MH]^+$=414.3.

Example 308: $N^3$-Methyl-$N^5$-((1S,2S)-2-methylcyclopropyl)-1-(3-(2-morpholinoethoxy)benzyl)-2-oxo-1,2-dihydropyridine-3,5-dicarboxamide

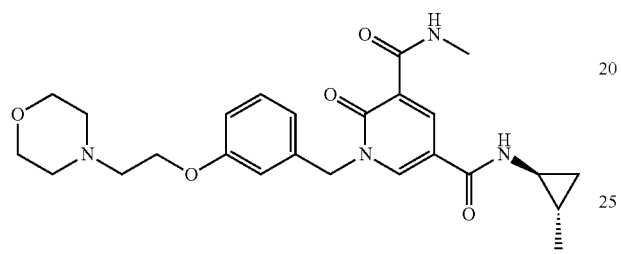

A mixture of 1-(3-hydroxybenzyl)-$N^3$-methyl-$N^5$-((1S,2S)-2-methylcyclopropyl)-2-oxo-1,2-dihydropyridine-3,5-dicarboxamide (45.6 mg, 0.13 mmol), 2-morpholinoethanol (31.0 μL, 0.26 mmol; commercially available from, for example, Acros) and 2-(tributylphosphoranylidene)acetonitrile (67.3 μL, 0.26 mmol; commercially available from, for example, TCI) in toluene (1.0 mL) in a sealed vial was heated at 100° C. for a total of 1 h in a microwave reactor. The mixture was evaporated under a stream of nitrogen to remove the solvent and the residue was re-dissolved in methanol (1 mL) and purified by MDAP (1×1 mL injection, high pH). The required fraction had the solvent evaporated under a stream of nitrogen to give a cream solid; $N^3$-methyl-$N^5$-((1S,2S)-2-methylcyclopropyl)-1-(3-(2-morpholinoethoxy)benzyl)-2-oxo-1,2-dihydropyridine-3,5-dicarboxamide (41.6 mg, 0.09 mmol, 69% yield)

LCMS (2 min formic) Rt=0.51 min, m/z=469 for $[MH]^+$

Example 309: 1-(3-((R)-2-Hydroxypropoxy)benzyl)-$N^3$-methyl-$N^5$-((1S,2S)-2-methylcyclopropyl)-2-oxo-1,2-dihydropyridine-3,5-dicarboxamide

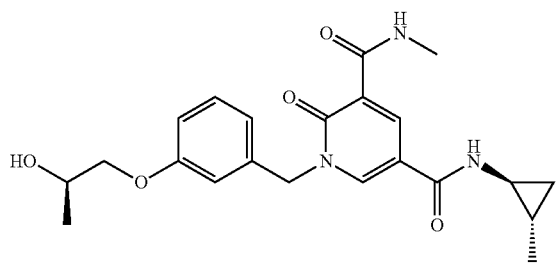 [SMILES: CNC(=O)c1cc(C(=O)N[C@H]2C[C@@H]2C)cn(Cc2cccc(OC[C@@H](C)O)c2)c1=O]

A mixture of 1-(3-hydroxybenzyl)-$N^3$-methyl-$N^5$-((1S,2S)-2-methylcyclopropyl)-2-oxo-1,2-dihydropyridine-3,5-dicarboxamide (43.6 mg, 0.12 mmol), (R)-2-methyloxirane (43.0 μL, 0.61 mmol; commercially available from, for example, Alfa Aesar), triethylamine (34.2 μL, 0.25 mmol) and DMF (1 mL) in a sealed vial was heated at 150° C. for 30 min in a microwave reactor. Further (R)-2-methyloxirane (43.0 μL, 0.61 mmol) and triethylamine (34.2 μL, 0.25 mmol) were added, the vial was re-sealed and the mixture heated at 150° C. for a further 2 h. The mixture was concentrated under a stream of nitrogen to a volume of approximately 0.3 mL, was diluted to 1 mL with methanol and directly purified by MDAP (1×1 mL injection, formic). The required fraction had the solvent evaporated under a stream of nitrogen to give a cream solid; 1-(3-((R)-2-hydroxypropoxy)benzyl)-$N^3$-methyl-$N^5$-((1S,2S)-2-methylcyclopropyl)-2-oxo-1,2-dihydropyridine-3,5-dicarboxamide (29.4 mg, 0.07 mmol, 58.0% yield)

LCMS (2 min formic) Rt=0.82 min, m/z=414 for $[MH]^+$

Example 310: (+/−)-1-((1H-Indol-4-yl)methyl)-$N^3$-ethyl-$N^5$-((trans)-2-methylcyclopropyl)-2-oxo-1,2-dihydropyridine-3,5-dicarboxamide

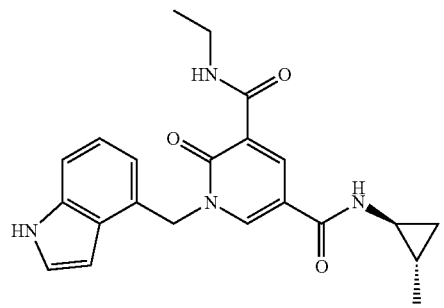 [SMILES: CCNC(=O)c1cc(C(=O)N[C@H]2C[C@@H]2C)cn(Cc2cccc3[nH]ccc23)c1=O]

A solution of (+/−)-$N^3$-ethyl-$N^5$-((trans)-2-methylcyclopropyl)-2-oxo-1-((1-tosyl-1H-indol-4-yl)methyl)-1,2-dihydropyridine-3,5-dicarboxamide (50 mg, 0.08 mmol), NaOH (6.44 mg, 0.16 mmol) in methanol (2 mL) was stirred under nitrogen at 70° C. for 3 h. The reaction mixture was then cooled to rt, diluted with water (50 mL) and extracted with EtOAc (2×50 mL). The combined organic layer was dried over anhydrous $Na_2SO_4$, filtered and the filtrate was concentrated to afford the crude compound. This was purified by flash chromatography using a 100-200 mesh silica gel column and eluting with 0-5% MeOH in DCM. The pure fractions were collected, concentrated and dried to obtain (+/−)-1-((1H-indol-4-yl)methyl)-$N^3$-ethyl-$N^5$-((trans)-2-methylcyclopropyl)-2-oxo-1,2-dihydropyridine-3,5-dicarboxamide (30 mg, 0.07 mmol, 85% yield) as a yellow solid.

Separately, a solution of (+/−)-$N^3$-ethyl-$N^5$-((trans)-2-methylcyclopropyl)-2-oxo-1-((1-tosyl-1H-indol-4-yl)methyl)-1,2-dihydropyridine-3,5-dicarboxamide (100 mg, 0.16 mmol), NaOH (12.88 mg, 0.32 mmol) in methanol (2 mL) was stirred under nitrogen at 70° C. for 3 h. The reaction mixture was then cooled to rt, diluted with water (50 mL) and extracted with EtOAc (2×50 mL). The combined organic layer was dried over anhydrous $Na_2SO_4$, filtered and the filtrate was concentrated to obtain the crude compound. This was purified by flash chromatography using a 100-200 mesh silica gel column and eluting with 0-5% MeOH in DCM. The pure fractions were collected, concentrated and dried to obtain (+/−)-1-((1H-indol-4-yl)methyl)-$N^3$-ethyl-$N^5$-((trans)-2-methylcyclopropyl)-2-oxo-1,2-dihydropyridine-3,5-dicarboxamide (70 mg, 0.15 mmol, 93% yield) as a yellow solid.

The two batches of product were combined and submitted for preparative HPLC following the conditions outlined below:
HPLC Preparative Conditions:
Mobile Phase A: 10 mM Ammonium Bicarbonate (aq.)
Mobile Phase B: acetonitrile
Column: Kromosil packed C18 (250*25 mm)
Method T/% B=0/50, 11/50, 11.5/100, 18/100, 18.5/50, 22/50
Flow rate: 20 mL/min
Solubility: ACN+Water+THF
Temp: Ambient After preparative purification, the compound fraction was lyophilized to afford (+/−)-1-((1H-indol-4-yl)methyl)-$N^3$-ethyl-$N^5$-((trans)-2-methylcyclopropyl)-2-oxo-1,2-dihydropyridine-3,5-dicarboxamide (35 mg, 0.09 mmol, 41% yield) as an off white solid.

LCMS (4.5 min RND-FA-4.5-MIN): Rt=1.97 min, [MH]$^+$=393.2.
LCMS Conditions: RND-FA-4.5-MIN
Column: Acquity BEH C18 (50 mm×2.1 mm, 1.7 μm)
Mobile Phase: B: 0.05% formic acid in ACN; A: 0.05% formic acid in water
Time (min)/% B: 0/3, 0.4/3, 3.2/98, 3.8/98, 4.2/3, 4.5/3
Column Temp: 35° C., Flow Rate: 0.6 mL/min Example 311: 1-Benzyl-$N^5$-((1S*,2R*)-2-(2-hydroxyethyl)cyclopropyl)-$N^3$-methyl-2-oxo-1,2-dihydropyridine-3,5-dicarboxamide Example 312: 1-Benzyl-$N^5$-((1R*,2S*)-2-(2-hydroxyethyl)cyclopropyl)-$N^3$-methyl-2-oxo-1,2-dihydropyridine-3,5-dicarboxamide

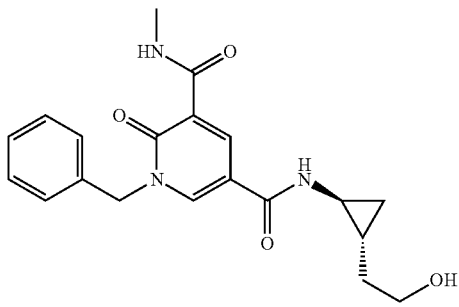

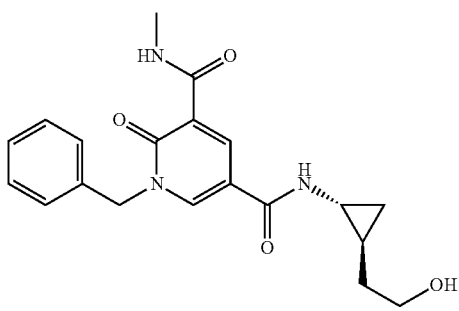

The racemate, (+/−)-1-benzyl-N5-((trans)-2-(2-hydroxyethyl)cyclopropyl)-$N^3$-methyl-2-oxo-1,2-dihydropyridine-3,5-dicarboxamide (31 mg) was dissolved in EtOH (2 mL) with heat. Injection: 2 mL was injected onto the column (30% EtOH/heptane, flow rate=30 mL/min), detection: UV wavelength, 215 nm, 4. Ref 550, 100), Column: 30 mm×25 cm Chiralcel OJ-H (5 μm) Lot No. OJH10027-01. Fractions from 10.5-13 min were bulked and labelled peak 1. Fractions from 17-21 min were bulked and labelled peak 2. The bulked fractions were concentrated in vacuo, then transferred to weighed flasks.

The fractions corresponding to peak 1 were collected to afford Example 311 (12 mg)
LCMS (2 min high pH): Rt=0.83 min, [MH]$^+$=370.3.
The fractions corresponding to peak 2 were collected to afford Example 312 (13 mg)
LCMS (2 min high pH): Rt=0.83 min, [MH]$^+$=370.3.

Example 313: (+/−)-1-((1H-Indol-4-yl)methyl)-$N^5$-((trans)-2-(2-hydroxyethyl)cyclopropyl)-$N^3$-methyl-2-oxo-1,2-dihydropyridine-3,5-dicarboxamide

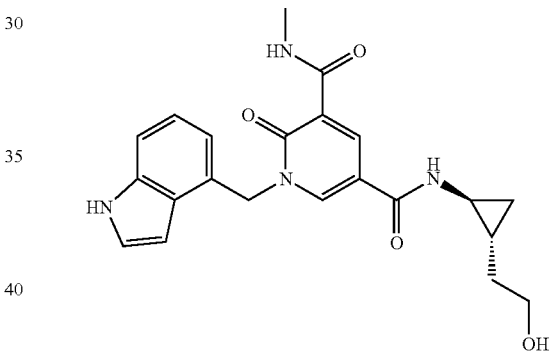

1-((1H-Indol-4-yl)methyl)-$N^5$-((1S,2R)-2-(2-((tert-butyldimethylsilyl)oxy)ethyl)cyclopropyl)-$N^3$-methyl-2-oxo-1,2-dihydropyridine-3,5-dicarboxamide (203 mg, 0.39 mmol) was taken up in THF (10 mL) and TBAF (1M in THF, 0.777 mL, 0.78 mmol) was added. The reaction was stirred at rt for 4 h. The reaction was quenched with water (10 mL) then partitioned between EtOAc and brine (25 mL each). The aqueous layer was re-extracted with EtOAc (25 mL) and the combined organics were dried with Na$_2$SO$_4$, filtered through a hydrophobic frit and concentrated in vacuo to yield an orange oil. The crude product was applied to a 10 g ULTRA SNAP cartridge in the minimum of DCM and purified by flash chromatography eluting with 10-50% (3:1 EtOAc:EtOH) in DCM. The appropriate fractions were concentrated in vacuo to give (+/−)-1-((1H-indol-4-yl)methyl)-$N^5$-((trans)-2-(2-hydroxyethyl)cyclopropyl)-$N^3$-methyl-2-oxo-1,2-dihydropyridine-3,5-dicarboxamide (148 mg, 0.34 mmol, 89% yield) as a cream solid.

LCMS (2 min High pH): Rt=0.79 min, [MH]$^+$=409.4

Example 314: (+/−)-N³-Ethyl-1-(indolin-4-ylm-ethyl)-N⁵-((trans)-2-methylcyclopropyl)-2-oxo-1,2-dihydropyridine-3,5-dicarboxamide

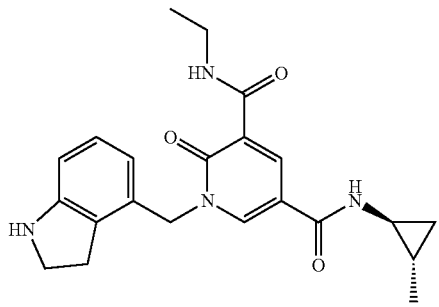

To a solution of (+/−)-tert-butyl 4-((3-(ethylcarbamoyl)-5-(((trans)-2-methylcyclopropyl)carbamoyl)-2-oxopyridin-1(2b)-yl)methyl)indoline-1-carboxylate (400 mg, 0.26 mmol) in DCM (10 mL) stirred under nitrogen at 0° C., was added TFA (1.396 mL, 18.12 mmol). The reaction mixture was stirred at rt for 30 min. The reaction mixture was then concentrated to afford the crude product. This was purified by flash chromatography using a 100-200 mesh silica gel column and eluting with 0-10% MeOH in DCM. The pure fractions were collected, concentrated and dried to afford the desired product which was still impure. The product was further purified by preparative HPLC following the conditions below:

Preparative HPLC Conditions:
Mobile Phase A: 10 mM ammonium acetate (aq., pH 9)
Mobile Phase B: acetonitrile
Column: Xselect CSH C18 (150*19 mm), 5 μm
Method T/% B=0/35, 9.5/35, 10/100, 13/100, 13.5/35, 16/35
Flow rate: 18 mL/min
Solubility: ACN+Water+THF
Temp: Ambient After preparative purification, the compound was lyophilized and diluted with DCM (100 mL), washed with water and the organic phase was then washed with saturated brine (25 mL), dried over sodium sulphate, filtered and evaporated in vacuo to afford the desired product. The compound was triturated with n-pentane and filtered, the filtrate was concentrated to give (+/−)-N³-ethyl-1-(indolin-4-ylmethyl)-N⁵-((trans)-2-methylcyclopropyl)-2-oxo-1,2-dihydropyridine-3,5-dicarboxamide (30 mg, 0.07 mmol, 28% yield) as an off white solid.

LCMS (4.5 min RND-FA-4.5-MIN): Rt=1.43 min, [MH]⁺=395.2.
LCMS Conditions: RND-FA-4.5-MIN
Column: Acquity BEH C18 (50 mm×2.1 mm, 1.7 μm)
Mobile Phase: B: 0.05% formic acid in ACN; A: 0.05% formic acid in water
Time (min)/% B: 0/3, 0.4/3, 3.2/98, 3.8/98, 4.2/3, 4.5/3
Column Temp: 35° C., Flow Rate: 0.6 mL/min

Example 315: (+/−)-N³-Ethyl-1-(3-(2-hydroxyethoxy)benzyl)-N⁵-((trans)-2-methylcyclopropyl)-2-oxo-1,2-dihydropyridine-3,5-dicarboxamide

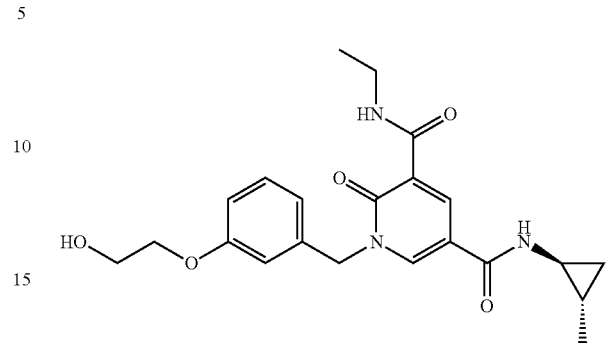

A solution of (+/−)-N³-ethyl-1-(3-hydroxybenzyl)-N⁵-((trans)-2-methylcyclopropyl)-2-oxo-1,2-dihydropyridine-3,5-dicarboxamide (150 mg, 0.40 mmol), 1,3-dioxolan-2-one (139 mg, 1.58 mmol) and K₂CO₃ (164 mg, 1.19 mmol) in DMF (2 mL) was stirred under nitrogen at 90° C. for 6 h. The reaction mixture was then quenched with water and extracted with DCM (2×25 mL). The organic phase was washed with saturated brine (25 mL), dried over sodium sulphate, filtered and evaporated in vacuo to afford the crude product. This was purified by flash chromatography using a 100-200 mesh silica gel column and eluting with 0-10% MeOH in DCM. The pure fractions were collected, concentrated and dried to give (+/−)-N³-ethyl-1-(3-(2-hydroxyethoxy)benzyl)-N⁵-((trans)-2-methylcyclopropyl)-2-oxo-1,2-dihydropyridine-3,5-dicarboxamide (45 mg, 0.10 mmol, 26% yield) as a white solid.

LCMS (4.5 min RND-FA-4.5-MIN): Rt=1.74 min, [MH]⁺=414.2.
LCMS Conditions: RND-FA-4.5-MIN
Column: Acquity BEH C18 (50 mm×2.1 mm, 1.7 μm)
Mobile Phase: B: 0.05% formic acid in ACN; A: 0.05% formic acid in water
Time (min)/% B: 0/3, 0.4/3, 3.2/98, 3.8/98, 4.2/3, 4.5/3
Column Temp: 35° C., Flow Rate: 0.6 mL/min

Example 316: (+/−)-1-((1H-Indol-4-yl)methyl)-N⁵-((trans)-2-(2-((2-aminoethyl)(methyl)amino)ethyl)cyclopropyl)-N³-methyl-2-oxo-1,2-dihydropyridine-3,5-dicarboxamide

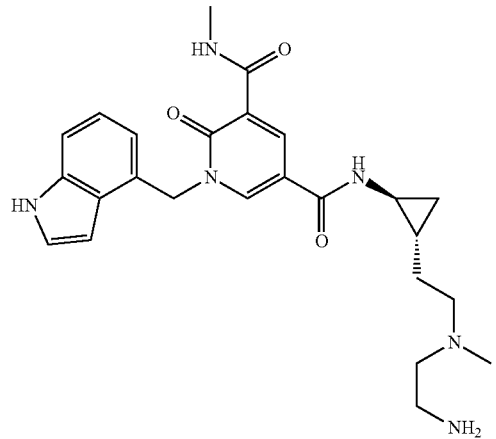 [SMILES: CNC(=O)c1cc(C(=O)N[C@H]2C[C@@H]2CCN(C)CCN)cn(Cc2cccc3[nH]ccc23)c1=O]

(+/−)-tert-Butyl (2-((2-((trans)-2-(1-((1H-indol-4-yl)methyl)-5-(methylcarbamoyl)-6-oxo-1,6-dihydropyridine-3-carboxamido)cyclopropyl)ethyl)(methyl)amino)ethyl)carbamate (44 mg, 0.08 mmol) was taken up in DCM (5 mL) and TFA (0.5 mL, 6.49 mmol) added. The reaction was stirred at rt. After 90 min the reaction was concentrated in vacuo. The crude product was purified by MDAP (high pH). The appropriate fractions were concentrated in vacuo to give (+/−)-1-((1H-indol-4-yl)methyl)-$N^5$-((trans)-2-(2-((2-aminoethyl)(methyl)amino)ethyl)cyclopropyl)-$N^3$-methyl-2-oxo-1,2-dihydropyridine-3,5-dicarboxamide (3.9 mg, 7.98 μmol, 10% yield) as a cream solid.

LCMS (2 min High pH): Rt=0.81 min, [MH]$^+$=465.4.

Example 317: 1-((1H-Indol-4-yl)methyl)-$N^5$-(trans-3-hydroxycyclobutyl)-$N^3$-methyl-2-oxo-1,2-dihydropyridine-3,5-dicarboxamide

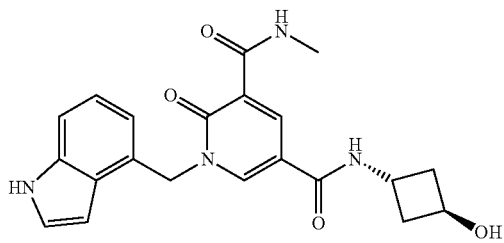

To a mixture of 1-((1H-indol-4-yl)methyl)-5-(methylcarbamoyl)-6-oxo-1,6-dihydropyridine-3-carboxylic acid (56.0 mg, 0.17 mmol) and HATU (101.1 mg, 0.27 mmol) was added a solution of trans-3-aminocyclobutanoyl, hydrochloride (30.7 mg, 0.25 mmol, commercially available from, for example, Activate Scientific) in DMF (1.5 mL). N,N-Diisopropylethylamine (0.105 mL, 0.602 mmol) was added and the mixture was stirred at rt for 1 h. The reaction mixture was concentrated under a stream of nitrogen, diluted with acetonitrile to a total volume of 2 mL and directly purified by MDAP (2×1 mL injection, formic). The required fractions from both injections were combined and evaporated in vacuo. The residue was suspended in dichloromethane and methanol (1:1, ~6 mL), transferred to a tared vial and the solvent evaporated under a stream of nitrogen to give a cream solid; 1-((1H-indol-4-yl)methyl)-$N^5$-(trans-3-hydroxycyclobutyl)-$N^3$-methyl-2-oxo-1,2-dihydropyridine-3,5-dicarboxamide (60.7 mg, 0.15 mmol, 89% yield)

LCMS (2 min formic) Rt=0.70 min, m/z=395 for [MH]$^+$

Example 318: $N^5$-Cyclopropyl-$N^3$-methyl-2-oxo-1-(3-(trifluoromethyl)benzyl)-1,2-dihydropyridine-3,5-dicarboxamide

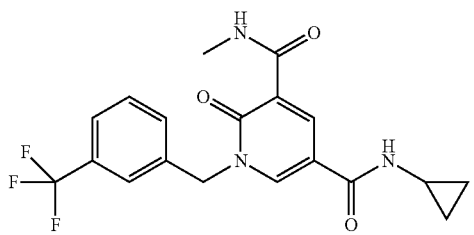 [SMILES: CNC(=O)c1cc(C(=O)NC2CC2)cn(Cc2cccc(C(F)(F)F)c2)c1=O]

To a mixture of $N^5$-cyclopropyl-$N^3$-methyl-2-oxo-1,2-dihydropyridine-3,5-dicarboxamide (51.0 mg, 0.217 mmol) in toluene (1 mL) was added (3-(trifluoromethyl)phenyl)methanol (0.038 mL, 0.28 mmol, commercially available from, for example, Alfa Aesar) and 2-(tributylphosphoranylidene)acetonitrile (0.114 mL, 0.43 mmol; commercially available from, for example, TCI) in a microwave vial. The vial was sealed and the mixture heated in a microwave reactor at 100° C. for 30 min. The volatiles were evaporated under a stream of nitrogen to give a dark brown viscous oil which was redissolved in DMSO (2 mL) and directly purified by MDAP (2×1 mL injection, high pH). The required fractions from both injections were evaporated under a stream of nitrogen, redissolved in methanol (approx. 0.5 mL each) and dichloromethane (approx. 2 mL each) and combined. This solution was evaporated under a stream of nitrogen and the residue dried in vacuo to give a light yellow oily solid which was redissolved in DMSO (2 mL) and further purified by MDAP (2×1 mL injection, formic). The required fractions from both injections were evaporated under a stream of nitrogen, redissolved in methanol (approx. 2 mL each) and dichloromethane (approx. 2 mL each) and combined. This solution was evaporated under a stream of nitrogen and the residue dried in vacuo to give a light yellow oily solid. This was further purified by redissolving the sample in dichloromethane (approx. 3 mL) and directly applying it to the top of a 10 g SNAP cartridge to be purified by SP4 flash column chromatography. The column was eluted with a gradient of 0-50% ethyl acetate:ethanol (3:1) in cyclohexane. The required fractions were combined and evaporated in vacuo to give a white solid; $N^5$-cyclopropyl-$N^3$-methyl-2-oxo-1-(3-(trifluoromethyl)benzyl)-1,2-dihydropyridine-3,5-dicarboxamide (54.7 mg, 0.14 mmol, 64% yield).

LCMS (2 min high pH) Rt=0.98 min, m/z=394 for [MH]$^+$

Example 319: (+/−)-1-((1H-Indol-4-yl)methyl)-$N^5$-((trans)-2-(2-((2-acetamidoethyl)(methyl)amino)ethyl)cyclopropyl)-$N^3$-methyl-2-oxo-1,2-dihydropyridine-3,5-dicarboxamide

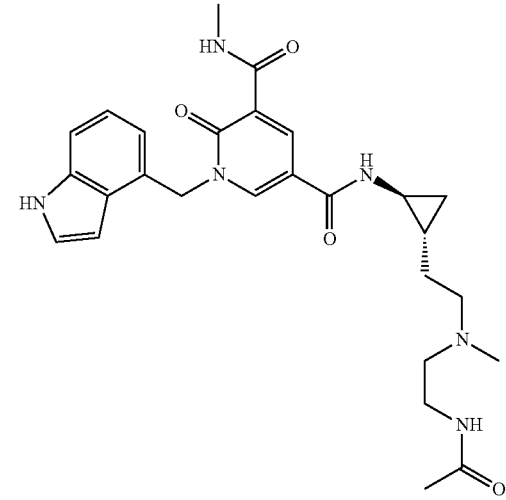 [SMILES: CNC(=O)c1cc(C(=O)N[C@H]2C[C@@H]2CCN(C)CCNC(C)=O)cn(Cc2cccc3[nH]ccc23)c1=O]

(+/−)-1-((1H-Indol-4-yl)methyl)-N-((trans)-2-(2-((2-aminoethyl)(methyl)amino)ethyl)cyclopropyl)-$N^3$-methyl-2-oxo-1,2-dihydropyridine-3,5-dicarboxamide (36.2 mg, 0.08 mmol) was taken up in DCM (5 mL). Et$_3$N (0.022 mL, 0.16 mmol) then AcCl (6.09 µl, 0.09 mmol) was added and the reaction stirred at rt overnight. The reaction was concentrated in vacuo and purified by MDAP (high pH). The appropriate fractions were concentrated in vacuo to give (+/−)-1-((1H-indol-4-yl)methyl)-$N^5$-((trans)-2-(2-((2-acetamidoethyl)(methyl)amino)ethyl)cyclopropyl)-$N^3$-methyl-2-oxo-1,2-dihydropyridine-3,5-dicarboxamide (9.7 mg, 0.02 mmol, 23% yield) as a cream solid.

LCMS (2 min High pH): Rt=0.79 min, [MH]$^+$=507.4.

Example 320: 1-Benzyl-$N^3$-methyl-$N^5$-((1R*,2R'-2-(2-morpholinoethyl)cyclopropyl)-2-oxo-1,2-dihydropyridine-3,5-dicarboxamide Example 321: 1-Benzyl-$N^3$-methyl-$N^5$-((1S*,2S*)-2-(2-morpholinoethyl)cyclopropyl)-2-oxo-1,2-dihydropyridine-3,5-dicarboxamide

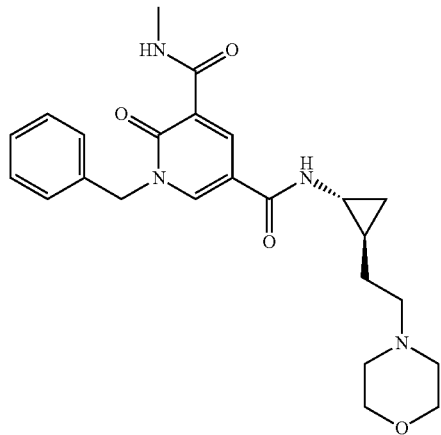 [SMILES: CNC(=O)c1cc(C(=O)N[C@@H]2C[C@H]2CCN2CCOCC2)cn(Cc2ccccc2)c1=O]

(+/−)-1-Benzyl-$N^3$-methyl-$N^5$-((trans)-2-(2-morpholinoethyl)cyclopropyl)-2-oxo-1,2-dihydropyridine-3,5-dicarboxamide (80 mg) was purified by chiral HPLC. The racemate was dissolved in EtOH (2 mL) with heat. Injection: 1 mL of the solution was injected onto the column (15% EtOH (+0.2% isopropylamine)/heptane (+0.2% isopropylamine), flow rate=30 mL/min, detection wavelength=215 nm, 4. Ref 550, 100, Column 30 mm×25 cm Chiralcel OJ-H (5 µm), lot no. OJH10027-01). Total number of injections=2. Fractions from 21-25 min were bulked and labelled peak 1. Fractions from 29-34 min were bulked and labelled peak 2. The bulked fractions were concentrated in vacuo and then transferred to weighed flasks. The final compounds were recovered from DCM and heptane in order to obtain a solid.

The fractions corresponding to peak 1 were collected to afford 1-benzyl-$N^3$-methyl-$N^5$-((1R*,2R*)-2-(2-morpholinoethyl)cyclopropyl)-2-oxo-1,2-dihydropyridine-3,5-dicarboxamide (24 mg, 0.06 mmol as a single unknown enantiomer (example 320).

LCMS (2 min Formic): Rt=0.58 min, [MH]$^+$=439.4.

The fractions corresponding to peak 2 were collected to afford 1-benzyl-$N^3$-methyl-$N^5$-((1S*,2S*)-2-(2-morpholinoethyl)cyclopropyl)-2-oxo-1,2-dihydropyridine-3,5-dicarboxamide (25 mg, 0.06 mmol) as a single unknown enantiomer (example 321).

LCMS (2 min Formic): Rt=0.58 min, [MH]$^+$=439.4.

Example 322: (+/−)-1-Benzyl-$N^3$-methyl-$N^5$-((trans)-2-(2-morpholinoethyl)cyclopropyl)-2-oxo-1,2-dihydropyridine-3,5-dicarboxamide

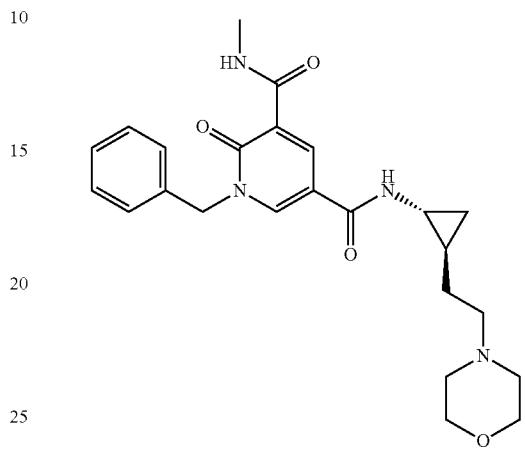

(+/−)-1-Benzyl-$N^5$-((trans)-2-(2-hydroxyethyl)cyclopropyl)-$N^3$-methyl-2-oxo-1,2-dihydropyridine-3,5-dicarboxamide (100 mg, 0.27 mmol) was suspended in DCM (5 mL), then Dess-Martin periodinane (230 mg, 0.54 mmol) was added and the mixture was stirred overnight at rt, then washed with water and the organic layer dried and evaporated in vacuo to give a colourless gummy solid. The crude product was suspended in DCM (5 mL) and morpholine (0.047 ml, 0.541 mmol) was added, followed by sodium triacetoxyborohydride (287 mg, 1.353 mmol). The mixture was stirred for 2 h, then washed with saturated sodium bicarbonate solution, then the organic layer was dried and evaporated in vacuo and the residue purified by MDAP (High pH) to give (+/−)-1-benzyl-$N^3$-methyl-$N^5$-((trans)-2-(2-morpholinoethyl)cyclopropyl)-2-oxo-1,2-dihydropyridine-3,5-dicarboxamide (80 mg, 0.18 mmol, 67% yield)

LCMS (2 min High pH): Rt=0.88 min, [MH]$^+$=439.4.

Example 323: 1-Benzyl-$N^3$-methyl-2-oxo-1,2-dihydropyridine-3,5-dicarboxamide

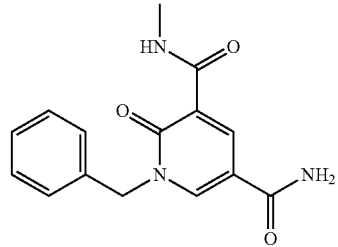 [SMILES: CNC(=O)c1cc(C(N)=O)cn(Cc2ccccc2)c1=O]

2,4,6-Trichlorophenyl 1-benzyl-5-(methylcarbamoyl)-6-oxo-1,6-dihydropyridine-3-carboxylate (1 g, 2.15 mmol) was taken up in THF (25 mL) and ammonia (21.47 mL, 10.74 mmol) was added. The reaction was heated to 50° C. overnight. A thick precipitate formed. The reaction mixture was cooled and partitioned between EtOAc and sat. NaHCO$_3$ (50 mL each). The aqueous phase was re-extracted with EtOAc (2×50 mL) and the combined organics were eluted through a hydrophobic frit then concentrated in vacuo to give a white semi-solid. The crude product was taken up in the minimum volume of 20% MeOH in DCM and silica (~2 g) added. The solvent was removed in vacuo and the silica was applied to a 25 g SNAP cartridge and was purified by flash chromatography, eluting with 10-100% (3:1 EtOAc: EtOH) in cyclohexane. The appropriate fractions were concentrated in vacuo to give 1-benzyl-N³-methyl-2-oxo-1,2-dihydropyridine-3,5-dicarboxamide (128 mg, 0.43 mmol, 20% yield) as a cream solid.

Due to the poor recovery, the experiment was repeated. 2,4,6-trichlorophenyl 1-benzyl-5-(methylcarbamoyl)-6-oxo-1,6-dihydropyridine-3-carboxylate (1 g, 2.15 mmol) was taken up in THF (25 mL) and ammonia (21.47 mL, 10.74 mmol) was added. The reaction was stirred at 50° C. for 5 h in total. The reaction was then cooled and filtered. The filter cake was washed with EtOAc (5 mL) and dried in the vacuum oven over the weekend to give 1-benzyl-N³-methyl-2-oxo-1,2-dihydropyridine-3,5-dicarboxamide (562 mg, 1.87 mmol, 87% yield) as a white solid.

LCMS (2 min High pH): Rt=0.74 min, [MH]⁺=286.3.

Example 324: (R*)—N⁵-Cyclopropyl-1-(2-hydroxy-1-phenylethyl)-N³-methyl-2-oxo-1,2-dihydropyridine-3,5-dicarboxamide Example 325: (S*)—N⁵-Cyclopropyl-1-(2-hydroxy-1-phenylethyl)-N³-methyl-2-oxo-1,2-dihydropyridine-3,5-dicarboxamide

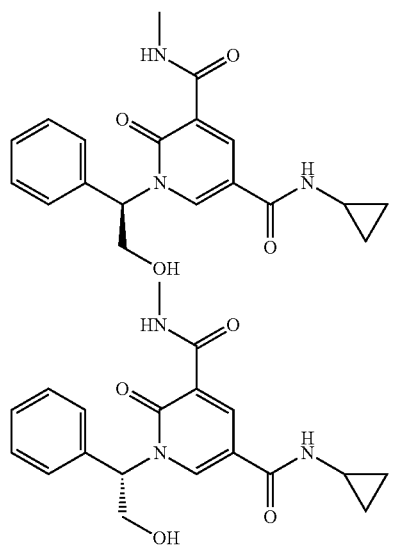

To a flask containing N⁵-cyclopropyl-N³-methyl-2-oxo-1,2-dihydropyridine-3,5-dicarboxamide (100 mg, 0.43 mmol) in trifluoroethanol (4 mL) was added 2-phenyloxirane (0.06 mL, 0.553 mmol, commercially available from, for example, Sigma-Aldrich) at rt. The reaction was heated to 75° C. and stirred for 1 h at rt. The reaction was then heated for a further 16 h. The reaction mixture was concentrated in vacuo, and the crude starting material was redissolved in ethanol (4 mL) and pyridine (0.069 mL, 0.85 mmol) followed by further 2-phenyloxirane (0.063 mL, 0.55 mmol) were added and the reaction heated to reflux for 2 h. The reaction mixture was allowed to cool to rt and concentrated in vacuo to afford the crude product as a dark oil. This was taken up in DCM and purified by flash SP4 chromatography (10 g SNAP silica cartridge) eluting with 0-40% (25% EtOH/EtOAc)/cyclohexane. The product containing fractions were collected together and concentrated in vacuo to afford the crude product as an orange foam. NMR showed the presence of two products in an 80:20 ratio, with the major component assigned as the undesired secondary alcohol: (+/−)-N⁵-cyclopropyl-1-(2-hydroxy-2-phenylethyl)-N³-methyl-2-oxo-1,2-dihydropyridine-3,5-dicarboxamide) with the desired product: (+/−)-N⁵-cyclopropyl-1-(2-hydroxy-1-phenylethyl)-N³-methyl-2-oxo-1,2-dihydropyridine-3,5-dicarboxamide) as the minor component.

The crude product was purified by chiral HPLC. The crude product (120 mg) was dissolved in EtOH (3 mL). Injection: 1 mL of the solution was injected onto the column (40% EtOH (+0.2% isopropylamine)/heptane (+0.2% isopropylamine), flow rate=30 mL/min, detection wavelength=215 nm, 4. Ref 550, 100, Column 30 mm×25 cm Chiralcel IC (5 μm), lot no. IC10028-01). Total number of injections=3. Fractions from 12.5-14 min were bulked and labelled peak 1. Fractions from 15-16 min were bulked and labelled peak 2—this required a further chiral purification using the same method. Fractions from 18.5-21 min were bulked and labelled peak 3. Fractions from 29-31.5 min were bulked and labelled peak 4. The bulked fractions were concentrated in vacuo and then transferred to weighed flasks. The final compounds were recovered from DCM and heptane in order to obtain a solid.

Peaks 1 and 3 were confirmed as corresponding to both enantiomers of the undesired regioisomeric alcohol.

The fractions corresponding to peak 2 were collected to afford: Example 324—(R*)—N⁵-cyclopropyl-1-(2-hydroxy-1-phenylethyl)-N³-methyl-2-oxo-1,2-dihydropyridine-3,5-dicarboxamide (6 mg, 0.02 mmol, 4% yield)

LCMS (2 min Formic): Rt=0.74 min, [MH]⁺=356.3.

The fractions corresponding to peak 4 were collected to afford: Example 325—(S*)—N⁵-cyclopropyl-1-(2-hydroxy-1-phenylethyl)-N³-methyl-2-oxo-1,2-dihydropyridine-3,5-dicarboxamide (8 mg, 0.02 mmol, 5% yield)

LCMS (2 min Formic): Rt=0.74 min, [MH]⁺=356.3.

Example 326: (S*)—N⁵-Cyclopropyl-1-(2-methoxy-1-phenylethyl)-N³-methyl-2-oxo-1,2-dihydropyridine-3,5-dicarboxamide

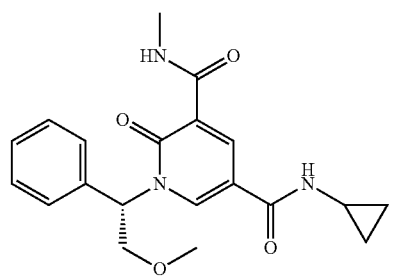 [SMILES: CNC(=O)c1cc(C(=O)NC2CC2)cn([C@H](COC)c2ccccc2)c1=O]

To a solution of (S*)—N⁵-cyclopropyl-1-(2-hydroxy-1-phenylethyl)-N³-methyl-2-oxo-1,2-dihydropyridine-3,5-dicarboxamide (4.5 mg, 0.01 mmol) in DCM (1 mL) at rt was added Proton Sponge (27.1 mg, 0.13 mmol), followed by Meerwein's salt (9.4 mg, 0.06 mmol). The reaction was stirred for 2 h. Further Proton Sponge (27.1 mg, 0.13 mmol) and Meerwein's salt (9.4 mg, 0.06 mmol) were added and the reaction stirred overnight, during which time the DCM evaporated. Further DCM (1 mL) was added. The reaction was stirred for a further 2 h. Further Proton Sponge (27.1 mg, 0.13 mmol) and Meerwein's salt (9.4 mg, 0.06 mmol) were added and the reaction stirred for a further 4 h and then over the weekend, during which time the DCM evaporated. The reaction was diluted with DCM and quenched with sat. aq. NaHCO₃ solution (10 mL) and diluted with DCM (10 mL). The layers were separated and the aqueous layer was extracted with further DCM (2×10 mL). The combined organics were dried and concentrated in vacuo. In order to remove the proton sponge the crude product was taken up in MeOH (20 mL) and added to a preconditioned SCX cartridge (1 g). The product was eluted from this column using MeOH with the proton sponge retained. The MeOH fractions were concentrated in vacuo to afford the crude product. The crude product was purified by SNAP (10 g cartridge) SP4 silica chromatography eluting with 40% EtOAc/cyclohexane. The fractions were left overnight to allow partial evaporation and the appropriate fractions were then concentrated in vacuo to afford the desired product as a yellow oil—(S*)—$N^5$-cyclopropyl-1-(2-methoxy-1-phenylethyl)-$N^3$-methyl-2-oxo-1,2-dihydropyridine-3,5-dicarboxamide (2.0 mg, 5.41 μmol, 43% yield)

LCMS (2 min Formic): Rt=0.88 min, $[MH]^+$=370.2.

Examples 327-341

Examples 324-341 were prepared in an analogous manner to the previous examples

| Ex No. | Name | Structure | [MH]⁺ | Rt (min)* |
|---|---|---|---|---|
| 327 | $N^5$-Cyclopropyl-$N^3$-methyl-1-((2-methylbenzo[d]oxazol-7-yl)methyl)-2-oxo-1,2-dihydropyridine-3,5-dicarboxamide | 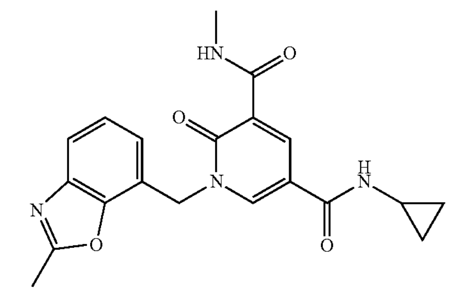 [SMILES: CNC(=O)c1cc(C(=O)NC2CC2)cn(Cc2cccc3nc(C)oc23)c1=O] | 381.2 (formic) | 0.73 |
| 328 | 1-((R*)-1-(3-Methoxyphenyl)ethyl)-$N^3$-methyl-$N^5$-((1S,2S)-2-methylcyclopropyl)-2-oxo-1,2-dihydropyridine-3,5-dicarboxamide | 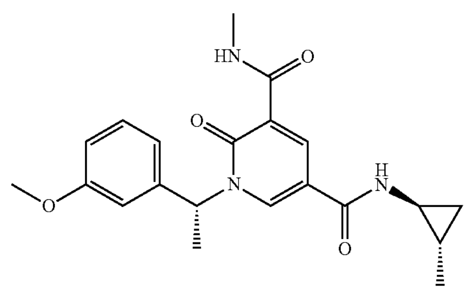 [SMILES: CNC(=O)c1cc(C(=O)N[C@H]2C[C@@H]2C)cn([C@H](C)c2cccc(OC)c2)c1=O] | 384.2 (formic) | 0.97 |
| 329 | (+/−)-1-Benzyl-$N^5$-((trans)-2-((dimethylamino)methyl)cyclopropyl)-$N^3$-methyl-2-oxo-1,2-dihydropyridine-3,5-dicarboxamide | 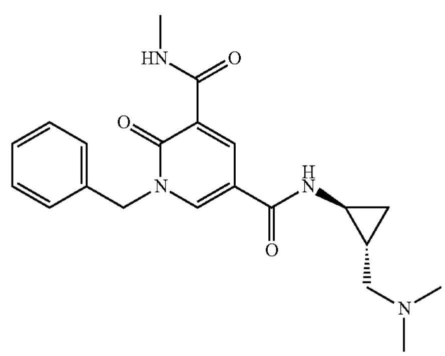 [SMILES: CNC(=O)c1cc(C(=O)N[C@H]2C[C@@H]2CN(C)C)cn(Cc2ccccc2)c1=O] | 383.2 (formic) | 0.52 |
| 330 | 1-((1H-pyrrolo[2,3-c]pyridin-3-yl)methyl)-$N^5$-cyclopropyl-$N^3$-methyl-2-oxo-1,2-dihydropyridine-3,5-dicarboxamide, hydrochloride | 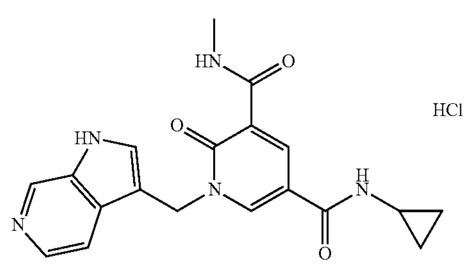 [SMILES: CNC(=O)c1cc(C(=O)NC2CC2)cn(Cc2c[nH]c3cnccc23)c1=O ; Cl] | 366.3 (formic) | 0.36 |

| Ex No. | Name | Structure | [MH]+ | Rt (min)* |
|---|---|---|---|---|
| 331 | 1-((6-Methoxypyridin-2-yl)methyl)-N$^3$-methyl-N$^5$-((1S,2S)-2-methylcyclopropyl)-2-oxo-1,2-dihydropyridine-3,5-dicarboxamide | 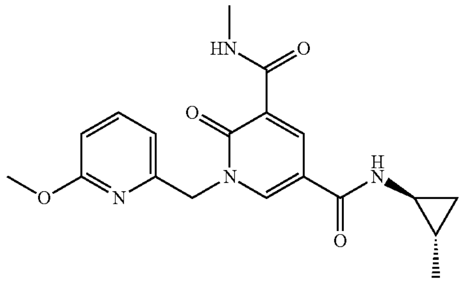 [SMILES: CNC(=O)c1cc(C(=O)N[C@H]2C[C@@H]2C)cn(Cc2cccc(OC)n2)c1=O] | 371.3 (formic) | 0.86 |
| 332 | N$^3$-Methyl-N$^5$-((1S,2S)-2-methylcyclopropyl)-2-oxo-1-(1-(pyridin-2-yl)ethyl)-1,2-dihydropyridine-3,5-dicarboxamide, 1:1 mixture of diastereomers at undefined stereocentre | 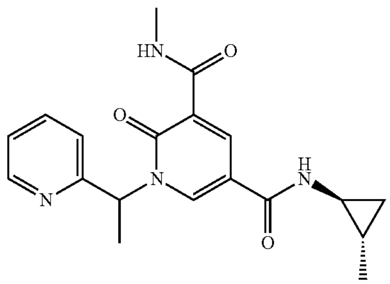 [SMILES: CNC(=O)c1cc(C(=O)N[C@H]2C[C@@H]2C)cn(C(C)c2ccccn2)c1=O] | 355.2 (formic) | 0.75 |
| 333 | N$^3$-Methyl-N$^5$-((1S,2S)-2-methylcyclopropyl)-2-oxo-1-(pyridin-2-ylmethyl)-1,2-dihydropyridine-3,5-dicarboxamide | 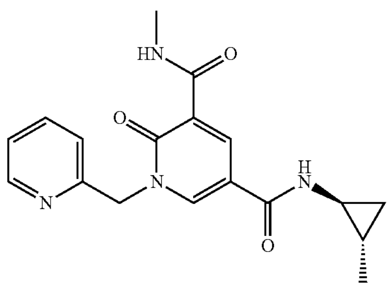 [SMILES: CNC(=O)c1cc(C(=O)N[C@H]2C[C@@H]2C)cn(Cc2ccccn2)c1=O] | 341.2 (formic) | 0.65 |
| 334 | 1-((4-Methoxypyridin-2-yl)methyl)-N$^3$-methyl-N$^5$-((1S,2S)-2-methylcyclopropyl)-2-oxo-1,2-dihydropyridine-3,5-dicarboxamide | 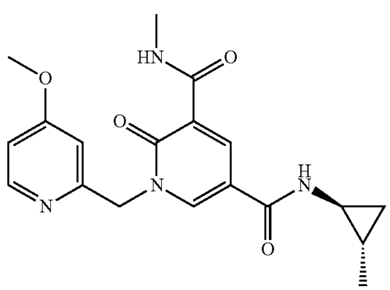 [SMILES: CNC(=O)c1cc(C(=O)N[C@H]2C[C@@H]2C)cn(Cc2cc(OC)ccn2)c1=O] | 371.3 (formic) | 0.51 |
| 335 | N$^3$-Methyl-N$^5$-((1S,2S)-2-methylcyclopropyl)-1-((4-methylpyridin-2-yl)methyl)-2-oxo-1,2-dihydropyridine-3,5-dicarboxamide | 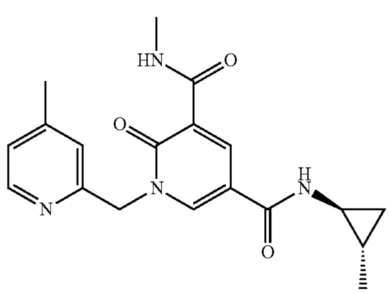 [SMILES: CNC(=O)c1cc(C(=O)N[C@H]2C[C@@H]2C)cn(Cc2cc(C)ccn2)c1=O] | 355.3 (formic) | 0.63 |

| Ex No. | Name | Structure | [MH]+ | Rt (min)* |
|---|---|---|---|---|
| 336 | 1-Benzyl-N⁵-((1R,2S)-2-((dimethylamino)methyl)cyclopropyl)-N³-methyl-2-oxo-1,2-dihydropyridine-3,5-dicarboxamide, formic acid salt | 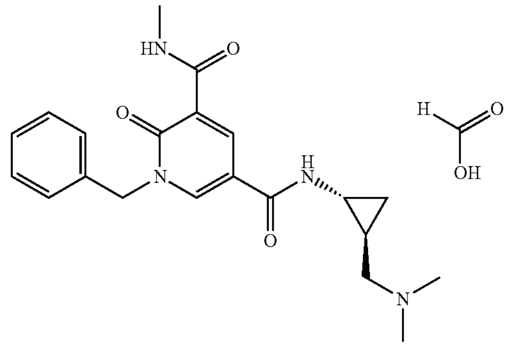 [SMILES: CNC(=O)c1cc(C(=O)N[C@@H]2C[C@H]2CN(C)C)cn(Cc2ccccc2)c1=O ; O=CO] | 383.5 (formic) | 0.52 |
| 337 | 1-(3,5-Dimethoxybenzyl)-N³-methyl-N⁵-((1S,2S)-2-methylcyclopropyl)-2-oxo-1,2-dihydropyridine-3,5-dicarboxamide | 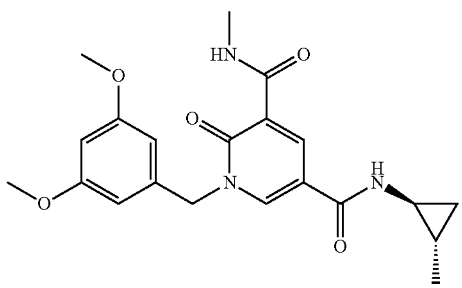 [SMILES: CNC(=O)c1cc(C(=O)N[C@H]2C[C@@H]2C)cn(Cc2cc(OC)cc(OC)c2)c1=O] | 400.4 (formic) | 0.93 |
| 338 | Methyl 4-((3-(methylcarbamoyl)-5-(((1S,2S)-2-methylcyclopropyl)carbamoyl)-2-oxopyridin-1(2H)-yl)methyl)benzoate | 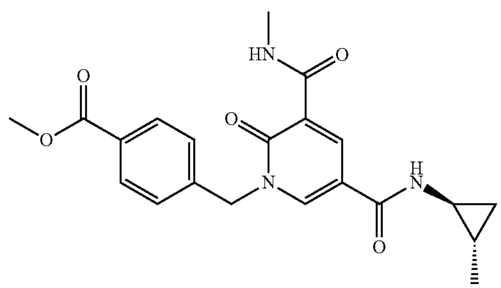 [SMILES: CNC(=O)c1cc(C(=O)N[C@H]2C[C@@H]2C)cn(Cc2ccc(C(=O)OC)cc2)c1=O] | 398.4 (high pH) | 0.93 |
| 339 | 4-((3-(Methylcarbamoyl)-5-(((1S,2S)-2-methylcyclopropyl)carbamoyl)-2-oxopyridin-1(2H)-yl)methyl)benzoic acid | 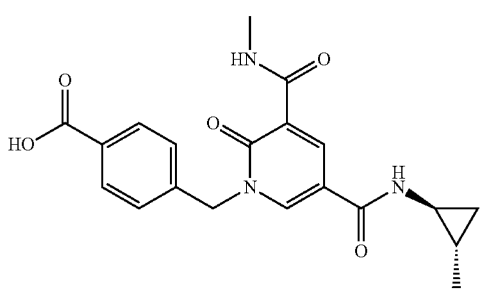 [SMILES: CNC(=O)c1cc(C(=O)N[C@H]2C[C@@H]2C)cn(Cc2ccc(C(=O)O)cc2)c1=O] | 384.3 (high pH) | 0.56 |
| 340 | 1-(4-(2-Aminoethoxy)benzyl)-N³-methyl-N⁵-((1S,2S)-2-methylcyclopropyl)-2-oxo-1,2-dihydropyridine-3,5-dicarboxamide, hydrochloride | 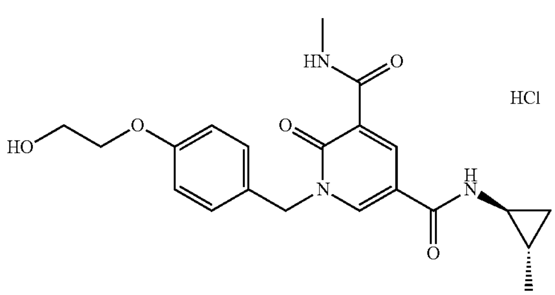 [SMILES: CNC(=O)c1cc(C(=O)N[C@H]2C[C@@H]2C)cn(Cc2ccc(OCCO)cc2)c1=O ; Cl] | 399.4 (high pH) | 0.77 |

| Ex No. | Name | Structure | [MH]+ | Rt (min)* |
|---|---|---|---|---|
| 341 | 1-Benzyl-$N^5$-((trans)-3-hydroxycyclobutyl)-$N^3$-methyl-2-oxo-1,2-dihydropyridine-3,5-dicarboxamide | 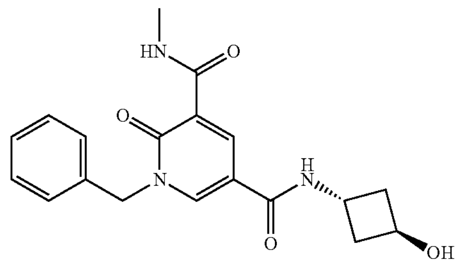 [SMILES: CNC(=O)c1cc(C(=O)N[C@H]2C[C@H](O)C2)cn(Cc2ccccc2)c1=O] | 356.3 (formic) | 0.73 |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

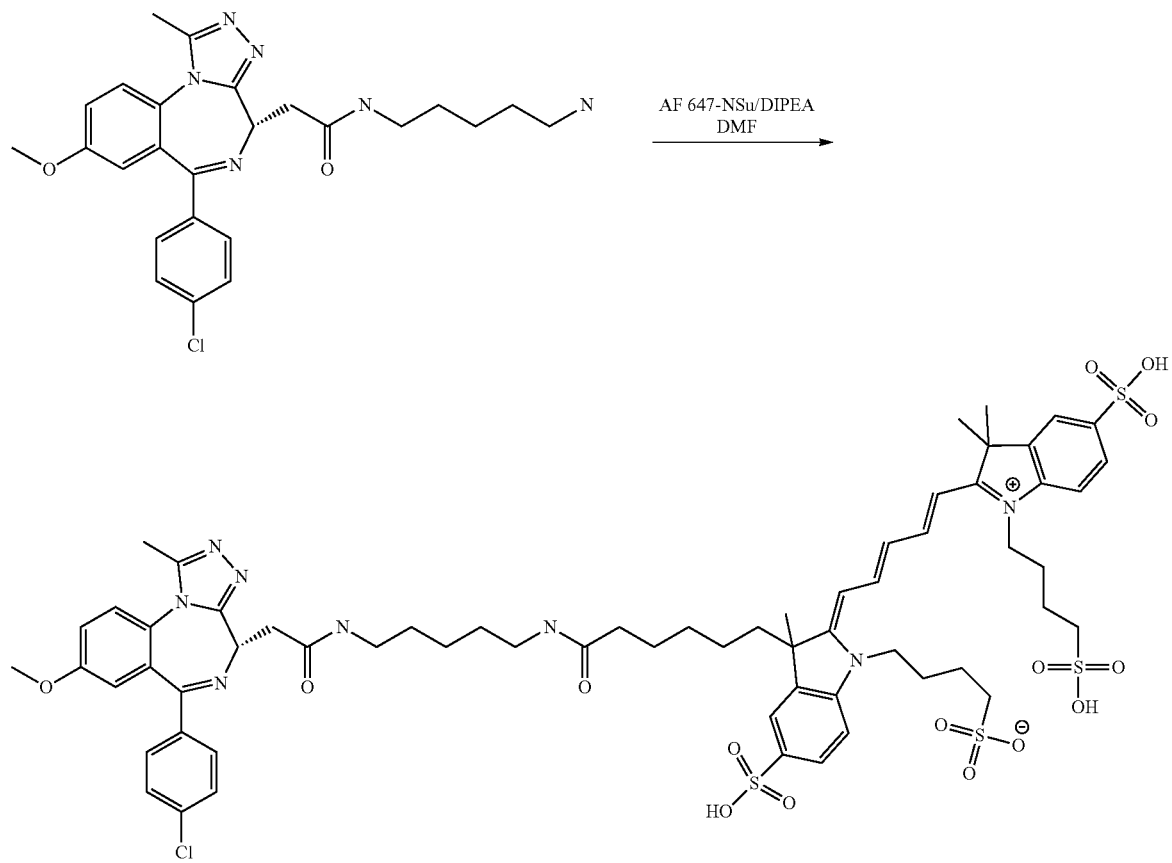

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µl) was added a solution of AlexaFluor647-ONSu (2.16 mg, 1.966 µmol) also in DMF (100 µl). The mixture was basified with DIPEA (1 µl, 5.73 µmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly greatly reduced in comparison to the non mutated, wild type tandem BET proteins (>1000 fold reduction in Kd). The affinities of the single mutated bromdomain tandem proteins for Reference Compound X were equi-potent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 µsecs, measuring emission of the donor and acceptor fluorophores at A615 nm and A665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10^x/10^c)^d)$$

Where 'a' is the minimum, 'b' is the Hill slope, 'c' is the pIC$_{50}$ and 'd' is the maximum.

All compounds (Examples 1-341) were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All tested compounds were found to have a pIC$_{50}$≥4.0 in at least one assay described above.

Examples 159, 160, 163, 168, 169, 171, 173, 177-180, 185, 186, 190, 194, 196, 198-201, 206, 208, 211, 213, 214, 217, 219, 222, 243, 248, 250, 267, 268, 324, 334, 335 and 339 were found to have a pIC$_{50}$≥4.0 and <6.0 in the BRD4 BD2 assay.

All other tested compounds were found to have a pIC$_{50}$≥6.0 in the BRD4 BD2 assay.

Example 1 had a mean pIC$_{50}$ of 7.1 (n=13) in the the BRD4 BD2 TR-FRET assay described above, and a mean pIC$_{50}$ of 4.8 (n=11) in the BRD4 BD1 TR-FRET assay described above.

Example 102 had a mean pIC$_{50}$ of 7.6 (n=17) in the the BRD4 BD2 TR-FRET assay described above, and a mean pIC$_{50}$ of 5.1 (n=17) in the BRD4 BD1 TR-FRET assay described above.

Example 153 had a mean pIC$_{50}$ of 7.2 (n=9) in the the BRD4 BD2 TR-FRET assay described above, and a mean pIC$_{50}$ of 4.5 (n=10) in the BRD4 BD1 TR-FRET assay described above.

Calculation of Selectivity for BRD4 BD2 Over BRD4 BD1

Selectivity for BRD4 BD2 over BRD4 BD1 was calculated as follows:

$$\text{Selectivity} = \text{BRD4BD2pIC}_{50} - \text{BRD4BD1pIC}_{50}$$

Examples 1-167, 170-172, 174-184, 186-207, 209-213, 215-267 and 269-341 were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1-156, 215, 221, 223, 224, 228, 229, 231-236, 238-242, 244-247, 249, 251-266 and 269-321 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Example 1 was found to have selectivity for BRD4 BD2 over BRD4 BD1 of 2.4 log units in at least one of the TR-FRET assays described above, and hence is at least 100-fold selective for BRD4 BD2 over BRD4 BD1.

Example 102 was found to have a selectivity for BRD4 BD2 over BRD4 BD1 of 2.5 log units in at least one of the TR-FRET assays described above, and hence is at least 100-fold selective for BRD4 BD2 over BRD4 BD1.

Example 153 was found to have a selectivity for BRD4 BD2 over BRD4 BD1 of 2.7 log units in at least one of the TR-FRET assays described above, and hence is at least 100-fold selective for BRD4 BD2 over BRD4 BD1.

The invention claimed is:

1. A pharmaceutical composition comprising a compound which is

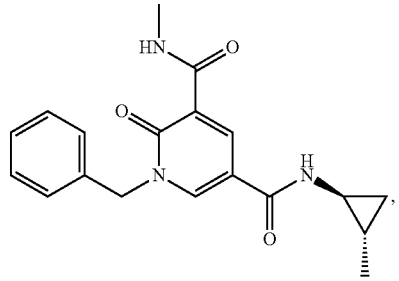 [SMILES: CNC(=O)c1cc(C(=O)N[C@H]2C[C@@H]2C)cn(Cc2ccccc2)c1=O]

or a pharmaceutically acceptable salt thereof, and a pharmaceutically acceptable excipient.

2. The pharmaceutical composition according to claim 1, wherein the composition is suitable for oral administration.

3. The pharmaceutical composition according to claim 2 in the form of a tablet.

4. The pharmaceutical composition according to claim 2 in the form of a capsule.

5. A pharmaceutical composition comprising a compound which is

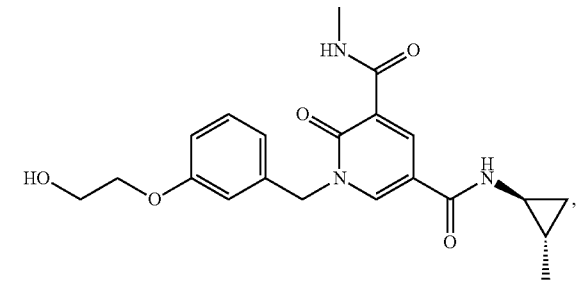 [SMILES: CNC(=O)c1cc(C(=O)N[C@H]2C[C@@H]2C)cn(Cc2cccc(OCCO)c2)c1=O]

or a pharmaceutically acceptable salt thereof, and a pharmaceutically acceptable excipient.

6. The pharmaceutical composition according to claim 5, wherein the composition is suitable for oral administration.

7. The pharmaceutical composition according to claim 6 in the form of a tablet.

8. The pharmaceutical composition according to claim 6 in the form of a capsule.

* * * * *